US012570648B2

(12) United States Patent
Novák et al.

(10) Patent No.: US 12,570,648 B2
(45) Date of Patent: Mar. 10, 2026

(54) 6,7-DIHYDRO-5H-PYRIDO[2,3-C]PYRIDAZINE DERIVATIVES AND RELATED COMPOUNDS AS BCL-XL PROTEIN INHIBITORS AND PRO-APOPTOTIC AGENTS FOR TREATING CANCER

(71) Applicants: LES LABORATOIRES SERVIER, Suresnes (FR); VERNALIS (R&D) LTD, Cambridge (GB)

(72) Inventors: Tibor Novák, Budapest (HU); James Edward Paul Davidson, Great Shelford (GB); Attila Paczal, Budapest (HU); Jérôme-Benoît Starck, Rueil-Malmaison (FR); András Kotschy, Törökbálint (HU); James Brooke Murray, Linton (GB); Simon Bedford, Harlow (GB); Maïa Chanrion, Issy les Moulineaux (FR); Frédéric Colland, Puiseux-en-France (FR); Mark Philip Dodsworth, Manchester (GB); András Herner, Tata (HU); Ana Leticia Maragno, Croissy-sur-Seine (FR); Emma Sanders, London (GB); Mátyás Pál Timári, Budapest (HU); Paul Webb, Chatteris (GB)

(73) Assignees: LES LABORATOIRES SERVIER, Suresnes (FR); VERNALIS (R&D) LTD, Cambridge (GB)

( * ) Notice: Subject to any disclaimer, the term of this patent is extended or adjusted under 35 U.S.C. 154(b) by 884 days.

(21) Appl. No.: 17/630,673

(22) PCT Filed: Jul. 28, 2020

(86) PCT No.: PCT/EP2020/071181
§ 371 (c)(1),
(2) Date: Jan. 27, 2022

(87) PCT Pub. No.: WO2021/018858
PCT Pub. Date: Feb. 4, 2021

(65) Prior Publication Data
US 2022/0363677 A1 Nov. 17, 2022

(30) Foreign Application Priority Data
Jul. 29, 2019 (EP) .................................... 19188749

(51) Int. Cl.
| | |
|---|---|
| *A61P 37/00* | (2006.01) |
| *A61K 31/428* | (2006.01) |
| *A61K 31/4709* | (2006.01) |
| *A61K 31/5025* | (2006.01) |
| *A61K 31/538* | (2006.01) |
| *A61P 35/00* | (2006.01) |
| *A61P 35/02* | (2006.01) |
| *A61P 37/02* | (2006.01) |
| *A61P 37/06* | (2006.01) |
| *C07D 401/12* | (2006.01) |
| *C07D 401/14* | (2006.01) |
| *C07D 403/12* | (2006.01) |
| *C07D 417/14* | (2006.01) |
| *C07D 471/04* | (2006.01) |
| *C07D 487/04* | (2006.01) |

(52) U.S. Cl.
CPC ............ *C07D 417/14* (2013.01); *A61P 35/00* (2018.01); *A61P 35/02* (2018.01); *C07D 471/04* (2013.01); *C07D 487/04* (2013.01)

(58) Field of Classification Search
None
See application file for complete search history.

(56) References Cited

FOREIGN PATENT DOCUMENTS

| | | | | |
|---|---|---|---|---|
| RU | 2017123942 | 1/2019 | | |
| WO | WO2010080503 | 7/2010 | | |
| WO | WO2013855897 | 4/2013 | | |
| WO | WO 2016/094505 | 6/2016 | | |
| WO | WO 2016/094509 | 6/2016 | | |
| WO | WO 2016/094517 | 6/2016 | | |
| WO | WO-2017097870 A1 * | 6/2017 | .......... | C07D 417/12 |
| WO | WO2017214233 | 12/2017 | | |

OTHER PUBLICATIONS

Golub et al., Science, vol. 286, Oct. 15, 1999, pp. 531-537 (Year: 1999).*

(Continued)

*Primary Examiner* — Kortney L. Klinkel
*Assistant Examiner* — Alison Azar Salamatian
(74) *Attorney, Agent, or Firm* — HUESCHEN AND SAGE

(57) ABSTRACT

Compounds of formula (I):

wherein Het, Het$_1$, Het$_2$, A$_4$, A$_5$, Z$_1$, R$_1$, R$_2$ and R$_3$ defined in the description.
Medicaments.

39 Claims, 2 Drawing Sheets
Specification includes a Sequence Listing.

(56) References Cited

OTHER PUBLICATIONS

Heil et al,. WO-2017097870-A1, 2017—English Translation (Year: 2017).*

International Search Report for PCT/EP2020/871181 dated Aug. 17, 2020.

Velentza, et al., Bioorganic & Medicinal Chemistry Letters, 2003, 13, 3465-3470.

\* cited by examiner

Figure 1 : Tumor volume (mm³) of MOLT-4-grafted female NOD SCID mice upon treatment with vehicle (HPBCD/HCl) or Example 24 (2.5, 5 and 7.5 mg/kg, administered IV, Q3D6, n=7).
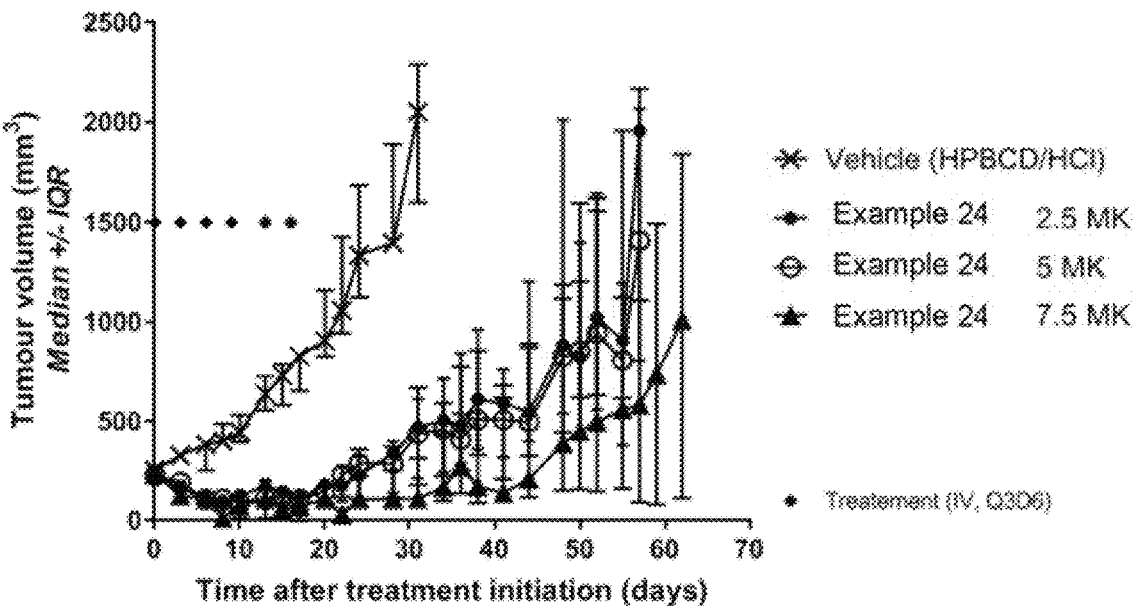

Figure 2 : % of body weight loss of MOLT-4-grafted female NOD SCID mice upon treatment with vehicle (HPBCD/HCl) or Example 24 (2.5, 5 and 7.5 mg/kg, administered IV, Q3D6, n=7).
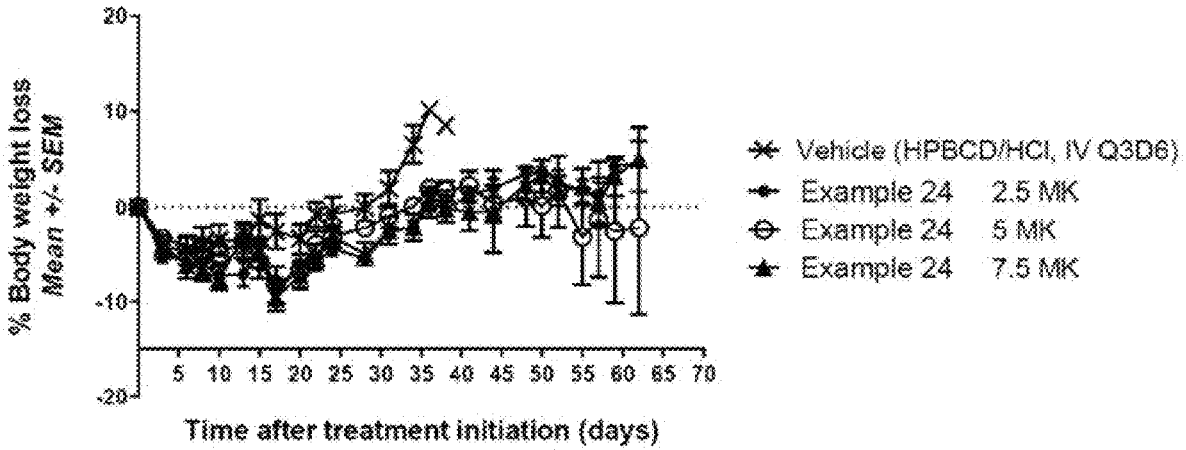

6,7-DIHYDRO-5H-PYRIDO[2,3-C]PYRIDAZINE DERIVATIVES AND RELATED COMPOUNDS AS BCL-XL PROTEIN INHIBITORS AND PRO-APOPTOTIC AGENTS FOR TREATING CANCER

INCORPORATION-BY-REFERENCE OF MATERIAL SUBMITTED ELECTRONICALLY

Incorporated by reference in its entirety is a computer-readable nucleotide/amino acid sequence listing submitted concurrently herewith and identified as follows: One, 6,831 Bytes ASCII (Text) file named "Sequence_listing.txt," created on 12 Jan. 2022.

FIELD OF THE INVENTION

The present invention relates to 6,7-dihydro-5H-pyrido [2,3-c]pyridazin-8-yl derivatives, to pharmaceutical compositions containing them and their uses as pro-apoptotic agents. The compounds of the present invention inhibit the activity of the Bcl-xL protein and may be of interest in the treatment of cancer, immune and autoimmune diseases.

BACKGROUND OF THE INVENTION

Apoptosis (programmed cell death) is an evolutionarily conserved pathway essential for tissue homeostasis, development and removal of damaged cells. Deregulation of apoptosis contributes to human diseases, including malignancies, neurodegenerative disorders, diseases of the immune system and autoimmune diseases (Hanahan and Weinberg, *Cell.* 2011 Mar. 4; 144(5):646-74; Marsden and Strasser, *Annu Rev Immunol.* 2003; 21:71-105; Vaux and Flavell, *Curr Opin Immunol.* 2000 Dec.; 12(6):719-24). Evasion of apoptosis is recognized as a hallmark of cancer, participating in the development as well as the sustained expansion of tumors and the resistance to anti-cancer treatments (Hanahan and Weinberg, *Cell.* 2000 Jan. 7; 100(1): 57-70).

The Bcl-2 protein family comprises key regulators of cell survival which can suppress (e.g., Bcl-2, Bcl-xL, Mcl-1) or promote (e.g., Bad, Bax) apoptosis (Gross et al., *Genes Dev.* 1999 Aug. 1; 13(15):1899-911, Youle and Strasser, *Nat. Rev. Mol. Cell Biol.* 2008 Jan.; 9(1):47-59).

In the face of stress stimuli, whether a cell survives or undergoes apoptosis is dependent on the extent of pairing between the Bcl-2 family members that promote cell death with family members that promote cell survival. For the most part, these interactions involve the docking of the Bcl-2 homology 3 (BH3) domain of proapoptotic family members into a groove on the surface of pro-survival members. The presence of Bcl-2 homology (BH) domain defines the membership of the Bcl-2 family, which is divided into three main groups depending upon the particular BH domains present within the protein. The prosurvival members such as Bcl-2, Bcl-xL, and Mcl-1 contain BH domains 1-4, whereas Bax and Bak, the proapoptotic effectors of mitochondrial outer membrane permeabilization during apoptosis, contain BH domains 1-3 (Youle and Strasser, *Nat. Rev. Mol. Cell Biol.* 2008 Jan.; 9(1):47-59).

Overexpression of the prosurvival members of the Bcl-2 family is a hallmark of cancer and it has been shown that these proteins play an important role in tumor development, maintenance and resistance to anticancer therapy (Czabotar et al., *Nat. Rev. Mol. Cell Biol.* 2014 Jan.; 15(1):49-63). Bcl-xL (also named BCL2L1, from BCL2-like 1) is frequently amplified in cancer (Beroukhim et al., *Nature* 2010 Feb. 18; 463(7283):899-905) and it has been shown that its expression inversely correlates with sensitivity to more than 120 anti-cancer therapeutic molecules in a representative panel of cancer cell lines (NCI-60) (Amundson et al., *Cancer Res.* 2000 Nov. 1; 60(21):6101-10).

In addition, several studies using transgenic knockout mouse models and transgenic overexpression of Bcl-2 family members highlighted the importance of these proteins in the diseases of the immune system and autoimmune diseases (for a review, see Merino et al., Apoptosis 2009 Apr.; 14(4):570-83. doi: 10.1007/s10495-008-0308-4.PMID: 19172396). Transgenic overexpression of Bcl-xL within the T-cell compartment resulted in resistance to apoptosis induced by glucocorticoid, g-radiation and CD3 crosslinking, suggesting that transgenic Bcl-xL overexpression can reduce apoptosis in resting and activated T-cells (Droin et al., *Biochim Biophys Acta* 2004 Mar. 1; 1644(2-3):179-88. doi: 10.1016/j.bbamcr.2003.10.011.PMID: 14996502). In patient samples, persistent or high expression of antiapoptotic Bcl-2 family proteins has been observed (Pope et al., *Nat Rev Immunol.* 2002 Jul.; 2(7):527-35. doi: 10.1038/ nri846.PMID: 12094227). In particular, T-cells isolated from the joints of rheumatoid arthritis patients exhibited increased Bcl-xL expression and were resistant to spontaneous apoptosis (Salmon et al., *J Clin Invest.* 1997 Feb. 1; 99(3):439-46. doi: 10.1172/JCII 19178.PMID: 9022077). The use of BH3 mimetics has also shown benefit in preclinical models of diseases of the immune system and autoimmune diseases. Treatment with ABT-737 (Bcl-2, Bcl-xL, and Bcl-w inhibitor) resulted in potent inhibition of lymphocyte proliferation in vitro. Importantly, mice treated with ABT-737 in animal models of arthritis and lupus showed a significant decrease in disease severity (Bardwell et al., *J Clin Invest.* 1997 Feb. 1; 99(3):439-46. doi: 10.1172/ JCI119178.PMID: 9022077). In addition, it has been shown that ABT-737 prevented allogeneic T-cell activation, proliferation, and cytotoxicity in vitro and inhibited allogeneic T- and B-cell responses after skin transplantation with high selectivity for lymphoid cells (Cippa et al., Transpl Int. 2011 Jul.; 24(7):722-32. doi: 10.1111/j.1432-2277.2011.01272.x. Epub 2011 May 25.PMID: 21615547).

The findings indicated above motivated the discovery and development of a new class of drugs named BH3 mimetics. These molecules are able to disrupt the interaction between the proapoptotic and antiapoptotic members of the Bcl-2 family and are potent inducers of apoptosis. This new class of drugs includes inhibitors of Bcl-2, Bcl-xL, Bcl-w and Mcl-1. The first BH3 mimetics described were ABT-737 and ABT-263, targeting Bcl-2, Bcl-xL and Bcl-w (Park et al., *J. Med. Chem.* 2008 Nov. 13; 51(21):6902-15; Roberts et al., *J. Clin. Oncol.* 2012 Feb. 10; 30(5):488-96). After that, selective inhibitors of Bcl-2 (ABT-199 and S55746—Souers et al., *Nat Med.* 2013 Feb.; 19(2):202-8; Casara et al., *Oncotarget* 2018 Apr. 13; 9(28):20075-20088), Bcl-xL (A-1155463 and A-1331852—Tao et al., *ACS Med Chem Lett.* 2014 Aug. 26; 5(10):1088-93; Leverson et al., *Sci Transl Med.* 2015 Mar. 18; 7(279):279ra40) and Mcl-1 (A-1210477, S63845, S64315, AMG-176 and AZD-5991— Leverson et al., *Cell Death Dis.* 2015 Jan. 15; 6:e1590.; Kotschy et al., *Nature* 2016, 538, 477-482; Maragno et al., *AACR* 2019, Poster #4482; Kotschy et al., WO 2015/ 097123; Caenepeel et al., *Cancer Discov.* 2018 Dec.; 8(12): 1582-1597; Tron et al., *Nat. Commun.* 2018 Dec. 17; 9(1): 5341) were also discovered. The selective Bcl-2 inhibitor ABT-199 is now approved for the treatment of patients with CLL and AML in combination therapy, while the other inhibitors are still under pre-clinical or clinical development. In pre-clinical models, ABT-263 has shown activity in several hematological malignancies and solid tumors (Shoemaker et al., *Clin. Cancer Res.* 2008 Jun. 1; 14(11):3268-77; Ackler et al., *Cancer Chemother. Pharmacol.* 2010 October; 66(5):869-80; Chen et al., *Mol. Cancer Ther.* 2011 Dec.; 10(12):2340-9). In clinical studies, ABT-263 exhibited objective antitumor activity in lymphoid malignancies (Wilson et al., *Lancet Oncol.* 2010 Dec.; 11(12):1149-59; Roberts et al., *J. Clin. Oncol.* 2012 Feb. 10; 30(5):488-96) and its activity is being investigated in combination with several therapies in solid tumors. The selective Bcl-xL inhibitors, A-1155463 or A-1331852, exhibited in vivo activity in pre-clinical models of T-ALL (T-cell Acute Lymphoblastic Leukemia) and different types of solid tumors (Tao et al., *ACS Med. Chem. Lett.* 2014 Aug. 26; 5(10):1088-93; Leverson et al., *Sci. Transl. Med.* 2015 Mar. 18; 7(279):279ra40). The Mcl-1 selective inhibitors have shown promising in vivo activity in several types of hematological cell malignancies in preclinical models and three of them, S64315, AMG176 and AZD5991, are currently being investigated in clinical trials (Yang et al., *Eur. J. Med. Chem.* 2019 May 8; 177:63-75).

Therefore, BH3 mimetics represent a highly attractive approach for the development of novel therapies in oncology and in the field of immune and autoimmune diseases. In particular, the need exists for small molecules that inhibit selectively the Bcl-xL protein. The present invention fulfills this need.

SUMMARY OF THE INVENTION

The present invention provides potent selective Bcl-xL inhibitors of formula (I) as defined below. We have shown that these compounds are able to induce apoptosis of cancer cells in vivo, triggering tumor regression in mice. Based on their pro-apoptotic properties, the compounds of the invention could be of interest for the treatment of pathologies involving a deregulation in apoptosis, such as, for example, cancer, auto-immune diseases and diseases of the immune system. In addition, these compounds were well tolerated in mice, with no clinically relevant body weight loss upon treatment with efficacious doses, indicating a possible therapeutic margin for the use of these Bcl-xL-targeting small molecules in cancer treatment. In agreement with the previously described role of Bcl-xL in the regulation of platelets life-span (Zhang et al., *Cell Death Differ.* 2007 May; 14(5): 943-51; Mason et al., *Cell.* 2007 Mar. 23; 128(6):1173-86), we observed a reduction in the number of circulating platelets after treatment of mice with these inhibitors, with recovery after treatment discontinuation. Considering this effect in platelet survival, the Bcl-xL inhibitors of the present invention could also be used for treating diseases or conditions characterized by an excess or a deregulated activity of platelets, such as, for example, pro-thrombotic conditions.

BRIEF DESCRIPTION OF THE DRAWINGS

FIG. 1 shows the tumor volume (mm³) of MOLT-4-grafted female NOD SCID mice upon treatment with vehicle (HPBCD/HCl) or Example 24 (2.5, 5 and 7.5 mg/kg, administered IV, Q3D6, n=7).

FIG. 2 shows the % of body weight loss of MOLT-4-grafted female NOD SCID mice upon treatment with vehicle (HPBCD/HCl) or Example 24 (2.5, 5 and 7.5 mg/kg, administered IV, Q3D6, n=7).

DETAILED DESCRIPTION OF THE INVENTION

In a first embodiment (E1), the present invention provides compounds of formula (I):

wherein:

the Het moiety represents a fused aromatic or non-aromatic ring composed of from 5 to 7 ring members, which may contain, in addition to the nitrogen, one additional heteroatom or group selected from oxygen, sulphur and C=O, $A_4$ and $A_5$ independently of one another represent a carbon or a nitrogen atom, preferably $A_4$ and $A_5$ represent each a nitrogen atom, $Z_1$ represents a bond, —N(R)—, or —O—, wherein R represents a hydrogen or a linear or branched $C_1$-$C_6$alkyl, $R_1$ represents a group selected from: hydrogen; linear or branched $C_1$-$C_6$alkyl optionally substituted by a hydroxyl or a $C_1$-$C_6$alkoxy group; $C_3$-$C_6$cycloalkyl; trifluoromethyl; linear or branched $C_1$-$C_6$alkylene-heterocycloalkyl wherein the heterocycloalkyl group is optionally substituted by a linear or branched $C_1$-$C_6$alkyl group;

$R_2$ represents a hydrogen or a methyl;

$R_3$ represents a group selected from: hydrogen; linear or branched $C_1$-$C_4$alkyl; —$X_1$—$NR_aR_b$; —$X_1$—$N^+$ $R_aR_bR_c$; —$X_1$—O—Re; —$X_1$—$COOR_c$; —$X_1$—PO $(OH)_2$; —$X_1$—$SO_2(OH)$; —$X_1$—$N_3$ and:

$$—X_1—{\equiv\!\!\equiv}CH,$$

$R_a$ and $R_b$ independently of one another represent a group selected from: hydrogen; heterocycloalkyl; —$SO_2$-phenyl wherein the phenyl may be substituted by a linear or branched $C_1$-$C_6$alkyl; linear or branched $C_1$-$C_6$alkyl optionally substituted by one or two hydroxyl groups; $C_1$-$C_6$alkylene-$SO_2OH$; $C_1$-$C_6$alkylene-$SO_2O$—; $C_1$-$C_6$alkylene-COOH; $C_1$-$C_6$alkylene-PO$(OH)_2$; $C_1$-$C_6$alkylene-NR$_dR_e$; $C_1$-$C_6$alkylene-N+R$_dR_eR_f$; $C_1$-$C_6$alkylene-phenyl wherein the phenyl may be substituted by a $C_1$-$C_6$alkoxy group; the group:

or $R_a$ and $R_b$ form with the nitrogen atom carrying them a cycle $B_1$;

or $R_a$, $R_b$ and $R_e$ form with the nitrogen atom carrying them a bridged $C_3$-$C_8$ heterocycloalkyl, $R_c$, $R_d$, $R_e$, $R_f$ independently of one another represents a hydrogen or a linear or branched $C_1$-$C_6$alkyl group, or $R_d$ and $R_e$ form with the nitrogen atom carrying them a a cycle $B_2$, or $R_d$, $R_e$ and $R_f$ form with the nitrogen atom carrying them a bridged $C_3$-$C_8$ heterocycloalkyl, Het$_1$ represents a group selected from:

Het₂ represents a group selected from:

A₁ is —NH—, —N(C₁-C₃alkyl), O, S or Se,

A₂ is N, CH or C(R₅),

G is selected from the group consisting of:

—C(O)OR$_{G3}$, —C(O)NR$_{G1}$R$_{G2}$, —C(O)R$_{G2}$, —NR$_{G1}$C(O)R$_{G2}$, —NR$_{G1}$C(O)NR$_{G1}$R$_{G2}$, —OC(O)NR$_{G1}$R$_{G2}$, —NR$_{G1}$C(O)OR$_{G3}$, —C(=NOR$_{G1}$)NR$_{G1}$R$_{G2}$, —NR$_{G1}$C(=NCN)NR$_{G1}$R$_{G2}$, —NR$_{G1}$S(O)₂NR$_{G1}$R$_{G2}$, —S(O)₂R$_{G3}$, —S(O)₂NR$_{G1}$R$_{G2}$, —NR$_{G1}$S(O)₂R$_{G2}$, —NR$_{G1}$C(=NR$_{G2}$)NR$_{G1}$R$_{G2}$, —C(=S)NR$_{G1}$R$_{G2}$, —C(=NR$_{G1}$)NR$_{G1}$R$_{G2}$, halogen, —NO₂, and —CN, in which:

R$_{G1}$ and R$_{G2}$ at each occurrence are each independently selected from the group consisting of hydrogen, C₁-C₆alkyl optionally substituted by 1 to 3 halogen atoms, C₂-C₆alkenyl, C₂-C₆alkynyl, C₃-C₆cycloalkyl, phenyl and —(CH₂)₁₋₄-phenyl;

R$_{G3}$ is selected from the group consisting of C₁-C₆alkyl optionally substituted by 1 to 3 halogen atoms, C₂-C₆alkenyl, C₂-C₆alkynyl, C₃-C₆cycloalkyl, phenyl and —(CH₂)₁₋₄-phenyl; or R$_{G1}$ and R$_{G2}$, together with the atom to which each is attached are combined to form a C₃-C₈heterocycloalkyl; or in the alternative, G is selected from the group consisting of:

-continued wherein $R_{G4}$ is selected from $C_1$-$C_6$alkyl optionally substituted by 1 to 3 halogen atoms, $C_2$-$C_6$alkenyl, $C_2$-$C_6$alkynyl and $C_3$-$C_6$cycloalkyl, $R_4$ represents a hydrogen, fluorine, chlorine or bromine atom, a methyl, a hydroxyl or a methoxy group, $R_5$ represents a group selected from: $C_1$-$C_6$alkyl optionally substituted by 1 to 3 halogen atoms; $C_2$-$C_6$alkenyl; $C_2$-$C_6$alkynyl; halogen or —CN, $R_6$ represents a group selected from:

hydrogen;

—$C_2$-$C_6$alkenyl;

—$X_2$—O—$R_7$;

—$X_2$—NSO$_2$—$R_7$;

—C=C($R_9$)—$Y_1$—O—$R_7$;

$C_3$-$C_6$cycloalkyl;

$C_3$-$C_6$heterocycloalkyl optionally substituted by a hydroxyl group;

$C_3$-$C_6$cycloalkylene-$Y_2$—$R_7$;

$C_3$-$C_6$heterocycloalkylene-$Y_2$—$R_7$ group, an heteroarylene-$R_7$ group optionally substituted by a linear or branched $C_1$-$C_6$alkyl group, $R_7$ represents a group selected from: linear or branched $C_1$-$C_6$alkyl group; ($C_3$-$C_6$)cycloalkylene-$R_8$; or:

-continued wherein Cy represents a $C_3$-$C_8$cycloalkyl, $R_8$ represents a group selected from: hydrogen; linear or branched $C_1$-$C_6$alkyl, —NR'$_a$R'$_b$; —NR'$_a$—CO—OR'$_c$; —NR'$_a$—CO—R'$_c$; —N$^+$R'$_a$R'$_b$R'$_c$; —O—R'$_c$; —NH—X'$_2$—N$^+$R'$_a$R'$_b$R'C; —O—X'$_2$—NR'$_a$R'$_b$, —X'$_2$—NR'$_a$R'$_b$, —NR'$_c$—X'$_2$—N$_3$ and:

$$-NR'_c - X'_2 - \equiv CH,$$

$R_9$ represents a group selected from linear or branched $C_1$-$C_6$alkyl, trifluoromethyl, hydroxyl, halogen, $C_1$-$C_6$alkoxy, $R_{10}$ represents a group selected from hydrogen, fluorine, chlorine, bromine, —CF$_3$ and methyl, $R_{11}$ represents a group selected from hydrogen, halogen, $C_1$-$C_3$alkylene-$R_8$, —O—$C_1$-$C_3$alkylene-$R_8$, —CO—NR$_h$R$_i$ and —CH=CH—$C_1$-$C_4$alkylene-NR$_h$R$_i$, —CH=CH—CHO, $C_3$-$C_8$cycloalkylene-CH$_2$—$R_8$, $C_3$-$C_8$heterocycloalkylene-CH$_2$—$R_8$, $R_{12}$ and $R_{13}$, independently of one another, represent a hydrogen atom or a methyl group, $R_{14}$ and $R_{15}$, independently of one another, represent a hydrogen or a methyl group, or $R_{14}$ and $R_{15}$ form with the carbon atom carrying them a a cyclohexyl, $R_h$ and $R_i$, independently of one another, represent a hydrogen or a linear or branched $C_1$-$C_6$alkyl group, $X_1$ represents a linear or branched $C_1$-$C_4$alkylene group optionally substituted by one or two groups selected from trifluoromethyl, hydroxyl, halogen, $C_1$-$C_6$alkoxy, $X_2$ represents a linear or branched $C_1$-$C_6$alkylene group optionally substituted by one or two groups selected from trifluoromethyl, hydroxyl, halogen, $C_1$-$C_6$alkoxy, $X'_2$ represents a linear or branched $C_1$-$C_6$alkylene, $R'_a$ and $R'_b$ independently of one another, represent a group selected from: hydrogen; heterocycloalkyl; —SO$_2$-phenyl wherein the phenyl may be substituted by a linear or branched $C_1$-$C_6$alkyl; linear or branched $C_1$-$C_6$alkyl optionally substituted by one or two hydroxyl or $C_1$-$C_6$alkoxy groups; $C_1$-$C_6$alkylene-SO$_2$OH; $C_1$-$C_6$alkylene-SO$_2$O—; $C_1$-$C_6$alkylene- COOH; $C_1$-$C_6$alkylene-PO(OH)$_2$; $C_1$-$C_6$alkylene-NR'$_d$R'$_e$; $C_1$-$C_6$alkylene-N$^+$R'$_d$R'$_e$R' $C_1$-$C_6$alkylene-O—$C_1$-$C_6$alkylene-OH; $C_1$-$C_6$alkylene-phenyl wherein the phenyl may be substituted by a hydroxyl or a $C_1$-$C_6$alkoxy group; the group:

or R'$_a$ and R'$_b$ form with the nitrogen atom carrying them a cycle B$_3$, or R'$_a$, R'$_b$ and R'$_e$ form with the nitrogen atom carrying them a bridged $C_3$-$C_8$heterocycloalkyl, R'$_c$, R'$_d$, R'$_e$, R'$_f$ independently of one another, represents a hydrogen or a linear or branched $C_1$-$C_6$alkyl group, or R'$_a$ and R'$_e$ form with the nitrogen atom carrying them a cycle B$_4$, or R'$_d$, R'$_e$ and R'$_f$ form with the nitrogen atom carrying them a bridged $C_3$-$C_8$heterocycloalkyl, $Y_1$ represents a linear or branched $C_1$-$C_4$alkylene, $Y_2$ represents a bond, —O—, —O—CH$_2$—, —O—CO—, —O—SO$_2$—, —CH$_2$—, —CH$_2$—O—, —CH$_2$—CO—, —CH$_2$—SO$_2$—, —C$_2$H$_5$—, —CO—, —CO—O—, —CO—CH$_2$—, —CO—NH—CH$_2$—, —SO$_2$—, —SO$_2$—CH$_2$—, —NH—CO—, —NH—SO$_2$—, m=0, 1 or 2, p=1, 2, 3 or 4, $B_1$, $B_2$, $B_3$ and $B_4$, independently of one another, represents a $C_3$-$C_8$heterocycloalkyl group, which group can: (i) be a mono- or bi-cyclic group, wherein bicyclic group includes fused, bridged or spiro ring system, (ii) can contain, in addition to the nitrogen atom, one or two hetero atoms selected independently from oxygen, sulphur and nitrogen, (iii) be substituted by one or two groups selected from: fluorine, bromine, chlorine, linear or branched $C_1$-$C_6$alkyl, hydroxyl, —NH$_2$, oxo or piperidinyl, it also being understood that:

"aryl" means a phenyl, naphthyl, biphenyl or indenyl group,

"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens), "cycloalkyl" means any mono- or bi-cyclic non-aromatic carbocyclic group containing from 3 to 10 ring members, which may include fused, bridged or spiro ring systems, "heterocycloalkyl" means any mono- or bi-cyclic non-aromatic carbocyclic group, composed of from 3 to 10 ring members, and containing from one to 3 hetero atoms selected from oxygen, sulphur, SO, SO$_2$ and nitrogen, it being understood that bicyclic group may be fused or spiro type, heteroarylene, cycloalkylene, heterocycloalkylene mean a divalent heteroaryl, cycloalkyl and heterocycloalkyl, its enantiomers and diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid and camphoric acid.

Among the pharmaceutically acceptable bases there may be mentioned, without implying any limitation, sodium hydroxide, potassium hydroxide, triethylamine and tert-butylamine.

Further enumerated embodiments (E) of the invention are described herein. It will be recognized that features specified in each embodiment may be combined with other specified features to provide further embodiments of the present invention.

E2 The compound according to E1, which is a compound of formula (IA):

E3. The compound according to E1 or E2 wherein $Z_1$ represents —NH— or —O—.

E4 The compound according to any of E1 to E3 wherein $R_3$ represents —X$_1$—NR$_a$R$_b$, preferably the group —C$_2$H$_5$—NH—CH$_3$.

E5 The compound according to E1 or E2, which is selected from:

-continued

E6 The compound according to E5, which is a compound of formula (IB):

E7 The compound according to E6 wherein $Z_1$ represents a bond and $R_3$ represents a hydrogen atom.

E8 The compound according to E1, which is a compound of formula (IC):

wherein $A_3$ represents an oxygen or a sulphur atom.

E9. The compound according to any one of E1 to E8 wherein $R_1$ represents a hydrogen atom, a methyl or a cyclopropyl group, preferably a methyl.

E10. The compound according to any one of E1 to E9 wherein $Het_1$ represents:

or

E11. The compound according to any one of E1 to E10 wherein $Het_2$ represents:

E12. The compound according to any one of E1 to E10 wherein $Het_2$ represents:

E13. The compound according to E11 wherein $R_6$ represents a $—X_2—O—R_7$ group wherein $X_2$ is a propylene group.

E14 The compound according to E13 wherein $R_7$ represents the following group:

E15 The compound according to E13 wherein $R_7$ represents the following group:

E16 The compound according to E13 wherein $R_7$ represents the following group:

E17. The compound according to any of E14 to E16 wherein $R_8$ represents $NR'_aR'_b$.

E18 The compound according to any of E14 to E16 wherein $R_8$ represents a group selected from: dimethylamino, diethylamino, diisopropylamino, diisobutylamino, methylamino, ethylamino, ethyl(methyl)amino, 4-methylpiperazin-1-yl, piperazin-1-yl, pyrrolidin-1-yl, azetidin-1-yl, 1-piperidyl, 4-morpholinyl, 4,4-difluoropiperidin-1-yl, 3,3-difluoropiperidin-1-yl, 3-hydroxy-1-piperidyl, (1S,5R)-3-azabicyclo[3.1.0]hexan-3-yl, 4-(1-piperidyl)-1-piperidyl, 3-oxo-2,8-diazaspiro[4.5]decan-8-yl, (1S,5R)-6,6-difluoro-3-azabicyclo[3.1.0]hexan-3-yl, 2-(dimethylamino)ethylamino, 3-piperazin-1-yl, (3R,5S)-3,5-dimethylpiperazin-1-yl, (but-3-yn-1-yl)amino, (but-3-yn-1-yl)(methyl)amino, (3-azidopropyl)amino, (3-azidopropyl)(methyl)amino (3-aminopropyl)amino, (pent-4-yn-1-yl)amino, methyl (pent-4-yn-1-yl)amino, (prop-2-yn-1-yl)amino, (hex-5-yn-1-yl)amino, 3-[(hex-5-yn-1-yl)(methyl)amino, (4-azidobutyl)amino, (4-azidobutyl)(methyl)amino, [2-(2-hydroxyethoxy)ethyl](methyl)amino, and:

E19. The compound according to any of E14 to E16 wherein $R_8$ represents a group selected from: bis[(3S)-3,4-dihydroxybutyl]amino, amino, [(3S)-3,4-dihydroxybutyl]amino, [(3R)-3,4-dihydroxybutyl]amino, acetyl(methyl)amino, 3-hydroxypropylamino.

E20. The compound according to E13 wherein $R_7$ represents:

wherein $R_{11}$ is selected from 3-(dimethylamino)propyl, 3-(methylamino)propyl, aminomethyl, 2-(dimethylamino)ethyl, 4-(dimethylamino)butyl, 2-(methylamino)ethyl, 4-(methylamino)butyl, 3-(azetidin-1-yl)propyl, 3-(4-methylpiperazin-1-yl)propyl, 3-pyrrolidin-1-ylpropyl, 3-morpholinopropyl, 3-(1-piperidyl)propyl, 3-[(1R,5S)-6,6-difluoro-3-azabicyclo[3.1.0]hexan-3-yl and 3-(3-oxo-2,8-diazaspiro[4.5]decan-8-yl)propyl.

E21. The compound according to E13 wherein $R_7$ represents a group selected from:

E22. The compound according to E12 wherein $R_6$ represents:

E23. The compound according to E22 wherein $R_7$ represents a group selected from:

wherein $R_8$ represents —O—X'2-$NR'_aR'_b$ or —X'2-$NR'_aR'_b$.

E24. The compound according to E22 wherein $R_7$ represents a group selected from:

wherein $R_8$ represents a group selected from: hydrogen, 2-(methylamino)ethoxy, 2-(dimethylamino)ethoxy, 2-[(2-sulfoethyl)amino]ethoxy, 2-[methyl(2-sulfoethyl)amino] ethoxy, 4-methylpiperazin-1-yl and:

E25 The compound according to E22 wherein $R_7$ represents a group selected from:

wherein $R_8$ represents a group selected from: 2-pyrrolidin-1-ylethoxy, 2-(4-methylpiperazin-1-yl)ethoxy, 2-[[(3R)-3,4-dihydroxybutyl]-methyl-amino]ethoxy, 2-(4-hydroxybuty-lamino)ethoxy, 2-[[3-hydroxy-2-(hydroxymethyl)propyl] amino]ethoxy, 2-[bis(2-hydroxyethyl)amino]ethoxy, 2-[[2-hydroxy-1-(hydroxymethyl)ethyl]amino]ethoxy, 2-[2-(2-hydroxyethoxy)ethylamino]ethoxy, 2-[bis(3-hydroxypropyl)amino]ethoxy, 2-(3-hydroxypropylamino)

ethoxy, 2-[bis(4-hydroxybutyl)amino]ethoxy, 2-morpholinoethoxy, 2-(1-piperidyl)ethoxy, 2-piperazin-1-ylethoxy, 2-(azepan-1-yl)ethoxy, 2-(4-isopropylpiperazin-1-yl) ethoxy, 2-[[(4-hydroxyphenyl)methylamino]ethoxy, 2-[2-hydroxyethyl(methyl)amino]ethoxy, 2-[3-methoxypropyl (methyl)amino]ethoxy, 2-[4-hydroxybutyl(methyl)amino] ethoxy, 3-pyrrolidin-1-ylpropyl, 3-(dimethylamino)propyl, 3-(4-methylpiperazin-1-yl)propyl, 3-morpholinopropyl, 3-(3-hydroxypropylamino)propyl, 3-(4-hydroxybuty-lamino)propyl, 3-[[(3S)-3,4-dihydroxybutyl]amino]propyl, 3-hydroxy-2-(hydroxymethyl)propyl]amino]propyl, 3-[4-hydroxybutyl(methyl)amino]propyl, 3-[3-hydroxypropyl (methyl)amino]propyl, 3-[3-[bis(3-hydroxypropyl)amino] propyl, 3-piperazin-1-ylpropyl.

E26 The compound according to any of E1, E2 and E6 wherein $R_3$ represents —$X_1$—PO(OH)$_2$, —$X_1$—SO$_2$(OH), —$X_1$—NR$_a$R$_b$; —$X_1$—N$^+$R$_a$R$_b$R$_c$, wherein R$_a$ or R$_b$, or both of them, represent a group selected from C$_1$-C$_6$alkylene-SO$_2$OH, C$_1$-C$_6$alkylene-SO$_2$O— and C$_1$-C$_6$alkylene-PO(OH)$_2$.

E27 The compound according to any one of E1, E2 and E6 wherein $R_8$ represents —NR'$_a$R'$_b$; —N$^+$R'$_a$R'$_b$R'$_c$; —NH—X'2-N$^+$R'$_a$R'$_b$R'$_e$, wherein R'$_a$ and R'$_b$, or both of them, represent a group selected from C$_1$-C$_6$alkylene-SO$_2$OH and C$_1$-C$_6$alkylene-PO(OH)$_2$.

E28. A compound according to E1 selected in the following group:

2-[3-(1,3-Benzothiazol-2-ylamino)-4-methyl-6,7-dihydro-5H-pyrido[2,3-c]pyridazin-8-yl]-5-[3-[4-[3-(dimethyl-amino)prop-1-ynyl]-2-fluoro-phenoxy]propyl]thiazole-4-carboxylic acid, 2-{3-[(1,3-Benzothiazol-2-yl)amino]-4-methyl-5H,6H,7H,8H-pyrido[2,3-c]pyridazin-8-yl}-5-(3-{2-fluoro-4-[3-(methylamino)prop-1-yn-1-yl]phenoxy}propyl)-1,3-thi-azole-4-carboxylic acid, 2-{3-[(1,3-Benzothiazol-2-yl)amino]-4-methyl-5H,6H,7H,8H-pyrido[2,3-c]pyridazin-8-yl}-5-(3-{4-[3-(dimethyl-amino)propyl]-2-fluorophenoxy}propyl)-1,3-thiazole-4-carboxylic acid, 2-[3-(1,3-Benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)but-1-ynyl]phenoxy]propyl]thiaz-ole-4-carboxylic acid, 2-[3-(1,3-Benzothiazol-2-ylamino)-4-methyl-6,7-dihydro-5H-pyrido[2,3-c]pyridazin-8-yl]-5-[3-[2-fluoro-4-(3-pyr-rolidin-1-ylprop-1-ynyl)phenoxy]propyl]thiazole-4-car-boxylic acid, 5-(3-{4-[3-(Azetidin-1-yl)prop-1-yn-1-yl]-2-fluorophenoxy}propyl)-2-{3-[(1,3-benzothiazol-2-yl) amino]-4-methyl-5H,6H,7H,8H-pyrido[2,3-c]pyridazin-8-yl}-1,3-thiazole-4-carboxylic acid, 2-[3-(1,3-Benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)prop-1-ynyl]phenoxy]propyl]thiaz-ole-4-carboxylic acid, 2-{3-[(1,3-Benzothiazol-2-yl)amino]-4-methyl-5H,6H,7H,8H-pyrido[2,3-c]pyridazin-8-yl}-5-(3-{4-[3-(4,4-difluo-ropiperidin-1-yl)prop-1-yn-1-yl]-2-fluorophenoxy}propyl)-1,3-thiazole-4-carboxylic acid, 2-{3-[(1,3-Benzothiazol-2-yl)amino]-4-methyl-5H,6H,7H,8H-pyrido[2,3-c]pyridazin-8-yl}-5-(3-{4-[3-(3,3-difluo-ropiperidin-1-yl)prop-1-yn-1-yl]-2-fluorophenoxy}propyl)-1,3-thiazole-4-carboxylic acid, 2-[3-(1,3-Benzothiazol-2-ylamino)-4-methyl-6,7-dihydro-5H-pyrido[2,3-c]pyridazin-8-yl]-5-[3-[2-fluoro-4-[3-(3-oxo-2,8-diazaspiro[4.5]decan-8-yl)prop-1-ynyl]phenoxy] propyl]thiazole-4-carboxylic acid, 2-[3-(1,3-Benzothiazol-2-ylamino)-4-methyl-6,7-dihydro-5H-pyrido[2,3-c]pyridazin-8-yl]-5-[3-[4-[3-[(1S,5R)-6,6-difluoro-3-azabicyclo[3.1.0]hexan-3-yl]prop-1-ynyl]-2-fluoro-phenoxy]propyl]thiazole-4-carboxylic acid, 2-[3-(1,3-Benzothiazol-2-ylamino)-4-methyl-6,7-dihydro-5H-pyrido[2,3-c]pyridazin-8-yl]-5-[3-[2-fluoro-4-(3-piperazin-1-ylprop-1-ynyl)phenoxy]propyl]thiazole-4-carboxylic acid, 2-[3-(1,3-Benzothiazol-2-ylamino)-4-methyl-6,7-dihydro-5H-pyrido[2,3-c]pyridazin-8-yl]-5-[3-[4-[3-[(3R,5S)-3,5-dimethylpiperazin-1-yl]prop-1-ynyl]-2-fluoro-phenoxy]propyl]thiazole-4-carboxylic acid, 2-[3-(1,3-Benzothiazol-2-ylamino)-4-methyl-6,7-dihydro-5H-pyrido[2,3-c]pyridazin-8-yl]-5-[3-[4-[3-(diethyl-amino)prop-1-ynyl]-2-fluoro-phenoxy]propyl]thiazole-4-carboxylic acid, 2-[3-(1,3-Benzothiazol-2-ylamino)-4-methyl-6,7-dihydro-5H-pyrido[2,3-c]pyridazin-8-yl]-5-[3-[4-[3-(diisopropy-lamino)prop-1-ynyl]-2-fluoro-phenoxy]propyl]thiazole-4-carboxylic acid, 2-[3-(1,3-Benzothiazol-2-ylamino)-4-methyl-6,7-dihydro-5H-pyrido[2,3-c]pyridazin-8-yl]-5-[3-[4-[3-[2-(dimethyl-amino)ethylamino]prop-1-ynyl]-2-fluoro-phenoxy]pro-pyl]thiazole-4-carboxylic acid, 2-{3-[(1,3-Benzothiazol-2-yl)amino]-4-methyl-6-[2-(meth-ylamino)ethoxy]-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylic acid, 2-[3-(1,3-Benzothiazol-2-ylamino)-4-methyl-6,7-dihydro-5H-pyrido[2,3-c]pyridazin-8-yl]-5-[3-[4-[1-[(dimethyl-amino)methyl]-3-bicyclo[1.1.1]pentanyl]-2-fluoro-phe-noxy]propyl]thiazole-4-carboxylic acid, 2-[3-(1,3-Benzothiazol-2-ylamino)-4-methyl-6,7-dihydro-5H-pyrido[2,3-c]pyridazin-8-yl]-5-[3-[2-fluoro-4-[3-methyl-3-(methylamino)but-1-ynyl]phenoxy]propyl]thi-azole-4-carboxylic acid, 2-[3-(1,3-benzothiazol-2-ylamino)-4-methyl-6,7-dihydro-5H-pyrido[2,3-c]pyridazin-8-yl]-5-[3-[2-fluoro-4-[3-(prop-2-ynylamino)prop-1-ynyl]phenoxy]propyl]thiaz-ole-4-carboxylic acid, 6-{3-[(1,3-benzothiazol-2-yl)amino]-4-methyl-6,7-dihydro-pyrido[2,3-c]pyridazin-8(5H)-yl}-3-[1-({3-[2-(dimethyl-amino)ethoxy]-5,7-dimethyladamantan-1-yl}methyl)-5-methyl-1H-pyrazol-4-yl]pyridine-2-carboxylic acid, 6-{3-[(1,3-benzothiazol-2-yl)amino]-4-methyl-6,7-dihydro-pyrido[2,3-c]pyridazin-8(5H)-yl}-3-[1-({3,5-dimethyl-7-[2-(methylamino)ethoxy]adamantan-1-yl}methyl)-5-methyl-1H-pyrazol-4-yl]pyridine-2-carboxylic acid, 2-{3-[(1,3-benzothiazol-2-yl)amino]-4-methyl-6,7-dihydro-pyrido[2,3-c]pyridazin-8(5H)-yl}-5-(3-{4-[3-(ethyl-amino)-3-methylbut-1-yn-1-yl]-2-fluorophenoxy}propyl)-1,3-thiazole-4-carboxylic acid, 3-{1-[(Adamantan-1-yl)methyl]-5-methyl-1H-pyrazol-4-yl}-6-{3-[(1,3-benzothiazol-2-yl)amino]-4-methyl-5H,6H,7H,8H-pyrido[2,3-c]pyridazin-8-yl}pyridine-2-car-boxylic acid, its enantiomers and diastereoisomers, and addition salts thereof with a pharmaceutically acceptable acid or base.

E29. A compound according to E1 selected in the follow-ing group:

6-{3-[(1,3-benzothiazol-2-yl)amino]-4-methyl-6,7-dihydro-pyrido[2,3-c]pyridazin-8(5H)-yl}-3-[1-({3-[2-(dimethyl-amino)ethoxy]-5,7-dimethyladamantan-1-yl}methyl)-5-methyl-1H-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3,5-dimethyl-7-

(2-pyrrolidin-1-ylethoxy)-1-adamantyl]methyl]-5-methyl-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3,5-dimethyl-7-[2-(4-methylpiperazin-1-yl)ethoxy]-1-adamantyl]methyl]-5-methyl-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3-[2-(3-hydroxy-propylamino)ethoxy]-5,7-dimethyl-1-adamantyl]methyl]-5-methyl-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3-[2-(4-hydroxy-butylamino)ethoxy]-5,7-dimethyl-1-adamantyl]methyl]-5-methyl-pyrazol-4-yl]pyridine-2-carboxylic acid, 6-{3-[(1,3-benzothiazol-2-yl)amino]-4-methyl-6,7-dihydro-pyrido[2,3-c]pyridazin-8(5H)-yl}-3-(1-{[3-(2-{[(3S)-3,4-dihydroxybutyl]amino}ethoxy)-5,7-dimethyladamantan-1-yl]methyl}-5-methyl-1H-pyrazol-4-yl)pyridine-2-carboxylic acid, 6-{3-[(1,3-benzothiazol-2-yl)amino]-4-methyl-6,7-dihydro-pyrido[2,3-c]pyridazin-8(5H)-yl}-3-(1-{[3-(2-{[(3R)-3,4-dihydroxybutyl]amino}ethoxy)-5,7-dimethyladaman-tan-1-yl]methyl}-5-methyl-1H-pyrazol-4-yl)pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3-[2-[2-hydroxy-ethyl(methyl)amino]ethoxy]-5,7-dimethyl-1-adamantyl]methyl]-5-methyl-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3-[2-[4-hydroxy-butyl(methyl)amino]ethoxy]-5,7-dimethyl-1-adamantyl]methyl]-5-methyl-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3-[2-[[(3R)-3,4-dihydroxybutyl]-methyl-amino]ethoxy]-5,7-dimethyl-1-adamantyl]methyl]-5-methyl-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3,5-dimethyl-7-(2-piperazin-1-ylethoxy)-1-adamantyl]methyl]-5-methyl-pyrazol-4-yl]pyridine-2-carboxylic acid, 6-{3-[(1,3-benzothiazol-2-yl)amino]-4-methyl-6,7-dihydro-pyrido[2,3-c]pyridazin-8(5H)-yl}-3-[1-({3,5-dimethyl-7-[2-(methylamino)ethoxy]adamantan-1-yl}methyl)-5-methyl-1H-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3,5-dimethyl-7-[2-(1-piperidyl)ethoxy]-1-adamantyl]methyl]-5-methyl-pyrazol-4-yl]pyridine-2-carboxylic acid, 3-[1-[[3-[2-(azepan-1-yl)ethoxy]-5,7-dimethyl-1-adaman-tyl]methyl]-5-methyl-pyrazol-4-yl]-6-[3-(1,3-benzothi-azol-2-ylamino)-4-methyl-6,7-dihydro-5H-pyrido[2,3-c]pyridazin-8-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3-[2-(4-isopropy-lpiperazin-1-yl)ethoxy]-5,7-dimethyl-1-adamantyl]methyl]-5-methyl-pyrazol-4-yl]pyridine-2-carboxylic acid, 6-[3-(1,3-benzothiazol-2-ylamino)-4-methyl-6,7-dihydro-5H-pyrido[2,3-c]pyridazin-8-yl]-3-[1-[[3,5-dimethyl-7-(2-morpholinoethoxy)-1-adamantyl]methyl]-5-methyl-pyrazol-4-yl]pyridine-2-carboxylic acid, 6-[3-(1,3-benzothiazol-2-ylamino)-4-methyl-6,7-dihydro-
5H-pyrido[2,3-c]pyridazin-8-yl]-3-[1-[[3-[2-[3-methoxy-
propyl(methyl)amino]ethoxy]-5,7-dimethyl-1-adaman-
tyl]methyl]-5-methyl-pyrazol-4-yl]pyridine-2-carboxylic
acid, 6-[3-(1,3-benzothiazol-2-ylamino)-4-methyl-6,7-dihydro-
5H-pyrido[2,3-c]pyridazin-8-yl]-3-[1-[[3-[2-[2-(2-hy-
droxyethoxy)ethylamino]ethoxy]-5,7-dimethyl-1-ada-
mantyl]methyl]-5-methyl-pyrazol-4-yl]pyridine-2-
carboxylic acid, 6-[3-(1,3-benzothiazol-2-ylamino)-4-methyl-6,7-dihydro-
5H-pyrido[2,3-c]pyridazin-8-yl]-3-[1-[[3-[2-[[2-hy-
droxy-1-(hydroxymethyl)ethyl]amino]ethoxy]-5,7-dim-
ethyl-1-adamantyl]methyl]-5-methyl-pyrazol-4-yl]
pyridine-2-carboxylic acid, 6-[3-(1,3-benzothiazol-2-ylamino)-4-methyl-6,7-dihydro-
5H-pyrido[2,3-c]pyridazin-8-yl]-3-[1-[[3-[2-[[3-hy-
droxy-2-(hydroxymethyl)propyl]amino]ethoxy]-5,7-dim-
ethyl-1-adamantyl]methyl]-5-methyl-pyrazol-4-yl]
pyridine-2-carboxylic acid, 6-[3-(1,3-benzothiazol-2-ylamino)-4-methyl-6,7-dihydro-
5H-pyrido[2,3-c]pyridazin-8-yl]-3-[1-[[3-[2-[bis(2-hy-
droxyethyl)amino]ethoxy]-5,7-dimethyl-1-adamantyl]
methyl]-5-methyl-pyrazol-4-yl]pyridine-2-carboxylic
acid, 6-[3-(1,3-benzothiazol-2-ylamino)-4-methyl-6,7-dihydro-
5H-pyrido[2,3-c]pyridazin-8-yl]-3-[1-[[3-[2-[bis(3-hy-
droxypropyl)amino]ethoxy]-5,7-dimethyl-1-adamantyl]
methyl]-5-methyl-pyrazol-4-yl]pyridine-2-carboxylic
acid, 6-[3-(1,3-benzothiazol-2-ylamino)-4-methyl-6,7-dihydro-
5H-pyrido[2,3-c]pyridazin-8-yl]-3-[1-[[3-[2-[bis(4-hy-
droxybutyl)amino]ethoxy]-5,7-dimethyl-1-adamantyl]
methyl]-5-methyl-pyrazol-4-yl]pyridine-2-carboxylic
acid, 6-{3-[(1,3-benzothiazol-2-yl)amino]-4-methyl-6,7-dihydro-
pyrido[2,3-c]pyridazin-8(5H)-yl}-3-{1-[(3,5-dimethyl-7-
{2-[(2-sulfoethyl)amino]ethoxy}adamantan-1-yl)
methyl]-5-methyl-1H-pyrazol-4-yl}pyridine-2-
carboxylic acid, 6-[3-(1,3-benzothiazol-2-ylamino)-4-methyl-6,7-dihydro-
5H-pyrido[2,3-c]pyridazin-8-yl]-3-[1-[[3-[2-[(4-hy-
droxyphenyl)methylamino]ethoxy]-5,7-dimethyl-1-ada-
mantyl]methyl]-5-methyl-pyrazol-4-yl]pyridine-2-
carboxylic acid, 2-[3-(1,3-Benzothiazol-2-ylamino)-4-methyl-6,7-dihydro-
5H-pyrido[2,3-c]pyridazin-8-yl]-5-[3-[4-[3-(dimethyl-
amino)prop-1-ynyl]-2-fluoro-phenoxy]propyl]thiazole-4-
carboxylic acid, 2-[3-(1,3-benzothiazol-2-ylamino)-4-methyl-6,7-dihydro-
5H-pyrido[2,3-c]pyridazin-8-yl]-5-[3-[4-[3-[[(3S)-3,4-di-
hydroxybutyl]amino]prop-1-ynyl]-2-fluoro-phenoxy]
propyl]thiazole-4-carboxylic acid, 2-[3-(1,3-benzothiazol-2-ylamino)-4-methyl-6,7-dihydro-
5H-pyrido[2,3-c]pyridazin-8-yl]-5-[3-[2-fluoro-4-[3-(3-
hydroxypropylamino)prop-1-ynyl]phenoxy]propyl]thiaz-
ole-4-carboxylic acid, its enantiomers and diastereoisomers, and addition salts
thereof with a pharmaceutically acceptable acid or base.

E30, Process for the preparation of a compound of for-
mula (I) according to E6, which process is characterized in
that there is used as starting material the compound of
formula (II):

(II)

which compound of formula (II) is subjected to a leaving
group incorporation (using iodination preferably) to yield
the compounds of formula (III):

(III)

wherein L.G represents a leaving group (preferably a halo-
gen atom, more preferably iodine), which compound of
formula (III) is further subjected to a coupling reaction, in an
aqueous or organic medium (preferably acetone), in the
presence of a base (preferably cesium carbonate), with a
compound of formula (IV):

(IV)

wherein G1 represents a $C_1$-$C_6$alkyl group or a (4-methoxy-
phenyl)methyl group and

represents a protecting group (preferably a tert-butoxycarbonyl group), to yield the compound of formula (V):

(V)

which amino group of the compound of formula (V) is deprotected (using preferably 1,1,1,3,3,3-hexafluoroisopropanol) to yield the compound of formula (VI):

(VI)

which compound of formula (VI) is subjected to a Suzuki coupling reaction, in an aqueous or organic medium, in the presence of a phosphine palladium complex (preferably Pd(AtaPhos)$_2$Cl$_2$), of a base (preferably Cs$_2$CO$_3$) and of a compound of formula (VII):

(VII)

wherein R$_7$ is as defined in formula (I), to yield the compound of formula (VIII):

(VIII)

which compound of formula (VIII) is further subjected to an intramolecular Buchwald coupling reaction, in an aqueous or organic medium, in the presence of a phosphine palladium complex (preferably Pd(AtaPhos)$_2$Cl$_2$) and at least one base (preferably Cs$_2$CO$_3$ and DIPEA) to yield the compound of formula (IX):

(IX)

which compound of formula (IX) is subjected to a Buchwald reaction, in an aqueous or organic medium, in the presence of a palladium catalyst (preferably Pd$_2$(dba)$_3$), of a base (preferably DIPEA), of a phosphine (preferably Xantphos) and of the compound of formula (X):

(X)

wherein $R_4$ and m are as defined in formula (I), to yield the compound of formula (XI):

(XI)

the ester function of which compound of formula (XI) is hydrolysed (using preferably $LiOH \times H_2O$ or TFA) to yield the compound of formula (I), which compound of formula (I) may be purified according to a conventional separation technique, which may be converted into its addition salts with a pharmaceutically acceptable acid or base and which is optionally separated into its isomers according to a conventional separation technique, it being understood that, at any time considered appropriate in the course of the above-described process, hydroxy, amino, carboxylic and phosphono groups of the reagents or intermediates of synthesis may be protected and then deprotected according to the requirements of synthesis.

E31. Process according to E30 wherein the group $R_7$ is selected from:

wherein $R_8$, $R_{12}$ and $R_{13}$ are as defined in formula (I).

E32. Process for the preparation of a compound of formula (I) according to E6, which process is characterized in that there is used as starting material the compound of formula (II):

(II)

which compound of formula (II) is subjected to a Mitsunobu reaction in the presence of triphenylphosphine in toluene, an appropriate coupling reagent (preferably di-tert-butylazodi-carboxylate) and of the compound of formula (XII-a) or (XII-b):

(XII-a)

or (XII-b)

wherein $A_1$, $A_2$ and $R_6$ are as defined in formula (I), G1 represents a $C_1$-$C_6$alkyl group or a (4-methoxyphenyl) methyl group and

P.G represents a protecting group (preferably a tert-butoxycar-bonyl group), to yield the compound of formula (XIII-a) or (XIII-b):

(XIII-a)

or

-continued (XIII-b)

(XV-a)

which amino group of the compound of formula (XIII-a) or (XIII-b) is further deprotected to yield the compound of formula (XIV-a) or (XIV-b):

(XIV-a)

(XV-b)

(XIV-b)

which compound of formula (XV-a) or (XV-b) is subjected to a Buchwald reaction, in an aqueous or organic medium, in the presence of a palladium catalyst (preferably Pd$_2$(dba)$_3$), of a base (preferably DIPEA), of a phosphine (preferably Xantphos) and of the compound of formula (X):

(i) which compound of formula (XIV-a) is further subjected to an intramolecular coupling reaction, in an aqueous or organic medium, in the presence of a base (preferably Cs$_2$CO$_3$) to yield the compound of formula (XV-a), or (ii) which compound of formula (XIV-b) is further subjected to an intramolecular Buchwald coupling reaction, in an aqueous or organic medium, in the presence of a phosphine palladium complex (preferably Pd(Ata-Phos)$_2$C$_{12}$) and at least one base (preferably Cs$_2$CO$_3$ and DIPEA) to yield the compound of formula (XV-b), (X)

to yield the compound of formula (XVI-a) or (XVI-b):

E3 Synthesis intermediate according to E30 or E31 selected in the following group:

(XVI-a)

or (XVI-b)

the ester function of which compound of formula (XVI-a) or (XVI-b) is hydrolysed (using preferably LiOH×H$_2$O or with TFA) to yield the compound of formula (I), which compound of formula (I) may be purified according to a conventional separation technique, which may be converted into its addition salts with a pharmaceutically acceptable acid or base and which is optionally separated into its isomers according to a conventional separation technique, it being understood that, at any time considered appropriate in the course of the above-described process, hydroxy, amino, carboxylic and phosphono groups of the reagents or intermediates of synthesis may be protected and then deprotected according to the requirements of synthesis.

(VI)

(VIII)

(IX)

wherein R$_7$ is as defined in formula (I) and G1 represents a C$_1$-C$_6$alkyl group, preferably a methyl group, or a (4-methoxyphenyl)methyl group.

E34. Synthesis intermediate according to E32 selected in the following group:

(XIII-a)

-continued (XIII-b)

(XV-a)

(XV-b)

wherein $R_6$ is as defined in formula (I) and G1 represents a $C_1$-$C_6$alkyl group, preferably a methyl group, or a (4-methoxyphenyl)methyl group.

E35 The compound according to E1 wherein $R_4$ represents a hydrogen, fluorine, chlorine or bromine atom, a methyl or a methoxy group.

E36 The compound according to E1 wherein $R_8$ represents a group selected from: hydrogen; linear or branched $C_1$-$C_6$alkyl, —NR'$_a$R'$_b$; —NR'$_a$—CO—OR'$_e$; —N$^+$R'$_a$R'$_b$R'$_c$; —O—R'$_e$; —NH—X'$_2$—N$^+$R'$_a$R'$_b$R'$_e$; —O—X'2-NR'$_a$R'$_b$, —NR'$_e$—X'$_2$—N$_3$ and:

$$\text{—NR'}_c\text{—X'}_2\text{—}{\equiv}\text{CH}$$

E37. The compound according to E1 wherein R'$_a$ and R'$_b$ independently of one another, represent a group selected from: hydrogen; heterocycloalkyl; —SO$_2$-phenyl wherein the phenyl may be substituted by a linear or branched $C_1$-$C_6$alkyl; linear or branched $C_1$-$C_6$alkyl optionally substituted by one or two hydroxyl groups; $C_1$-$C_6$alkylene-SO$_2$OH; $C_1$-$C_6$alkylene-SO$_2$O—; $C_1$-$C_6$alkylene-COOH; $C_1$-$C_6$alkylene-PO(OH)$_2$; $C_1$-$C_6$alkylene-NR'$_a$R'$_e$;

$C_1$-$C_6$alkylene-N$^+$R'$_a$R'$_e$R' $\qquad$ $C_1$-$C_6$alkylene-O—$C_1$-$C_6$alkylene-OH; $C_1$-$C_6$alkylene-phenyl wherein the phenyl may be substituted by a $C_1$-$C_6$alkoxy group; the group:

or R'$_a$ and R'$_b$ form with the nitrogen atom carrying them a cycle B$_3$, or R'$_a$, R'$_b$ and R'$_e$ form with the nitrogen atom carrying them a bridged $C_3$-$C_8$heterocycloalkyl.

E38. Compound according to any of E1 to E27 wherein m=1.

Pharmacological study of the compounds of the invention has shown that they have pro-apoptotic properties. The ability to reactivate the apoptotic process in cells is of major therapeutic interest in the treatment of cancers and of immune and auto-immune diseases. In particular, the compounds according to the invention will be useful in the treatment of chemo- or radio-resistant cancers.

In another embodiment, the compounds of the invention could be used for treating diseases or conditions characterized by an excess or a deregulated activity of platelets, especially pro-thrombotic conditions.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

Among the cancer treatments envisaged there may be mentioned, without implying any limitation, the treatment of haematological malignancies and solid tumors. Haematological malignancies include myeloma, especially multiple myeloma, lymphoma, especially Non-Hodgkin Lymphoma (NHL) and more especially Diffuse Large B-cell Lymphoma (DLBCL), and leukemia, especially Chronic Lymphocytic Leukemia (CLL), T-cell Acute Lymphoblastic Leukemia (T-ALL), B-cell Acute Lymphoblastic Leukemia (B-ALL) and Acute Myelogenous Leukemia (AML). Solid tumors include the bladder, brain, breast, uterus, cesophagus and liver cancers, colorectal cancer, renal cancer, melanoma, ovarian cancer, prostate cancer, pancreatic cancer and lung cancer, especially non-small-cell lung cancer and small-cell lung cancer.

In particular, T-ALL results from the leukemic transformation of thymic cell precursors and their arrest at specific stages of differentiation. Despite recent and extensive insights into the molecular and cellular mechanisms responsible for T-ALL onset and progression, this knowledge has not been translated into efficient targeted therapies. Current clinical treatments include chemotherapy associated or not with hematopoietic stem cell transplantation with survival rates remaining around 50 and 70% in adult and pediatric cases, respectively. Both in pediatric and adult cases, relapses show very poor prognosis, reinforcing the need of the discovery of novel therapeutic options (Passaro et al., *Immunol. Rev.* 2016 May; 271(1):156-72). It has been shown that dual Bcl-2/Bcl-xL inhibitors, like ABT-263 and ABT-737, have promising activity in T-ALL patient derived xenograft models (Van Delft et al. *Cancer Cell* 2006; 10:389-99; Suryani et al., *Clin. Cancer Res.* 2014, 20:4520-31). Other studies have reported a differential requirement for Bcl-xL or Bcl-2 for survival of mature versus very immature (ETP subgroup) T-ALL (Chonghaile et al., *Cancer Discov.* 2014; 4:1074-87). The selective Bcl-xL inhibitor A-1331852 described previously have also shown to have in vitro and in vivo activity in the mature T-ALL cell line xenograft model Molt-4 (Leverson et al., *Sci. Transl. Med.* 2015 Mar. 18; 7(279):279ra40). In a particular embodiment, tumor growth inhibition was also observed in MOLT-4 xenograft model upon treatment with the Bcl-xL inhibitors of the invention. These data support the use of the present compounds in the treatment of T-ALL.

Among the treatments of autoimmune diseases envisaged there may be mentioned, without implying any limitation, the treatment of rheumatoid arthritis (RA) and systemic lupus erythematosus (SLE).

The present invention relates also to pharmaceutical compositions comprising at least one compound of formula (I), as the active ingredient, in combination with one or more pharmaceutically acceptable excipients. In particular, these pharmaceutical compositions are interesting for use as pro-apoptotic and/or anti-proliferative agents, particularly, in the treatment of cancers and of auto-immune and immune system diseases.

Suitable excipients according to the invention include diluents, lubricants, binders, disintegration agents, stabilis-ers, preservatives, absorbents, colorants, sweeteners and flavourings.

By way of non-limiting example there may be mentioned:
as diluents: lactose, dextrose, sucrose, mannitol, sorbitol, cellulose, glycerol,
as lubricants: silica, talc, stearic acid and its magnesium and calcium salts, polyethylene glycol,
as binders: magnesium aluminium silicate, starch, gelatin, tragacanth, methylcellulose, sodium carboxymethyl-cellulose and polyvinylpyrrolidone,
as disintegrants: agar, alginic acid and its sodium salt, effervescent mixtures.

Among the pharmaceutical compositions according to the invention there may be mentioned more especially those that are suitable for oral, parenteral, nasal, per- or trans-cutane-ous, rectal, perlingual, ocular or respiratory administration, especially tablets, dragées, sublingual tablets, capsules, glossettes, capsules, lozenges, injectable or drinkable prepa-rations, aerosols, eye or nose drops, suppositories, creams, ointments, dermal gels.

Actual dosage levels of the active ingredients in the pharmaceutical compositions of this invention may be var-ied so as to obtain an amount of the active ingredient which is effective to achieve the desired therapeutic response for a particular patient, composition, and mode of administration, without being toxic to the patient. The selected dosage level will depend upon a variety of factors including the activity of the particular compound of the present invention employed, the route of administration, the time of adminis-tration, the rate of excretion or metabolism of the particular compound being employed, the rate and extent of absorp-tion, the duration of the treatment, other drugs, compounds and/or materials used in combination with the particular compound employed, the age, sex, weight, condition, general health and prior medical history of the patient being treated, and like factors well known in the medical arts.

A suitable daily dose of a compound of the invention will depend upon the factors described above and may range from 0.01 mg to 2.5 g per day in one or more administration (s).

In another aspect, the present invention relates also to the combination of a compound of formula (I) with an antican-cer agent selected from genotoxic agents, mitotic poisons, anti-metabolites, proteasome inhibitors, kinase inhibitors and antibodies, and also to pharmaceutical compositions comprising that type of combination and their use in the manufacture of medicaments for use in the treatment of cancer.

In another aspect, the compounds of the invention can be used in combination with radiotherapy in the treatment of cancer.

Alternatively, the compounds of the invention may be linked to monoclonal antibodies. Antibody Drug Conjugates (ADCs) represent a new class of therapeutics that is formed by chemically linking a cytotoxic drug to a monoclonal antibody through a linker. The monoclonal antibody of an ADC selectively binds to a target antigen of a cell (e.g. cancer cell) and releases the drug into the cell. ADCs have therapeutic potential because they combine the specificity of the antibody and the cytotoxic potential of the drug. None-theless, developing ADCs as therapeutic agents has thus far met with limited success owing to a variety of factors such as unfavorable toxicity profiles, low efficacies and poor pharmacological parameters.

Accordingly, there is still a need for new ADCs that overcome these problems and can selectively deliver Bcl-xL to target cancer cells.

In another aspect, the compounds of the invention may be linked to fragments of monoclonal antibodies or linked to scaffold proteins that can be related or not to monoclonal antibodies.

Antibody fragments must be understood as fragments of Fv, scFv, Fab, F(ab')$_2$, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra, *J Mol. Recogn.* 2000, 13, 167-187): phylogenetically good conser-vation, robust architecture with a well-known three-dimen-sional molecular organization (such as, for example, crys-tallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra, *J. Biotechnol.*

2001, 74, 257-75), the protein Z derivative from the domain B of staphylococcal protein A, thioredoxin A or any protein with a repeated domain such as an "ankyrin repeat" (Kohl et al. *PNAS* 2003, 100, 1700-1705), "armadillo repeat", "leucine-rich repeat" or "tetratricopeptide repeat". There could also be mentioned a scaffold derivative from toxins (such as, for example, scorpion, insect, plant or mollusc toxins) or protein inhibitors of neuronal nitric oxide synthase (PIN).

The following Examples illustrate the invention but do not limit it in any way. All intermediates for preparing Examples are either commercially available or can be obtained by the person skilled in the art using conventional chemical reactions described in the literature.

General Procedure

All reagents obtained from commercial sources were used without further purification.

Anhydrous solvents were obtained from commercial sources and used without further drying.

Column Chromatography

Automated flash column chromatography was performed on ISCO CombiFlash® Rf 200 or CombiFlash® Rf+ Lumen™ using RediSep® Rf Normal-phase Silica Flash Columns (35-70 μm, 60 Å), RediSep Rf Gold® Normal-phase Silica High Performance Columns (20-40 μm, 60 Å), RediSep® Rf Reversed-phase C18 Columns (40-63 m, 60 Å), or RediSep Rf Gold® Reversed-phase C18 High Performance Columns (20-40 m, 100 Å).

TLC

Thin layer chromatography was conducted with 5×10 cm plates coated with Merck Type 60 $F_{254}$ silica-gel.

Microwave Reactions

Microwave heating was performed with a CEM Discover® SP, or with an Anton Paar Monowave Microwave Reactor.

NMR

1H-NMR measurements were performed on a Bruker Avance III 500 MHz spectrometer, a Bruker Avance III 400 MHz spectrometer, or a Bruker DPX-400 spectrometer using DMSO-$d_6$ or CDCl$_3$ as solvent. 1H NMR data is in the form of delta values, given in part per million (ppm), using the residual peak of the solvent (2.50 ppm for DMSO-$d_6$ and 7.26 ppm for CDCl$_3$) as internal standard. Splitting patterns are designated as: s (singlet), d (doublet), t (triplet), q (quartet), quint (quintet), sept (septet), m (multiplet), br s (broad singlet), dd (doublet of doublets), td (triplet of doublets), dt (doublet of triplets), ddd (doublet of doublet of doublets).

Analytical LC-MS

Certain compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/H$_2$O (1:1) with 5 μL loop injection. LCMS analyses were performed on two instruments, one of which was operated with basic, and the other with acidic eluents.

Basic LCMS: Gemini-NX, 3 μm, C18, 50 mm×3.00 mm i.d. column at 23° C., at a flow rate of 1 mL min-1 using 5 mM ammonium bicarbonate (Solvent A) and acetonitrile (Solvent B) with a gradient starting from 100% Solvent A and finishing at 100% Solvent B over various/certain duration of time.

Acidic LCMS: KINATEX XB-C18-100 Å, 2.6 m, 50 mm*2.1 mm column at 40° C., at a flow rate of 1 mL min-1 using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

Certain other compounds of the present invention were characterized HPLC-MS under specific named methods as follows. For all of these methods UV detection was by diode array detector at 230, 254, and 270 nm. Sample injection volume was 1 μL. Gradient elutions were run by defining flow rates and percentage mixtures of the following mobile phases, using HPLC-grade solvents:

Solvent A: 10 mM aqueous ammonium formate+0.04% (v/v) formic acid

Solvent B: Acetonitrile+5.3% (v/v) Solvent A+0.04% (v/v) formic acid.

Retention times (RT) for these named methods are reported in minutes. Ionisation is recorded in positive mode, negative mode, or positive-negative switching mode. Specific details for individual methods follow.

LCMS-V-B methods

Using an Agilent 1200 SL series instrument linked to an Agilent MSD 6140 single quadrupole with an ESI-APCI multimode source (Methods LCMS-V-B1 and LCMS-V-B2) or using an Agilent 1290 Infinity II series instrument connected to an Agilent TOF 6230 with an ESI-jet stream source (Method LCMS-V-B1); column: Thermo Accucore 2.6 m, C18, 50 mm×2.1 mm at 55° C. Gradient details for methods LCMS-V-B1 and LCMS-V-B2:

| | LCMS-V-B1 | | LCMS-V-B2 | | |
|---|---|---|---|---|---|
| Time (min) | Solvent A (%) | Solvent B (%) | Solvent A (%) | Solvent B (%) | Flow (mL/min) |
| 0 | 95 | 5 | 60 | 40 | 1.1 |
| 0.12 | 95 | 5 | 60 | 40 | 1.3 |
| 1.30 | 5 | 95 | 2 | 98 | 1.3 |
| 1.35 | 5 | 95 | 2 | 98 | 1.6 |
| 1.85 | 5 | 95 | 2 | 98 | 1.6 |
| 1.90 | 5 | 95 | 2 | 98 | 1.3 |
| 1.95 | 95 | 5 | 95 | 5 | 1.3 |

LCMS-V-C method

Using an Agilent 1200 SL series instrument linked to an Agilent MSD 6140 single quadrupole with an ESI-APCI multimode source; column: Agilent Zorbax Eclipse plus 3.5 m, C18(2), 30 mm×2.1 mm at 35° C. Gradient details for method LCMS-V-C:

| Time (min) | Solvent A (%) | Solvent B (%) | Flow (mL/min) |
|---|---|---|---|
| 0 | 95 | 5 | 1 |
| 0.25 | 95 | 5 | 1 |
| 2.50 | 95 | 5 | 1 |
| 2.55 | 5 | 95 | 1.7 |
| 3.60 | 5 | 95 | 1.7 |
| 3.65 | 5 | 95 | 1 |
| 3.70 | 95 | 5 | 1 |
| 3.75 | 95 | 5 | 1 |

Preparative HPLC

Certain compounds of the present invention were purified by high performance liquid chromatography (HPLC) on an Armen Spot Liquid Chromatography or Teledyne EZ system with a Gemini-NX® 10 μM C18, 250 mm×50 mm i.d. column running at a flow rate of 118 mL min-1 with UV diode array detection (210-400 nm) using 25 mM aqueous $NH_4HCO_3$ solution and MeCN or 0.10% TFA in water and MeCN as eluents.

Certain other compounds of the present invention were purified by HPLC under specific named methods as follows:

HPLC-V-A methods

These were performed on a Waters FractionLynx MS autopurification system, with a Gemini® 5 μm C18(2), 100 mm×20 mm i.d. column from Phenomenex, running at a flow rate of 20 cm³ min⁻¹ with UV diode array detection (210-400 nm) and mass-directed collection. The mass spectrometer was a Waters Micromass ZQ2000 spectrometer, operating in positive or negative ion electrospray ionisation modes, with a molecular weight scan range of 150 to 1000.

Method HPLC-V-A1 (pH 4):

Solvent A: 10 mM aqueous ammonium acetate+0.08% (v/v) formic acid; Solvent B: acetonitrile+5% (v/v) Solvent A+0.08% (v/v) formic acid Method HPLC-V-A2 (pH 9):

Solvent A: 10 mM aqueous ammonium acetate+0.08% (v/v) conc. ammonia; Solvent B: acetonitrile+5% (v/v) Solvent A+0.08% (v/v) conc. ammonia HPLC-V-B methods Performed on an AccQPrep HP125 (Teledyne ISCO) system, with a Gemini® NX 5 μm C18(2), 150 mm×21.2 mm i.d. column from Phenomenex, running at a flow rate of 20 cm³ min⁻¹ with UV (214 and 254 nm) and ELS detection.

Method HPLC-V-B1 (pH 4):

Solvent A: water+0.08% (v/v) formic acid; solvent B: acetonitrile+0.08% (v/v) formic acid.

Method HPLC-V-B2 (pH 9):

Solvent A: water+0.08% (v/v) conc. ammonia; solvent B: acetonitrile+0.08% (v/v) conc. ammonia.

Method HPLC-V-B3 (neutral):

Solvent A: water; Solvent B: acetonitrile.

Analytical GC-MS

Combination gas chromatography and low resolution mass spectrometry (GC-MS) was performed on Agilent 6850 gas chromatograph and Agilent 5975C mass spectrometer using 15 m×0.25 mm column with 0.25 μm HP-5MS coating and helium as carrier gas. Ion source: EI+, 70 eV, 230° C., quadrupole: 150° C., interface: 300° C.

High-resolution MS

High-resolution mass spectra were acquired on an Agilent 6230 time-of-flight mass spectrometer equipped with a Jet Stream electrospray ion source in positive ion mode. Injections of 0.5 d were directed to the mass spectrometer at a flow rate 1.5 ml/min (5 mM ammonium-formate in water and acetonitrile gradient program), using an Agilent 1290 Infinity HPLC system. Jet Stream parameters: drying gas (N2) flow and temperature: 8.0 l/min and 325° C., respectively; nebulizer gas (N2) pressure: 30 psi; capillary voltage: 3000 V; sheath gas flow and temperature: 325° C. and 10.0 l/min; TOFMS parameters: fragmentor voltage: 100 V; skimmer potential: 60 V; OCT 1 RF Vpp:750 V. Full-scan mass spectra were acquired over the m/z range 105-1700 at an acquisition rate of 995.6 ms/spectrum and processed by Agilent MassHunter B.04.00 software.

Chemical Naming

IUPAC-preferred names were generated using ChemAxon's 'Structure to Name' (s2n) functionality within *Marvin-Sketch or JChem for Excel* (JChem versions 16.6.13-18.22.3), or with the chemical naming functionality provided by Biovia® Draw 4.2.

Abbreviations

Ahx 6-hexanoic acid monomer

AgOTf silver trifluoromethanesulfonate tBuOH tert-butanol cc. concentrated

CyOH cyclohexanol dba (1E,4E)-1,5-diphenylpenta-1,4-dien-3-one, dibenzylideneacetone DCM dichloromethane DIPA N-isopropylpropan-2-amine, diisopropylamine DIPEA N-ethyl-N-isopropyl-propan-2-amine, diisopropylethylamine DMAP 4-dimethylaminopyridine ee. enatiomeric excess eq. equivalent EtOAc ethyl acetate HFxPyr Hydrogen fluoride pyridine hs *Homo sapiens*

LDA lithium diisopropylamide

MeCN acetonitrile

MeOH methanol

NMP N-methyl-2-pyrrolidone $Pd(AtaPhos)_2Cl_2$ bis(di-tert-butyl(4-dimethylaminophenyl)phosphine)dichloropalladium(II)

rt room temperature

RT retention time (in minutes)

on overnight

TBAF tetrabutylammonium fluoride

TBAOH tetrabutylammonium hydroxide

TBDPS-Cl tert-butyl-chloro-diphenyl-silane

TBSCl tert-butyl-chloro-dimethyl-silane

TEA NN-diethylethanamine

TFA 2,2,2-trifluoroacetic acid pTSA 4-methylbenzenesulfonic acid

THF tetrahydrofuran

TMP-MgCl 2,2,6,6-tetramethylpiperidinylmagnesium chloride lithium chloride complex solution DIAD diisopropylazodicarboxylate Xantphos 4,5-Bis(diphenylphosphino)-9,9-dimethylxanthene BrettPhos 2-(Dicyclohexylphosphino)-3,6-dimethoxy-2',4',6'-triisopropyl-1,1'-biphenyl JosiPhos (2R)-1-[(1R)-1-(Dicyclohexylphosphino)ethyl]-2-(diphenylphosphino)ferrocene JosiPhos Pd G3 {(R)-1-[(Sp)-2-(Dicyclohexylphosphino)ferrocenyl]ethyldi-tert-butylphosphine}[2-(2'-amino-1,1'-biphenyl)]palladium(II) methanesulfonate Xantphos Pd G3 [(4,5-Bis(diphenylphosphino)-9,9-dimethylxanthene)-2-(2'-amino-1,1'-biphenyl)]palladium(II) methanesulfonate BINAP 2,2'-Bis(diphenylphosphino)-1,1'-binaphthyl rac-BINAP Pd G3 [(2,2'-Bis(diphenylphosphino)-1,1'-binaphthyl)-2-(2'-amino-1,1'-biphenyl)]palladium(II) methanesulfonate $Pd(dppf)C_{12}·CH_2Cl_2$ [1,1'-Bis(diphenylphosphino)ferrocene]dichloropalladium(II)

$Pd_2(dba)_3$ Tris(dibenzylideneacetone)dipalladium(0)

Named General Procedures

The following are representative experimental procedures that are referred to by name in subsequent Preparations.

Sonogashira General Procedure

The mixture of 1 eq. of aryl halogenide, 2 eq. of acetylene, 0.05 eq. of Pd(PPh3)2Cl2, 0.05 eq. of CuI, and DIPA (1 mL/mmol) in THF (5 mL/mmol) was kept at 60° C. After reaching an appropriate conversion the volatiles were removed under reduced pressure, the crude intermediate was purified via flash chromatography using heptane/EtOAc as eluents.

Deprotection with HFIP General Procedure

Substrate in HFIP (10 mL/mmol) was kept at 100-120° C. in a pressure bottle. After reaching an appropriate conversion the volatiles were removed under reduced pressure, the crude intermediate was purified via flash chromatography using heptane/EtOAc as eluents.

Deprotection and Hydrolysis General Procedure

The mixture of 1 eq. of substrate and 100 eq. of HFxPyr in MeCN (15 mL/mmol) was stirred at 60° C. After reaching an appropriate conversion, the volatiles were removed under reduced pressure, the residue was suspended in a 1:1 mixture of THF—water (30 mL/mmol), 150 eq. of LiOHxH$_2$O was added, and the mixture was stirred at rt. After reaching an appropriate conversion, the volatiles were removed under reduced pressure; the crude product was purified via flash chromatography using DCM and MeOH (containing 1.2% NH3) as eluents.

Alkylation General Procedure

The mixture of 1 eq. of phenol/carbamate, 1-2 eq. of alkyl iodide/bromide, and 2-3 eq. of Cs$_2$CO$_3$ in acetone (5 mL/mmol) was stirred at rt for phenols and at 55° C. for carbamates. After reaching an appropriate conversion the volatiles were removed under reduced pressure, the crude intermediate was purified via flash chromatography using heptane/EtOAc as eluents.

Alkylation with tosylate General Procedure

An oven-dried vial was equipped with a PTFE-coated magnetic stirring bar, and was charged with 1 eq. tosylate and 5 eq. as the appropriate amine were suspended in MeCN (5 mL/mmol). The reaction mixture was then warmed up to 50° C. and stirred at that temperature until no further conversion was observed. The reaction mixture was diluted with DCM then it was injected onto a DCM preconditioned silica gel column. Then it was purified via flash chromatography using DCM and MeOH (1.2% NH3) as eluents.

Alkylation of Silyl-Protected Phenols General Procedure

The mixture of 1 eq. of silyl-protected phenol, 1 eq. of alkyl iodide, and 1.15 eq. of TBAF (1 M in THF) in THF (2 mL/mmol) was stirred at rt. After reaching an appropriate conversion the volatiles were removed under reduced pressure, the crude intermediate was purified via flash chromatography using heptane/EtOAc as eluents.

Buchwald General Procedure I

The mixture of 1 eq. of chloro-substrate, 2 eq. of 1,3-benzothiazol-2-amine, 0.1 eq. of Pd2(dba)$_3$, 0.2 eq. of XantPhos, and 3 eq. of DIPEA in CyOH (5 mL/mmol) was kept at 140° C. After reaching an appropriate conversion, the reaction mixture was diluted with DCM (10 mL/mmol), injected onto a preconditioned silica gel column and was purified via flash chromatography using heptane/EtOAc as eluents.

Buchwald General Procedure II

The mixture of chloro compound, 2 eq. of 1,3-benzothiazol-2-amine, 10 mol % of JosiPhos Pd (G3) and 3 eq. of DIPE suspended in 1,4-dioxane (5 mL/mmol) were stirred at reflux until no further conversion was observed. Celite was added to the reaction mixture and the volatiles were removed under reduced pressure. Then it was purified via flash chromatography on 120 g silica gel column using heptane-EtOAc or DCM-MeOH (1.2% NH$_3$) as eluents.

Mitsunobu General Procedure

To the mixture of 1 eq. of aliphatic alcohol, 1 eq. of carbamate/phenol, and 1 eq. triphenylphosphine in toluene (5 mL/mmol) was added 1 eq. of di-tert-butyl azodicarboxylate.

The mixture was stirred at 50° C. for the carbamate and at rt for the phenol. After reaching an appropriate conversion the volatiles were removed under reduced pressure, the crude intermediate was purified via flash chromatography using heptane/EtOAc as eluents.

Finkelstein General Procedure

The mixture of 1 eq. of alkyl chloride and 2 eq. of NaI in acetone (5 mL/mmol) was kept at reflux. After reaching an appropriate conversion the volatiles were removed under reduced pressure, the crude intermediate was purified via flash chromatography using heptane/EtOAc as eluents.

Quaternary salt formation General Procedure

An oven-dried vial was equipped with a PTFE-coated magnetic stirring bar, and was charged with 1 eq. tosylate and 20 eq. as the appropriate amine were suspended in CyOH (5 mL/mmol). The reaction mixture was then warmed up to 140° C. and stirred at that temperature until no further conversion was observed. The reaction mixture was diluted with DCM then it was injected onto a DCM preconditioned silica gel column. Then it was purified via flash chromatography using DCM and MeOH (1.2% NH3) as eluents.

Quaternary salt deprotection General Procedure

To a THF (5 mL/mmol) solution of the appropriate quaternary salt 3 eq. TBAF was added, and then it was stirred at rt until no further conversion was observed. The reaction mixture was the evaporated to dry under reduced pressure. To a suspension of 1 eq. desalilated quaternary salt in dry MeCN (15 mL/mmol), 100 eq. of HFxPyr added, and then was stirred at 60° C. After reaching an appropriate conversion, the volatiles were removed under reduced pressure, the residue was suspended in a 1:1 mixture of THF—water (30 mL/mmol), 150 eq. of LiOHxH$_2$O was added, and the mixture was stirred at rt. After reaching an appropriate conversion, the volatiles were removed under reduced pressure. The crude product was purified via flash chromatography using DCM and MeOH (containing 1.2% NH3) as eluents.

Proparylic Amine Preparation General Procedure

An oven-dried vial was equipped with a PTFE-coated magnetic stirring bar, it was charged with 2 eq. PPh3 and 2 eq. imidazole then DCM (5 mL/mmol) was added. To the resulting mixture 2 eq. iodine was added portionwise then stirred for 15 min at rat. To the resulting mixture 1 eq. of the appropriate alcohol was added dissolved in DCM and stirred at rt until no further conversion was observed. To the generated iodo compound 20 eq. of the appropriate amine was added and then stirred for 30 min at rt, while full conversion was observed. Celite was added to the reaction mixture and the volatiles were removed under reduced pressure. Then it was purified via flash chromatography using DCM and MeOH (1.2% NH$_3$) eluents.

Silver Catalyzed Propargylic Amine Preparation General Procedure

A 24 ml vial was equipped with a stirring bar, and charged with 1 eq. of 2-[3-(1,3-benzothiazol-2-ylamino)-4-methyl-6,7-dihydro-5H-pyrido[2,3-c]pyridazin-8-yl]-5-[3-(4-ethynyl-2-fluoro-phenoxy)propyl]thiazole-4-carboxylic acid, 20 eq. paraformaldehyde/acetone and 20 eq. of the appropriate amine were stirred in dry ethanol (5 ml/mmol) in presence of 20 mol % silver tosylate at 80° C. until no further conversion was observed. Celite was added to the reaction mixture and the volatiles were removed under reduced pressure. Then it was purified via flash chromatography using DCM and MeOH (1.2% NH₃) as eluents.

Hydrolysis General Procedure

The appropriate methyl ester was suspended in a 1:1 mixture of THF—water (5 mL/mmol) and 10 eq. of LiOH× H₂O was added, and the mixture was stirred at 50° C. After reaching an appropriate conversion, the volatiles were removed under reduced pressure; the crude product was purified via flash chromatography using DCM and MeOH (containing 1.2% NH₃) as eluents.

Amine Substitution and Hydrolysis General Procedure

To the product from any of the Preparations 12, 13 and 14 in a 1:1 mixture of acetonitrile and N-methyl-2-pyrrolidone (10 ml/mmol), was added the appropriate amine (3-10 eq), and the reaction mixture was stirred at 50° C. for 2-24 h. After the purification of the substitution product by column chromatography (silica gel, using DCM and MeOH as eluents), the product was dissolved in THF (10 ml/mmol), and water (2 ml/mmol) and LiOH×H₂O(3-5 equ) was added.

Then, the reaction mixture was stirred at 20-40° C. for 1-4 h. The hydrolysed product was purified by preparative HPLC (using acetonitrile and 5 mM aqueous NH₄HCO₃ solution as eluents) to give the desired product.

Preparations

The following experimental details describe the preparation of synthetic intermediates.

Preparation 1a: Methyl 2-(tert-butoxycarbonylamino)-5-[3-(2-fluoro-4-iodo-phenoxy)propyl] thiazole-4-carboxylate

Step A: methyl 2-(tert-butoxycarbonylamino)-5-iodo-thiazole-4-carboxylate 50.00 g methyl 2-(tert-butoxycarbonylamino)thiazole-4-carboxylate (193.55 mmol, 1 equiv) was suspended in 600 mL dry MeCN. 52.25 g N-iodo succinimide (232.30 mmol,) was added and the resulting mixture was stirred overnight at room temperature.

The reaction mixture was diluted with saturated brine, then it was extracted with EtOAc. The combined organic layers were extracted with 1 M Na₂S₂O₃, then with brine again. Then dried over Na₂SO₄, filtered and the filtrate was concentrated under reduced pressure. The crude product was purified via flash chromatography using heptane as eluent to obtain 60 g of the desired product (156 mmol, 80% Yield).

$^1$H NMR (400 MHz, DMSO-d₆): δ ppm 12.03/11.06 (br s), 3.78 (s, 3H), 1.47 (s, 9H); $^{13}$C NMR (100 MHz, DMSO-d₆) δ ppm 153.8, 82.5, 77.7, 52.3, 28.3; HRMS-ESI (m/z): [M+H]⁺ calcd for C₁₀H₁₄IN₂O₄S: 384.9713; found 384.9708.

Step B: methyl 2-(tert-butoxycarbonylamino)-5-(3-hydroxyprop-1-ynyl)thiazole-4-carboxylate A 500 mL oven-dried, one-necked, round-bottom flask was equipped with a PTFE-coated magnetic stirring bar and fitted with a reflux condenser. It was charged with 9.6 g of the product from Step A (25 mmol, 1 equiv), 2.80 g prop-2-yn-1-ol (2.91 mL, 50 mmol, 2 equiv) and 36.10 g DIPA (50 mL, 356.8 mmol, 14.27 equiv) then 125 mL dry THF was added and the system was flushed with argon. After 5 minutes stirring under inert atmosphere 549 mg Pd(PPh3)₂Cl₂ (1.25 mmol, 0.05 equiv) and 238 mg CuI (1.25 mmol, 0.05 equiv) was added. The resulting mixture was then warmed up to 60° C. and stirred at that temperature until no further conversion was observed. Celite was added to the reaction mixture and the volatiles were removed under reduced pressure. Then it was purified via flash chromatography using heptane and EtOAc as eluents to give 7.30 g of the desired product (23 mmol, 93% Yield) as a yellow solid.

$^1$H NMR (400 MHz, DMSO-d₆): δ ppm 12.1 (br s, 1H), 5.45 (t, 1H), 4.36 (d, 2H), 3.79 (s, 3H), 1.48 (s, 9H); $^{13}$C NMR (100 MHz, DMSO-d₆) δ ppm 12.1 (br s, 1H), 5.45 (t, 1H), 4.36 (d, 2H), 3.79 (s, 3H), 1.48 (s, 9H); HRMS-ESI (m/z): [M+H]⁺ calcd for C₁₃H₁₇N₂O₅S: 313.0852, found 313.0866.

Step C: methyl 2-(tert-butoxycarbonylamino)-5-(3-hydroxypropyl)thiazole-4-carboxylate An 1 L oven-dried pressure bottle equipped with a PTFE-coated magnetic stir bar was charged with 44.75 g of the product from Step B (143.3 mmol, 1 equiv), 7.62 Pd/C (7.17 mmol, 0.05 equiv) in 340 mL ethanol, and then placed under a nitrogen atmosphere using hydrogenation system. After that, it was filled with 4 bar H₂ gas and stirred at rt overnight. Full conversion was observed, but only the olefin product was formed. After filtration of the catalysts through a pad of Celite, the whole procedure was repeated with 5 mol % new catalysts. The resulting mixtures were stirred overnight to get full conversion. Celite was added to the reaction mixtures and the volatiles were removed under reduced pressure. Then it was purified via flash chromatography column using heptane and EtOAc as eluents to give 31.9 g of the desired product (101 mmol, 70.4% Yield) as light-yellow crystals $^1$H NMR (500 MHz, DMSO-d₆): δ ppm 11.61 (br s, 1H), 4.54 (t, 1H), 3.76 (s, 3H), 3.43 (m, 2H), 3.09 (t, 2H), 1.74 (m, 2H), 1.46 (s, 9H); $^{13}$C NMR (125 MHz, DMSO-d₆) δ ppm 162.8, 143.1, 135.4, 60.3, 51.9, 34.5, 28.3, 23.4; HRMS-ESI (m/z): [M+H]⁺ calcd for C₁₃H₂₁N₂O₅S: 317.1165, found 317.1164 (M+H).

Step D: methyl 2-(tert-butoxycarbonylamino)-5-[3-(2-fluoro-4-iodo-phenoxy)propyl]thiazole-4-carboxylate A 250 mL oven-dried, one-necked, round-bottomed flask equipped with a PTFE-coated magnetic stir bar, was charged with 3.40 g 2-fluoro-4-iodo-phenol (14 mmol, 1 equiv), 5.00 g of the product from Step C (16 mmol, 1.1 equiv) and 4.10 g PPh₃ (16 mmol, 1.1 equiv) dissolved in 71 mL dry toluene. After 5 min stirring under nitrogen atmosphere, 3.10 mL DIAD (3.20 g, 16 mmol, 1.1 equiv) was added in one portion while the reaction mixture warmed up. Then the reaction mixture was heated up to 50° C. and stirred at that temperature for 30 min, when the reaction reached complete conversion.

The reaction mixture was directly injected onto a preconditioned silica gel column, and then it was purified via flash chromatography using heptane and EtOAc as eluents. The crude product was crystalized from MeOH to give 4.64 g of the desired product (9.24 mmol, 66% Yield).

$^1$H NMR (500 MHz, DMSO-d₆) δ ppm 11.64 (br s, 1H), 7.59 (dd, 1H), 7.45 (dd, 1H), 6.98 (t, 1H), 4.06 (t, 2H), 3.73 (s, 3H), 3.22 (t, 2H), 2.06 (m, 2H), 1.46 (s, 9H); $^{13}$C NMR (125 MHz, DMSO-d₆) δ ppm 134, 124.9, 117.6, 68.2, 51.9, 30.5, 28.3, 23.2; HRMS-ESI (m/z): [M+H]⁺ calcd for C₁₉H₂₃N₂O₅FSI: 537.0350; found 537.0348.

Preparation 1b: Methyl 2-(tert-butoxycarbonylamino)-5-[3-[4-[3-[tert-butoxycarbonyl(methyl)amino]prop-1-ynyl]-2-fluoro-phenoxy]propyl]thiazole-4-carboxylate A 500 mL oven-dried, one-necked, round-bottom flask was equipped with a PTFE-coated magnetic stirring bar and fitted with a reflux condenser. It was charged with 13.41 g Preparation 1a (25 mmol, 1 equiv), 8.46 g tert-butyl N-methyl-N-prop-2-ynyl-carbamate (50 mmol, 2 equiv) and 50 mL DIPA (36.10 g, 50 mL, 356.8 mmol, 14.27 equiv) then 125 mL dry THF was added and the system was flushed with argon. After 5 minutes stirring under inert atmosphere 549 mg Pd(PPh$_3$)$_2$Cl$_2$ (1.25 mmol, 0.05 equiv) and 238 mg CuI (1.25 mmol, 0.05 equiv) were added. The resulting mixture was then warmed up to 60° C. and stirred at that temperature until no further conversion was observed. Celite was added to the reaction mixture and the volatiles were removed under reduced pressure. Then it was purified via flash chromatography using heptane and EtOAc as eluents to give 10.5 g of the desired product (18.2 mmol, 72.7% Yield).

$^1$H NMR (500 MHz, DMSO-d$_6$) δ ppm 11.65 (br s, 1H), 7.31 (br d, 1H), 7.21 (br d, 1H), 7.14 (t, 1H), 4.23 (s, 2H), 4.1 (t, 2H), 3.73 (s, 3H), 3.23 (t, 2H), 2.86 (s, 3H), 2.07 (m, 2H), 1.46/1.41 (s, 18H); $^{13}$C NMR (125 MHz, DMSO-d$_6$) δ ppm 129.1, 119.2, 115.4, 68.1, 51.9, 38.6, 33.8, 30.5, 23.2; HRMS-ESI (m/z): [M+H]$^+$ calcd for C$_{28}$H$_{37}$FN$_3$O$_7$S: 578.2330; found 578.2331.

Preparation 1c: Methyl 2-(tert-butoxycarbo-nylamino)-5-[3-[4-[3-(dimethylamino)prop-1-ynyl]-2-fluoro-phenoxy]propyl]thiazole-4-carboxylate A 250 mL oven-dried, one-necked, round-bottom flask was equipped with a PTFE-coated magnetic stirring bar and fitted with a reflux condenser. It was charged with 5.36 g Preparation 1a (10 mmol, 1 equiv), 1.66 g N,N-dimethyl-prop-2-yn-1-amine (20 mmol, 2 equiv) and 20 mL DIPA (142.7 mmol, 14.27 equiv) then 50 mL dry THF was added and the system was flushed with argon. After 5 minutes stirring under inert atmosphere 220 mg Pd(PPh$_3$)$_2$Cl$_2$ (0.5 mmol, 0.05 equiv) and 95 CuI (0.5 mmol, 0.05 equiv) were added. The resulting mixture was then warmed up to 60° C. and stirred at that temperature until no further conversion was observed. Celite was added to the reaction mixture and the volatiles were removed under reduced pressure. Then it was purified via flash chromatography using DCM and MeOH (1.2% NH$_3$) as eluents to give 4.5 g of the desired product (7.8 mmol, 78% Yield).

$^1$H NMR (500 MHz, DMSO-d$_6$) δ ppm 11.66 (s, 1H), 7.29 (dd, 1H), 7.19 (m, 1H), 7.12 (t, 1H), 4.09 (t, 2H), 3.73 (s, 3H), 3.44 (s, 2H), 3.23 (t, 2H), 2.24 (s, 6H), 2.07 (m, 2H), 1.45 (s, 9H); $^{13}$C NMR (125 MHz, DMSO-d$_6$) δ ppm 162.8, 147.3, 129, 119.2, 115.4, 84.3, 68, 51.9, 48.1, 44.2, 30.6, 28.3, 23.2; HRMS-ESI (m/z): [M+H]$^+$ calcd for C$_{24}$H$_{31}$FN$_3$O$_5$S: 492.1962; found 492.1956 (M+H).

Preparation 1d: Methyl 2-{[(tert-butoxy)carbonyl]amino}-5-(3-iodopropyl)-1,3-thiazole-4-carboxylate To a solution of the product from Preparation 1a, Step C (5 g, 15.8 mmol, 1 eq) in diethyl ether (175 mL) and acetonitrile (35 mL) was added imidazole (1.57 mL, 23.71 mmol, 1.5 eq) followed by triphenylphosphine (3.73 g, 14.22 mmol, 1.5 eq) and iodine (6.02 g, 23.71 mmol, 1.5 eq). The mixture was stirred at ambient temperature for 1 h. The reaction was partitioned between ethyl acetate (150 mL) and 10% aqueous sodium thiosulfate (250 mL), and the organic phase was successively washed with water (200 mL) and brine (150 mL), dried (magnesium sulfate) and concentrated in vacuo. The residue was dissolved in diethyl ether and left to age at fridge temperature overnight. The resultant crystals were removed by filtration and the filtrate was concentrated in vacuo. Purification by automated flash chromatography (Combiflash R$_f$, Silica 80 g RediSep column) eluting with a gradient of 0-50% ethyl acetate in iso-heptane afforded the desired product (5.77 g, 13.53 mmol, 85%) as a white solid.

LC/MS (C$_{13}$H$_{19}$IN$_2$O$_4$S) 427 [M+H]$^+$; RT 0.88 (LCMS-V-B2)

$^1$H NMR (400 MHz, DMSO-d6) δ 11.67 (s, 1H), 3.79 (s, 3H), 3.29 (t, J=6.8 Hz, 2H), 3.20-3.12 (m, 2H), 2.09 (dq, J=8.7, 6.8 Hz, 2H), 1.48 (s, 9H).

Preparation 2a: 3-(3,6-Dichloro-5-methyl-pyridazin-4-yl)propan-1-ol

Step A: [(pent-4-yn-1-yloxy)methyl]benzene

To an oven-dried flask was added 4-pentyn-1-ol (11.1 mL, 119 mmol, 1 eq) in THF (100 mL) and the solution was cooled to 0° C. Sodium hydride (60% dispersion; 7.13 g, 178 mmol, 1.5 eq) was added portionwise and the mixture was allowed to stir for 30 min at 0° C. before the dropwise addition of benzyl bromide (15.6 mL, 131 mmol, 1.1 eq). The mixture was allowed to warm to ambient temperature and was stirred for 16 h, then cooled to 0° C., quenched with saturated aqueous ammonium chloride (30 mL) and diluted with water (30 mL). The mixture was extracted with ethyl acetate (2×150 mL), and the combined organic extracts were washed successively with dilute aqueous ammonium hydroxide ammonium hydroxide (150 mL) and brine (100 mL), dried (magnesium sulfate) and concentrated in vacuo. Purification by automated flash column chromatography (CombiFlash Rf, 330 g RediSep™ silica cartridge) eluting with a gradient of 0-10% ethyl acetate in iso-heptane afforded the desired product as a yellow liquid (19.5 g, 112 mmol, 94%).

LC/MS (C$_{12}$H$_{14}$O) 175 [M+H]$^+$; RT 1.28 (LCMS-V-B1)

$^1$H NMR (400 MHz, Chloroform-d) δ 7.37-7.32 (m, 4H), 7.31-7.27 (m, 1H), 4.52 (s, 2H), 3.58 (t, J=6.1 Hz, 2H), 2.32 (td, J=7.1, 2.6 Hz, 2H), 1.95 (t, J=2.7 Hz, 1H), 1.83 (tt, J=7.1, 6.2 Hz, 2H).

Step B: [(hex-4-yn-1-yloxy)methyl]benzene

To an oven-dried flask was added the product from Step A (19.5 g, 112 mmol, 1 eq) and tetrahydrofuran (200 mL) and the solution was cooled to −78° C. n-Butyllithium (66.9 mL, 135 mmol, 1.2 eq) was added dropwise over 30 min and the reaction was stirred for 1 h then iodomethane (10.5 mL, 168 mmol, 1.5 eq) was added dropwise and the mixture was allowed to warm to 0° C. over 1 h. The reaction was quenched by the addition of saturated aqueous ammonium chloride (40 mL), diluted with water (40 mL), extracted with ethyl acetate (3×100 mL), and the combined organic extracts were successively washed with 2M aqueous sodium thio-sulfate (200 mL) and brine (200 mL), dried (magnesium sulfate) and concentrated in vacuo. Purification by auto-mated flash column chromatography (CombiFlash Rf, 330 g RediSep™ silica cartridge) eluting with a gradient of 0-10% ethyl acetate in iso-heptane afforded the desired product as a yellow liquid (19.2 g, 0.1 mol, 91%).

LC/MS (C$_{13}$H$_{16}$O) 189 [M+H]$^+$; RT 1.34 (LCMS-V-B1)

$^1$H NMR (400 MHz, DMSO-d6) δ 7.41-7.23 (m, 5H), 4.46 (s, 2H), 3.48 (t, J=6.3 Hz, 2H), 2.23-2.14 (m, 2H), 1.72 (s, 3H), 1.70-1.65 (m, 2H).

Step C: 4-[3-(benzyloxy)propyl]-3,6-dichloro-5-methylpyridazine

A solution of 3,6-dichloro-1,2,4,5-tetrazine (5 g, 33.1 mmol, 1 eq) and the product from Step B (7.48 g, 39.8 mmol, 1.2 eq) in tetrahydrofuran (30 mL) was heated at 160° C. for 19 h in a sealed flask. The reaction was allowed to cool to ambient temperature then concentrated in vacuo. Purification by automated flash column chromatography (CombiFlash Rf, 220 g RediSep™ silica cartridge) eluting with a gradient of 0-30% ethyl acetate in iso-heptane afforded the desired product as an orange oil (7.32 g, 23.5 mmol, 71%).

LC/MS ($C_{15}H_{16}Cl_2N_2O$) 311 [M+H]$^+$; RT 1.35 (LCMS-V-B1)

$^1$H NMR (400 MHz, DMSO-d6) δ 7.45-7.18 (m, 5H), 4.48 (s, 2H), 3.53 (t, J=5.9 Hz, 2H), 2.96-2.83 (m, 2H), 2.42 (s, 3H), 1.88-1.69 (m, 2H).

Step D: 3-(3,6-dichloro-5-methylpyridazin-4-yl)propan-1-ol

To a cooled solution of the product from Step C (7.32 g, 23.5 mmol, 1 eq) in dichloromethane (100 mL) was added boron trichloride solution (1 M in dichloromethane; 58.8 mL, 58.8 mmol, 2.5 eq) dropwise and the mixture was allowed to stir at ambient temperature for 1 h. The reaction was quenched by the addition of methanol and concentrated in vacuo. The residue was partitioned between dichloromethane (100 mL) and saturated aqueous sodium bicarbonate (150 mL), and the organic phase was washed with brine (150 mL), dried (magnesium sulfate) and concentrated in vacuo. Purification by automated flash column chromatography (CombiFlash Rf, 80 g RediSep™ silica cartridge) eluting with a gradient of 0-80% ethyl acetate in iso-heptane afforded the desired product as a yellow oil (4.19 g, 19 mmol, 81%).

LC/MS ($C_8H_{11}C_{12}N_2O$) 221 [M+H]$^+$; RT 0.84 (LCMS-V-B1)

$^1$H NMR (400 MHz, DMSO-d6) δ 4.67 (t, J=5.1 Hz, 1H), 3.49 (td, J=6.0, 5.1 Hz, 2H), 2.91-2.80 (m, 2H), 2.43 (s, 3H), 1.72-1.59 (m, 2H).

Preparation 2b: 2-[tert-butyl(diphenyl)silyl]oxy-3-(3,6-dichloro-5-methyl-pyridazin-4-yl)propan-1-ol (enantiopure, from Enantiomer 2 of Step A)

Step A: ethyl 3-(3,6-dichloro-5-methyl-pyridazin-4-yl)-2-hydroxy-propanoate To 3,6-dichloro-4,5-dimethyl-pyridazine (26.5 g, 150 mmol) in dry THF (375 mL) was added dropwise TMP-MgCl×LiCl (165 mL, 165 mmol, 1.1 eq.) at −78° C., then the resulting mixture was stirred for 2 h at 0° C. The generated Mg salt was transferred to a solution of ethyl 2-oxoacetate (45.9 g, 225 mmol, 1.5 eq.) in dry THF (375 mL) at 0° C., then it was stirred for 30 min at 0° C. After quenching the reaction with saturated aqueous NH$_4$Cl solution and extraction with EtOAc, the combined organic layers were dried, filtered, concentrated, and purified via flash chromatography on silica gel using heptane and EtOAc as eluents to give 11 g (26.3%) of the desired compound.

$^1$H NMR (500 MHz, DMSO-d$_6$) δ ppm 5.85 (d, 1H), 4.33 (m, 1H), 4.12 (q, 2H), 3.19 (d, 2H), 2.45 (s, 3H), 1.17 (t, 3H); $^{13}$C NMR (125 MHz, DMSO-d$_6$) δ ppm 172.8, 157.6, 157.2, 141.4, 139.3, 68.8, 61.2, 35.2, 17.3, 14.4. HRMS-ESI (m/z): [M+H]$^+$ calcd for $C_{10}H_{13}Cl_2N_2O_3$: 279.0303, found 279.0301.

Enantiomers of the desired product was separated on a AS-V chiral column (100*500 mm, 20 m) using 10:90

EtOH-heptane as eluents to give the Enantiomer 1 (eluded first) of 99.6% ee and Enantiomer 2 (eluded last) of 99.1% ee.

Step B: ethyl 2-[tert-butyl(diphenyl)silyl]oxy-3-(3, 6-dichloro-5-methyl-pyridazin-4-yl)propanoate To the Enantiomer 2 of Step A (4500 mg, 16 mmol, imidazole (2200 mg, 2.0 eq.) in THF (81 mL) was added dropwise TBDPS-Cl (8900 mg, 2.0 eq.), then it was stirred at rt for 18 h. The product was purified via flash chromatography using heptane and EtOAc as eluents to give the desired product (6200 mg, 74%).

$^1$H NMR (400 MHz, DMSO-d$_6$) δ ppm 7.52-7.27 (m, 1OH), 4.46 (dd, 1H), 3.83 (m, 2H), 3.35 (dd, 1H), 3.19 (dd, 1H), 2.34 (s, 3H), 0.93 (t, 3H), 0.87 (s, 9H).

Step C: 2-[tert-butyl(diphenyl)silyl]oxy-3-(3,6-di-chloro-5-methyl-pyridazin-4-yl)propan-1-ol To the enantiopure product of Step B (3600 mg, 6.95 mmol) in MeOH (35 mL) was added portionwise NaBH$_4$ (2.63 g, 10 eq.) at 0° C. over a period of 5 min and stirred at that temperature for 30 min. After quenching the reaction with the addition of saturated aqueous solution of NH$_4$Cl, it was extracted twice with EtOAc. The combined organic layers were dried, filtered, concentrated, and purified via flash chromatography on silica gel using heptane and EtOAc as eluents to give the desired product (1.6 g, 48%).

$^1$H NMR (500 MHz, DMSO-d$_6$) δ ppm 7.57-7.3 (m, 1OH), 4.9 (brs, 1H), 4.05 (m, 1H), 3.38/3.32 (dd+dd, 2H), 3.13/3.11 (dd+dd, 2H), 2.3 (s, 3H), 0.8 (s, 9H); $^{13}$C NMR (125 MHz, DMSO-d$_6$) ppm 72.7, 65.5, 35.5, 26.9, 17.2; HRMS-ESI (m/z): [M+H]$^+$ calcd for $C_{24}H_{29}Cl_2N_2O_2Si$: 475.1369, found 475.1362.

Preparation 2c: 2-(3,6-Dichloro-5-methyl-pyridazin-4-yl)ethanol

Step A: 3-(3,6-dichloro-5-methyl-pyridazin-4-yl) propane-1,2-diol

To 700 mg (2.5 mmol) of the product from Preparation 2b, Step A in 3 mL of methanol was added 285 mg (3 eq.) of NaBH$_4$ at 0° C. and the mixture was stirred at 0° C. for 0.5 h. After quenching the reaction with a saturated solution of NH$_4$Cl, the crude product was purified via flash chromatography on silica gel using DCM and MeOH (1.2% NH$_3$) as eluents to give 500 mg (84%) of the desired compound.

$^1$H NMR (400 MHz, DMSO-d$_6$) δ ppm 4.90 (bd, 1H), 4.83 (bs, 1H), 3.75 (m, 1H), 3.47 (dd, 1H), 3.38 (m, 1H), 3.00 (dd, 1H), 2.87 (dd, 1H), 2.45 (s, 3H).

Step B: 2-(3,6-dichloro-5-methyl-pyridazin-4-yl) acetaldehyde

To a solution of 237 mg of the product from Step A (1 mmol.) in a 5 mL acetone/H$_2$O (4:1) were cooled to 0° C., then 427 mg sodium periodate (2 mmol, 2 eq.) was added portionwise. After 2 h stirring at rt, the mixture was purified by flash chromatography using heptane-EtOAc as eluents to give 200 mg of the desired product (97%).

$^1$H NMR (400 MHz, DMSO-d$_6$) δ ppm 9.71 (s, 1H), 4.27 (s, 1H), 2.35 (s, 3H).

Step C: 2-(3,6-dichloro-5-methyl-pyridazin-4-yl)ethanol

To a solution of 200 mg of the product from Step B (0.97 mmol) in 3 mL of methanol was added in small portions 110 mg (2.92 mmol, 3 eq.) of sodium borohydride at 0° C. After 15 min stirring, the reaction mixture was diluted with saturated aqueous NH$_4$Cl solution and extracted with EtOAc. The combined organic layers were dried, filtered, concentrated, and purified by flash chromatography using heptane-EtOAc as eluents to give 180 mg (89%) of the desired product.

$^1$H NMR (500 MHz, DMSO-d$_6$) δ ppm 4.9 (t, 1H), 3.65 (m, 2H), 3 (t, 2H), 2.45 (s, 3H); $^{13}$C NMR (125 MHz, DMSO-d$_6$) δ ppm 157.5, 157.2, 140.9, 140.7, 59.1, 34, 17.1; HRMS-ESI (m/z): [M+H]$^+$ calcd for C$_7$H9Cl$_2$N$_2$O: 207.0086, found 207.0083.

Preparation 2e:
3-(3,6-Dichloro-5-methylpyridazin-4-yl)propanal

To an oven-dried flask was added dimethyl sulfoxide (3.08 mL, 43.4 mmol, 2.4 eq) and dichloromethane (100 mL) and the solution was cooled to −78° C. Oxalyl chloride (2M in dichloromethane; 13.6 mL, 27.1 mmol, 1.5 eq) was added dropwise and the reaction was allowed to stir for 1 h. A solution of the product from Preparation 2a (4 g, 18.1 mmol, 1 eq) in dichloromethane (20 mL) was then added dropwise and the mixture was allowed to stir for 1 h. Triethylamine (15.1 mL, 109 mmol, 6 eq) was added and the reaction was allowed to warm to 0° C. over 1 h. The reaction was quenched with water (50 mL), then partitioned between saturated sodium bicarbonate (50 mL) and dichloromethane (200 mL), the aqueous phase was extracted with dichloromethane (200 mL), and the combined organic extracts were washed with brine (100 mL), dried (magnesium sulfate) and concentrated in vacuo. Purification by automated flash column chromatography (CombiFlash Rf, 24 g RediSep™ silica cartridge) eluting with a gradient of 0-50% ethyl acetate in iso-heptane afforded the desired product as an off-white solid (2.27 g, 10.4 mmol, 57%).

LC/MS (CH$_8$Cl$_2$N$_2$O) 219 [M+H]$^+$; RT 0.87 (LCMS-V-B1)

$^1$H NMR (400 MHz, DMSO-d6) δ 9.71 (s, 1H), 3.03 (dd, J=8.7, 7.0 Hz, 2H), 2.86-2.69 (m, 2H), 2.44 (s, 3H).

Preparation 3a: Methyl 2-(3-chloro-4-methyl-6,7-dihydro-5H-pyrido[2,3-c]pyridazin-8-yl)-5-[3-(2-fluoro-4-iodo-phenoxy)propyl]thiazole-4-carboxylate

Step A: methyl 2-{[(tert-butoxy)carbonyl][3-(3,6-dichloro-5-methylpyridazin-4-yl)propyl]amino}-5-[3-(2-fluoro-4-iodophenoxy)propyl]-1,3-thiazole-4-carboxylate Using Mitsunobu General Procedure starting from 4.85 g Preparation 1a (9.04 mmol, 1 equiv) as the appropriate carbamate and 2 g Preparation 2a (9.04 mmol, 1 equiv) as the appropriate alcohol, 4.6 g of the desired product (69% Yield) was obtained.

$^1$H NMR (500 MHz, DMSO-d$_6$) δ ppm 7.56 (dd, 1H), 7.44 (dm, 1H), 7.08 (m, 2H), 6.96 (t, 1H), 4.05 (t, 2H), 3.75 (s, 3H), 3.21 (t, 2H), 2.82 (m, 2H), 2.4 (s, 3H), 2.06 (m, 2H), 1.88 (m, 2H), 1.48 (s, 9H); $^{13}$C NMR (125 MHz, DMSO-d$_6$) δ ppm 162.7, 157.6, 156.7, 156.5/153.2, 152.2, 147, 139.8, 134, 124.9, 117.6, 84, 82.4, 68.1, 52.1, 46.1, 30.4, 28.1, 27.5, 25.8, 23.1, 16.4; HRMS-ESI (m/z): [M+H]$^+$ calcd for C$_{27}$H$_{31}$Cl$_2$FIN$_4$O$_5$S: 739.0415, found 739.0395.

Step B: methyl 2-[3-(3,6-dichloro-5-methyl-pyridazin-4-yl)propylamino]-5-[3-(2-fluoro-4-iodo-phenoxy)propyl]thiazole-4-carboxylate Using Deprotection with HFIPA General Procedure starting from the product from Step A as the appropriate carbamate, 3.70 g the desired product (97% Yield) was obtained.

$^1$H NMR (500 MHz, DMSO-d$_6$) δ ppm 7.71 (t, 1H), 7.59 (dd, 1H), 7.44 (dm, 1H), 6.96 (t, 1H), 4.03 (t, 2H), 3.7 (s, 3H), 3.29 (m, 2H), 3.11 (t, 2H), 2.84 (m, 2H), 2.39 (s, 3H), 2 (m, 2H), 1.76 (m, 2H); $^{13}$C NMR (125 MHz, DMSO-d$_6$) δ ppm 164.6, 163, 152.3, 147.1, 134.1, 124.8, 117.6, 82.4, 68.1, 51.9, 44, 30.7, 28, 26.9, 23.3, 16.4; HRMS-ESI (m/z): [M+H]$^+$ calcd for C$_{22}$H$_{23}$Cl$_2$FIN$_4$O$_3$S: 638.9891, found 638.9888.

Step C: methyl 2-(3-chloro-4-methyl-6,7-dihydro-5H-pyrido[2,3-c]pyridazin-8-yl)-5-[3-(2-fluoro-4-iodo-phenoxy)propyl]thiazole-4-carboxylate A suspension of 3 g of the product from Step B (4.69 mmol, 1 eq) and 1.81 g cesium carbonate (9.3853 mmol, 2 eq.) were stirred at 80° C. for 3 h in 25 mL dry 1,4-dioxane to reach complete conversion. Reaction mixture directly was evaporated to Celite, and then purified by flash chromatography on using DCM-MeOH as eluents to obtain 2.67 g of the title compound (94% Yield).

$^1$H NMR (500 MHz, DMSO-d$_6$) δ ppm 7.57 (dd, 1H), 7.43 (dm, 1H), 6.97 (t, 1H), 4.23 (t, 2H), 4.08 (t, 2H), 3.77 (s, 3H), 3.22 (t, 2H), 2.86 (t, 2H), 2.29 (s, 3H), 2.08 (m, 2H), 2.03 (m, 2H);

$^{13}$C NMR (125 MHz, DMSO-d$_6$) δ ppm 163.1, 155.4, 152.2, 151.6, 151.2, 147, 142.5, 136, 134.8, 134, 128.9, 124.9, 117.6, 82.3, 68.4, 51.9, 46.3, 30.7, 24.2, 23, 19.7, 15.7; HRMS-ESI (m/z): [M+H]$^+$ calcd for C$_{22}$H$_{22}$ClFIN$_4$O$_3$S: 603.0124, found 603.0108.

Preparation 3b: Methyl 5-(3-hydroxypropyl)-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate

Step A: methyl 2-(tert-butoxycarbonylamino)-5-[3-[tert-butyl(dimethyl)silyl]oxyprop-1-ynyl]thiazole-4-carboxylate A 1 L oven-dried, one-necked, round-bottomed flask equipped with a PTFE-coated magnetic stir bar was charged with 20 g Preparation 1a, Step A (52.05 mmol, 1.0 eq.), 17.73 g tert-butyl-dimethyl-prop-2-ynoxy-silane (21 mL, 104.1 mmol, 2.0 eq.) dissolved in 250 mL dry THF/25 mL DIPA and then placed under a nitrogen atmosphere through a gas inlet. Then this solution was charged with 572 mg Pd(PPh$_3$)$_2$Cl$_2$ (1.30 mmol, 0.025 eq.) and 247 mg CuI (1.30 mmol, 0.025 eq.). The reaction mixture was then warmed up to reflux and stirred at that temperature until no further conversion was observed. Celite was added to the reaction mixture and the volatiles were removed under reduced pressure. Then it was purified in two parts via flash chromatography using heptane and EtOAc as eluents to obtain 18.00 g of the desired product (81% Yield).

$^1$H NMR (400 MHz, DMSO-d$_6$) δ ppm 12.13 (br., 1H), 4.62 (s, 2H), 3.79 (s, 3H), 1.48 (s, 9H), 0.89 (s, 9H), 0.13 (s, 6H); $^{13}$C NMR (100 MHz, DMSO-d$_6$) δ ppm 161.2, 52.4, 52.4, 28.3, 26.2,-4.6; HRMS-ESI (m/z): [M+H]$^+$ calcd for C$_{19}$H$_{31}$N$_2$O$_5$SSi: 427.1717, found 427.1711.

Step B: methyl 2-(tert-butoxycarbonylamino)-5-[3-[tert-butyl(dimethyl)silyl]oxypropyl]thiazole-4-carboxylate 13 g of the product from Step A (30.42 mmol, 1.0 eq.) was dissolved in 150 mL EtOH and charged with 3.23 g Pd/C (3.04 mmol, 0.1 eq.). A 250 mL oven-dried autoclave equipped with a PTFE-coated magnetic stir bar was charged with the solution, and then placed under a nitrogen atmosphere using the hydrogenation system. After that it was filled with 10 bar H$_2$ gas. After 2 hours stirring at rt the reaction reached complete conversion. Celite was added to the reaction mixture and the volatiles were removed under reduced pressure. Then it was purified via flash chromatography heptane and EtOAc as eluents to obtain 9.95 g of the desired product (78% Yield).

$^1$H NMR (500 MHz, DMSO-d$_6$) δ ppm 11.62 (br., 1H), 3.76 (s, 3H), 3.62 (t, 2H), 3.12 (t, 2H), 1.78 (quint., 2H), 1.46 (s, 9H), 0.86 (s, 9H), 0.03 (s, 6H); $^{13}$C NMR (125 MHz, DMSO-d$_6$) δ ppm 162.8, 62, 51.9, 34.3, 28.3, 26.3, 23.3, −4.9; HRMS-ESI (m/z): [M+H]$^+$ calcd for C$_{19}$H$_{35}$N$_2$O$_5$SSi: 431.2030, found 431.2025.

Step C: methyl 2-[tert-butoxycarbonyl-[3-(3,6-dichloro-5-methyl-pyridazin-4-yl)propyl]amino]-5-[3-[tert-butyl(dimethyl)silyl]oxypropyl]thiazole-4-carboxylate Using Mitsunobu General Procedure starting from 9.91 g of the product from Step B (23.0 mmol, 1 eq.) as the appropriate carbamate and 5.1 g Preparation 2a (23.0 mmol, 1 equiv) as the appropriate alcohol, 13.02 g of the desired product (89% Yield) was obtained.

$^1$H NMR (500 MHz, DMSO-d$_6$) δ ppm 4.09 (t, 2H), 3.77 (s, 3H), 3.61 (t, 2H), 3.12 (t, 2H), 2.82 (t, 2H), 2.41 (s, 3H), 1.88 (qn, 2H), 1.79 (qn, 2H), 1.39 (s, 9H), 0.85 (s, 9H), 0.02 (s, 6H);

$^{13}$C NMR (125 MHz, DMSO-d$_6$) δ ppm 162.8, 157.7, 156.3, 156.1, 152.8, 144.5, 142.1, 139.9, 135.3, 79.4, 62.1, 52.1, 46.1, 34.1, 28.6, 27.5, 26.3, 25.9, 23.2, 18.4, 16.4, −4.9; HRMS-ESI (m/z): [M+H]$^+$ calcd for C$_{27}$H$_{43}$Cl$_2$N$_4$O$_5$SSi: 633.2095, found 633.2091.

Step D: methyl 5-[3-[tert-butyl(dimethyl)silyl]oxypropyl]-2-[3-(3,6-dichloro-5-methyl-pyridazin-4-yl)propylamino]thiazole-4-carboxylate Using Deprotection with HFIPA General Procedure starting from the product from Step C as the appropriate carbamate, 10.4 g of the desired product (95% Yield) was obtained.

$^1$H NMR (500 MHz, DMSO-d$_6$) δ ppm 7.69 (t, 1H), 3.71 (s, 3H), 3.60 (t, 2H), 3.30 (q, 2H), 3.01 (t, 2H), 2.85 (t, 2H), 2.41 (s, 3H), 1.78 (qn, 2H), 1.71 (qn, 2H), 0.86 (s, 9H), 0.02 (s, 6H); $^{13}$C NMR (125 MHz, DMSO-d$_6$) δ ppm 164.3, 163.1, 157.7, 156.9, 142.5, 140.0, 137.6, 136.5, 62.0, 51.7, 44.1, 34.4, 28.0, 26.9, 26.3, 23.4, 18.5, 16.5, −4.9; HRMS-ESI (m/z): [M+H]$^+$ calcd for C$_{22}$H$_{35}$Cl$_2$N$_4$O$_3$SSi: 533.1570, found 533.1566.

Step E: methyl 5-[3-[tert-butyl(dimethyl)silyl]oxypropyl]-2-(3-chloro-4-methyl-6,7-dihydro-5H-pyrido[2,3-c]pyridazin-8-yl)thiazole-4-carboxylate A 250 mL oven-dried one-necked, round-bottom flask equipped with a PTFE-coated magnetic stir bar was charged with 10.4 g of the product from Step D (19.57 mmol, 1.0 eq.), 12.75 g Cs$_2$CO$_3$ (39.13 mmol, 2.0 eq.) and 100 mL dry 1,4-dioxane. The reaction mixture was then warmed up to reflux temperature and stirred at that temperature for 8 h. Celite was added to the reaction mixture and the volatiles were removed under reduced pressure. Then it was purified via flash chromatography using heptane and EtOAc as eluents to obtain 6.40 g of the desired product (66% Yield).

$^1$H NMR (500 MHz, DMSO-d$_6$) δ ppm 4.26 (t, 2H), 3.79 (s, 3H), 3.65 (t, 2H), 3.14 (t, 2H), 2.89 (t, 2H), 2.32 (s, 3H), 2.04 (m, 2H), 1.82 (m, 2H), 0.87 (s, 9H), 0.04 (s, 6H); $^{13}$C NMR (125 MHz, DMSO-d$_6$) δ ppm 163.1, 155.3, 151.8, 151.3, 143.4, 136.1, 134.6, 129.0, 62.1, 52.0, 46.3, 34.4, 26.3, 24.2, 23.1, 19.7, 15.7, −4.8; HRMS-ESI (m/z): [M+H]$^+$ calcd for C$_{22}$H$_{34}$ClN$_4$O$_3$SSi: 497.1804, found 497.1796.

Step F: methyl 2-[3-(1,3-benzothiazol-2-ylamino)-4-methyl-6,7-dihydro-5H-pyrido[2,3-c]pyridazin-8-yl]-5-[3-[tert-butyl(dimethyl)silyl]oxypropyl]thiazole-4-carboxylate A 250 mL oven-dried, one-necked, round-bottom flask was equipped with a PTFE-coated magnetic stirring bar and fitted with a reflux condenser. It was charged with 6.43 g of the product from Step E (12.94 mmol, 1.0 eq.), 3.88 g 1,3-benzothiazol-2-amine (25.87 mmol, 2.0 equiv) and 6.75 mL DIPEA (38.81 mmol, 3.0 eq.) then 65 mL CyOH was added. And then the system was flushed with argon. After 5 minutes stirring under inert atmosphere 1.18 g Pd$_2$(dba)$_3$ (1.29 mmol, 0.1 eq.) and 1.49 g XantPhos (2.587 mmol, 0.2 eq.) were added. The resulting mixture was then warmed up to 140° C. and stirred at that temperature for 1 hour to reach complete conversion. The reaction mixture was diluted with DCM, and directly injected onto a preconditioned silica gel column, and then it was purified via flash chromatography using heptane and EtOAc as eluents to obtain 6.85 g of the desired product (87% Yield).

$^1$H NMR (500 MHz, DMSO-d$_6$) δ ppm 7.82 (br., 1H), 7.52 (br., 1H), 7.37 (t, 1H), 7.19 (t, 1H), 4.25 (t, 2H), 3.80 (s, 3H), 3.66 (t, 2H), 3.16 (t, 2H), 2.87 (t, 2H), 2.33 (s, 3H), 2.04 (m, 2H), 1.84 (m, 2H), 0.92 (s, 9H), 0.07 (s, 6H); $^{13}$C NMR (125 MHz, DMSO-d$_6$) δ ppm 163.2, 155.6, 148.8, 148.6, 142.3, 134.5, 127.6, 126.5, 122.5, 122, 62.0, 51.9, 46.3, 34.4, 26.4, 23.9, 22.9, 20.3, 12.8, −4.8; HRMS-ESI (m/z): [M+H]$^+$ calcd for C$_{29}$H$_{39}$N$_6$O$_3$S$_2$Si: 611.2288, found 611.2284.

Step G: methyl 5-[3-[tert-butyl(dimethyl)silyl]oxypropyl]-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate 5.00 g of the product from Step F (8.18 mmol, 1.0 eq.) was dissolved in 50 mL dry DCM and 50 mg DMAP (0.41 mmol, 0.05 eq.) and 2.85 mL DIPEA (16.37 mmol, 2.0 eq.) was added at 0° C. Then 2.24 mL 2-(chloromethoxy)ethyl-trimethyl-silane (12.69 mmol, 1.5 eq.) was added over 5 minutes period of time at 0° C., and the resulting mixture was put in the fridge for a night, while complete conversion was observed. Celite was added to the reaction mixture and the volatiles were removed under reduced pressure. Then it was purified via flash chromatography using heptane and EtOAc as eluents to obtain 3.85 g of the desired product (63% Yield).

$^1$H NMR (500 MHz, DMSO-d$_6$) δ ppm 7.6-7.15 (m, 4H), 5.83 (s, 2H), 4.42 (t, 2H), 3.92 (s, 3H), 3.74 (t, 2H), 3.73 (t, 2H), 3.24 (t, 2H), 2.86 (t, 2H), 2.37 (s, 3H), 2.12 (m, 2H), 1.97 (m, 2H), 0.96 (t, 2H), 0.95 (s, 9H), 0.1 (s, 6H), −0.07 (s, 9H); $^{13}$C NMR (125 MHz, DMSO-d$_6$) δ ppm 163.6, 157.7, 156.4, 154.7, 148.5, 143.7, 137.6, 134.1, 132.6, 126.1, 125.6, 73.2, 66.9, 62.5, 51.9, 46, 34.3, 26.1, 24.2, 23.4, 20.6, 18.0, 12.9, −1.4, −5.2; HRMS-ESI (m/z): [M+H]$^+$ calcd for C$_{35}$H$_{53}$N$_6$O$_4$S2Si$_2$: 741.3102, found 741.3098.

Step H: methyl 5-(3-hydroxypropyl)-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate 3.85 g of the product from Step G (5.19 mmol, 1.0 eq.) and 362 mg camphor sulfonic acid (1.56 mmol, 0.3 eq.) were dissolved in 40 mL DCM/MeOH (2:1). The reaction mixture was then warmed up to 50° C. and stirred at that temperature overnight. The reaction reached complete conversion. The reaction mixture was cooled to room temperature and quenched by the addition of saturated aqueous NaHCO$_3$ solution and then then it was extracted with EtOAc for two times.

Celite was added to the combined organic layers and the volatiles were removed under reduced pressure. Then it was purified via flash chromatography using heptane and EtOAc as eluents to give 2.50 g title compound (76% Yield).

$^1$H NMR (500 MHz, DMSO-d$_6$) δ ppm 7.83 (dm, 1H), 7.44 (dm, 1H), 7.42 (m, 1H), 7.23 (m, 1H), 5.84 (s, 2H), 4.57 (brs, 1H), 4.26 (t, 2H), 3.80 (s, 3H), 3.72 (m, 2H), 3.48 (t, 2H), 3.14 (m, 2H), 2.86 (t, 2H), 2.36 (s, 3H), 2.04 (m, 2H), 1.81 (m, 2H), 0.91 (m, 2H), −0.11 (s, 9H); $^{13}$C NMR (125 MHz, DMSO-d$_6$) δ ppm 127.1, 123.3, 123.2, 111.9, 72.9, 66.7, 60.6, 51.9, 46.4, 35.0, 23.8, 23.2, 20.4, 17.8, 13, −1.0; HRMS-ESI (m/z): [M+H]$^+$ calcd for C$_{29}$H$_{39}$N$_6$O$_4$S2Si: 627.2237, found 627.2236.

Preparation 3c: 2-[3-(1,3-Benzothiazol-2-ylamino)-4-methyl-6,7-dihydro-5H-pyrido[2,3-c]pyridazin-8-yl]-5-[3-(4-ethynyl-2-fluoro-phenoxy)propyl]thiazole-4-carboxylic acid Step A: methyl 2-(3-chloro-4-methyl-6,7-dihydro-5H-pyrido[2,3-c]pyridazin-8-yl)-5-[3-[2-fluoro-4-(2-trimethylsilylethynyl)phenoxy]propyl]thiazole-4-carboxylate A 250 mL oven-dried, one-necked, round-bottom flask was equipped with a PTFE-coated magnetic stirring bar and fitted with a reflux condenser. It was charged with 5 g Preparation 3a (8.29 mmol, 1 eq.), 2.34 mL ethynyl(trimethyl)silane (16.58 mmol, 2 eq.) and 10 mL DIPEA, then 40 mL dry THF was added and the system was flushed with argon. After 5 minutes stirring under inert atmosphere 182 mg Pd(PPh$_3$)$_2$Cl$_2$ (0.41 mmol, 0.05 eq.) and 79 mg (0.41 mmol, 0.05 eq.) were added. The resulting mixture was then warmed up to 60° C. and stirred at that temperature for 2 hours to reach complete conversion. Celite was added to the reaction mixture and the volatiles were removed under reduced pressure. Then it was purified via flash chromatography using Heptane-EtOAc as eluents to give 4.26 g of the desired product (89% Yield).

$^1$H NMR (500 MHz, DMSO-d$_6$) δ ppm 7.31 (dd, 1H), 7.23 (dn, 1H), 7.13 (t, 1H), 4.25 (t, 2H), 4.12 (t, 2H), 3.77 (s, 3H), 3.24 (t, 2H), 2.87 (t, 2H), 2.31 (s, 3H), 2.1 (m, 2H), 2.03 (m, 2H), 0.21 (s, 9H); $^{13}$C NMR (125 MHz, DMSO-d$_6$) δ ppm 163.0, 155.3, 151.7, 151.3, 136.1, 129.4, 129.0, 119.4, 115.3, 104.6, 93.7, 68.2, 51.9, 46.3, 30.7, 24.1, 23.0, 19.7, 15.7, 0.4; HRMS-ESI (m/z): [M]+ calcd for C$_{27}$H$_{30}$ClFN$_4$O$_3$SSi: 572.1481, found 572.1480.

Step B: methyl 2-[3-(1,3-benzothiazol-2-ylamino)-4-methyl-6,7-dihydro-5H-pyrido[2,3-c]pyridazin-8-yl]-5-[3-[2-fluoro-4-(2-trimethylsilylethynyl) phenoxy]propyl]thiazole-4-carboxylate A 100 mL oven-dried, one-necked, round-bottom flask with a PTFE-coated magnetic stirring bar was charged with 4.25 g of the product from Step A (7.4 mmol, 1.0 eq.), 2.23 g 1,3-benzothiazol-2-amine (14.8 mmol, 2.0 eq.) and 3.87 mL DIPEA (2.87 mg, 22.2 mmol, 3.0 eq.) then 40 mL cyclohexanol was added and the system was flushed with argon. After 5 minutes stirring under inert atmosphere 679 mg Pd$_2$(dba)$_3$ (0.74 mmol, 0.10 eq.) and 858 mg XantPhos (1.48 mmol, 0.20 eq.) were added. The resulting mixture was then warmed up to 140° C. and stirred at that temperature for 30 min to reach complete conversion. The reaction mixture was diluted with DCM and directly injected onto a preconditioned silica gel column, and then it was purified via flash chromatography using heptane and EtOAc as eluents. The pure fractions were combined and concentrated under reduced pressure to give 3.90 g of the desired product (77% Yield).

$^1$H NMR (500 MHz, DMSO-d$_6$) δ ppm 12.27/10.91 (brs, 1H), 8.1-7.1 (brm, 4H), 7.34 (dd, 1H), 7.24 (dm, 1H), 7.16 (t, 1H), 4.25 (t, 2H), 4.15 (t, 2H), 3.78 (s, 3H), 3.28 (t, 2H), 2.87 (t, 2H), 2.34 (s, 3H), 2.13 (m, 2H), 2.04 (m, 2H), 0.19 (s, 9H); HRMS-ESI (m/z): [M+H]$^+$ calcd for C$_{34}$H$_{36}$FN$_6$O$_3$S$_2$Si: 687.2038, found 687.2020.

Step C: 2-[3-(1,3-benzothiazol-2-ylamino)-4-methyl-6,7-dihydro-5H-pyrido[2,3-c]pyridazin-8-yl]-5-[3-(4-ethynyl-2-fluoro-phenoxy)propyl]thiazole-4-carboxylic acid A 10 mL oven-dried, one-necked, round-bottom flask was equipped with a PTFE-coated magnetic stirring bar and fitted with a reflux condenser. It was charged with 343 mg of the product from Step B (0.5 mmol, 1.0 eq.) dissolved in 2.5 mL THF/H$_2$O (4:1). Then 105 mg LiOH×H$_2$O (2.50 mmol, 5.0 eq.) was added and the resulting mixture was heated to 60° C. and stirred for 4 h at this temp. The reaction reached complete conversion. Celite gel was added to the reaction mixture and the volatiles were removed under reduced pressure. Then it was purified via flash chromatography using DCM and MeOH (1.2% NH$_3$) as eluents to give 200 mg title compound (66% Yield).

$^1$H NMR (500 MHz, DMSO-d$_6$) δ ppm 7.88 (d, 1H), 7.49 (br., 1H), 7.37 (t, 1H), 7.36 (dd, 1H), 7.25 (dm, 1H), 7.19 (t, 1H), 7.16 (t, 1H), 4.27 (t, 2H), 4.15 (t, 2H), 4.11 (s, 1H), 3.27 (t, 2H), 2.87 (t, 2H), 2.33 (s, 3H), 2.14 (m, 2H), 2.04 (m, 2H); $^{13}$C NMR (125 MHz, DMSO-d$_6$) δ ppm 164.2, 151.5, 147.9, 129.4, 126.5, 122.5, 122.3, 119.5, 115.5, 114.5, 82.9, 80.5, 68.5, 46.2, 31.0, 23.9, 23.1, 20.3, 12.9; HRMS-ESI (m/z): [M+H]$^+$ calcd for C$_{30}$H$_{26}$FN$_6$O$_3$S$_2$: 601.1486, found 601.1498.

Preparation 3d: Methyl 2-[3-(1,3-benzothiazol-2-ylamino)-4-methyl-6,7-dihydro-5H-pyrido[2,3-c]pyridazin-8-yl]-5-[3-[2-fluoro-4-(3-hydroxyprop-1-ynyl)phenoxy]propyl]thiazole-4-carboxylate Step A: methyl 5-[3-[4-[3-[tert-butyl(dimethyl)silyl]oxyprop-1-ynyl]-2-fluoro-phenoxy]propyl]-2-(3-chloro-4-methyl-6,7-dihydro-5H-pyrido[2,3-c]pyridazin-8-yl)thiazole-4-carboxylate Using Sonogashira General Procedure starting from 4.00 g of Preparation 3a (6.63 mmol, 1.0 eq.) and 2.26 g tert-butyl-dimethyl-prop-2-ynoxy-silane (13.27 mmol, 2 eq.) as the appropriate acetylene, 2.80 g of the desired product (65% Yield) was obtained.

$^1$H NMR (500 MHz, DMSO-d$_6$) δ ppm 7.27 (dd, 1H), 7.19 (dd, 1H), 7.14 (t, 1H), 4.51 (s, 1H), 4.25 (m, 2H), 4.12 (t, 2H), 3.77 (s, 3H), 3.24 (t, 2H), 2.87 (t, 2H), 2.3 (s, 3H), 2.1 (quint., 2H), 2.03 (m, 2H), 0.88 (s, 9H), 0.12 (s, 6H); $^{13}$C NMR (125 MHz, DMSO-d$_6$) δ ppm 163.0, 128.9, 119.1, 115.5, 68.3, 52.1, 51.9, 46.3, 30.7, 26.2, 24.2, 23.0, 19.7, 15.7, −4.6; HRMS-ESI (m/z): [M+H]$^+$ calcd for C$_{31}$H$_{39}$ClFN$_4$O$_4$SSi: 645.2128, found 645.2120.

Step B: methyl 2-[3-(1,3-benzothiazol-2-ylamino)-4-methyl-6,7-dihydro-5H-pyrido[2,3-c]pyridazin-8-yl]-5-[3-[4-[3-[tert-butyl(dimethyl)silyl]oxyprop-1-ynyl]-2-fluoro-phenoxy]propyl]thiazole-4-carboxylate Using Buchwald General Procedure II starting from 2.8 g of the product from Step A (4.34 mmol, 1.0 eq.) and 1.30 g 1,3-benzothiazol-2-amine (8.67 mmol, 2.0 eq.), 2.1 g of the desired product (64% Yield) was obtained.

$^1$H NMR (500 MHz, DMSO-d$_6$) δ ppm 12.25/10.91 (brs 1H), 7.88 (br, 1H), 7.51 (br, 1H), 7.37 (t, 1H), 7.29 (dd, 1H), 7.2 (t, 1H), 7.2 (dd, 1H), 7.17 (t, 1H), 4.49 (s, 2H), 4.25 (t, 2H), 4.14 (t, 2H), 3.77 (s, 3H), 3.27 (t, 2H), 2.86 (t, 2H), 2.32 (s, 3H), 2.13 (qn, 2H), 2.04 (qn, 2H), 0.87 (s, 9H), 0.1 (s, 6H); $^{13}$C NMR (125 MHz, DMSO-d$_6$) δ ppm 163.2, 155.7, 151.6, 148.5, 147.6, 141.5, 128.9, 127.6, 126.5, 122.5, 122.3, 119.1, 116.9, 115.5, 114.8, 88.2, 84, 68.4, 52.1, 51.9, 46.4, 31, 26.2, 24, 23.1, 20.4, 12.9, −4.6; HRMS-ESI (m/z): [M+H]$^+$ calcd for C$_{38}$H$_{44}$FN$_6$O$_4$S$_2$Si: 759.2613, found 759.2609.

Step C: methyl 2-[3-(1,3-benzothiazol-2-ylamino)-4-methyl-6,7-dihydro-5H-pyrido[2,3-c]pyridazin-8-yl]-5-[3-[2-fluoro-4-(3-hydroxyprop-1-ynyl)phenoxy]propyl]thiazole-4-carboxylate A 100 mL oven-dried, one-necked, round-bottom flask was equipped with a PTFE-coated magnetic stirring bar and fitted with a reflux condenser. It was charged with 2.10 g of the product from Step B (2.76 mmol, 1.0 eq.) dissolved in 15 mL THF. Then 3.32 mL TBAF (3.32 mmol, 1.2 eq., 1 M in THF) was added dropwise via syringe over a period of 2 minutes, and stirred at that temperature for 30 min. The reaction mixture was quenched with saturated NH$_4$Cl, then directly evaporated to Celite and it was purified via flash chromatography using heptane-EtOAc as eluents to give 1.6 g of the desired product (90% Yield).

$^1$H NMR (500 MHz, DMSO-d$_6$) δ ppm 11.14 (brs, 1H), 7.83 (brd, 1H), 7.49 (brs, 1H), 7.36 (m, 1H), 7.24 (dd, 1H), 7.19 (m, 1H), 7.18 (dm, 1H), 7.15 (t, 1H), 5.08 (t, 1H), 4.28 (m, 2H), 4.27 (d, 2H), 4.17 (t, 2H), 3.8 (s, 3H), 3.29 (m, 2H), 2.89 (m, 2H), 2.35 (s, 3H), 2.15 (m, 2H), 2.07 (m, 2H); HRMS-ESI (m/z): [M+H]$^+$ calcd for C$_{32}$H$_{30}$FN$_6$O$_4$S$_2$: 645.1748, found 645.1738.

Preparation 3e: Methyl 2-[3-(1,3-benzothiazol-2-ylamino)-4-methyl-6,7-dihydro-5H-pyrido[2,3-c]pyridazin-8-yl]-5-[3-[2-fluoro-4-(3-hydroxypropyl)phenoxy]propyl]thiazole-4-carboxylate

Step A: methyl 2-(tert-butoxycarbonylamino)-5-[3-[4-[3-[tert-butyl(dimethyl)silyl]oxyprop-1-ynyl]-2-fluoro-phenoxy]propyl]thiazole-4-carboxylate Using Sonogashira General Procedure starting from 4.00 g of Preparation 1a (7.45 mmol, 1.0 eq.) and 2.54 g tert-butyl-dimethyl-prop-2-ynoxy-silane (14.90 mmol, 2.0 eq.) as the appropriate acetylene, 1.70 g of the desired product (39% Yield) was obtained.

$^1$H NMR (500 MHz, DMSO-d$_6$) δ ppm 11.64 (s, 1H), 7.27 (dd, 1H), 7.19 (dm, 1H), 7.14 (t, 1H), 4.51 (s, 2H), 4.1 (t, 2H), 3.73 (s, 3H), 3.23 (t, 2H), 2.07 (m, 2H), 1.46 (s, 9H), 0.89 (s, 9H), 0.12 (s, 6H); $^{13}$C NMR (125 MHz, DMSO-d$_6$) δ ppm 88.2, 83.8.

Step B: methyl 2-(tert-butoxycarbonylamino)-5-[3-[4-[3-[tert-butyl(dimethyl)silyl]oxypropyl]-2-fluoro-phenoxy]propyl]thiazole-4-carboxylate A 50 mL oven-dried autoclave was equipped with a PTFE-coated magnetic stirring bar. It was charged with 1.70 g of the product from Step A (2.9 mmol, 1.0 eq.), 310 mg Pd/C (0.29 mmol, 0.10 eq.) and 15 mL ethanol, and then inertized using vacuum and nitrogen, finally filled with 10 bar pressure hydrogen gas. Then the mixture was stirred at rt temperature for 3 hours to reach complete conversion. Celite was added to the reaction mixture and the volatiles were removed under reduced pressure. Then it was purified via flash chromatography using heptane and EtOAc as eluents to give 1.2 g of the desired product (70% Yield).

$^1$H NMR (500 MHz, DMSO-d$_6$) δ ppm 11.64 (br., 1H), 7.02 (t, 1H), 7.01 (d, 1H), 6.89 (d, 1H), 4.02 (t, 2H), 3.74 (s, 3H), 3.54 (t, 2H), 3.22 (t, 2H), 2.54 (t, 2H), 2.04 (quint., 2H), 1.70 (quint., 2H), 1.45 (s, 9H), 0.85 (s, 9H), 0 (s, 6H); $^{13}$C NMR (125 MHz, DMSO-d$_6$) δ ppm 162.8, 156.2/153.5, 152.0, 144.7, 141.9, 135.8, 135.5, 124.6, 116.2, 115.5, 68.1, 62.0, 51.9, 34.3, 30.8, 30.8, 28.3, 26.2, 23.2, −4.9.

Step C: methyl 2-[tert-butoxycarbonyl-[3-(3,6-dichloro-5-methyl-pyridazin-4-yl)propyl]amino]-5-[3-[4-[3-[tert-butyl(dimethyl)silyl]oxypropyl]-2-fluoro-phenoxy]propyl]thiazole-4-carboxylate Using Mitsunobu General Procedure starting from 1.16 g of the product from Step B (2.0 mmol, 1.0 eq.) as the appropriate carbamate and 484 mg of Preparation 2a (2.2 mmol, 1.1 eq.) as the appropriate alcohol, 1.2 g of the desired product (77% Yield) was obtained.

$^1$H NMR (500 MHz, DMSO-d$_6$) δ ppm 7.02 (m, 1H), 6.99 (d, 1H), 6.89 (m, 1H), 4.08 (t, 2H), 4.02 (t, 2H), 3.75 (s, 3H), 3.54 (t, 2H), 3.22 (t, 2H), 2.81 (t, 2H), 2.53 (t, 2H), 2.40 (s, 3H), 2.05 (quint., 2H), 1.87 (m, 2H), 1.70 (quint., 2H), 1.48 (s, 9H), 0.85 (s, 9H), 0.00 (s, 6H); $^{13}$C NMR (125 MHz, DMSO-d$_6$) δ ppm 162.7, 156.4/153, 152.0, 144.7, 143.6, 142/139.8, 141.9, 135.5, 124.6, 116.2, 115.4, 68.1, 62.0, 52.0, 46.1, 34.2, 30.8, 30.7, 28.0, 27.5, 26.2, 25.8, 23.2, 16.4, −4.9;

Step D: methyl 5-[3-[4-[3-[tert-butyl(dimethyl)silyl]oxypropyl]-2-fluoro-phenoxy]propyl]-2-[3-(3,6-dichloro-5-methyl-pyridazin-4-yl)propylamino]thiazole-4-carboxylate Using Deprotection with HFIPA General Procedure starting from 1.2 g of the product from Step C as the appropriate carbamate, 790 mg of the desired product (75% Yield) was obtained.

Step E: methyl 5-[3-[4-[3-[tert-butyl(dimethyl)silyl]oxypropyl]-2-fluoro-phenoxy]propyl]-2-(3-chloro-4-methyl-6,7-dihydro-5H-pyrido[2,3-c]pyridazin-8-yl)thiazole-4-carboxylate A 25 mL oven-dried pressure bottle equipped with a PTFE-coated magnetic stir bar was charged with 1.2 g of the product from Step D (1.75 mmol, 1.0 equiv) and 680 mg cesium carbonate (3.50 mmol, 2.0 equiv) suspended in 10 mL 1,4-dioxane. The reaction mixture was then warmed up to 80° C. and stirred at that temperature for 3 h, when the reaction reached complete conversion. Celite was added to the reaction mixture and the volatiles were removed under reduced pressure. Then it was purified via flash chromatography DCM and MeOH (containing 1.2%0NH₃) as eluents to give 1.0 g of the desired product (88% Yield).

Step F: methyl 2-[3-(1,3-benzothiazol-2-ylamino)-4-methyl-6,7-dihydro-5H-pyrido[2,3-c]pyridazin-8-yl]-5-[3-[4-[3-[tert-butyl(dimethyl)silyl]oxypropyl]-2-fluoro-phenoxy]propyl]thiazole-4-carboxylate Using Buchwald General Procedure II starting from 630 mg of the product from Step E (0.97 mmol, 1.0 eq.) and 291 mg 1,3-benzothiazol-2-amine (1.94 mmol, 2.0 eq.), 600 mg of the desired product (81%) was obtained.

Step G: methyl 2-[3-(1,3-benzothiazol-2-ylamino)-4-methyl-6,7-dihydro-5H-pyrido[2,3-c]pyridazin-8-yl]-5-[3-[2-fluoro-4-(3-hydroxypropyl)phenoxy]propyl]thiazole-4-carboxylate A 250 mL oven-dried, round-bottom flask was equipped with a PTFE-coated magnetic stirring bar. It was charged with 600 mg of the product from Step F (0.78 mmol, 1.0 eq.) dissolved in 10 mL THF, and then 936 uL TBAF (0.963 mmol, 1.2 eq.) was added dropwise. After 1 hour stirring full conversion was observed. Then reaction mixture was quenched with saturated aqueous NH₄Cl solution, Celite was added to the reaction mixture and the volatiles were removed under reduced pressure. Then it was purified via flash chromatography using heptane and EtOAc and MeOH (1.2% NH₃) as eluents to give 450 mg of the desired product (89% Yield).

$^1$H NMR (500 MHz, DMSO-d₆) δ ppm 7.87 (br, 1H), 7.49 (br, 1H), 7.37 (t, 1H), 7.19 (t, 1H), 7.06 (m, 1H), 7.05 (d, 1H), 6.92 (dd, 1H), 4.44 (br, 1H), 4.25 (t, 2H), 4.08 (t, 2H), 3.78 (s, 3H), 3.36 (t, 2H), 3.27 (t, 2H), 2.85 (t, 2H), 2.52 (t, 2H), 2.32 (s, 3H), 2.1 (qn, 2H), 2.04 (qn, 2H), 1.65 (qn, 2H); $^{13}$C NMR (500 MHz, dmso-d6) δ ppm 163.2, 155.6, 152.0, 148.5, 144.7, 141.7, 135.9, 134.8, 127.6, 126.5, 124.7, 122.5, 122.3, 116.3, 116.0, 115.6, 68.6, 60.4, 52.0, 46.4, 34.6, 31.2, 31.0, 23.9, 23.2, 20.4, 12.9.

Preparation 3f: Ethyl 2-{3-[(1,3-benzothiazol-2-yl)amino]-4-methyl-5H,6H,7H,8H-pyrido[2,3-c]pyridazin-8-yl}-1,3-thiazole-4-carboxylate Step A: ethyl 2-[(hex-4-yn-1-yl)amino]-1,3-thiazole-4-carboxylate To a solution of ethyl 2-bromo-1,3-thiazole-4-carboxylate (1.17 g, 4.97 mmol, 1 eq) in acetonitrile (16 mL) was added hex-4-yn-1-amine (725 mg, 7.46 mmol, 1.5 eq) and triethylamine (1.04 mL, 7.46 mmol, 1.5 eq) and the mixture was heated at 150° C. for 4 h under microwave irradiation. The reaction was partitioned between ethyl acetate and brine, and the organic phase was dried (magnesium sulfate) and concentrated in vacuo. Purification by automated flash column chromatography (CombiFlash Rf, 40 g RediSep™ silica cartridge) eluting with a gradient of 0-60% ethyl acetate in iso-heptane afforded the desired product as a beige solid (741 mg, 2.94 mmol, 59%).

LC/MS (C₁₂H₁₆N₂O₂S) 253 [M+H]f; RT 2.32 (LCMS-V-C)

Step B: ethyl 2-{3-chloro-4-methyl-5H,6H,7H,8H-pyrido[2,3-c]pyridazin-8-yl}-1,3-thiazole-4-carboxylate To a solution of 3,6-dichloro-1,2,4,5-tetrazine (443 mg, 2.94 mmol, 1 eq) in tetrahydrofuran (15 mL) was added the product from Step A (741 mg, 2.94 mmol, 1 eq) and the mixture was heated in a sealed tube at 110° C. overnight. The reaction was concentrated in vacuo and the residue was triturated with methanol, filtered and dried under vacuum to afford the desired product as a beige solid (607 mg, 1.79 mmol, 61%).

LC/MS (C₁₄H₁₅ClN₄O₂S) 339 [M+H]⁺; RT 2.41 (LCMS-V-C)

$^1$H NMR (400 MHz, DMSO-d6) δ 8.06 (s, 1H), 4.38-4.25 (m, 4H), 2.92 (t, J=6.3 Hz, 2H), 2.34 (s, 3H), 2.14-2.01 (m, 2H), 1.31 (t, J=7.1 Hz, 3H).

Step C: ethyl 2-{3-[(1,3-benzothiazol-2-yl)amino]-4-methyl-5H,6H,7H,8H-pyrido[2,3-c]pyridazin-8-yl}-1,3-thiazole-4-carboxylate To an oven-dried microwave vial was added the product from Step B (607 mg, 1.79 mmol, 1 eq), 2-aminobenzothiazole (404 mg, 2.69 mmol, 1.5 eq)), XantPhos (207 mg, 0.36 mmol, 0.2 eq), cesium carbonate (1.17 g, 3.58 mmol, 2 eq) and 1,4-dioxane (36 mL) and the vessel was evacuated and flushed with nitrogen then tris(dibenzylideneacetone)dipalladium(0) (164 mg, 0.18 mmol, 0.1 eq) was added and the mixture was sparged with nitrogen (10 mins) then heated at 150° C. for 4 hours under microwave irradiation. The reaction was diluted with ethyl acetate and filtered through celite, then washed with brine, dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded a solid that was triturated with diethyl ether, filtered and dried under vacuum to afford the desired product as a yellow solid (329 mg, 0.73 mmol, 41%).

LC/MS (C₂₁H₂₀N₆O₂S₂) 453 [M+H]⁺; RT 2.73 (LCMS-V-C)

$^1$H NMR (400 MHz, DMSO-d6) δ 7.99 (br s+s, 2H), 7.65 (br s, 1H), 7.43-7.31 (m, 1H), 7.28-7.15 (m, 1H), 4.35-4.25 (m, 4H), 2.96-2.85 (m, 2H), 2.36 (s, 3H), 2.15-2.00 (m, 2H), 1.32 (t, J=7.1 Hz, 3H).

Preparation 3g: Ethyl 5-(3-hydroxypropyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate Step A: ethyl 2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3f (11.7 g, 25.8 mmol, 1 eq) in dimethylformamide (700 mL) was added NN-diisopropylethylamine (13.5 mL, 77.4 mmol, 3 eq). After 5 min the mixture was cooled to 0° C. and 4-(dimethylamino)pyridine (630 mg, 5.16 mmol, 0.2 eq) and 2-(trimethylsilyl)ethoxymethyl chloride (13.6 mL, 77.4 mmol, 3 eq) were added and the mixture was stirred at ambient temperature overnight. The reaction was concentrated in vacuo, then partitioned between dichloromethane and brine, and the organic phase was dried (magnesium sulfate) and concentrated in vacuo. Purification by automated flash column chromatography (CombiFlash Rf, 330 g RediSep™ silica cartridge) eluting with a gradient of 0-40% ethyl acetate in iso-heptane afforded the desired product as a yellow solid (9.61 g, 16.5 mmol, 64%).

LC/MS ($C_{27}H_{34}N_6O_3SiS_2$) 583 [M+H]+; RT 2.90 (LCMS-V-C)

$^1$H NMR (400 MHz, DMSO-d6) δ 7.99 (s, 1H), 7.82 (dd, J=7.7, 1.1 Hz, 1H), 7.49-7.38 (m, 2H), 7.28-7.19 (m, 1H), 5.86 (s, 2H), 4.38-4.23 (m, 4H), 3.77-3.67 (m, 2H), 2.89 (t, J=6.2 Hz, 2H), 2.38 (s, 3H), 2.13-2.01 (m, 2H), 1.31 (t, J=7.1 Hz, 3H), 0.91 (dd, J=8.5, 7.4 Hz, 2H), −0.11 (s, 9H).

Step B: ethyl 5-bromo-2-(4-methyl-3-{[(2Z)-3-{[2-(trimethylsilyl)ethoxy]methyl}-2,3-dihydro-1,3-ben-zothiazol-2-ylidene]amino}-5H,6H,7H,8H-pyrido[2,3-c]pyridazin-8-yl)-1,3-thiazole-4-carboxylate To a solution of the product of Step A(9.61 g, 16.5 mmol, 1 eq) in dichloromethane (400 mL) was added N-bromo-succinimide (3.52 g, 19.8 mmol, 1.2 eq) and the mixture was stirred at ambient temperature overnight. The reaction was partitioned between dichloromethane and water, and the organic phase was washed with brine, dried (PTFE phase separator) and concentrated in vacuo. Purification by automated flash column chromatography (CombiFlash Rf, 220 g RediSep™ silica cartridge) eluting with a gradient of 0-40% ethyl acetate in iso-heptane afforded the desired product as a yellow solid (9.66 g, 14.6 mmol, 89%).

LC/MS ($C_{27}H_{33}BrN_6O_3SiS_2$) 663 [M+H]+; RT 3.13 (LCMS-V-C)

$^1$H NMR (400 MHz, DMSO-d6) δ 7.84 (dd, J=7.5, 1.1 Hz, 1H), 7.59-7.38 (m, 2H), 7.24 (ddd, J=8.3, 6.7, 1.7 Hz, 1H), 5.85 (s, 2H), 4.37-4.23 (m, 4H), 3.72 (dd, J=8.5, 7.4 Hz, 2H), 2.87 (t, J=6.2 Hz, 2H), 2.38 (s, 3H), 2.13-2.00 (m, 2H), 1.32 (t, 3H), 0.95-0.81 (m, 2H), −0.12 (s, 9H).

Step C: ethyl 5-[(JE)-3-[(tert-butyldimethylsilyl)oxy]prop-1-en-1-yl]-2-(4-methyl-3-{[(2Z)-3-{[2-(trimethylsilyl)ethoxy]methyl}-2,3-dihydro-1,3-ben-zothiazol-2-ylidene]amino}-5H,6H,7H,8H-pyrido[2,3-c]pyridazin-8-yl)-1,3-thiazole-4-carboxylate To an oven-dried sealed flask was added the product from Step B (9.66 g, 14.6 mmol, 1 eq), (E)-3-(tert-butyldimethylsilyloxy)propene-1-yl-boronic acid pinacol ester (5.74 mL, 17.5 mmol, 1.2 eq), potassium carbonate (6.05 g, 43.8 mmol, 3 eq), [1,1'-bis(diphenylphosphino)ferrocene]dichloropalladium(II) (1.19 g, 1.46 mmol, 0.1 eq), tetrahydrofuran (360 mL) and water (120 mL), and the mixture was sparged with nitrogen (10 min) then heated at 120° C. for 2 h. The reaction was partitioned between ethyl acetate and water, and the organic layer was washed with brine, dried (magnesium sulfate) and concentrated in vacuo. Purification by automated flash column chromatography (CombiFlash Rf, 220 g RediSep™ silica cartridge) eluting with a gradient of 0-30% ethyl acetate in iso-heptane afforded the desired product as a yellow solid (6.46 g, 8.58 mmol, 59%).

LC/MS ($C_{36}H_{52}N_6O_4Si_2S2$) 753 [M+H]+; RT 1.62 (LCMS-V-B2)

$^1$H NMR (400 MHz, DMSO-d6) δ 7.80 (dd, J=7.6, 1.0 Hz, 1H), 7.51-7.38 (m, 3H), 7.24 (ddd, J=8.3, 6.8, 1.8 Hz, 1H), 6.28 (dt, J=16.0, 4.3 Hz, 1H), 5.85 (s, 2H), 4.37 (dd, J=4.4, 2.1 Hz, 2H), 4.35-4.25 (m, 4H), 3.72 (dd, J=8.5, 7.4 Hz, 2H), 2.88 (t, J=6.3 Hz, 2H), 2.37 (s, 3H), 2.09-1.99 (m, 2H), 1.31 (t, J=7.1 Hz, 3H), 0.93 (s, 9H), 0.92-0.83 (m, 2H), 0.11 ((s, 6H), −0.11 (s, 9H).

Step D: ethyl 5-{3-[(tert-butyldimethylsilyl)oxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Step C (6.46 g, 8.58 mmol, 1 eq) in ethyl acetate (300 mL) was added platinum (IV) oxide (390 mg, 1.72 mmol, 0.2 eq) under a nitrogen atmosphere. The vessel was evacuated and backfilled with nitrogen (×3), then evacuated, placed under an atmosphere of hydrogen, and shaken for 3 days at ambient temperature. The reaction was filtered through celite, eluted with ethyl acetate and concentrated in vacuo to afford the desired product as a brown gum (6.72 g, 8.9 mmol, >100%).

LC/MS ($C_{36}H_{54}N_6O_4Si_2S2$) 755 [M+H]+; RT 1.67 (LCMS-V-B2)

$^1$H NMR (400 MHz, DMSO-d6) δ 7.76 (d, 1H), 7.48-7.35 (m, 2H), 7.24 (ddd, J=8.2, 6.5, 1.9 Hz, 1H), 5.84 (s, 2H), 4.33-4.22 (m, 4H), 3.76-3.62 (m, 4H), 3.15 (t, J=7.5 Hz, 2H), 2.87 (t, J=6.4 Hz, 2H), 2.37 (s, 3H), 2.10-1.98 (m, 3H), 1.91-1.79 (m, 2H), 1.31 (t, J=7.1 Hz, 3H), 0.95-0.85 (m, 11H), 0.06 (s, 6H), −0.12 (s, 9H).

Step E: ethyl 5-(3-hydroxypropyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Step D (6.72 g, 8.9 mmol, 1 eq) in 1,4-dioxane (400 mL) was added hydrochloric acid (4M in dioxane; 67 mL, 267 mmol, 30 eq) and the mixture was stirred at ambient temperature for 1 h. The reaction cooled to 0° C. and neutralised with 1N aqueous sodium hydroxide (300 mL), then partitioned between ethyl acetate and water, and the organic phase was dried (magnesium sulfate) and concentrated in vacuo. Purification by automated flash column chromatography (CombiFlash Rf, 120 g RediSep™ silica cartridge) eluting with a gradient of 0-80% ethyl acetate in iso-heptane gave a solid that was triturated with diethyl ether, filtered and dried under vacuum to afford the desired product as a white solid (3.87 g, 6.04 mmol, 68%).

LC/MS ($C_{30}H_{40}N_6O_4SiS_2$) 641 [M+H]+; RT 2.80 (LCMS-V-C)

$^1$H NMR (400 MHz, DMSO-d6) δ 7.83 (dd, J=7.6, 1.1 Hz, 1H), 7.48-7.37 (m, 2H), 7.23 (ddd, J=8.3, 6.7, 1.8 Hz, 1H), 5.85 (s, 2H), 4.56 (t, J=5.1 Hz, 1H), 4.33-4.22 (m, 4H), 3.72 (dd, J=8.6, 7.3 Hz, 2H), 3.48 (td, J=6.3, 5.1 Hz, 2H), 3.17-3.08 (m, 2H), 2.88 (t, J=6.4 Hz, 2H), 2.38 (s, 3H), 2.11-1.99 (m, 2H), 1.87-1.75 (m, 2H), 1.31 (t, J=7.1 Hz, 3H), 0.96-0.86 (m, 2H), −0.11 (s, 9H).

Preparation 4a: 4-[1-[(Dimethylamino)methyl]-3-bicyclo[1.1.1]pentanyl]-2-fluoro-phenol

Step A: tricyclo[1.1.1.0$^{1,3}$]pentane

A 1 L 3-neck flask equipped with a stirrer bar was assembled with a still-head attached to a condenser and 250 mL collection flask with schlenk tap, a 250 mL dropping funnel, and a thermometer [all glassware was assembled hot, then connected to the Schlenk line and allowed to cool under a stream of nitrogen]. A solution of 1,1-dibromo-2,2-bis (chloromethyl)cyclopropane (59.4 g, 200 mmol, 1 eq) in diethyl ether (200 mL) was cooled to −45° C. and phenyl-lithium (1.9 M in n-butyl ether; 211 mL, 400 mmol, 2 eq) was added over 25 min by dropping funnel. After complete addition the mixture was allowed to warm to 0° C. and stirred for 2 h. After this time the receiving flask was cooled to −78° C., and the connection to the manifold was briefly closed and replaced with a vacuum pump attachment (with pressure-equalising inlet connected to the nitrogen mani-fold). Before switching on the pump the dropping funnel and thermometer were replaced with pre-greased glass stoppers. The pump was brought to a pressure of 200 mbar and then the connection was opened. Over 3 mins the pressure was gradually reduced to 120 mbar and then the reaction vessel was allowed to warm to ambient temperature. The pressure was then cautiously reduced to 45 mbar and this pressure was maintained for 45 mins. After this time the vacuum was released with nitrogen and the resultant clear and colourless distillate was stored at −20° C. The concentration of the desired product was determined to be 0.45 M by ¹H NMR.

¹H NMR (400 MHz, Chloroform-d) δ 2.04 (s, 6H).

Step B: bromo(3-fluoro-4-methoxyphenyl)magnesium

To a 3-neck 50 mL flask equipped with a stirrer bar and condenser was added magnesium (681 mg, 28 mmol, 1.4 eq) and the apparatus was heated strongly (~500° C.) with a heat gun for 5 mins with vigorous stirring and then allowed to cool to ambient temperature under nitrogen.

Diethyl ether (5 mL) was added followed by 1,2-dibro-moethane (172 μL, 2 mmol, 0.1 eq). The mixture was heated to reflux 4-5 times over 5 mins and then left to stand for 10 mins after which time a gentle reflux was observed. The mixture was brought to a steady reflux with hand-heat, and then slow stirring was initiated. At this point a solution of 4-bromo-2-fluoroanisole (4.1 g, 20 mmol, 1 eq) in diethyl ether (10 mL) was added at such a rate as to maintain steady reflux and stirring speed was increased (300 rpm). Addition was complete after 15 mins. The mixture was allowed to stir at ambient temperature for 0.5 h after which time a clear biphasic system had resulted. The lower dark straw-colored layer (10.15 mL) was transferred to a dry Schlenk flask via syringe through a 0.2 μm PTFE filter. The concentration of the solution was calculated to be 1.38 M by titration against a solution of iodine in dry tetrahydrofuran. The product solution was used directly in the next step without further characterisation.

Step C: ethyl 3-(3-fluoro-4-methoxyphenyl)bicyclo [1.1.1]pentane-1-carboxylate To an oven-dried 50 mL ACE pressure vessel equipped with a stirrer bar was added the product from Step B (1.38M in diethyl ether; 4.83 mL, 6.67 mmol, 1 eq) followed by the product from Step A (0.45M in diethyl ether, 14.8 mL, 6.67 mmol, 1 eq) and the vessel was sealed with a teflon screw-top fitted with a front O-ring, and placed in a pre-heated heater block behind a blast shield at 105° C. for 3 h. The mixture was allowed to cool at ambient temperature for 20 mins, and then in ice-water for 10 mins. The teflon screw top was replaced with a subaseal attached to the nitrogen line, and the reaction was cooled to −78° C. Ethyl chloro-formate (5.1 mL, 53.3 mmol, 4 eq) was added and the mixture was allowed to warm to ambient temperature for 1.5 h. The reaction was partitioned between saturated aqueous ammonium chloride and diethyl ether, and the aqueous phase was extracted with ether. The combined organic extracts were washed with brine, dried (magnesium sulfate) and concentrated in vacuo. Purification by automated flash column chromatography (CombiFlash Rf, 80 g RediSep™ silica cartridge) eluting with a gradient of 0-10% ethyl acetate in iso-heptane afforded the desired product as a colourless liquid that was a mixture of desired product and byproduct. This material was further purified by automated flash column chromatography (CombiFlash Torrent, 200 g RediSep™ silica cartridge) eluting with a gradient of 0-80% dichloromethane in heptane afforded the desired product (640 mg, 3.78 mmol, 56%).

¹H NMR (500 MHz, DMSO-d6) δ ppm 7.09 (t, 1H), 7.09 (dd, 1H), 6.98 (dm, 1H), 4.08 (q, 2H), 3.8 (s, 3H), 2.22 (s, 6H), 1.2 (t, 3H). 13C NMR (500 MHz, dmso-d6) δ ppm 169.8, 151.8, 146.6, 133.0, 122.8, 114.2, 114.2, 60.6, 56.5, 53.2, 41.0, 36.9, 14.6.

HRMS-EI (m/z): M+ calcd for C15H17 F O3: 264.1162, found 264.1156.

Step D: 1-(3-fluoro-4-methoxy-phenyl)bicyclo [1.1.1]pentane-3-carboxylic acid 200 mg of the product from Step C (0.76 mmol, 1 eq.) and 159 mg of LiOH×H₂O(3.78 mmol, 5 eq.) were mixed in 1,4-dioxane (2 mL/mmol) and water (2 mL/mmol) then stirred at rt for 1 h when full conversion was observed. Reaction mixture was made basic with 1:1 HCl solution then the precipitation was filtered and washed with water then dried in vacuum for o.n. 170 mg (95%) of the desired product was isolated as a white solid.

¹H NMR (500 MHz, DMSO-d₆) δ ppm 12.41 (s, 1H), 7.09 (m, 1H), 7.09 (m, 1H), 6.97 (dm, 1H), 3.80 (s, 3H), 2.18 (s, 6H); ¹³C NMR (125 MHz, DMSO-d₆) δ ppm 171.7, 151.8, 146.6, 133.3, 122.7, 114.2, 114.1, 56.5, 53.1, 40.8, 37.0; GC-MS-EI (m/z): [M]⁺ calcd for C₁₃H₁₃FO₃: 236.0849, found 236.0840.

Step E: 1-(3-fluoro-4-methoxy-phenyl)-N,N-dim-ethyl-bicyclo[1.1.1]pentane-3-carboxamide 164 mg of the product from Step D (1.04 mmol, 1 eq.) and 278 mg of N,N-diethylethanamine (1.39 mmol, 2 eq.) were mixed in EtOAc (3 mL/mmol) then 663 mg of 2,4,6-tripropyl-1,3,5,2λ^{5}, 4λ^{5},6'λ^{5}-trioxatriphosphi-nane 2,4,6-trioxide (50w % in EtOAc, 1.04 mmol, 1.5 eq.) was added in one portion then stirred at rt for 40 min. After the reaction time 0.52 mL of N-methylmethanamine (2 M in MeOH, 1.04 mmol, 1.5 eq.) was added and stirred at rt until full conversion was observed (60 min). Reaction mixture was diluted with DCM then washed with cc. NaHCO₃ then the organic phase was washed with cc. NaCl, dried over MgSO₄, filtered, concentrated, dried in vacuo to give 187 mg (quant.) of the desired product as a solid with peach color.

¹H NMR (500 MHz, DMSO-d₆) δ ppm 7.14 (m, 2H), 6.86 (m, 2H), 3.72 (s, 3H), 3.08 (s, 3H), 2.81 (s, 3H), 2.26 (s, 6H); ¹³C NMR (125 MHz, DMSO-d₆) δ ppm 168.9, 158.6, 132.5, 127.6, 114.1, 55.5, 54.2, 42.0, 39.0, 37.4, 35.9; HRMS-ESI (m/z): [M+H]⁺ calcd for C₁₅H₁₉FNO₂: 264.1394, found 264.1389.

Step F: 1-[3-(3-fluoro-4-methoxy-phenyl)-1-bicyclo [1.1.1]pentanyl]-N,N-dimethyl-methanamine 182 mg of the product from Step E (0.69 mmol, 1 eq.) was dissolved in THF (5 mL/mmol) then 1.38 mL of LiAlH₄ (1

M in THF, 1.38 mmol, 2 eq.) was added under nitrogen atmosphere at ambient temperature then stirred until full conversion was achieved (ca. 1 h). The mixture cooled to 0° C. then quenched with cc. NH$_4$Cl. After quenching –5 mL water and –10 mL EtOAc were added and shaked well. 2 M HCl was added and the (acidic) water phase was separated then the organic phase was extracted with further 2 M HCl. The combined water phases were made basic with 2 M NaOH and extracted with DCM. The combined organic phases was washed with brine, dried over MgSO$_4$ and concentrated, dried in vacuo. 119 mg (69%) of the desired product was obtained as viscous oil.

$^1$H NMR (500 MHz, DMSO-d$_6$) δ ppm 7.07 (t, 1H), 7.01 (dd, 1H), 6.93 (dm, 1H), 3.79 (s, 3H), 2.35 (s, 2H), 2.16 (s, 6H), 1.90 (s, 6H); $^{13}$C NMR (125 MHz, DMSO-d$_6$) δ ppm 151.8, 146.2, 134.5, 122.5, 114.1, 114.0, 60.7, 56.5, 52.9, 46.6, 41.7, 38.0; HRMS-ESI (m/z): [M+H]$^+$ calcd for C$_{15}$H$_{21}$FNO: 250.1602, found 250.1596.

Step G: 4-[1-[(dimethylamino)methyl]-3-bicyclo [1.1.1]pentanyl]-2-fluoro-phenol 113 mg of the product from Step F (0.45 mmol, 1 eq.) was dissolved in DCM (5 mL/mmol) then 1.36 mL of BBr$_3$ (1 M in DCM, 1.36 mmol, 3 eq.) was added under nitrogen atmosphere at 0° C. then stirred for 15 min at 0° C. and at rt until full conversion was achieved (ca. 45 min). DCM was added then poured into NaHCO$_3$ solution, stirred for a few minutes then made it neutral with cc. NH$_4$Cl. Separated and washed with brine, dried over MgSO$_4$ and concentrated, dried in vacuo. 47 mg (quant.) of the crude desired product was obtained as viscous oil.

$^1$H NMR (400 MHz, CDCl$_3$) δ ppm 6.95 (t, 1H), 6.90 (dd, 1H), 6.85 (dm, 1H), 3.84 (s, 2H), 3.17 (s, 6H), 2.24 (s, 6H); $^{13}$C NMR (100 MHz, CDCl$_3$) δ ppm 122.4, 117.4, 113.4, 59.5, 54.8, 46.0, 43.8, 34.8; HRMS-ESI (m/z): [M+H]$^+$ calcd for C$_{14}$H$_{19}$FNO: 236.1445, 236.1445.

Preparation 4b: 4-[3-(Dimethylamino)prop-1-ynyl]-2-fluoro-phenol

Using Sonogashira General Procedure starting from 10.00 g of 2-fluoro-4-iodo-phenol (42.0 mmol, 1 eq.) as the appropriate phenol and 5.24 g of NN-dimethylprop-2-yn-1-amine (63 mmol, 1.5 eq.) as the alkyne, 7.30 g (90%) of the desired product was obtained.

$^1$H NMR (500 MHz, DMSO-d$_6$) δ ppm 7.20 (dd, 1H), 7.07 (dm, 1H), 6.91 (m, 1H), 3.39 (m, 2H), 2.21 (m, 3H); $^{13}$C NMR (125 MHz, DMSO-d$_6$) δ ppm 150.9, 146.2, 128.9, 119.5, 118.4, 113.6, 84.5, 84.2, 48.2, 44.3; HRMS-ESI (m/z): [M+H]$^+$ calcd for C$_{11}$H$_{13}$FNO: 194.0976, found 194.0981.

Preparation 4c: tert-Butyl N-[3-(3-fluoro-4-hydroxy-phenyl)prop-2-ynyl]-N-methyl-carbamate Using Sonogashira General Procedure starting from 10.00 g of 2-fluoro-4-iodo-phenol (42.0 mmol, 1 eq.) as the appropriate phenol and 10.67 g of tert-butyl N-methyl-N-prop-2-ynyl-carbamate (63.1 mmol, 1.5 eq.) as the alkyne, 10.8 g (92%) of the desired product was obtained.

$^1$H NMR (500 MHz, DMSO-d$_6$) δ ppm 10.32 (s, 1H), 7.22 (brd, 1H), 7.08 (dm, 1H), 6.92 (dd, 1H), 4.21 (s, 2H), 2.85 (s, 3H), 1.41 (s, 9H); $^{13}$C NMR (125 MHz, DMSO-d$_6$) δ ppm 150.8, 146.4, 129.0, 119.6, 118.4, 113.2, 84.4, 82.7, 38.5, 33.8, 28.5; HRMS-ESI (m/z): [M-C$_4$H$_8$+H]$^+$ calcd for C$_{11}$H$_{11}$FNO$_3$: 224.0717, found 224.0720.

Preparation 4d: 4-[3-(Dimethylamino)propyl]-2-fluorophenol

To a solution of the product from Preparation 4b (1.5 g, 7.76 mmol, 1 eq) in ethyl acetate (54 mL) and ethanol (18 mL) under nitrogen was added platinum(IV) oxide hydrate (353 mg, 1.55 mmol, 0.2 eq). The vessel was evacuated and backfilled with nitrogen (×3), then evacuated, subjected to an atmosphere of hydrogen, and shaken at ambient temperature overnight. The reaction was filtered through celite, eluted with ethyl acetate and concentrated in vacuo. Purification by automated flash column chromatography (CombiFlash Rf, 24 g RediSep™ silica cartridge) eluting with a gradient of 0-10% 1N methanolic ammonia in dichloromethane afforded the desired product (652 mg, 3.31 mmol, 42%) as an off-white solid.

LC/MS (C$_{11}$H$_{16}$FNO) 198 [M+H]$^+$; RT 0.44 (LCMS-V-C)

$^1$H NMR (400 MHz, DMSO-d6) δ 9.52 (s, 1H), 6.96 (dd, J=12.5, 1.9 Hz, 1H), 6.88-6.76 (m, 2H), 2.47 (dd, J=8.5, 6.8 Hz, 2H), 2.20-2.13 (m, 2H), 2.11 (s, 6H), 1.69-1.57 (m, 2H).

Preparation 4e: 4-[2-(Dimethylamino)ethoxy]phenol

Step A: 4-(methoxymethoxy)phenol

To a solution of hydroquinone (0.76 mL, 9.08 mmol, 1 eq) in acetone (30 mL) was added potassium carbonate (2.51 g, 18.2 mmol, 2 eq) and chloromethyl methyl ether (0.69 mL, 9.08 mmol, 1 eq) and the mixture was stirred at ambient temperature overnight. The reaction was partitioned between ethyl acetate and water, and the organic phase was dried (magnesium sulfate) and concentrated in vacuo. Purification by automated flash column chromatography (CombiFlash Rf, 24 g RediSep™ silica cartridge) eluting with a gradient of 0-20% ethyl acetate in iso-heptane afforded the desired product as a brown oil (601 mg, 3.9 mmol, 43%).

$^1$H NMR (400 MHz, DMSO-d6) δ 9.03 (s, 1H), 6.91-6.80 (m, 2H), 6.72-6.62 (m, 2H), 5.05 (s, 2H), 3.36 (s, 3H).

Step B: {2-[4-(methoxymethoxy)phenoxy]ethyl}dimethylamine

To a solution of the product from Step A (400 mg, 2.59 mmol, 1 eq) in tetrahydrofuran (20 mL) was added NN-dimethylethanolamine (526 μL, 5.19 mmol, 2 eq), di-tert-butyl azodicarboxylate (1.19 g, 5.19 mmol, 2 eq) and triphenylphosphine (1.36 g, 5.19 mmol, 2 eq) and the mixture was heated at 50° C. for 3 h. The reaction was concentrated in vacuo, partitioned between dichloromethane and saturated aqueous sodium bicarbonate, and the organic phase was separated (PTFE phase separator) and concentrated in vacuo. Purification by automated flash column chromatography (CombiFlash Rf, 24 g RediSep™ silica cartridge) eluting with a gradient of 0-7% methanol in dichloromethane afforded the desired product as a brown oil (383 mg, 1.7 mmol, 66%).

LC/MS (C$_{12}$H$_{19}$NO$_3$) 226 [M+H]$^+$; RT 0.88 (LCMS-V-C)

$^1$H NMR (400 MHz, DMSO-d6) δ 6.99-6.90 (m, 2H), 6.94-6.82 (m, 2H), 5.10 (s, 2H), 3.98 (t, J=5.8 Hz, 2H), 3.36 (s, 3H), 2.59 (t, J=5.9 Hz, 2H), 2.20 (s, 6H).

Step C: 4-[2-(dimethylamino)ethoxy]phenol

A solution of the product from Step B (383 mg, 1.7 mmol, 1 eq) in hydrochloric acid (4M in 1,4-dioxane; 5 mL, 20 mmol, 11.7 eq) was stirred at ambient temperature for 1 h. The reaction was concentrated in vacuo, then dissolved in methanol, loaded onto a methanol-wet SCX cartridge (10 g), washed with methanol, and eluted with 1.75N methanolic ammonia and concentrated in vacuo to afford the desired product as a brown solid (249 mg, 1.37 mmol, 812%).

LC/MS ($C_{10}H_{15}NO_2$) 182 [M+H]$^+$; RT 0.24 (LCMS-V-C)

$^1$H NMR (400 MHz, DMSO-d6) δ 8.91 (s, 1H), 6.79-6.70 (m, 2H), 6.70-6.62 (m, 2H), 3.92 (t, J=5.9 Hz, 2H), 2.57 (t, J=5.9 Hz, 2H), 2.20 (s, 6H).

Preparation 4f: 4-[2-(Pyrrolidin-1-yl)ethoxy]phenol

Step A: 1-{2-[4-(methoxymethyl)phenoxy]ethyl}pyrrolidine

To a solution of the product from Preparation 4e, Step A (525 mg, 3.41 mmol, 1 eq) in tetrahydrofuran (20 mL) was added 1-(2-hydroxyethyl)pyrrolidine (0.8 mL, 6.81 mmol, 2 eq), di-tert-butyl azodicarboxylate (1.57 g, 6.81 mmol, 2 eq) and triphenylphosphine (1.79 g, 6.81 mmol, 2 eq) and the mixture was heated at 50° C. overnight. The reaction was concentrated in vacuo and partitioned between dichloromethane and saturated aqueous sodium bicarbonate, and the organic phase was separated (PTFE phase separator) and concentrated in vacuo. Purification by automated flash column chromatography (CombiFlash Rf, 40 g RediSep™ silica cartridge) eluting with a gradient of 0-7% methanol in dichloromethane afforded the desired product as a brown oil (556 mg, 2.21 mmol, 65%).

LC/MS ($C_{14}H_{21}NO_3$) 252 [M+H]$^+$; RT 1.09 (LCMS-V-C)

$^1$H NMR (400 MHz, DMSO-d6) δ 6.98-6.91 (m, 2H), 6.91-6.82 (m, 2H), 5.10 (s, 2H), 4.00 (t, J=5.9 Hz, 2H), 3.36 (d, J=6.0 Hz, 3H), 2.75 (t, J=6.0 Hz, 2H), 2.50-2.42 (m, 4H), 1.74-1.61 (m, 4H).

Step B: 4-[2-(pyrrolidin-1-yl)ethoxy]phenol

A solution of the product from Step A (556 mg, 2.21 mmol, 1 eq) in hydrochloric acid (4M in 1,4-dioxane; 7 mL, 28 mmol, 12.7 eq) was stirred at ambient temperature for 30 min. The reaction was concentrated in vacuo, then dissolved in methanol, loaded onto a methanol-wet SCX cartridge (10 g), washed with methanol, eluted with 1.75N methanolic ammonia and concentrated in vacuo to afford the desired product as a brown solid (453 mg, 2.19 mmol, 99%).

LC/MS ($C_{12}H_{17}NO_2$) 208 [M+H]$^+$; RT 0.28 (LCMS-V-C)

$^1$H NMR (400 MHz, DMSO-d6) δ 8.90 (s, 1H), 6.79-6.70 (m, 2H), 6.70-6.62 (m, 2H), 3.94 (t, J=6.0 Hz, 2H), 3.17 (d, J=4.3 Hz, 2H), 2.73 (t, J=6.0 Hz, 2H), 2.49 (dt, J=4.1, 1.4 Hz, 2H), 1.74-1.60 (m, 4H).

Preparation 4g: 4-[2-(Dimethylamino)ethyl]-2-fluorophenol

Step A: 2-fluoro-1-methoxy-4-[(E)-2-nitroethenyl]benzene

To a solution of 3-fluoro-4-methoxybenzaldehyde (400 mg, 2.6 mmol, 1 eq) and nitromethane (339 μL, 6.23 mmol, 2.4 eq) in methanol (50 mL), cooled to 0° C., was added 1M aqueous sodium hydroxide (20 mL, 20 mmol, 7.71 eq) dropwise and the resultant mixture was stirred at 0° C. for 1 h. The mixture was added portionwise to 8M aqueous hydrochloric acid (12 mL, 96 mmol, 37 eq), cooled to 0° C., and the resultant suspension was allowed to warm to ambient temperature and stir for 30 min. The precipitate was collected by filtration, washed with water and dried under vacuum to afford the desired product (393 mg, 1.99 mmol, 76%) as a yellow solid.

$^1$H NMR (400 MHz, DMSO-d6) δ 8.20 (d, J=13.6 Hz, 1H), 8.10 (dd, J=13.5, 1.0 Hz, 1H), 7.88 (dd, J=12.6, 2.1 Hz, 1H), 7.70 (dt, J=8.6, 1.5 Hz, 1H), 7.29 (t, J=8.8 Hz, 1H), 3.92 (s, 3H).

Step B: 2-(3-fluoro-4-methoxyphenyl)ethan-1-amine

To a solution of the product from Step A (393 mg, 1.99 mmol, 1 eq) in tetrahydrofuran (12 mL) was added lithium aluminium hydride (1M in tetrahydrofuran; 5.98 mL, 5.98 mmol, 3 eq) and the mixture was heated at 40° C. overnight. The reaction was quenched with water (1.2 mL) and concentrated in vacuo. The residue was dissolved in 2N aqueous hydrochloric acid (20 mL) and washed with ethyl acetate (×2). Tartaric acid (2.1 g) was added to the aqueous phase and the pH was adjusted to pH 11 with concentrated ammonium hydroxide. The mixture was extracted with dichloromethane (×3) and the combined organic extracts were separated (PTFE phase separator) and concentrated in vacuo to afford the desired product as a yellow oil (252 mg, 1.49 mmol, 75%).

LC/MS ($C_9H_{12}FNO$) 170 [M+H]$^+$; RT 0.14 (LCMS-V-B1)

$^1$H NMR (400 MHz, DMSO-d6) δ 7.16-7.03 (m, 3H), 3.80 (s, 3H), 3.38-3.30 (m, 2H), 2.79-2.69 (m, 2H), 2.62-2.54 (m, 2H).

Step C: [2-(3-fluoro-4-methoxyphenyl)ethyl]dimethylamine

To a solution of the product from Step B (252 mg, 1.49 mmol, 1 eq) in methanol (5 mL) was added formaldehyde (13.4M in water; 123 μL, 4.47 mmol, 3 eq) followed by sodium triacetoxyborohydride (947 mg, 4.47 mmol, 3 eq) and glacial acetic acid (0.05 mL) and the mixture was stirred at ambient temperature for 1 h. The reaction was partitioned between ethyl acetate and saturated aqueous sodium bicarbonate, and the organic phase was dried (magnesium sulfate) and concentrated in vacuo. Purification by automated flash column chromatography (CombiFlash Rf, 4 g RediSep™ silica cartridge) eluting with a gradient of 0-10% methanol in dichloromethane afforded the desired product as a yellow oil (92 mg, 0.47 mmol, 31%).

LC/MS ($C_{11}H_{16}FNO$) 198 [M+H]$^+$; RT 0.82 (LCMS-V-C)

$^1$H NMR (400 MHz, DMSO-d6) δ 7.16-6.94 (m, 3H), 3.80 (s, 3H), 2.64 (dd, J=8.5, 6.7 Hz, 2H), 2.41 (dd, J=8.5, 6.7 Hz, 2H), 2.16 (s, 6H).

Step D: 4-[2-(dimethylamino)ethyl]-2-fluorophenol

To a solution of the product from Step C (92 mg, 0.47 mmol, 1 eq) in dichloromethane (3.5 mL), cooled to 0° C., was added boron tribromide (1M in dichloromethane, 1.4 mL, 1.4 mmol, 3 eq) and the mixture was stirred at ambient temperature overnight. The reaction was cooled to 0° C. and quenched with methanol, then concentrated in vacuo. The residue was dissolved in methanol, loaded onto a methanol-wet SCX cartridge (5 g), washed with methanol, eluted with 1.75N methanolic ammonia, and concentrated in vacuo to afford the desired product as a brown oil (41 mg, 0.22 mmol, 48%).

LC/MS ($C_{10}H_{14}FNO$) 184 [M+H]$^+$; RT 0.36 (LCMS-V-C)

$^1$H NMR (400 MHz, DMSO-d6) δ 9.55 (s, 1H), 7.03-6.95 (m, 1H), 6.88-6.78 (m, 2H), 2.59 (dd, J=8.7, 6.7 Hz, 2H), 2.38 (dd, J=8.6, 6.7 Hz, 2H), 2.15 (s, 6H).

Preparation 4h: 3-[(Dimethylamino)methyl]-5-fluoro-1-methyl-1H-indol-6-ol

Step A: 6-(benzyloxy)-5-fluoro-1H-indole-2-carboxylic acid

To a stirred solution of 6-benzyloxy-5-fluoro-1H-indole-2-carboxylic acid methyl ester (2.5 g, 8.35 mmol, 1 eq) in a mixture of tetrahydrofuran (25 mL) and methanol (25 mL) was added a solution of sodium hydroxide (4 g, 100 mmol, 12 eq) in water (30 mL) and the mixture was stirred for 2.5 h. The reaction was cooled in ice-water and acidified with stirring by slow addition of 2N aqueous hydrochloric acid (60 mL) resulting in precipitation. Water (80 mL) was added and the mixture was stirred for 45 min, then the solids were collected by filtration, washed with water and dried under vacuum to afford the desired product (2.25 g, 7.89 mmol, 94%) as an off-white solid.

LC/MS ($C_{16}H_{12}FNO_3$) 284 [M−H]$^-$; RT 1.16 (LCMS-V-B1)

$^1$H NMR (400 MHz, DMSO-d6) δ 12.85 (s, 1H), 11.71 (d, J=2.3 Hz, 1H), 7.54-7.39 (m, 5H), 7.39-7.32 (m, 1H), 7.10 (dd, J=7.4, 0.8 Hz, 1H), 7.01 (dd, J=2.2, 0.8 Hz, 1H), 5.19 (s, 2H).

Step B: 6-(benzyloxy)-5-fluoro-1H-indole

A mixture of the product from Step A (1.25 g, 4.38 mmol, 1 eq) and diphenyl ether (60 mL) was heated at 290° C. (external) for 45 min. The reaction was allowed to cool to ambient temperature then diluted with heptane (180 mL) and loaded onto a hexane-wet pre-packed silica column (80 g) under vacuum. Purification by automated flash chromatography (CombiFlash Rf, Silica 80 g RediSep column) eluting with a gradient of 0-80% ethyl acetate in hexane afforded the desired product (372 mg, 1.54 mmol, 35%) as a beige solid.

LC/MS ($C_{15}H_{12}FNO$) 242 [M+H]$^+$; RT 1.26 (LCMS-V-B1)

$^1$H NMR (400 MHz, DMSO-d6) δ 11.00 (s, 1H), 7.52-7.45 (m, 2H), 7.49-7.37 (m, 2H), 7.41-7.30 (m, 2H), 7.25 (t, J=2.8 Hz, 1H), 7.13 (dd, J=7.3, 0.8 Hz, 1H), 6.34 (ddd, J=3.0, 2.0, 0.8 Hz, 1H), 5.18 (s, 2H).

Step C: 6-(benzyloxy)-5-fluoro-1-methyl-1H-indole

To a stirred solution of the product from Step B (365 mg, 1.51 mmol, 1 eq) in dimethylformamide (10 mL), cooled in an ice-water bath, was added sodium hydride (60% dispersion; 72.6 mg, 3.03 mmol, 2 eq) and the mixture was stirred for 15 min. Iodomethane (0.11 mL, 1.82 mmol, 1.2 eq) was added, then the mixture was allowed to warm to ambient temperature and stir for 1 h. The reaction was cooled in ice, then quenched by dropwise addition of saturated aqueous ammonium chloride and slowly poured onto stirring ice-water (40 mL) resulting in precipitation. Further ice was added (20 mL) and after 30 min stirring the solids were collected by filtration, washed successively with ice-cold water (2×30 mL) and hexane (2×10 mL) and dried under vacuum to afford the desired product (259 mg, 1.01 mmol, 67%) as a beige solid.

LC/MS ($C_{16}H_{14}FNO$) 256 [M+H]$^+$; RT 1.36 (LCMS-V-B1)

$^1$H NMR (400 MHz, DMSO-d6) δ 7.55-7.48 (m, 2H), 7.47-7.38 (m, 2H), 7.40-7.29 (m, 3H), 7.25 (d, J=3.1 Hz, 1H), 6.33 (dd, J=3.1, 0.8 Hz, 1H), 5.21 (s, 2H), 3.76 (s, 3H).

Step D: {[6-(benzyloxy)-5-fluoro-1-methyl-1H-indol-3-yl]methyl}dimethylamine To a stirred mixture of 1,4-dioxane (5 mL) and glacial acetic acid (5 mL) was added aqueous formaldehyde (37 wt %; 1.18 mL, 14.54 mmol, 14.6 eq) followed by aqueous dimethylamine (40 wt %; 1.42 mL, 12.6 mmol, 12.6 eq). This solution (1.6 mL) was added to a stirred solution of the product of Step C (255 mg, 1 mmol, 1 eq) in 1,4-dioxane (1 mL) and the mixture was stirred at ambient temperature for 4 h. The reaction was concentrated in vacuo, then 2N aqueous sodium hydroxide (4 mL) was added and the resultant thick suspension was diluted with water (10 mL), stirred and cooled in ice-water for 15 min, then filtered, washed with water (×3) and dried under vacuum to afford the desired product (290 mg, 0.93 mmol, 93%) as a cream solid.

LC/MS ($C_{19}H_{21}FN_2O$) 268 [M+H−NHMe₂]+; RT 0.99 (LCMS-V-B1)

$^1$H NMR (400 MHz, DMSO-d6) δ 7.55-7.47 (m, 2H), 7.47-7.38 (m, 2H), 7.40-7.31 (m, 2H), 7.28 (d, J=7.3 Hz, 1H), 7.13 (s, 1H), 5.20 (s, 2H), 3.71 (s, 3H), 3.44 (s, 2H), 2.12 (s, 6H).

Step E: 3-[(dimethylamino)methyl]-5-fluoro-1-methyl-1H-indol-6-ol

A flask was charged with 10% Pd/C (50 mg, 0.05 eq), then evacuated and flushed with nitrogen (×2). A solution of the product from Step D (285 mg, 0.91 mmol, 1 eq) in ethanol (20 mL) was added and the flask was evacuated and flushed with nitrogen (×3), then evacuated and flushed with hydrogen (×3), then subjected to an atmosphere of hydrogen and shaken for 4 h at ambient temperature. The reaction was filtered through an HM-N cartridge, eluted with ethanol, and concentrated in vacuo. Purification by reverse phase automated flash chromatography (CombiFlash Rf, C18 50 g Gold RediSep column) eluting with a gradient of 10-100% acetonitrile in water afforded the desired product (69.8 mg, 0.27 mmol, 29%) as an off-white solid (hydrochloride salt).

LC/MS ($C_{12}H_{15}FN_2O$) 178 [M+H−NHMe₂]+; RT 0.36 (LCMS-V-B1)

$^1$H NMR (400 MHz, DMSO-d6) δ 10.08 (s, 1H), 9.66 (s, 1H), 7.60 (d, J=11.8 Hz, 1H), 7.40 (s, 1H), 6.96 (d, J=7.5 Hz, 1H), 4.29 (s, 2H), 3.71 (s, 3H), 2.66 (s, 6H), 1.23 (d, J=6.5 Hz, 1H).

Preparation 4i: 4-[4-(Dimethylamino)butyl]-2-fluorophenol

Step A: [3-(1,3-dioxo-2,3-dihydro-1H-isoindol-2-yl)propyl]triphenylphosphanium bromide N-(3-bromopropyl)phthalimide (2.75 g, 10.26 mmol, 1 eq) and triphenylphosphine (2.69 g, 10.3 mmol, 1 eq) were stirred in toluene (25 mL) and heated at reflux overnight. The reaction was allowed to cool to ambient temperature and the solids were collected by filtration and dried under vacuum to afford the desired product as a white solid (2.55 g, 4.81 mmol, 47%).

$^1$H NMR (400 MHz, DMSO-d6) δ 7.95-7.85 (m, 7H), 7.82-7.71 (m, 12H), 3.80-3.64 (m, 4H), 1.99-1.90 (m, 2H).

Step B: 2-[(3E)-4-(3-fluoro-4-methoxyphenyl)but-3-en-1-yl]-2,3-dihydro-1H-isoindole-1,3-dione To a solution of the product from Step A (2.55 g, 4.81 mmol, 1 eq) in toluene (25 mL) was added 3-Fluoro-4-methoxybenzaldehyde (741 mg, 4.81 mmol, 1 eq), followed by 18-crown-6 (108 μL, 0.48 mmol, 0.1 eq) and the mixture was stirred at ambient temperature overnight. The reaction was partitioned between ethyl acetate and water, and the organic phase was dried (magnesium sulfate) and concentrated in vacuo. Purification by automated flash column chromatography (CombiFlash Rf, 24 g RediSep™ silica cartridge) eluting with a gradient of 0-30% ethyl acetate in iso-heptane afforded the desired product as a white solid (1.48 g, 4.55 mmol, 95%).

LC/MS (C$_{19}$H$_{16}$FNO$_3$) 302 [OTHER]; RT 2.25 (LCMS-V-C)

$^1$H NMR (400 MHz, DMSO-d6) δ 7.91-7.79 (m, 4H), 7.13-6.98 (m, 3H), 6.43-6.33 (m, 1H), 5.61 (dt, J=11.7, 7.4 Hz, 1H), 3.82 (s, 3H), 3.70 (t, 2H), 2.64 (qd, J=7.2, 1.8 Hz, 2H).

Step C: (3E)-4-(3-fluoro-4-methoxyphenyl)but-3-en-1-amine

To a solution of the product from Step B (1.48 g, 4.55 mmol, 1 eq) in ethanol (60 mL) was added methylamine (2M in methanol; 24 mL, 665 mmol, 146 eq) and the mixture was heated at reflux overnight. The reaction was allowed to cool to ambient temperature and was concentrated in vacuo. The residue was triturated with diethyl ether, filtered and dried under vacuum. The crude solid was dissolved in ethyl acetate and extracted with 1N aqueous hydrochloric acid (3×100 mL). The combined aqueous extracts were basified with 4M aqueous potassium hydroxide, extracted with ethyl acetate (×2), and the combined organic extracts were dried (magnesium sulfate) and concentrated in vacuo to afford the desired product as a pink gum (395 mg, 2.02 mmol, 45%).

LC/MS (C$_{11}$H$_{14}$FNO) 196 [M+H]$^+$; RT 1.25 (LCMS-V-C)

$^1$H NMR (400 MHz, DMSO-d6) δ 7.24-7.04 (m, 4H), 6.44-6.30 (m, 1H), 5.63 (dt, J=11.6, 7.2 Hz, 1H), 2.65 (t, 2H), 2.37 (qd, J=7.1, 2.0 Hz, 2H).

Step D: 4-(3-fluoro-4-methoxyphenyl)butan-1-amine

To a solution of the product from Step C (395 mg, 2.02 mmol, 1 eq) in methanol (10 mL) was added platinum(IV) oxide (45.9 mg, 0.2 mmol, 0.1 eq) under a nitrogen atmosphere. The vessel was evacuated and backfilled with nitrogen (×3), evacuated, then placed under an atmosphere of hydrogen and shaken at ambient temperature overnight. The reaction was filtered through celite, eluted with methanol and concentrated in vacuo. The residue was dissolved in methanol, loaded onto a methanol-wet SCX cartridge (5 g), washed with methanol, eluted with 1.75N methanolic ammonia and concentrated in vacuo to afford the desired product as a peach gum (219 mg, 1.11 mmol, 55%).

LC/MS (C$_{11}$H$_{16}$FNO) 198 [M+H]$^+$; RT 1.18 (LCMS-V-C)

$^1$H NMR (400 MHz, DMSO-d6) δ 7.10-7.01 (m, 2H), 6.99-6.90 (m, 1H), 3.80 (s, 3H), 2.57-2.44 (m, 2H), 1.61-1.42 (m, 4H), 1.39-1.26 (m, 2H).

Step E: [4-(3-fluoro-4-methoxyphenyl)butyl]dimethylamine

To a solution of the product from Step D (219 mg, 1.11 mmol, 1 eq) in methanol (5 mL) was added aqueous formaldehyde (37 wt %; 91.8 μL, 13.4 M, 3.33 mmol, 3 eq), sodium triacetoxyborohydride (706 mg, 3.33 mmol, 3 eq) and glacial acetic acid (6.36 μL, 0.11 mmol, 0.1 eq) and the mixture was stirred at ambient temperature overnight. The reaction was concentrated in vacuo, then partitioned between ethyl acetate and saturated aqueous sodium bicarbonate, and the organic phase was dried (magnesium sulfate) and concentrated in vacuo. Purification by automated flash column chromatography (CombiFlash Rf, 4 g RediSep™ silica cartridge) eluting with a gradient of 0-10% methanol in dichloromethane afforded the desired product as a clear oil (163 mg, 0.72 mmol, 65%).

LC/MS (C$_{13}$H$_{20}$FNO) 226 [M+H]$^+$; RT 1.30 (LCMS-V-C)

$^1$H NMR (400 MHz, DMSO-d6) δ 7.10-7.00 (m, 2H), 6.98-6.90 (m, 1H), 3.80 (s, 3H), 2.56-2.47 (m, 2H), 2.23-2.15 (m, 2H), 2.09 (s, 6H), 1.59-1.47 (m, 2H), 1.43-1.31 (m, 2H).

Step F: 4-[4-(dimethylamino)butyl]-2-fluorophenol

To a solution of the product of Step E (163 mg, 0.72 mmol, 1 eq) in dichloromethane (5 mL), cooled to 0° C., was added boron tribromide (1M in dichloromethane; 2.17 mL, 2.17 mmol, 3 eq) and the mixture was stirred at ambient temperature overnight. The reaction was cooled to 0° C., quenched with methanol and concentrated in vacuo. The residue was dissolved in methanol, loaded onto a methanol-wet SCX cartridge (5 g), washed with methanol, eluted with 1.75N methanolic ammonia and concentrated in vacuo to afford the desired product as a yellow oil (110 mg, 0.52 mmol, 72%).

LC/MS (C$_{12}$H$_{18}$FNO) 212 [M+H]$^+$; RT 0.96 (LCMS-V-C)

$^1$H NMR (400 MHz, DMSO-d6) δ 9.54 (s, 1H), 6.94 (dd, J=12.5, 2.0 Hz, 1H), 6.88-6.75 (m, 2H), 2.47 (t, J=7.6 Hz, 2H), 2.21-2.13 (m, 2H), 2.08 (s, 6H), 1.56-1.44 (m, 2H), 1.42-1.30 (m, 2H).

Preparation 41: tert-butyl N-[2-(3-fluoro-4-hydroxyphenyl)ethyl]-N-methylcarbamate

Step A: ethyl N-[2-(3-fluoro-4-methoxyphenyl)ethyl]carbamate

To a solution of 2-(3-fluoro-4-methoxyphenyl)ethan-1-amine (263 mg, 1.55 mmol, 1 eq) in dichloromethane (10 mL) was added triethylamine (315 mg, 3.11 mmol, 2 eq) and the mixture was cooled to 0° C. before the addition of ethyl chloroformate (149 μL, 1.55 mmol, 1 eq) and the mixture was stirred at ambient temperature overnight. The reaction was partitioned between dichloromethane and saturated aqueous sodium bicarbonate, and the organic phase was separated (PTFE phase separator) and concentrated in vacuo. Purification by automated flash column chromatography (CombiFlash Rf, 12 g RediSep™ silica cartridge) eluting with a gradient of 0-1% methanol in dichloromethane afforded the desired product as a white wax (245 mg, 1.02 mmol, 65%).

LC/MS ($C_{12}H_{16}FNO_3$) 242 [M+H]$^+$; RT 1.81 (LCMS-V-C)

$^1$H NMR (400 MHz, DMSO-d6) δ 7.13 (t, 1H), 7.11-7.01 (m, 2H), 6.98-6.92 (m, 1H), 3.96 (q, J=7.1 Hz, 2H), 3.80 (s, 3H), 3.16 (td, J=7.3, 5.8 Hz, 2H), 2.64 (t, J=7.3 Hz, 2H), 1.13 (t, J=7.1 Hz, 3H).

Step B: [2-(3-fluoro-4-methoxyphenyl)ethyl](methyl)amine

A solution of the product from Step A (245 mg, 1.02 mmol, 1 eq) in tetrahydrofuran (3 mL) was cooled to 0° C. Lithium aluminium hydride (1M in tetrahydrofuran, 2.54 mL, 2.54 mmol, 2.5 eq) was added and the mixture was heated at reflux overnight. The reaction was cooled to 0° C. and water (96 μL) was added, followed by 15% aqueous sodium hydroxide (96 μL), then water (288 μL). Further tetrahydrofuran was added to aid stirring and the mixture was stirred at ambient temperature for 30 min. Magnesium sulfate was added, followed by ethyl acetate, the mixture was stirred for 15 min, then filtered through celite and eluted with ethyl acetate.

Solvents were removed in vacuo and purification by automated flash column chromatography (CombiFlash Rf, 4 g RediSep™ silica cartridge) eluting with a gradient of 0-10% methanol in dichloromethane afforded the desired product as a clear oil (89 mg, 0.49 mmol, 48%).

LC/MS ($C_{10}H_{14}FNO$) 184 [M+H]$^+$; RT 0.75 (LCMS-V-C)

$^1$H NMR (400 MHz, DMSO-d6) δ 7.15-7.01 (m, 2H), 6.96 (ddd, J=8.3, 2.0, 1.0 Hz, 1H), 3.80 (s, 3H), 2.69-2.57 (m, 4H), 2.27 (s, 3H).

Step C: 2-fluoro-4-[2-(methylamino)ethyl]phenol

To a solution of the product of Step B (89 mg, 0.49 mmol, 1 eq) in dichloromethane (4 mL), cooled to 0° C., was added boron tribromide (1M in dichloromethane, 1.46 mL, 1.46 mmol, 3 eq) and the mixture was stirred at ambient temperature for 4 h. The reaction was cooled to 0° C. and quenched with methanol, then concentrated in vacuo. The residue was dissolved in methanol, loaded onto a methanol-wet SCX cartridge (5 g), washed with methanol, eluted with 1.75N methanolic ammonia and concentrated in vacuo to afford the desired product as a brown gum (62 mg, 0.37 mmol, 75%).

LC/MS ($C_9H_{12}FNO$) 170 [M+H]$^+$; RT 0.24 (LCMS-V-C)

$^1$H NMR (400 MHz, DMSO-d6) δ 7.02-6.93 (m, 1H), 6.88-6.76 (m, 2H), 2.67-2.53 (m, 4H), 2.27 (s, 3H).

Step D: tert-butyl N-[2-(3-fluoro-4-hydroxyphenyl)ethyl]-N-methylcarbamate

To a solution of the product from Step C (62 mg, 0.37 mmol, 1 eq) in dichloromethane (5 mL) was added triethylamine (153 μL, 1.1 mmol, 3 eq) and 4-(dimethylamino)pyridine (4.48 mg, 0.04 mmol, 0.1 eq), followed by di-tert-butyl dicarbonate (0.09 mL, 0.44 mmol, 1.2 eq) and the mixture was stirred at ambient temperature for 3 h. The reaction was partitioned between dichloromethane and saturated aqueous sodium bicarbonate, and the organic phase was dried (PTFE phase separator) and concentrated in vacuo. Purification by automated flash column chromatography (CombiFlash Rf, 4 g RediSep™ silica cartridge) eluting with a gradient of 0-85% ethyl acetate in iso-heptane afforded the desired product as a clear oil (48 mg, 0.18 mmol, 49%).

LC/MS ($C_{14}H_{20}FNO_3$) 170 [M-Boc+H]$^+$; RT 2.54 (LCMS-V-C)

$^1$H NMR (400 MHz, DMSO-d6) δ 9.60 (s, 1H), 6.95 (d, J=12.3 Hz, 1H), 6.89-6.72 (m, 2H), 3.34-3.27 (m, 2H), 2.73 (s, 3H), 2.64 (t, J=7.1 Hz, 2H), 1.28 (s, 9H).

Preparation 4k: tert-Butyl N-[4-(3-fluoro-4-hydroxyphenyl)butyl]-N-methylcarbamate

Step A: ethyl N-[(3E)-4-(3-fluoro-4-methoxyphenyl)but-3-en-1-yl]carbamate

To a solution of the product from Preparation 4i, Step C (397 mg, 2.03 mmol, 1 eq) in dichloromethane (20 mL) was added triethylamine (0.57 mL, 4.07 mmol, 2 eq) and the mixture was cooled to 0° C. Ethyl chloroformate (194 μL, 2.03 mmol, 1 eq) was added and the mixture was allowed to warm to ambient temperature and stir overnight. The reaction was partitioned between dichloromethane and saturated aqueous sodium bicarbonate, and the organic phase was separated (PTFE phase separator) and concentrated in vacuo. Purification by automated flash column chromatography (CombiFlash Rf, 12 g RediSep™ silica cartridge) eluting with a gradient of 0-25% ethyl acetate in iso-heptane afforded the desired product as a clear oil (310 mg, 1.16 mmol, 57%).

LC/MS ($C_{14}H_{18}FNO_3$) 268 [M+H]$^+$; RT 2.06 (LCMS-V-C)

$^1$H NMR (400 MHz, DMSO-d6) δ 7.24-7.05 (m, 3H), 6.42-6.33 (m, 1H), 5.57 (dt, J=11.7, 7.2 Hz, 1H), 4.00 (dq, J=26.6, 7.1 Hz, 2H), 3.84 (s, 3H), 3.08 (q, J=6.8 Hz, 2H), 2.42 (qd, J=7.1, 1.9 Hz, 2H), 1.16 (t, 3H).

Step B: ethyl N-[4-(3-fluoro-4-methoxyphenyl)butyl]carbamate

To a solution of the product from Step A (310 mg, 1.16 mmol, 1 eq) in methanol (12 mL) was added platinum(IV) oxide (26.3 mg, 0.12 mmol, 0.1 eq) under a nitrogen atmosphere. The vessel was evacuated and backfilled with nitrogen (×3), evacuated, placed under an atmosphere of hydrogen and shaken at ambient temperature overnight. The reaction was filtered through celite, eluted with methanol and concentrated in vacuo to afford the desired product as a clear oil (275 mg, 1.02 mmol, 88%).

LC/MS ($C_{14}H_{20}FNO_3$) 270 [M+H]$^+$; RT 2.07 (LCMS-V-C)

$^1$H NMR (400 MHz, DMSO-d6) δ 7.12-7.00 (m, 3H), 6.99-6.91 (m, 1H), 3.96 (q, J=7.1 Hz, 2H), 3.80 (s, 3H), 2.97 (q, J=6.7 Hz, 2H), 2.52-2.45 (m, 2H), 1.51 (p, J=7.8, 7.4 Hz, 2H), 1.37 (p, J=7.2 Hz, 2H), 1.14 (t, J=7.1 Hz, 3H).

Step C: [4-(3-fluoro-4-methoxyphenyl)butyl](methyl)amine

To a solution of the product from Step B (417 mg, 1.55 mmol, 1 eq) in tetrahydrofuran (5 mL), cooled to 0° C., was added lithium aluminium hydride (1M in tetrahydrofuran; 3.87 mL, 3.87 mmol, 2.5 eq) and the mixture was heated at reflux overnight. The reaction was cooled to 0° C., water (150 μL) was added, followed by 15% aqueous sodium hydroxide (150 μL) and water (450 μL). The mixture was diluted with tetrahydrofuran and stirred for 30 min. Magnesium sulfate and ethyl acetate were added, and the mixture was filtered through celite and concentrated in vacuo. Purification by automated flash column chromatography (CombiFlash Rf, 4 g RediSep™ silica cartridge) eluting with a gradient of 0-15% methanol in dichloromethane afforded the desired product as a clear oil (222 mg, 1.05 mmol, 68%).

LC/MS ($C_{12}H_{18}FNO$) 212 [M+H]$^+$; RT 1.28 (LCMS-V-C)

$^1$H NMR (400 MHz, DMSO-d6) δ 7.09-6.99 (m, 2H), 6.94 (dd, 1H), 3.80 (s, 3H), 2.51-2.48 (m, 2H), 2.44 (t, 2H), 2.24 (s, 3H), 1.61-1.47 (m, 2H), 1.47-1.31 (m, 2H).

Step D: 2-fluoro-4-[4-(methylamino)butyl]phenol

To a solution of the product of Step C (222 mg, 1.05 mmol, 1 eq) in dichloromethane (10 mL), cooled at 0° C., was added boron tribromide (1M in dichloromethane, 3.15 mL, 3.15 mmol, 3 eq) and the mixture was stirred at ambient temperature for 3 h. The reaction was cooled to 0° C., quenched with methanol and concentrated in vacuo. The residue was dissolved in methanol, loaded onto a methanol-wet SCX cartridge (5 g), washed with methanol, eluted with 1.4N methanolic ammonia and concentrated in vacuo to afford the desired product as a brown gum (63 mg, 0.32 mmol, 30%).

LC/MS ($C_{11}H_{16}FNO$) 198 [M+H]$^+$; RT 1.01 (LCMS-V-C)

$^1$H NMR (400 MHz, DMSO-d6) δ 7.00-6.91 (m, 1H), 6.88-6.75 (m, 2H), 2.49-2.40 (m, 4H), 2.24 (s, 3H), 1.58-1.45 (m, 2H), 1.43-1.33 (m, 2H).

Step E: tert-butyl N-[4-(3-fluoro-4-hydroxyphenyl)butyl]-N-methylcarbamate

To a solution of the product of Step D (63 mg, 0.32 mmol, 1 eq) in dichloromethane (5 mL) was added triethylamine (133 μL, 0.96 mmol, 3 eq) and 4-(dimethylamino)pyridine (3.9 mg, 0.03 mmol, 0.1 eq) and the mixture was cooled to 0° C. and di-tert-butyl dicarbonate (66 μL, 0.29 mmol, 0.9 eq) was added and the mixture was stirred at ambient temperature for 1 h. The reaction was partitioned between dichloromethane and saturated aqueous sodium bicarbonate, and the organic phase was separated (PTFE phase separator) and concentrated in vacuo. Purification by automated flash column chromatography (CombiFlash Rf, 4 g RediSep™ silica cartridge) eluting with a gradient of 0-35% ethyl acetate in iso-heptane afforded the desired product (33 mg, 0.11 mmol, 35%).

LC/MS ($C_{16}H_{24}FNO_3$) 198 [M-Boc+H]$^+$; RT 2.18 (LCMS-V-C)

$^1$H NMR (400 MHz, DMSO-d6) δ 9.54 (s, 1H), 6.95 (dd, J=12.4, 2.0 Hz, 1H), 6.88-6.74 (m, 2H), 3.21-3.11 (m, 2H), 2.74 (s, 3H), 2.49-2.41 (m, 2H), 1.53-1.40 (m, 4H), 1.37 (s, 9H).

Preparation 5a: 1-(1-Adamantylmethyl)-5-methyl-4-(4,4,5,5-tetramethyl-1,3,2-dioxaborolan-2-yl)pyrazole

Step A: 1-(1-adamantylmethyl)-4-iodo-pyrazole

The mixture of 35.9 g of 1-adamantylmethanol (216 mmol), 73.48 g of triphenylphosphine (280 mmol, 1.3 eq.), 54.25 g of 4-iodo-1H-pyrazole (280 mmol, 1.3 eq.) and 64.4 g of tert-butyl N-(tert-butoxycarbonyliminomethylene)carbamate (266 mmol. 1.3 eq.) in 1078 mL of THF was stirred at rt for 48 h. After the addition of extra 10.94 g of 4-iodo-1H-pyrazole (56 mmol, 0.26 eq.), 12.81 g of tert-butyl N-(tert-butoxycarbonyliminomethylene)carbamate (53 mmol, 0.26 eq.) and 14.69 g of triphenylphosphine (56 mmol, 0.26 eq.), the reaction was stirred at rt for 24 h then concentrated, purified via flash column chromatography using DCM as eluent, triturated in cold MeOH, and filtered off to give 53.6 g (73%) of the desired product as white powder.

Step B: 1-(1-adamantylmethyl)-4-iodo-5-methyl-pyrazole

To 9.8 mL of diisopropylamine (69.5 mmol, 1.1 eq.) in 180 mL of THF was added dropwise 33.4 mL of a 2.5 M solution of butyl lithium (84 mmol, 1.3 eq.) at −78° C. and the mixture was stirred at −78° C. for 0.5 h, treated with 22.0 g of the product from Step A (64.28 mmol, 1 eq.) in 90 mL of THF, stirred at −78° C. for 1 h, treated with 4.67 mL of methyliodide (73.3 mmol, 1.14 eq.), and stirred at −78° C. for 18 h. After quenching with cc. NH₄Cl, the reaction was extracted with EtOAc and the combined organic phases were washed with brine, dried, concentrated, triturated in MeOH, and filtered off to give 21 g (92%) of the desired product.

Step C: 1-(1-adamantylmethyl)-5-methyl-4-(4,4,5,5-tetramethyl-1,3,2-dioxaborolan-2-yl)pyrazole To 21 g of the product from Step B (58.95 mmol, 1 eq.) in 300 mL of THF was added 28.3 mL of a 2.5 M solution of butyllithium (70.8 mmol, 1.2 eq) at −78° C. and the mixture was stirred at −78° C. for 0.5 h, treated with 16.4 g of 2-isopropoxy-4,4,5,5-tetramethyl-1,3,2-dioxaborolane (88.1 mmol, 1.5 eq.) (addition in portions over 40 min), and kept at −78° C. for 24 h. After quenching with cc. NH₄Cl at rt, the reaction was extracted with EtOAc and the combined organic phases were washed with brine, dried, concentrated, triturated in MeOH, and filtered off to give 19.7 g (94%) of the desired product as off-white crystals.

$^1$H NMR (500 MHz, DMSO-d₆) δ ppm 7.45 (s, 1H), 3.69 (s, 2H), 2.36 (s, 3H), 1.91 (m, 1H), 1.64/1.54 (m, 6H), 1.50 (m, 6H), 1.24 (s, 12H); $^{13}$C NMR (500 MHz, DMSO-d₆) δ ppm 146.9, 144.1, 104.6, 59.7, 40.6, 36.8, 35.4, 28.1, 25.1, 12.1; HRMS-ESI (m/z): [M+H]$^+$ calcd for $C_{21}H_{34}BN_2O_2$: 357.2713, found 357.2704.

Preparation 5b: 1-{[1-(3-Methoxypropyl)cyclooctyl]methyl}-5-methyl-4-(4,4,5,5-tetramethyl-1,3,2-di-oxaborolan-2-yl)-1H-pyrazole

Step A: methyl 1-(3-methoxypropyl)cyclooctanecarboxylate

To 4.74 g (1.14 eq.) of diisopropylamine in 90 mL of tetrahydrofuran was added 18.8 mL (1.14 eq.) of a 2.5 M solution of butyl lithium at −78° C. and after 0.5 h at −78° C., 7.0 g (41.1 mmol) of methyl cyclooctanecarboxylate in 40 mL of tetrahydrofuran was added over 1 h. After 1 h at −78° C., 7.2 g (1.14 eq.) of 1-bromo-3-methoxy-propane was added and the mixture was stirred for 18 h. After quenching the reaction with the addition of saturated NH₄Cl solution, the mixture was extracted with EtOAc and the organic phases were dried over MgSO₄ and concentrated to give 8.0 g (80%) of the desired product.

1H NMR (400 MHz, CDCl$_3$) δ ppm 3.66 (s, 3H), 3.33 (t, 2H), 3.31 (s, 3H), 2.03-1.94 (m, 2H), 1.64-1.38 (m, 16H).

Step B: [1-(3-methoxypropyl)cyclooctyl]methanol

To 9.0 g (37.13 mmol) of the product from Step A in 93 mL of diethyl ether was added 1.76 g (1.25 eq.) of lithium aluminum hydride portion wise at 0° C. After stirring at rt for 2 h, the reaction was quenched by the addition of icy water and EtOAc and a 10% solution of NaOH were added. The mixture was extracted with EtOAc, dried, and concentrated to give 7.4 g (93%) of the desired product.
$^1$H NMR (400 MHz, CDCl$_3$) δ ppm 3.37 (t, 2H), 3.34 (s, 3H), 3.30 (s, 2H), 1.61-1.23 (m, 18H).

Step C: 4-iodo-1-[[1-(3-methoxypropyl)cyclooctyl] methyl]-1H-pyrazole

To 1.39 g (6.5 mmol) of the product from Step B and 1.64 g (1.3 eq.) of 4-iodo-1H-pyrazole in 33 mL of tetrahydrofuran was added 2.22 g (1.3 eq.) of triphenylphosphine and 1.95 g (1.3 eq.) of di-tert-butyl azodicarboxylate and the mixture was stirred at rt for 67 h. To the mixture was added 278 mg of 4-iodo-1H-pyrazole, 444 mg of triphenylphosphine, and 390 mg of di-tert-butyl azodicarboxylate and was stirred at rt for 24 h. After the addition of reagents and stirring at rt for 24 h was repeated (115 h stirring in total), the mixture was concentrated and purified via flash column chromatography (silica gel) using heptane and EtOAc as eluents to give 1.24 g (49%) of the desired product.
$^1$H NMR (400 MHz, CDCl$_3$) δ ppm 7.47 (s, 1H), 7.42 (s, 1H), 3.93 (s, 2H), 3.37 (t, 2H), 3.36 (s, 3H), 1.68-1.18 (m, 18H).

Step D: 4-iodo-1-[[1-(3-methoxypropyl)cyclooctyl] methyl]-5-methyl-1H-pyrazole To 1.2 g (3.07 mmol) of the product from Step C in 5 mL of tetrahydrofuran was added 3.7 mL (1.2 eq.) of a 1 M solution of LDA at −78° C. After 0.6 h at −78° C., 0.5 mL (1.14 eq.) of methyl iodide was added dropwise to the mixture and it was let to warm up to rt over 20 h. Reaction was quenched with a saturated solution of NH$_4$Cl and extracted with EtOAc. The combined organic phases were dried, concentrated, and purified via flash column chromatography (silica gel) using heptane and EtOAc as eluents to give 0.79 g (64%) of the desired product.
$^1$H NMR (400 MHz, CDCl$_3$) δ ppm 7.43 (s, 1H), 3.85 (s, 2H), 3.38 (t, 2H), 3.35 (s, 3H), 2.29 (s, 3H), 1.69-1.24 (m, 18H).

Step E: 1-[[1-(3-methoxypropyl)cyclooctyl]methyl]-5-methyl-4-(4,4,5,5-tetramethyl-1,3,2-dioxaborolan-2-yl)-1H-pyrazole To the solution of 0.81 g (2 mmol) of the product from Step D in 15 mL of tetrahydrofuran was added 0.96 mL (1.2 eq.) of a 2.5 M solution of butyl lithium dropwise at −78° C. After 0.5 h, 0.5 mL (1.2 eq.) of 2-isopropoxy-4,4,5,5-tetramethyl-1,3,2-dioxaborolane was added over 20 min and the mixture was kept at −78° C. for 6 h and at rt for 6 h. After quenching the reaction with saturated solution of NH$_4$Cl and extracting with EtOAc, the combined organic phases were washed with brine, dried, and purified via flash column chromatography (silica gel) using heptane and EtOAc as eluents to give 0.33 g (34%) of the desired product.

$^1$H NMR (500 MHz, dmso-d6) δ ppm 7.46 (s, 1H), 3.75 (s, 2H), 3.27 (t, 2H), 3.21 (s, 3H), 2.36 (s, 3H), 1.66-1.1 (m, 14H), 1.57 (m, 2H), 1.24 (s, 12H), 1.24 (m, 2H). $^{13}$C NMR (500 MHz, dmso-d6) δ ppm 147.3, 144.5, 104.5, 73.2, 58.2, 54.4, 40.5, 33.2, 25.1, 23.6, 11.8. IR: 2922, 1556, 1246, 1144, 1055. HRMS-ESI (m/z): [M+H]$^+$ calcd for C$_{23}$H$_{42}$N$_2$O$_3$B: 405.3289, found 405.3329.

Preparation 5c: 1-{[1-(3-Methoxypropyl)cyclo-hexyl]methyl}-5-methyl-4-(4,4,5,5-tetramethyl-1,3, 2-dioxaborolan-2-yl)-1H-pyrazole

Step A: methyl 1-(3-methoxypropyl)cyclohexanecarboxylate

To 6.84 g (1.09 eq.) of diisopropylamine in 130 mL of tetrahydrofuran was added 27 mL (1.09 eq.) of a 2.5 M solution of butyl lithium at −78° C. and after 0.5 h at −78° C., 8.8 g of methyl cyclohexanecarboxylate in 50 mL of tetrahydrofuran was added over 1 h. After 1 h at −78° C., 10.7 g (1.13 eq.) of 1-bromo-3-methoxy-propane was added and the mixture was stirred for 18 h. After quenching the reaction with the addition of saturated NH$_4$Cl solution, the mixture was extracted with EtOAc and the organic phases were dried over MgSO$_4$ and concentrated to give 12 g (92%) of the desired product.
$^1$H NMR (400 MHz, CDCl$_3$) δ ppm 3.67 (s, 3H), 3.35 (d, 1H), 3.32 (d, 1H), 3.31 (s, 3H), 2.11-2.03 (m, 2H), 1.60-1.16 (m, 12H).

Step B: [1-(3-methoxypropyl)cyclohexyl]methanol

To 12 g (56.41 mmol) of the product from Step A in 140 mL of diethyl ether was added 2.68 g (1.25 eq.) of lithium aluminum hydride portion wise at 0° C. After stirring at rt for 2 h, the reaction was quenched by the addition of icy water and EtOAc and a 10% solution of NaOH were added. The mixture was extracted with EtOAc, dried, and concentrated to give 9.37 g (89%) of the desired product.
$^1$H NMR (400 MHz, CDCl$_3$) δ ppm 3.41 (s, 2H), 3.38 (t, 2H), 3.35 (s, 3H), 1.56-1.27 (m, 14H).

Step C: 4-iodo-1-[[1-(3-methoxypropyl)cyclohexyl] methyl]pyrazole

To 1.21 g (6.5 mmol) of the product from Step B and 2.58 g (2.05 eq.) of 4-iodo-1H-pyrazole in 33 mL of tetrahydrofuran was added 3.5 g (2.05 eq.) of triphenylphosphine and 3.07 g (2.05 eq.) of di-tert-butyl azodicarboxylate and the mixture was stirred at rt for 2 h. To the mixture was added 140 mg of 4-iodo-1H-pyrazole, 230 mg of triphenylphosphine, and 200 mg of di-tert-butyl azodicarboxylate and was stirred at rt for 24 h. After the addition of reagents and stirring at rt for 24 h was repeated twice (96 h stirring in total), the mixture was concentrated and purified via flash column chromatography (silica gel) using heptane and EtOAc as eluents to give 1.4 g (59.5%) of the desired product.
$^1$H NMR (400 MHz, CDCl$_3$) δ ppm 7.47 (s, 1H), 7.41 (s, 1H), 4.00 (s, 2H), 3.36 (t, 2H), 3.35 (s, 3H), 1.62-1.21 (m, 14H).

Step D: 4-iodo-1-[[1-(3-methoxypropyl)cyclohexyl] methyl]-5-methyl-pyrazole

To 3.7 g (10.21 mmol) of the product from Step C in 15 mL of tetrahydrofuran was added 12.3 mL (1.2 eq.) of a 1 M solution of LDA in tetrahydrofuran at −78° C. After 0.6 h at −78° C., 0.73 mL (1.14 eq.) of methyl iodide was added dropwise to the mixture and it was let to warm up to rt over 20 h. Reaction was quenched with a saturated solution of NH$_4$Cl and extracted with EtOAc. The combined organic phases were dried, concentrated, and purified via flash column chromatography (silica gel) using heptane and EtOAc as eluents to give 2.85 g (74%) of the desired product.

$^1$H NMR (400 MHz, CDCl$_3$) δ ppm 7.44 (s, 1H), 3.92 (s, 2H), 3.38 (t, 2H), 3.35 (s, 3H), 2.29 (s, 3H), 1.58-1.13 (m, 14H).

Step E: 1-[[1-(3-methoxypropyl)cyclohexyl] methyl]-5-methyl-4-(4,4,5,5-tetramethyl-1,3,2-di-oxaborolan-2-yl)pyrazole To the solution of 5.0 g (13.3 mmol) of the product from Step D in 71 mL of tetrahydrofuran was added 6.38 mL (1.2 eq.) of a 2.5 M solution of butyl lithium dropwise at −78° C. After 0.5 h, 4.1 mL (1.5 eq.) of 2-isopropoxy-4,4,5,5-tetramethyl-1,3,2-dioxaborolane was added over 40 min and the mixture was kept at −78° C. for 6 h and at rt for 6 h. After quenching the reaction with saturated solution of NH$_4$Cl and extracting with EtOAc, the combined organic phases were washed with brine, dried, and purified via flash column chromatography (silica gel) using heptane and EtOAc as eluents to give 2.3 g (46%) of the desired product.

$^1$H NMR (500 MHz, dmso-d6) δ ppm 7.47 (s, 1H), 3.84 (s, 2H), 3.27 (t, 2H), 3.2 (s, 3H), 2.37 (s, 3H), 1.54-1.07 (m, 1OH), 1.46 (m, 2H), 1.32 (m, 2H), 1.24 (s, 12H). $^{13}$C NMR (500 MHz, dmso-d6) δ ppm 147.3, 144.4, 104.6, 73.1, 58.2, 55.7, 37.9, 30.6, 25.1, 23.1, 12.0. IR: 2927, 1556, 1257, 1144, 1053. HRMS-ESI (m/z): [M+H]$^+$ calcd for C$_{21}$H$_{38}$N$_2$O$_3$B: 376.2897, found 376.3019.

Preparation 6a: Ethyl 5-bromo-2-(4-methyl-3-{ [(2Z)-3-{[2-(trimethylsilyl)ethoxy]methyl}-2,3-di-hydro-1,3-benzothiazol-2-ylidene]amino}-5H,6H, 7H-pyrrolo[2,3-c]pyridazin-7-yl)-1,3-thiazole-4-carboxylate

Step A: ethyl 2-[(pent-3-yn-1-yl)amino]-1,3-thiaz-ole-4-carboxylate

To a solution of ethyl 2-bromo-1,3-thiazole-4-carboxylate (538 mg, 2.28 mmol, 1 eq) in acetonitrile (10 mL) was added pent-3-yn-1-amine hydrochloride (300 mg, 2.51 mmol, 1.1 eq) and triethylamine (0.7 mL, 5.02 mmol, 2.2 eq) and the mixture was heated at 150° C. for 3 h under microwave irradiation. The reaction was partitioned between ethyl acetate and brine, and the organic phase was dried (magnesium sulfate) and concentrated in vacuo. Purification by automated flash column chromatography (CombiFlash Rf, 24 g RediSep™ silica cartridge) eluting with a gradient of 0-40% ethyl acetate in iso-heptane afforded the desired product as a beige solid (221 mg, 0.93 mmol, 41%).

LC/MS (C$_{11}$H$_{14}$N$_2$O$_2$S) 239 [M+H]$^+$; RT 2.22 (LCMS-V-C)

$^1$H NMR (400 MHz, DMSO-d6) δ 7.93 (t, J=5.7 Hz, 1H), 7.52 (s, 1H), 4.22 (q, J=7.1 Hz, 2H), 3.38-3.28 (m, 2H), 2.44-2.33 (m, 2H), 1.75 (t, J=2.5 Hz, 3H), 1.27 (t, J=7.1 Hz, 3H).

Step B: ethyl 2-{3-chloro-4-methyl-5H,6H,7H-pyr-rolo[2,3-c]pyridazin-7-yl}-1,3-thiazole-4-carboxy-late To a solution of 3,6-dichloro-1,2,4,5-tetrazine (140 mg, 0.93 mmol, 1 eq) in tetrahydrofuran was added the product from Step A (221 mg, 0.93 mmol, 1 eq) and the mixture was heated at reflux overnight. The reaction was concentrated in vacuo and the residue was triturated with dichloromethane, filtered, and dried under vacuum to afford the desired product as an off-white solid (148 mg, 0.46 mmol, 49%).

LC/MS (C$_{13}$H$_{13}$ClN$_4$O$_2$S) 325 [M+H]$^+$; RT 2.32 (LCMS-V-C)

$^1$H NMR (400 MHz, DMSO-d6) δ 8.11 (s, 1H), 4.41 (dd, J=8.8, 7.7 Hz, 2H), 4.30 (q, J=7.1 Hz, 2H), 3.34-3.24 (m, 2H), 2.29 (d, J=1.1 Hz, 3H), 1.31 (t, J=7.1 Hz, 3H).

Step C: ethyl 2-{3-[(1,3-benzothiazol-2-yl)amino]-4-methyl-5H,6H,7H-pyrrolo[2,3-c]pyridazin-7-yl}-1,3-thiazole-4-carboxylate To an-oven dried microwave vial was added the product from Step B (148 mg, 0.46 mmol, 1 eq), 2-aminobenzothi-azole (103 mg, 0.68 mmol, 1.5 eq), XantPhos (52.7 mg, 0.09 mmol, 0.2 eq), cesium carbonate (297 mg, 0.91 mmol, 2 eq), and 1,4-dioxane (20 mL) and the vessel was evacuated and flushed with nitrogen then tris(dibenzylideneacetone)dipal-ladium(0) (41.7 mg, 0.05 mmol, 0.1 eq) was added and the mixture was sparged with nitrogen (10 min) then heated at 150° C. for 2 h under microwave irradiation. The reaction was diluted with ethyl acetate, filtered through celite, washed with brine, dried (magnesium sulfate) and concen-trated in vacuo. Purification by automated flash column chromatography (CombiFlash Rf, 24 g RediSep™ silica cartridge) eluting with a gradient of 0-10% methanol in dichloromethane afforded the desired product as a yellow solid (103 mg, 0.23 mmol, 52%).

LC/MS (C$_{20}$H$_{18}$N$_6$O$_2$S$_2$) 439 [M+H]$^+$; RT 2.67 (LCMS-V-C)

$^1$H NMR (400 MHz, DMSO-d6) δ 10.94 (br s, 1H), 8.06 (s, 1H), 7.95 (br s, 1H), 7.66 (br s, 1H), 7.44-7.33 (m, 1H), 7.28-7.15 (m, 1H), 4.42-4.34 (m, 2H), 4.30 (q, 2H), 3.32-3.28 (m, 2H), 2.34 (s, 3H), 1.32 (t, J=7.1, 2.4 Hz, 3H).

Step D: ethyl 2-(4-methyl-3-{[(2Z)-3-{[2-(trimeth-ylsilyl)ethoxy]methyl}-2,3-dihydro-1,3-benzothi-azol-2-ylidene]amino}-5H,6H,7H-pyrrolo[2,3-c] pyridazin-7-yl)-1,3-thiazole-4-carboxylate To a cooled solution of the product of Step C (103 mg, 0.23 mmol, 1 eq) in tetrahydrofuran (15 mL) and dimeth-ylformamide (5 mL) was added N,N-diisopropylethylamine (81.8 μL, 0.47 mmol, 2 eq). After 5 min, 4-dimethylamino-pyridine (5.74 mg, 0.05 mmol, 0.2 eq) and [2-(chlo-romethoxy)ethyl]trimethylsilane (103 μL, 0.59 mmol, 2.5 eq) were added and the mixture was stirred at ambient temperature overnight. The reaction was partitioned between ethyl acetate and water, and the organic phase was dried (magnesium sulfate) and concentrated in vacuo. Puri-fication by automated flash column chromatography (Com-biFlash Rf, 24 g RediSep™ silica cartridge) eluting with a gradient of 0-70% ethyl acetate in iso-heptane afforded the desired product as an off white solid (98 mg, 0.17 mmol, 73%).

LC/MS (C$_{26}$H$_{32}$N$_6$O$_3$SiS$_2$) no ionisation; RT 3.08 (LCMS-V-C)

$^1$H NMR (400 MHz, DMSO-d6) δ 8.14 (s, 1H), 7.91 (d, J=7.6 Hz, 1H), 7.60-7.51 (m, 2H), 7.39-7.30 (m, 1H), 5.96 (s, 2H), 4.48 (t, J=8.1 Hz, 2H), 4.40 (q, J=7.1 Hz, 2H), 3.87-3.78 (m, 2H), 3.48-3.36 (m, 2H), 2.44 (s, 3H), 1.42 (t, J=7.1 Hz, 3H), 1.07-0.98 (m, 2H), 0.00 (s, 9H).

Step E: ethyl 5-bromo-2-(4-methyl-3-{[(2Z)-3-{[2-(trimethylsilyl)ethoxy]methyl}-2,3-dihydro-1,3-benzothiazol-2-ylidene]amino}-5H,6H,7H-pyrrolo[2,3-c]pyridazin-7-yl)-1,3-thiazole-4-carboxylate To a solution of the product of Step D (98 mg, 0.17 mmol, 1 eq) in dichloromethane (15 mL) was added N-bromosuccinimide (39.9 mg, 0.22 mmol, 1.3 eq) and the mixture was stirred at ambient temperature for 3 h. Purification by automated flash column chromatography (CombiFlash Rf, 12 g RediSep™ silica cartridge) eluting with a gradient of 0-50% ethyl acetate in iso-heptane afforded the desired product as an off-white solid (98 mg, 0.15 mmol, 88%).

LC/MS ($C_{26}H_{31}BrN_6O_3SiS_2$) no ionisation; RT 3.22 (LCMS-V-C)

$^1$H NMR (400 MHz, DMSO-d6) δ 7.81 (dd, J=7.6, 1.1 Hz, 1H), 7.50-7.39 (m, 2H), 7.28-7.21 (m, 1H), 5.85 (s, 2H), 4.40-4.24 (m, 4H), 3.68-3.58 (m, 2H), 3.27 (t, J=8.0 Hz, 2H), 2.32 (s, 3H), 1.31 (t, J=7.1 Hz, 3H), 1.02 (dd, J=8.5, 7.4 Hz, 2H), −0.12 (s, 9H).

Preparation 7: tert-butyl-diphenyl-[2-[[3,5-dimethyl-7-[[5-methyl-4-(4,4,5,5-tetramethyl-1,3,2-dioxaborolan-2-yl)pyrazol-1-yl]methyl]-1-adamantyl]oxy]ethoxy]silane

Step A: 3-bromo-5,7-dimethyladamantane-1-carboxylic acid

After stirring iron (6.7 g, 120 mmol) in bromine (30.7 mL, 600 mmol, 5 eq) at 0° C. for 1 h, 3,5-dimethyladamantane-1-carboxylic acid (25 g, 1 eq) was added and the reaction mixture was stirred at rt for 2 days. After the addition of EtOAc, the reaction mixture was treated carefully with a saturated solution of sodium-thiosulfate at 0° C. and stirred for 15 min. After filtration through a pad of Celite and rinsing with EtOAc, the organic phase was separated, washed with a saturated solution of sodium-thiosulfate and brine, dried, concentrated to give the desired product (34.28 g, 74.6%), which was used without further purification.

$^1$H NMR (400 MHz, DMSO-d$_6$): δ ppm 12.33 (br., 1H), 2.21 (s, 2H), 1.96/1.91 (d+d, 4H), 1.50/1.43 (d+d, 4H), 1.21/1.14 (dm+dm, 2H), 0.86 (s, 6H); $^{13}$C NMR (100 MHz, DMSO-d$_6$) δ ppm 176.8, 66.8, 54.0, 48.7, 48.5, 45.7, 43.3, 35.5, 29.4; HRMS-ESI (m/z): [M−H]−calcd for $C_{13}H_{18}BrO_2$: 285.0496; found 285.0498.

Step B: 3-bromo-5,7-dimethyl-1-adamantyl-methanol

To the product from Step A (34.3 g, 119 mmol) in THF (77.6 mL) was added slowly a 1 M solution of BH$_3$-THF in THF (358 mL, 3 eq) and the reaction mixture was stirred for 18 h. After the addition of methanol and stirring for 30 min, purification by column chromatography (silica gel, heptane and MTBE as eluents) afforded the desired product (16.19 g, 49.6%).

$^1$H NMR (400 MHz, DMSO-d$_6$): δ ppm 4.51 (t, 1H), 3.05 (d, 2H), 1.91 (s, 2H), 1.91 (s, 4H), 1.19/1.09 (d+d, 2H), 1.19/1.05 (d+d, 4H), 0.85 (s, 6H)$^{13}$C NMR (100 MHz, DMSO-d$_6$) δ ppm 70.4, 68.9, 54.9, 49.8, 49.3, 43.8, 41.4, 35.7, 29.7; HRMS-ESI (m/z): [M-Br]− calcd for $C_{13}H_{21}O$: 193.1598 found: 193.1589.

Step C: 1-[3-bromo-5,7-dimethyl-1-adamantyl]methyl]pyrazole

To the product from Step B (16.19 g, 59.26 mmol) and 1H-pyrazole (4.841 g, 1.2 eq) in toluene (178 mL) was

---

78 added cyanomethylenetributylphosphorane (18.64 mL, 1.2 eq) in one portion and the reaction mixture was stirred at 90° C. for 2 h. Purification by column chromatography (silica gel, heptane and MTBE as eluents) afforded the desired product (17.88 g, 93%).

$^1$H NMR (400 MHz, DMSO-d$_6$): δ ppm 7.63 (d, 1H), 7.43 (d, 1H), 6.23 (t, 1H), 3.90 (s, 2H), 1.92-1.02 (m, 12H), 0.83 (s, 6H); $^{13}$C NMR (100 MHz, DMSO-d$_6$) δ ppm 139.0, 131.8, 105.2, 67.7, 61.4, 54.4/48.8/44.6, 50.4, 35.7, 29.6; HRMS-ESI (m/z): [M]+ calcd for $C_{16}H_{23}BrN_2$: 322.1045 found: 322.1014.

Step D: 5-methyl-1-[[3-bromo-5,7-dimethyl-1-adamantyl]methyl]pyrazole

To the solution of the product from Step C (17.88 g, 55.3 mmol) in THF (277 mL) was added butyllithium (2.5 M in THF, 66 mL, 3 eq) at −78° C., then after 1 h, iodomethane (17.2 mL, 5 eq) was added. After 10 min, the reaction mixture was quenched with a saturated solution of NH$_4$Cl, extracted with EtOAc and the combined organic layers were dried and concentrated to give the desired product (18.7 g, 100%), which was used in the next step without further purification.

$^1$H NMR (400 MHz, DMSO-d$_6$): δ ppm 7.31 (d, 1H), 6.00 (d, 1H), 3.79 (s, 2H), 2.23 (s, 3H), 2.01 (s, 2H), 1.89/1.85 (d+d, 4H), 1.23/1.15 (d+d, 4H), 1.16/1.05 (d+d, 2H), 0.83 (s, 6H); $^{13}$C NMR (100 MHz, DMSO-d$_6$) δ ppm 139.2, 138.0, 105.2, 67.8, 57.8, 54.4, 50.6, 48.8, 44.8, 41.5, 35.7, 29.6, 11.8; HRMS-ESI (m/z): [M+H]$^+$ calcd for $C_{17}H_{26}BrN_2$: 337.1279 found: 337.1289.

Step E: 2-[[3,5-dimethyl-7-[(5-methylpyrazol-1-yl)methyl]-1-adamantyl]oxy]ethanol The mixture of the product from Step D (18.7 g, 55.3 mmol), ethylene glycol (123 mL, 40 eq), and DIPEA (48.2 mL, 5 eq) was stirred at 120° C. for 6 h. After the reaction mixture was diluted with water and extracted with EtOAc, the combined organic layers were dried and concentrated to give the desired product (18.5 g, 105%), which was used in the next step without further purification.

$^1$H NMR (400 MHz, DMSO-d$_6$): δ ppm 7.29 (d, 1H), 5.99 (d, 1H), 4.45 (t, 1H), 3.78 (s, 2H), 3.39 (q, 2H), 3.32 (t, 2H), 2.23 (s, 3H), 1.34 (s, 2H), 1.27/1.21 (d+d, 4H), 1.13/1.07 (d+d, 4H), 1.04/0.97 (d+d, 2H), 0.84 (s, 6H); $^{13}$C NMR (100 MHz, DMSO-d$_6$) δ ppm 139.0, 137.8, 105.1, 74.0, 62.1, 61.5, 58.5, 50.1, 47.0, 46.1, 43.3, 39.7, 33.5, 30.2, 11.9; HRMS-ESI (m/z): [M+H]$^+$ calcd for $C_{19}H_{31}N_2O_2$: 319.2386 found: 319.2387.

Step F: tert-butyl-diphenyl-[2-[[3,5-dimethyl-7-[(5-methylpyrazol-1-yl)methyl]-1-adamantyl]oxy]ethoxy]silane To the mixture of the product from Step E (17.6 g, 55.3 mmol) and imidazole (5.65 g, 1.5 eq) in DCM (150 ml) was added tert-butyl-chloro-diphenyl-silane (18.6 g, 1.2 eq) and the reaction mixture was stirred for 1 h. Purification by column chromatography (silica gel, heptane and MTBE as eluents) afforded the desired product (27.0 g, 87.8%).

$^1$H NMR (400 MHz, DMSO-d$_6$): δ ppm 7.72-7.34 (m, 10H), 7.29 (d, 1H), 5.99 (br., 1H), 3.78 (s, 2H), 3.67 (t, 2H), 3.44 (t, 2H), 2.21 (s, 3H), 1.33 (s, 2H), 1.26/1.18 (d+d, 4H), 1.12/1.06 (d+d, 4H), 1.03/0.96 (d+d, 2H), 0.98 (s, 9H), 0.82 (s, 6H); $^{13}$C NMR (100 MHz, DMSO-d$_6$) δ ppm 139.0, 137.8, 105.1, 74.2, 64.4, 61.7, 58.5, 50.0, 46.9, 46.0, 43.4, 39.6, 33.5, 30.1, 27.1, 19.3, 11.9; HRMS-ESI (m/z): [M+H]⁺ calcd for $C_{35}H_{49}N_2O_2Si$: 557.3563 found: 557.3564.

Step G: tert-butyl-diphenyl-[2-[[3-[(4-iodo-5-methyl-pyrazol-1-yl)methyl]-5,7-dimethyl-1-adamantyl]oxy]ethoxy]silane To the solution of the product from Step F (27.0 g, 48.56 mmol) in DMF (243 mL) was added N-iodosuccinimide (13.6 g, 1.25 eq) and the reaction mixture was stirred for 2 h. After the dilution with water, the mixture was extracted with DCM. The combined organic layers were washed with saturated solution of sodium-thiosulphate and brine, dried, and concentrated to afford the desired product (30.1 g, 90%).

$^1$H NMR (400 MHz, DMSO-d$_6$): δ ppm 7.68-7.37 (m, 1OH), 7.45 (s, 1H), 3.89 (s, 2H), 3.67 (t, 2H), 3.44 (t, 2H), 2.23 (s, 3H), 1.30 (s, 2H), 1.26/1.17 (d+d, 4H), 1.12/1.05 (d+d, 4H), 1.00/0.96 (d+d, 2H), 0.98 (s, 9H), 0.82 (s, 6H); $^{13}$C NMR (100 MHz, DMSO-d$_6$) δ ppm 142.5, 140.8, 133.7, 64.4, 61.7, 60.3, 59.9, 49.9, 46.8, 45.9, 43.2, 39.7, 33.5, 30.1, 27.1, 19.3, 12.2; HRMS-ESI (m/z): [M+H]⁺ calcd for $C_{35}H_{48}N_2O_2Si$ 683.2530 found: 683.2533.

Step H: tert-butyl-diphenyl-[2-[[3,5-dimethyl-7-[[5-methyl-4-(4,4,5,5-tetramethyl-1,3,2-dioxaborolan-2-yl)pyrazol-1-yl]methyl]-1-adamantyl]oxy]ethoxy]silane To the product from Step G (17.5 g, 25.6 mmol) in THF (128 mL) was added chloro(isopropyl)magnesium-LiCl (1.3 M in THF, 24 mL, 1.2 eq) at 0° C., stirred for 40 min, treated with 2-isopropoxy-4,4,5,5-tetramethyl-1,3,2-dioxaborolane (15.7 mL, 3 eq), and the reaction mixture was stirred for 10 min. After dilution with a saturated solution NH$_4$Cl and extraction with EtOAc, the combined organic phases were concentrated and was purified by column chromatography (silica gel, heptane and MTBE as eluents) to give the desired product (15.2 g, 86.9%).

$^1$H NMR (400 MHz, DMSO-d$_6$): δ ppm 7.65 (dm, 4H), 7.47 (s, 1H), 7.45 (tin, 2H), 7.40 (tin, 4H), 3.80 (s, 2H), 3.66 (t, 2H), 3.44 (t, 2H), 2.35 (s, 3H), 1.35-0.94 (m, 12H), 1.24 (s, 12H), 0.97 (s, 9H), 0.83 (s, 6H); $^{13}$C NMR (100 MHz, DMSO-d$_6$) δ ppm 146.9, 144.3, 135.6, 130.2, 128.2, 104.7, 83.0, 74.2, 64.4, 61.7, 58.4, 30.1, 27.1, 25.2, 19.3, 12.0; HRMS-ESI (m/z): [M+H]⁺ calcd for $C_{41}H_6OBN_2O_4Si$ 683.4415 found: 683.4423.

Preparation 8: tert-butyl-[3-[3,5-dimethyl-7-[[5-methyl-4-(4,4,5,5-tetramethyl-1,3,2-dioxaborolan-2-yl)pyrazol-1-yl]methyl]-1-adamantyl]propoxy]-diphenyl-silane

Step A: 1-[[3-allyl-5,7-dimethyl-1-adamantyl]methyl]-5-methyl-pyrazole

To the product of Step D of Preparation 7 (15.66 g, 46.43 mmol) and AgOTf (597 mg, 0.05 eq) in THF (232 mL) was added a 2 M solution of allyl-Mg—Cl in THF (46.4 mL, 2 eq) and the reaction mixture was stirred for 0.5 h. After quenching with a saturated solution of NH$_4$Cl and extracting with EtOAc, the combined organic phases were concentrated and purified by column chromatography (silica gel, heptane and MTBE as eluents) to give the desired product (11.32 g, 81.7%).

$^1$H NMR (400 MHz, DMSO-d$_6$): δ ppm 7.27 (d, 1H), 5.98 (m, 1H), 5.76 (m, 1H), 5.01/4.96 (dm+dm, 2H), 3.73 (s, 2H), 2.22 (s, 3H), 1.83 (d, 2H), 1.15-0.93 (m, 12H), 0.78 (s, 6H);

$^{13}$C NMR (100 MHz, DMSO-d$_6$) δ ppm 139.0, 137.7, 135.0, 117.7, 105.0, 59.0, 47.8, 44.2, 35.0, 31.8, 30.6, 11.9; HRMS-ESI (m/z): [M+H]⁺ calcd for $C_{20}H_{31}N_2$: 299.2487 found: 299.2485.

Step B: 3-[3,5-dimethyl-7-[(5-methylpyrazol-1-yl)methyl]-1-adamantyl]propan-1-ol To the product of Step A (10.2 g, 34.17 mmol), in THF (85 mL) was added a 1 M solution of BH$_3$-THF in THF (85.4 mL, 2 eq) and the reaction mixture was stirred for 1 h. After treatment with a 10 M solution of NaOH (24 mL, 7 eq) and a 33% solution of hydrogen peroxide (73 mL, 25 eq) at 0° C., the reaction was stirred at rt for 1 h. Then, it was quenched with aqueous HCl solution, extracted with EtOAc, and purified by column chromatography (silica gel, heptane and MTBE as eluents) to give the desired product (9.75 g, 90%).

$^1$H NMR (400 MHz, DMSO-d$_6$): δ ppm 7.28 (d, 1H), 5.98 (m, 1H), 4.33 (t, 1H), 3.73 (s, 2H), 3.32 (m, 2H), 2.22 (brs, 3H), 1.32 (m, 2H), 1.12-0.92 (m, 12H), 1.06 (m, 2H), 0.78 (s, 6H); $^{13}$C NMR (100 MHz, DMSO-d$_6$) δ ppm 137.7, 105.0, 62.1, 59.1, 39.7, 30.7, 26.5, 11.9, HRMS-ESI (m/z): [M+H]⁺ calcd for $C_{20}H_{33}N_2O$: 317.2593 found: 317.2590

Step C: tert-butyl-[3-[3,5-dimethyl-7-[(5-methylpyrazol-1-yl)methyl]-1-adamantyl]propoxy]-diphenyl-silane To the product of Step B (9.75 g, 30.8 mmol) and imidazole (3.1 g, 1.5 eq) in DCM (92 ml) was added tert-butyl-chloro-diphenyl-silane (9.45 mL, 1.2 eq) and the reaction mixture was stirred for 1 h. Purification by column chromatography (silica gel, heptane and MTBE as eluents) afforded the desired product (12.5 g, 73%).

$^1$H NMR (400 MHz, DMSO-d$_6$): δ ppm 7.63-7.39 (m, 1OH), 7.27 (d, 1H), 5.98 (d, 1H), 3.72 (s, 2H), 3.59 (t, 2H), 2.21 (s, 3H), 1.42 (m, 2H), 1.1-0.92 (br., 12H), 1.09 (m, 2H), 0.98 (s, 9H), 0.77 (s, 6H); $^{13}$C NMR (100 MHz, DMSO-d$_6$) δ ppm 137.7, 105.0, 64.8, 59.1, 39.3, 38.0, 34.2, 31.8, 30.6, 27.2, 26.1, 19.2, 11.9; HRMS-ESI (m/z): [M+H]⁺ calcd for $C_{36}H_{51}N_2OSi$: 555.3771 found: 555.3770.

Step D: tert-butyl-[3-[3-[(4-iodo-5-methyl-pyrazol-1-yl)methyl]-5,7-dimethyl-1-adamantyl]propoxy]-diphenyl-silane To the product of Step C (12.5 g, 22.54 mmol) in DMF (112 mL) was added N-iodosuccinimide (6.34 g, 1.25 eq) and the reaction mixture was stirred for 2 h. After quenching with a saturated solution of sodium thiosulfate and extraction with DCM, the combined organic phases were washed with saturated sodium thiosulphate and brine, dried, and evaporated to afford the desired product (16.3 g, 105%). LC/MS ($C_{36}H_{50}IN_2OSi$) 681 [M+H]⁺.

Step E: tert-butyl-[3-[3,5-dimethyl-7-[[5-methyl-4-(4,4,5,5-tetramethyl-1,3,2-dioxaborolan-2-yl)pyrazol-1-yl]methyl]-1-adamantyl]propoxy]-diphenyl-silane To the product of Step D (16.25 g, 23.9 mmol) in THF (119 mL) was added chloro(isopropyl)magnesium-LiCl (1.3 M in THF, 22 mL, 1.2 eq.) at 0° C., the mixture was stirred for 40 min, treated with 2-isopropoxy-4,4,5,5-tetramethyl-1,3,2-dioxaborolane (14.6 mL, 3 eq), and stirred for 10 min. After dilution with a saturated solution NH$_4$Cl and extraction with EtOAc, the combined organic phases were concentrated and was purified by column chromatography (silica gel, heptane and MTBE as eluents) to give the desired product (11.4 g, 70%).

$^1$H NMR (400 MHz, DMSO-d$_6$): δ ppm 7.59 (d, 4H), 7.46 (s, 1H), 7.45 (t, 2H), 7.43 (t, 4H), 3.74 (s, 2H), 3.59 (t, 2H), 2.35 (s, 3H), 1.41 (qn, 2H), 1.24 (s, 12H), 1.09 (m, 2H), 1.08 (s, 4H), 1.05 (s, 2H), 0.98 (s, 9H), 0.98 (s, 2H), 0.94 (s, 4H), 0.78 (s, 6H); $^{13}$C NMR (100 MHz, DMSO-d$_6$) δ ppm 146.9, 144.2, 135.5, 133.8, 130.3, 128.3, 104.6, 83.0, 64.7, 64.7, 59.0, 50.6, 48.2, 46.5, 44.1, 39.2, 37.9, 31.8, 30.7, 27.2, 26.1, 25.2, 19.2, 12.0; HRMS-ESI (m/z): [M+H]$^+$ calcd for C$_{42}$H$_{62}$BN$_2$O$_3$Si: 681.4623 found: 681.4631.

Preparation 9: tert-butyl-[2-[[3-[[5-methyl-4-(4,4,5, 5-tetramethyl-1,3,2-dioxaborolan-2-yl)pyrazol-1-yl] methyl]-1-adamantyl]oxy]ethoxy]-diphenyl-silane

Step A: (3-bromo-1-adamantyl)methanol

To 3-bromoadamantane-1-carboxylic acid (10.0 g, 38.6 mmol) in THF (25 mL) was added slowly a 1 M solution of BH3-THF in THF (115 mL, 3 eq) and the mixture was stirred for 48 h. After the addition of methanol and stirring for 30 min, purification by column chromatography (silica gel, heptane and MTBE as eluents) afforded the desired product (8.37 g, 88%).

$^1$H NMR (400 MHz, DMSO-d$_6$): δ ppm 4.50 (t, 1H), 3.02 (d, 2H), 2.28/2.21 (dm+dm, 4H), 2.11 (m, 2H), 2.07 (s, 2H), 1.66/1.56 (dm+dm, 2H), 1.48/1.39 (dm+dm, 4H); $^{13}$C NMR (100 MHz, DMSO-d$_6$) δ ppm 70.9, 69.3, 51.3, 49.0, 40.6, 37.3, 35.1, 32.3.

Step B: 1-[(3-bromo-1-adamantyl)methyl]pyrazole

To the product from Step A (8.37 g, 34.1 mmol), 1H-pyrazole (2.79 g, 1.2 eq) in toluene (100 mL) was added (cyanomethylene)tributylphosphorane (10.7 mL, 1.2 eq) and the reaction mixture was stirred at 90° C. for 2 h. Purification by column chromatography (silica gel, heptane and MTBE as eluents) afforded the desired product (8.50 g, 84%).

$^1$H NMR (400 MHz, DMSO-d$_6$): δ ppm 7.63 (dd, 1H), 7.43 (dd, 1H), 6.23 (t, 1H), 3.87 (s, 2H), 2.24/2.13 (m+m, 4H), 2.1 (m, 2H), 2.07 (s, 2H), 1.63/1.50 (m+m, 2H), 1.47/1.43 (m+m, 4H); $^{13}$C NMR (100 MHz, DMSO-d$_6$) δ ppm 138.9, 131.7, 105.1, 68.0, 61.8, 51.8, 48.5, 39.8, 38.3, 34.6, 32.1; HRMS-ESI (m/z): [M+H]$^+$ calcd for C$_{14}$H$_{20}$BrN$_2$: 295.0810 found: 295.0804.

Step C: 1-[(3-bromo-1-adamantyl)methyl]-5-methyl-pyrazole

To the product from Step B (1.70 g, 5.76 mmol) in THF (30 mL) was added butyllithium (2.5 M in THF, 12 mL, 5 eq) at −78° C. After 1 h, iodomethane (7.2 mL, 5 eq) was added to the mixture. After 10 min, the reaction mixture was quenched with a saturated solution of NH$_4$Cl, extracted with EtOAc and the combined organic layers were dried and concentrated to give the desired product (2.0 g, 112%), which was used in the next step without further purification.

$^1$H NMR (400 MHz, DMSO-d$_6$): δ ppm 7.31 (d, 1H), 6.01 (d, 1H), 3.76 (s, 2H), 2.25/2.15 (d+d, 4H), 2.24 (s, 3H), 2.16 (s, 2H), 2.10 (m, 2H), 1.63/1.52 (d+d, 2H), 1.52/1.49 (d+d, 4H); $^{13}$C NMR (100 MHz, DMSO-d$_6$) δ ppm 139.2, 138.0, 105.2, 68.2, 58.3, 52.1, 48.5, 40.5, 38.4, 34.5, 32.2, 11.8; HRMS-ESI (m/z): [M+H]$^+$ calcd for C$_{15}$H$_{22}$BrN$_2$: 309.0966 found: 309.0962.

Step D: 2-[[3-[(5-methylpyrazol-1-yl)methyl]-1-adamantyl]oxy]ethanol

The mixture of the product from Step C (2.00 g, 6.47 mmol), ethylene glycol (14.4 mL, 40 eq), and DIPEA (5.6 mL, 5 eq) was stirred at 120° C. for 6 h. After diluting with water and extracting with EtOAc, the combined organic phases were purified by column chromatography (silica gel, heptane and MTBE as eluents) to give the desired product (1.62 g, 86.6%).

$^1$H NMR (400 MHz, DMSO-d$_6$): δ ppm 7.28 (d, 1H), 5.99 (m, 1H), 4.46 (t, 1H), 3.75 (s, 2H), 3.40 (m, 2H), 3.32 (m, 2H), 2.23 (brs, 3H), 2.13 (m, 2H), 1.61/1.52 (m+m, 4H), 1.47/1.43 (m+m, 2H), 1.45 (s, 2H), 1.44-1.35 (m, 4H); $^{13}$C NMR (100 MHz, DMSO-d$_6$) δ ppm 137.8, 105.1, 61.8, 61.5, 59.0, 44.6, 40.8, 39.6, 35.7, 30.0, 11.9; HRMS-ESI (m/z): [M+H]$^+$ calcd for C$_{17}$H$_{27}$N$_2$O$_2$: 291.2073 found: 291.2069.

Step E: tert-butyl-[2-[[3-[(5-methylpyrazol-1-yl) methyl]-1-adamantyl]oxy]ethoxy]-diphenyl-silane To the product from Step D (6.52 g, 22.5 mmol) and imidazole (2.29 g, 1.5 eq) in DCM (67 ml) was added tert-butyl-chloro-diphenyl-silane (6.9 mL, 1.2 eq) and the reaction mixture was stirred for 1 h. Purification by column chromatography (silica gel, heptane and MTBE as eluents) afforded the desired product (11.0 g, 92.7%). LC/MS (C$_{33}$H$_{45}$N$_2$O$_2$Si) 529 [M+H]$^+$.

Step F: tert-butyl-[2-[[3-[(4-iodo-5-methyl-pyrazol-1-yl)methyl]-1-adamantyl]oxy]ethoxy]-diphenyl-silane To the product from Step E (11.0 g, 20.8 mmol) in DMF (105 mL) was added N-iodosuccinimide (5.85 g, 1.25 eq.) and the reaction mixture was stirred for 3 h. After the reaction mixture was diluted with water and extracted with DCM, the combined organic phases were washed with saturated sodium thiosulphate and brine, dried, and evaporated to get the desired product (11.0 g, 81%).

$^1$H NMR (400 MHz, DMSO-d$_6$): δ ppm 7.70-7.36 (m, 10H), 7.44 (s, 1H), 3.86 (s, 2H), 3.67 (t, 2H), 3.45 (t, 2H), 2.24 (s, 3H), 2.12 (m, 2H), 1.66-1.32 (m, 12H), 0.98 (s, 9H)$^{13}$C NMR (100 MHz, DMSO-d$_6$) δ ppm 142.4, 140.9, 64.4, 61.4, 60.4, 60.3, 30.0, 27.1, 12.2; HRMS-ESI (m/z): [M+H]$^+$ calcd for C$_{33}$H$_{44}$IN$_2$O$_2$Si: 655.2217 found: 655.2217.

Step G: tert-butyl-[2-[[3-[[5-methyl-4-(4,4,5,5-tetramethyl-1,3,2-dioxaborolan-2-yl)pyrazol-1-yl] methyl]-1-adamantyl]oxy]ethoxy]-diphenyl-silane To the product from Step F (11.0 g, 16.8 mmol) in THF (84 mL) was added chloro(isopropyl)magnesium-LiCl (1.3 M in THF, 17 mL, 1.2 eq) at 0° C., and the reaction mixture was stirred for 40 min, treated with 2-isopropoxy-4,4,5,5-tetramethyl-1,3,2-dioxaborolane (10.3 mL, 3 eq), and stirred for 10 min. After dilution with a saturated solution NH$_4$Cl and extraction with EtOAc, the combined organic phases were concentrated and purified by column chromatography (silica gel, heptane and MTBE as eluents) to give the desired product (9.0 g, 82%).

$^1$H NMR (400 MHz, DMSO-d$_6$): δ ppm 7.66 (d, 4H), 7.47 (s, 1H), 7.45 (t, 2H), 7.40 (t, 4H), 3.77 (s, 2H), 3.67 (t, 2H), 3.44 (t, 2H), 2.36 (s, 3H), 2.11 (br, 2H), 1.60/1.48 (d+d, 4H), 1.44 (d, 2H), 1.44 (s, 2H), 1.40 (d, 4H), 1.23 (s, 12H), 0.97 (s, 9H); $^{13}$C NMR (100 MHz, DMSO-d$_6$) δ ppm 146.9, 144.2, 133.8, 130.2, 128.3, 125.7, 104.6, 83.0, 72.5, 64.4, 61.4, 58.9, 44.6, 40.7, 39.6, 38.7, 35.6, 30.0, 27.1, 25.2, 19.3, 12.1; HRMS-ESI (m/z): [M+H]$^+$ calcd for $C_{39}H_{56}BN_2O_4Si$: 655.4102 found: 655.4108.

Preparation 10: methyl 3-bromo-6-[3-(3,6-dichloro-5-methyl-pyridazin-4-yl)propylamino]pyridine-2-carboxylate

Step A: methyl 6-[bis(tert-butoxycarbonyl)amino]-3-bromo-pyridine-2-carboxylate To methyl 6-amino-3-bromo-pyridine-2-carboxylate (25.0 g, 108.2 mmol) and DMAP (1.3 g, 0.1 eq) in DCM (541 mL) was added Boc2O (59.0 g, 2.5 eq) at 0° C. and the reaction mixture was stirred for 2.5 h. After the addition of a saturated solution of NaHCO$_3$ and extraction with DCM, the combined organic phases were dried and concentrated to afford the desired product (45.0 g, 72.3%).

LC/MS ($C_{17}H_{23}BrN_2O_6Na$) 453 [M+Na]$^+$.

Step B: methyl 3-bromo-6-(tert-butoxycarbonylamino)pyridine-2-carboxylate

To the product from Step A (42.7 g, 74.34 mmol) in DCM (370 mL) was added TFA (17.1 mL, 3 eq) at 0° C. and the reaction mixture was stirred for 18 h. After washing with a saturated solution of NaHCO$_3$ and brine, the combined organic phases were dried, concentrated, and purified by column chromatography (silica gel, heptane and EtOAc as eluents) to give the desired product (28.3 g, 115.2%).

$^1$H NMR (400 MHz, DMSO-d$_6$): δ ppm 10.29 (s, 1H), 8.11 (d, 1H), 7.88 (d, 1H), 3.87 (s, 3H), 1.46 (s, 9H)$^{13}$C NMR (100 MHz, DMSO-d$_6$) δ ppm 165.6, 153.1, 151.8/148.3, 143.5, 116.3, 109.2, 53.2, 28.4. LC/MS ($C_{12}H_{15}BrN_2O_4Na$) 353 [M+Na]$^+$.

Step C: methyl 3-bromo-6-[tert-butoxycarbonyl-[3-(3,6-dichloro-5-methyl-pyridazin-4-yl)propyl]amino]pyridine-2-carboxylate To the product from Step B (10.0 g, 30.1967 mmol) in acetone (150 mL), were added Cs$_2$CO$_3$ (29.5 g, 3 eq) and 3,6-dichloro-4-(3-iodopropyl)-5-methyl-pyridazine (9.9 g, 1 eq) and the reaction mixture was stirred for 18 h. After dilution with water and extraction with EtOAc, the combined organic phases were washed with brine, dried and concentrated to give the desired product (17.5 g, 108%).

$^1$H NMR (400 MHz, DMSO-d$_6$): δ ppm 8.13 (d, 1H), 7.78 (d, 1H), 3.91 (t, 2H), 3.89 (s, 3H), 2.79 (m, 2H), 2.38 (s, 3H), 1.82 (m, 2H), 1.46 (s, 9H); $^{13}$C NMR (100 MHz, DMSO-d$_6$) δ ppm 165.3, 157.6, 156.6, 153.2, 152.9, 147.2, 143.1, 142.2, 139.7, 122.6, 111.8, 82.2, 53.3, 46.4, 28.1, 27.7, 26.5, 16.3; HRMS-ESI (m/z): [M+Na]$^+$ calcd for $C_{20}H_{23}BrCl_2N_4NaO_4$: 555.0177 found: 555.0172.

Step D: methyl 3-bromo-6-[3-(3,6-dichloro-5-methyl-pyridazin-4-l)propylamino]pyridine-2-carboxylate The product from Step C (17.5 g, 32.7 mmol) in 1,1,1,3,3,3-hexafluoroisopropanol (330 mL) was stirred at 110° C. for 18 h. Purification by column chromatography (silica gel, heptane and EtOAc as eluents) afforded the desired product (9.9 g, 70%).

$^1$H NMR (400 MHz, DMSO-d$_6$): δ ppm 7.63 (d, 1H), 7.22 (t, 1H), 6.57 (d, 1H), 3.83 (s, 3H), 3.30 (m, 2H), 2.83 (m, 2H), 2.37 (s, 3H), 1.74 (m, 2H)$^{13}$C NMR (100 MHz, DMSO-d$_6$) δ ppm 166.5, 141.5, 112.6, 52.9, 40.9, 28.0, 27.0, 16.4.

Preparation 11: (4-methoxyphenyl)methyl 3-bromo-6-[3-(3,6-dichloro-5-methyl-pyridazin-4-yl)propylamino]pyridine-2-carboxylate

Step A: 3-bromo-6-[3-(3,6-dichloro-5-methyl-pyridazin-4-yl)propylamino]pyridine-2-carboxylic acid The mixture of the product from Preparation 10 (35.39 g, 81.52 mmol) and LiOH×H$_2$O(13.68 g, 4 eq) in 1,4-dioxane (408 mL) and water (82 mL) was stirred at 60° C. for 1 h. After quenching with a 1 M solution of HCl and extraction with EtOAc, the combined organic phases were dried, concentrated, and purified by flash chromatography (silica gel, using DCM and MeOH as eluents) to give the desired product (27.74 g, 81%).

LC/MS ($C_{14}H_{14}BrCl_2N_4O_2$) 421 [M+H]V.

Step B: (4-methoxyphenyl)methyl 3-bromo-6-[3-(3,6-dichloro-5-methyl-pyridazin-4-yl)propylamino]pyridine-2-carboxylate To the product of Step A (27.7 g, 65.9 mmol), (4-methoxyphenyl)methanol (16.4 mL, 2 eq), and PPh$_3$ (34.6 g, 2 eq) in toluene (660 mL) and THF (20 ml) was added dropwise diisopropyl azodicarboxylate (26 mL, 2 eq) and the reaction mixture was stirred at 50° C. for 1 h. Purification by flash chromatography (silica gel, using heptane and EtOAc as eluents) afforded the desired product (23.65 g, 66.4%).

$^1$H NMR (500 MHz, dmso-d6) δ ppm 7.62 (d, 1H), 7.37 (dn, 2H), 7.21 (t, 1H), 6.91 (dm, 2H), 6.56 (d, 1H), 5.25 (s, 2H), 3.74 (s, 3H), 3.30 (q, 2H), 2.81 (m, 2H), 2.33 (s, 3H), 1.73 (m, 2H); $^{13}$C NMR (500 MHz, dmso-d6) δ ppm 165.9, 159.7, 157.6, 157.5, 156.8, 148.0, 142.7, 141.5, 139.7, 130.6, 127.8, 114.3, 112.6, 101.6, 67.0, 55.6, 40.9, 28.0, 27.1, 16.4; HRMS-ESI (m/z): [M+H]$^+$ calcd for $C_{22}H_{22}BrCl_2N_4O_3$: 539.0252, found: 539.0246.

Preparation 12: methyl 6-[3-(1,3-benzothiazol-2-ylamino)-4-methyl-6,7-dihydro-5H-pyrido[2,3-c]pyridazin-8-yl]-3-[1-[[3,5-dimethyl-7-[2-(p-tolylsulfonyloxy)ethoxy]-1-adamantyl]methyl]-5-methyl-pyrazol-4-yl]pyridine-2-carboxylate

Step A: methyl 6-[3-(3,6-dichloro-5-methyl-pyridazin-4-yl)propylamino]-3-[5-methyl-1-[[3-[2-[tert-butyl(diphenyl)silyl]oxyethoxy]-5,7-dimethyl-1-adamantyl]methyl]pyrazol-4-yl]pyridine-2-carboxylate The mixture of the product from Preparation 10 (15.0 g, 34.55 mmol), the product from Preparation 7 (30.7 g, 1.3 eq), Cs$_2$CO$_3$ (33.8 g, 3.0 eq), and Pd(AtaPhos)$_2$Cl$_2$ (1.53 g, 0.1 eq) in 1,4-dioxane (207 mL) and H$_2$O (34.5 mL) was stirred at 80° C. for 1.5 h. Purification by column chromatography (silica gel, heptane and EtOAc as eluents) afforded the desired product (18.5 g, 58%).

$^1$H NMR (400 MHz, DMSO-d$_6$): δ ppm 7.69-7.37 (m, 1OH), 7.32 (d, 1H), 7.23 (s, 1H), 6.98 (t, 1H), 6.63 (d, 1H), 3.82 (s, 2H), 3.67 (t, 2H), 3.58 (s, 3H), 3.46 (t, 2H), 3.35 (m, 2H), 2.86 (m, 2H), 2.40 (s, 3H), 2.06 (s, 3H), 1.78 (m, 2H), 1.35 (s, 2H), 1.27/1.2 (m+m, 4H), 1.15/1.09 (m+m, 4H), 1.05/0.97 (m+m, 2H), 0.97 (s, 9H), 0.84 (s, 6H); HRMS-ESI (m/z): [M+H]$^+$ calcd for $C_{50}H_{63}Cl_2N_6O_4Si$: 909.4057 found: 909.4053.

Step B: methyl 6-(3-chloro-4-methyl-6,7-dihydro-5H-pyrido[2,3-c]pyridazin-8-yl)-3-[5-methyl-1-[[[2-[tert-butyl(diphenyl)silyl]oxyethoxy]-5,7-dimethyl-1-adamantyl]methyl]pyrazol-4-yl]pyridine-2-carboxylate The mixture of the product from Step A (18.5 g, 20.3 mmol), $Cs_2CO_3$ (13.2 g, 2 eq), DIPEA (7.1 mL, 2 eq), and $Pd(Ataphos)_2Cl_2$ (900 mg, 0.1 eq) in 1,4-dioxane (102 mL) was stirred at 110° C. for 18 h. After filtration and concentration, the residue was taken up with DCM, washed with water, and purified by column chromatography (silica gel, DCM and EtOAc as eluents) to give the desired product (12.6 g, 71%).

$^1$H NMR (400 MHz, DMSO-d$_6$): δ ppm 7.85 (d, 1H), 7.69 (d, 1H), 7.66 (dm, 4H), 7.47-7.36 (m, 6H), 7.38 (s, 1H), 3.97 (t, 2H), 3.87 (s, 2H), 3.68 (t, 2H), 3.66 (s, 3H), 3.47 (t, 2H), 2.87 (t, 2H), 2.30 (s, 3H), 2.14 (s, 3H), 1.99 (br., 2H), 1.38 (s, 2H), 1.32-0.96 (br., 1OH), 0.98 (s, 9H), 0.85 (s, 6H); $^{13}$C NMR (100 MHz, DMSO-d$_6$) δ ppm 139.9, 137.6, 120.5, 64.4, 61.7, 58.9, 52.3, 46.0, 43.4, 30.2, 27.1, 24.6, 21.0, 15.5, 10.9; HRMS-ESI (m/z): [M+H]$^+$ calcd for $C_{50}H_{62}ClN_6O_4Si$: 873.4290 found: 873.4291.

Step C: methyl 6-(3-chloro-4-methyl-6,7-dihydro-5H-pyrido[2,3-c]pyridazin-8-yl)-3-[1-[[3-(2-hydroxyethoxy)-5,7-dimethyl-1-adamantyl]methyl]-5-methyl-pyrazol-4-yl]pyridine-2-carboxylate To the product from Step B (8.46 g, 9.68 mmol) in THF (95 mL) was added a 1 M solution of TBAF in THF (10.6 mL, 1.1 eq) at 0° C. and the reaction mixture was stirred for 2 h. After quenching with a saturated solution of $NH_4Cl$ and extraction with EtOAc, the combined organic phases were washed with brine, dried, and purified by column chromatography (silica gel, DCM and MeOH as eluents) to give the desired product (5.38 g, 88%).

$^1$H NMR (400 MHz, DMSO-d$_6$): δ ppm 7.86 (d, 1H), 7.71 (d, 1H), 7.38 (s, 1H), 4.46 (t, 1H), 3.97 (t, 2H), 3.87 (s, 2H), 3.70 (s, 3H), 3.40 (m, 2H), 3.35 (t, 2H), 2.87 (t, 2H), 2.30 (s, 3H), 2.15 (s, 3H), 1.99 (m, 2H), 1.42-0.95 (m, 12H), 0.87 (s, 6H); HRMS-ESI (m/z): [M+H]$^+$ calcd for $C_{34}H_{44}ClN_6O_4$: 635.3113 found: 635.3112.

Step D: methyl 6-[3-(1,3-benzothiazol-2-ylamino)-4-methyl-6,7-dihydro-5H-pyrido[2,3-c]pyridazin-8-yl]-3-[1-[[3-(2-hydroxyethoxy)-5,7-dimethyl-1-adamantyl]methyl]-5-methyl-pyrazol-4-yl]pyridine-2-carboxylate Using Buchwald General Procedure I at 130° C. for 1 h, starting from 3.7 g of the product from Step C (5.78 mmol) and 1.74 g of 1,3-benzothiazol-2-amine (2 eq), 3.1 g of the desired product (72% Yield) were obtained.

$^1$H NMR (400 MHz, DMSO-d$_6$): δ ppm 7.96 (d, 1H), 7.82 (br., 1H), 7.70 (d, 1H), 7.50 (br., 1H), 7.38 (s, 1H), 7.35 (t, 1H), 7.17 (t, 1H), 4.46 (br., 1H), 4.00 (t, 2H), 3.88 (s, 2H), 3.70 (s, 3H), 3.40 (brt., 2H), 3.35 (t, 2H), 2.86 (t, 2H), 2.32 (s, 3H), 2.16 (s, 3H), 2.03-1.94 (m, 2H), 1.42-0.96 (m, 12H), 0.87 (s, 6H); $^{13}$C NMR (100 MHz, DMSO-d$_6$) δ ppm 139.8, 137.5, 126.4, 122.4, 122.1, 119.0, 62.1, 61.5, 59.0, 52.6, 45.4, 30.2, 24.3, 21.7, 12.6, 10.9; HRMS-ESI (m/z): [M+H]$^+$ calcd for $C_4H_{49}N_8O_4S$: 749.3597 found: 749.3595.

Step E: methyl 6-[3-(1,3-benzothiazol-2-ylamino)-4-methyl-6,7-dihydro-5H-pyrido[2,3-c]pyridazin-8-yl]-3-[1-[[3,5-dimethyl-7-[2-(p-tolylsulfonyloxy)ethoxy]-1-adamantyl]methyl]-5-methyl-pyrazol-4-yl]pyridine-2-carboxylate To the product from Step D (3.85 g, 5.14 mmol) and triethylamine (2.15 mL, 3 eq) in DCM (50 mL) was added p-tolylsulfonyl 4-methylbenzenesulfonate (2.51 g, 1.5 eq) and the reaction mixture was stirred for 1 h. Purification by column chromatography (silica gel, heptane and EtOAc as eluents) afforded the desired product (3.2 g, 69%).

$^1$H NMR (400 MHz, DMSO-d$_6$): δ ppm 7.96 (d, 1H), 7.81 (br., 1H), 7.77 (d, 2H), 7.70 (d, 1H), 7.50 (br., 1H), 7.46 (d, 2H), 7.39 (s, 1H), 7.35 (t, 1H), 7.17 (t, 1H), 4.06 (t, 2H), 4.00 (t, 2H), 3.85 (s, 2H), 3.69 (s, 3H), 3.49 (t, 2H), 2.86 (t, 2H), 2.40 (s, 3H), 2.32 (s, 3H), 2.15 (s, 3H), 1.99 (m, 2H), 1.32-0.93 (m, 12H), 0.84 (s, 6H); $^{13}$C NMR (100 MHz, DMSO-d$_6$) δ ppm 139.8, 137.6, 130.6, 128.1, 126.4, 122.4, 122.1, 119, 71.5, 58.8, 58.4, 52.6, 45.4, 30.1, 24.3, 21.7, 21.6, 12.6, 10.9; HRMS-ESI (m/z): [M+H]$^+$ calcd for $C_{48}H_{55}NO_6S_2$: 903.3686 found: 903.3685.

Preparation 13: (4-methoxyphenyl)methyl 6-[3-(1,3-benzothiazol-2-ylamino)-4-methyl-6,7-dihydro-5H-pyrido[2,3-c]pyridazin-8-yl]-3-[1-[[3,5-dimethyl-7-[3-(p-tolylsulfonyloxy)propyl]-1-adamantyl]methyl]-5-methyl-pyrazol-4-yl]pyridine-2-carboxylate Step A: (4-methoxyphenyl)methyl 3-[1-[[3-[3-[tert-butyl(diphenyl)silyl]oxypropyl]-5,7-dimethyl-1-adamantyl]methyl]-5-methyl-pyrazol-4-yl]-6-[3-(3,6-dichloro-5-methyl-pyridazin-4-yl)propylamino]pyridine-2-carboxylate The mixture of the product from Preparation 11 (3.67 g, 6.79 mmol), the product from Preparation 8 (5.09 g, 1.1 eq), $Pd(AtaPhos)_2Cl_2$ (301 mg, 0.1 eq), and $Cs_2CO_3$ (6.64 g, 3 eq) in 1,4-dioxane (41 mL) and $H_2O$ (6.8 mL) was stirred at 80° C. for 18 h. Purification by column chromatography (silica gel, heptane and EtOAc as eluents) afforded the desired product (4.43 g, 64%).

$^1$H NMR (400 MHz, DMSO-d$_6$): δ ppm 7.62-7.38 (m, 1OH), 7.32 (d, 1H), 7.26 (s, 1H), 7.10 (m, 2H), 6.98 (t, 1H), 6.83 (m, 2H), 6.63 (d, 1H), 4.98 (s, 2H), 3.74 (s, 2H), 3.70 (s, 3H), 3.58 (t, 2H), 3.35 (m, 2H), 2.84 (m, 2H), 2.34 (s, 3H), 2.02 (s, 3H), 1.77 (m, 2H), 1.43 (m, 2H), 1.18-0.85 (m, 12H), 1.09 (t, 2H), 0.97 (s, 9H), 0.77 (s, 6H); HRMS-ESI (m/z): [M+H]$^+$ calcd for $C_{58}H_{71}Cl_2N_6O_4Si$: 1013.4683 found: 1013.4683;

Step B: (4-methoxyphenyl)methyl 3-[1-[[3-[3-[tert-butyl(diphenyl)silyl]oxypropyl]-5,7-dimethyl-1-adamantyl]methyl]-5-methyl-pyrazol-4-yl]-6-(3-chloro-4-methyl-6,7-dihydro-5H-pyrido[2,3-c]pyridazin-8-yl)pyridine-2-carboxylate The mixture of the product from Step A (4.43 g, 4.37 mmol), $Cs_2CO_3$ (2.84 g, 2 eq), DIPEA (1.5 mL, 2 eq) and $Pd(Ataphos)_2Cl_2$ (193 mg, 0.1 eq) in 1,4-dioxane (22 mL) was stirred at 110° C. for 18 h. After quenching with water and extracting with EtOAc, the combined organic phases were dried, concentrated, and purified by column chromatography (silica gel, DCM and EtOAc as eluents) to give the desired product (2.83 g, 66%).

$^1$H NMR (400 MHz, DMSO-d$_6$): δ ppm 7.84 (d, 1H), 7.68 (d, 1H), 7.59 (d, 4H), 7.44 (t, 2H), 7.42 (t, 4H), 7.38 (s, 1H), 7.14 (d, 2H), 6.87 (d, 2H), 5.07 (s, 2H), 3.96 (t, 2H), 3.78 (s, 2H), 3.71 (s, 3H), 3.59 (t, 2H), 2.86 (t, 2H), 2.29 (s, 3H), 2.08 (s, 3H), 1.97 (qn, 2H), 1.43 (qn, 2H), 1.12 (s, 4H), 1.10 (s, 2H), 1.09 (t, 2H), 0.97 (s, 9H), 0.95 (s, 2H), 0.94/0.91 (d+d, 4H), 0.78 (s, 6H); $^{13}$C NMR (100 MHz, DMSO-d$_6$) δ ppm 166.9, 159.6, 156.3, 153.6, 150.8, 147.7, 140.1, 137.5, 137.3, 136.0, 135.5, 133.8, 130.3, 130.1, 129.1, 128.3, 127.6, 123.1, 120.5, 115.5, 114.3, 66.8, 64.8, 64.8, 59.6, 55.6, 50.5, 48.1, 46.4, 46.0, 44.2, 39.3, 38.1, 31.7, 30.6, 27.2, 26.1, 24.6, 21.0, 19.3, 15.5, 10.9; HRMS-ESI (m/z): [M+H]$^+$ calcd for C$_{58}$H$_{70}$ClN$_6$O$_4$Si: 977.4916 found: 977.4915.

Step C: (4-methoxyphenyl)methyl 6-(3-chloro-4-methyl-6,7-dihydro-5H-pyrido[2,3-c]pyridazin-8-yl)-3-[1-[[3-(3-hydroxypropyl)-5,7-dimethyl-1-adamantyl]methyl]-5-methyl-pyrazol-4-yl]pyridine-2-carboxylate To the product from Step B (2.83 g, 2.89 mmol) in THF (95 mL) was added a 1 M solution of TBAF in THF (3.2 mL, 1.1 eq) at 0° C. and the reaction mixture was stirred for 2 h. After quenching with a saturated solution of NH$_4$Cl and extracted with EtOAc, the combined organic phases were washed with brine, dried, concentrated, and purified by column chromatography (silica gel, DCM and MeOH as eluents) to give the desired product (2.21 g, 103%).

$^1$H NMR (400 MHz, DMSO-d$_6$): δ ppm 7.85 (d, 1H), 7.70 (d, 1H), 7.39 (s, 1H), 7.17 (d, 2H), 6.90 (d, 2H), 5.09 (s, 2H), 4.34 (t, 1H), 3.96 (t, 2H), 3.79 (s, 2H), 3.74 (s, 3H), 3.32 (q, 2H), 2.86 (t, 2H), 2.29 (s, 3H), 2.09 (s, 3H), 1.98 (qn, 2H), 1.34 (qn, 2H), 1.13 (s, 2H), 1.13 (s, 4H), 1.06 (t, 2H), 0.99/0.95 (d+d, 4H), 0.97 (s, 2H), 0.78 (s, 6H); $^{13}$C NMR (100 MHz, DMSO-d$_6$) δ ppm 166.9, 159.7, 156.4, 153.6, 150.8, 147.7, 140.2, 137.5, 137.3, 136.0, 130.2, 129.1, 127.6, 123.1, 120.4, 115.5, 114.3, 66.8, 66.8, 62.1, 59.7, 55.6, 50.6, 48.2, 46.5, 46.0, 44.3, 39.7, 38.1, 31.8, 30.6, 26.5, 24.6, 21.0, 15.5, 10.9; HRMS-ESI (m/z): [M+H]$^+$ calcd for C$_{42}$H$_{52}$ClN$_6$O$_4$: 739.3739 found: 739.3739.

Step D: (4-methoxyphenyl)methyl 6-[3-(1,3-benzo-thiazol-2-ylamino)-4-methyl-6,7-dihydro-5H-pyrido[2,3-c]pyridazin-8-yl]-3-[1-[[3-(3-hydroxypropyl)-5,7-dimethyl-1-adamantyl]methyl]-5-methyl-pyrazol-4-yl]pyridine-2-carboxylate The mixture of the product from Step C (1.71 g, 2.31 mmol), 1,3-benzothiazol-2-amine (695 mg, 2 eq), Pd$_2$dba$_3$ (212 mg, 0.1 eq), XantPhos (268 mg, 0.2 eq), and DIPEA (1.2 mL, 3 eq) in cyclohexanol (14 mL) was stirred at 130° C. for 1 h. Purification by column chromatography (silica gel, heptane, DCM and MeCN as eluents) afforded the desired product (1.25 g, 63%).

$^1$H NMR (400 MHz, DMSO-d$_6$): δ ppm 12.08/10.87 (brs/brs, 1H), 7.95 (d, 1H), 7.81 (br, 1H), 7.68 (d, 1H), 7.50 (br, 1H), 7.39 (s, 1H), 7.35 (t, 1H), 7.18 (d, 2H), 7.17 (t, 1H), 6.90 (d, 2H), 5.10 (s, 2H), 4.34 (t, 1H), 3.99 (t, 2H), 3.79 (s, 2H), 3.74 (s, 3H), 3.33 (q, 2H), 2.85 (t, 2H), 2.32 (s, 3H), 2.11 (s, 3H), 1.98 (qn, 2H), 1.34 (qn, 2H), 1.14 (s, 4H), 1.14 (s, 2H), 1.07 (t, 2H), 1.00/0.95 (d+d, 2H), 0.99/0.95 (d+d, 4H), 0.79 (s, 6H); $^{13}$C NMR (100 MHz, DMSO-d$_6$) δ ppm 140.0, 137.6, 130.2, 126.4, 122.4, 122.0, 119.0, 114.3, 66.7, 62.1, 59.6, 55.6, 50.6, 48.2, 46.5, 45.4, 44.3, 39.7, 30.6, 26.5, 24.3, 21.7, 12.6, 11.0; HRMS-ESI (m/z): [M+H]$^+$ calcd for C$_{49}$H$_{57}$N$_8$O$_4$S: 853.4223 found: 853.4229.

Step E: (4-methoxyphenyl)methyl 6-[3-(1,3-benzo-thiazol-2-ylamino)-4-methyl-6,7-dihydro-5H-pyrido[2,3-c]pyridazin-8-yl]-3-[1-[[3,5-dimethyl-7-[3-(p-tolylsulfonyloxy)propyl]-1-adamantyl]methyl]-5-methyl-pyrazol-4-yl]pyridine-2-carboxylate To the product from Step D (1.25 g, 1.47 mmol) and triethylamine (0.61 mL, 3 eq) in DCM (15 mL) was added p-tolylsulfonyl 4-methylbenzenesulfonate (717 mg, 1.5 eq) and the reaction mixture was stirred for 1 h. Purification by column chromatography (silica gel, heptane and EtOAc as eluents) afforded 800 mg (54%) of the desired product.

$^1$H NMR (400 MHz, DMSO-d$_6$): δ ppm 7.95 (d, 1H), 7.88 (brs, 1H), 7.77 (m, 2H), 7.68 (d, 1H), 7.62 (brs, 1H), 7.47 (m, 2H), 7.39 (s, 1H), 7.35 (brs, 1H), 7.17 (brs, 1H), 7.10 (m, 2H), 6.90 (m, 2H), 5.09 (s, 2H), 4.00 (m, 2H), 3.98 (t, 2H), 3.77 (s, 2H), 3.74 (s, 3H), 2.85 (t, 2H), 2.40 (s, 3H), 2.32 (s, 3H), 2.09 (s, 3H), 1.98 (m, 2H), 1.45 (m, 2H), 1.17-0.8 (m, 12H), 0.98 (m, 2H), 0.77 (s, 6H); HRMS-ESI (m/z): [M+H]$^+$ calcd for C$_{56}$H$_6$3N$_8$O$_6$S$_2$: 1007.4312 found: 1007.4318.

Preparation 14: (4-methoxyphenyl)methyl 6-[3-(1,3-benzothiazol-2-ylamino)-4-methyl-6,7-dihydro-5H-pyrido[2,3-c]pyridazin-8-yl]-3-[5-methyl-1-[[3-[2-(p-tolylsulfonyloxy)ethoxy]-1-adamantyl]methyl]pyrazol-4-yl]pyridine-2-carboxylate

Step A: (4-methoxyphenyl)methyl 3-[1-[[3-[2-[tert-butyl(diphenyl)silyl]oxyethoxy]-1-adamantyl]methyl]-5-methyl-pyrazol-4-yl]-6-[3-(3,6-dichloro-5-methyl-pyridazin-4-yl)propylamino]pyridine-2-carboxylate The mixture of the product from Preparation 11 (3.67 g, 6.79 mmol), the product from Preparation 9 (4.89 g, 1.1 eq), Pd(AtaPhos)$_2$Cl$_2$ (301 mg, 0.1 eq), and Cs$_2$CO$_3$ (6.64 g, 3 eq) in 1,4-dioxane (41 mL) and H$_2$O (6.8 mL) was stirred at 80° C. for 12 h. Purification by column chromatography (silica gel, heptane and EtOAc as eluents) afforded the desired product (3.0 g, 45%).

$^1$H NMR (400 MHz, DMSO-d$_6$): δ ppm 7.69-7.37 (m, 10H), 7.31 (d, 1H), 7.24 (s, 1H), 7.12 (m, 2H), 6.98 (t, 1H), 6.83 (m, 2H), 6.62 (d, 1H), 4.99 (s, 2H), 3.76 (s, 2H), 3.70 (s, 3H), 3.66 (t, 2H), 3.45 (t, 2H), 3.35 (m, 2H), 2.85 (m, 2H), 2.34 (s, 3H), 2.12 (m, 2H), 2.02 (s, 3H), 1.77 (m, 2H), 1.65-1.33 (m, 12H), 0.97 (s, 9H); HRMS-ESI (m/z): [M+H]$^+$ calcd for C$_{55}$H$_{65}$Cl$_2$N$_6$O$_5$Si: 987.4163 found: 987.4158.

Step B: (4-methoxyphenyl)methyl 3-[1-[[3-[2-[tert-butyl(diphenyl)silyl]oxyethoxy]-1-adamantyl]methyl]-5-methyl-pyrazol-4-yl]-6-(3-chloro-4-methyl-6,7-dihydro-5H-pyrido[2,3-c]pyridazin-8-yl)pyridine-2-carboxylate The mixture of the product from Step A (3.00 g, 3.00 mmol), Cs$_2$CO$_3$ (1.95 g, 2 eq), DIPEA (1.0 mL, 2 eq), and Pd(Ataphos)$_2$Cl$_2$ (212 mg, 0.1 eq) in 1,4-dioxane (15 mL) was stirred at 110° C. for 18 h. Purification by column chromatography (silica gel, DCM and MeOH as eluents) afforded the desired product (1.74 g, 60%).

$^1$H NMR (400 MHz, DMSO-d$_6$): δ ppm 7.84 (d, 1H), 7.68 (d, 1H), 7.68-7.37 (m, 10H), 7.36 (s, 1H), 7.16 (m, 2H), 6.87 (m, 2H), 5.08 (s, 2H), 3.96 (m, 2H), 3.81 (s, 2H), 3.72 (s, 3H), 3.67 (t, 2H), 3.46 (t, 2H), 2.87 (t, 2H), 2.29 (s, 3H), 2.13 (m, 2H), 2.09 (s, 3H), 1.98 (m, 2H), 1.65-1.37 (m, 12H), 0.97 (s, 9H); HRMS-ESI (m/z): [M+H]$^+$ calcd for C$_{55}$H$_4$ClN$_6$O$_5$Si: 951.4396 found: 951.4397.

Step C: (4-methoxyphenyl)methyl 6-(3-chloro-4-methyl-6,7-dihydro-5H-pyrido[2,3-c]pyridazin-8-yl)-3-[1-[[3-(2-hydroxyethoxy)-1-adamantyl]methyl]-5-methyl-pyrazol-4-yl]pyridine-2-carboxylate To the product from Step B (1.73 g, 1.82 mmol) in THF (20 mL) was added a 1 M solution of TBAF in THF (2.0 mL, 1.1 eq) at 0° C. and the reaction mixture was stirred for 2 h. Purification by column chromatography (silica gel, DCM and MeOH as eluents) afforded the desired product (1.06 g, 82%).

$^1$H NMR (400 MHz, DMSO-d$_6$): δ ppm 7.85 (d, 1H), 7.71 (d, 1H), 7.36 (s, 1H), 7.19 (m, 2H), 6.90 (m, 2H), 5.10 (s, 2H), 4.47 (t, 1H), 3.96 (m, 2H), 3.81 (s, 2H), 3.75 (s, 3H), 3.40 (m, 2H), 3.34 (t, 2H), 2.87 (t, 2H), 2.29 (s, 3H), 2.14 (m, 2H), 2.10 (s, 3H), 1.98 (m, 2H), 1.67-1.36 (m, 12H); HRMS-ESI (m/z): [M+H]$^+$ calcd for C$_{39}$H$_{46}$ClN$_6$O$_5$: 713.3218 found: 713.3217.

Step D: (4-methoxyphenyl)methyl 6-[3-(1,3-benzo-thiazol-2-ylamino)-4-methyl-6,7-dihydro-5H-pyrido[2,3-c]pyridazin-8-yl]-3-[1-[[3-(2-hydroxyethoxy)-1-adamantyl]methyl]-5-methyl-pyrazol-4-yl]pyridine-2-carboxylate The mixture of the product from Step C (1.00 g, 1.40 mmol), 1,3-benzothiazol-2-amine (421 mg, 2 eq), Pd$_2$dba$_3$ (128 mg, 0.1 eq), XantPhos (162 mg, 0.2 eq), and DIPEA (0.72 mL, 3 eq) in cyclohexanol (10 mL) was stirred at 130° C. for 1 h. Purification by column chromatography (silica gel, heptane, then DCM and MeOH as eluents) afforded the desired product (600 mg, 53%).

$^1$H NMR (400 MHz, DMSO-d$_6$): δ ppm 12.18/10.84 (brs/brs, 1H), 7.94 (d, 1H), 7.83 (br, 1H), 7.69 (d, 1H), 7.57 (br, 1H), 7.36 (s, 1H), 7.35 (brt, 1H), 7.20 (d, 2H), 7.17 (brt, 1H), 6.91 (d, 2H), 5.11 (s, 2H), 4.47 (brt, 1H), 4.00 (t, 2H), 3.81 (s, 2H), 3.75 (s, 3H), 3.41 (brq, 2H), 3.35 (t, 2H), 2.85 (t, 2H), 2.32 (s, 3H), 2.14 (m, 2H), 2.12 (s, 3H), 1.99 (qn, 2H), 1.62/1.53 (d+d, 4H), 1.53 (s, 2H), 1.49/1.44 (d+d, 2H), 1.44 (s, 4H); $^{13}$C NMR (100 MHz, DMSO-d$_6$) δ ppm 139.9, 137.6, 130.1, 126.4, 122.4, 122.0, 118.9, 114.2, 66.7, 61.9, 61.5, 59.5, 55.6, 45.4, 44.7, 40.8, 39.5, 35.6, 30.1, 24.3, 21.7, 12.6, 10.8; HRMS-ESI (m/z): [M+H]$^+$ calcd for C$_{46}$H$_{51}$N$_8$O$_5$S: 827.3703 found: 827.3709.

Step E: (4-methoxyphenyl)methyl 6-[3-(1,3-benzo-thiazol-2-ylamino)-4-methyl-6,7-dihydro-5H-pyrido[2,3-c]pyridazin-8-yl]-3-[5-methyl-1-[[3-[2-(p-tolylsulfonyloxy)ethoxy]-1-adamantyl]methyl]pyrazol-4-yl]pyridine-2-carboxylate To the product from Step D (600 mg, 0.726 mmol) and NN-diethylethanamine (0.31 mL, 3 eq) in dichloromethane (7 mL) was added p-tolylsulfonyl 4-methylbenzenesulfonate (357 mg, 1.5 eq) and the reaction mixture was stirred for 18 h. Purification by flash chromatography (silica gel, using DCM and MeOH as eluents) afforded 354 mg (50%) of the desired product.

$^1$H NMR (500 MHz, dmso-d6) δ ppm 12.22/10.85 (brs/brs, 1H), 7.94 (d, 1H), 7.81 (br, 1H), 7.77 (d, 2H), 7.70 (d, 1H), 7.52 (br, 1H), 7.45 (d, 2H), 7.37 (s, 1H), 7.35 (t, 1H), 7.19 (d, 2H), 7.17 (t, 1H), 6.89 (d, 2H), 5.10 (s, 2H), 4.05 (t, 2H), 4.00 (t, 2H), 3.79 (s, 2H), 3.74 (s, 3H), 3.49 (t, 2H), 2.86 (t, 2H), 2.40 (s, 3H), 2.32 (s, 3H), 2.11 (m, 2H), 2.11 (s, 3H), 1.99 (qn, 2H), 1.55-1.36 (m, 12H); $^{13}$C NMR (500 MHz, dmso-d6) δ ppm 139.9, 137.6, 130.5, 130.3, 128.1, 126.4, 122.4, 122.0, 118.9, 114.2, 71.4, 66.8, 59.4, 58.2, 55.6, 45.4, 30.0, 24.2, 21.6, 21.6, 12.6, 10.9; HRMS-ESI (m/z): [M+H]$^+$ calcd for C$_{53}$H$_{57}$NO$_7$S$_2$: 981.3792 found: 981.3795.

Preparation 15: ethyl 2-(3-chloro-4-methyl-6,7-di-hydro-5H-pyrido[2,3-c]pyridazin-8-yl)-5-[3-(2-fluoro-4-iodo-phenoxy)propyl]thiazole-4-carboxy-late

Step A: 2-(3-chloro-4-methyl-6,7-dihydro-5H-pyrido[2,3-c]pyridazin-8-yl)-5-[3-(2-fluoro-4-iodo-phenoxy)propyl]thiazole-4-carboxylic acid The mixture of the product from Preparation 3a (35.39 g, 81.52 mmol) and LiOH×H$_2$O(4 eq) in 1,4-dioxane (408 mL) and water (82 mL) was stirred at 60° C. for 1 h. After quenching with a 1 M solution of HCl and extraction with EtOAc, the combined organic phases were dried, concentrated, and purified by flash chromatography (silica gel, using DCM and MeOH as eluents) to give the desired product (27.7 g, 81%).

$^1$H NMR (500 MHz, dmso-d6) δ ppm 7.56 (dd, 1H), 7.43 (brd., 1H), 6.96 (t, 1H), 4.18 (t, 2H), 4.05 (t, 2H), 3.28 (t, 2H), 2.84 (t, 2H), 2.29 (s, 3H), 2.07 (m, 2H), 1.97 (m, 2H); $^{13}$C NMR (500 MHz, dmso-d6) δ ppm 166.4, 154.8, 152.1, 151.8, 151.1, 147.1, 143.9, 135.7, 134.0, 133.8, 129.0, 124.9, 117.6, 82.3, 68.8, 46.3, 31.0, 24.0, 22.5, 19.8, 15.7; HRMS-ESI (m/z): [M+H]$^+$ calcd for C$_{21}$H$_{20}$ClFIN$_4$O$_3$S: 588.9973 found: 588.9969.

Step B: ethyl 2-(3-chloro-4-methyl-6,7-dihydro-5H-pyrido[2,3-c]pyridazin-8-yl)-5-[3-(2-fluoro-4-iodo-phenoxy)propyl]thiazole-4-carboxylate To the mixture of the product of Step A (27.7 g, 65.9 mmol), ethanol (2 eq) and PPh$_3$ (2 eq) in toluene (660 mL) and THF (20 ml) was added dropwise diisopropyl azodicar-boxylate (2 eq) and the reaction was stirred at 50° C. 1 h. Purification by flash chromatography (silica gel, using heptane and EtOAc as eluents) afforded the desired product (23.65 g, 66.4%).

$^1$H NMR (500 MHz, dmso-d6) δ ppm 7.59 (dd, 1H), 7.44 (dm, 1H), 6.98 (t, 1H), 4.29 (m, 2H), 4.25 (q, 2H), 4.08 (t, 2H), 3.24 (t, 2H), 2.89 (t, 2H), 2.32 (s, 3H), 2.09 (m, 2H), 2.04 (m, 2H), 1.28 (t, 3H); $^{13}$C NMR (500 MHz, dmso-d6) δ ppm 162.6, 155.4, 152.2, 151.7, 151.3, 147.0, 134.0, 124.9, 117.6, 82.4, 68.3, 60.7, 46.3, 30.8, 24.1, 23.1, 19.7, 15.7, 14.6; HRMS-ESI (m/z): [M+H]$^+$ calcd for C$_{23}$H$_{24}$ClFIN$_4$O$_3$S: 617.0286, found: 617.0282.

Example 1: 2-{6-[(1,3-Benzothiazol-2-yl)amino]-1,
2,3,4-tetrahydroquinolin-1-yl}-1,3-thiazole-4-car-
boxylic acid

Step A: ethyl 2-(6-bromo-1,2,3,4-tetrahydroquino-lin-1-yl)-1,3-thiazole-4-carboxylate To a solution of benzoyl isothiocyanate (380 μL, 2.83 mmol, 1.2 eq) in acetone (10 mL) was added 6-bromo-1,2,3,4-tetrahydroquinoline (500 mg, 2.36 mmol, 1 eq) and the mixture was heated at reflux for 1 h. The mixture was poured onto ice water and the precipitate filtered, washed with water and dried to give a pale yellow solid. The solid was added to 1N aqueous sodium hydroxide (10 mL) and the suspension was heated at 80° C. for 30 min, cooled to ambient temperature and poured onto cold 1N aqueous hydrochloric acid. The pH was adjusted to pH 8 with saturated aqueous sodium carbonate and the solids were collected by filtration and washed with water to afford a yellow solid. A suspension of the solid and ethyl bromopyruvate (296 μL, 2.36 mmol, 1 eq) in ethanol (10 mL) was heated at reflux for 2 h. The mixture was allowed to cool to ambient temperature, then partitioned between ethyl acetate and water. The aqueous phase was extracted with ethyl acetate (3×50 mL) and the combined organic extracts were washed with brine (50 mL), dried (magnesium sulfate) and concentrated in vacuo. Purification by automated flash column chromatography (CombiFlash Rf, 24 g RediSep™ silica cartridge) eluting with a gradient of 0-10% ethyl acetate in iso-heptane afforded the desired product as a yellow gum (232 mg, 0.63 mmol, 27%).

LC/MS ($C_{15}H_{15}BrN_2O_2S$) 367 [M+H]$^+$; RT 1.42 (LCMS-V-B1)

$^1$H NMR (400 MHz, DMSO-d6) δ 7.99 (d, 1H), 7.87 (s, 1H), 7.53-7.48 (m, 1H), 7.44-7.38 (m, 1H), 4.27 (q, 2H), 3.83 (t, 2H), 2.83-2.73 (m, 2H), 2.00-1.90 (m, 2H), 1.29 (t, 3H).

Step B: ethyl 2-{6-[(1,3-benzothiazol-2-yl)amino]-1,2,3,4-tetrahydroquinolin-1-yl}-1,3-thiazole-4-car-boxylate To an oven-dried microwave vial was added the product from Step A (93.8 mg, 0.26 mmol, 1 eq), 2-aminobenzothiazole (46.0 mg, 0.31 mmol, 1.2 eq), cesium carbonate (166 mg, 0.51 mmol, 2 eq) and 1,4-dioxane (4 mL), and the mixture was sparged with nitrogen (10 mins) before adding BrettPhos (13.7 mg, 0.03 mmol, 0.1 eq) and tris(dibenzylideneacetone)dipalladium(0) (23.4 mg, 0.03 mmol, 0.1 eq), and heating at 120° C. for 2 h under microwave irradiation. The reaction was partitioned between ethyl acetate and water, the aqueous phase was extracted with ethyl acetate (3×50 mL), and the combined organic extracts were washed with brine (50 mL), dried (magnesium sulfate) and concentrated in vacuo. Purification by automated flash column chromatography (CombiFlash Rf, 12 g RediSep™ silica cartridge) eluting with a gradient of 0-20% ethyl acetate in iso-heptane afforded the desired product as a yellow gum (85.1 mg, 0.19 mmol, 76%).

LC/MS ($C_{22}H_{20}N_4O_2S2$) 437 [M+H]$^+$; RT 1.40 (LCMS-V-B1)

$^1$H NMR (400 MHz, DMSO-d6) δ 7.87 (d, 1H), 7.83-7.78 (m, 1H), 7.69-7.65 (m, 1H), 7.63-7.57 (m, 2H), 7.36-7.29 (m, 1H), 7.18-7.13 (m, 1H), 7.03-6.98 (m, 1H), 4.28 (q, J=7.08 Hz, 2H), 3.92-3.84 (m, 2H), 2.80 (t, J=6.30 Hz, 2H), 2.00-1.89 (m, 2H), 1.30 (t, J=7.09 Hz, 2H).

Step C: 2-{6-[(1,3-benzothiazol-2-yl)amino]-1,2,3,4-tetrahydroquinolin-1-yl}-1,3-thiazole-4-carboxylic acid To a solution of the product from Step B (85.1 mg, 0.19 mmol, 1 eq) in tetrahydrofuran (2 mL) and methanol (1 mL), was added a 1N aqueous sodium hydroxide (0.39 mL, 0.39 mmol, 2 eq) and the mixture was heated at 50° C. for 3 h. The reaction was partitioned between ethyl acetate and water, the aqueous phase was extracted with ethyl acetate (3×30 mL), and the combined organic extracts were washed with brine (50 mL), dried (magnesium sulfate) and concentrated in vacuo. Purification by automated flash column chromatography (CombiFlash Rf, 12 g RediSep™ silica cartridge) eluting with a gradient of 0-6% methanol in dichloromethane afforded material that was further purified by preparative HPLC (HPLC-V-A2) to afford the desired product as a cream solid (1.2 mg, 1.5%).

HRMS-ESI (m/z) [M+H]+ calcd for $C_{20}H_{17}N_4O_2S_2$: 409.0793, found 409.0830

Example 2: 2-{5-[(1,3-Benzothiazol-2-yl)amino]-1H-indol-1-yl}-1,3-thiazole-4-carboxylic acid

Step A: methyl 2-(5-bromo-1H-indol-1-yl)-1,3-thi-azole-4-carboxylate

To a cooled solution of 5-bromoindole (150 mg, 0.77 mmol, 1 eq) in dimethylformamide (2 mL) was added sodium hydride (60% dispersion; 36.7 mg, 1.53 mmol, 2 eq) portionwise and the mixture was stirred at 0° C. for 30 min, before the addition of methyl 2-chloro-4-thiazolecarboxylate (272 mg, 1.53 mmol, 2 eq), then allowing to warm to ambient temperature and stir overnight. The reaction was partitioned between ethyl acetate and water, the aqueous phase was extracted with ethyl acetate (3×30 mL), and the combined organic extracts were washed with brine (3×30 mL), dried (magnesium sulfate) and concentrated in vacuo. Purification by automated flash column chromatography (CombiFlash Rf, 12 g RediSep™ silica cartridge) eluting with a gradient of 0-20% ethyl acetate in iso-heptane afforded the desired product as a yellow solid (72.8 mg, 0.22 mmol, 28%).

LC/MS ($C_{13}H_9BrN_2O_2S$) 339 [M+H]$^+$; RT 1.35 (LCMS-V-B1)

$^1$H NMR (400 MHz, DMSO-d6) δ 8.41-8.38 (m, 1H), 8.37 (s, 1H), 8.02 (d, J=3.5 Hz, 1H), 7.93 (d, J=2.0 Hz, 1H), 7.57 (dd, J=8.8, 2.0 Hz, 1H), 6.86 (dd, J=3.5, 0.8 Hz, 1H), 3.89 (s, 3H).

Step B: methyl 2-{5-[(1,3-benzothiazol-2-yl) amino]-1H-indol-1-yl}-1,3-thiazole-4-carboxylate To an oven-dried microwave vial was added the product from Step A (72.8 mg, 0.22 mmol, 1 eq), 2-aminobenzothi-azole (38.9 mg, 0.26 mmol, 1.2 eq), cesium carbonate (141 mg, 0.43 mmol, 2 eq) and 1,4-dioxane (2 mL) and the mixture was sparged with nitrogen (10 mins) before adding BrettPhos (11.6 mg, 0.02 mmol, 0.1 eq) and tris(diben-zylideneacetone)dipalladium(0) (19.8 mg, 0.02 mmol, 0.1 eq), then heating at 120° C. for 2 h under microwave irradiation. The reaction was partitioned between ethyl acetate and water, the aqueous phase was extracted with ethyl acetate (3×30 mL), and the combined organic extracts were washed with brine (30 mL), dried (magnesium sulfate) and concentrated in vacuo. Purification by automated flash column chromatography (CombiFlash Rf, 12 g RediSep™ silica cartridge) eluting with a gradient of 0-20% ethyl acetate in iso-heptane afforded the desired product as a pale yellow solid (10.5 mg, 0.03 mmol, 12%).

LC/MS ($C_{20}H_{14}N_4O_2S_2$) 407 [M+H]$^+$; RT 1.35 (LCMS-V-B1)

$^1$H NMR (400 MHz, DMSO-d6) δ 8.39 (d, J=8.9 Hz, 1H), 8.34 (d, J=4.4 Hz, 1H), 7.96 (d, J=3.6 Hz, 1H), 7.84-7.78 (m, 1H), 7.67-7.57 (m, 2H), 7.39-7.30 (m, 2H), 7.20-7.12 (m, 1H), 6.92 (d, J=3.7 Hz, 1H), 3.90 (s, 3H).

Step C: 2-{5-[(1,3-benzothiazol-2-yl)amino]-1H-indol-1-yl}-1,3-thiazole-4-carboxylic acid To a solution of the product from Step B (10.5 mg, 0 mol, 1 eq) in tetrahydrofuran (2 mL) and methanol (1 mL) was added 1N aqueous sodium hydroxide (0.05 mL, 0.05 mmol, 2 eq) and the mixture was heated at 50° C. for 2 h. The reaction was partitioned between ethyl acetate and water, the aqueous phase was extracted with ethyl (3×30 mL), and the combined organic extracts were washed with brine (50 mL), dried (magnesium sulfate) and concentrated in vacuo. Purification by preparative HPLC (HPLC-V-A2) afforded the desired product as a cream solid (3.5 mg, 0.01 mmol, 35%).

HRMS-ESI (m/z) [M+H]+ calcd for $C_{19}H_{13}N_4O_2S_2$: 393.0480, found 393.0503

Example 3: 2-{5-[(1,3-Benzothiazol-2-yl)amino]-2, 3-dihydro-1H-indol-1-yl}-1,3-thiazole-4-carboxylic acid

Step A: ethyl 2-(5-bromo-2,3-dihydro-1H-indol-1-yl)-1,3-thiazole-4-carboxylate To a solution of benzoyl isothiocyanate (0.33 mL, 2.42 mmol, 1.2 eq) in acetone (10 mL) was added 5-bromoin-doline (400 mg, 2.02 mmol, 1 eq) and the mixture was heated at reflux for 1 h. The reaction was poured onto ice water and the precipitate filtered, washed with water and dried to give a pale yellow solid. The solid was added to 1N aqueous sodium hydroxide (10 mL) and the suspension was heated at 80° C. for 30 min, allowed to cool to ambient temperature and poured onto cold 1N aqueous hydrochloric acid. The pH was adjusted to pH 8 with saturated aqueous sodium carbonate, and the solids were collected by filtration and washed with water to afford a yellow solid. A suspension of the solid and ethyl bromopyruvate (253 μL, 2.02 mmol, 1 eq) in ethanol (10 mL) was heated at reflux for 2 h then allowed to cool to ambient temperature. The reaction was partitioned between ethyl acetate and water, the aqueous phase was extracted with ethyl acetate (3×50 mL), and the combined organic extracts were washed with brine (50 mL), dried (magnesium sulfate) and concentrated in vacuo. Puri-fication by automated flash column chromatography (Com-biFlash Rf, 24 g RediSep™ silica cartridge) eluting with a gradient of 0-20% ethyl acetate in iso-heptane afforded the desired product as a yellow solid (377 mg, 1.07 mmol, 53%).

LC/MS ($C_{14}H_{13}BrN_2O_2S$) 353 [M+H]$^+$; RT 1.39 (LCMS-V-B1)

$^1$H NMR (400 MHz, DMSO-d6) δ 8.00 (d, J=8.4 Hz, 1H), 7.92 (s, 1H), 7.57-7.53 (m, 1H), 7.47-7.44 (m, 1H), 4.30 (q, J=7.1 Hz, 2H), 4.08 (t, 2H), 3.34-3.26 (m, 2H), 1.31 (t, 3H).

Step B: ethyl 2-{5-[(1,3-benzothiazol-2-yl)amino]-2,3-dihydro-1H-indol-1-yl}-1,3-thiazole-4-carboxy-late To an oven-dried microwave vial was added the product from Step A (100 mg, 0.28 mmol, 1 eq), 2-aminobenzothi-azole (51.0 mg, 0.34 mmol, 1.2 eq), cesium carbonate (129 mg, 0.4 mmol, 2 eq), and 1,4-dioxane (2 mL) and the mixture was sparged with nitrogen (10 mins) before adding BrettPhos (10.6 mg, 0.02 mmol, 0.1 eq) and tris(diben-zylideneacetone)dipalladium(0) (18.2 mg, 0.02 mmol, 0.1 eq), then heating at 120° C. for 1 h under microwave irradiation. The reaction was partitioned between ethyl acetate and water, the aqueous phase was extracted with ethyl acetate (3×50 mL), and the combined organic extracts were washed with brine (50 mL), dried (magnesium sulfate) and concentrated in vacuo. Purification by automated flash column chromatography (CombiFlash Rf, 24 g RediSep™ silica cartridge) eluting with a gradient 0-40% ethyl acetate in iso-heptane afforded the desired product as a brown gum (29.8 mg, 0.07 mmol, 36%).

LC/MS (C$_{21}$H$_{18}$N$_4$O$_2$S$_2$) 423 [M+H]$^+$; RT 1.38 (LCMS-V-B1)

$^1$H NMR (400 MHz, DMSO-d6) δ 8.01 (d, 1H), 7.87 (s, 1H), 7.83-7.78 (m, 1H), 7.61-7.57 (m, 1H), 7.45 (s, 1H), 7.33-7.28 (m, 1H), 7.18-7.10 (m, 1H), 7.00 (td, J=1.24, 7.55 Hz, 1H), 4.31 (q, J=7.12 Hz, 2H), 4.13-4.06 (m, 2H), 3.43-3.34 (m, 2H), 1.33 (t, J=7.12 Hz, 3H).

Step C: 2-{5-[(1,3-benzothiazol-2-yl)amino]-2,3-dihydro-1H-indol-1-yl}-1,3-thiazole-4-carboxylic acid To a solution of the product from Step B (29.8 mg, 0.07 mmol, 1 eq) in tetrahydrofuran (2 mL) and methanol (1 mL), was added 1N aqueous sodium hydroxide (0.14 mL, 0.14 mmol, 2 eq) and the mixture was heated at 50° C. for 1 h. The reaction was partitioned between ethyl acetate and water, the aqueous phase was extracted with ethyl acetate (3×30 mL), and the combined organic extracts were washed with brine (50 mL), dried (magnesium sulfate) and concentrated in vacuo. Purification by automated flash column chromatography (CombiFlash Rf, 4 g RediSep™ silica cartridge) eluting with a gradient of 0-15% methanol in dichloromethane afforded material that was further purified by preparative HPLC (HPLC-V-A2) to afford the desired product as a cream solid (3.7 mg, 0.01 mmol, 13%).

HRMS-ESI (m/z) [M+H]+ calcd for C$_{19}$H$_{15}$N$_4$O$_2$S$_2$: 395.0636, found 395.0659

Example 4: 2-{7-[(1,3-Benzothiazol-2-yl)amino]-3,4-dihydro-2H-1,4-benzoxazin-4-yl}-1,3-thiazole-4-carboxylic acid

Step A: ethyl 2-(7-bromo-3,4-dihydro-2H-1,4-benzoxazin-4-yl)-1,3-thiazole-4-carboxylate To a solution of benzoyl isothiocyanate (301 μL, 2.24 mmol, 1.2 eq) in acetone (10 mL) was added 7-bromo-3,4-dihydro-2H-benzo[b][1,4]oxazine (400 mg, 1.87 mmol, 1 eq) and the mixture was heated at reflux for 1 h. The reaction was poured onto ice water and the precipitate filtered, washed with water and dried to give a pale yellow solid. The solid was added to 1N sodium hydroxide (10 mL) and the suspension was heated at 80° C. for 30 min, cooled to ambient temperature and poured onto cold 1N aqueous hydrochloric acid. The pH was adjusted to pH 8 with saturated aqueous sodium carbonate, the solids were collected by filtration and washed with water to afford a yellow solid. A suspension of the solid and ethyl bromopyruvate (235 μL, 1.87 mmol, 1 eq) in ethanol (10 mL) was heated at reflux for 2 h then allowed to cool to ambient temperature. The reaction was partitioned between ethyl acetate and water, the aqueous phase was extracted with ethyl acetate (3×50 mL), and the combined organic extracts were washed with brine (50 mL), dried (magnesium sulfate) and concentrated in vacuo. Purification by automated flash column chromatography (CombiFlash Rf, 24 g RediSep™ silica cartridge) eluting with a gradient 0-20% ethyl acetate in iso-heptane afforded the desired product as a yellow solid (264 mg, 0.71 mmol, 38%).

LC/MS (C$_{14}$H$_{13}$BrN$_2$O$_3$S) 369 [M+H]$^+$; RT 1.36 (LCMS-V-B1)

$^1$H NMR (400 MHz, DMSO-d6) δ 8.14 (d, J=8.76 Hz, 1H), 7.94 (s, 1H), 7.26-7.11 (m, 2H), 4.37-4.21 (m, 4H), 4.07-3.99 (m, 2H), 1.29 (t, 3H).

Step B: ethyl 2-{7-[(1,3-benzothiazol-2-yl)amino]-3,4-dihydro-2H-1,4-benzoxazin-4-yl}-1,3-thiazole-4-carboxylate To an oven-dried microwave vial was added the product from Step A (173 mg, 0.47 mmol, 1 eq), 2-aminobenzothiazole (105 mg, 0.7 mmol, 1.5 eq), potassium tert-butoxide (105 mg, 0.94 mmol, 2 eq) and 1,4-dioxane (5 mL), and the mixture was sparged with nitrogen (10 mins) before adding BrettPhos (37.7 mg, 0.07 mmol, 0.15 eq) and tris(dibenzylideneacetone)dipalladium(0) (42.9 mg, 0.05 mmol, 0.1 eq), then heating at 140° C. for 1 h under microwave irradiation. The reaction was partitioned between ethyl acetate and water, the aqueous phase was extracted with ethyl acetate (3×50 mL), and the combined organic extracts were washed with brine (50 mL), dried (magnesium sulfate) and concentrated in vacuo. Purification by automated flash column chromatography (CombiFlash Rf, 12 g RediSep™ silica cartridge) eluting with a gradient of 0-30% ethyl acetate in iso-heptane afforded the desired product as a pale yellow solid (91.4 mg, 0.21 mmol, 45%) that was used directly in the next step without further purification.

LC/MS (C$_{21}$H$_{18}$N$_4$O$_3$S2) 439 [M+H]$^+$; RT 1.35 (LCMS-V-B1) Step C: 2-{7-[(1,3-benzothiazol-2-yl)amino]-3,4-dihydro-2H-1,4-benzoxazin-4-yl}-1,3-thiazole-4-carboxylic acid To a solution of the product from Step B (91.4 mg, 0.21 mmol, 1 eq) in tetrahydrofuran (3 mL) and methanol (1 mL), was added 1N aqueous sodium hydroxide (0.42 mL, 0.42 mmol, 2 eq) and the mixture was heated at 50° C. for 2 h. The reaction was partitioned between ethyl acetate and water, the aqueous phase was extracted with ethyl acetate (3×30 mL), and the combined organic extracts were washed with brine (50 mL), dried (magnesium sulfate) and concentrated in vacuo. Purification by preparative HPLC (HPLC-V-A1) afforded the desired product as a cream solid (1.5 mg, 2%).

LC/MS (C$_{19}$H$_{14}$N$_4$O$_3$S2) 411 [M+H]$^+$; RT 1.18 (LCMS-V-B1)

$^1$H NMR (400 MHz, DMSO-d6) δ 10.51 (s, 1H), 8.02 (d, J=8.9 Hz, 1H), 7.81 (dd, J=7.8, 1.2 Hz, 1H), 7.69-7.59 (m,

3H), 7.33 (td, J=7.7, 1.3 Hz, 1H), 7.24 (dd, J=8.9, 2.5 Hz, 1H), 7.16 (td, J=7.6, 1.2 Hz, 1H), 4.30 (t, J=4.4 Hz, 2H), 4.03 (t, J=4.5 Hz, 2H).

HRMS-ESI (m/z) [M+H]+ calcd for $C_{19}H_{15}N_4O_3S_2$: 411.0586, found 411.0610

Example 5: 6-{5-[(1,3-Benzothiazol-2-yl)amino]-1H-indol-1-yl}pyridine-2-carboxylic acid

Step A: 6-(5-iodo-1H-indol-1-yl)pyridine-2-carboxylic acid

To a stirred solution of 5-iodoindole (170 mg, 0.7 mmol, 1 eq) in 1,4-dioxane (5 mL)/dimethylformamide (1 mL) was added sodium hydride (60% dispersion; 20.1 mg, 0.84 mmol, 1.2 eq) portionwise over 20 minutes, then the mixture was stirred for 30 min before the addition of ethyl 6-chloropicolinate (143 mg, 0.77 mmol, 1.1 eq) and stirring at 70° C. overnight. The reaction was partitioned between ethyl acetate and water, the aqueous phase was extracted with ethyl acetate (3×30 mL), and the combined organic extracts were washed with brine (3×30 mL), dried (magnesium sulfate) and concentrated in vacuo. Purification by automated flash column chromatography (CombiFlash Rf, 12 g RediSep™ silica cartridge) eluting with a gradient of 0-30% ethyl acetate in iso-heptane afforded the desired product as a yellow solid (38.3 mg, 0.11 mmol, 15%).

LC/MS ($C_{14}H_9IN_9N_2O_2$) 365 [M+H]+; RT 1.22 (LCMS-V-B1)

$^1$H NMR (400 MHz, DMSO-d6) δ 13.47 (s, 1H), 8.64 (d, J=8.8 Hz, 1H), 8.20-8.17 (m, 1H), 8.16-8.13 (m, 1H), 8.08-8.02 (m, 2H), 7.93 (dd, J=7.5, 0.8 Hz, 1H), 7.59 (dd, J=1.8 Hz, 1H), 6.78 (dd, J=3.6, 0.7 Hz, 1H).

Step B: 6-{5-[(1,3-benzothiazol-2-yl)amino]-1H-indol-1-yl}pyridine-2-carboxylic acid To an oven-dried microwave vial was added the product from Step A (38.3 mg, 0.11 mmol, 1 eq), 2-aminobenzothiazole (19 mg, 0.13 mmol, 1.2 eq), sodium tert-butoxide (20.2 mg, 0.21 mmol, 2 eq) and 1,4-dioxane (2 mL) and the mixture was sparged with nitrogen (10 mins) before adding BrettPhos (5.65 mg, 0.01 mmol, 0.1 eq) and tris(dibenzylideneacetone)dipalladium(0) (9.63 mg, 0.01 mmol, 0.1 eq), then heating at 140° C. for 4 h under microwave irradiation. The reaction was partitioned between ethyl acetate and water, the aqueous phase was extracted with ethyl acetate (3×50 mL), and the combined organic extracts were washed with brine (50 mL), dried (magnesium sulfate) and concentrated in vacuo. Purification by preparative HPLC (HPLC-V-A2) afforded the desired product as a cream solid (0.8 mg, 2%).

HRMS-ESI (m/z) [M+H]+ calcd for $C_{21}H_{15}N_4O_2S$: 387.0916, found 387.0943

Example 6: 2-{5-[(1,3-Benzothiazol-2-yl)amino]-1H-pyrrolo[2,3-b]pyridin-1-yl}-1,3-thiazole-4-carboxylic acid

Step A: ethyl 2-{5-bromo-1H-pyrrolo[2,3-b]pyridin-1-yl}-1,3-thiazole-4-carboxylate To a solution of 5-bromo-1H-pyrrolo[2,3-b]pyridine (250 mg, 1.27 mmol, 1 eq) in 1,4-dioxane (5 mL) and dimethylformamide (2 mL) was added sodium hydride (60% dispersion; 36.5 mg, 1.52 mmol, 1.2 eq) portionwise over 20 mins and the mixture was stirred at ambient temperature for 30 min before the addition of ethyl 2-bromo-1,3-thiazole-4-carboxylate (449 mg, 1.9 mmol, 1.5 eq). The mixture was heated at reflux for 2 h then allowed to cool to ambient temperature and the resultant precipitate was collected by filtration and dried under vacuum to afford the desired product as a cream solid (300 mg, 0.85 mmol, 67%).

LC/MS ($C_{13}H_{10}BrN_3O_2S$) 352 [M+H]+; RT 1.41 (LCMS-V-B1)

$^1$H NMR (400 MHz, DMSO-d6) δ 8.61 (d, J=2.2 Hz, 1H), 8.48 (d, J=2.2 Hz, 1H), 8.38 (s, 1H), 8.33 (d, J=3.9 Hz, 1H), 6.88 (d, J=3.8 Hz, 1H), 4.34 (q, J=7.1 Hz, 2H), 1.34 (t, J=7.1 Hz, 3H).

Step B: ethyl 2-{5-[(1,3-benzothiazol-2-yl)amino]-1H-pyrrolo[2,3-b]pyridin-1-yl}-1,3-thiazole-4-carboxylate To an oven-dried microwave vial was added the product from Step A (200 mg, 0.57 mmol, 1 eq), 2-aminobenzothiazole (128 mg, 0.85 mmol, 1.5 eq), cesium carbonate (370 mg, 1.14 mmol, 2 eq) and 1,4-dioxane (3 mL) and the mixture was sparged with nitrogen (10 mins) before the addition of tris(dibenzylideneacetone)dipalladium(0) (52 mg, 0.06 mmol, 0.1 eq) and Xantphos (64.8 mg, 0.12 mmol, 0.2 eq) then heating at 120° C. for 6 h under microwave irradiation. The reaction was partitioned between ethyl acetate and water, the aqueous phase was extracted with ethyl acetate (3×30 mL), and the combined organic extracts were washed with brine (30 mL), dried (magnesium sulfate) and concentrated in vacuo. Purification by automated flash column chromatography (CombiFlash Rf, 12 g RediSep™ silica cartridge) eluting with a gradient of 0-70% ethyl acetate in iso-heptane afforded the crude desired product as a yellow gum that was used directly in the subsequent step without further purification.

LC/MS ($C_{20}H_{15}N_5O_2S_2$) 422 [M+H]$^+$; RT 1.37 (LCMS-V-B1)

Step C: 2-{5-[(1,3-benzothiazol-2-yl)amino]-1H-pyrrolo[2,3-b]pyridin-1-yl}-1,3-thiazole-4-carboxylic acid To a solution of the product from Step B (61.2 mg, 0.15 mmol, 1 eq) in tetrahydrofuran (3 mL) and methanol (1 mL), was added 1N aqueous sodium hydroxide (0.29 mL, 0.29 mmol, 2 eq) and the mixture was heated at 50° C. for 2 h. The reaction was concentrated in vacuo and the residue suspended in water and acidified to pH 6 with 1N aqueous hydrochloric acid. The mixture was partitioned between ethyl acetate and water, the aqueous phase was extracted with ethyl acetate (3×30 mL), and the combined organic extracts were washed with brine (50 mL), dried (magnesium sulfate) and concentrated in vacuo. Purification by reverse phase automated flash chromatography (CombiFlash Rf, C18 5.5 g RediSep column) eluting with a gradient of 5-95% acetonitrile in water afforded the desired product as a white solid (2.5 mg, 0.01 mmol, 4%).

HRMS-ESI (m/z) [M+H]+ calcd for $C_{18}H_{12}N_5O_2S_2$: 394.0432, found 394.0459

Example 7: 2-{5-[(1,3-Benzothiazol-2-yl)amino]-1H-pyrrolo[2,3-c]pyridin-1-yl}-1,3-thiazole-4-carboxylic acid

Step A: ethyl 2-{5-chloro-1H-pyrrolo[2,3-c]pyridin-1-yl}-1,3-thiazole-4-carboxylate To a solution of 5-chloro-1H-pyrrolo[2,3-c]pyridine (300 mg, 1.97 mmol, 1 eq) in 1,4-dioxane (5 mL) and dimethylformamide (2 mL) was added sodium hydride (60% dispersion; 56.6 mg, 2.36 mmol, 1.2 eq) portionwise over 20 mins and the mixture was stirred at ambient temperature for 30 min, before the addition of ethyl 2-bromo-1,3-thiazole-4-carboxylate (696 mg, 2.95 mmol, 1.5 eq) and heating at reflux for 2 h. The reaction was allowed to cool to ambient temperature and the resultant precipitate was collected by filtration and drying under vacuum to afford the desired product as a pale brown solid (518 mg, 1.68 mmol, 86%).

LC/MS ($C_{13}H_{10}ClN_3O_2S$) 308 [M+H]$^+$; RT 1.19 (LCMS-V-B1)

$^1$H NMR (400 MHz, DMSO-d6) δ 9.48 (s, 1H), 8.39 (s, 1H), 8.33 (d, J=3.5 Hz, 1H), 7.85 (d, J=0.9 Hz, 1H), 6.93 (dd, J=3.5, 0.8 Hz, 1H), 4.37 (q, J=7.1 Hz, 2H), 1.36 (t, J=7.1 Hz, 3H).

Step B: ethyl 2-{5-[(1,3-benzothiazol-2-yl)amino]-1H-pyrrolo[2,3-c]pyridin-1-yl}-1,3-thiazole-4-carboxylate To an oven-dried microwave vial was added the product from Step A (300 mg, 0.97 mmol, 1 eq), 2-aminobenzothiazole (220 mg, 1.46 mmol, 1.5 eq), cesium carbonate (635 mg, 1.95 mmol, 2 eq), and 1,4-dioxane (7 mL) and the mixture was sparged with nitrogen (10 mins) before the addition of tris(dibenzylideneacetone)dipalladium(0) (89.3 mg, 0.1 mmol, 0.1 eq) and Xantphos (113 mg, 0.19 mmol, 0.2 eq) then heating at 130° C. for 8 h under microwave irradiation. The reaction was partitioned between ethyl acetate and water, the aqueous phase was extracted with ethyl acetate (3×50 mL), and the combined organic extracts were washed with brine (30 mL), dried (magnesium sulfate) and concentrated in vacuo. Purification by automated flash column chromatography (CombiFlash Rf, 12 g RediSep™ silica cartridge) eluting with a gradient of 0-70% ethyl acetate in iso-heptane afforded the desired product as a yellow solid (17.3 mg, 0.04 mmol, 4%).

LC/MS ($C_{20}H_{15}N_5O_2S_2$) 422 [M+H]$^+$; RT 1.34 (LCMS-V-B1)

$^1$H NMR (400 MHz, DMSO-d6) δ 11.52 (s, 1H), 9.53 (t, J=0.9 Hz, 1H), 8.34 (s, 1H), 8.22 (d, J=3.5 Hz, 1H), 7.87 (d, 1H), 7.61 (d, J=8.1 Hz, 1H), 7.54-7.49 (m, 1H), 7.40-7.27 (m, 1H), 7.21-7.14 (m, 1H), 6.94 (dd, J=3.5, 0.7 Hz, 1H), 4.40 (q, J=7.1 Hz, 2H), 1.38 (t, J=7.1 Hz, 3H).

Step C: 2-{5-[(1,3-benzothiazol-2-yl)amino]-1H-pyrrolo[2,3-c]pyridin-1-yl}-1,3-thiazole-4-carboxylic acid To a solution of the product from Step B (17.3 mg, 0.04 mmol, 1 eq) in tetrahydrofuran (3 mL) and methanol (1 mL), was added 1N aqueous sodium hydroxide (0.08 mL, 0.08 mmol, 2 eq) and the mixture was heated at 50° C. for 2 h. The reaction was concentrated in vacuo and the residue was suspended in water and acidified to pH 7 with 1N aqueous hydrochloric acid. The solids were collected by filtration, washed with methanol, then diethyl ether, and dried under vacuum to afford the desired product as a cream solid (9.1 mg, 0.02 mmol, 56%).

HRMS-ESI (m/z) [M+H]+ calcd for $C_{18}H_{12}N_5O_2S_2$: 394.0432, found 394.0452

Example 8: 2-{3-[(1,3-Benzothiazol-2-yl)amino]-7H-pyrrolo[2,3-c]pyridazin-7-yl}-1,3-thiazole-4-carboxylic acid

Step A: ethyl 2-{3-chloro-7H-pyrrolo[2,3-c]pyridazin-7-yl}-1,3-thiazole-4-carboxylate To a solution of 3-chloro-7H-pyrrolo[2,3-c]pyridazine (285 mg, 1.86 mmol, 1 eq) in 1,4-dioxane (5 mL) and dimethylformamide (2 mL) was added sodium hydride (60% dispersion; 53.4 mg, 2.23 mmol, 1.2 eq) portionwise over 20 mins, then the mixture was stirred at ambient temperature for 30 min, before the addition of ethyl 2-chlorothiazole-4-carboxylate (533 mg, 2.78 mmol, 1.5 eq) and heating at reflux for 2 h. The reaction was partitioned between ethyl acetate and water, the aqueous phase was extracted with ethyl acetate (3×40 mL), and the combined organic extracts were washed with brine, dried (magnesium sulfate) and concentrated in vacuo. Purification by automated flash column chromatography (CombiFlash Rf, 24 g RediSep™ silica cartridge) eluting with a gradient of 0-40% ethyl acetate in iso-heptane afforded the desired product as a peach solid (388 mg, 1.26 mmol, 68%).

LC/MS ($C_{12}H_9ClN_4O_2S$) 309 [M+H]$^+$; RT 1.14 (LCMS-V-B1)

$^1$H NMR (400 MHz, DMSO-d6) δ 8.69 (d, J=3.8 Hz, 1H), 8.46 (s, 1H), 8.30 (s, 1H), 6.97 (d, J=3.8 Hz, 1H), 4.36 (q, J=7.1 Hz, 2H), 1.35 (t, J=7.1 Hz, 3H).

Step B: ethyl 2-{3-[(1,3-benzothiazol-2-yl)amino]-7H-pyrrolo[2,3-c]pyridazin-7-yl}-1,3-thiazole-4-carboxylate To an oven-dried microwave vial was added the product from Step A (388 mg, 1.26 mmol, 1 eq), 2-aminobenzothiazole (283 mg, 1.89 mmol, 1.5 eq), cesium carbonate (819 mg, 2.51 mmol, 2 eq), and 1,4-dioxane (10 mL) and the mixture was sparged with nitrogen (10 mins) before the addition of tris(dibenzylideneacetone)dipalladium(0) (115 mg, 0.13 mmol, 0.1 eq) and Xantphos (145 mg, 0.25 mmol, 0.2 eq), then heating at 130° C. for 6 h under microwave irradiation. The reaction was partitioned between ethyl acetate and water, the aqueous phase was extracted with ethyl acetate (3×50 mL), and the combined organic extracts were washed with brine (30 mL), dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a brown solid (112 mg, 0.27 mmol, 21%).

LC/MS ($C_{19}H_{14}N_6O_2S_2$) 423 [M+H]$^+$; RT 1.29 (LCMS-V-B1)

$^1$H NMR (400 MHz, DMSO-d6) δ 11.84 (s, 1H), 8.58 (d, J=3.9 Hz, 1H), 8.41 (s, 1H), 7.95 (d, J=7.8 Hz, 1H), 7.91 (s, 1H), 7.71-7.63 (m, 1H), 7.40 (ddd, J=8.2, 7.2, 1.3 Hz, 1H), 7.24 (td, J=7.6, 1.1 Hz, 1H), 6.99 (d, J=3.9 Hz, 1H), 4.36 (q, J=7.1 Hz, 3H), 1.35 (t, J=7.1 Hz, 3H).

Step C: 2-{3-[(1,3-benzothiazol-2-yl)amino]-7H-pyrrolo[2,3-c]pyridazin-7-yl}-1,3-thiazole-4-carboxylic acid To a solution of the product from Step B (112 mg, 0.27 mmol, 1 eq) in tetrahydrofuran (5 mL) and methanol (1.5 mL) was added 1N aqueous sodium hydroxide (0.53 mL, 0.53 mmol, 2 eq) and the mixture was heated at 50° C. for 2 h. The reaction was concentrated in vacuo, the residue was suspended in water, and the solids were collected by filtration. Purification by reverse phase automated flash chromatography (CombiFlash Rf, C18 5.5 g RediSep column)

eluting with a gradient of 5-95% acetonitrile in water afforded the desired product as a pale yellow solid (4.9 mg, 0.01 mmol, 5%).

HRMS-ESI (m/z) [M+H]+ calcd for $C_{17}H_{11}N_6O_2S_2$: 395.0385, found 395.0406

Example 9: 2-{3-[(1,3-Benzothiazol-2-yl)amino]-7H-pyrrolo[2,3-c]pyridazin-7-yl}-5-[3-(2-fluorophenoxy)propyl]-1,3-thiazole-4-carboxylic acid

Step A: ethyl 5-bromo-2-acetamido-1,3-thiazole-4-carboxylate

To a solution of ethyl 2-amino-5-bromothiazole-4-carboxylate (4 g, 15.9 mmol, 1 eq) in dichloromethane (70 mL) was added acetic anhydride (1.65 mL, 17.5 mmol, 1.1 eq) and 4-dimethylaminopyridine (2.24 g, 18.3 mmol, 1.15 eq) and the mixture was stirred at ambient temperature overnight. The reaction was allowed to cool to ambient temperature, then washed with water followed by brine, dried (magnesium sulfate) and concentrated in vacuo. The resultant solid was triturated with diethyl ether, filtered, and dried under vacuum to afford the desired product as an off-white solid (4.15 g, 14.15 mmol, 89%).

LC/MS ($C_8H_9BrN_{203}S$) 294 [M+H]$^+$; RT 0.82 (LCMS-V-B1)

$^1$H NMR (400 MHz, DMSO-d6) δ 12.80 (s, 1H), 4.28 (q, J=7.1 Hz, 2H), 2.15 (s, 3H), 1.30 (t, J=7.1 Hz, 3H).

Step B: ethyl 2-acetamido-5-(3-hydroxyprop-1-yn-1-yl)-1,3-thiazole-4-carboxylate Tetrakis(triphenylphosphine)palladium(0) (813 mg, 0.7 mmol, 0.05 eq) was added to a solution of the product from Step A (4.13 g, 14.1 mmol, 1 eq), propargyl alcohol (1.64 mL, 28.2 mmol, 2 eq), triethylamine (5.87 mL, 42.2 mmol, 3 eq) and copper (I) iodide (0.27 g, 1.41 mmol, 0.1 eq) in dimethylformamide (60 mL) under a nitrogen atmosphere, and the mixture was heated at 100° C. for 3 h. The reaction was concentrated in vacuo and purification by automated flash column chromatography (CombiFlash Rf, 120 g RediSep™ silica cartridge) eluting with a gradient of 0-10% methanol in dichloromethane afforded the desired product as a cream solid (3 g, 11.2 mmol, 79%).

LC/MS ($Cn1H_{12}N_2O_4S$) 269 [M+H]$^+$; RT 0.63 (LCMS-V-B1)

$^1$H NMR (400 MHz, DMSO-d6) δ 12.80 (s, 1H), 5.45 (t, J=6.0 Hz, 1H), 4.37 (d, J=6.0 Hz, 2H), 4.27 (q, J=7.1 Hz, 2H), 2.16 (s, 3H), 1.30 (t, J=7.1 Hz, 3H).

Step C: ethyl 2-acetamido-5-(3-hydroxypropyl)-1,3-thiazole-4-carboxylate

Ethyl acetate (30 mL) and methanol (30 mL) were added to a flask containing the product from Step B (3 g, 11.2 mmol, 1 eq) and platinum(IV) oxide hydrate (508 mg, 2.23 mmol, 0.2 eq) under a nitrogen atmosphere. The vessel was evacuated and back-filled with nitrogen (×3), then evacuated and placed under an atmosphere of hydrogen and shaken at ambient temperature for 24 h. The reaction was filtered through celite (10 g), eluted with methanol, and the solvent removed in vacuo. Purification by automated flash column chromatography (CombiFlash Rf, 80 g RediSep™ silica cartridge) eluting with a gradient of 0-10% methanol in dichloromethane afforded the desired product as a brown solid (1.89 g, 6.94 mmol, 62%).

LC/MS ($C_{11}H_{16}N_2O_4S$) 273 [M+H]$^+$; RT 0.61 (LCMS-V-B1)

$^1$H NMR (400 MHz, DMSO-d6) δ 12.38 (s, 1H), 4.54 (t, J=5.1 Hz, 1H), 4.25 (q, J=7.1 Hz, 2H), 3.44 (q, J=6.1 Hz, 2H), 3.20-3.08 (m, 2H), 2.12 (s, 3H), 1.82-1.68 (m, 2H), 1.29 (t, J=7.1 Hz, 3H).

Step D: ethyl 2-amino-5-(3-hydroxypropyl)-1,3-thiazole-4-carboxylate

To a solution of the product from Step C (500 mg, 1.84 mmol, 1 eq) in ethanol (15 mL) was added hydrochloric acid (4M in 1,4-dioxane; 4.59 mL, 4 M, 18.4 mmol, 10 eq) and the mixture was heated at 60° C. overnight. The reaction was allowed to cool to ambient temperature and then concentrated in vacuo. Purification by automated flash column chromatography (CombiFlash Rf, 12 g RediSep™ silica cartridge) eluting with a gradient of 0-10% methanol in dichloromethane afforded the desired product as a beige solid (422 mg, 1.83 mmol, 100%).

LC/MS ($C_9H_{14}N_2O_3S$) 231 [M+H]$^+$; RT 0.50 (LCMS-V-B1)

$^1$H NMR (400 MHz, DMSO-d6) δ 8.04 (br s, 2H), 4.26 (q, J=7.1 Hz, 2H), 3.44 (t, J=6.3 Hz, 2H), 3.05-2.96 (m, 2H), 1.76-1.64 (m, 2H), 1.29 (t, J=7.1 Hz, 3H).

Step E: ethyl 2-bromo-5-(3-hydroxypropyl)-1,3-thiazole-4-carboxylate tert-Butyl nitrate (0.26 mL, 2.2 mmol, 1.2 eq) was added dropwise to a stirred solution of copper (II) bromide (491 mg, 2.2 mmol, 1.2 eq) in acetonitrile (6 mL) and the mixture was heated to 60° C. then a suspension of the product from Step D (422 mg, 1.83 mmol, 1 eq) in acetonitrile (8 mL) was added slowly. The mixture was maintained at 60° C. for 2 h then allowed to cool to ambient temperature and quenched by the addition of 2N aqueous sodium hydroxide, then extracted with ethyl acetate. The organic extract was washed with water, brine, dried (magnesium sulfate) and concentrated in vacuo. Purification by automated flash column chromatography (CombiFlash Rf, 12 g RediSep™ silica cartridge) eluting with a gradient of 0-50% ethyl acetate in iso-heptane afforded the desired product as a colourless oil (271 mg, 0.92 mmol, 50%).

LC/MS ($C_9H_{12}BrNO_3S$) 296 [M+H]$^+$; RT 0.76 (LCMS-V-B1)

$^1$H NMR (400 MHz, DMSO-d6) δ 4.59 (t, J=5.1 Hz, 1H), 4.29 (q, J=7.1 Hz, 2H), 3.44 (td, J=6.3, 5.1 Hz, 2H), 3.24-3.15 (m, 2H), 1.81-1.69 (m, 2H), 1.31 (t, J=7.1 Hz, 3H).

Step F: ethyl 2-bromo-5-[3-(2-fluorophenoxy)propyl]-1,3-thiazole-4-carboxylate A solution of the product from Step E (271 mg, 0.92 mmol, 1 eq), 2-fluorophenol (0.12 mL, 1.38 mmol, 1.5 eq) and triphenylphosphine (362 mg, 1.38 mmol, 1.5 eq) in tetrahydrofuran (10 mL) was cooled in an ice-bath then diisopropyl azodicarboxylate (0.27 mL, 1.38 mmol, 1.5 eq) was added slowly and the mixture was stirred at 0° C. for 30 min then at ambient temperature for 3 h. The reaction was partitioned between ethyl acetate and water, and the organic phase was washed with brine, dried (magnesium sulfate) and concentrated in vacuo. Purification by automated flash column chromatography (CombiFlash Rf, 40 g RediSep™ silica cartridge) eluting with a gradient of 0-60% ethyl acetate in iso-heptane afforded the desired product as an orange oil (302 mg, 0.78 mmol, 85%).

LC/MS ($C_{15}H_{15}BrFNO_3S$) 390 [M+H]$^+$; RT 1.23 (LCMS-V-B1)

$^1$H NMR (400 MHz, DMSO-d6) δ 7.26-7.07 (m, 3H), 7.01-6.88 (m, 1H), 4.27 (q, J=7.1 Hz, 2H), 4.09 (t, J=6.1 Hz, 2H), 3.39-3.29 (m, 2H), 2.16-2.03 (m, 2H), 1.28 (t, J=7.1 Hz, 3H).

Step G: ethyl 2-{3-chloro-7H-pyrrolo[2,3-c]pyridazin-7-yl}-5-[3-(2-fluorophenoxy)propyl]-1,3-thiazole-4-carboxylate To a stirred solution of 3-chloro-7H-pyrrolo[2,3-c]pyridazine (179 mg, 1.17 mmol, 1.5 eq) in 1,4-dioxane (10 mL) and dimethylformamide (3 mL) was added sodium hydride (60% dispersion; 22.4 mg, 0.93 mmol, 1.2 eq) portionwise over 20 minutes and the mixture was stirred for 30 mins before the addition of the product from Step F (302 mg, 0.78 mmol, 1 eq) and stirring at ambient temperature for 2 h and at reflux overnight. The reaction was partitioned between ethyl acetate and water, the aqueous phase was extracted with ethyl acetate (3×30 mL), and the combined organic extracts were washed with brine, dried (magnesium sulfate) and concentrated in vacuo. Purification by automated flash column chromatography (CombiFlash Rf, 12 g RediSep™ silica cartridge) eluting with a gradient of 0-50% ethyl acetate in iso-heptane afforded the desired product as a pale yellow solid (122 mg, 0.27 mmol, 34%).

LC/MS ($C_{21}H_{18}C_1FN_4O_3S$) 461 [M+H]$^+$; RT 1.41 (LCMS-V-B1)

$^1$H NMR (400 MHz, DMSO-d6) δ 8.63 (d, J=3.8 Hz, 1H), 8.28 (s, 1H), 7.26-7.07 (m, 3H), 6.99-6.87 (m, 2H), 4.32 (q, J=7.1 Hz, 2H), 4.15 (t, J=6.1 Hz, 2H), 3.48-3.37 (m, 2H), 2.28-2.14 (m, 2H), 1.32 (t, J=7.1 Hz, 3H).

Step H: ethyl 2-{3-[(1,3-benzothiazol-2-yl)amino]-7H-pyrrolo[2,3-c]pyridazin-7-yl}-5-[3-(2-fluorophenoxy)propyl]-1,3-thiazole-4-carboxylate To a microwave vial was added the product from Step G (122 mg, 0.27 mmol, 1 eq), 2-aminobenzothiazole (59.7 mg, 0.4 mmol, 1.5 eq), cesium carbonate (173 mg, 0.53 mmol, 2 eq), tris(dibenzylideneacetone)dipalladium(0) (24.3 mg, 0.03 mmol, 0.1 eq), Xantphos (15.3 mg, 0.03 mmol, 0.1 eq) and 1,4-dioxane (7.5 mL), and the mixture was heated at 120° C. for 6 h under microwave irradiation. The mixture was partitioned between ethyl acetate and water, and the aqueous phase was extracted with ethyl acetate (3×40 mL), washed with brine, dried (magnesium sulfate) and concentrated in vacuo. Purification by automated flash column chromatography (CombiFlash Rf, 12 g RediSep™ silica cartridge) eluting with a gradient of 0-50% ethyl acetate in iso-heptane afforded the desired product as a yellow solid (42.8 mg, 0.07 mmol, 28%).

LC/MS ($C_{28}H_{23}FN_6O_3S_2$) 575 [M+H]$^+$; RT 1.47 (LCMS-V-B1)

$^1$H NMR (400 MHz, DMSO-d6) δ 11.80 (br s, 1H), 8.53 (d, J=3.8 Hz, 1H), 7.95 (d, J=7.7 Hz, 1H), 7.88 (s, 1H), 7.69-7.63 (m, 1H), 7.40 (ddd, J=8.2, 7.3, 1.3 Hz, 1H), 7.26-7.16 (m, 3H), 7.15-7.11 (m, 1H), 6.98-6.91 (m, 2H), 4.32 (q, J=7.1 Hz, 2H), 4.17 (t, J=6.1 Hz, 2H), 3.48-3.39 (m, 2H), 2.28-2.17 (m, 2H), 1.33 (t, J=7.1 Hz, 3H).

Step I: 2-{3-[(1,3-benzothiazol-2-yl)amino]-7H-pyrrolo[2,3-c]pyridazin-7-yl}-5-[3-(2-fluorophenoxy)propyl]-1,3-thiazole-4-carboxylic acid To a solution of the product from Step H (42.8 mg, 0.07 mmol, 1 eq) in 1,4-dioxane (2 mL) was added 1.25M aqueous lithium hydroxide (0.12 mL, 0.15 mmol, 2 eq) and the mixture was heated at reflux for 2 h. The reaction was concentrated in vacuo and purification by preparative HPLC (HPLC-V-A2) afforded the desired product as a yellow solid (2.3 mg, 6%).

HRMS-ESI (m/z) [M+H]+ calcd for $C_{26}H_{20}FN_6O_3S_2$: 547.1022, found 547.1010.

Example 10: 2-{3-[(1,3-Benzothiazol-2-yl)amino]-5H,6H,7H-pyrrolo[2,3-c]pyridazin-7-yl}-1,3-thiazole-4-carboxylic acid

Step A: tert-butyl 3-chloro-5H,6H,7H-pyrrolo[2,3-c]pyridazine-7-carboxylate

To a solution of N-(but-3-yn-1-yl)-6-chloro-1,2,4,5-tetrazin-3-amine (381 mg, 2.08 mmol, 1 eq) in tetrahydrofuran (15 mL) was added di-tert-butyl dicarbonate (1.36 g, 6.23 mmol, 3 eq) and 4-dimethylaminopyridine (12.7 mg, 0.1 mmol, 0.05 eq) and the mixture was stirred at ambient temperature overnight. Purification by automated flash column chromatography (CombiFlash Rf, 24 g RediSep™ silica cartridge) eluting with a gradient of 0-70% ethyl acetate in iso-heptane afforded the desired product as a red solid (89 mg, 0.35 mmol, 17%).

LC/MS ($C_{11}H_{14}ClN_3O_2$) 256 [M+H]$^+$; RT 2.06 (LCMS-V-C)

$^1$H NMR (400 MHz, DMSO-d6) δ 7.62 (t, J=1.6 Hz, 1H), 3.97 (dd, J=8.9, 7.9 Hz, 2H), 3.10 (ddd, J=9.4, 7.8, 1.6 Hz, 2H), 1.51 (s, 9H).

Step B: 3-chloro-5H,6H,7H-pyrrolo[2,3-c] pyridazine

To a solution of the product from Step A (89 mg, 0.35 mmol, 1 eq) in dichloromethane (3 mL) was added trifluoroacetic acid (1.5 mL) and the mixture was stirred at ambient temperature for 1 h. The reaction was concentrated in vacuo then loaded onto a methanol-washed SCX cartridge (5 g), washed with methanol, then eluted with 1.4N methanolic ammonia to afford the desired product as a beige solid (51 mg, 0.33 mmol, 94%).

LC/MS ($C_6H_6ClN_3$) 156 [M+H]$^+$; RT 0.37 (LCMS-V-C)

$^1$H NMR (400 MHz, DMSO-d6) δ 7.27 (br s, 1H), 7.24-7.20 (m, 1H), 3.55 (td, J=8.2, 1.1 Hz, 2H), 3.06 (ddd, J=9.7, 7.8, 1.7 Hz, 1H).

Step C: ethyl 2-{3-chloro-5H,6H,7H-pyrrolo[2,3-c] pyridazin-7-yl}-1,3-thiazole-4-carboxylate To an oven-dried microwave vial was added the product from Step B (51 mg, 0.33 mmol, 1 eq), ethyl 2-bromo-1,3-thiazole-4-carboxylate (92.9 mg, 0.39 mmol, 1.2 eq), trans-N,N'-dimethylcyclohexane-1,2-diamine (10.3 μL, 0.07 mmol, 0.2 eq), copper(I) iodide (6.24 mg, 0.03 mmol, 0.1 eq) and potassium phosphate tribasic (139 mg, 0.66 mmol, 2 eq), and 1,4-dioxane (3 mL) and the vessel was evacuated and flushed with nitrogen then heated at 150° C. for 1 hour under microwave irradiation. The reaction was diluted with ethyl acetate, filtered through celite, then washed with brine, dried (magnesium sulfate) and concentrated in vacuo. Purification by automated flash column chromatography (CombiFlash Rf, 12 g RediSep™ silica cartridge) eluting with a gradient of 0-3% methanol in dichloromethane afforded the crude desired product as a beige solid (19 mg, 0.06 mmol, 19%) that was used directly in the next step without further purification.

LC/MS ($C_{12}HClN_4O_2S$) 311 [M+H]$^+$; RT 2.24 (LCMS-V-C)

Step D: ethyl 2-{3-[(1,3-benzothiazol-2-yl)amino]-5H,6H,7H-pyrrolo[2,3-c]pyridazin-7-yl}-1,3-thiazole-4-carboxylate To an oven-dried microwave vial was added the product from Step C (19 mg, 0.06 mmol, 1 eq), 2-aminobenzothiazole (13.8 mg, 0.09 mmol, 1.5 eq), Xantphos (7.08 mg, 0.01 mmol, 0.2 eq), cesium carbonate (39.8 mg, 0.12 mmol, 2 eq), and 1,4-dioxane (3 mL) and the vessel was evacuated and flushed with nitrogen then tris(dibenzylideneacetone) dipalladium(0) (5.6 mg, 0.01 mmol, 0.1 eq) was added and the mixture was sparged with nitrogen (10 mins) then heated at 150° C. for 1 h under microwave irradiation. The reaction was diluted with ethyl acetate and filtered through celite, washed with brine, dried (magnesium sulfate) and concentrated in vacuo. Purification by automated flash column chromatography (CombiFlash Rf, 12 g RediSep™ silica cartridge) eluting with a gradient of 0-10% methanol in dichloromethane afforded the desired product as a brown solid (9 mg, 0.02 mmol, 35%).

LC/MS ($C_{19}H_{16}N_6O_2S_2$) 425 [M+H]$^+$; RT 2.53 (LCMS-V-C)

$^1$H NMR (400 MHz, DMSO-d6) δ 7.95-7.89 (m, 1H), 7.69-7.58 (m, 2H), 7.41-7.35 (m, 1H), 7.33-7.29 (m, 1H), 7.25-7.15 (m, 1H), 4.40-4.26 (m, 4H), 1.33 (t, 3H).

Step E: 2-{3-[(1,3-benzothiazol-2-yl)amino]-5H,6H, 7H-pyrrolo[2,3-c]pyridazin-7-yl}-1,3-thiazole-4-carboxylic acid To a solution of the product from Step D (9 mg, 0.02 mmol, 1 eq) in 1,4-dioxane (2 mL) was added lithium hydroxide monohydrate (3.56 mg, 0.08 mmol, 4 eq) and the mixture was heated at reflux for 6 h. The reaction was concentrated in vacuo, then dissolved in methanol and loaded onto a methanol-washed PE-AX cartridge (5 g), washed with methanol, eluted with 10:1 dichloromethane/ formic acid, and concentrated in vacuo. The crude material was triturated with dichloromethane, filtered, and dried under vacuum to afford the desired product as a beige solid (2.42 mg, 0.01 mmol, 29%), as a formic acid salt.

HRMS-ESI (m/z) [M+H]+ calcd for $C_{17}H_{13}N_6O_2S_2$: 397.0541, found 397.0529.

Example 11: 2-{3-[(1,3-Benzothiazol-2-yl)amino]- 4-methyl-5H,6H,7H-pyrrolo[2,3-c]pyridazin-7-yl}- 1,3-thiazole-4-carboxylic acid Step A: 3-chloro-4-methyl-5H,6H,7H-pyrrolo[2,3-c] pyridazine To a solution 3,6-dichloro-1,2,4,5-tetrazine (600 mg, 3.97 mmol, 1 eq) in tetrahydrofuran (16 mL) was added pent-3-yn-1-amine hydrochloride (475 mg, 3.97 mmol, 1 eq) and triethylamine (553 μL, 3.97 mmol, 1 eq) and the mixture was heated at 110° C. in a sealed tube for 8 hours. The reaction was diluted with methanol, filtered through a pad of celite, and the filtrate was partitioned between dichloromethane and saturated aqueous sodium bicarbonate, the aqueous phase was extracted with dichloromethane, and the combined organic extracts were dried (magnesium sulfate) and concentrated in vacuo. Purification by automated flash column chromatography (CombiFlash Rf, 40 g RediSep™ silica cartridge) eluting with a gradient of 0-10% methanol in dichloromethane afforded the desired product as a beige solid (96 mg, 0.57 mmol, 14%).

LC/MS ($C_7H_8ClN_3$) 170 [M+H]+; RT 0.54 (LCMS-V-C)

$^1$H NMR (400 MHz, DMSO-d6) δ 7.12 (s, 1H), 3.56 (td, J=8.4, 1.2 Hz, 2H), 3.04 (ddd, J=9.2, 7.9, 1.3 Hz, 2H), 2.13 (d, J=1.3 Hz, 3H).

Step B: ethyl 2-{3-chloro-4-methyl-5H,6H,7H-pyr-rolo[2,3-c]pyridazin-7-yl}-1,3-thiazole-4-carboxy-late To an oven-dried microwave vial was added the product from Step A (96 mg, 0.57 mmol, 1 eq), ethyl 2-bromo-1,3- thiazole-4-carboxylate (187 mg, 0.79 mmol, 1.4 eq), trans-N,N'-dimethylcyclohexane-1,2-diamine (17.9 μL, 0.11 mmol, 0.2 eq), copper (I) iodide (10.8 mg, 0.06 mmol, 0.1 eq), potassium phosphate tribasic (240 mg, 1.13 mmol, 2 eq), and 1,4-dioxane (8 mL) and the vessel was evacuated and flushed with nitrogen then heated at 150° C. for 1 h under microwave irradiation. The reaction was diluted with ethyl acetate, filtered through celite, washed with brine, dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product as a beige solid (18 mg, 0.06 mmol, 10%).

LC/MS ($C_1H_{13}ClN_4O_2S$) 325 [M+H]+; RT 2.32 (LCMS-V-C)

$^1$H NMR (400 MHz, DMSO-d6) δ 8.11 (s, 1H), 4.41 (dd, J=8.8, 7.6 Hz, 2H), 4.30 (q, J=7.1 Hz, 2H), 3.34-3.27 (m, 2H), 2.29 (d, J=1.2 Hz, 3H), 1.31 (t, J=7.1 Hz, 3H).

Step C: ethyl 2-{3-[(1,3-benzothiazol-2-yl)amino]- 4-methyl-5H,6H,7H-pyrrolo[2,3-c]pyridazin-7-yl}- 1,3-thiazole-4-carboxylate To an oven-dried microwave vial was added the product from Step B (27 mg, 0.08 mmol, 1 eq), 2-aminobenzothi-azole (18.7 mg, 0.12 mmol, 1.5 eq), Xantphos (9.62 mg, 0.02 mmol, 0.2 eq), cesium carbonate (54.2 mg, 0.17 mmol, 2 eq) and 1,4-dioxane (4 mL), and the vessel was evacuated and flushed with nitrogen then tris(dibenzylideneacetone) dipalladium(0) (7.61 mg, 0.01 mmol, 0.1 eq) was added and the mixture was sparged with nitrogen (10 mins) then heated at 150° C. for 1 h under microwave irradiation. The reaction was diluted with ethyl acetate and filtered through celite, then washed with brine, dried (magnesium sulfate) and concentrated in vacuo. Purification by automated flash column chromatography (CombiFlash Rf, 4 g RediSep™ silica cartridge) eluting with a gradient of 0-100% ethyl acetate in iso-heptane afforded the desired product as a yellow solid (15 mg, 0.03 mmol, 41%).

LC/MS ($C_{20}H_{18}N_6O_2S_2$) 439 [M+H]+; RT 2.67 (LCMS-V-C)

$^1$H NMR (400 MHz, DMSO-d6) δ 8.06 (s, 1H), 7.88 (s, 1H), 7.53 (br s, 1H), 7.38 (t, J=7.5 Hz, 1H), 7.20 (t, J=7.6 Hz, 1H), 4.38 (t, J=8.0 Hz, 2H), 4.31 (q, J=7.1 Hz, 2H), 3.32-3.21 (m, 2H), 2.33 (s, 3H), 1.32 (t, J=7.1 Hz, 3H).

Step D: 2-{3-[(1,3-benzothiazol-2-yl)amino]-4-methyl-5H,6H,7H-pyrrolo[2,3-c]pyridazin-7-yl}-1, 3-thiazole-4-carboxylic acid To a solution of the product from Step C (15 mg, 0.03 mmol, 1 eq) in 1,4-dioxane (2 mL) was added lithium hydroxide monohydrate (5.74 mg, 0.14 mmol, 4 eq) and the mixture was heated at reflux for 3 h. The reaction was concentrated in vacuo, dissolved in methanol, loaded onto a methanol-washed PE-AX cartridge (5 g), washed with methanol, eluted with 9:1 dichloromethane/formic acid and concentrated in vacuo. The residue was triturated with dichloromethane, filtered and dried under vacuum to afford the desired product as a cream solid (9.03 mg, 0.02 mmol, 64%).

HRMS-ESI (m/z) [M+H]+ calcd for $C_{18}H_{15}N_6O_2S_2$: 411.0698, found 411.0701.

Example 12: 2-{3-[(1,3-Benzothiazol-2-yl)amino]-5H,6H,7H,8H-pyrido[2,3-c]pyridazin-8-yl}-1,3-thiazole-4-carboxylic acid Step A: pent-4-yn-1-yl methanesulfonate To a solution of 4-pentyn-1-ol (3.32 mL, 35.7 mmol, 1 eq) in dichloromethane (60 mL) was added triethylamine (6.45 mL, 46.4 mmol, 1.3 eq) and the mixture was cooled to 0° C. before the dropwise addition of methanesulfonyl chloride (3.31 mL, 42.8 mmol, 1.2 eq) and stirring at ambient temperature overnight. The reaction was partitioned between dichloromethane and water, and the organic phase was washed successively with saturated sodium bicarbonate and brine, dried (magnesium sulfate) and concentrated in vacuo to afford the desired product as an amber oil (5.8 g, 35.8 mmol, 100%).

$^1$H NMR (400 MHz, DMSO-d6) δ 4.26 (t, J=6.2 Hz, 2H), 3.19 (s, 3H), 2.88 (t, J=2.7 Hz, 1H), 2.29 (td, J=7.1, 2.7 Hz, 2H), 1.91-1.80 (m, 2H).

Step B: 5-azidopent-1-yne

To a solution of the product from Step A (5.8 g, 35.8 mmol, 1 eq) in dimethylformamide (30 mL) was added sodium azide (5.81 g, 89.4 mmol, 2.5 eq) and the mixture was heated at 70° C. for 3 h. The reaction was diluted with water, the aqueous phase was extracted with diethyl ether (×3), and the combined organics were dried (magnesium sulfate) and concentrated in vacuo to afford the desired product as a yellow oil (5.65 g, 51.8 mmol, >100%).

$^1$H NMR (400 MHz, DMSO-d6) δ 3.42 (t, J=6.7 Hz, 2H), 2.85 (t, J=2.7 Hz, 1H), 2.25 (td, J=7.0, 2.7 Hz, 2H), 1.75-1.64 (m, 2H).

Step C: pent-4-yn-1-amine

A solution of the product from Step B (3.9 g, 35.7 mmol, 1 eq) in diethyl ether (40 mL) was cooled to 0° C., triphenylphosphine (14.1 g, 53.6 mmol, 1.5 eq) was added and the reaction stirred at 0° C. for 6 h. The reaction was quenched by the addition of water (5 mL) and stirred at ambient temperature overnight. The mixture was poured onto 4N aqueous hydrochloric acid (300 mL) and extracted with diethyl ether (×3). The aqueous phase was basified with portionwise addition of sodium hydroxide and further extracted with diethyl ether (×2). The combined organic extracts were dried (magnesium sulfate) and concentrated in vacuo to afford the desired product as a yellow oil (1.51 g, 18.16 mmol, 51%).

$^1$H NMR (400 MHz, DMSO-d6) δ 2.73 (t, 1H), 2.58 (t, J=6.7 Hz, 2H), 2.19 (td, J=7.2, 2.7 Hz, 2H), 1.55-1.44 (m, 2H).

Step D: ethyl 2-[(pent-4-yn-1-yl)amino]-1,3-thiazole-4-carboxylate

To a solution of ethyl 2-bromo-1,3-thiazole-4-carboxylate (750 mg, 3.18 mmol, 1 eq) in acetonitrile (15 mL) was added the product from Step C (396 mg, 4.77 mmol, 1.5 eq) and triethylamine (0.66 mL, 4.77 mmol, 1.5 eq) and the mixture was heated at 150° C. for 10 h under microwave irradiation. The reaction was partitioned between ethyl acetate and brine, and the organic phase was dried (MgSO$_4$) and concentrated in vacuo. Purification by automated flash column chromatography (CombiFlash Rf, 24 g RediSep™ silica cartridge) eluting with a gradient of 0-50% ethyl acetate in iso-heptane afforded the desired product as a colourless solid (263 mg, 1.1 mmol, 35%).

LC/MS (C$_{11}$H$_{14}$N$_2$O$_2$S) 239 [M+H]$^+$; RT 2.20 (LCMS-V-C)

$^1$H NMR (400 MHz, DMSO-d6) δ 7.84 (t, J=5.4 Hz, 1H), 7.51 (s, 1H), 4.22 (q, J=7.1 Hz, 2H), 3.28 (td, J=6.9, 5.4 Hz, 2H), 2.82 (t, J=2.6 Hz, 1H), 2.25 (td, J=7.1, 2.7 Hz, 2H), 1.73 (p, J=7.0 Hz, 2H), 1.26 (t, J=7.1 Hz, 3H).

Step E: ethyl 2-{3-chloro-5H,6H,7H,8H-pyrido[2,3-c]pyridazin-8-yl}-1,3-thiazole-4-carboxylate To a solution of 3,6-dichloro-1,2,4,5-tetrazine (103 mg, 0.68 mmol, 1 eq) in tetrahydrofuran (12 mL) was added the product from Step D (163 mg, 0.68 mmol, 1 eq) and the mixture was heated at 90° C. overnight. Purification by automated flash column chromatography (CombiFlash Rf, 24 g RediSep™ silica cartridge) eluting with a gradient of 0-70% ethyl acetate in iso-heptane afforded the desired product as an off white solid (141 mg, 0.43 mmol, 64%).

LC/MS (C$_{13}$H$_{13}$ClN$_4$O$_2$S) 325 [M+H]$^+$; RT 2.42 (LCMS-V-C)

$^1$H NMR (400 MHz, DMSO-d6) δ 8.08 (s, 1H), 7.77-7.71 (m, 1H), 4.40-4.33 (m, 2H), 4.30 (q, 2H), 2.94 (t, J=6.1 Hz, 2H), 2.11-2.00 (m, 2H), 1.32 (t, J=7.1 Hz, 3H).

Step F: ethyl 2-{3-[(1,3-benzothiazol-2-yl)amino]-5H,6H,7H,8H-pyrido[2,3-c]pyridazin-8-yl}-1,3-thiazole-4-carboxylate To an oven-dried microwave vial was added the product from Step E (141 mg, 0.43 mmol, 1 eq), 2-aminobenzothiazole (97.8 mg, 0.65 mmol, 1.5 eq), Xantphos (50.2 mg, 0.09 mmol, 0.2 eq), cesium carbonate (283 mg, 0.87 mmol, 2 eq) and 1,4-dioxane (15 mL) and the vessel was evacuated and flushed with nitrogen then tris(dibenzylideneacetone)dipalladium(0) (39.8 mg, 0.04 mmol, 0.1 eq) was added and the mixture was sparged with nitrogen (10 mins) then heated at 150° C. for 2 h under microwave irradiation. The reaction was diluted with ethyl acetate and filtered through celite, washed with brine, dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product as a yellow solid (29 mg, 0.07 mmol, 15%).

LC/MS (C$_{20}$H$_{18}$N$_6$O$_2$S$_2$) 439 [M+H]$^+$; RT 2.64 (LCMS-V-C)

$^1$H NMR (400 MHz, DMSO-d6) δ 11.67 (s, 1H), 8.02 (s, 1H), 7.98 (d, 1H), 7.66 (d, J=7.9 Hz, 1H), 7.42 (dt, J=15.0, 7.2 Hz, 1H), 7.35 (s, 1H), 7.23 (t, J=7.5 Hz, 1H), 4.41-4.24 (m, 4H), 2.96 (t, 2H), 2.12-2.02 (m, 2H), 1.32 (t, J=7.1 Hz, 3H).

Step G: 2-{3-[(1,3-benzothiazol-2-yl)amino]-5H,6H, 7H,8H-pyrido[2,3-c]pyridazin-8-yl}-1,3-thiazole-4-carboxylic acid To a solution of the product from Step F (29 mg, 0.07 mmol, 1 eq) in 1,4-dioxane (6 mL) was added lithium hydroxide monohydrate (13.9 mg, 0.33 mmol, 5 eq) and the mixture was heated at reflux for 5 h. The reaction was concentrated in vacuo, dissolved in methanol, then loaded onto a methanol-washed PE-AX cartridge (5 g), washed with methanol, eluted with 9:1 dichloromethane/formic acid, and concentrated in vacuo. The residue was triturated dichloromethane, filtered and dried under vacuum to afford the desired product as a cream solid (9.86 mg, 0.02 mmol, 36%), as a formic acid salt.

HRMS-ESI (m/z) [M+H]+ calcd for $C_{18}H_{15}N_6O_2S_2$: 411.0698, found 411.0722

Example 13: 5-{1-[(Adamantan-1-yl)methyl]-5-methyl-1H-pyrazol-4-yl}-2-{3-[(1,3-benzothiazol-2-yl)amino]-4-methyl-5H,6H,7H-pyrrolo[2,3-c]pyridazin-7-yl}-1,3-thiazole-4-carboxylic acid

Step A: ethyl 5-{1-[(adamantan-1-yl)methyl]-5-methyl-1H-pyrazol-4-yl}-2-(4-methyl-3-{[(2Z)-3-{[2-(trimethylsilyl)ethoxy]methyl}-2,3-dihydro-1,3-benzothiazol-2-ylidene]amino}-5H,6H,7H-pyrrolo[2,3-c]pyridazin-7-yl)-1,3-thiazole-4-carboxylate To an oven-dried microwave vial was added the product from Preparation 6a (98 mg, 0.15 mmol, 1 eq), the product from Preparation 5a (64.7 mg, 0.18 mmol, 1.2 eq), potassium carbonate (62.7 mg, 0.45 mmol, 3 eq), [1,1'-bis(diphenylphosphino)ferrocene]dichloropalladium(II) (11.1 mg, 0.02 mmol, 0.1 eq), tetrahydrofuran (3 mL) and water (1 mL) and the mixture was sparged with nitrogen (10 min) then heated at 120° C. for 1 h under microwave irradiation. The reaction was partitioned between ethyl acetate and water, and the organic layer was washed with brine, dried (magnesium sulfate) and concentrated in vacuo. Purification by automated flash column chromatography (CombiFlash Rf, 12 g RediSep™ silica cartridge) eluting with a gradient of 0-50% ethyl acetate in iso-heptane afforded the desired product as a cream solid (57 mg, 0.07 mmol, 47%).

1H NMR (400 MHz, DMSO-d6) δ 7.78 (d, 1H), 7.56 (s, 1H), 7.48-7.38 (m, 2H), 7.27-7.20 (m, 1H), 5.85 (s, 2H), 4.37 (t, J=8.1 Hz, 2H), 4.17 (q, J=7.1 Hz, 2H), 3.79 (s, 2H), 3.76-3.67 (m, 2H), 3.45-3.36 (m, 2H), 2.34 (s, 3H), 2.23 (s, 3H), 2.02-1.90 (m, 3H), 1.73-1.52 (m, 12H), 1.16 (t, 3H), 0.96-0.87 (m, 2H), −0.11 (s, 9H).

Step B: ethyl 5-{1-[(adamantan-1-yl)methyl]-5-methyl-]H-pyrazol-4-yl}-2-{3-[(1,3-benzothiazol-2-yl)amino]-4-methyl-5H,6H,7H-pyrrolo[2,3-c]pyridazin-7-yl}-1,3-thiazole-4-carboxylate To a cooled solution of the product from Step A (57 mg, 0.07 mmol, 1 eq) in dichloromethane (6 mL) was added trifluoroacetic acid (0.6 mL) and after 10 min the mixture was allowed to warm to ambient temperature and stir overnight. The reaction was partitioned between dichloromethane and saturated aqueous sodium bicarbonate, dried (PTFE phase separator) and concentrated in vacuo. Purification by automated flash column chromatography (CombiFlash Rf, 4 g RediSep™ silica cartridge) eluting with a gradient of 0-100% ethyl acetate in iso-heptane afforded the desired product as a yellow solid (17 mg, 0.03 mmol, 36%).

LC/MS ($C_{35}H_{38}N_8O_2S_2$) 667 [M+H]⁺; RT 1.55 (LCMS-V-B2)

¹H NMR (400 MHz, DMSO-d6) δ 7.85 (d, J=7.6 Hz, 1H), 7.62-7.44 (m, 2H), 7.42-7.31 (m, 1H), 7.20 (t, J=7.6 Hz, 1H), 4.37 (t, J=8.1 Hz, 2H), 4.18 (q, J=7.1 Hz, 2H), 3.80 (s, 2H), 3.34-3.24 (m, 2H), 2.34 (d, J=3.4 Hz, 3H), 2.24 (s, 3H), 2.02-1.93 (m, 3H), 1.74-1.51 (m, 12H), 1.18 (t, 3H).

Step C: 5-{1-[(adamantan-1-yl)methyl]-5-methyl-1H-pyrazol-4-yl}-2-{3-[(1,3-benzothiazol-2-yl)amino]-4-methyl-5H,6H,7H-pyrrolo[2,3-c]pyridazin-7-yl}-1,3-thiazole-4-carboxylic acid To a solution of the product from Step B (17 mg, 0.03 mmol, 1 eq) in 1,4-dioxane (6 mL) was added lithium hydroxide monohydrate (10.7 mg, 0.25 mmol, 10 eq) and the mixture was heated at reflux for 5 h. The reaction was concentrated in vacuo, dissolved in methanol, loaded onto a methanol-washed PE-AX cartridge (5 g), washed with methanol, eluted with 9:1 dichloromethane/formic acid, and concentrated in vacuo. The residue was triturated with diethyl ether and acetonitrile, filtered and dried under vacuum to afford the desired product as a beige solid (2.4 mg, 3.7 μmol, 15%).

HRMS-ESI (m/z) [M+H]+ calcd for $C_{33}H_{35}N_8O_2S_2$: 639.2324, found 639.2310

Example 14: 2-{3-[(1,3-Benzothiazol-2-yl)amino]-4-methyl-5H,6H,7H-pyrrolo[2,3-c]pyridazin-7-yl}-5-(1-{[1-(3-methoxypropyl)cyclooctyl]methyl}-5-methyl-1H-pyrazol-4-yl)-1,3-thiazole-4-carboxylic acid Step A: ethyl 5-(1-{[1-(3-methoxypropyl)cyclooctyl]methyl}-5-methyl-1H-pyrazol-4-yl)-2-(4-methyl-3-{[(2Z)-3-{[2-(trimethylsilyl)ethoxy]methyl}-2,3-dihydro-1,3-benzothiazol-2-ylidene]amino}-5H,6H,7H-pyrrolo[2,3-c]pyridazin-7-yl)-1,3-thiazole-4-carboxylate To an oven dried microwave vial was added the product from Preparation 6a (34 mg, 0.05 mmol, 1 eq), the product from Preparation 5b (25.5 mg, 0.06 mmol, 1.2 eq), potassium carbonate (21.8 mg, 0.16 mmol, 3 eq), [1,1'-bis(diphenylphosphino)ferrocene]dichloropalladium(II) (3.84 mg, 0.01 mmol, 0.1 eq), tetrahydrofuran (3 mL) and water (1 mL) and the mixture was sparged with nitrogen (10 min) then heated at 120° C. for 1 h under microwave irradiation. The reaction was partitioned between ethyl acetate and water, and the organic layer was washed with brine, dried (magnesium sulfate) and concentrated in vacuo. Purification by automated flash column chromatography (CombiFlash Rf, 4 g RediSep™ silica cartridge) eluting with a gradient of 0-50% ethyl acetate in iso-heptane afforded the desired product as a white solid (29 mg, 0.03 mmol, 65%).

LC/MS ($C_{43}H_{60}N_8O_4SiS_2$) 845 [M+H]$^+$; RT 1.79 (LCMS-V-B2)

$^1$H NMR (400 MHz, DMSO-d6) δ 7.77 (d, 1H), 7.58 (s, 1H), 7.49-7.38 (m, 2H), 7.27-7.19 (m, 1H), 5.85 (s, 2H), 4.37 (t, J=8.2 Hz, 2H), 4.17 (q, J=7.1 Hz, 2H), 3.85 (s, 2H), 3.77-3.66 (m, 2H), 3.45-3.34 (m, 2H), 3.31-3.26 (m, 4H), 3.23 (s, 3H), 2.33 (s, 3H), 2.22 (s, 3H), 1.74-1.48 (m, 8H), 1.47-1.20 (m, 8H), 1.18 (t, 3H), 0.96-0.87 (m, 2H), −0.11 (s, 9H).

Step B: ethyl 2-{3-[(1,3-benzothiazol-2-yl)amino]-4-methyl-5H,6H,7H-pyrrolo[2,3-c]pyridazin-7-yl}-5-(1-{[1-(3-methoxypropyl)cyclooctyl]methyl}-5-methyl-1H-pyrazol-4-yl)-1,3-thiazole-4-carboxylate To a cooled solution of the product from Step A (29 mg, 0.03 mmol, 1 eq) in dichloromethane (5 mL) was added trifluoroacetic acid (0.9 mL) and after 10 min the mixture was allowed to warm to ambient temperature and stirred overnight. The reaction was partitioned between dichloromethane and saturated aqueous sodium bicarbonate, dried (PTFE phase separator) and concentrated in vacuo afforded the desired product as a yellow solid (13 mg, 0.02 mmol, 54%).

LC/MS ($C_{37}H_{46}N_8O_3S2$) 715 [M+H]$^+$; RT 1.59 (LCMS-V-B2)

$^1$H NMR (400 MHz, DMSO-d6) δ 7.86 (s, 1H), 7.59 (br s+s, 2H), 7.37 (t, 1H), 7.20 (t, J=7.6 Hz, 1H), 4.37 (t, J=8.1 Hz, 2H), 4.19 (q, J=7.0 Hz, 2H), 3.87 (s, 2H), 3.34-3.26 (m, 6H), 3.25 (s, 3H), 2.34 (s, 3H), 2.23 (s, 3H), 1.73-1.49 (m, 8H), 1.48-1.21 (m, 8H), 1.18 (t, 3H).

Step C: 2-{3-[(1,3-benzothiazol-2-yl)amino]-4-methyl-5H,6H,7H-pyrrolo[2,3-c]pyridazin-7-yl}-5-(1-{[1-(3-methoxypropyl)cyclooctyl]methyl}-5-methyl-1H-pyrazol-4-yl)-1,3-thiazole-4-carboxylic acid To a solution of the product from Step B (13 mg, 0.02 mmol, 1 eq) in 1,4-dioxane (3 mL) was added lithium hydroxide monohydrate (11.5 mg, 0.27 mmol, 15 eq) and the mixture was heated at reflux for 5 h. The reaction was concentrated in vacuo, and the residue was triturated with water, filtered and dried under vacuum to afford the desired product as a yellow solid (5.64 mg, 0.01 mmol, 45%), as a lithium salt.

HRMS-ESI (m/z) [M+H]+ calcd for $C_{35}H_{43}N_8O_3S_2$: 687.2900, found 687.2932

Example 15: 2-{3-[(1,3-Benzothiazol-2-yl)amino]-4-methyl-5H,6H,7H,8H-pyrido[2,3-c]pyridazin-8-yl}-1,3-thiazole-4-carboxylic acid Step A: 2-{3-[(1,3-benzothiazol-2-yl)amino]-4-methyl-5H,6H,7H,8H-pyrido[2,3-c]pyridazin-8-yl}-1,3-thiazole-4-carboxylic acid To a solution of the product from Preparation 3f (24 mg, 0.05 mmol, 1 eq) in 1,4-dioxane (6 mL) was added lithium hydroxide monohydrate (33.4 mg, 0.8 mmol, 15 eq) and the mixture was heated at reflux for 7 h. The reaction was concentrated in vacuo, then dissolved in methanol, loaded onto a methanol-wet PE-AX cartridge (5 g), washed with methanol, eluted with 9:1 dichloromethane/formic acid and concentrated in vacuo. The residue was triturated with dichloromethane, filtered and dried under vacuum to afford the desired product as a beige solid (13.5 mg, 0.03 mmol, 60%), as a formic acid salt.

HRMS-ESI (m/z) [M+H]+ calcd for $C_{19}H_{17}N_6O_2S_2$: 425.0854, found 425.0845.

Example 16: 2-{3-[(1,3-Benzothiazol-2-yl)amino]-6-methyl-5H,6H,7H-pyrrolo[2,3-c]pyridazin-7-yl}-1,3-thiazole-4-carboxylic acid

Step A: ethyl 2-[(pent-4-yn-2-yl)amino]-1,3-thiazole-4-carboxylate

To a solution of ethyl 2-bromo-1,3-thiazole-4-carboxylate (1.87 g, 7.93 mmol, 1 eq) in acetonitrile (18 mL) was added pent-4-yn-2-amine (989 mg, 11.9 mmol, 1.5 eq) and triethylamine (1.66 mL, 11.9 mmol, 1.5 eq) and the mixture was heated at 170° C. in a sealed tube overnight. The reaction was partitioned between ethyl acetate and brine, and the organic phase was dried (magnesium sulfate) and concentrated in vacuo. Purification by automated flash column chromatography (CombiFlash Rf, 40 g RediSep™ silica cartridge) eluting with a gradient of 0-50% ethyl acetate in iso-heptane afforded the desired product as a yellow oil (555 mg, 2.33 mmol, 29%).

LC/MS ($C_{11}H_{14}N_2O_2S$) 239 [M+H]$^+$; RT 2.21 (LCMS-V-C)

$^1$H NMR (400 MHz, DMSO-d6) δ 7.85 (d, J=7.4 Hz, 1H), 7.51 (s, 1H), 4.27 (q, 2H), 3.91-3.79 (m, 1H), 2.89 (t, J=2.6 Hz, 1H), 2.51-2.45 (m, 1H), 2.44-2.41 (m, 1H), 1.30-1.21 (m, 6H).

Step B: ethyl 2-{3-chloro-6-methyl-5H,6H,7H-pyrrolo[2,3-c]pyridazin-7-yl}-1,3-thiazole-4-carboxylate To a solution of 3,6-dichloro-1,2,4,5-tetrazine (352 mg, 2.33 mmol, 1 eq) in tetrahydrofuran (15 mL) was added the product from Step A (555 mg, 2.33 mmol, 1 eq) and the mixture was heated at reflux overnight. The reaction was concentrated in vacuo and purification by automated flash column chromatography (CombiFlash Rf, 24 g RediSep™ silica cartridge) eluting with a gradient of 0-100% ethyl acetate in iso-heptane afforded the desired product as a red solid (124 mg, 0.38 mmol, 16%).

LC/MS ($C_{13}H_{13}ClN_4O_2S$) 325 [M+H]$^+$; RT 2.39 (LCMS-V-C)

$^1$H NMR (400 MHz, DMSO-d6) δ 8.12 (s, 1H), 7.71 (t, J=1.6 Hz, 1H), 5.11-4.97 (m, 1H), 4.31 (q, J=7.1, 1.4 Hz, 2H), 3.65-3.53 (m, 1H), 3.00-2.88 (m, 1H), 1.50 (d, J=6.3 Hz, 3H), 1.31 (t, 3H).

Step C: ethyl 2-{3-[(1,3-benzothiazol-2-yl)amino]-6-methyl-5H,6H,7H-pyrrolo[2,3-c]pyridazin-7-yl}-1,3-thiazole-4-carboxylate To an oven-dried microwave vial was added the product from Step B (124 mg, 0.38 mmol, 1 eq), 2-aminobenzothiazole (86 mg, 0.57 mmol, 1.5 eq), Xantphos (44.2 mg, 0.08 mmol, 0.2 eq), cesium carbonate (249 mg, 0.76 mmol, 2 eq), 1,4-dioxane (4 mL) and tris(dibenzylideneacetone)dipalladium(0) (35 mg, 0.04 mmol, 0.1 eq) and the mixture was sparged with nitrogen (10 mins) then heated at 150° C. for 2 h under microwave irradiation. The reaction was diluted with ethyl acetate and filtered through celite, then washed with brine, dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded a solid that was triturated with diethyl ether, filtered and dried under vacuum to afford the desired product as a beige solid (37 mg, 0.08 mmol, 22%).

LC/MS ($C_{20}H_{18}N_6O_2S_2$) 439 [M+H]$^+$; RT 2.62 (LCMS-V-C)

$^1$H NMR (400 MHz, DMSO-d6) δ 11.69 (s, 1H), 8.07 (s, 1H), 7.95 (d, J=7.9 Hz, 1H), 7.66 (d, J=8.1 Hz, 1H), 7.44-7.37 (m, 1H), 7.36 (s, 1H), 7.23 (td, J=7.6, 1.1 Hz, 1H), 5.07-4.95 (m, 1H), 4.31 (q, 2H), 3.65-3.52 (m, 1H), 3.03-2.93 (m, 1H), 1.49 (d, J=6.3 Hz, 3H), 1.32 (t, J=7.1 Hz, 3H).

Step D: 2-{3-[(1,3-benzothiazol-2-yl)amino]-6-methyl-5H,6H,7H-pyrrolo[2,3-c]pyridazin-7-yl}-1,3-thiazole-4-carboxylic acid To a solution of the product from Step C (37 mg, 0.08 mmol, 1 eq) in 1,4-dioxane (8 mL) was added lithium hydroxide monohydrate (53.1 mg, 1.27 mmol, 15 eq) and the mixture was heated at reflux for 7 h. The reaction was concentrated in vacuo, dissolved in methanol, then loaded onto a methanol-wet PE-AX cartridge (10 g), washed with methanol, eluted with 9:1 dichloromethane/formic acid and concentrated in vacuo. The residue was triturated with dichloromethane, filtered and dried under vacuum to afford the desired product as a beige solid (24.8 mg, 0.06 mmol, 72%), as a formic acid salt.

HRMS-ESI (m/z) [M+H]+ calcd for $C_{18}H_{15}N_6O_2S_2$: 411.0698, found 411.0695.

Example 17: 2-{3-[(1,3-Benzothiazol-2-yl)amino]-4-methyl-5H,6H,7H-pyrrolo[2,3-c]pyridazin-7-yl}-5-(1-{[1-(3-methoxypropyl)cyclohexyl]methyl}-5-methyl-1H-pyrazol-4-yl)-1,3-thiazole-4-carboxylic acid Step A: ethyl 5-(1-{[1-(3-methoxypropyl)cyclo-
hexyl]methyl}-5-methyl-1H-pyrazol-4-yl)-2-(4-
methyl-3-{[(2Z)-3-{[2-(trimethylsilyl)ethoxy]
methyl}-2,3-dihydro-1,3-benzothiazol-2-ylidene]
amino}-5H,6H,7H-pyrrolo[2,3-c]pyridazin-7-yl)-1,
3-thiazole-4-carboxylate To an oven-dried microwave vial was added the product
from Preparation 6a (37 mg, 0.06 mmol, 1 eq), the product
from Preparation 5c (25.8 mg, 0.07 mmol, 1.2 eq), potas-
sium carbonate (23.7 mg, 0.17 mmol, 3 eq), [1,1'-bis(diphe-
nylphosphino)ferrocene]dichloropalladium(II) (4.18 mg,
0.01 mmol, 0.1 eq), tetrahydrofuran (3 mL) and water (1
mL) and the mixture was sparged with nitrogen (10 min)
then heated at 120° C. for 1 h under microwave irradiation.
The reaction was partitioned between ethyl acetate and
water, and the organic phase was washed with brine, dried
(magnesium sulfate) and concentrated in vacuo. Purification
by automated flash column chromatography (CombiFlash
Rf, 4 g RediSep™ silica cartridge) eluting with a gradient of
0-60% ethyl acetate in iso-heptane afforded the desired
product as a white solid (22 mg, 0.03 mmol, 47%).
LC/MS (C$_{41}$H$_{56}$N$_8$O$_4$SiS$_2$) 818 [M+H]$^+$; RT 3.45
(LCMS-V-C)
$^1$H NMR (400 MHz, DMSO-d6) δ 7.79-7.74 (m, 1H),
7.58 (s, 1H), 7.48-7.38 (m, 2H), 7.27-7.20 (m, 1H), 5.85 (s,
2H), 4.37 (t, J=8.1 Hz, 2H), 4.17 (q, J=7.1 Hz, 2H), 3.93 (s,
2H), 3.76-3.66 (m, 2H), 3.44-3.36 (m, 2H), 3.34-3.25 (m,
2H), 3.23 (s, 3H), 2.33 (s, 3H), 2.23 (s, 3H), 1.60-1.27 (m,
14H), 1.18 (t, J=7.1 Hz, 3H), 0.98-0.85 (m, 2H), −0.11 (s,
9H).

Step B: ethyl 2-{3-[(1,3-benzothiazol-2-yl)amino]-
4-methyl-5H,6H,7H-pyrrolo[2,3-c]pyridazin-7-yl}-
5-(1-{[1-(3-methoxypropyl)cyclohexyl]methyl}-5-
methyl-1H-pyrazol-4-yl)-1,3-thiazole-4-carboxylate To a cooled solution of the product from Step A (22 mg,
0 mol, 1 eq) in dichloromethane (5 mL) was added trifluo-
roacetic acid (1.5 mL) and after 10 min the mixture was
allowed to warm to ambient temperature and stir overnight.
The reaction was partitioned between dichloromethane and
saturated aqueous sodium bicarbonate, dried (PTFE phase
separator) and concentrated in vacuo. Purification by auto-
mated flash column chromatography (CombiFlash Rf, 4 g
RediSep™ silica cartridge) eluting with a gradient of
0-100% ethyl acetate in iso-heptane afforded the desired
product as a yellow solid (10 mg, 0.01 mmol, 54%).
LC/MS (C$_{35}$H$_{42}$N$_8$O$_3$S2) 688 [M+H]$^+$; RT 3.02 (LCMS-
V-C)
$^1$H NMR (400 MHz, DMSO-d6) δ 7.91-7.79 (m, 1H),
7.59 (br s+s, 2H), 7.38 (t, J=7.7 Hz, 1H), 7.25-7.13 (m, 1H),
4.38 (t, J=8.2 Hz, 2H), 4.19 (q, J=7.0 Hz, 2H), 3.95 (s, 2H),
3.34-3.27 (m, 4H), 3.25 (s, 3H), 2.34 (s, 3H), 2.24 (s, 3H),
1.60-1.45 (m, 6H), 1.44-1.29 (m, 6H), 1.28-1.22 (m, 2H),
1.18 (t, 3H).

Step C: 2-{3-[(1,3-benzothiazol-2-yl)amino]-4-
methyl-5H,6H,7H-pyrrolo[2,3-c]pyridazin-7-yl}-5-
(1-{[1-(3-methoxypropyl)cyclohexyl]methyl}-5-
methyl-1H-pyrazol-4-yl)-1,3-thiazole-4-carboxylic
acid To a solution of the product from Step B (10 mg, 0.01
mmol, 1 eq) in 1,4-dioxane (3 mL) was added lithium
hydroxide monohydrate (12.2 mg, 0.29 mmol, 20 eq) and
the mixture was heated at reflux for 5 h. The reaction was concentrated in vacuo, triturated with water, filtered and
dried under vacuum to afford the desired product as a yellow
solid (5.71 mg, 0.01 mmol, 60%).
HRMS-ESI (m/z) [M+H]+ calcd for C$_{33}$H$_{39}$N$_8$O$_3$S$_2$:
659.2587, found 659.2577.

Example 18: 2-{4-Methyl-3-[(1,3-thiazol-2-yl)
amino]-5H,6H,7H-pyrrolo[2,3-c]pyridazin-7-yl}-1,
3-thiazole-4-carboxylic acid Step A: ethyl 2-{4-methyl-3-[(1,3-thiazol-2-yl)
amino]-5H,6H,7H-pyrrolo[2,3-c]pyridazin-7-yl}-1,
3-thiazole-4-carboxylate To an oven-dried microwave vial was added the product
from Preparation 6a, Step B (100 mg, 0.31 mmol, 1 eq),
2-aminothiazole (46.3 mg, 0.46 mmol, 1.5 eq), Xantphos
(35.6 mg, 0.06 mmol, 0.2 eq), cesium carbonate (201 mg,
0.62 mmol, 2 eq), 1,4-dioxane (4 mL) and tris(dibenzylide-
neacetone)dipalladium(0) (28.2 mg, 0.03 mmol, 0.1 eq) and
the mixture was sparged with nitrogen (10 min) then heated
at 150° C. for 1 h under microwave irradiation. The reaction
was diluted with ethyl acetate, filtered through celite,
washed with brine, dried (magnesium sulfate) and concen-
trated in vacuo. Purification by automated flash column
chromatography (CombiFlash Rf, 12 g RediSep™ silica
cartridge) eluting with a gradient of 0-10% methanol in
dichloromethane gave a solid that was triturated with
acetonitrile, filtered and dried under vacuum to afford the
desired product as a yellow solid (23 mg, 0.06 mmol, 19%).
LC/MS (C$_{16}$H$_{16}$N$_6$O$_2$S$_2$) 389 [M+H]$^+$; RT 2.29 (LCMS-
V-C)
$^1$H NMR (400 MHz, DMSO-d6) δ 10.57 (br s, 1H), 8.04
(s, 1H), 7.44 (br s, 1H), 7.06 (br s, 1H), 4.40-4.32 (m, 2H),
4.29 (q, 2H), 3.30-3.22 (m, 2H), 2.31 (s, 3H), 1.32 (t, 3H).

Step B: 2-{4-methyl-3-[(1,3-thiazol-2-yl)amino]-
5H,6H,7H-pyrrolo[2,3-c]pyridazin-7-yl}-1,3-thiaz-
ole-4-carboxylic acid To a solution of the product from Step A (23 mg, 0.06
mmol, 1 eq) in 1,4-dioxane (6 mL) was added lithium
hydroxide monohydrate (37.3 mg, 0.89 mmol, 15 eq) and
the mixture was heated at reflux for 5 h. The reaction was
concentrated in vacuo, dissolved in methanol, loaded onto a
methanol-wet PE-AX cartridge (5 g), washed with metha-
nol, eluted with 9:1 dichloromethane/formic acid and con-
centrated in vacuo. The residue was triturated with dichlo-
romethane and methanol, filtered and dried under vacuum to
afford the desired product as a beige solid (8.84 mg, 0.02
mmol, 41%).
HRMS-ESI (m/z) [M+H]+ calcd for C$_{14}$H$_{13}$N$_6$O$_2$S$_2$:
361.0541, found 361.0531.

Example 19: 2-{3-[(4,5-Dimethyl-1,3-thiazol-2-yl)amino]-4-methyl-5H,6H,7H-pyrrolo[2,3-c]pyridazin-7-yl}-1,3-thiazole-4-carboxylic acid Example 20: 6-{3-[(1,3-Benzothiazol-2-yl)amino]-4-methyl-5H,6H,7H-pyrrolo[2,3-c]pyridazin-7-yl}pyridine-2-carboxylic acid Step A: ethyl 2-{3-[(4,5-dimethyl-1,3-thiazol-2-yl)amino]-4-methyl-5H,6H,7H-pyrrolo[2,3-c]pyridazin-7-yl}-1,3-thiazole-4-carboxylate To an oven-dried microwave vial was added the product from Preparation 6a, Step B (100 mg, 0.31 mmol, 1 eq), 4,5-dimethyl-1,3-thiazol-2-amine (59.2 mg, 0.46 mmol, 1.5 eq), Xantphos (35.6 mg, 0.06 mmol, 0.2 eq), cesium carbonate (201 mg, 0.62 mmol, 2 eq), 1,4-dioxane (3 mL) then tris(dibenzylideneacetone)dipalladium(0) (28.2 mg, 0.03 mmol, 0.1 eq) and the mixture was sparged with nitrogen (10 mins) then heated at 150° C. for 1 h under microwave irradiation. The reaction was diluted with ethyl acetate and filtered through celite, then washed with brine, dried (magnesium sulfate) and concentrated in vacuo. The residue was triturated with methanol, filtered and dried under vacuum to afford the desired product as a yellow solid (64 mg, 0.15 mmol, 50%).

LC/MS ($C_{18}H_{20}N_6O_2S_2$) 417 [M+H]$^+$; RT 2.42 (LCMS-V-C)

$^1$H NMR (400 MHz, DMSO-d6) δ 8.03 (s, 1H), 4.39-4.21 (m, 4H), 3.25 (t, J=8.0 Hz, 2H), 2.27 (s, 3H), 2.23 (s, 3H), 2.16 (s, 3H), 1.31 (t, J=7.1 Hz, 3H).

Step B: 2-{3-[(4,5-dimethyl-1,3-thiazol-2-yl)amino]-4-methyl-5H,6H,7H-pyrrolo[2,3-c]pyridazin-7-yl}-1,3-thiazole-4-carboxylic acid To a solution of the product from Step A (64 mg, 0.15 mmol, 1 eq) in 1,4-dioxane (15 mL) was added lithium hydroxide monohydrate (96.7 mg, 2.3 mmol, 15 eq) and the mixture was heated at reflux for 5 h. The reaction was concentrated in vacuo, dissolved in methanol, then loaded onto a methanol-wet PE-AX cartridge (10 g), washed with methanol, eluted with 9:1 dichloromethane/formic acid and concentrated in vacuo. The residue was triturated with methanol, filtered and dried under vacuum to afford the desired product as a beige solid (17.9 mg, 0.05 mmol, 30%).

HRMS-ESI (m/z) [M+H]+ calcd for $C_{16}H_{17}N_6O_2S_2$: 389.0854, found 389.0847.

Step A: tert-butyl 6-[(pent-3-yn-1-yl)amino]pyridine-2-carboxylate

To a solution of tert-butyl 6-fluoropyridine-2-carboxylate (219 mg, 1.11 mmol, 1 eq) in dimethylacetamide (5 mL) was added pent-3-yn-1-amine hydrochloride (133 mg, 1.11 mmol, 1 eq) and NN-diisopropylethylamine (0.39 mL, 2.22 mmol, 2 eq) and the mixture was heated at 120° C. overnight in a sealed tube. The reaction was partitioned between ethyl acetate and water, and the organic phase was dried (magnesium sulfate) and concentrated in vacuo. Purification by automated flash column chromatography (CombiFlash Rf, 12 g RediSep™ silica cartridge) eluting with a gradient of 0-30% ethyl acetate in iso-heptane afforded the desired product as a clear oil (48 mg, 0.18 mmol, 17%).

LC/MS ($C_{15}H_{20}N_2O_2$) 261 [M+H]$^+$; RT 2.42 (LCMS-V-C)

$^1$H NMR (400 MHz, DMSO-d6) δ 7.49 (dd, J=8.4, 7.2 Hz, 1H), 7.11 (dd, J=7.3, 0.8 Hz, 1H), 6.89 (t, J=5.7 Hz, 1H), 6.66 (dd, J=8.5, 0.8 Hz, 1H), 3.45-3.29 (m, 2H), 2.44-2.35 (m, 2H), 1.75 (t, J=2.6 Hz, 3H), 1.53 (s, 9H).

Step B: tert-butyl 6-{3-chloro-4-methyl-5H,6H,7H-pyrrolo[2,3-c]pyridazin-7-yl}pyridine-2-carboxylate To a solution of 3,6-dichloro-1,2,4,5-tetrazine (27.8 mg, 0.18 mmol, 1 eq) in tetrahydrofuran (3 mL) was added the product from Step A (48 mg, 0.18 mmol, 1 eq) and the mixture was heated at 110° C. for 1 h under microwave irradiation. The reaction was concentrated in vacuo and purification by automated flash column chromatography (CombiFlash Rf, 4 g RediSep™ silica cartridge) eluting with a gradient of 0-30% ethyl acetate in iso-heptane afforded the desired product as a pink solid (12 mg, 0.03 mmol, 19%).

LC/MS ($C_{17}H_{19}ClN_4O_2$) 347 [M+H]$^+$; RT 2.67 (LCMS-V-C)

$^1$H NMR (400 MHz, DMSO-d6) δ 8.84 (dd, J=8.6, 0.8 Hz, 1H), 8.01 (dd, J=8.6, 7.4 Hz, 1H), 7.65 (dd, J=7.4, 0.8 Hz, 1H), 4.36 (dd, J=8.9, 7.8 Hz, 2H), 3.22 (t, J=8.3 Hz, 2H), 2.27 (s, 3H), 1.57 (s, 9H).

Step C: tert-butyl 6-{3-[(1,3-benzothiazol-2-yl)amino]-4-methyl-5H,6H,7H-pyrrolo[2,3-c]pyridazin-7-yl}pyridine-2-carboxylate To an oven-dried microwave vial was added the product from Step B (26 mg, 0.07 mmol, 1 eq), 2-aminothiazole (16.9 mg, 0.11 mmol, 1.5 eq), Xantphos (8.68 mg, 0.01 mmol, 0.2 eq), cesium carbonate (48.9 mg, 0.15 mmol, 2 eq), 1,4-dioxane (4 mL) then tris(dibenzylideneacetone) dipalladium(0) (6.87 mg, 0.01 mmol, 0.1 eq) and the mixture was sparged with nitrogen (10 mins) then heated at 150° C. for 1 h under microwave irradiation. The reaction was diluted with ethyl acetate, filtered through celite, washed with brine, dried (magnesium sulfate) and concentrated in vacuo. Purification by automated flash column chromatography (CombiFlash Rf, 4 g RediSep™ silica cartridge) eluting with a gradient of 0-40% ethyl acetate in iso-heptane gave a solid that was triturated with diethyl ether, filtered and dried under vacuum to afford the desired product as a yellow solid (7 mg, 0.02 mmol, 20%).

LC/MS ($C_{24}H_{24}N_6O_2S$) 461 [M+H]⁺; RT 2.69 (LCMS-V-C)

¹H NMR (400 MHz, DMSO-d6) δ 8.98 (d, J=8.7 Hz, 1H), 8.01 (t, J=8.0 Hz, 1H), 7.88 (s, 1H), 7.68-7.57 (m, 2H), 7.38 (t, J=7.5 Hz, 1H), 7.28-7.14 (m, 1H), 4.32 (t, J=8.2 Hz, 2H), 3.20 (t, J=8.1 Hz, 2H), 2.33 (s, 3H), 1.58 (s, 8H).

Step D: 6-{3-[(1,3-benzothiazol-2-yl)amino]-4-methyl-5H,6H,7H-pyrrolo[2,3-c]pyridazin-7-yl}pyridine-2-carboxylic acid To a solution of the product from Step C (7 mg, 0.02 mmol, 1 eq) in 1,4-dioxane (3 mL) was added lithium hydroxide monohydrate (9.57 mg, 0.23 mmol, 15 eq) and the mixture was heated at reflux for 6 h. The reaction was concentrated in vacuo, then dissolved in methanol, loaded onto a methanol-wet PE-AX cartridge (5 g), washed with methanol, eluted with 9:1 dichloromethane/formic acid and concentrated in vacuo. The residue was triturated with dichloromethane and methanol, filtered and dried under vacuum to afford the desired product as a yellow solid (2.0 mg, 32%).

HRMS-ESI (m/z) [M+H]+ calcd for $C_{20}H_{17}N_6O_2S$: 405.1134, found 405.1122.

Example 21: 6-{3-[(1,3-Benzothiazol-2-yl)amino]-4-methyl-5H,6H,7H,8H-pyrido[2,3-c]pyridazin-8-yl}pyridine-2-carboxylic acid

Step A: ethyl 6-{[3-(3,6-dichloro-5-methylpyridazin-4-yl)propyl]amino}pyridine-2-carboxylate To a solution of the product from Preparation 2e (500 mg, 2.28 mmol, 1 eq) and ethyl 6-aminopicolinate (455 mg, 2.74 mmol, 1.2 eq) in methanol (18 mL) and acetic acid (6 mL)

was added sodium triacetoxyborohydride (968 mg, 4.56 mmol, 2 eq) and the mixture was stirred at ambient temperature for 16 h. The reaction was quenched by the addition of 1N aqueous sodium hydroxide (50 mL), extracted with ethyl acetate (3×50 mL), and the combined organic extracts were successively washed with saturated aqueous sodium bicarbonate and brine, dried (magnesium sulfate) and concentrated in vacuo. Purification by automated flash column chromatography (CombiFlash Rf, 40 g RediSep™ silica cartridge) eluting with a gradient of 0-60% ethyl acetate in iso-heptane afforded the desired product as a white solid (400 mg, 1.08 mmol, 47%).

LC/MS ($C_{16}H_{18}Cl_2N_4O_2$) 369 [M+H]⁺; RT 1.19 (LCMS-V-B1)

¹H NMR (400 MHz, DMSO-d6) δ 7.52 (dd, J=8.4, 7.2 Hz, 1H), 7.18 (dd, 1H), 6.99 (t, J=5.7 Hz, 1H), 6.69 (dd, J=8.5, 0.8 Hz, 1H), 4.27 (q, J=7.1 Hz, 2H), 3.42-3.35 (m, 2H), 2.92-2.82 (m, 2H), 2.41 (s, 3H), 1.87-1.74 (m, 2H), 1.29 (t, J=7.1 Hz, 3H).

Step B: methyl 6-{3-chloro-4-methyl-5H,6H,7H, 8H-pyrido[2,3-c]pyridazin-8-yl}pyridine-2-carboxylate To a solution of the product from Step A (170 mg, 0.46 mmol, 1 eq) in alpha,alpha,alpha-trifluorotoluene (4 mL) was added cesium carbonate (300 mg, 0.92 mmol, 2 eq) and the mixture was heated in a sealed tube at 160° C. for 5 days. The reaction was allowed to cool to ambient temperature and concentrated in vacuo. Purification by automated flash column chromatography (CombiFlash Rf, 24 g RediSep™ silica cartridge) eluting with a gradient of 0-10% methanol in dichloromethane afforded the desired product as a cream solid (74 mg, 0.23 mmol, 50%).

LC/MS ($C_{15}H_{15}ClN_4O_2$) 319 [M+H]⁺; RT 1.10 (LCMS-V-B1)

¹H NMR (400 MHz, DMSO-d6) δ 7.97-7.84 (m, 2H), 7.75 (dd, J=7.1, 1.2 Hz, 1H), 4.05-3.96 (m, 2H), 3.89 (s, 3H), 2.92-2.81 (m, 2H), 2.31 (s, 3H), 2.05-1.92 (m, 2H).

Step C: methyl 6-{3-[(1,3-benzothiazol-2-yl) amino]-4-methyl-5H,6H,7H,8H-pyrido[2,3-c] pyridazin-8-yl}pyridine-2-carboxylate To a solution of the product from Step B (74 mg, 0.23 mmol, 1 eq), 2-aminobenzothiazole, (52.3 mg, 0.35 mmol, 1.5 eq) and N,N-diisopropylethylamine (0.12 mL, 0.7 mmol, 3 eq) in 1,4-dioxane (5 mL) was added Xantphos (13.4 mg, 0.02 mmol, 0.1 eq) and tris(dibenzylideneacetone)dipalladium(0) (10.6 mg, 0.01 mmol, 0.05 eq) and the mixture was heated in a sealed tube at 150° C. for 20 h. The reaction was allowed to cool to ambient temperature, then partitioned between ethyl acetate (20 mL) and brine (25 mL), and the organic phase was dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product as a yellow solid (20 mg, 0.05 mmol, 20%).

LC/MS ($C_{22}H_{20}N_6O_2S$) 433 [M+H]⁺; RT 1.15 (LCMS-V-B1)

¹H NMR (400 MHz, DMSO-d6) δ 8.03 (dd, J=8.5, 0.9 Hz, 1H), 7.87 (dd, J=8.5, 7.3 Hz, 1H), 7.83 (br s, 1H), 7.68 (d, J=7.3 Hz, 1H), 7.53 (br s, 1H), 7.36 (t, J=7.6 Hz, 1H), 7.17 (t, J=7.6 Hz, 1H), 4.11-3.99 (m, 2H), 3.90 (s, 3H), 2.86 (t, J=6.5 Hz, 2H), 2.33 (s, 3H), 2.05-1.94 (m, 2H).

Step D: 6-{3-[(1,3-benzothiazol-2-yl)amino]-4-
methyl-5H,6H,7H,8H-pyrido[2,3-c]pyridazin-8-
yl}pyridine-2-carboxylic acid To a solution of the product from Step C (15 mg, 0.03 mmol, 1 eq) in 1,4-dioxane (2 mL) was added lithium hydroxide monohydrate (2.91 mg, 0.07 mmol, 2 eq) and the mixture was heated at reflux for 1 h. The reaction was allowed to cool to ambient temperature and concentrated in vacuo. Purification by reverse phase automated flash chromatography (CombiFlash Rf, C18 4.3 g RediSep column) eluting with a gradient of 5-95% acetonitrile in water afforded the desired product as a cream solid (10 mg, 0.02 mmol, 69%).

HRMS-ESI (m/z) [M+H]+ calcd for $C_{21}H_{19}N_6O_2S$: 419.1290, found 419.1287.

Example 22: 2-{3-[(1,3-Benzothiazol-2-yl)amino]-
4-methyl-5H,6H,7H-pyrrolo[2,3-c]pyridazin-7-yl}-
5-(3-{4-[3-(dimethylamino)prop-1-yn-1-yl]-2-
fluorophenoxy}propyl)-1,3-thiazole-4-carboxylic
acid Step A: ethyl 5-[(1E)-3-[(tert-butyldimethylsilyl)
oxy]prop-1-en-1-yl]-2-(4-methyl-3-{[(2Z)-3-{[2-
(trimethylsilyl)ethoxy]methyl}-2,3-dihydro-1,3-ben-
zothiazol-2-ylidene]amino}-5H,6H,7H-pyrrolo[2,3-
c]pyridazin-7-yl)-1,3-thiazole-4-carboxylate To an oven-dried sealed flask was added the product from Preparation 6a (3 g, 4.63 mmol, 1 eq), (E)-3-(tert-butyldi-methylsilyloxy)propene-1-yl-boronic acid pinacol ester (1.82 mL, 5.56 mmol, 1.2 eq), potassium carbonate (1.92 g, 13.9 mmol, 3 eq), [1,1'-bis(diphenylphosphino)ferrocene] dichloropalladium(II) (339 mg, 0.46 mmol, 0.1 eq), tetra-hydrofuran (150 mL) and water (50 mL) and the mixture was sparged with nitrogen (10 min) then heated at 120° C. for 1.5 h. The reaction was allowed to cool to ambient temperature then partitioned between ethyl acetate and water, and the organic phase washed with brine, dried (magnesium sulfate) and concentrated in vacuo. Purification by automated flash column chromatography (CombiFlash Rf, 80 g RediSep™ silica cartridge) eluting with a gradient of 0-70% ethyl acetate in iso-heptane afforded the desired product as a cream solid (1.86 g, 2.52 mmol, 54%).

LC/MS ($C_{35}H_{50}N_6O_4Si_2S2$) 739 [M+H]$^+$; RT 3.69 (Shortneg2)

$^1$H NMR (400 MHz, DMSO-d6) δ 7.80 (d, J=7.6 Hz, 1H), 7.55-7.38 (m, 3H), 7.30-7.20 (m, 1H), 6.30 (dt, J=15.9, 4.3 Hz, 1H), 5.85 (s, 2H), 4.41-4.26 (m, 4H), 3.77-3.67 (m, 2H), 3.45-3.20 (m, 4H), 2.32 (s, 3H), 1.32 (t, J=7.1 Hz, 3H), 0.93 (s, 9H), 0.92-0.86 (m, 2H), 0.11 (s, 6H), −0.11 (s, 9H).

Step B: ethyl 5-{3-[(tert-butyldimethylsilyl)oxy]
propyl}-2-(4-methyl-3-{[(2Z)-3-{[2-(trimethylsilyl)
ethoxy]methyl}-2,3-dihydro-1,3-benzothiazol-2-
ylidene]amino}-5H,6H,7H-pyrrolo[2,3-c]pyridazin-
7-yl)-1,3-thiazole-4-carboxylate To a solution of the product from Step A (900 mg, 1.22 mmol, 1 eq) in ethyl acetate (600 mL) was added a catalytic amount of platinum (IV) oxide under a nitrogen atmosphere. The mixture was evacuated and backfilled with nitrogen (×3), then evacuated and backfilled with hydrogen and shaken for 3 days at ambient temperature under an atmosphere of hydrogen. The reaction was filtered through celite, eluted with ethyl acetate and evaporated under reduced pressure to afford the desired product as a beige solid (950 mg, 1.28 mmol, >100%%).

LC/MS ($C_{35}H_{52}N_6O_4Si_2S2$) 741 [M+H]$^+$; RT 1.88 (LCMS-V-B2)

$^1$H NMR (400 MHz, DMSO-d6) δ 7.77 (d, J=7.6 Hz, 1H), 7.50-7.39 (m, 2H), 7.28-7.18 (m, 1H), 5.85 (s, 2H), 4.37-4.22 (m, 4H), 3.77-3.62 (m, 4H), 3.31-3.14 (m, 4H), 2.32 (s, 3H), 1.93-1.80 (m, 2H), 1.31 (t, J=7.1 Hz, 3H), 0.96-0.80 (m, 11H), 0.06 (s, 6H), −0.11 (s, 9H).

Step C: ethyl 5-(3-hydroxypropyl)-2-(4-methyl-3-
{[(2Z)-3-{[2-(trimethylsilyl)ethoxy]methyl}-2,3-
dihydro-1,3-benzothiazol-2-ylidene]amino}-5H,6H,
7H-pyrrolo[2,3-c]pyridazin-7-yl)-1,3-thiazole-4-
carboxylate To a solution of the product from Step B (950 mg, 1.28 mmol, 1 eq) in 1,4-dioxane (150 mL) was added hydrochloric acid (4M in dioxane; 50 mL, 200 mmol, 156 eq) and the mixture was stirred at ambient temperature for 1 h. The reaction was partitioned between ethyl acetate and saturated aqueous sodium bicarbonate, dried (magnesium sulfate) and concentrated in vacuo. Purification by automated flash column chromatography (CombiFlash Rf, 40 g RediSep™ silica cartridge) eluting with a gradient of 0-80% ethyl acetate in iso-heptane afforded the desired product as an off-white solid (577 mg, 0.92 mmol, 72%).

LC/MS ($C_{29}H_{38}N_6O_4SiS_2$) 627 [M+H]$^+$; RT 2.68 (LCMS-V-C)

$^1$H NMR (400 MHz, DMSO-d6) δ 7.80 (d, J=7.5 Hz, 1H), 7.49-7.38 (m, 2H), 7.28-7.19 (m, 1H), 5.85 (s, 2H), 4.57 (t, J=5.2 Hz, 1H), 4.37-4.22 (m, 4H), 3.76-3.67 (m, 2H), 3.53-3.44 (m, 2H), 3.30-3.13 (m, 4H), 2.32 (s, 3H), 1.86-1.77 (m, 2H), 1.31 (t, J=7.1 Hz, 3H), 0.96-0.86 (m, 2H), −0.11 (s, 9H).

Step D: ethyl 5-(3-chloropropyl)-2-(4-methyl-3-{
[(2Z)-3-{[2-(trimethylsilyl)ethoxy]methyl}-2,3-di-
hydro-1,3-benzothiazol-2-ylidene]amino}-5H,6H,
7H-pyrrolo[2,3-c]pyridazin-7-yl)-1,3-thiazole-4-
carboxylate The product from Step C (577 mg, 0.92 mmol, 1 eq) was dissolved in thionyl chloride (30 mL) and stirred at ambient temperature for 5 h. The reaction was concentrated in vacuo, then partitioned between dichloromethane and brine, and the organic phase was dried (PTFE phase separator) and concentrated in vacuo. Purification by automated flash column chromatography (CombiFlash Rf, 24 g RediSep™ silica cartridge) eluting with a gradient of 0-50% ethyl acetate in iso-heptane afforded the desired product as a beige solid (341 mg, 0.53 mmol, 57%).

LC/MS ($C_{29}H_{37}ClN_6O_3SiS_2$) 645 [M+H]$^+$; RT 2.91 (LCMS-V-C)

$^1$H NMR (400 MHz, DMSO-d6) δ 7.80 (d, 1H), 7.50-7.39 (m, 2H), 7.29-7.18 (m, 1H), 5.85 (s, 2H), 4.38-4.22 (m, 4H), 3.78-3.67 (m, 4H), 3.30-3.21 (m, 2H), 2.32 (s, 3H), 2.20-2.06 (m, 2H), 1.31 (t, J=7.1 Hz, 2H), 0.97-0.86 (m, 2H), −0.11 (s, 9H).

Step E: ethyl 5-(3-{4-[3-(dimethylamino)prop-1-yn-1-yl]-2-fluorophenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H-pyrrolo[2,3-c]pyridazin-7-yl)-1,3-thiazole-4-carboxylate To an oven dried sealed flask was added the product from Preparation 4b (133 mg, 0.69 mmol, 1.3 eq) in dimethyl-formamide (70 mL). Sodium hydride (60% dispersion; 52.8 mg, 1.32 mmol, 2.5 eq) was added to the solution and the mixture stirred for 2 min. A solution of the product from Step D (341 mg, 0.53 mmol, 1 eq) in dimethylformamide (30 mL) was added and the mixture was sparged with nitrogen (10 min) and heated at 100° C. for 1 h. The reaction was partitioned between ethyl acetate and water, and the organic phase was dried (magnesium sulfate) and concentrated in vacuo. Purification by automated flash column chromatography (CombiFlash Rf, 24 g RediSep™ silica cartridge) eluting with a gradient of 0-7% methanol in dichloromethane afforded the desired product as a beige solid (203 mg, 0.25 mmol, 48%).

LC/MS ($C_{40}H_{48}FN_7O_4SiS_2$) 802 [M+H]V; RT 2.59 (LCMS-V-C)

$^1$H NMR (400 MHz, DMSO-d6) δ 7.79 (d, 1H), 7.47-7.38 (m, 2H), 7.31 (dd, 1H), 7.27-7.11 (m, 3H), 5.84 (s, 2H), 4.36-4.20 (m, 4H), 4.13 (t, 2H), 3.75-3.66 (m, 2H), 3.39 (s, 2H), 3.31-3.19 (m, 4H), 2.30 (s, 3H), 2.19 (s, 6H), 2.18-2.09 (m, 2H), 1.28 (t, 3H), 0.95-0.84 (m, 2H), −0.11 (s, 9H).

Step F: ethyl 2-{3-[(1,3-benzothiazol-2-yl)amino]-4-methyl-5H,6H,7H-pyrrolo[2,3-c]pyridazin-7-yl}-5-(3-{4-[3-(dimethylamino)prop-1-yn-1-yl]-2-fluorophenoxy}propyl)-1,3-thiazole-4-carboxylate To a solution of the product from Step E (203 mg, 0.25 mmol, 1 eq) in dichloromethane (10 mL) was added trif-luoroacetic acid (5.0 mL, 65.8 mmol, 260 eq) and the mixture was stirred at rt for 6 h. The reaction was diluted with dichloromethane, cooled to 0° C. and neutralised by the addition of 2M aqueous sodium hydroxide. The organic phase was dried (PTFE phase separator) and concentrated in vacuo. Purification by automated flash column chromatography (CombiFlash Rf, 24 g RediSep™ silica cartridge) eluting with a gradient of 0-5% methanol in dichloromethane afforded the desired product as a yellow solid (114 mg, 0.17 mmol, 67%).

LC/MS ($C_{34}H_{34}FN_7O_3S_2$) 672 [M+H]$^+$; RT 2.04 (LCMS-V-C)

$^1$H NMR (400 MHz, DMSO-d6) δ 11.36 (br s, 1H), 7.89 (d, J=7.9 Hz, 1H), 7.58-7.47 (m, 1H), 7.43-7.28 (m, 2H), 7.26-7.12 (m, 3H), 4.33 (t, 2H), 4.27 (q, 2H), 4.15 (t, J=6.1 Hz, 2H), 3.40 (s, 2H), 3.34-3.22 (m, 4H), 2.33 (s, 3H), 2.21 (s, 6H), 2.16 (t, 2H), 1.29 (t, J=7.1 Hz, 3H).

Step G: 2-{3-[(1,3-benzothiazol-2-yl)amino]-4-methyl-5H,6H,7H-pyrrolo[2,3-c]pyridazin-7-yl}-5-(3-{4-[3-(dimethylamino)prop-1-yn-1-yl]-2-fluorophenoxy}propyl)-1,3-thiazole-4-carboxylic acid To a solution of the product from Step F (114 mg, 0.17 mmol, 1 eq) in 1,4-dioxane (15 mL) was added lithium hydroxide monohydrate (71.2 mg, 1.7 mmol, 10 eq) and the mixture was heated at reflux for 7 h. The reaction was concentrated in vacuo, and the residue was triturated with water and acetonitrile, filtered and dried under vacuum to afford the desired product as a yellow solid (64.7 mg, 0.1 mmol, 59%), as a lithium salt.

HRMS-ESI (m/z) [M+H]+ calcd for $C_{32}H_{31}FN_7O_3S_2$: 644.1914, found 644.1908.

Example 23: 3-{1-(Adamantan-1-yl)methyl]-5-methyl-1H-pyrazol-4-yl}-6-{3-[(1,3-benzothiazol-2-yl)amino]-4-methyl-7H-pyrrolo[2,3-c]pyridazin-7-yl}pyridine-2-carboxylic acid

Step A: tert-butyl N-(pent-3-yn-1-yl)carbamate

To a solution of pent-3-yn-1-amine hydrochloride (5 g, 41.8 mmol, 1 eq) in tetrahydrofuran (130 mL) and water (130 mL) was added sodium bicarbonate (10.5 g, 125 mmol, 3 eq), followed by di-tert-butyl dicarbonate (9.12 g, 41.8 mmol, 1 eq) and the mixture was stirred at ambient temperature overnight. The reaction was diluted with ethyl acetate, successively washed with saturated aqueous sodium bicarbonate and brine, dried (magnesium sulfate) and concentrated in vacuo to afford the desired product as a yellow oil (8.2 g, 44.8 mmol, >100%).

$^1$H NMR (400 MHz, DMSO-d6) δ 6.89 (t, J=5.9 Hz, 1H), 2.99 (td, J=7.3, 5.9 Hz, 2H), 2.25-2.15 (m, 2H), 1.73 (t, J=2.6 Hz, 3H), 1.38 (s, 9H).

Step B: ethyl 3-bromo-6-{[(tert-butoxy)carbonyl](pent-3-yn-1-yl)amino}pyridine-2-carboxylate To an oven-dried sealed flask was added the product from Step A (8.2 g, 44.8 mmol, 1 eq), ethyl 3,6-dibromopicolinate (13.8 g, 44.8 mmol, 1 eq), Xantphos (2.59 g, 4.47 mmol, 0.1 eq), cesium carbonate (29.2 g, 89.5 mmol, 2 eq) and 1,4-dioxane (180 mL). The vessel was evacuated and flushed with nitrogen then tris(dibenzylideneacetone)dipal-ladium(0) (2.05 g, 2.24 mmol, 0.05 eq) was added and the mixture was sparged with nitrogen (10 mins) then heated at 130° C. for 1 h. The reaction was diluted with ethyl acetate and filtered through celite, then successively washed with water and brine, dried (magnesium sulfate) and concentrated in vacuo. Purification by automated flash column chromatography (CombiFlash Rf, 330 g RediSep™ silica cartridge) eluting with a gradient of 0-8% ethyl acetate in iso-heptane afforded the desired product as a yellow oil (9.95 g, 24.2 mmol, 54%).

LC/MS ($C_{18}H_{23}BrN_2O_4$) 357 [M-tBu]$^+$; RT 2.59 (LCMS-V-C)

$^1$H NMR (400 MHz, DMSO-d6) δ 8.14 (d, J=8.9 Hz, 1H), 7.71 (d, J=8.9 Hz, 1H), 4.38 (q, J=7.1 Hz, 2H), 3.96-3.87 (m, 2H), 2.49-2.38 (m, 2H), 1.66 (t, J=2.5 Hz, 3H), 1.48 (s, 9H), 1.33 (t, J=7.1 Hz, 3H).

Step C: ethyl 3-bromo-6-[(pent-3-yn-1-yl)amino] pyridine-2-carboxylate

To a solution of the product from Step B (9.95 g, 24.2 mmol, 1 eq) in dichloromethane (120 mL) was added trifluoroacetic acid (19.9 mL, 260 mmol, 10.8 eq) and the mixture was stirred at ambient overnight. The reaction was diluted with dichloromethane, cooled to 0° C. and neutralised by the addition of 4M aqueous sodium hydroxide. The organic phase was dried (phase separator) and concentrated in vacuo. Purification by automated flash column chromatography (CombiFlash Rf, 220 g RediSep™ silica cartridge) eluting with a gradient of 0-30% ethyl acetate in iso-heptane afforded the desired product as a yellow oil (6.68 g, 21.5 mmol, 89%).

LC/MS ($C_{13}H_{15}BrN_2O_2$) 313 [M+H]$^+$; RT 2.12 (LCMS-V-C)

$^1$H NMR (400 MHz, DMSO-d6) δ 7.63 (d, J=9.0 Hz, 1H), 7.20 (t, J=5.8 Hz, 1H), 6.58 (d, J=9.0 Hz, 1H), 4.32 (q, J=7.1 Hz, 2H), 3.29 (td, J=7.1, 5.7 Hz, 2H), 2.41-2.29 (m, 2H), 1.74 (t, J=2.6 Hz, 3H), 1.30 (t, J=7.1 Hz, 3H).

Step D: ethyl 3-bromo-6-{3-chloro-4-methyl-7H-pyrrolo[2,3-c]pyridazin-7-yl}pyridine-2-carboxylate To a solution of the product from Step C (6.68 g, 21.5 mmol, 1 eq) in 1,4-dioxane (220 mL) was added 3,6-dichloro-1,2,4,5-tetrazine (6.48 g, 42.9 mmol, 2 eq) and the mixture was heated in a sealed flask at 120° C. for 72 h. The reaction was diluted with methanol, filtered through a phase separator and concentrated in vacuo. Purification by automated flash column chromatography (CombiFlash Rf, 120 g RediSep™ silica cartridge) eluting with a gradient of 0-40% ethyl acetate in iso-heptane afforded the desired product as a red solid (1.49 g, 3.77 mmol, 18%).

LC/MS ($C_{15}H_{12}BrClN_4O_2$) 397 [M+H]$^+$; RT 2.36 (LCMS-V-C)

$^1$H NMR (400 MHz, DMSO-d6) δ 8.93 (d, J=8.9 Hz, 1H), 8.63 (d, J=3.9 Hz, 1H), 8.53 (d, J=8.9 Hz, 1H), 7.11 (d, J=3.9 Hz, 1H), 4.45 (q, J=7.1 Hz, 2H), 2.64 (s, 3H), 1.37 (t, J=7.1 Hz, 3H).

Step E: ethyl 3-{1-[(adamantan-1-yl)methyl]-5-methyl-1H-pyrazol-4-yl}-6-{3-chloro-4-methyl-7H-pyrrolo[2,3-c]pyridazin-7-yl}pyridine-2-carboxylate To a solution of the product from Step D (1.49 g, 3.77 mmol, 1 eq) in tetrahydrofuran (5 mL) and water (15 mL) was added the product from Preparation 5a (1.48 g, 4.14 mmol, 1.1 eq) and potassium carbonate (1.56 g, 11.3 mmol, 3 eq). The vessel was evacuated and flushed with nitrogen then Pd(dppf)C$_{12}$·CH$_2$Cl$_2$ (308 mg, 0.38 mmol, 0.1 eq) was added and the mixture was sparged with nitrogen (10 mins)

then heated at 90° C. overnight in a sealed flask. The reaction was partitioned between ethyl acetate and water, and the organic phase was dried (magnesium sulfate) and concentrated in vacuo. Purification by automated flash column chromatography (CombiFlash Rf, 80 g RediSep™ silica cartridge) eluting with a gradient of 0-40% ethyl acetate in iso-heptane afforded the desired product as a white solid (1.08 g, 1.98 mmol, 53%).

LC/MS ($C_{30}H_{33}ClN_6O_2$) 545 [M+H]$^+$; RT 2.72 (LCMS-V-C)

$^1$H NMR (400 MHz, DMSO-d6) δ 8.97 (d, J=8.6 Hz, 1H), 8.69 (d, J=3.9 Hz, 1H), 8.17 (d, J=8.6 Hz, 1H), 7.43 (s, 1H), 7.10 (d, J=3.9 Hz, 1H), 4.22 (q, J=7.1 Hz, 2H), 3.80 (s, 2H), 2.65 (s, 3H), 2.23 (s, 3H), 2.03-1.89 (m, 3H), 1.73-1.50 (m, 12H), 1.16 (t, 3H).

Step F: ethyl 3-{1-[(adamantan-1-yl)methyl]-5-methyl-1H-pyrazol-4-yl}-6-{3-[(1,3-benzothiazol-2-yl)amino]-4-methyl-7H-pyrrolo[2,3-c]pyridazin-7-yl}pyridine-2-carboxylate To an oven-dried sealed flask was added the product from Step E (1.08 mg, 1.98 mmol, 1 eq), 2-aminothiazole (594 mg, 3.96 mmol, 2 eq), NN-diisopropylethylamine (1.03 mL, 5.93 mmol, 3 eq) and 1,4-dioxane (80 mL). The vessel was evacuated and flushed with nitrogen then JosiPhos (183 mg, 0.2 mmol, 0.1 eq) was added and the mixture was sparged with nitrogen (10 mins) then heated at 150° C. for 2 days. The reaction was diluted with ethyl acetate, successively washed with water and brine, and the organic phase was dried (magnesium sulfate) and concentrated in vacuo. Purification by automated flash column chromatography (CombiFlash Rf, 40 g RediSep™ silica cartridge) eluting with a gradient of 0-70% ethyl acetate in iso-heptane afforded the desired product as an orange solid (510 mg, 0.77 mmol, 39%).

LC/MS ($C_{37}H_{38}N_{802}S$) 659 [M+H]$^+$; RT 2.9 (LCMS-V-C)

$^1$H NMR (400 MHz, DMSO-d6) δ 9.13 (d, J=8.6 Hz, 1H), 8.61 (d, J=3.9 Hz, 1H), 8.16 (d, J=8.6 Hz, 1H), 7.91 (br s, 1H), 7.62 (br s, 1H), 7.44 (s, 1H), 7.41-7.32 (m, 1H), 7.27-7.11 (m, 1H), 6.99 (d, J=3.9 Hz, 1H), 4.22 (q, J=7.1 Hz, 2H), 3.80 (s, 2H), 2.65 (s, 3H), 2.23 (s, 3H), 2.03-1.89 (m, 3H), 1.76-1.52 (m, 12H), 1.16 (t, 3H).

Step G: 3-{1-[(adamantan-1-yl)methyl]-5-methyl-1H-pyrazol-4-yl}-6-{3-[(1,3-benzothiazol-2-yl)amino]-4-methyl-7H-pyrrolo[2,3-c]pyridazin-7-yl}pyridine-2-carboxylic acid To a solution of the product from Step F (400 mg, 0.61 mmol, 1 eq) in 1,4-dioxane (15 mL) was added lithium hydroxide monohydrate (255 mg, 6.07 mmol, 10 eq) and the mixture was heated at reflux overnight. The reaction was concentrated in vacuo, and the residue was triturated in water, filtered and dried under vacuum. Purification by automated flash column chromatography (CombiFlash Rf, 40 g RediSep™ silica cartridge) eluting with a gradient of 0-14% methanol in dichloromethane afforded a pale yellow solid that was triturated with methanol, filtered and dried under vacuum to afford the desired product as a yellow solid (154 mg, 0.24 mmol, 40%).

HRMS-ESI (m/z) [M+H]+ calcd for $C_{35}H_{35}N_8O_2S$: 631.2604, found 631.2600.

Example 24: 3-{1-(Adamantan-1-yl)methyl]-5-methyl-1H-pyrazol-4-yl}-6-{3-[(1,3-benzothiazol-2-yl)amino]-4-methyl-5H,6H,7H,8H-pyrido[2,3-c]pyridazin-8-yl}pyridine-2-carboxylic acid Step A: ethyl 3-{1-[(adamantan-1-yl)methyl]-5-methyl-1H-pyrazol-4-yl}-6-aminopyridine-2-carboxylate A biphasic solution of ethyl 6-amino-3-bromopicolinate (5.14 g, 21 mmol, 1 eq), the product from Preparation 5a (7.47 g, 21 mmol, 1 eq) and potassium carbonate (8.7 g, 62.9 mmol, 3 eq) in tetrahydrofuran (100 mL) and water (20 mL) was mixed vigorously while sparging with nitrogen (10 min). Pd(dppf)C$_{12}$·CH$_2$Cl$_2$ (2.57 g, 3.15 mmol, 0.15 eq) was added and the mixture was heated at reflux for 16 h. The reaction was allowed to cool to ambient temperature and was filtered through celite. The filtrate was diluted with ethyl acetate (200 mL), washed with water (100 mL), and the organic phase was washed with brine, dried (magnesium sulfate) and concentrated in vacuo. Purification by automated flash column chromatography (CombiFlash Rf, 220 g RediSep™ silica cartridge) eluting with a gradient of 0-90% ethyl acetate in iso-heptane afforded the desired product as a cream solid (5.28 g, 13.4 mmol, 64%).

LC/MS (C$_{23}$H$_{30}$N$_4$O$_2$) 395 [M+H]$^+$; RT 1.32 (LCMS-V-B1)

$^1$H NMR (400 MHz, DMSO-d6) δ 7032 (d, 1H), 7.21 (s, 1H), 6.58 (d, 1H), 6.24 (s, 2H), 4.05 (q, 2H), 3.72 (s, 2H), 2.10 (s, 3H), 1.98-1.88 (m, 3H), 1.71-1.47 (m, 12H), 1.10 (t, J=7.1 Hz, 3H).

Step B: ethyl 3-{1-[(adamantan-1-yl)methyl]-5-methyl-1H-pyrazol-4-yl}-6-{[3-(3,6-dichloro-5-methylpyridazin-4-yl)propyl]amino}pyridine-2-carboxylate To a solution of the product from Preparation 2e (1.92 g, 8.76 mmol, 1 eq) and the product from Step A (3.8 g, 9.64 mmol, 1.1 eq) in methanol (40 mL) was added acetic acid (15 mL) and sodium cyanoborohydride (2.75 g, 43.8 mmol, 5 eq) portionwise and the mixture was heated at reflux for 1 h. The reaction was allowed to cool to ambient temperature then poured onto 1N aqueous sodium hydroxide (50 mL) and extracted with ethyl acetate (3×50 mL). The organic phase was successively washed with saturated aqueous sodium bicarbonate (100 mL) and brine (100 mL), dried (magnesium sulfate) and concentrated in vacuo. Purification by automated flash column chromatography (CombiFlash Rf, 40 g RediSep™ silica cartridge) eluting with a gradient of 0-70% ethyl acetate in iso-heptane afforded the desired product as a white solid (3.99 g, 6.68 mmol, 76%).

LC/MS (C$_{31}$H$_{38}$Cl$_2$N$_6$O$_2$) 597 [M+H]$^+$; RT 1.53 (LCMS-V-B1)

$^1$H NMR (400 MHz, DMSO-d6) δ 7.34 (d, J=8.6 Hz, 1H), 7.22 (s, 1H), 6.95 (t, J=5.7 Hz, 1H), 6.63 (d, J=8.6 Hz, 1H), 4.06 (q, J=7.1 Hz, 2H), 3.72 (s, 2H), 3.41-3.31 (m, 2H), 2.92-2.83 (m, 2H), 2.42 (s, 3H), 2.10 (s, 3H), 1.98-1.89 (m, 3H), 1.86-1.74 (m, 2H), 1.71-1.48 (m, 12H), 1.08 (t, J=7.1 Hz, 3H).

Step C: ethyl 3-{1-[(adamantan-1-yl)methyl]-5-methyl-1H-pyrazol-4-yl}-6-{3-chloro-4-methyl-5H,6H,7H,8H-pyrido[2,3-c]pyridazin-8-yl}pyridine-2-carboxylate To a solution of the product from Step B (3.99 g, 6.68 mmol, 1 eq) in alpha,alpha,alpha-trifluorotoluene (150 mL) was added cesium carbonate (4.35 g, 13.4 mmol, 2 eq) and the mixture was heated in a sealed tube at 160° C. for 3 days. The reaction was allowed to cool to ambient temperature and concentrated in vacuo. Purification by automated flash column chromatography (CombiFlash Rf, 120 g RediSep™ silica cartridge) eluting with a gradient of 0-70% ethyl acetate in iso-heptane afforded the desired product as a white solid (0.95 g, 1.69 mmol, 25%).

LC/MS (C$_{31}$H$_{37}$ClN$_6$O$_2$) 561 [M+H]$^+$; RT 1.55 (LCMS-V-B1)

$^1$H NMR (400 MHz, DMSO-d6) δ 7.85 (d, J=8.6 Hz, 1H), 7.71 (d, J=8.6 Hz, 1H), 7.35 (s, 1H), 4.15 (q, J=7.1 Hz, 2H), 4.01-3.92 (m, 2H), 3.77 (s, 2H), 2.88 (t, J=6.6 Hz, 2H), 2.31 (s, 3H), 2.19 (s, 3H), 2.04-1.88 (m, 5H), 1.73-1.50 (m, 12H), 1.13 (t, J=7.1 Hz, 3H).

Step D: ethyl 3-{1-[(adamantan-1-yl)methyl]-5-methyl-1H-pyrazol-4-yl}-6-{3-[(1,3-benzothiazol-2-yl)amino]-4-methyl-5H,6H,7H,8H-pyrido[2,3-c]pyridazin-8-yl}pyridine-2-carboxylate To a solution of the product from Step C (946 mg, 1.69 mmol, 1 eq), 2-aminobenzothiazole, (380 mg, 2.53 mmol, 1.5 eq) and NN-diisopropylethylamine (0.88 mL, 5.06 mmol, 3 eq) in 1,4-dioxane (30 mL) was added Xantphos (97.6 mg, 0.17 mmol, 0.1 eq) and tris(dibenzylideneacetone) dipalladium(0) (77.2 mg, 0.08 mmol, 0.05 eq) and the mixture was heated in a sealed flask at 160° C. for 60 h. The reaction was allowed to cool to ambient temperature and was diluted with ethyl acetate (20 mL), washed with brine (25 mL), dried (magnesium sulfate) and concentrated in vacuo. Purification by automated flash column chromatography (CombiFlash Rf, 80 g RediSep™ silica cartridge) eluting with a gradient of 0-75% ethyl acetate in iso-heptane afforded the desired product as an orange solid (606 mg, 0.9 mmol, 53%).

LC/MS (C$_{38}$H$_{42}$N$_8$O$_2$S) 675 [M+H]$^+$; RT 1.61 (LCMS-V-B1)

$^1$H NMR (400 MHz, DMSO-d6) δ 7.95 (d, J=9.6 Hz, 1H), 7.83 (br s, 1H), 7.69 (d, 1H), 7.57 (br s, 1H), 7.40-7.31 (m, 2H), 7.18 (t, J=7.5 Hz, 1H), 4.15 (q, J=7.1 Hz, 2H), 4.05-3.97 (m, 2H), 3.77 (s, 2H), 2.86 (t, J=6.5 Hz, 2H), 2.33 (s, 3H), 2.20 (s, 3H), 2.04-1.89 (m, 5H), 1.72-1.50 (m, 12H), 1.13 (t, 3H).

Step E: 3-{1-[(adamantan-1-yl)methyl]-5-methyl-1H-pyrazol-4-yl}-6-{3-[(1,3-benzothiazol-2-yl)amino]-4-methyl-5H,6H,7H,8H-pyrido[2,3-c]pyridazin-8-yl}pyridine-2-carboxylic acid To a solution of the product from Step D (600 mg, 0.89 mmol, 1 eq) in 1,4-dioxane (10 mL) was added lithium hydroxide monohydrate (74.6 mg, 1.78 mmol, 2 eq) and the mixture was heated at reflux for 1 h. The reaction was allowed to cool to ambient temperature and concentrated in vacuo. The residue was taken up in water, acidified to pH 4 and the solids were collected by filtration, washed with water and dried. Purification by automated flash column chromatography (CombiFlash Rf, 12 g RediSep™ silica cartridge) eluting with a gradient of 0-10% methanol in dichloromethane afforded the desired product as a yellow solid (93 mg, 0.14 mmol, 16%).

HRMS-ESI (m/z) [M+H]+ calcd for $C_{36}H_{39}N_8O_2S$: 647.2917, found 647.2913.

Example 25: 2-{3-[(1,3-Benzothiazol-2-yl)amino]-4-methyl-5H,6H,7H,8H,9H-pyridazino[3,4-b]aze-pin-9-yl}-1,3-thiazole-4-carboxylic acid Step A: ethyl 2-{[(tert-butoxy)carbonyl](hept-5-yn-1-yl)amino}-1,3-thiazole-4-carboxylate To ethyl 2-{[(tert-butoxy)carbonyl]amino}-1,3-thiazole-4-carboxylate (1.62 g, 5.94 mmol, 1 eq) in tetrahydrofuran (50 mL) was added hept-5-yn-1-ol (1 g, 8.92 mmol, 1.5 eq) and triphenylphosphine (2.34 g, 8.92 mmol, 1.5 eq), followed by dropwise addition of diethyl azodicarboxylate (1.62 mL, 8.92 mmol, 1.5 eq) and the mixture was stirred at ambient temperature for 16 h. The reaction was partitioned between dichloromethane and brine, and the organic phase was dried (PTFE phase separator) and concentrated in vacuo. Purification by automated flash column chromatography (CombiFlash Rf, 40 g RediSep™ silica cartridge) eluting with a gradient of 0-15% ethyl acetate in iso-heptane afforded the desired product as a yellow oil (1.92 g, 5.24 mmol, 88%).

LC/MS ($C18H_{26}N_2O_4S$) 367 [M+H]⁺; RT 2.53 (LCMS-V-C)

¹H NMR (400 MHz, DMSO-d6) δ 8.07 (s, 1H), 4.27 (q, J=7.1 Hz, 2H), 4.11-4.00 (m, 2H), 2.22-2.13 (m, 2H), 1.79-1.68 (m, 5H), 1.55 (s, 9H), 1.48-1.34 (m, 2H), 1.30 (t, J=7.1 Hz, 2H).

Step B: ethyl 2-[(hept-5-yn-1-yl)amino]-1,3-thiaz-ole-4-carboxylate

To a solution of the product from Step A (1.97 g, 5.38 mmol, 1 eq) in dichloromethane (50 mL) was added trifluoroacetic acid (4.94 mL, 64.5 mmol, 12 eq) and the mixture was stirred at ambient temperature overnight. The reaction was cooled to 0° C. and diluted with dichloromethane, basified with 2N aqueous sodium hydroxide, and the organic phase was dried (PTFE phase separator) and concentrated in vacuo to afford the desired product as a yellow oil (1.46 g, 5.48 mmol, >100%).

LC/MS ($C_{13}H_{18}N_2O_2S$) 267 [M+H]⁺; RT 1.91 (LCMS-V-C)

¹H NMR (400 MHz, DMSO-d6) δ 7.81 (t, J=5.4 Hz, 1H), 7.49 (s, 1H), 5.77 (s, 1H), 4.21 (q, J=7.1 Hz, 2H), 3.21 (td, J=6.9, 5.3 Hz, 2H), 2.19-2.07 (m, 2H), 1.73 (t, J=2.6 Hz, 3H), 1.67-1.55 (m, 2H), 1.54-1.41 (m, 2H), 1.26 (t, J=7.1 Hz, 3H).

Step C: ethyl 2-{3-chloro-4-methyl-5H,6H,7H,8H, 9H-pyridazino[3,4-b]azepin-9-yl}-1,3-thiazole-4-carboxylate To a solution of 3,6-dichloro-1,2,4,5-tetrazine (827 mg, 5.48 mmol, 1 eq) in tetrahydrofuran (20 mL) was added the product from Step B (1.46 g, 5.48 mmol, 1 eq) and the mixture was heated at 120° C. in a sealed flask for 48 h. The reaction was concentrated in vacuo. And purification by automated flash column chromatography (CombiFlash Rf, 40 g RediSep™ silica cartridge) eluting with a gradient of 0-60% ethyl acetate in iso-heptane afforded the desired product as a pink solid (0.92 g, 2.61 mmol, 48%).

LC/MS ($C_{15}H_{17}ClN_4O_2S$) 353 [M+H]⁺; RT 2.00 (LCMS-V-C)

¹H NMR (400 MHz, DMSO-d6) δ 7.85 (s, 1H), 4.28 (q, J=7.1 Hz, 3H), 4.22-4.13 (m, 2H), 2.95-2.88 (m, 2H), 2.40 (s, 3H), 2.02-1.89 (m, 2H), 1.84-1.75 (m, 2H), 1.30 (t, J=7.1 Hz, 3H).

Step D: ethyl 2-{3-[(1,3-benzothiazol-2-yl)amino]-4-methyl-5H,6H,7H,8H,9H-pyridazino[3,4-b]aze-pin-9-yl}-1,3-thiazole-4-carboxylate To an oven-dried microwave vial was added the product from Step C (920 mg, 2.61 mmol, 1 eq), 2-aminothiazole (470 mg, 3.13 mmol, 1.2 eq), Xantphos (151 mg, 0.26 mmol, 0.1 eq), N,N-diisopropylethylamine (1.36 mL, 7.82 mmol, 3 eq) and 1,4-dioxane (15 mL). The vessel was evacuated and flushed with nitrogen then tris(dibenzylideneacetone)dipalladium(0) (119 mg, 0.13 mmol, 0.05 eq) was added and the mixture was sparged with nitrogen (10 min) then heated at 150° C. for 8 h under microwave irradiation. The reaction was partitioned between ethyl acetate and brine, and the organic phase was dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane gave a solid that was triturated with acetonitrile, filtered and dried under vacuum to afford the desired product as a yellow solid (0.81 g, 1.74 mmol, 67%).

LC/MS ($C_{22}H_{22}N_6O_2S_2$) 467 [M+H]⁺; RT 2.20 (LCMS-V-C)

¹H NMR (400 MHz, DMSO-d6) δ 7.88 (br s, 1H), 7.75 (s, 1H), 7.49 (br s, 1H), 7.44-7.34 (m, 1H), 7.27-7.16 (m, 1H), 4.28 (q, J=7.1 Hz, 2H), 4.14-4.01 (s, 2H), 2.90-2.78 (m, 2H), 2.42 (s, 3H), 1.96-1.83 (m, 2H), 1.82-1.70 (m, 2H), 1.31 (t, J=7.1 Hz, 3H).

Step E: 2-{3-[(1,3-benzothiazol-2-yl)amino]-4-methyl-5H,6H,7H,8H,9H-pyridazino[3,4-b]azepin-9-yl}-1,3-thiazole-4-carboxylic acid To a solution of the product from Step D (30 mg, 0.06 mmol, 1 eq) in 1,4-dioxane (6 mL) was added lithium hydroxide monohydrate (27 mg, 0.64 mmol, 10 eq) and the mixture was heated at reflux for 6 h. The reaction was concentrated in vacuo, then dissolved in MeOH, loaded onto a methanol-wet PE-AX cartridge (5 g), washed with methanol, eluted with 9:1 dichloromethane/formic acid and concentrated in vacuo. The residue was triturated with dichloromethane and methanol, filtered and dried under vacuum to afford the desired product as an off-white solid (22.4 mg, 0.05 mmol, 79%).

HRMS-ESI (m/z) [M+H]+ calcd for $C_{20}H_{19}N_6O_2S_2$: 439.1011, found 439.1003.

Example 26: 3-{3-[(1,3-Benzothiazol-2-yl)amino]-4-methyl-5H,6H,7H,8H-pyrido[2,3-c]pyridazin-8-yl}benzoic acid

Step A: ethyl 3-{[3-(3,6-dichloro-5-methylpyridazin-4-yl)propyl]amino}benzoate To a solution of the product from Preparation 2e (100 mg, 0.46 mmol, 1 eq) and ethyl 3-aminobenzoate (79.2 mg, 0.48 mmol, 1.05 eq) in methanol (6 mL) was added acetic acid (2 mL) and sodium cyanoborohydride (57.4 mg, 0.91 mmol, 2 eq) portionwise and the mixture was stirred overnight. The reaction was quenched by the addition of 1N aqueous sodium hydroxide and extracted with ethyl acetate (3×50 mL), and the combined organic extracts were washed with brine, dried (magnesium sulfate) and concentrated in vacuo. Purification by automated flash column chromatography (CombiFlash Rf, 12 g RediSep™ silica cartridge) eluting with a gradient of 0-40% ethyl acetate in iso-heptane afforded the desired product as a colourless oil (88 mg, 0.24 mmol, 52%).

LC/MS ($C_{17}H_{19}Cl_2N_3O_2$) 332 [M−HCl+H]⁺; RT 1.34 (LCMS-V-B1)

¹H NMR (400 MHz, Chloroform-d) δ 7.40 (dt, J=7.6, 1.3 Hz, 1H), 7.28 (dd, J=2.6, 1.5 Hz, 1H), 7.23 (t, J=7.9 Hz, 1H), 6.78 (ddd, J=8.1, 2.6, 1.0 Hz, 1H), 4.36 (q, J=7.2 Hz, 2H), 3.32 (t, J=6.7 Hz, 2H), 2.98-2.86 (m, 2H), 2.40 (s, 3H), 1.96-1.83 (m, 2H), 1.38 (t, J=7.1 Hz, 3H).

Step B: ethyl 3-{3-chloro-4-methyl-5H,6H,7H,8H-pyrido[2,3-c]pyridazin-8-yl}benzoate To a solution of the product from Step A (88 mg, 0.24 mmol, 1 eq) in dichloromethane (3 mL) was added trifluoroacetic acid (0.1 mL) and the mixture was stirred at ambient temperature overnight. The reaction was neutralised by addition of 1N aqueous sodium hydroxide and the mixture was extracted with dichloromethane (2×20 mL). The combined organic extracts were washed with brine, dried (magnesium sulfate) and concentrated in vacuo to afford the desired product as a yellow solid (48 mg, 0.14 mmol, 61%).

LC/MS ($C_{17}H_{18}ClN_3O_2$) 332 [M+H]⁺; RT 1.27 (LCMS-V-B1)

¹H NMR (400 MHz, DMSO-d6) δ 7.90 (t, J=1.9 Hz, 1H), 7.80 (dt, J=7.6, 1.5 Hz, 1H), 7.66-7.60 (m, 1H), 7.56 (t, J=7.7 Hz, 1H), 4.33 (q, J=7.1 Hz, 2H), 3.76-3.70 (m, 2H), 2.87 (t, J=6.5 Hz, 2H), 2.25 (s, 3H), 2.09-1.97 (m, 2H), 1.32 (t, J=7.1 Hz, 3H).

Step C: ethyl 3-{3-[(1,3-benzothiazol-2-yl)amino]-4-methyl-5H,6H,7H,8H-pyrido[2,3-c]pyridazin-8-yl}benzoate To a solution of the product from Step B (80 mg, 0.24 mmol, 1 eq), 2-aminobenzothiazole, (43.5 mg, 0.29 mmol, 1.2 eq), N,N-diisopropylethylamine (0.13 mL, 0.72 mmol, 3 eq) and 1,4-dioxane (5 mL) was added Xantphos (14 mg, 0.02 mmol, 0.1 eq) and tris(dibenzylideneacetone)dipalladium(0) (11 mg, 0.01 mmol, 0.05 eq) and the mixture was heated in a sealed tube at 160° C. for 24 h. The reaction was allowed to cool to ambient temperature, then partitioned between ethyl acetate (20 mL) and brine (25 mL) and the organic phase was dried (magnesium sulfate) and concentrated in vacuo. Purification by reverse phase automated flash chromatography (CombiFlash Rf, C18 4.3 g RediSep column) eluting with a gradient of 5-95% acetonitrile in water afforded the crude desired product as a yellow glass (18 mg, 0.04 mmol, 17%) that was used directly in the subsequent step without further purification.

LC/MS ($C_{24}H_{23}N_5O_2S$) 446 [M+H]⁺; RT 1.31 (LCMS-V-B1) Step D: 3-{3-[(1,3-benzothiazol-2-yl)amino]-4-methyl-5H,6H,7H,8H-pyrido[2,3-c]pyridazin-8-yl}benzoic acid To a solution of the product from Step C (18 mg, 0.04 mmol, 1 eq) in 1,4-dioxane (5 mL) was added lithium hydroxide monohydrate (3.39 mg, 0.08 mmol, 2 eq) and the mixture was heated at reflux for 1 h. The reaction was allowed to cool to ambient temperature and concentrated in vacuo. The residue was taken up in water, acidified with 1N aqueous hydrochloric acid and concentrated in vacuo. Purification by preparative HPLC (HPLC-V-A1) afforded the desired product as a yellow solid (10.6 mg, 0.03 mmol, 63%).

HRMS-ESI (m/z) [M+H]+ calcd for $C_{22}H_{20}N_5O_2S$: 418.1338, found 418.1334.

Example 27: 2-[3-(1,3-Benzothiazol-2-ylamino)-4-methyl-6,7-dihydro-5H-pyrido[2,3-c]pyridazin-8-yl]-5-[3-[4-[3-(dimethylamino)prop-1-ynyl]-2-fluoro-phenoxy]propyl]thiazole-4-carboxylic acid Using Propargylic amine preparation General Procedure starting from Preparation 3d and dimethylamine as the appropriate amine. Then Hydrolysis General Procedure starting from the appropriate methyl ester, the desired product was obtained.

HRMS-ESI (m/z): [M+H]$^+$ calcd for $C_{34}H_{35}FN_7O_3S_2$: 672.2221, found 672.2205.

Example 28: 2-{3-[(1,3-Benzothiazol-2-yl)amino]-4-cyclopropyl-5H,6H,7H-pyrrolo[2,3-c]pyridazin-7-yl}-1,3-thiazole-4-carboxylic acid Step A: ethyl 2-{[(tert-butoxy)carbonyl](4-iodobut-3-yn-1-yl)amino}-1,3-thiazole-4-carboxylate To ethyl 2-{[(tert-butoxy)carbonyl]amino}-1,3-thiazole-4-carboxylate (3.16 g, 11.6 mmol, 1 eq) in tetrahydrofuran (150 mL) was added 4-iodobut-3-yn-1-ol (3.41 g, 17.4 mmol, 1.5 eq) and triphenylphosphine (4.56 g, 17.4 mmol, 1.5 eq), followed by dropwise addition of diethyl azodicarboxylate (2.74 mL, 17.4 mmol, 1.5 eq) and the mixture was stirred at ambient temperature for 16 h. The reaction was partitioned between ethyl acetate and brine, and the organic phase was dried (magnesium sulfate) and concentrated in vacuo. Purification by automated flash column chromatography (CombiFlash Rf, 120 g RediSep™ silica cartridge) eluting with a gradient of 0-15% ethyl acetate in iso-heptane afforded the desired product as a white solid (3.75 g, 8.33 mmol, 72%).

LC/MS ($C_{15}H_{19}1N_2O_4S$) 451 [M+H]$^+$; RT 2.45 (LCMS-V-C)

$^1$H NMR (400 MHz, DMSO-d6) δ 8.09 (s, 1H), 4.28 (q, J=7.1 Hz, 2H), 4.16 (t, J=6.7 Hz, 2H), 2.77 (t, J=6.7 Hz, 2H), 1.56 (s, 9H), 1.30 (t, J=7.1 Hz, 3H).

Step B: ethyl 2-[(4-iodobut-3-yn-1-yl)amino]-1,3-thiazole-4-carboxylate

To a solution of the product from Step A (3.75 g, 8.33 mmol, 1 eq) in dichloromethane (50 mL) was added trifluoroacetic acid (15.3 mL, 200 mmol, 24 eq) and the mixture was stirred at ambient temperature for 1 h. The reaction was cooled to 0° C., diluted with dichloromethane, basified with 2N aqueous sodium hydroxide, and the organic phase was dried (PTFE phase separator) and concentrated in vacuo to afford the desired product as a white solid (2.74 g, 7.82 mmol, 94%).

LC/MS ($C_{10}H_{11}IN_2O_2S$) 351 [M+H]$^+$; RT 1.84 (LCMS-V-C)

$^1$H NMR (400 MHz, DMSO-d6) δ 7.98 (t, J=5.7 Hz, 1H), 7.53 (s, 1H), 4.22 (q, J=7.1 Hz, 2H), 3.40-3.30 (m, 2H), 2.61 (t, J=6.8 Hz, 2H), 1.26 (t, J=7.1 Hz, 3H).

Step C: ethyl 2-{3-chloro-4-iodo-5H,6H,7H-pyrrolo[2,3-c]pyridazin-7-yl}-1,3-thiazole-4-carboxylate To a solution of 3,6-dichloro-1,2,4,5-tetrazine (1.18 g, 7.82 mmol, 1 eq) in tetrahydrofuran (80 mL) was added the product from Step B (2.74 g, 7.82 mmol, 1 eq) and the mixture was heated at reflux overnight. The reaction was allowed to cool to ambient temperature and the precipitate was collected by filtration, washed with tetrahydrofuran and dried under vacuum to afford the desired product as an off-white solid (1.06 g, 2.43 mmol, 31%).

LC/MS ($C_{12}H_{10}ClIN_4O_2S$) 437 [M+H]$^+$; RT 1.99 (LCMS-V-C)

$^1$H NMR (400 MHz, DMSO-d6) δ 8.17 (s, 1H), 4.45 (t, J=8.1 Hz, 2H), 4.31 (q, J=7.1 Hz, 2H), 3.46-3.33 (m, 2H), 1.31 (t, J=7.1 Hz, 3H).

Step D: ethyl 2-{3-chloro-4-cyclopropyl-5H,6H,7H-pyrrolo[2,3-c]pyridazin-7-yl}-1,3-thiazole-4-carboxylate To a sealed tube was added the product from Step C (120 mg, 0.27 mmol, 1 eq), potassium cyclopropyltrifluoroborate (102 mg, 0.69 mmol, 2.5 eq), potassium carbonate (114 mg, 0.82 mmol, 3 eq), tetrahydrofuran (16 mL) and water (4 mL). The vessel was evacuated and flushed with nitrogen then Pd(dppf)Cl$_2$·CH$_2$Cl$_2$ (44.9 mg, 0.05 mmol, 0.2 eq) was added and the mixture was sparged with nitrogen (10 min) then heated at 150° C. for 40 h under microwave irradiation. The reaction was partitioned between ethyl acetate and brine and the organic phase was dried (magnesium sulfate) and concentrated in vacuo. Purification by automated flash column chromatography (CombiFlash Rf, 12 g RediSep™ silica cartridge) eluting with a gradient of 0-90% ethyl acetate in iso-heptane afforded the desired product as a white solid (40 mg, 0.11 mmol, 42%).

LC/MS ($C_{15}H_{15}ClN_4O_2S$) 351 [M+H]$^+$; RT 2.00 (LCMS-V-C)

$^1$H NMR (400 MHz, DMSO-d6) δ 8.12 (d, J=9.9 Hz, 1H), 4.43-4.23 (m, 4H), 3.42-3.29 (m, 2H), 2.03-1.94 (m, 1H), 1.30 (t, 3H), 1.14-1.04 (m, 2H), 0.98-0.84 (m, 2H).

Step E: ethyl 2-{3-[(1,3-benzothiazol-2-yl)amino]-4-cyclopropyl-5H,6H,7H-pyrrolo[2,3-c]pyridazin-7-yl}-1,3-thiazole-4-carboxylate To an oven-dried microwave vial was added the product from Step D (40 mg, 0.11 mmol, 1 eq), 2-aminothiazole (25.7 mg, 0.17 mmol, 1.5 eq), NN-diisopropylethylamine (59.6 μL, 0.34 mmol, 3 eq) and 1,4-dioxane (3 mL). The vessel was evacuated and flushed with nitrogen then JosiPhos (10.5 mg, 0.01 mmol, 0.1 eq) was added and the mixture was sparged with nitrogen (10 min) then heated at 150° C. for 1 h under microwave irradiation. The reaction was partitioned between ethyl acetate and brine, and the organic phase was dried (magnesium sulfate) and concentrated in vacuo. Purification by automated flash column chromatography (CombiFlash Rf, 4 g RediSep™ silica cartridge) eluting with a gradient of 0-100% ethyl acetate in iso-heptane afforded the desired product as a yellow solid (18 mg, 0.04 mmol, 34%).

LC/MS ($C_{22}H_{20}N_6O_2S_2$) 464 [M+H]$^+$; RT 2.31 (LCMS-V-C)

$^1$H NMR (400 MHz, DMSO-d6) δ 10.58 (br s, 1H), 8.06 (s, 1H), 8.02-7.89 (m, 1H), 7.76-7.62 (m, 1H), 7.47-7.32 (m, 1H), 7.30-7.13 (m, 1H), 4.42-4.25 (m, 4H), 3.46-3.37 (m, 2H), 2.20-2.01 (m, 1H), 1.32 (t, J=7.1 Hz, 3H), 1.21-1.06 (m, 2H), 0.93-0.74 (m, 2H).

Step F: 2-{3-[(1,3-benzothiazol-2-yl)amino]-4-cyclopropyl-5H,6H,7H-pyrrolo[2,3-c]pyridazin-7-yl}-1,3-thiazole-4-carboxylic acid To a solution of the product from Step E (18 mg, 0.04 mmol, 1 eq) in 1,4-dioxane (6 mL) was added lithium hydroxide monohydrate (16.3 mg, 0.39 mmol, 10 eq) and the mixture was heated at reflux for 8 h. The reaction was concentrated in vacuo, dissolved in methanol, then loaded onto a methanol-wed PE-AX cartridge (10 g), washed with methanol, eluted with 9:1 dichloromethane/formic acid and concentrated in vacuo. The residue was successively triturated with dichloromethane and water, filtered and dried under vacuum to afford the desired product as a beige solid (2.44 mg, 0.01 mmol, 14.43%), as a formic acid salt.

HRMS-ESI (m/z) [M+H]+ calcd for $C_{20}H_{17}N_6O_2S_2$: 437.0854, found 437.0853.

Example 29: 3-{1-[(Adamantan-1-yl)methyl]-5-methyl-1H-pyrazol-4-yl}-6-{3-[(1,3-benzothiazol-2-yl)amino]-4-methyl-5H,6H,7H,8H,9H-pyridazino[3,4-b]azepin-9-yl}pyridine-2-carboxylic acid

Step A: [(hex-5-yn-1-yloxy)methyl]benzene

To a stirred solution of 5-hexyn-1-ol (5.36 g, 54.6 mmol, 1 eq) in tetrahydrofuran (35 mL), cooled to 0° C., was added sodium hydride (60% dispersion; 3.28 g, 81.9 mmol, 1.5 eq) portionwise and the mixture was allowed to stir for 30 min. Benzyl bromide (6.49 mL, 54.6 mmol, 1 eq) was added dropwise and the mixture was allowed to warm to ambient temperature and stir for 90 h. The reaction was cooled to 0° C. and quenched by the addition of saturated aqueous ammonium chloride (30 mL) then diluted with water (30 mL). The mixture was extracted with ethyl acetate (2×150 mL), and the combined organic extracts were washed with brine (100 mL), dried (magnesium sulfate) and concentrated in vacuo. Purification by automated flash column chromatography (CombiFlash Rf, 120 g RediSep™ silica cartridge) eluting with a gradient of 0-10% ethyl acetate in iso-heptane afforded the desired product as a yellow oil (10.2 g, 54.2 mmol, 99%).

LC/MS ($C_{13}H_{16}O$) 189 [M+H]$^+$; RT 2.21 (LCMS-V-C)

$^1$H NMR (400 MHz, Chloroform-d) δ 7.40-7.24 (m, 5H), 4.45 (s, 2H), 3.44 (t, J=6.3 Hz, 2H), 2.77 (t, J=2.7 Hz, 1H), 2.17 (td, J=7.0, 2.6 Hz, 2H), 1.70-1.57 (m, 2H), 1.56-1.37 (m, 2H).

Step B: [(hept-5-yn-1-yloxy)methyl]benzene

A solution of the product from Step A (10.2 g, 54.2 mmol, 1 eq) in tetrahydrofuran (90 mL) was cooled to −78° C. and n-butyllithium (2.5M in hexanes; 26 mL, 65 mmol, 1.2 eq) was added dropwise over 30 min. After stirring for 1 h, iodomethane (4.05 mL, 65 mmol, 1.2 eq) was added dropwise and the mixture was allowed to warm to 0° C. over 1 h. The reaction was quenched with aqueous saturated ammonium chloride (40 mL), diluted with water (40 mL), and extracted with ethyl acetate (3×100 mL). The combined organic extracts were successively washed with 2N aqueous sodium thiosulfate (200 mL) and brine (200 mL), dried (magnesium sulfate) and concentrated in vacuo. Purification by automated flash column chromatography (CombiFlash Rf, 220 g RediSep™ silica cartridge) eluting with a gradient of 0-6% ethyl acetate in iso-heptane afforded the desired product as a clear oil (10.4 g, 51.3 mmol, 95%).

LC/MS ($C_{14}H_{18}O$) 203 [M+H]$^+$; RT 2.37 (LCMS-V-C)

$^1$H NMR (400 MHz, DMSO-d6) δ 7.40-7.24 (m, 5H), 4.45 (s, 2H), 3.43 (t, J=6.4 Hz, 2H), 2.17-2.08 (m, 2H), 1.73 (t, J=2.6 Hz, 3H), 1.67-1.55 (m, 2H), 1.54-1.41 (m, 2H).

Step C: 4-[4-(benzyloxy)butyl]-3,6-dichloro-5-methylpyridazine

A solution of 3,6-dichloro-1,2,4,5-tetrazine (3.23 g, 21.4 mmol, 1 eq) and the product from Step B (5.2 g, 25.7 mmol, 1.2 eq) in toluene (40 mL) was heated at 130° C. overnight in a sealed flask. The reaction was allowed to cool to ambient temperature and was concentrated in vacuo. Purification by automated flash column chromatography (CombiFlash Rf, 120 g RediSep™ silica cartridge) eluting with a gradient of 0-30% ethyl acetate in iso-heptane afforded the desired product as a red oil (3.27 g, 10.1 mmol, 47%).

LC/MS ($C_{16}H_{18}C_2N_2O$) 325 [M+H]$^+$; RT 2.32 (LCMS-V-C)

$^1$H NMR (400 MHz, DMSO-d6) δ 7.40-7.24 (m, 5H), 4.46 (s, 2H), 3.49 (t, J=6.1 Hz, 2H), 2.87-2.78 (m, 2H), 2.41 (s, 3H), 1.74-1.62 (m, 2H), 1.61-1.51 (m, 2H).

Step D: 4-(3,6-dichloro-5-methylpyridazin-4-yl)butan-1-ol

To a solution of the product from Step C (3.27 g, 10.1 mmol, 1 eq) in dichloromethane (50 mL), cooled in an ice-water bath, was added boron trichloride (1M in dichloromethane; 50.3 mL, 50.3 mmol, 5 eq) dropwise and the mixture was allowed to warm to ambient temperature and stir for 1 h. The reaction was cooled to 0° C., quenched by the addition of methanol and concentrated in vacuo. The residue was partitioned between dichloromethane (100 mL) and saturated aqueous sodium bicarbonate (150 mL), and the organic phase was washed with brine (150 mL), dried (magnesium sulfate) and concentrated in vacuo. Purification by automated flash column chromatography (CombiFlash Rf, 40 g RediSep™ silica cartridge) eluting with a gradient of 0-80% ethyl acetate in iso-heptane afforded the desired product as a yellow oil (2.21 g, 9.4 mmol, 94%).

LC/MS ($C_9H_{12}Cl_2N_2O$) 235 [M+H]$^+$; RT 1.36 (LCMS-V-C)

$^1$H NMR (400 MHz, DMSO-d6) δ 4.44 (t, J=5.1 Hz, 1H), 3.45 (dd, J=6.0, 5.0 Hz, 2H), 2.87-2.76 (m, 2H), 2.43 (s, 3H), 1.62-1.48 (m, 4H).

Step E: 4-(3,6-dichloro-5-methylpyridazin-4-yl)butanal

An oven-dried flask was charged with dimethyl sulfoxide (1.6 mL, 22.6 mmol, 2.4 eq) and dichloromethane (60 mL) and the mixture was cooled to −78° C. Oxalyl chloride (2M in dichloromethane; 7.05 mL, 14.1 mmol, 1.5 eq) was added dropwise and the mixture was stirred for 1 h. A solution of the product from Step D (2.21 g, 9.4 mmol, 1 eq) in dichloromethane (20 mL) was added dropwise and the mixture was stirred for 1 h. Triethylamine (7.84 mL, 56.4 mmol, 6 eq) was added and the mixture was allowed to warm to 0° C. over 1 h. The reaction was quenched with water (50 mL), diluted with saturated aqueous sodium bicarbonate (50 mL) and extracted with dichloromethane (2×200 mL). The combined organic extracts were washed with brine (100 mL), dried (magnesium sulfate) and concentrated in vacuo. Purification by automated flash column chromatography (CombiFlash Rf, 40 g RediSep™ silica cartridge) eluting with a gradient of 0-70% ethyl acetate in iso-heptane afforded the desired product as a yellow oil (6.58 g, 6.78 mmol, 72%).

LC/MS ($C_9H_{10}Cl_2N_2O$) 233 [M+H]$^+$; RT 1.51 (LCMS-V-C)

$^1$H NMR (400 MHz, DMSO-d6) δ 9.70 (t, J=1.1 Hz, 1H), 2.86-2.76 (m, 2H), 2.63 (td, J=7.0, 1.1 Hz, 2H), 2.45 (s, 3H), 1.81-1.68 (m, 2H).

Step F: ethyl 3-{1-[(adamantan-1-yl)methyl]-5-methyl-1H-pyrazol-4-yl}-6-{[4-(3,6-dichloro-5-methylpyridazin-4-yl)butyl]amino}pyridine-2-carboxylate To a solution of the product from Step E (1.04 g, 4.45 mmol, 1 eq) and the product from Example 24, Step A (1.93 g, 4.89 mmol, 1.1 eq) in methanol (30 mL) and acetic acid (10 mL) was added sodium cyanoborohydride (559 mg, 8.89 mmol, 2 eq) and the mixture was stirred at ambient temperature overnight. The reaction was quenched with 1N aqueous sodium hydroxide (50 mL) and extracted with ethyl acetate (3×50 mL). The combined organic extracts were successively washed with saturated aqueous sodium bicarbonate and brine, dried (magnesium sulfate) and concentrated in vacuo. Purification by automated flash column chromatography (CombiFlash Rf, 40 g RediSep™ silica cartridge) eluting with a gradient of 0-70% ethyl acetate in iso-heptane afforded the desired product as a white gum (1.71 g, 2.8 mmol, 63%).

LC/MS ($C_{32}H_{40}Cl_2N_6O_2$) 611 [M+H]$^+$; RT 2.65 (LCMS-V-C)

$^1$H NMR (400 MHz, DMSO-d6) δ 7.32 (d, J=8.6 Hz, 1H), 7.21 (s, 1H), 6.81 (t, J=5.4 Hz, 1H), 6.60 (d, J=8.6 Hz, 1H), 4.05 (q, J=7.1 Hz, 2H), 3.72 (s, 2H), 3.32-3.23 (m, 2H), 2.90-2.81 (m, 2H), 2.43 (s, 3H), 2.10 (s, 3H), 1.94 (s, 3H), 1.74-1.48 (m, 16H), 1.07 (t, J=7.1 Hz, 3H).

Step G: ethyl 3-{1-[(adamantan-1-yl)methyl]-5-methyl-1H-pyrazol-4-yl}-6-{3-chloro-4-methyl-5H,6H,7H,8H,9H-pyridazino[3,4-b]azepin-9-yl}pyridine-2-carboxylate To a solution of the product from Step F (646 mg, 1.06 mmol, 1 eq) in alpha,alpha,alpha-trifluorotoluene (6 mL) was added cesium carbonate (1.03 g, 3.17 mmol, 3 eq) and XantPhos Pd G3 (50.1 mg, 0.05 mmol, 0.05 eq) and the mixture was sparged with nitrogen (10 min) then heated at 120° C. overnight. The reaction was partitioned between ethyl acetate and water, and the organic phase was dried (magnesium sulfate) and concentrated in vacuo. Purification by automated flash column chromatography (CombiFlash Rf, 12 g RediSep™ silica cartridge) eluting with a gradient of 0-60% ethyl acetate in iso-heptane afforded the desired product as an off-white solid (119 mg, 0.21 mmol, 20%).

LC/MS ($C_{32}H_{39}ClN_6O_2$) 575 [M+H]$^+$; RT 2.66 (LCMS-V-C)

$^1$H NMR (400 MHz, DMSO-d6) δ 7.47 (d, J=8.8 Hz, 1H), 7.29 (s, 1H), 6.80 (d, J=8.7 Hz, 1H), 4.22-4.16 (m, 2H), 4.12 (q, 2H), 3.73 (s, 2H), 2.89-2.81 (m, 2H), 2.45 (s, 3H), 2.14 (s, 3H), 2.00-1.89 (m, 3H), 1.80-1.49 (m, 16H), 1.10 (t, 3H).

Step H: ethyl 3-{1-[(adamantan-1-yl)methyl]-5-methyl-1H-pyrazol-4-yl}-6-{3-[(1,3-benzothiazol-2-yl)amino]-4-methyl-5H,6H,7H,8H,9H-pyridazino[3,4-b]azepin-9-yl}pyridine-2-carboxylate To a solution of the product from Step G (119 mg, 0.21 mmol, 1 eq), 2-aminobenzothiazole, (62.2 mg, 0.41 mmol, 2 eq) and NN-diisopropylethylamine (108 μL, 0.62 mmol, 3 eq) in 1,4-dioxane (8 mL) was added JosiPhos (19.2 mg, 0.02 mmol, 0.1 eq) and the mixture was heated in a sealed tube at 150° C. for 72 h. The reaction was allowed to cool to ambient temperature, then diluted with ethyl acetate (20 mL), washed with brine (25 mL), dried (magnesium sulfate) and concentrated in vacuo. Purification by automated flash column chromatography (CombiFlash Rf, 12 g RediSep™ silica cartridge) eluting with a gradient of 0-50% ethyl acetate in iso-heptane afforded the crude desired product as a yellow gum (49 mg, 0.07 mmol, 34%) that was used directly in the subsequent step without further purification.

LC/MS ($C_{39}H_{44}N_8O_2S$) 690 [M+H]$^+$; RT 2.81 (LCMS-V-C)

Step I: 3-{1-[(adamantan-1-yl)methyl]-5-methyl-]H-pyrazol-4-yl}-6-{3-[(1,3-benzothiazol-2-yl)amino]-4-methyl-5H,6H,7H,8H,9H-pyridazino[3,4-b]aze-pin-9-yl}pyridine-2-carboxylic acid To a solution of the product from Step H (49 mg, 0.07 mmol, 1 eq) in 1,4-dioxane (15 mL) was added lithium hydroxide monohydrate (44.8 mg, 1.07 mmol, 15 eq) and the mixture was heated at reflux for 1 h. The reaction was cooled to ambient temperature and concentrated in vacuo. Purification by reverse phase automated flash chromatography (CombiFlash Rf, C18 4.3g RediSep column) eluting with a gradient of 5-95% acetonitrile in water afforded the desired product as a yellow solid (6.24 mg, 0.01 mmol, 13%).

HRMS-ESI (m/z) [M+H]+ calcd for $C_{37}H_{41}N_8O_2S$: 661.3073, found 661.3097

Example 30: 2-{3-[(1,3-Benzothiazol-2-yl)amino]-4-cyclopropyl-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylic acid

Step A: tert-butyl[(5-cyclopropylpent-4-yn-1-yl)oxy]dimethylsilane

To a solution of cyclopropylacetylene (8 mL, 94.5 mmol, 1.1 eq) in tetrahydrofuran (200 mL), cooled to −78° C., was added n-butyllithium (2.0M in hexanes; 47.3 mL, 94.5 mmol, 1.1 eq) and the mixture was stirred at this temperature for 2.5 h. 1,3-dimethyl-3,4,5,6-tetrahydro-2(1H)-pyrimidinone (12 mL, 98.8 mmol, 1.15 eq) was added and after 15 min (3-bromopropoxy)-tert-butyldimethylsilane (15 mL, 85.9 mmol, 1 eq) was added dropwise and the mixture was allowed to warm to ambient temperature and stir overnight. The reaction was partitioned between ethyl acetate and saturated aqueous ammonium chloride, and the organic phase was dried (magnesium sulfate) and concentrated in vacuo. Purification by automated flash column chromatography (CombiFlash Rf, 330 g RediSep™ silica cartridge) eluting with a gradient of 0-6% ethyl acetate in iso-heptane afforded the crude desired product as a clear oil (8.62 g, 36.2 mmol, 42%) that was used directly in the subsequent step without further purification.

Step B: 5-cyclopropylpent-4-yn-1-ol

To a solution of the product from Step A (8.62 g, 36.2 mmol, 1 eq) in tetrahydrofuran (150 mL) was added tetra-butylammonium fluoride (1M in tetrahydrofuran; 39.8 mL, 39.8 mmol, 1.1 eq) and the mixture was stirred at ambient temperature for 1 h. The reaction was concentrated in vacuo, partitioned between ethyl acetate and water, and the organic phase was dried (magnesium sulfate) and concentrated in vacuo. Purification by automated flash column chromatography (CombiFlash Rf, 120 g RediSep™ silica cartridge) eluting with a gradient of 0-50% ethyl acetate in iso-heptane afforded the desired product as a clear oil (2.14 g, 17.2 mmol, 48%).

$^1$H NMR (400 MHz, DMSO-d6) δ 4.43 (t, J=5.2 Hz, 1H), 3.46-3.38 (m, 2H), 2.12 (td, J=7.1, 2.0 Hz, 2H), 1.58-1.47 (m, 2H), 1.29-1.16 (m, 1H), 0.74-0.65 (m, 2H), 0.54-0.46 (m, 2H).

Step C: ethyl 2-{[(tert-butoxy)carbonyl](5-cyclopropylpent-4-yn-1-yl)amino}-1,3-thiazole-4-carboxylate To a solution of ethyl 2-[(tert-butoxycarbonyl)amino]-1,3-thiazole-4-carboxylate (3.13 g, 11.5 mmol, 1 eq) and the product from Step B (2.14 g, 17.2 mmol, 1.5 eq) in tetrahydrofuran (80 mL) was added polymer-supported triphenylphosphine (4.52 g, 17.23 mmol, 1.5 eq) and the mixture was cooled to 0° C. and diethyl azodicarboxylate (2.73 mL, 17.2 mmol, 1.5 eq) was added dropwise then the mixture was allowed to warm to ambient temperature and stir overnight. The reaction was partitioned between dichloromethane and water, separated (PTFE phase separator) and concentrated in vacuo. Purification by automated flash column chromatography (CombiFlash Rf, 80 g RediSep™ silica cartridge) eluting with a gradient of 0-15% ethyl acetate in iso-heptane afforded the desired product as a colourless solid (3.86 g, 10.2 mmol, 89%).

LC/MS ($C_{19}H_{26}N_2O_4S$) 379 [M+H]$^+$; RT 2.60 (LCMS-V-C)

$^1$H NMR (400 MHz, DMSO-d6) δ 8.07 (s, 1H), 4.28 (q, J=7.1 Hz, 2H), 4.11 (t, J=7.0 Hz, 2H), 2.21-2.13 (m, 2H), 1.84-1.75 (m, 2H), 1.58 (s, 9H), 1.55 (s, 4H), 1.29 (t, 3H), 1.23-1.14 (m, 1H), 0.73-0.61 (m, 2H), 0.56-0.45 (m, 2H).

Step D: ethyl 2-{3-chloro-4-cyclopropyl-5H,6H,7H,8H-pyrido[2,3-c]pyridazin-8-yl}-1,3-thiazole-4-carboxylate To a solution of the product of Step C (3.86 g, 10.2 mmol, 1 eq) in toluene (120 mL) was added 3,6-dichloro-1,2,4,5-tetrazine (1.54 g, 10.2 mmol, 1 eq) and the mixture was heated in a sealed flask at 130° C. for 24 h. The reaction was concentrated in vacuo. Purification by automated flash column chromatography (CombiFlash Rf, 80 g RediSep™ silica cartridge) eluting with a gradient of 0-60% ethyl acetate in iso-heptane afforded the desired product (677 mg, 1.86 mmol, 18%).

LC/MS (C$_{16}$H$_{17}$ClN$_4$O$_2$S) 365 [M+H]$^+$; RT 2.18 (LCMS-V-C)

$^1$H NMR (400 MHz, TFA added/DMSO-d6) δ 8.04 (s, 1H), 4.36-4.22 (m, 4H), 3.07 (t, J=6.2 Hz, 2H), 2.11-2.00 (m, 2H), 1.92-1.81 (m, 1H), 1.31 (t, J=7.1 Hz, 3H), 1.20-1.06 (m, 2H), 0.76-0.67 (m, 2H).

Step E: ethyl 2-{3-[(1,3-benzothiazol-2-yl)amino]-4-cyclopropyl-5H,6H,7H,8H-pyrido[2,3-c]pyridazin-8-yl}-1,3-thiazole-4-carboxylate To an oven-dried sealed tube was added the product from Step D (627 mg, 1.72 mmol, 1 eq), 2-aminobenzothiazole (387 mg, 2.58 mmol, 1.5 eq), NN-diisopropylethylamine (0.9 mL, 5.16 mmol, 3 eq) and 1,4-dioxane (22 mL) and the mixture was sparged with nitrogen (10 min) then Josiphos Pd G3 (162 mg, 0.17 mmol, 0.1 eq) was added and the mixture was heated at 150° C. for 20 h. The reaction was partitioned between ethyl acetate and brine, and the organic phase was dried (magnesium sulfate) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a beige solid (261 mg, 0.55 mmol, 32%).

LC/MS (C$_{23}$H$_{22}$N$_6$O$_2$S$_2$) 479 [M+H]$^+$; RT 2.44 (LCMS-V-C)

$^1$H NMR (400 MHz, TFA added/DMSO-d6) δ 10.45 (s, 1H), 8.07-7.92 (m, 2H), 7.75-7.60 (m, 1H), 7.40 (t, 1H), 7.30-7.16 (m, 1H), 4.38-4.22 (m, 4H), 3.08 (t, J=6.1 Hz, 2H), 2.15-2.01 (m, 2H), 1.98-1.85 (m, 1H), 1.32 (t, J=7.1 Hz, 3H), 1.27-1.12 (m, 2H), 0.74-0.53 (m, 2H).

Step F: ethyl 2-{3-[(1,3-benzothiazol-2-yl)({[2-(trimethylsilyl)ethoxy]methyl})amino]-4-cyclopropyl-5H,6H,7H,8H-pyrido[2,3-c]pyridazin-8-yl}-1,3-thiazole-4-carboxylate To a solution of the product of Step E (1.47 g, 3.07 mmol, 1 eq) in dimethylformamide (240 mL) was added N,N-diisopropylethylamine (1.61 mL, 9.21 mmol, 3 eq) and after 5 min the mixture was cooled to 0° C. and 4-(dimethylamino)pyridine (75.1 mg, 0.61 mmol, 0.2 eq) and 2-(trimethylsilyl)ethoxymethyl chloride (1.62 mL, 9.21 mmol, 3 eq) were added and the mixture was allowed to warm to ambient temperature and stir overnight. The reaction was concentrated in vacuo, then partitioned between dichloromethane and brine, separated (PTFE phase separator) and the organic phase was concentrated in vacuo. Purification by automated flash column chromatography (CombiFlash Rf, 40 g RediSep™ silica cartridge) eluting with a gradient of 0-50% ethyl acetate in iso-heptane afforded the desired product as a yellow gum (1.36 g, 2.23 mmol, 73%).

LC/MS (C$_{29}$H$_{36}$N$_6$O$_3$SiS$_2$) 609 [M+H]$^+$; RT 2.96 (LCMS-V-C)

$^1$H NMR (400 MHz, DMSO-d6) δ 7.97 (s, 1H), 7.80 (d, 1H), 7.48-7.37 (m, 2H), 7.22 (ddd, J=8.3, 7.0, 1.5 Hz, 1H), 5.82 (s, 2H), 4.36-4.21 (m, 4H), 3.76-3.66 (m, 2H), 3.06 (t, J=6.2 Hz, 2H), 2.13-2.02 (m, 2H), 1.95-1.84 (m, 1H), 1.31 (t, J=7.1 Hz, 3H), 1.23-1.15 (m, 2H), 1.13-1.05 (m, 2H), 0.93-0.84 (m, 2H), −0.10 (s, 9H).

Step G: ethyl 2-{3-[(1,3-benzothiazol-2-yl)({[2-(trimethylsilyl)ethoxy]methyl})amino]-4-cyclopropyl-5H,6H,7H,8H-pyrido[2,3-c]pyridazin-8-yl}-5-bromo-1,3-thiazole-4-carboxylate To a solution of the product of Step F (1.36 g, 2.23 mmol, 1 eq) in dichloromethane (40 mL) was added N-bromosuccinimide (596 mg, 3.35 mmol, 1.5 eq) and the mixture was stirred at ambient temperature overnight. The reaction was partitioned between dichloromethane and brine, and the organic phase was dried (PTFE phase separator) and concentrated in vacuo. Purification by automated flash column chromatography (CombiFlash Rf, 40 g RediSep™ silica cartridge) eluting with a gradient of 0-40% ethyl acetate in iso-heptane afforded the desired product as a yellow solid (1.43 g, 2.08 mmol, 93%).

LC/MS (C$_{29}$H$_{35}$BrN$_6$O$_3$SiS$_2$) 689 [M+H]$^+$; RT 3.17 (LCMS-V-C)

$^1$H NMR (400 MHz, DMSO-d6) δ 7.86-7.81 (m, 1H), 7.50-7.39 (m, 2H), 7.27-7.20 (m, 1H), 5.82 (s, 2H), 4.32 (q, 2H), 4.29-4.21 (m, 2H), 3.75-3.66 (m, 2H), 2.13-2.01 (m, 2H), 1.98-1.86 (m, 1H), 1.32 (t, 3H), 1.28-1.16 (m, 2H), 1.15-1.05 (m, 2H), 0.94-0.83 (m, 2H), −0.10 (s, 9H).

Step H: ethyl 5-[(1E)-3-[(tert-butyldimethylsilyl)oxy]prop-1-en-1-yl]-2-(4-cyclopropyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To an oven-dried sealed flask was added the product from Step G (1.43 g, 2.08 mmol, 1 eq), (E)-3-(tert-butyldimethylsilyloxy)propene-1-yl-boronic acid pinacol ester (0.82 mL, 2.5 mmol, 1.2 eq), potassium carbonate (862 mg, 6.24 mmol, 3 eq), [1,1'-bis(diphenylphosphino)ferrocene]dichloropalladium(II) (170 mg, 0.21 mmol, 0.1 eq), tetrahydrofuran (60 mL) and water (20 mL) and the mixture was sparged with nitrogen (10 min) then heated at 120° C. for 1.5 h. The reaction was partitioned between ethyl acetate and water, and the organic phase was washed with brine, dried (magnesium sulfate) and concentrated in vacuo. Purification by automated flash column chromatography (CombiFlash Rf, 80 g RediSep™ silica cartridge) eluting with a gradient of 0-30% ethyl acetate in iso-heptane afforded the desired product as a yellow solid (1.05 g, 1.35 mmol, 65%).

LC/MS (C$_{38}$H$_{54}$N$_6$O$_4$Si$_2$S2) 779 [M+H]$^+$; RT 1.66 (LCMS-V-B2)

$^1$H NMR (400 MHz, DMSO-d6) δ 7.79 (d, 1H), 7.51-7.37 (m, 3H), 7.27-7.18 (m, 1H), 6.27 (dt, J=16.0, 4.3 Hz, 1H), 5.82 (s, 2H), 4.40-4.34 (m, 2H), 4.34-4.23 (m, 4H), 3.75-3.66 (m, 2H), 3.06 (t, J=6.1 Hz, 2H), 2.13-2.01 (m, 2H), 1.96-1.84 (m, 1H), 1.31 (t, J=7.1 Hz, 3H), 1.22-1.14 (m, 2H), 1.13-1.04 (m, 2H), 0.93 (s, 9H), 0.89-0.82 (m, 2H), 0.11 (s, 6H), −0.10 (s, 9H).

Step I: ethyl 5-{3-[(tert-butyldimethylsilyl)oxy]propyl}-2-(4-cyclopropyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Step H (1.05 g, 1.35 mmol, 1 eq) in ethyl acetate (60 mL) was added platinum (IV) oxide (91.8 mg, 0.4 mmol, 0.3 eq) under a nitrogen atmosphere. The vessel was evacuated and back-filled with nitrogen (×3), then evacuated, placed under an atmosphere of hydrogen, and shaken at ambient temperature for 2 days. The reaction was filtered through celite, eluted with ethyl acetate and concentrated in vacuo. Purification by automated flash column chromatography (CombiFlash Rf, 24 g RediSep™ silica cartridge) eluting with a gradient of 0-40% ethyl acetate in iso-heptane afforded the desired product as a clear gum (913 mg, 1.17 mmol, 87%).

LC/MS $(C_{38}H_{56}N_6O_4Si_2S_2)$ 781 [M+H]⁺; RT 1.71 (LCMS-V-B2)

¹H NMR (400 MHz, DMSO-d6) δ 7.74 (d, 1H), 7.49-7.36 (m, 2H), 7.27-7.20 (m, 1H), 5.82 (s, 2H), 4.34-4.21 (m, 4H), 3.75-3.62 (m, 4H), 3.15 (t, J=7.5 Hz, 2H), 3.05 (t, J=6.3 Hz, 2H), 2.12-2.00 (m, 2H), 1.96-1.78 (m, 3H), 1.31 (t, 3H), 1.21-1.16 (m, 2H), 1.13-1.05 (m, 2H), 0.91 (s, 9H), 0.87-0.81 (m, 2H), 0.06 (s, 6H), −0.10 (m, 9H).

Step J: ethyl 2-(4-cyclopropyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-5-(3-hydroxypropyl)-1,3-thiazole-4-carboxylate To a solution of the product from Step I (819 mg, 1.05 mmol, 1 eq) in 1,4-dioxane (18 mL) was added tetrabutylammonium fluoride (1M in tetrahydrofuran; 1.15 mL, 1.15 mmol, 1.1 eq) and the mixture was stirred at ambient temperature for 2 h. The reaction was partitioned between ethyl acetate and water, and the organic phase was dried (magnesium sulfate) and concentrated in vacuo. Purification by automated flash column chromatography (CombiFlash Rf, 24 g RediSep™ silica cartridge) eluting with a gradient of 0-50% ethyl acetate in dichloromethane afforded the desired product as a yellow gum (650 mg, 0.97 mmol, 93%).

LC/MS $(C_{32}H_{42}N_6O_4SiS_2)$ 667 [M+H]⁺; RT 2.85 (LCMS-V-C)

¹H NMR (400 MHz, DMSO-d6) δ 7.81 (dd, J=7.5, 1.0 Hz, 1H), 7.48-7.36 (m, 2H), 7.27-7.17 (m, 1H), 5.81 (s, 2H), 4.56 (t, J=5.1 Hz, 1H), 4.34-4.21 (m, 4H), 4.12 (q, J=7.1 Hz, 3H), 3.75-3.66 (m, 2H), 3.48 (td, J=6.3, 5.1 Hz, 2H), 3.17-3.08 (m, 2H), 3.05 (t, J=6.3 Hz, 2H), 1.96-1.84 (m, 1H), 1.83-1.74 (m, 2H), 1.31 (t, J=7.1 Hz, 3H), 1.20-1.15 (m, 2H), 1.13-1.04 (m, 2H), 0.93-0.85 (m, 2H), −0.10 (s, 9H).

Step K: ethyl 5-(3-chloropropyl)-2-(4-cyclopropyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate The product from Step J (291 mg, 0.44 mmol, 1 eq) was dissolved in thionyl chloride (10 mL) and stirred at ambient temperature for 8 h. The reaction was concentrated in vacuo, then partitioned between dichloromethane and brine, and the organic phase was dried (PTFE phase separator) and concentrated in vacuo. Purification by automated flash column chromatography (CombiFlash Rf, 12 g RediSep™ silica cartridge) eluting with a gradient of 0-40% ethyl acetate in iso-heptane afforded the desired product as an orange gum (147 mg, 0.21 mmol, 49%).

LC/MS $(C_{32}H_{41}ClN_6O_3SiS_2)$ 685 [M+H]⁺; RT 3.15 (LCMS-V-C)

¹H NMR (400 MHz, DMSO-d6) δ 7.80 (dd, J=7.4, 1.0 Hz, 1H), 7.48-7.36 (m, 2H), 7.27-7.18 (m, 1H), 5.81 (s, 2H), 4.34-4.21 (m, 4H), 3.78-3.64 (m, 4H), 3.27-3.18 (m, 2H), 3.05 (t, J=6.2 Hz, 2H), 2.16-1.96 (m, 4H), 1.98-1.81 (m,

1H), 1.32 (t, J=7.1 Hz, 3H), 1.22-1.14 (m, 2H), 1.13-1.01 (m, 2H), 0.95-0.82 (m, 2H), −0.11 (s, 9H).

Step L: ethyl 2-(4-cyclopropyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-5-(3-{4-[3-(dimethylamino)prop-1-yn-1-yl]-2-fluorophenoxy}propyl)-1,3-thiazole-4-carboxylate To a solution of the product from Preparation 4b (53.9 mg, 0.28 mmol, 1.3 eq) in dimethylformamide (30 mL) was added sodium hydride (60% dispersion; 21.5 mg, 0.54 mmol, 2.5 eq) and the mixture stirred for 2 min. A solution of the product from Step K (147 mg, 0.21 mmol, 1 eq) in dimethylformamide (10 mL) was added and the mixture was heated at 100° C. for 1.5 h. The reaction was partitioned between ethyl acetate and water, and the organic phase was dried (magnesium sulfate) and concentrated in vacuo. Purification by automated flash column chromatography (CombiFlash Rf, 24 g RediSep™ silica cartridge) eluting with a gradient of 0-5% methanol in dichloromethane afforded the desired product as a yellow gum (145 mg, 0.17 mmol, 80%).

LC/MS $(C_{43}H_{52}FN_7O_4SiS_2)$ 842 [M+H]V; RT 2.76 (LCMS-V-C)

¹H NMR (400 MHz, DMSO-d6) δ 7.79 (dd, J=7.5, 1.1 Hz, 1H), 7.48-7.36 (m, 2H), 7.34-7.27 (m, 1H), 7.26-7.12 (m, 3H), 5.81 (s, 2H), 4.30-4.20 (m, 4H), 4.14 (t, J=6.1 Hz, 2H), 3.75-3.66 (m, 2H), 3.38 (s, 2H), 3.27 (t, J=6.3 Hz, 2H), 3.05 (t, 2H), 2.19 (s, 6H), 2.17-2.09 (m, 2H), 2.08-1.99 (m, 2H), 1.94-1.83 (m, 1H), 1.29 (t, 3H), 1.21-1.14 (m, 2H), 1.13-1.05 (m, 2H), 0.94-0.82 (m, 2H), −010 (s, 9H).

Step M: ethyl 2-{3-[(1,3-benzothiazol-2-yl)amino]-4-cyclopropyl-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylate To a solution of the product from Step L (175 mg, 0.21 mmol, 1 eq) in dichloromethane (6 mL) was added trifluoroacetic acid (6 mL) and the mixture was stirred at ambient temperature for 7.5 h. The reaction was diluted with dichloromethane, cooled to 0° C. and neutralised with 2N aqueous sodium hydroxide. The organic phase was dried (PTFE phase separator) and concentrated in vacuo. Purification by automated flash column chromatography (CombiFlash Rf, 12 g RediSep™ silica cartridge) eluting with a gradient of 0-7% methanol in dichloromethane afforded the desired product as a yellow gum (16 mg, 0.02 mmol, 11%).

LC/MS $(C_{37}H_{38}FN_7O_3S2)$ 712 [M+H]⁺; RT 2.18 (LCMS-V-C)

¹H NMR (400 MHz, DMSO-d6) δ 7.94 (d, J=7.7 Hz, 1H), 7.60 (d, J=8.0 Hz, 1H), 7.43-7.34 (m, 1H), 7.30 (dd, J=11.9, 2.0 Hz, 1H), 7.26-7.10 (m, 3H), 4.30-4.20 (m, 4H), 4.14 (t, J=6.1 Hz, 2H), 3.36 (s, 2H), 3.30-3.23 (m, 2H), 3.10-3.00 (m, 2H), 2.19 (s, 6H), 2.16-2.09 (m, 2H), 2.08-1.99 (m, 2H), 1.95-1.86 (m, 1H), 1.28 (t, J=7.1 Hz, 3H), 1.25-1.21 (m, 2H), 1.21-1.13 (m, 2H).

Step N: 2-{3-[(1,3-benzothiazol-2-yl)amino]-4-cyclopropyl-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylic acid To a solution of the product from Step M (16 mg, 0.02 mmol, 1 eq) in 1,4-dioxane (5 mL) was added lithium hydroxide monohydrate (9.43 mg, 0.22 mmol, 10 eq) and the mixture was heated at reflux overnight. The reaction was concentrated in vacuo, and the residue was triturated in water then diethyl ether, filtered and dried under vacuum to afford the desired product as a yellow solid (10.4 mg, 0.02 mmol, 68%), as a lithium salt.

HRMS-ESI (m/z) [M+H]+ calcd for $C_{35}H_{35}FN_7O_3S_2$: 684.2227, found 684.2223.

Example 31: 2-{3-[(1,3-Benzothiazol-2-yl)amino]-4-methyl-5H,6H,7H,8H,9H-pyridazino[3,4-b]aze-pin-9-yl}-5-(3-{4-[3-(dimethylamino)prop-1-yn-1-yl]-2-fluorophenoxy}propyl)-1,3-thiazole-4-carboxylic acid

Step A: ethyl 2-(4-methyl-3-{[(2Z)-3-{[2-(trimeth-ylsilyl)ethoxy]methyl}-2,3-dihydro-1,3-benzothi-azol-2-ylidene]amino}-5H,6H,7H,8H,9H-pyridazino[3,4-b]azepin-9-yl)-1,3-thiazole-4-carboxylate To a solution of Example 25 (4.97 g, 10.7 mmol, 1 eq) in dimethylformamide (180 mL) was added NN-diisopropyl-ethylamine (5.57 mL, 32 mmol, 3 eq). After 5 min the mixture was cooled to 0° C. and 4-(dimethylamino)pyridine (260 mg, 2.13 mmol, 0.2 eq) and 2-(trimethylsilyl)ethoxym-ethyl chloride (5.61 mL, 32 mmol, 3 eq) were added and the mixture was stirred at ambient temperature overnight. The reaction was concentrated in vacuo, partitioned between ethyl acetate and water, and the organic phase was dried (magnesium sulfate) and concentrated in vacuo. Purification by automated flash column chromatography (CombiFlash Rf, 120 g RediSep™ silica cartridge) eluting with a gradient of 0-40% ethyl acetate in iso-heptane afforded the desired product as a yellow gum (5.21 g, 8.73 mmol, 82%).

LC/MS $(C_{28}H_{36}N_6O_3SiS_2)$ 597 [M+H]$^+$; RT 2.87 (LCMS-V-C)

$^1$H NMR (400 MHz, DMSO-d6) δ 7.82 (dd, J=7.7, 1.1 Hz, 1H), 7.74 (s, 1H), 7.52-7.39 (m, 2H), 7.25 (td, J=7.5, 1.4 Hz, 1H), 5.88 (s, 2H), 4.27 (q, J=7.1 Hz, 2H), 4.15-4.01 (m, 2H), 3.72 (dd, J=8.4, 7.4 Hz, 2H), 2.89-2.81 (m, 2H), 2.43 (s, 3H), 1.95-1.83 (m, 2H), 1.82-1.69 (m, 2H), 1.29 (t, J=7.1 Hz, 3H), 0.91 (dd, J=8.5, 7.4 Hz, 2H), −0.11 (s, 9H).

Step B: ethyl 5-bromo-2-(4-methyl-3-{[(2Z)-3-{[2-(trimethylsilyl)ethoxy]methyl}-2,3-dihydro-1,3-ben-zothiazol-2-ylidene]amino}-5H,6H,7H,8H,9H-pyridazino[3,4-b]azepin-9-yl)-1,3-thiazole-4-carboxylate To a solution of the product of Step A (5.21 g, 8.73 mmol, 1 eq) in dichloromethane (100 mL) was added N-bromosuccinimide (1.71 g, 9.6 mmol, 1.1 eq) and the mixture was stirred at ambient temperature overnight. The reaction was partitioned between dichloromethane and 10% aqueous sodium thiosulfate, and the organic phase was washed with brine, dried (PTFE phase separator) and concentrated in vacuo. Purification by automated flash column chromatog-raphy (CombiFlash Rf, 120 g RediSep™ silica cartridge) eluting with a gradient of 0-30% ethyl acetate in iso-heptane afforded the desired product as a yellow gum (5.23 g, 7.74 mmol, 89%).

LC/MS $(C_{28}H_{35}BrN_6O_3SiS_2)$ 677 [M+H]$^+$; RT 3.08 (LCMS-V-C)

$^1$H NMR (400 MHz, DMSO-d6) δ 7.84 (dd, J=7.9, 1.1 Hz, 1H), 7.52-7.38 (m, 2H), 7.31-7.20 (m, 1H), 5.88 (s, 2H), 4.30 (q, J=7.1 Hz, 2H), 4.18 (dd, J=6.8, 4.6 Hz, 2H), 3.78-3.66 (m, 2H), 2.95-2.85 (m, 2H), 2.44 (s, 3H), 2.01-1.88 (m, 2H), 1.86-1.72 (m, 2H), 1.31 (t, J=7.1 Hz, 3H), 0.96-0.87 (m, 2H), −0.10 (s, 9H).

Step C: ethyl 5-[(1E)-3-[(tert-butyldimethylsilyl)oxy]prop-1-en-1-yl]-2-(4-methyl-3-{[(2Z)-3-{[2-(trimethylsilyl)ethoxy]methyl}-2,3-dihydro-1,3-ben-zothiazol-2-ylidene]amino}-5H,6H,7H,8H,9H-pyridazino[3,4-b]azepin-9-yl)-1,3-thiazole-4-carboxylate To an oven-dried sealed flask was added the product from Step B (5.23 g, 7.74 mmol, 1 eq), (E)-3-(tert-butyldimeth-ylsilyloxy)propene-1-yl-boronic acid pinacol ester (3.04 mL, 9.29 mmol, 1.2 eq), potassium carbonate (3.21 g, 23.2 mmol, 3 eq), [1,1'-bis(diphenylphosphino)ferrocene]dichlo-ropalladium(II) (632 mg, 0.77 mmol, 0.1 eq), tetrahydro-furan (150 mL) and water (50 mL) and the mixture was sparged with nitrogen (10 min) then heated at 120° C. for 1 h. The reaction was partitioned between ethyl acetate and water, and the organic phase was washed with brine, dried (magnesium sulfate) and concentrated in vacuo. Purification by automated flash column chromatography (CombiFlash Rf, 120 g RediSep™ silica cartridge) eluting with a gradient of 0-40% ethyl acetate in iso-heptane afforded the desired product as an orange oil (5.17 g, 6.74 mmol, 87%). LC/MS $(C_{37}H_{54}N_6O_4Si_2S2)$ 767 [M+H]$^+$; RT 1.60 (LCMS-V-B2)

$^1$H NMR (400 MHz, DMSO-d6) δ 7.82 (dd, J=7.8, 1.2 Hz, 1H), 7.53-7.35 (m, 3H), 7.26 (ddd, J=8.3, 7.2, 1.3 Hz, 1H), 6.01 (dt, J=15.9, 4.3 Hz, 1H), 5.88 (s, 2H), 4.36-4.235 (m, 4H), 4.12-3.99 (m, 2H), 3.78-3.67 (m, 2H), 2.89-2.78 (m, 2H), 2.43 (s, 3H), 1.95-1.82 (m, 2H), 1.81-1.68 (m, 2H), 1.30 (t, J=7.1 Hz, 3H), 0.97-0.84 (m, 11H), 0.07 (s, 6H), −0.12 (s, 9H).

Step D: ethyl 5-{3-[(tert-butyldimethylsilyl)oxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H,9H-pyridazino[3,4-b]azepin-9-yl)-1,3-thiazole-4-carboxylate To a solution of the product from Step C (5.17 g, 6.74 mmol, 1 eq) in ethyl acetate (120 mL) was added platinum (IV) oxide (459 mg, 2.02 mmol, 0.3 eq) under a nitrogen atmosphere. The vessel was evacuated and backfilled with nitrogen (×3), then evacuated, placed under an atmosphere of hydrogen and shaken at ambient temperature for 2 days. The reaction was filtered through celite, eluted with ethyl acetate and concentrated in vacuo. Purification by automated flash column chromatography (CombiFlash Rf, 120 g RediSep™ silica cartridge) eluting with a gradient of 0-40% ethyl acetate in iso-heptane afforded the desired product as an orange oil (4.46 g, 5.8 mmol, 86%).

LC/MS ($C_{37}H_{56}N_6O_4Si_2S_2$) 769 [M+H]⁺; RT 1.62 (LCMS-V-B2)

¹H NMR (400 MHz, DMSO-d6) δ 7.79 (dd, J=7.9, 1.2 Hz, 1H), 7.53-7.40 (m, 2H), 7.31-7.21 (m, 1H), 5.87 (s, 2H), 4.26 (q, J=7.1 Hz, 2H), 4.10-3.97 (m, 2H), 3.77-3.66 (m, 2H), 3.61 (t, J=6.1 Hz, 2H), 3.60 (t, J=7.6 Hz, 2H), 3.11-2.99 (m, 2H), 2.88-2.76 (m, 2H), 2.44 (s, 3H), 1.96-1.81 (m, 2H), 1.81-1.67 (m, 4H), 1.29 (t, 3H), 0.91-0.81 (m, 11H), 0.01 (s, 6H), −0.11 (s, 9H).

Step E: ethyl 5-(3-hydroxypropyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H,9H-pyridazino[3,4-b]azepin-9-yl)-1,3-thiazole-4-carboxylate To a solution of the product from Step D (4.46 g, 5.8 mmol, 1 eq) in tetrahydrofuran (150 mL) was added tetra-butylammonium fluoride (1M in tetrahydrofuran, 8.7 mL, 8.7 mmol, 1.5 eq) and the mixture was stirred at rt for 1.5 h. The reaction was partitioned between ethyl acetate and water, and the organic phase was dried (magnesium sulfate) and concentrated in vacuo. Purification by automated flash column chromatography (CombiFlash Rf, 80 g RediSep™ silica cartridge) eluting with a gradient of 0-50% ethyl acetate in dichloromethane afforded the desired product as a beige gum (2.63 g, 4.02 mmol, 69%).

LC/MS ($C_{31}H_{42}N_6O_4SiS_2$) 655 [M+H]⁺; RT 2.77 (LCMS-V-C)

¹H NMR (400 MHz, DMSO-d6) δ 7.83 (dd, J=7.9, 1.2 Hz, 1H), 7.52-7.39 (m, 2H), 7.25 (ddd, J=8.3, 7.1, 1.3 Hz, 1H), 5.88 (s, 2H), 4.50 (t, J=5.1 Hz, 1H), 4.26 (q, J=7.1 Hz, 2H), 4.07-3.98 (m, 2H), 3.72 (t, J=7.9 Hz, 2H), 3.42 (td, J=6.3, 5.1 Hz, 2H), 3.04 (dd, J=8.9, 6.4 Hz, 2H), 2.90-2.77 (m, 2H), 2.43 (s, 3H), 1.95-1.82 (m, 2H), 1.81-1.65 (m, 4H), 1.29 (t, J=7.1 Hz, 3H), 0.91 (dd, J=8.4, 7.4 Hz, 2H), −0.12 (s, 9H).

Step F: ethyl 5-(3-chloropropyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H,9H-pyridazino[3,4-b]azepin-9-yl)-1,3-thiazole-4-carboxylate The product from Step E (1.35 g, 2.06 mmol, 1 eq) was dissolved in thionyl chloride (20 mL) and stirred at ambient temperature for 5 h. The reaction was concentrated in vacuo, then partitioned between dichloromethane and brine, and the organic phase was dried (PTFE phase separator) and concentrated in vacuo. Purification by automated flash column chromatography (CombiFlash Rf, 40 g RediSep™ silica cartridge) eluting with a gradient of 0-50% ethyl acetate in iso-heptane afforded the desired product as a yellow gum (989 mg, 1.47 mmol, 71%).

LC/MS ($C_{31}H_{41}ClN_6O_3SiS_2$) 673 [M+H]⁺; RT 3.02 (LCMS-V-C)

¹H NMR (400 MHz, DMSO-d6) δ 7.82 (dd, J=7.8, 1.2 Hz, 1H), 7.52-7.39 (m, 2H), 7.30-7.21 (m, 1H), 5.87 (s, 2H), 4.27 (q, J=7.1 Hz, 2H), 4.11-3.98 (m, 2H), 3.72 (t, 2H), 3.67 (t, 2H), 3.19-3.09 (m, 2H), 2.88-2.80 (m, 2H), 2.44 (s, 3H), 2.07-1.96 (m, 2H), 1.94-1.83 (m, 2H), 1.82-1.69 (m, 2H), 1.31 (t, J=7.1 Hz, 3H), 0.91 (dd, J=8.4, 7.4 Hz, 2H), −0.11 (s, 9H).

Step G: ethyl 5-(3-{4-[3-(dimethylamino)prop-1-yn-1-yl]-2-fluorophenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H,9H-pyridazino[3,4-b]azepin-9-yl)-1,3-thiazole-4-carboxylate To a solution of the product from Preparation 4b (369 mg, 1.91 mmol, 1.3 eq) in dimethylformamide (150 mL) was added sodium hydride (147 mg, 3.67 mmol, 2.5 eq) and the mixture stirred for 2 min. A solution of the product from Step F (989 mg, 1.47 mmol, 1 eq) in dimethylformamide (50 mL) was added and the mixture was heated at 100° C. for 1.5 h. The reaction was partitioned between ethyl acetate and water, and the organic phase was dried (magnesium sulfate) and concentrated in vacuo. Purification by automated flash column chromatography (CombiFlash Rf, 40 g RediSep™ silica cartridge) eluting with a gradient of 0-5% methanol in dichloromethane afforded the desired product as a yellow oil (728 mg, 0.88 mmol, 60%).

LC/MS ($C_{42}H_{52}FN_7O_4SiS_2$) 830 [M+H]V; RT 2.61 (LCMS-V-C)

¹H NMR (400 MHz, DMSO-d6) δ 7.82 (dd, J=7.7, 1.1 Hz, 1H), 7.52-7.39 (m, 2H), 7.31-7.22 (m, 2H), 7.21-7.15 (m, 1H), 7.12 (t, J=8.7 Hz, 1H), 5.88 (s, 2H), 4.24 (q, J=7.1 Hz, 2H), 4.10 (t, 2H), 4.08-3.99 (m, 2H), 3.77-3.68 (m, 2H), 3.38 (s, 2H), 3.18 (t, J=7.6 Hz, 2H), 2.86-2.77 (m, 2H), 2.43 (s, 3H), 2.20 (s, 6H), 2.11-1.98 (m, 2H), 1.94-1.83 (m, 2H), 1.82-1.69 (m, 2H), 1.27 (t, J=7.1 Hz, 3H), 0.91 (dd, J=8.4, 7.4 Hz, 2H), −0.12 (s, 9H).

Step H: ethyl 2-{3-[(1,3-benzothiazol-2-yl)amino]-4-methyl-5H,6H,7H,8H,9H-pyridazino[3,4-b]aze-pin-9-yl}-5-(3-{4-[3-(dimethylamino)prop-1-yn-1-yl]-2-fluorophenoxy}propyl)-1,3-thiazole-4-carboxylate To a solution of the product from Step G (728 mg, 0.88 mmol, 1 eq) in tetrahydrofuran (18 mL) was added ethyl-enediamine (176 µL, 2.63 mmol, 3 eq) and tetrabutylam-monium fluoride (1M in tetrahydrofuran; 2.64 mL, 2.63 mmol, 3 eq) and the mixture was heated at 60° C. for 24 h. The reaction was partitioned between ethyl acetate and water and the organic phase was washed with brine, dried (magnesium sulfate) and concentrated in vacuo. Purification by automated flash column chromatography (CombiFlash Rf, 40 g RediSep™ silica cartridge) eluting with a gradient of 0-7% methanol in dichloromethane afforded the desired product as a yellow gum (224 mg, 0.32 mmol, 37%).

LC/MS ($C_{36}H_{38}FN_7O_3S_2$) 700 [M+H]⁺; RT 2.05 (LCMS-V-C)

¹H NMR (400 MHz, DMSO-d6) δ 11.67 (br s, 1H), 7.87 (d, 1H), 7.51 (d, J=8.0 Hz, 1H), 7.38 (ddd, J=8.2, 7.3, 1.3 Hz, 1H), 7.26 (dd, J=12.0, 2.0 Hz, 1H), 7.23-7.16 (m, 2H), 7.12 (t, J=8.7 Hz, 1H), 4.24 (q, J=7.1 Hz, 2H), 4.09 (t, 2H), 4.05-3.97 (m, 2H), 3.38 (s, 2H), 3.17 (t, J=7.6 Hz, 2H), 2.86-2.77 (m, 2H), 2.40 (s, 3H), 2.20 (s, 6H), 2.11-1.96 (m, 2H), 1.92-1.82 (m, 2H), 1.80-1.69 (m, 2H), 1.27 (t, J=7.1 Hz, 3H).

Step I: 2-{3-[(1,3-benzothiazol-2-yl)amino]-4-methyl-5H,6H,7H,8H,9H-pyridazino[3,4-b]azepin-9-yl}-5-(3-{4-[3-(dimethylamino)prop-1-yn-1-yl]-2-fluorophenoxy}propyl)-1,3-thiazole-4-carboxylic acid To a solution of the product from Step H (224 mg, 0.32 mmol, 1 eq) in 1,4-dioxane (15 mL) was added lithium hydroxide monohydrate (134 mg, 3.2 mmol, 10 eq) and the mixture was heated at reflux overnight. The reaction was concentrated in vacuo, and the residue was triturated with water, filtered and dried under vacuum to afford the desired product as a yellow solid (202 mg, 0.3 mmol, 94%), as a lithium salt.

HRMS-ESI (m/z) [M+H]+ calcd for $C_{34}H_{35}FN_7O_3S_2$: 672.2227, found 672.225.

Example 32: 2-{3-[(1,3-Benzothiazol-2-yl)amino]-4-methyl-5H,6H,7H,8H-pyrido[2,3-c]pyridazin-8-yl}-5-(3-{2-fluoro-4-[3-(methylamino)prop-1-yn-1-yl]phenoxy}propyl)-1,3-thiazole-4-carboxylic acid

Step A: ethyl 5-{3-[4-(3-{[(tert-butoxy)carbonyl](methyl)amino}prop-1-yn-1-yl)-2-fluorophenoxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3g (500 mg, 0.78 mmol, 1 eq) in toluene (15 mL) was added the product from Preparation 4c (327 mg, 1.17 mmol, 1.5 eq), followed by triphenylphosphine (307 mg, 1.17 mmol, 1.5 eq) and diisopropyl azodicarboxylate (230 μL, 1.17 mmol, 1.5 eq) and the mixture was heated at reflux overnight. The reaction was partitioned between dichloromethane and water, and the organic phase was dried (PTFE phase separator) and concentrated in vacuo. Purification by automated flash column chromatography (CombiFlash Rf, 24 g RediSep™ silica cartridge) eluting with a gradient of 0-50% ethyl acetate in iso-heptane afforded the desired product as an off-white foam (715 mg, 0.79 mmol, >100%).

LC/MS $(C_{45}H_{56}FN_7O_6SiS_2)$ 902 [M+H]$^+$; RT 1.46 (LCMS-V-B2)

$^1$H NMR (400 MHz, DMSO-d6) δ 7.82 (dt, J=7.6, 0.9 Hz, 1H), 7.48-7.37 (m, 2H), 7.33 (d, J=11.6 Hz, 1H), 7.28-7.13 (m, 3H), 5.84 (s, 2H), 4.32-4.17 (m, 6H), 4.15 (t, J=6.1 Hz, 2H), 3.72 (dd, J=8.5, 7.4 Hz, 2H), 3.27 (d, J=15.4 Hz, 2H), 2.93-2.75 (m, 5H), 2.36 (s, 3H), 2.19-2.10 (m, 2H), 2.10-1.98 (m, 2H), 1.40 (s, 9H), 1.28 (t, 3H), 0.96-0.89 (m, 2H), −0.11 (s, 9H).

Step B: ethyl 2-{3-[(1,3-benzothiazol-2-yl)amino]-4-methyl-5H,6H,7H,8H-pyrido[2,3-c]pyridazin-8-yl}-5-(3-{2-fluoro-4-[3-(methylamino)prop-1-yn-1-yl]phenoxy}propyl)-1,3-thiazole-4-carboxylate To a solution of the product from Step A (1.67 g, 1.85 mmol, 1 eq) in acetonitrile (17 mL) was added hydrogen fluoride-pyridine (3.22 mL, 37 mmol, 20 eq) and the mixture was heated at 60° C. for 2 h. The reaction was partitioned between 3:1 dichloromethane/isopropanol and 2N aqueous sodium hydroxide, and the organic phase was washed with brine, dried (PTFE phase separator) and concentrated in vacuo. Purification by automated flash column chromatography (CombiFlash Rf, 80 g RediSep™ silica cartridge) eluting with a gradient of 0-7% methanol in dichloromethane afforded the desired product as a yellow solid (1.02 g, 1.52 mmol, 82%).

LC/MS $(C_{34}H_{34}FN_7O_3S_2)$ 672 [M+H]$^+$; RT 2.06 (LCMS-V-C)

$^1$H NMR (400 MHz, DMSO-d6) δ 7.89 (dd, J=7.8, 1.2 Hz, 1H), 7.50 (d, J=8.1 Hz, 1H), 7.38 (ddd, J=8.2, 7.3, 1.2 Hz, 1H), 7.32-7.25 (m, 1H), 7.23-7.12 (m, 3H), 4.32-4.21 (m, 4H), 4.15 (t, J=6.1 Hz, 2H), 3.45 (s, 2H), 3.32-3.23 (m, 2H), 2.89 (t, J=6.4 Hz, 2H), 2.35 (s, 3H), 2.31 (s, 3H), 2.20-2.10 (m, 2H), 2.09-1.97 (m, 2H), 1.30 (t, J=7.1 Hz, 3H).

Step C: 2-{3-[(1,3-benzothiazol-2-yl)amino]-4-methyl-5H,6H,7H,8H-pyrido[2,3-c]pyridazin-8-yl}-5-(3-{2-fluoro-4-[3-(methylamino)prop-1-yn-1-yl]phenoxy}propyl)-1,3-thiazole-4-carboxylic acid To a solution of the product from Step B (1.02 g, 1.52 mmol, 1 eq) in 1,4-dioxane (50 mL) was lithium hydroxide monohydrate (637 mg, 15.2 mmol, 10 eq) and the mixture was heated at 110° C. overnight. Purification by automated flash column chromatography (CombiFlash Rf, 80 g RediSep™ silica cartridge) eluting with a gradient of 0-70% 0.7N methanolic ammonia in dichloromethane gave a solid that was triturated with acetonitrile, filtered and dried under vacuum to afford the desired product as a yellow solid (657 mg, 1.02 mmol, 67%).

HRMS-ESI (m/z) [M+H]+ calcd for $C_{32}H_{31}FN_7O_3S_2$: 644.1914, found 644.1930.

Example 33: 2-[(6R)-3-[(1,3-Benzothiazol-2-yl)amino]-6-hydroxy-4-methyl-5H,6H,7H,8H-pyrido[2,3-c]pyridazin-8-yl]-1,3-thiazole-4-carboxylic acid Step A: (4S)-3-[2-(benzyloxy)acetyl]-4-(propan-2-yl)-1,3-oxazolidin-2-one To a solution of (S)-4-isopropyl-2-oxazolidinone (10 g, 77.4 mmol, 1 eq) in tetrahydrofuran (200 mL) was slowly added sodium hydride (60% dispersion; 3.72 g, 92.9 mmol, 1.2 eq) at 0° C. After 1 h, benzyloxyacetyl chloride (12.8 mL, 81.3 mmol, 1.05 eq) was added dropwise and the mixture was stirred for 1 h. The reaction was quenched by the dropwise addition of saturated aqueous ammonium chloride (20 mL) at 0° C., and extracted with ethyl acetate (250 mL). The organic extract was washed successively with water (250 mL) and brine (2×250 mL), dried (magnesium sulfate) and concentrated in vacuo. The solids were suspended in heptane (250 mL) and stirred vigorously for 1 h, then filtered, washed with heptane (2×100 mL) and dried under vacuum to afford the desired product as a white powder (19.9 g, 71.7 mmol, 93%).

LC/MS ($C_{15}H_{19}NO_4$) 278 [M+H]⁺; RT 1.19 (LCMS-V-B1)

1H NMR (400 MHz, DMSO-d6) δ 7.42-7.35 (m, 4H), 7.34-7.28 (m, 1H), 4.64 (d, 2H), 4.57 (d, J=0.8 Hz, 2H), 4.42-4.29 (m, 3H), 2.26-2.15 (m, 1H), 0.85 (dd, J=20.8, 6.9 Hz, 6H).

Step B: (4S)-3-[(2R)-2-(benzyloxy)hex-4-ynoyl]-4-(propan-2-yl)-1,3-oxazolidin-2-one To a solution of the product from Step A (8.7 g, 31.4 mmol, 1 eq) in tetrahydrofuran (350 mL), cooled to −78° C., was added sodium bis(trimethylsilyl)amide (1M in tetrahydrofuran; 47.1 mL, 47.1 mmol, 1.5 eq) dropwise and the mixture was stirred for 1 h at this temperature. A solution of 1-iodobut-2-yne (16.9 g, 94.1 mmol, 3 eq) in tetrahydrofuran (30 mL) was added dropwise and the mixture was allowed to warm to −40° C. and stir for 3 h. The reaction was quenched with saturate aqueous ammonium chloride (200 mL), partitioned between ethyl acetate and water, and the organic phase was successively washed with water and brine, dried (magnesium sulfate) and concentrated in vacuo. Purification by automated flash column chromatography (CombiFlash Rf, 120 g RediSep™ silica cartridge) eluting with a gradient of 0-25% ethyl acetate in iso-heptane afforded the desired product as a yellow gum (4.17 g, 12.7 mmol, 40%).

LC/MS ($C_{19}H_{23}NO_4$) 330 [M+H]⁺; RT 1.31 (LCMS-V-B1PsNeg)

¹H NMR (400 MHz, DMSO-d6) δ 7.41-7.34 (m, 4H), 7.34-7.27 (m, 1H), 5.13 (t, J=5.7 Hz, 1H), 4.57 (d, J=11.9 Hz, 1H), 4.55-4.40 (m, 2H), 4.39-4.26 (m, 2H), 2.68-2.56 (m, 2H), 2.20-2.07 (m, 1H), 1.71 (t, J=2.6 Hz, 3H), 0.84 (dd, 6H).

Step C: (2R)-2-(benzyloxy)hex-4-yn-1-ol

To a cooled solution of the product from Step B (4.17 g, 12.7 mmol, 1 eq) in tetrahydrofuran (45 mL) was added a solution of sodium borohydride (623 mg, 16.5 mmol, 1.3 eq) in water (12 mL) and the mixture was stirred at ambient temperature for 3 h. The reaction was quenched with saturated aqueous ammonium chloride (100 mL) and partitioned between ethyl acetate and water. The organic phase was successively washed with water and brine, dried (magnesium sulfate) and concentrated in vacuo. Purification by automated flash column chromatography (CombiFlash Rf, 40 g RediSep™ silica cartridge) eluting with a gradient of 0-30% ethyl acetate in iso-heptane afforded the desired product as a colourless oil (2.01 g, 9.84 mmol, 78%).

¹H NMR (400 MHz, DMSO-d6) δ 7.41-7.31 (m, 4H), 7.31-7.23 (m, 1H), 4.70 (t, J=5.5 Hz, 1H), 4.59 (d, J=1.9 Hz, 2H), 3.57-3.40 (m, 3H), 2.46-2.27 (m, 2H), 1.75 (t, J=2.6 Hz, 3H).

Step D: {[(2R)-2-(benzyloxy)hex-4-yn-1-yl]oxy}(tert-butyl)diphenylsilane

To a cooled solution of the product from Step C (2.01 g, 9.84 mmol, 1 eq) in dichloromethane (50 mL) was added imidazole (1.34 g, 19.7 mmol, 2 eq) and tert-butyl(chloro)diphenylsilane (5.12 mL, 19.7 mmol, 2 eq) dropwise and the mixture was allowed to warm to ambient temperature and stir for 4 h. The reaction was quenched with 2M aqueous ammonium chloride and partitioned between dichloromethane and water. The organic phase was successively washed with water and brine, dried (PTFE phase separator) and concentrated in vacuo. Purification by automated flash column chromatography (CombiFlash Rf, 80 g RediSep™ silica cartridge) eluting with a gradient of 0-8% ethyl acetate in iso-heptane afforded the desired product as a colourless oil (3.66 g, 8.27 mmol, 84%).

LC/MS ($C_{29}H_{34}O_2Si$) weak ionisation; RT 1.73 (LCMS-V-B1P0sNeg)

¹H NMR (400 MHz, DMSO-d6) δ 7.68-7.61 (m, 4H), 7.51-7.38 (m, 6H), 7.37-7.32 (m, 4H), 7.32-7.25 (m, 1H), 4.65-4.52 (m, 2H), 3.83-3.68 (m, 2H), 3.67-3.56 (m, 1H), 2.49-2.41 (m, 2H), 1.71 (t, J=2.5 Hz, 3H), 1.00 (s, 9H).

Step E: 4-[(2R)-2-(benzyloxy)-3-[(tert-butyldiphenylsilyl)oxy]propyl]-3,6-dichloro-5-methylpyridazine A solution of 3,6-dichloro-1,2,4,5-tetrazine (4.99 g, 33.1 mmol, 4 eq) and the product from Step D (3.66 g, 8.27 mmol, 1 eq) in toluene (50 mL) was heated in a sealed flask at 150° C. overnight.

The reaction was concentrated in vacuo and purification by automated flash column chromatography (CombiFlash Rf, 80 g RediSep™ silica cartridge) eluting with a gradient of 0-15% ethyl acetate in iso-heptane afforded the desired product as a bright orange oil (3.76 g, 6.65 mmol, 80%).

LC/MS ($C_{31}H_{34}Cl_2N_2O_2Si$) 566 [M+H]; RT 1.72 (LCMS-V-B1)

¹H NMR (400 MHz, DMSO-d6) δ 7.72-7.62 (m, 4H), 7.56-7.40 (m, 6H), 7.27-7.11 (m, 3H), 6.93-6.84 (m, 2H), 4.44 (d, J=12.1 Hz, 1H), 4.10 (d, J=12.1 Hz, 1H), 3.91-3.78 (m, 2H), 3.76-3.66 (m, 1H), 3.15 (dd, J=13.8, 10.0 Hz, 1H), 3.00 (dd, J=13.8, 3.6 Hz, 1H), 2.27 (s, 3H), 1.04 (s, 9H).

Step F: (2R)-2-(benzyloxy)-3-(3,6-dichloro-5-methylpyridazin-4-yl)propan-1-ol

To a solution of the product from Step E (3.76 g, 6.65 mmol, 1 eq) in tetrahydrofuran (25 mL) was added tetrabutylammonium fluoride (1M in tetrahydrofuran; 7.31 mL, 7.31 mmol, 1.1 eq) and the mixture was stirred at ambient temperature for 1 h. The reaction was diluted with ethyl acetate (100 mL), successively washed with water (150 mL), saturated aqueous sodium bicarbonate (150 mL) and brine (2×100 mL), dried (magnesium sulfate) and concentrated in vacuo. Purification by automated flash column chromatography (CombiFlash Rf, 40 g RediSep™ silica cartridge)

eluting with a gradient of 0-80% ethyl acetate in iso-heptane afforded the desired product as an orange solid (1.68 g, 5.14 mmol, 77%).

LC/MS ($C_{15}H_{16}Cl_2N_2O_2$) 327 [M+H]$^+$; RT 1.06 (LCMS-V-B1)

$^1$H NMR (400 MHz, DMSO-d6) δ 7.25-7.12 (m, 3H), 7.01-6.93 (m, 2H), 4.99 (t, J=5.5 Hz, 1H), 4.53 (d, J=12.1 Hz, 1H), 4.22 (d, J=12.0 Hz, 1H), 3.69-3.51 (m, 3H), 3.08-2.91 (m, 2H), 2.29 (s, 3H).

Step G: ethyl 2-{[(2R)-2-(benzyloxy)-3-(3,6-di-chloro-5-methylpyridazin-4-yl)propyl]amino}-1,3-thiazole-4-carboxylate To a solution of the product from Step F (1.68 g, 5.14 mmol, 1 eq) in tetrahydrofuran (55 mL) was added triphenylphosphine (2.7 g, 10.3 mmol, 2 eq) and ethyl 2-[(tert-butoxycarbonyl)amino]-1,3-thiazole-4-carboxylate (1.68 g, 6.16 mmol, 1.2 eq), followed by diisopropyl azodicarboxylate (2.02 mL, 10.3 mmol, 2 eq) and the mixture was stirred at ambient temperature for 2 h. The reaction was partitioned between ethyl acetate and water and the organic phase was successively washed with water and brine (2×50 mL), dried (magnesium sulfate) and concentrated in vacuo. The material was dissolved in dichloromethane (30 mL) and trifluoroacetic acid (7.87 mL, 103 mmol, 20 eq) was added and the mixture was stirred at ambient temperature overnight. The reaction was diluted and neutralised with saturated aqueous sodium bicarbonate, the layers were separated and the aqueous phase was extracted with dichloromethane (3×100 mL). The combined organic extracts were washed with brine (150 mL), dried (PTFE phase separator) and concentrated in vacuo. Purification by automated flash column chromatography (CombiFlash Rf, 40 g RediSep™ silica cartridge) eluting with a gradient of 0-80% ethyl acetate in iso-heptane afforded the desired product as a yellow solid (1.94 g, 4.02 mmol, 78%).

LC/MS ($C_{21}H_{22}Cl_2N_4O_3S$) 482 [M+H]$^+$; RT 1.28 (LCMS-V-B1)

$^1$H NMR (400 MHz, DMSO-d6) δ 8.14 (t, J=5.9 Hz, 1H), 7.57 (s, 1H), 7.24-7.06 (m, 3H), 7.01-6.93 (m, 2H), 4.54 (d, J=11.9 Hz, 1H), 4.31-4.15 (m, 3H), 3.97-3.86 (m, 1H), 3.70-3.59 (m, 1H), 3.52-3.41 (m, 1H), 3.06 (dd, J=13.9, 10.2 Hz, 1H), 2.92 (dd, J=13.9, 3.2 Hz, 1H), 2.24 (s, 3H), 1.27 (t, J=7.1 Hz, 3H).

Step H: ethyl 2-[(6R)-6-(benzyloxy)-3-chloro-4-methyl-5H,6H,7H,8H-pyrido[2,3-c]pyridazin-8-yl]-1,3-thiazole-4-carboxylate To a solution of the product from Step G (2.09 g, 4.34 mmol, 1 eq) in acetonitrile (130 mL) was added potassium carbonate (1.2 g, 8.68 mmol, 2 eq) and copper (I) iodide (827 mg, 4.34 mmol, 1 eq) and the mixture was heated at reflux for 10 h. The reaction was diluted with water and extracted with ethyl acetate (3×60 mL). The combined organic extracts were washed with brine (2×50 mL), dried (magnesium sulfate) and concentrated in vacuo. Purification by reverse phase automated flash chromatography (CombiFlash Rf, C18 130 g RediSep column) eluting with a gradient of 5-95% acetonitrile in water afforded the desired product as a pale brown solid (0.7 g, 1.58 mmol, 36%).

LC/MS ($C_{21}H_{21}ClN_4O_3S$) 446 [M+H]$^+$; RT 1.36 (LCMS-V-B1)

$^1$H NMR (400 MHz, DMSO-d6) δ 8.05 (s, 1H), 7.32-7.17 (m, 5H), 4.99-4.86 (m, 1H), 4.59 (s, 2H), 4.39-4.23 (m, 3H), 4.07 (dd, J=13.6, 2.1 Hz, 1H), 3.29-3.02 (m, 2H), 2.32 (s, 3H), 1.32 (t, J=7.1 Hz, 3H).

Step I: ethyl 2-[(6R)-3-[(1,3-benzothiazol-2-yl)amino]-6-(benzyloxy)-4-methyl-5H,6H,7H,8H-pyrido[2,3-c]pyridazin-8-yl]-1,3-thiazole-4-carboxylate To an oven-dried sealed flask was added the product from Step H (700 mg, 1.57 mmol, 1 eq), 2-aminobenzothiazole (473 mg, 3.15 mmol, 2 eq), NN-diisopropylethylamine (0.82 mL, 4.72 mmol, 3 eq), JosiPhos Pd G3 (291 mg, 0.31 mmol, 0.2 eq) and 1,4-dioxane (17.5 mL) and the mixture was sparged with nitrogen (10 min) then heated at 100° C. for 3 days. The reaction was partitioned between saturated aqueous sodium bicarbonate and ethyl acetate, the aqueous phase was extracted with ethyl acetate (3×80 mL), and the combined organic extracts were washed with brine (70 mL), dried (magnesium sulfate) and concentrated in vacuo. Purification by automated flash column chromatography (CombiFlash Rf, 40 g RediSep™ silica cartridge) eluting with a gradient of 0-100% ethyl acetate in iso-heptane afforded the desired product as a yellow solid (548 mg, 0.98 mmol, 62%).

LC/MS ($C_{28}H_{26}N_6O_3S2$) 559 [M+H]$^+$; RT 1.03 (LCMS-V-B2)

$^1$H NMR (400 MHz, DMSO-d6) δ 8.00 (s, 1H), 7.89 (d, J=7.8 Hz, 1H), 7.50 (br s, 1H), 7.38 (td, J=7.7, 1.2 Hz, 1H), 7.33-7.16 (m, 6H), 4.96-4.85 (m, 1H), 4.61 (s, 2H), 4.38-4.25 (m, 3H), 4.15-4.05 (m, 1H), 3.25-3.14 (m, 1H), 3.13-3.02 (m, 1H), 2.35 (s, 3H), 1.33 (t, J=7.1 Hz, 3H).

Step J: ethyl 2-[(6R)-3-[(1,3-benzothiazol-2-yl)amino]-6-hydroxy-4-methyl-5H,6H,7H,8H-pyrido[2,3-c]pyridazin-8-yl]-1,3-thiazole-4-carboxylate To a cooled solution of the product from Step I (548 mg, 0.98 mmol, 1 eq) in dichloromethane (30 mL) was added boron trichloride (1M in dichloromethane; 4.9 mL, 4.9 mmol, 5 eq) dropwise and the mixture was stirred at ambient temperature for 2 h. The reaction was cooled to 0-5° C. and quenched with methanol (5 mL). Further methanol (5 mL) was added and the mixture was heated at reflux for 1.5 h. The reaction was concentrated in vacuo and purification by reverse phase automated flash chromatography (CombiFlash Rf, C18 43 g RediSep column) eluting with a gradient of 5-95% acetonitrile in water afforded the desired product as a yellow solid (328 mg, 0.7 mmol, 71%).

LC/MS ($C_{21}H_{20}N_6O_3S2$) 469 [M+H]$^+$; RT 0.71 (LCMS-V-B2)

$^1$H NMR (400 MHz, DMSO-d6) δ 8.01 (d, J=9.3 Hz, 1H), 7.89 (br s, 1H), 7.51 (br s, 1H), 7.38 (t, J=7.5 Hz, 1H), 7.20 (t, J=7.4 Hz, 1H), 5.38 (d, J=3.2 Hz, 1H), 4.47 (dd, J=12.8, 4.8 Hz, 1H), 4.41-4.34 (m, 1H), 4.30 (q, J=7.1 Hz, 2H), 4.19 (dd, J=12.9, 2.5 Hz, 1H), 3.08-2.88 (m, 2H), 2.35 (s, 3H), 1.33 (t, J=7.1 Hz, 3H).

Step K: 2-[(6R)-3-[(1,3-benzothiazol-2-yl)amino]-6-hydroxy-4-methyl-5H,6H,7H,8H-pyrido[2,3-c]pyridazin-8-yl]-1,3-thiazole-4-carboxylic acid To a solution of the product from Step J (60 mg, 0.13 mmol, 1 eq) in 1,4-dioxane (10 mL) was added a solution of lithium hydroxide monohydrate (10.8 mg, 0.26 mmol, 2 eq) in water (2 mL) and the mixture was heated at reflux for 2 h. Purification by reverse phase automated flash chromatography (CombiFlash Rf, C18 13 g RediSep column) eluting with a gradient of 5-95% acetonitrile in water afforded a yellow solid. The solid was dissolved in methanol, then loaded onto a methanol-wet PE-AX cartridge (10 g), washed successively with methanol and dichloromethane, eluted with 10% formic acid in dichloromethane, and concentrated in vacuo to afford the desired product as a yellow solid (11.4 mg, 0.03 mmol, 20%), as a formic acid salt.

HRMS-ESI (m/z) [M+H]+ calcd for $C_{19}H_{17}N_6O_3S_2$: 441.0804, found 441.0827.

Example 34: 2-{3-[(1,3-Benzothiazol-2-yl)amino]-4-methyl-5H,6H,7H,8H-pyrido[2,3-c]pyridazin-8-yl}-5-(3-{2-fluoro-4-[3-(methylamino)propyl]phenoxy}propyl)-1,3-thiazole-4-carboxylic acid

Step A: ethyl 5-{3-[4-(3-{[(tert-butoxy)carbonyl](methyl)amino}propyl)-2-fluorophenoxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the Example 32, Step A (447 mg, 0.5 mmol, 1 eq) in 1,4-dioxane (11 mL) was added platinum (IV) oxide (22.5 mg, 0.1 mmol, 0.2 eq) under a nitrogen atmosphere. The vessel was evacuated and back-filled with nitrogen (×3) then evacuated, placed under a hydrogen atmosphere and shaken at ambient temperature for 24 h. The reaction was filtered through celite, eluted with ethyl acetate and concentrated in vacuo. Purification by automated flash column chromatography (CombiFlash Rf, 24 g RediSep™ silica cartridge) eluting with a gradient of iso-heptane to 50% ethyl acetate in iso-heptane afforded the desired product as a yellow solid (424 mg, 0.47 mmol, 94%).

LC/MS ($C_{45}H_{60}FN_7O_6SiS_2$) 906 [M+H]+; RT 1.45 (LCMS-V-B2)

$^1$H NMR (400 MHz, DMSO-d6) δ 7.82 (d, 1H), 7.48-7.38 (m, 2H), 7.28-7.20 (m, 1H), 7.12-7.02 (m, 2H), 6.98-6.91 (m, 1H), 5.84 (s, 2H), 4.33-4.20 (m, 4H), 4.08 (t, J=6.2 Hz, 2H), 3.77-3.67 (m, 2H), 3.27 (t, J=7.6 Hz, 2H), 3.18-3.04 (m, 2H), 2.88 (t, J=6.3 Hz, 2H), 2.72 (s, 3H), 2.45 (t, J=7.3 Hz, 2H), 2.37 (s, 3H), 2.17-1.99 (m, 4H), 1.78-1.62 (m, 2H), 1.29 (t, 3H), 1.24 (s, 9H), −0.11 (s, 9H).

Step B: ethyl 2-{3-[(1,3-benzothiazol-2-yl)amino]-4-methyl-5H,6H,7H,8H-pyrido[2,3-c]pyridazin-8-yl}-5-(3-{2-fluoro-4-[3-(methylamino)propyl]phenoxy}propyl)-1,3-thiazole-4-carboxylate To a solution of the product from Step A (424 mg, 0.47 mmol, 1 eq) in acetonitrile (6 mL) was added hydrogen fluoride-pyridine (0.81 mL, 9.36 mmol, 20 eq) and the mixture was heated at 60° C. for 3 h. The reaction was partitioned between dichloromethane and 2N aqueous sodium hydroxide, and the organic phase was washed with brine, dried (PTFE phase separator) and concentrated in vacuo. Purification by automated flash column chromatography (CombiFlash Rf, 12 g RediSep™ silica cartridge) eluting with a gradient of 0-15% methanol in dichloromethane afforded the desired product as a yellow solid (147 mg, 0.22 mmol, 47%).

LC/MS ($C_{34}H_{38}FN_7O_3S_2$) 676 [M+H]$^+$; RT 2.06 (LCMS-V-C)

$^1$H NMR (400 MHz, DMSO-d6) δ 7.87 (dd, J=7.9, 1.1 Hz, 1H), 7.53-7.45 (m, 1H), 7.41-7.32 (m, 1H), 7.18 (td, J=7.6, 1.2 Hz, 1H), 7.12-7.01 (m, 2H), 6.97-6.89 (m, 1H), 4.34-4.19 (m, 4H), 4.09 (t, J=6.2 Hz, 2H), 3.32-3.21 (m, 4H), 2.88 (t, J=6.4 Hz, 2H), 2.41 (t, 2H), 2.34 (s, 3H), 2.24 (s, 3H), 2.17-1.99 (m, 4H), 1.69-1.57 (m, 2H), 1.30 (t, J=7.1 Hz, 3H).

Step C: 2-{3-[(1,3-benzothiazol-2-yl)amino]-4-methyl-5H,6H,7H,8H-pyrido[2,3-c]pyridazin-8-yl}-5-(3-{2-fluoro-4-[3-(methylamino)propyl]phenoxy}propyl)-1,3-thiazole-4-carboxylic acid To a solution of the product from Step B (147 mg, 0.22 mmol, 1 eq) in 1,4-dioxane (15 mL) was added lithium hydroxide monohydrate (91.3 mg, 2.18 mmol, 10 eq) and the mixture was heated at reflux overnight. Purification by automated flash column chromatography (CombiFlash Rf, 4 g RediSep™ silica cartridge) eluting with a gradient of 0-25% 7N methanolic ammonia in dichloromethane gave a solid that was triturated with acetonitrile, filtered and dried under vacuum to afford the desired product as a yellow solid (83.8 mg, 0.13 mmol, 60%).

HRMS-ESI (m/z) [M+H]+ calcd for $C_{32}H_{35}FN_7O_3S_2$: 648.2227, found 648.2246.

Example 35: 5-{3-[4-(Aminomethyl)-2-fluorophenoxy]propyl}-2-{3-[(1,3-benzothiazol-2-yl)amino]-4-methyl-5H,6H,7H,8H-pyrido[2,3-c]pyridazin-8-yl}-1,3-thiazole-4-carboxylic acid

Step A: ethyl 5-[3-(4-cyano-2-fluorophenoxy)propyl]-2-(4-methyl-3-{[(2Z)-3-{2-[2-(trimethylsilyl)ethoxy]ethyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3g (200 mg, 0.31 mmol, 1 eq) in toluene (6 mL) was added 3-fluoro-4- hydroxybenzonitrile (64.2 mg, 0.47 mmol, 1.5 eq), followed by triphenylphosphine (123 mg, 0.47 mmol, 1.5 eq) and diisopropyl azodicarboxylate (92.2 μL, 0.47 mmol, 1.5 eq) and the mixture was heated at reflux overnight. The reaction was partitioned between dichloromethane and water, and the organic phase was dried (PTFE phase separator) and concentrated in vacuo. Purification by automated flash column chromatography (CombiFlash Rf, 12 g RediSep™ silica cartridge) eluting with a gradient of 0-50% ethyl acetate in iso-heptane afforded the desired product as a beige solid (207 mg, 0.27 mmol, 87%).

LC/MS (C$_{37}$H$_{42}$FN$_7$O$_4$SiS$_2$) 760 [M+H]V; RT 3.00 (LCMS-V-C)

$^1$H NMR (400 MHz, DMSO-d6) δ 7.89-7.78 (m, 2H), 7.70-7.63 (m, 1H), 7.49-7.38 (m, 2H), 7.36 (t, J=8.6 Hz, 1H), 7.28-7.19 (m, 1H), 5.85 (s, 2H), 4.33-4.18 (m, 6H), 3.77-3.68 (m, 2H), 3.32-3.23 (m, 2H), 2.88 (t, J=6.2 Hz, 2H), 2.37 (s, 3H), 2.22-2.11 (m, 2H), 2.10-1.99 (m, 2H), 1.28 (t, J=7.1 Hz, 3H), 0.96-0.86 (m, 2H), −0.11 (s, 9H).

Step B: ethyl 5-{3-[4-(aminomethyl)-2-fluorophe-noxy]propyl}-2-(4-methyl-3-{[(2Z)-3-{2-[2-(trim-ethylsilyl)ethoxy]ethyl}-2,3-dihydro-1,3-benzothi-azol-2-ylidene]amino}-5H,6H,7H,8H-pyrido[2,3-c] pyridazin-8-yl)-1,3-thiazole-4-carboxylate A solution of the product from Step A (336 mg, 0.44 mmol, 1 eq) in ethyl acetate (60 mL) was hydrogenated using an H-Cube® Pro (ThalesNano) (110° C., 85 bar). The mixture was concentrated in vacuo and purification by automated flash column chromatography (CombiFlash Rf, 12 g RediSep™ silica cartridge) eluting with a gradient of 0-8% methanol in dichloromethane afforded the desired product as a yellow gum (282 mg, 0.37 mmol, 84%).

LC/MS (C$_{37}$H$_{46}$FN$_7$O$_4$SiS$_2$) 764 [M+H]$^+$; RT 1.31 (LCMS-V-B1)

$^1$H NMR (400 MHz, DMSO-d6) δ 7.84-7.78 (m, 1H), 7.48-7.37 (m, 2H), 7.28-7.13 (m, 2H), 7.12-7.00 (m, 2H), 5.84 (s, 2H), 5.87 (s, 2H), 4.33-4.20 (m, 4H), 4.09 (td, J=6.2, 1.9 Hz, 2H), 3.78-3.66 (m, 2H), 3.31-3.21 (m, 4H), 2.86 (t, J=6.3 Hz, 2H), 2.36 (s, 3H), 2.19-1.97 (m, 4H), 1.30 (t, J=7.1 Hz, 3H), 0.95-0.84 (m, 2H), −0.12 (s, 9H).

Step C: ethyl 5-{3-[4-(aminomethyl)-2-fluorophe-noxy]propyl}-2-{3-[(1,3-benzothiazol-2-yl)amino]-4-methyl-5H,6H,7H,8H-pyrido[2,3-c]pyridazin-8-yl}-1,3-thiazole-4-carboxylate To a solution of the product from Step B (94 mg, 0.12 mmol, 1 eq) in tetrahydrofuran (5 mL) was added tetrabuty-lammonium fluoride (1M in tetrahydrofuran, 0.74 mL, 0.74 mmol, 6 eq) and ethylenediamine (49.3 μL, 0.74 mmol, 6 eq) and the mixture was heated at 100° C. for 1 h under microwave irradiation. The reaction was partitioned between ethyl acetate and water, and the organic phase was washed with brine, dried (magnesium sulfate) and concentrated in vacuo. Purification by automated flash column chromatography (CombiFlash Rf, 4 g RediSep™ silica cartridge) eluting with a gradient of 0-10% methanol in dichloromethane afforded the desired product as a yellow solid (29 mg, 0.05 mmol, 37%).

LC/MS (C$_{31}$H$_{32}$FN$_7$O$_3$S$_2$) 634 [M+H]$^+$; RT 1.96 (LCMS-V-C)

$^1$H NMR (400 MHz, DMSO-d6) δ 7.84 (d, J=7.6 Hz, 1H), 7.46 (d, J=7.9 Hz, 1H), 7.38-7.30 (m, 1H), 7.26-7.00 (m,

4H), 4.32-4.21 (m, 4H), 4.09 (t, J=6.2 Hz, 2H), 3.32-3.21 (m, 4H), 2.87 (t, J=6.5 Hz, 2H), 2.33 (s, 3H), 2.17-1.98 (m, 4H), 1.29 (t, J=7.3 Hz, 3H).

Step D: 5-{3-[4-(aminomethyl)-2-fluorophenoxy] propyl}-2-{3-[(1,3-benzothiazol-2-yl)amino]-4-methyl-5H,6H,7H,8H-pyrido[2,3-c]pyridazin-8-yl}-1,3-thiazole-4-carboxylic acid To a solution of the product from Step C (29 mg, 0.05 mmol, 1 eq) in 1,4-dioxane (5 mL) was added lithium hydroxide monohydrate (19.2 mg, 0.46 mmol, 10 eq) and the mixture was heated at reflux overnight. Purification by automated flash column chromatography (CombiFlash Rf, 4 g RediSep™ silica cartridge) eluting with a gradient of 0-25% 7N methanolic ammonia in dichloromethane gave a solid that was triturated with diethyl ether, filtered and dried under vacuum to afford the desired product as a yellow solid (3.0 mg, 4.89 μmol, 28%). HRMS-ESI (m/z) [M+H]+ calcd for C$_{29}$H$_{29}$FN$_7$O$_3$S$_2$: 606.1757, found 606.1782.

Example 36: 2-{3-[(1,3-Benzothiazol-2-yl)amino]-4-methyl-5H,6H,7H,8H-pyrido[2,3-c]pyridazin-8-yl}-5-(3-{4-[3-(dimethylamino)propyl]-2-fluorophenoxy}propyl)-1,3-thiazole-4-carboxylic acid Step A: ethyl 5-(3-{4-[3-(dimethylamino)prop-1-yn-1-yl]-2-fluorophenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3g (1 g, 1.56 mmol, 1 eq) in toluene (30 mL) was added the product from Preparation 4b (452 mg, 2.34 mmol, 1.5 eq), followed by triphenylphosphine (614 mg, 2.34 mmol, 1.5 eq) and diiso-propyl azodicarboxylate (461 μL, 2.34 mmol, 1.5 eq) and the mixture was heated at reflux overnight. The reaction was partitioned between dichloromethane and water, and the organic phase was dried (PTFE phase separator) and concentrated in vacuo. Purification by automated flash column chromatography (CombiFlash Rf, 40 g RediSep™ silica cartridge) eluting with a gradient of 0-100% ethyl acetate in iso-heptane afforded the desired product as a brown gum (1.16 g, 1.42 mmol, 910%).

LC/MS ($C_{41}H_{50}FN_7O_4SiS_2$) 816 [M+H]$^+$; RT 2.70 (LCMS-V-C)

$^1$H NMR (400 MHz, DMSO-d6) δ 7.84-7.77 (m, 1H), 7.47-7.37 (m, 2H), 7.31 (dd, J=12.0, 1.9 Hz, 1H), 7.27-7.12 (m, 3H), 5.83 (s, 2H), 4.32-4.20 (m, 4H), 4.14 (t, J=6.1 Hz, 2H), 3.76-3.67 (m, 2H), 3.37 (s, 2H), 3.31-3.21 (m, 2H), 2.86 (t, J=6.3 Hz, 2H), 2.36 (s, 3H), 2.19 (s, 6H), 2.17-2.09 (m, 2H), 2.07-2.00 (m, 2H), 1.28 (t, J=7.1 Hz, 3H), 0.90 (dd, J=8.5, 7.4 Hz, 2H), −0.11 (s, 9H).

Step B: ethyl 2-{3-[(1,3-benzothiazol-2-yl)amino]-4-methyl-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylate To a solution of the product from Step A (262 mg, 0.32 mmol, 1 eq) in 1,4-dioxane (10 mL) was added ethylenediamine (21.4 µL, 0.32 mmol, 1 eq) and tetrabutylammonium fluoride (1M in tetrahydrofuran, 0.96 mL, 0.96 mmol, 3 eq) and the mixture was heated at 70° C. overnight. The reaction was partitioned between ethyl acetate and water, and the organic phase was dried (magnesium sulfate) and concentrated in vacuo. Purification by automated flash column chromatography (CombiFlash Rf, 12 g RediSep™ silica cartridge) eluting with a gradient of 0-6% methanol in dichloromethane afforded the desired product as a yellow gum (114 mg, 0.17 mmol, 52%).

LC/MS ($C_{35}H_{36}FN_7O_3S_2$) 686 [M+H]$^+$; RT 2.08 (LCMS-V-C)

$^1$H NMR (400 MHz, DMSO-d6) δ 11.43 (br s, 1H), 7.88 (d, J=7.6 Hz, 1H), 7.50 (d, J=8.0 Hz, 1H), 7.42-7.35 (m, 1H), 7.31 (dd, 1H), 7.26-7.12 (m, 3H), 4.32-4.22 (m, 4H), 4.15 (t, J=6.1 Hz, 2H), 3.40 (s, 2H), 3.28 (dd, J=8.6, 6.7 Hz, 2H), 2.88 (t, J=6.3 Hz, 2H), 2.35 (s, 3H), 2.21 (s, 6H), 2.20-2.10 (m, 2H), 2.07-2.02 (m, 2H), 1.30 (t, J=7.1 Hz, 3H).

Step C: ethyl 2-{3-[(1,3-benzothiazol-2-yl)amino]-4-methyl-5H,6H,7H,8H-pyrido[2,3-c]pyridazin-8-yl}-5-(3-{4-[3-(dimethylamino)propyl]-2-fluorophenoxy}propyl)-1,3-thiazole-4-carboxylate To a solution of the product from Step B (119 mg, 0.17 mmol, 1 eq) in ethyl acetate (40 mL) was added platinum (IV) oxide (7.88 mg, 0.03 mmol, 0.2 eq) under a nitrogen atmosphere and the vessel was evacuated and backfilled with nitrogen (×3), then evacuated, placed under a hydrogen atmosphere, and shaken at ambient temperature for 3 days. The reaction was filtered through celite, eluted with ethyl acetate and concentrated in vacuo. Purification by automated flash column chromatography (CombiFlash Rf, 4 g RediSep™ silica cartridge) eluting with a gradient of 0-10% methanol in dichloromethane afforded the desired product as a yellow gum (55 mg, 0.08 mmol, 46%).

LC/MS ($C_{35}H_{40}FN_7O_3S_2$) 690 [M+H]$^+$; RT 2.10 (LCMS-V-C)

$^1$H NMR (400 MHz, DMSO-d6) δ 11.44 (br s, 1H), 7.88 (dd, J=7.5, 1.1 Hz, 1H), 7.50 (d, J=8.1 Hz, 1H), 7.38 (td, J=7.7, 1.3 Hz, 1H), 7.20 (td, J=7.5, 1.1 Hz, 1H), 7.12-7.02 (m, 2H), 6.97-6.89 (m, 1H), 4.32-4.21 (m, 4H), 4.09 (t, 2H), 3.33-3.22 (m, 4H), 2.89 (t, J=6.3 Hz, 2H), 2.35 (s, 3H), 2.19-2.11 (m, 4H), 2.09 (s, 6H), 2.07-2.01 (m, 2H), 1.63 (p, J=7.4 Hz, 2H), 1.30 (t, J=7.1 Hz, 3H).

Step D: 2-{3-[(1,3-benzothiazol-2-yl)amino]-4-methyl-5H,6H,7H,8H-pyrido[2,3-c]pyridazin-8-yl}-5-(3-{4-[3-(dimethylamino)propyl]-2-fluorophenoxy}propyl)-1,3-thiazole-4-carboxylic acid To a solution of the product from Step C (55 mg, 0.08 mmol, 1 eq) in 1,4-dioxane (5 mL) was added lithium hydroxide monohydrate (33.5 mg, 0.8 mmol, 10 eq) and the mixture was heated at reflux overnight. Purification by automated flash column chromatography (CombiFlash Rf, 4 g RediSep™ silica cartridge) eluting with a gradient 0-20% 7N methanolic ammonia in dichloromethane gave a solid that was triturated with acetonitrile, filtered and dried under vacuum to afford the desired product as a yellow solid (32.8 mg, 0.05 mmol, 62%).

HRMS-ESI (m/z) [M+H]+ calcd for $C_{33}H_{37}FN_7O_3S_2$: 662.2383, found 662.2402.

Example 37: 2-[3-(1,3-Benzothiazol-2-ylamino)-4-methyl-5,6-dihydropyrrolo[2,3-c]pyridazin-7-yl]-5-[3-[2-fluoro-4-[3-(methylamino)prop-1-ynyl]phenoxy]propyl]thiazole-4-carboxylic acid

Step A: methyl 2-[tert-butoxycarbonyl-[2-(3,6-dichloro-5-methyl-pyridazin-4-yl)ethyl]amino]-5-[3-(2-fluoro-4-iodo-phenoxy)propyl]thiazole-4-carboxylate Using Mitsunobu General Procedure starting from 5.18 g of Preparation 1a (Step D) (9.6 mmol, 1.0 eq.) as the appropriate carbamate and 2.0 g of Preparation 2c (9.6 mmol, 1.0 eq.) as the appropriate alcohol, 5.6 g of the desired product (80% Yield) was obtained.

Step B: methyl 2-[2-(3,6-dichloro-5-methyl-pyridazin-4-yl)ethylamino]-5-[3-(2-fluoro-4-iodo-phenoxy)propyl]thiazole-4-carboxylate Using Deprotection with HFIP General Procedure starting from 5.65 g of the product from Step A as the appropriate carbamate, 2.9 g of the desired product (60%) was obtained.

$^1$H NMR (500 MHz, DMSO-d$_6$) δ ppm 7.76 (t, 1H), 7.59 (dd, 1H), 7.45 (dm, 1H), 6.97 (t, 1H), 4.02 (t, 2H), 3.71 (s, 3H), 3.48 (m, 2H), 3.13 (t, 2H), 3.1 (m, 2H), 2.44 (s, 3H), 1.99 (m, 2H); 13C NMR (125 MHz, DMSO-d$_6$) δ ppm 163.1, 134.2, 125, 117.7, 82.4, 67.9, 51.8, 41.6, 30.4, 30.4, 23.2, 16.8; HRMS-ESI (m/z): [M+H]+ calcd for C$_{21}$H$_{21}$Cl$_2$FIN$_4$O$_3$S: 624.9734, found 624.9740.

Step C: methyl 2-(3-chloro-4-methyl-5,6-dihydro-pyrrolo[2,3-c]pyridazin-7-yl)-5-[3-(2-fluoro-4-iodo-phenoxy)propyl]thiazole-4-carboxylate A suspension of 3.0 g of the product from Step B (4.79 mmol, 1 eq.) and 1.85 g cesium carbonate (9.59 mmol, 2 eq.) were stirred at 80° C. for 3 h in 25 mL dry 1,4-dioxane, while full conversion was observed. Reaction mixture directly was evaporated to Celite, and then purified by flash chromatography using DCM-MeOH as eluents to obtain 2.64 g of the desired product (93% Yield).

$^1$H NMR (400 MHz, DMSO-d$_6$) δ ppm 7.6 (dd, 1H), 7.46 (dm, 1H), 6.99 (t, 1H), 4.35 (t, 2H), 4.1 (t, 2H), 3.79 (s, 3H), 3.3 (m, 2H), 3.3 (m, 2H), 2.28 (s, 3H), 2.12 (m, 2H); $^{13}$C NMR (100 MHz, DMSO-d$_6$) δ ppm 134.2, 125.0, 117.7, 68.1, 52.2, 49.8, 30.7, 24.6, 23.5, 16.0; HRMS-ESI (m/z): [M+H]+ calcd for C$_{21}$H$_{20}$ClFFIN$_4$O$_3$S: 588.9967, found 588.9959.

Step D: methyl 5-[3-[4-[3-[tert-butoxycarbonyl (methyl)amino]prop-1-ynyl]-2-fluoro-phenoxy]pro-pyl]-2-(3-chloro-4-methyl-5,6-dihydropyrrolo[2,3-c] pyridazin-7-yl)thiazole-4-carboxylate A 100 mL oven-dried, one-necked, round-bottom flask was equipped with a PTFE-coated magnetic stirring bar and fitted with a reflux condenser. It was charged with 2.6 g the product from Step C (4.48 mmol, 1 eq.), 1.51 g tert-butyl N-methyl-N-prop-2-ynyl-carbamate (8.96 mmol, 2 eq.) and 4 mL DIPEA, then 16 mL dry THF was added and the system was flushed with argon. After 5 minutes stirring under inert atmosphere 42 mg mg Pd(PPh$_3$)$_2$Cl$_2$ (0.224 mmol, 0.05 eq.) and 79 mg (0.224 mmol, 0.05 eq.) were added. The resulting mixture was then warmed up to 60° C. and stirred at that temperature for 2 hours to reach complete conversion. Celite was added to the reaction mixture and the volatiles were removed under reduced pressure. Then it was purified via flash chromatography using Heptane-EtOAc as eluents to give 1.88 g of the desired product (67% Yield).

Step E: methyl 2-[3-(1,3-benzothiazol-2-ylamino)-4-methyl-5,6-dihydropyrrolo[2,3-c]pyridazin-7-yl]-5-[3-[4-[3-[tert-butoxycarbonyl(methyl)amino]prop-1-ynyl]-2-fluoro-phenoxy]propyl]thiazole-4-carboxylate A 4 mL oven-dried vial equipped with a PTFE-coated magnetic stir bar was charged with 80 mg the product from Step D (0.127 mmol, 1.0 eq.), 28 mg 1,3-benzothiazol-2-amine (0.19 mmol, 1.5 eq.) and 113 uL DIPEA (0.635 mmol, 5 equiv) suspended in 0.5 mL dry 1, 4-dioxane. Resulting mixture was flushed with nitrogen, and then 11 mg Pd$_2$ (dba)$_3$ (0.012 mmol, 0.1 eq.) and 14 mg XantPhos (0.024 mmol, 0.2 eq.) were added. The reaction mixture was then warmed up to 120° C. and stirred at that temperature for 2 h, when the reaction reached complete conversion. The reaction mixture directly was evaporated to Celite, and then purified by flash chromatography on using heptane-EtOAc as eluents to give 65 mg of the desired product (68% Yield).

Step F: 2-[3-(1,3-benzothiazol-2-ylamino)-4-methyl-5,6-dihydropyrrolo[2,3-c]pyridazin-7-yl]-5-[3-[2-fluoro-4-[3-(methylamino)prop-1-ynyl]phenoxy]propyl]thiazole-4-carboxylic acid Using Deprotection and Hydrolysis General Procedure starting from the product from Step E as the appropriate methyl ester, the desired product was obtained.

HRMS-ESI (m/z): [M+H]+ calcd for C$_{31}$H$_{29}$FN$_7$O$_3$S$_2$: 630.1752, found 630.1755.

Example 38: 2-[3-(1,3-Benzothiazol-2-ylamino)-6-hydroxy-4-methyl-6,7-dihydro-5H-pyrido[2,3-c] pyridazin-8-yl]-5-[3-[2-fluoro-4-[3-(methylamino) prop-1-ynyl]phenoxy]propyl]thiazole-4-carboxylic acid (enantiopure, from Enantiomer 2 of Preparation 2b, Step A)

Step A: methyl 2-[tert-butoxycarbonyl-[2-[tert-butyl (diphenyl)silyl]oxy-3-(3,6-dichloro-5-methyl-pyridazin-4-yl)propyl]amino]-5-[3-[4-[3-[tert-bu-toxycarbonyl(methyl)amino]prop-1-ynyl]-2-fluoro-phenoxy]propyl]thiazole-4-carboxylate(enantiopure, from Enantiomer 2 of Preparation 2b, Step A)

Using Mitsunobu General Procedure starting from 1.91 g Preparation 1b (3.4 mmol, 1.0 eq.) as the appropriate carbamate and 1.6 g Preparation 2b (3.4 mmol, 1.0 eq.) as the appropriate alcohol, 2.2 g of the desired product (63% Yield) was obtained.

$^1$H NMR (500 MHz, DMSO-d$_6$) δ ppm 7.54-7.26 (m, 10H), 7.29 (m, 1H), 7.18 (d, 1H), 7.08 (t, 1H), 4.76 (m, 1H), 4.34/3.84 (m, 2H), 4.06 (t, 2H), 3.75 (s, 3H), 3.23 (m, 2H), 2.96/2.89 (m, 2H), 2.86 (bs, 3H), 2.06 (m, 2H), 2.03 (bs, 3H), 1.4 (s, 18H), 1.22 (m, 2H), 0.81 (s, 9H); $^{13}$C NMR (125 MHz, DMSO-d$_6$) δ ppm 129.0, 119.2, 115.4, 68.8, 67.9, 52.0, 51.1, 36.1, 33.9, 30.4, 28.0, 26.9, 22.9, 22.7, 19.1, 16.8; HRMS-ESI (m/z): [M+H]+ calcd for C$_{52}$H$_{63}$Cl$_2$FN$_5$O$_8$SSi: 1034.3522, found 1034.3519.

Step B: methyl 5-[3-[4-[3-[tert-butoxycarbonyl(methyl)amino]prop-1-ynyl]-2-fluoro-phenoxy]propyl]-2-[[2-[tert-butyl(diphenyl)silyl]oxy-3-(3,6-dichloro-5-methyl-pyridazin-4-yl)propyl]amino]thiazole-4-carboxylate (enantiopure, from Enantiomer 2 of Preparation 2b, Step A)

Using Deprotection with HFIPA General Procedure starting from the product from Step A as the appropriate carbamate, 1.6 g of the desired product (81% Yield) was obtained.

$^1$H NMR (500 MHz, DMSO-d$_6$) δ ppm 7.76 (t, 1H), 7.56-7.26 (m, 10H), 7.31 (d, 1H), 7.21 (d, 1H), 7.12 (t, 1H), 4.46 (m, 1H), 4.23 (br., 2H), 4.06 (t, 2H), 3.68 (s, 3H), 3.38/3.25 (m+m, 2H), 3.11 (t, 2H), 3.05 (m, 2H), 2.86 (br., 3H), 2.11 (s, 3H), 1.98 (quint., 2H), 1.41 (s, 9H), 0.85 (s, 9H); $^{13}$C NMR (125 MHz, DMSO-d$_6$) δ ppm 162.9, 157.4, 157.3, 154.9, 151.5, 140.6, 139.8, 129.1, 119.3, 115.3, 69.9, 67.9, 51.7, 50.1, 38.5, 36.2, 33.8, 30.5, 28.5, 27.1, 23.2, 17.0; HRMS-ESI (m/z): [M+H]+ calcd for C$_{47}$H$_{55}$Cl$_2$FN$_5$O$_6$SSi: 934.2997, found 934.2994.

Step C: methyl 5-[3-[4-[3-[tert-butoxycarbonyl(methyl)amino]prop-1-ynyl]-2-fluoro-phenoxy]propyl]-2-[6-[tert-butyl(diphenyl) silyl]oxy-3-chloro-4-methyl-6,7-dihydro-5H-pyrido[2,3-c]pyridazin-8-yl]thiazole-4-carboxylate (enantiopure, from Enantiomer 2 of Preparation 2b, Step A)

A 40 mL oven-dried vial equipped with a PTFE-coated magnetic stir bar was charged with 1.50 g of the product from Step B (1.6 mmol, 1.0 equiv) dissolved in 8 mL 1,4-dioxane, then 620 mg cesium carbonate (3.2 mmol, 2.0 equiv) and 560 uL DIPEA (410 mg, 3.2 mmol, 2.0 equiv) were added, and then placed under an inert atmosphere. After addition of the 110 mg Pd(AtaPhos)$_2$Cl$_2$ (0.16 mmol, 0.10 eq.) the reaction mixture was then warmed up to 80° C. and stirred at that temperature for 30 min, when the reaction reached complete conversion. Celite was added to the reaction mixture and the volatiles were removed under reduced pressure. Then it was purified via flash chromatography using heptane and EtOAc as eluents to give 550 mg of the desired product (38% Yield).

$^1$H NMR (500 MHz, DMSO-d$_6$) δ ppm 7.47 (dm, 4H), 7.47/7.43 (tm+tm, 2H), 7.38/7.33 (tm+tm, 4H), 7.3 (dm, 1H), 7.18 (m, 1H), 7.11 (t, 1H), 4.72/3.86 (m+m, 2H), 4.63 (m, 1H), 4.22 (s, 2H), 4.11 (t, 2H), 3.79 (s, 3H), 3.27 (m, 2H), 2.95/2.87 (m+m, 2H), 2.85 (s, 3H), 2.14 (s, 3H), 2.12 (m, 2H), 1.41 (s, 9H), 0.8 (s, 9H); $^{13}$C NMR (125 MHz, DMSO-d$_6$) δ ppm 163.0, 156.0, 151.9, 151.6, 151.5, 151.4, 147.5, 142.2, 137.0, 135.6/135.5, 135.0, 133.2/133.1, 130.6/130.5, 129.1, 128.4/128.3, 126.8, 119.4, 115.4, 114.8, 85.3, 82.5, 79.8, 68.3, 63.1, 52.0, 51.8, 38.5, 33.8, 32.6, 30.7, 28.5, 26.8, 23.1, 19.1, 15.5; HRMS-ESI (m/z): [M+H]+ calcd for C$_{47}$H$_{54}$ClFN$_5$O$_6$SSi: 898.3231, found 898.3238.

Step D: methyl 2-[3-(1,3-benzothiazol-2-ylamino)-6-[tert-butyl(diphenyl)silyl]oxy-4-methyl-6,7-dihydro-5H-pyrido[2,3-c]pyridazin-8-yl]-5-[3-[4-[3-[tert-butoxycarbonyl(methyl)amino]prop-1-ynyl]-2-fluoro-phenoxy]propyl]thiazole-4-carboxylate (enantiopure, from Enantiomer 2 of Preparation 2b, Step A)

A 4 mL oven-dried vial equipped with a PTFE-coated magnetic stir bar was charged with 179 mg of the product from Step C (0.2 mmol, 1.0 eq.), 60 mg 1,3-benzothiazol- 2-amine (0.4 mmol, 2.0 eq.) and 104 uL DIPEA (0.6 mmol, 3 equiv) dissolved in 1 mL dry DMF. Resulting mixture was flushed with nitrogen, and then 18 mg Pd$_2$(dba)$_3$ (0.02 mmol, 0.1 eq.) and 23 mg XantPhos (0.04 mmol, 0.2 eq.) were added. The reaction mixture was then warmed up to 140° C. and stirred at that temperature for 30 min, when the reaction reached complete conversion. The reaction mixture was directly injected onto a preconditioned silica gel column, and then it was purified via flash chromatography using heptane and EtOAc as eluents to give 50 mg of the desired product (24% Yield).

Step E: 2-[3-(1,3-Benzothiazol-2-ylamino)-6-hydroxy-4-methyl-6,7-dihydro-5H-pyrido[2,3-c]pyridazin-8-yl]-5-[3-[2-fluoro-4-[3-(methylamino)prop-1-ynyl]phenoxy]propyl]thiazole-4-carboxylic acid (enantiopure, from Enantiomer 2 of Preparation 2b, Step A)

Using Deprotection and Hydrolysis General Procedure starting from the product from Step D as the appropriate methyl ester, the desired product was obtained.

HRMS-ESI (m/z): [M+H]+ calcd for C$_{32}$H$_{31}$FN$_7$O$_4$S$_2$: 660.1857, found 660.1847.

Example 39: 2-[(6R)-3-[(1,3-Benzothiazol-2-yl)amino]-4-methyl-6-{[2-(methylamino)ethyl]amino}-5H,6H,7H,8H-pyrido[2,3-c]pyridazin-8-yl]-5-(3-{4-[3-(dimethylamino)propyl]-2-fluorophenoxy}propyl)-1,3-thiazole-4-carboxylic acid Step A: tert-butyl (4R)-4-(2-hydroxyethyl)-2,2-dimethyl-1,3-oxazolidine-3-carboxylate To a solution of tert-butyl N-[(2R)-1,4-dihydroxybutan-2-yl]carbamate (10.5 g, 51.2 mmol, 1 eq) in dichloromethane (110 mL) was added 2,2-dimethoxypropane (12.5 mL, 102 mmol, 2 eq) and p-toluenesulfonic acid monohydrate (0.51 mL, 5.12 mmol, 0.1 eq) and the mixture was stirred at ambient temperature overnight. The reaction was quenched with 0.2N aqueous sodium hydroxide (50 mL) and the organic phase was dried (PTFE phase separator) and concentrated in vacuo. Purification by automated flash column chromatography (CombiFlash Rf, 220 g RediSep™ silica cartridge) eluting with a gradient of 0-60% ethyl acetate in iso-heptane afforded the desired product as a white solid (5.13 g, 20.9 mmol, 41%).

$^1$H NMR (400 MHz, DMSO-d6) δ 4.49-4.40 (m, 1H), 3.92-3.82 (m, 2H), 3.79 (d, J=7.8 Hz, 1H), 3.48-3.39 (m, 2H), 1.87-1.69 (m, 1H), 1.66-1.50 (m, 1H), 1.47 (s, 3H), 1.42 (s, 12H).

Step B: tert-butyl (4R)-2,2-dimethyl-4-(2-oxoethyl)-1,3-oxazolidine-3-carboxylate A solution of the product from Step A (5.13 g, 20.9 mmol, 1 eq) in dichloromethane (100 mL) was cooled to 0° C. Dess-Martin periodinane (9.31 g, 22 mmol, 1.05 eq) was added and the mixture was stirred at ambient temperature for 2.5 h. The reaction was partitioned between dichloromethane and saturated aqueous sodium bicarbonate, and the organic phase was dried (PTFE phase separator) and concentrated in vacuo. Purification by automated flash column chromatography (CombiFlash Rf, 220 g RediSep™ silica cartridge) eluting with a gradient of 0-40% ethyl acetate in iso-heptane afforded the desired product as a clear oil (3.23 g, 13.3 mmol, 64%).

$^1$H NMR (400 MHz, DMSO-d6) δ 9.65 (d, J=6.7 Hz, 2H), 4.22 (t, J=6.0 Hz, 2H), 4.09-3.98 (m, 1H), 3.71 (t, J=9.0 Hz, 1H), 2.76-2.61 (m, 2H), 1.48 (s, 3H), 1.40 (d, J=8.1 Hz, 12H).

Step C: tert-butyl (4R)-4-(3,3-dibromoprop-2-en-1-yl)-2,2-dimethyl-1,3-oxazolidine-3-carboxylate To a solution of tetrabromomethane (4.04 mL, 39.8 mmol, 3 eq) in dichloromethane (65 mL) was added a solution of triphenylphosphine (20.9 g, 79.7 mmol, 6 eq) in dichloromethane (100 mL) and the mixture was stirred for 10 min. To a solution of the product from Step B (3.23 g, 13.3 mmol, 1 eq) in dichloromethane (60 mL) was added triethylamine (16.6 mL, 120 mmol, 9 eq) and the mixture was cooled to 0° C. The first solution was added portionwise, and the resultant mixture was stirred at 0° C. for 2 h. The reaction was partitioned between dichloromethane and saturated aqueous sodium bicarbonate and the organic phase was washed with brine, dried (PTFE phase separator) and concentrated in vacuo. The residue was triturated with chilled diethyl ether, the solids were collected by filtration and washed with diethyl ether. Purification by automated flash column chromatography (CombiFlash Rf, 120 g RediSep™ silica cartridge) eluting with a gradient of 0-15% ethyl acetate in iso-heptane afforded the desired product as a clear oil (1.77 g, 4.43 mmol, 33%).

$^1$H NMR (400 MHz, DMSO-d6) δ 6.61 (t, J=7.5 Hz, 1H), 4.08-3.87 (m, 2H), 3.83-3.70 (m, 2H), 2.45-2.28 (m, 2H), 1.50 (s, 3H), 1.41 (d, 12H).

Step D: tert-butyl (4R)-4-(but-2-yn-1-yl)-2,2-dimethyl-1,3-oxazolidine-3-carboxylate To a solution of the product from Step C (1.77 g, 4.43 mmol, 1 eq) in tetrahydrofuran (40 mL), cooled to −78° C., was added n-butyllithium (2.5M in hexanes; 5.32 mL, 13.3 mmol, 3 eq) and the mixture was stirred at this temperature for 1 h. Iodomethane (1.38 mL, 22.2 mmol, 5 eq) was added and the mixture was allowed to warm to ambient temperature and stir overnight. The reaction was partitioned between ethyl acetate and saturated aqueous ammonium chloride, and the organic phase was dried (magnesium sulfate) and concentrated in vacuo. Purification by automated flash column chromatography (CombiFlash Rf, 24 g RediSep™ silica cartridge) eluting with a gradient of 0-15% ethyl acetate in iso-heptane afforded the desired product as a clear oil (1.04 g, 4.11 mmol, 93%).

$^1$H NMR (400 MHz, DMSO-d6) δ 4.02-3.92 (m, 1H), 3.90-3.75 (m, 2H), 2.46 (d, J=15.8 Hz, 1H), 2.37-2.20 (m, 1H), 1.75 (t, J=2.6 Hz, 3H), 1.48 (s, 3H), 1.41 (dd, J=8.2, 3.8 Hz, 12H).

Step E: tert-butyl N-[(2R)-1-hydroxyhex-4-yn-2-yl] carbamate

To a solution of the product of Step D (1.04 g, 4.11 mmol, 1 eq) in methanol (30 mL) was added p-toluenesulfonic acid monohydrate (0.08 mL, 0.82 mmol, 0.2 eq) and the mixture was stirred at ambient temperature overnight. The reaction was partitioned between ethyl acetate and saturated aqueous sodium bicarbonate, and the organic phase was dried (magnesium sulfate) and concentrated in vacuo. Purification by automated flash column chromatography (CombiFlash Rf, 12 g RediSep™ silica cartridge) eluting with a gradient of 0-60% ethyl acetate in iso-heptane afforded the desired product as a clear oil (724 mg, 3.39 mmol, 83%).

$^1$H NMR (400 MHz, DMSO-d6) δ 6.54 (d, J=8.3 Hz, 1H), 4.67 (t, J=5.7 Hz, 1H), 3.53-3.40 (m, 1H), 3.39-3.26 (m, 2H), 2.38-2.09 (m, 2H), 1.73 (t, J=2.6 Hz, 3H), 1.39 (s, 9H).

Step F: tert-butyl N-[(2R)-1-[(tert-butyldiphenylsilyl)oxy]hex-4-yn-2-yl]carbamate To a solution of the product from Step E (724 mg, 3.39 mmol, 1 eq) in dichloromethane (30 mL) was added imidazole (0.45 mL, 6.79 mmol, 2 eq) and the mixture was cooled to 0° C. then tert-butyl(chloro)diphenylsilane (0.93 mL, 3.56 mmol, 1.05 eq) was added and the mixture was stirred at ambient temperature overnight. The reaction was partitioned between dichloromethane and saturated aqueous ammonium chloride, and the organic phase was separated (PTFE phase separator) and concentrated in vacuo. Purification by automated flash column chromatography (CombiFlash Rf, 12 g RediSep™ silica cartridge) eluting with a gradient of 0-8% ethyl acetate in iso-heptane afforded the desired product as a clear oil (1.67 g, 3.7 mmol, 109%).

LC/MS ($C_{27}H_{37}NO_3Si$) 352 [M-Boc]+; RT 1.28 (LCMS-V-B2)

$^1$H NMR (400 MHz, DMSO-d6) δ 7.73-7.59 (m, 4H), 7.52-7.35 (m, 6H), 3.67-3.57 (m, 2H), 2.46-2.14 (m, 2H), 1.70 (t, J=2.5 Hz, 3H), 1.39 (s, 9H), 1.37-1.29 (m, 1H), 1.00 (s, 9H).

Step G: {[(2R)-2-aminohex-4-yn-1-yl]oxy}(tert-butyl)diphenylsilane

To a solution of the product from Step F (1.67 g, 3.7 mmol, 1 eq) in dichloromethane (35 mL), cooled to 0° C., was added trifluoroacetic acid (8.07 mL, 105 mmol, 28.5 eq) and the mixture was stirred at ambient temperature for 1 h. The reaction was partitioned between dichloromethane and 1N aqueous sodium hydroxide (120 mL), and the organic phase was separated (PTFE phase separator) and concentrated in vacuo. Purification by automated flash column chromatography (CombiFlash Rf, 24 g RediSep™ silica cartridge) eluting with a gradient of 0-70% ethyl acetate in iso-heptane afforded the desired product as a clear oil (997 mg, 2.84 mmol, 77%).

$^1$H NMR (400 MHz, DMSO-d6) δ 7.68-7.61 (m, 4H), 7.53-7.40 (m, 6H), 3.54 (d, J=5.7 Hz, 2H), 2.92-2.81 (m, 1H), 2.38-2.14 (m, 2H), 1.73 (t, J=2.6 Hz, 3H), 1.62-1.44 (m, 2H), 1.01 (s, 9H).

Step H: benzyl N-(2-{[(2R)-1-[(tert-butyldiphenyl-silyl)oxy]hex-4-yn-2-yl]amino}ethyl)-N-methylcar-bamate To a solution of the product of Step G (997 mg, 2.84 mmol, 1 eq) in tetrahydrofuran (24 mL) was added a solution of benzyl N-methyl-N-(2-oxoethyl)carbamate (647 mg, 3.12 mmol, 1.1 eq) in tetrahydrofuran (11.9 mL) and the mixture was cooled to 0° C. Sodium triacetoxyborohydride (1.8 g, 8.51 mmol, 3 eq) was added and the mixture was allowed to warm to ambient temperature and stir for 4 h. The reaction was partitioned between ethyl acetate and 1N aqueous sodium hydroxide, and the organic phase was dried (magnesium sulfate) and concentrated in vacuo. Purification by automated flash column chromatography (CombiFlash Rf, 24 g RediSep™ silica cartridge) eluting with a gradient of 0-40% ethyl acetate in iso-heptane afforded the desired product as a clear oil (1.46 g, 2.69 mmol, 95%).

LC/MS ($C_{33}H_{42}N_2O_3Si$) 543 [M+H]$^+$; RT 2.34 (LCMS-V-C)

$^1$H NMR (400 MHz, DMSO-d6) δ 7.63 (d, J=6.7 Hz, 4H), 7.52-7.39 (m, 6H), 7.37-7.24 (m, 5H), 5.03 (d, J=2.6 Hz, 2H), 3.64-3.52 (m, 2H), 3.28 (t, J=6.5 Hz, 2H), 2.86 (d, J=14.2 Hz, 3H), 2.74-2.60 (m, 2H), 2.35-2.23 (m, 2H), 1.68 (t, 3H), 1.63-1.50 (m, 1H), 0.99 (s, 9H).

Step I: benzyl N-(2-{[(benzyloxy)carbonyl](methyl) amino}ethyl)-N-[(2R)-1-[(tert-butyldiphenylsilyl) oxy]hex-4-yn-2-yl]carbamate To a solution of the product from Step H (1.46 g, 2.69 mmol, 1 eq) in ethyl acetate (30 mL) was added a solution of sodium bicarbonate (497 mg, 5.92 mmol, 2.2 eq) in water (8.5 mL) and the mixture was cooled to 0° C. then benzyl chloroformate (0.46 mL, 3.23 mmol, 1.2 eq) was added and the mixture was allowed to warm to ambient temperature and stir overnight. The reaction was partitioned between ethyl acetate and saturated aqueous sodium bicarbonate, and the organic phase was dried (magnesium sulfate) and concentrated in vacuo. Purification by automated flash column chromatography (CombiFlash Rf, 24 g RediSep™ silica cartridge) eluting with a gradient of 0-30% ethyl acetate in iso-heptane afforded the desired product as a clear oil (1.75 g, 2.59 mmol, 96%).

LC/MS ($C_{41}H_{48}N_2O_5Si$) 677 [M+H]$^+$; RT 1.32 (LCMS-V-B2)

$^1$H NMR (400 MHz, DMSO-d6) δ 7.67-7.50 (m, 4H), 7.49-7.22 (m, 16H), 5.16-4.90 (m, 4H), 4.19-4.07 (m, 1H), 3.79-3.51 (m, 2H), 3.44-3.34 (m, 2H), 3.28-3.15 (m, 2H), 2.92-2.71 (m, 3H), 2.45-2.17 (m, 2H), 1.64 (s, 3H), 0.95 (d, J=4.4 Hz, 9H).

Step J: benzyl N-(2-{[(benzyloxy)carbonyl](methyl) amino}ethyl)-N-[(2R)-1-[(tert-butyldiphenylsilyl) oxy]-3-(3,6-dichloro-5-methylpyridazin-4-yl)pro-pan-2-yl]carbamate To a solution of the product from Step I (1.75 g, 2.59 mmol, 1 eq) in toluene (35 mL) was added 3,6-dichloro-1, 2,4,5-tetrazine (1.56 g, 10.3 mmol, 4 eq) and the mixture was heated at 150° C. in a sealed flask for 3 days. The reaction was concentrated in vacuo and purification by automated flash column chromatography (CombiFlash Rf, 40 g RediSep™ silica cartridge) eluting with a gradient of 0-40% ethyl acetate in iso-heptane afforded the crude desired product as a red gum (1.2 g, 1.5 mmol, 58%) that was used directly in the subsequent step without further purification.

LC/MS ($C_{43}H_{48}N_4O_5SiCl_2$) 799 [M+H]$^+$; RT 1.32 (LCMS-V-B2) Step K: benzyl N-(2-{[(benzyloxy)carbonyl] (methyl)amino}ethyl)-N-[(2R)-1-(3,6-dichloro-5-meth-ylpyridazin-4-yl)-3-hydroxypropan-2-yl]carbamate To a solution of the product from Step J (1.2 g, 1.5 mmol, 1 eq) in methanol (55 mL) was added acetyl chloride (0.54 mL, 7.5 mmol, 5 eq) and the mixture was stirred at ambient temperature for 3 days. The reaction was concentrated in vacuo then partitioned between dichloromethane and water, and the organic phase was separated (PTFE phase separator) and concentrated in vacuo. Purification by automated flash column chromatography (CombiFlash Rf, 24 g RediSep™ silica cartridge) eluting with a gradient of 0-10% methanol in dichloromethane afforded the crude desired product as an orange gum (846 mg, 1.51 mmol, 100%) that was used directly in the subsequent step without further purification.

LC/MS ($C_{27}H_{30}Cl_2N_4O_5$) 561 [M+H]$^+$; RT 0.80 (LCMS-V-B2)

Step L: methyl 2-{[(tert-butoxy)carbonyl]amino}-5-(3-{4-[3-(dimethylamino)propyl]-2-fluorophenoxy}propyl)-1,3-thiazole-4-carboxylate To a solution of the product from Preparation 4d (652 mg, 3.31 mmol, 1.2 eq) in dimethylformamide (15 mL), cooled to 0° C., was added sodium hydride (60% dispersion; 264 mg, 6.61 mmol, 2.4 eq) and the mixture was stirred for 30 min. A solution of the product from Preparation 1d (1.17 g, 2.75 mmol, 1 eq) in dimethylformamide (15 mL) was added and the mixture was stirred at ambient temperature for 1 h. The reaction was partitioned between ethyl acetate and brine, and the organic phase was dried (magnesium sulfate) and concentrated in vacuo. Purification by automated flash column chromatography (CombiFlash Rf, 40 g RediSep™ silica cartridge) eluting with a gradient of 0-16% methanol in dichloromethane afforded the desired product as a clear gum (431 mg, 0.87 mmol, 32%).

LC/MS ($C_{24}H_{34}FN_3O_5S$) 496 [M+H]$^+$; RT 1.81 (LCMS-V-C)

$^1$H NMR (400 MHz, DMSO-d6) δ 11.64 (br s, 1H), 7.13-7.00 (m, 2H), 6.97-6.89 (m, 1H), 4.04 (t, J=6.2 Hz, 2H), 3.75 (s, 3H), 3.28-3.15 (m, 2H), 2.58-2.50 (m, 2H), 2.18 (t, J=7.2 Hz, 2H), 2.12 (s, 6H), 2.12-2.00 (m, 2H), 1.71-1.59 (m, 2H), 1.47 (s, 9H).

Step M: methyl 2-{[(2R)-2-{[(benzyloxy)carbonyl] (2-{[(benzyloxy)carbonyl](methyl)amino}ethyl) amino}-3-(3,6-dichloro-5-methylpyridazin-4-yl) propyl][(tert-butoxy)carbonyl]amino}-5-(3-{4-[3-(dimethylamino)propyl]-2-fluorophenoxy}propyl)-1, 3-thiazole-4-carboxylate To a solution of the product from Step K (422 mg, 0.75 mmol, 1 eq) in toluene (25 mL) was added the product from Step L (431 mg, 0.87 mmol, 1.16 eq), followed by triph-enylphosphine (394 mg, 1.5 mmol, 2 eq) and di-tert-butyl azodicarboxylate (346 mg, 1.5 mmol, 2 eq) and the mixture was stirred at ambient temperature for 3 h. The reaction was partitioned between dichloromethane and water, and the organic phase was washed with brine, separated (PTFE phase separator) and concentrated in vacuo. Purification by automated flash column chromatography (CombiFlash Rf, 24 g RediSep™ silica cartridge) eluting with a gradient of 0-10% methanol in dichloromethane afforded the desired product as an orange gum (517 mg, 0.5 mmol, 66%).

LC/MS $(C_{51}H_{62}Cl_2FN_7O_9S)$ 1040 $[M+H]^+$; RT 2.48 (LCMS-V-C)

$^1$H NMR (400 MHz, DMSO-d6) δ 7.31 (s, 27H), 7.24 (s, 2H), 7.11-6.95 (m, 8H), 6.90 (d, J=8.6 Hz, 3H), 5.76 (s, 3H), 5.22 (s, 1H), 5.05 (s, 1H), 4.97 (s, 4H), 4.78 (s, 1H), 4.50 (d, J=12.9 Hz, 1H), 4.00 (s, 7H), 3.69 (s, 6H), 2.94 (s, 3H), 2.82 (s, 3H), 2.76 (s, 1H), 2.37 (s, 1H), 2.30 (s, 1H), 2.20 (s, 7H), 2.13 (s, 17H), 2.09 (s, 1H), 2.05 (s, 3H), 1.96 (s, 5H), 1.64 (d, J=8.1 Hz, 8H), 1.50 (s, 5H), 1.43 (d, J=10.5 Hz, 6H).

Step N: methyl 2-{[(2R)-2-{[(benzyloxy)carbonyl] (2-{[(benzyloxy)carbonyl](methyl)amino}ethyl) amino}-3-(3,6-dichloro-5-methylpyridazin-4-yl) propyl]amino}-5-(3-{4-[3-(dimethylamino)propyl]- 2-fluorophenoxy}propyl)-1,3-thiazole-4-carboxylate To a solution of the product from Step M (517 mg, 0.5 mmol, 1 eq) in dichloromethane (10 mL) was added trifluoroacetic acid (4 mL, 52.2 mmol, 105 eq) and the mixture was stirred at ambient temperature for 1 h. The reaction was diluted with dichloromethane and cooled to 0° C. and quenched with 1N aqueous sodium hydroxide (60 mL), and the organic phase was washed with brine, separated (PTFE phase separator) and concentrated in vacuo. Purification by automated flash column chromatography (CombiFlash Rf, 12 g RediSep™ silica cartridge) eluting with a gradient of 0-8% 1N methanolic ammonia in dichloromethane afforded the desired product as an orange gum (461 mg, 0.49 mmol, 99%).

LC/MS $(C_{46}H_{54}Cl_2FN_7O_7S)$ 939 $[M+H]^+$; RT 2.16 (LCMS-V-C)

$^1$H NMR (400 MHz, DMSO-d6) δ 7.88 (s, 1H), 7.48-7.18 (m, 10H), 7.11-6.88 (m, 3H), 5.12-4.82 (m, 4H), 4.06-3.90 (m, 2H), 3.76-3.58 (m, 4H), 3.53-3.36 (m, 2H), 3.29-3.21 (m, 2H), 3.17-3.03 (m, 4H), 3.01-2.81 (m, 3H), 2.79-2.69 (m, 2H), 2.36-2.24 (m, 4H), 2.18 (t, 2H), 2.11 (s, 6H), 2.00-1.93 (m, 3H), 1.64 (p, J=7.3 Hz, 2H).

Step O: methyl 2-[(6R)-6-{[(benzyloxy)carbonyl] (2-{[(benzyloxy)carbonyl](methyl)amino}ethyl) amino}-3-chloro-4-methyl-5H,6H,7H,8H-pyrido[2, 3-c]pyridazin-8-yl]-5-(3-{4-[3-(dimethylamino) propyl]-2-fluorophenoxy}propyl)-1,3-thiazole-4- carboxylate To a solution of the product from Step N (461 mg, 0.49 mmol, 1 eq) in 1,4-dioxane (10 mL) was added cesium carbonate (320 mg, 0.98 mmol, 2 eq) and NN-diisopropylethylamine (171 μL, 0.98 mmol, 2 eq). The mixture was sparged with nitrogen (10 min) then bis(di-tert-butyl(4-dimethylaminophenyl)phosphine)dichloropalladium(II) (34.8 mg, 0.05 mmol, 0.1 eq) was added and the mixture was heated at 80° C. for 3 h under microwave irradiation. The reaction was partitioned between ethyl acetate and water, and the organic phase was washed with brine, dried (magnesium sulfate) and concentrated in vacuo. Purification by automated flash column chromatography (CombiFlash Rf, 12 g RediSep™ silica cartridge) eluting with a gradient of 0-12% methanol in dichloromethane afforded the desired product as an orange gum (285 mg, 0.32 mmol, 64%).

LC/MS $(C_{46}H_{53}ClFN_7O_7S)$ 902 $[M+H]^+$; RT 2.32 (LCMS-V-C)

$^1$H NMR (400 MHz, DMSO-d6) δ 7.52-7.21 (m, 9H), 7.15-7.00 (m, 4H), 5.21-4.91 (m, 4H), 4.84-4.63 (m, 1H), 4.39-4.22 (m, 1H), 4.07 (t, J=6.2 Hz, 2H), 4.05-3.91 (m, 1H), 3.77 (s, 3H), 3.56-3.43 (m, 2H), 3.41-3.36 (m, 2H), 3.31 (s, 2H), 3.30-3.23 (m, 2H), 3.01-2.75 (m, 4H), 2.28 (s, 2H), 2.18 (d, J=6.9 Hz, 4H), 2.11 (s, 6H), 1.64 (p, J=7.4 Hz, 2H).

Step P: methyl 2-[(6R)-3-[(1,3-benzothiazol-2-yl) amino]-6-{[(benzyloxy)carbonyl](2-{[(benzyloxy) carbonyl](methyl)amino}ethyl)amino}-4-methyl-5H, 6H,7H,8H-pyrido[2,3-c]pyridazin-8-yl]-5-(3-{4-[3- (dimethylamino)propyl]-2-fluorophenoxy}propyl)-1, 3-thiazole-4-carboxylate To a solution of the product from Step 0 (117 mg, 0.13 mmol, 1 eq) in 1,4-dioxane (5 mL) was added 2-aminobenzothiazole (39 mg, 0.26 mmol, 2 eq), NN-diisopropylethylamine (67.9 μL, 0.39 mmol, 3 eq) and Josiphos Pd G3 (24 mg, 0.03 mmol, 0.2 eq) and the mixture was sparged with nitrogen (10 min) then heated at 140° C. for 3 h under microwave irradiation. The reaction was partitioned between ethyl acetate and water, and the organic phase was washed with brine, dried (magnesium sulfate) and concentrated in vacuo. Purification by reverse phase automated flash chromatography (CombiFlash Rf, C18 13 g RediSep column) eluting with a gradient of 5-95% acetonitrile in water afforded the crude desired product as a yellow gum (23 mg, 0.02 mmol, 17%) that was used directly in the subsequent step without further purification.

LC/MS $(C_{53}H_{58}FN_9O_7S_2)$ 1017 $[M+H]^+$; RT 2.43 (LCMS-V-C)

Step O: 2-[(6R)-3-[(1,3-benzothiazol-2-yl)amino]-4- methyl-6-{[2-(methylamino)ethyl]amino}-5H,6H, 7H,8H-pyrido[2,3-c]pyridazin-8-yl]-5-(3-{4-[3-(di- methylamino)propyl]-2-fluorophenoxy}propyl)-1,3- thiazole-4-carboxylic acid To a solution of the product from Step P (23 mg, 0.02 mmol, 1 eq) in 1,4-dioxane (0.5 mL) was added concentrated hydrochloric acid (1.5 mL) and the mixture was stirred at ambient temperature for 3 days. The reaction was concentrated in vacuo and purification by automated flash column chromatography (CombiFlash Rf, 4 g RediSep™ silica cartridge) eluting with a gradient of 0-30% 7N methanolic ammonia in dichloromethane gave a solid that was triturated with diethyl ether, filtered and dried under vacuum to afford the desired solid as a yellow solid (9.5 mg, 0.01 mmol, 57%).

HRMS-ESI (m/z) [M+H]+ calcd for $C_{36}H_{45}FN_9O_3S_2$: 734.3071, found 734.3096.

Example 40: 2-{3-[(1,3-Benzothiazol-2-yl)amino]-4-methyl-5H,6H,7H,8H-pyrido[2,3-c]pyridazin-8-yl}-5-(3-{4-[3-(dimethylamino)prop-1-yn-1-yl]-2-(trifluoromethyl)phenoxy}propyl)-1,3-thiazole-4-carboxylic acid Step A: ethyl 5-{3-[4-bromo-2-(trifluoromethyl)phenoxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate Diisopropyl azodicarboxylate (0.09 ml, 0.47 mmol, 1.5 eq) was added dropwise to a solution of the product from Preparation 3g (200 mg, 0.31 mmol, 1 eq), 4-bromo-2-(trifluoromethyl)phenol (100 mg, 0.41 mmol, 1.33 eq) and triphenylphosphine (123 mg, 0.47 mmol, 1.5 eq) in toluene (10 mL). The mixture was stirred at ambient temperature for 18 h then concentrated in vacuo. Purification by flash column chromatography (20 g silica) eluting with a gradient of 0-25% ethyl acetate in iso-heptane afforded the desired product as a yellow solid (265 mg, 0.26 mmol, 84%).

LC/MS ($C_{37}H_{42}BrF_3N_6O_4SiS_2$) 863 [M+H]$^+$; RT 1.91 (LCMS-V-B1)

$^1$H NMR (400 MHz, CDCl$_3$) δ 7.71-7.64 (m, 1H), 7.62-7.52 (m, 2H), 7.39-7.34 (m, 2H), 7.24-7.17 (m, 1H), 6.88 (d, J=8.9 Hz, 1H), 5.84 (s, 2H), 4.50-4.30 (m, 4H), 4.12 (t, J=6.3 Hz, 2H), 3.82-3.68 (m, 2H), 3.39-3.30 (m, 2H), 2.87 (t, J=6.4 Hz, 2H), 2.38 (s, 3H), 2.33-2.22 (m, 2H), 2.18-2.07 (m, 2H), 1.40 (t, J=7.1 Hz, 3H), 1.01-0.90 (m, 2H), −0.08 (s, 9H).

Step B: ethyl 5-(3-{4-[3-(dimethylamino)prop-1-yn-1-yl]-2-(trifluoromethyl)phenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Step A (265 mg, 0.26 mmol, 1 eq) in 2-methyltetrahydrofuran (10 mL) was added copper(I) iodide (9.93 mg, 0.05 mmol, 0.2 eq) and tetrakis(triphenylphosphine)palladium(0) (30.1 mg, 0.03 mmol, 0.1 eq) and dimethyl(prop-2-yn-1-yl)amine (0.1 ml, 0.93 mmol, 3.5 eq). NN-diisopropylethylamine (0.14 ml, 0.78 mmol, 3 eq) was added and the mixture was heated at 75° C. for 96 h. The reaction was allowed to cool to ambient temperature and concentrated in vacuo. Purification by flash column chromatography (20 g silica) eluting with a gradient of 0-100% ethyl acetate in iso-heptane afforded the desired product as a dark yellow gum (170 mg, 0.2 mmol, 75%).

LC/MS ($C_{42}H_{50}F_3N_7O_4SiS_2$) 866 [M+H]$^+$; RT 1.57 (LCMS-V-B1)

$^1$H NMR (400 MHz, CDCl$_3$) δ 7.66 (d, J=2.3 Hz, 1H), 7.59 (dt, J=7.7, 0.9 Hz, 1H), 7.54-7.50 (m, 1H), 7.40-7.31 (m, 2H), 7.23-7.17 (m, 1H), 6.92 (d, J=8.6 Hz, 1H), 5.84 (s, 2H), 4.49-4.32 (m, 4H), 4.18-4.12 (m, 2H), 3.80-3.66 (m, 2H), 3.42 (s, 2H), 3.35 (dd, J=8.5, 6.6 Hz, 2H), 2.87 (t, J=6.4 Hz, 2H), 2.38 (s, 3H), 2.34 (s, 6H), 2.31-2.25 (m, 2H), 2.17-2.08 (m, 2H), 1.40 (t, J=7.1 Hz, 3H), 0.99-0.90 (m, 2H), −0.07 (s, 9H).

Step C: 2-{3-[(1,3-benzothiazol-2-yl)amino]-4-methyl-5H,6H,7H,8H-pyrido[2,3-c]pyridazin-8-yl}-5-(3-{4-[3-(dimethylamino)prop-1-yn-1-yl]-2-(trifluoromethyl)phenoxy}propyl)-1,3-thiazole-4-carboxylic acid To a solution of the product from Step B (160 mg, 0.18 mmol, 1 eq) in 1,4-dioxane (4.5 mL) at 0° C. was added trifluoroacetic acid (0.5 ml, 6.47 mmol, 35 eq) and the mixture was stirred for 36 h. The reaction was diluted with dichloromethane (50 mL) and successively washed with 1M aqueous ammonia (20 mL), water (20 mL) and brine (20 mL), dried magnesium sulfate and concentrated in vacuo. To a suspension of the crude material in a mixture of water (1.5 mL) and tetrahydrofuran (1.5 mL) was added lithium hydroxide monohydrate (23.3 mg, 0.55 mmol, 3 eq) and the mixture was stirred for 72 h at ambient temperature. Water (5 mL) was added and the suspension was neutralised with acetic acid. The solids were collected by filtration, washed with water (10 mL) and dried under vacuum to afford the desired product as a yellow solid (75 mg, 0.11 mmol, 57%).

HRMS-ESI (m/z) [M+H]+ calcd for $C_{34}H_{33}F_3N_7O_3S_2$: 708.2038, found 708.2058

Example 41: 2-[3-(1,3-Benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)but-1-ynyl]phenoxy]propyl]thiazole-4-carboxylic acid Step A: methyl 2-(3-chloro-4-methyl-6,7-dihydro-5H-pyrido[2,3-c]pyridazin-8-yl)-5-[3-[2-fluoro-4-[3-(4-methylpiperazin-1-yl)but-1-ynyl]phenoxy]propyl]thiazole-4-carboxylate A 24 mL oven-dried vial was equipped with a PTFE-coated magnetic stirring bar, and was charged with 250 mg 1-methylpiperazine (2.5 mmol, 5.0 eq.) dissolved in 2.5 mL dry THF Then 133 mg 3-bromobut-1-yne (1.0 mmol, 2.0 equiv) was added dropwise via syringe over a period of 5 minutes, and stirred at that temperature for 30 min. To the resulting mixture 301 mg of Preparation 3a (0.50 mmol, 1.0 eq.), 18.15 mg Pd(PPh₃)₂Cl₂ (0.025 mmol, 0.05 eq.) and 4.76 CuI (0.025 mmol, 0.05 eq.) were added, then it was heated to 60° C. and stirred for 2 h at that temperature. The reaction reached complete conversion. Celite was added to the reaction mixture and the volatiles were removed under reduced pressure. Then it was purified via flash chromatography using DCM and MeOH (1.2% NH₃) as eluents to give 300 mg (95% Yield) of the desired product.

Step B: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)but-1-ynyl]phenoxy]propyl]thiazole-4-carboxylate Using Buchwald General Procedure II starting from 300 mg of the product from Step A (0.47 mmol, 1.0 eq.) and 140 mg 1,3-benzothiazol-2-amine (0.94 mmol, 2.0 eq.), 150 mg (42%) mg of the desired product was obtained.

Step C: 2-[3-(1,3-benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)but-1-ynyl]phenoxy]propyl]thiazole-4-carboxylic acid Using Hydrolysis General Procedure starting from the product from Step B as the appropriate methyl ester, the desired product was obtained.

$^1$H NMR (500 MHz, DMSO-d₆) δ ppm 7.87 (d, 1H), 7.49 (d, 1H), 7.36 (t, 1H), 7.26 (dd, 1H), 7.2 (t, 1H), 7.16 (dd, 1H), 7.13 (t, 1H), 4.27 (t, 2H), 4.12 (t, 2H), 3.65 (q, 1H), 3.27 (t, 2H), 2.87 (t, 2H), 2.62-2.21 (brm, 8H), 2.14 (s, 3H), 2.13 (qn, 2H), 2.04 (qn, 2H), 1.33 (s, 3H), 1.25 (d, 3H); $^{13}$C NMR (125 MHz, DMSO-d₆) δ ppm 164.3, 155.4, 151.5, 151.4, 148.6, 147.2, 145.1, 140.2, 136.3, 130.2, 129.0, 129.0, 127.6, 126.5, 122.5, 122.3, 119.2, 116.4, 115.5, 115.4, 88.4, 84.1, 68.5, 51.7, 46.3, 46.1, 31, 23.9, 23.0, 20.3, 19.6, 12.9;

HRMS-ESI (m/z) [M+H]+ calcd for C₃₇H₄₀FN₈O₃S₂: 727.2649, found 727.2630

Example 42: 2-[3-(1,3-Benzothiazol-2-ylamino)-4-methyl-6,7-dihydro-5H-pyrido[2,3-c]pyridazin-8-yl]-5-[3-[2-fluoro-4-(3-pyrrolidin-1-ylprop-1-ynyl)phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[2-fluoro-4-(3-pyrrolidin-1-ylprop-1-ynyl)phenoxy]propyl]thiazole-4-carboxylate Using Propargylic amine preparation General Procedure starting from 258 mg of Preparation 3d (0.40 mmol, 1 eq.) as the appropriate propargylic alcohol and pyrrolidine (20 eq, 670 mg), 120 mg of the desired product (43%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-(3-pyrrolidin-1-ylprop-1-ynyl)phenoxy]propyl]thiazole-4-carboxylic acid Using Hydrolysis General Procedure starting from the product from Step A as the appropriate methyl ester, the desired product was obtained.

$^1$H NMR (500 MHz, DMSO-d₆) δ ppm 7.88 (d, 1H), 7.49 (d, 1H), 7.37 (t, 1H), 7.29 (dd, 1H), 7.2 (dd, 1H), 7.19 (t, 1H), 7.14 (t, 1H), 4.27 (t, 2H), 4.14 (t, 2H), 3.52 (s, 2H), 3.27 (t, 2H), 2.88 (t, 2H), 2.52 (t, 4H), 2.34 (s, 3H), 2.13 (qn, 2H), 2.04 (qn, 2H), 1.69 (t, 4H); $^{13}$C NMR (125 MHz, DMSO-d₆) δ ppm 151.5, 151.4, 148.6, 147.3, 145.1, 140.1, 136.7, 130.2, 129.0, 129.0, 127.5, 126.5, 122.5, 122.3, 119.2, 116.5, 115.5, 115.4, 85.9, 83.3, 68.6, 52.3, 46.3, 43.3, 31.1, 23.8, 23.8, 23.0, 20.4, 12.9; HRMS-ESI (m/z): [M+H]+ calcd for C₃₅H₃₅FN₇O₃S₂: 684.2221, found 684.2209.

Example 43: 2-[3-(1,3-Benzothiazol-2-ylamino)-4-methyl-6,7-dihydro-5H-pyrido[2,3-c]pyridazin-8-yl]-5-[3-[2-fluoro-4-(3-pyrrolidin-1-ylbut-1-ynyl)phenoxy]propyl]thiazole-4-carboxylic acid Step A: methyl 2-(3-chloro-4-methyl-6,7-dihydro-5H-pyrido[2,3-c]pyridazin-8-yl)-5-[3-[2-fluoro-4-(3-pyrrolidin-1-ylbut-1-ynyl)phenoxy]propyl]thiazole-4-carboxylate A 24 mL oven-dried vial was equipped with a PTFE-coated magnetic stirring bar, and was charged with 177 mg pyrrolidine (2.500 mmol, 5.0 eq.) dissolved in 2.5 mL dry THF Then 133 mg 3-bromobut-1-yne (1.0 mmol, 2.0 equiv) was added dropwise via syringe over a period of 5 minutes, and stirred at that temperature for 30 min. To the resulting mixture 301 mg of Preparation 3a (0.50 mmol, 1.0 eq.), 18.15 mg Pd(PPh$_3$)$_2$Cl$_2$ (0.025 mmol, 0.05 eq.) and 4.76 CuI (0.025 mmol, 0.05 eq.) were added, then it was heated to 60° C. and stirred for 2 h at that temperature. The reaction reached complete conversion. Celite was added to the reaction mixture and the volatiles were removed under reduced pressure. Then it was purified via flash chromatography using DCM and MeOH (1.2% NH$_3$) as eluents to give 220 mg (73% Yield) of the desired product.

$^1$H NMR (500 MHz, DMSO-d$_6$) δ ppm 7.41 (d, 1H), 7.28 (d, 1H), 7.18 (t, 1H), 4.51 (br., 1H), 4.26 (m, 2H), 4.13 (t, 2H), 3.77 (s, 3H), 3.5-2.97 (br., 4H), 3.25 (t, 2H), 2.88 (t, 2H), 2.32 (s, 3H), 2.11 (quint., 2H), 2.04 (m, 2H), 1.89 (br., 4H), 1.51 (brd., 3H); $^{13}$C NMR (125 MHz, DMSO-d$_6$) δ ppm 163.1, 129.4, 119.6, 115.4, 68.3, 52.4/50.2, 52.0, 51.7, 46.3, 30.7, 24.2, 23.6, 23.0, 19.7, 19.3, 15.7.

Step B: methyl 2-[3-(1,3-benzothiazol-2-ylamino)-4-methyl-6,7-dihydro-5H-pyrido[2,3-c]pyridazin-8-yl]-5-[3-[2-fluoro-4-(3-pyrrolidin-1-ylbut-1-ynyl)phenoxy]propyl]thiazole-4-carboxylate Using Buchwald General Procedure II starting from 220 mg of the product from Step A (0.47 mmol, 1.0 eq.) and 100 mg 1,3-benzothiazol-2-amine (0.668 mmol, 2.0 eq.), 150 mg (63% Yield) mg of the desired product was obtained.

Step C: 2-[3-(1,3-Benzothiazol-2-ylamino)-4-methyl-6,7-dihydro-5H-pyrido[2,3-c]pyridazin-8-yl]-5-[3-[2-fluoro-4-(3-pyrrolidin-1-ylbut-1-ynyl)phenoxy]propyl]thiazole-4-carboxylic acid Using Hydrolysis General Procedure starting from the product from Step B as the appropriate methyl ester, the desired product was obtained.

HRMS-ESI (m/z): [M+H]+ calcd for C$_{36}$H$_{37}$FN$_7$O$_3$S$_2$: 698.2377, found 698.2368.

Example 44: 2-{3-[(1,3-Benzothiazol-2-yl)amino]-4-methyl-5H,6H,7H,8H-pyrido[2,3-c]pyridazin-8-yl}-5-(3-{4-[2-(dimethylamino)ethoxy]phenoxy}propyl)-1,3-thiazole-4-carboxylic acid Step A: ethyl 5-(3-{4-[2-(dimethylamino)ethoxy]phenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3g (100 mg, 0.16 mmol, 1 eq) and the product from Preparation 4e (56.6 mg, 0.31 mmol, 2 eq) in tetrahydrofuran (5 mL) was added triphenylphosphine (81.9 mg, 0.31 mmol, 2 eq) and di-tert-butyl azodicarboxylate (71.9 mg, 0.31 mmol, 2 eq) and the mixture was heated at 50° C. for 8 h. The reaction was partitioned between ethyl acetate and brine, and the organic phase was dried (magnesium sulfate) and concentrated in vacuo. Purification by automated flash column chromatography (CombiFlash Rf, 4 g RediSep™ silica cartridge) eluting with a gradient of 0-11% methanol in dichloromethane afforded the desired product as a brown gum (35 mg, 0.04 mmol, 28%). LC/MS (C$_{40}$H$_{53}$N$_7$O$_5$SiS$_2$) 804 [M+H]$^+$; RT 2.72 (LCMS-V-C)

$^1$H NMR (400 MHz, DMSO-d6) δ 7.82 (dt, J=7.7, 0.9 Hz, 1H), 7.48-7.38 (m, 2H), 7.28-7.20 (m, 1H), 6.92-6.83 (m, 4H), 5.85 (s, 2H), 4.33-4.22 (m, 4H), 4.03-3.89 (m, 4H), 3.76-3.66 (m, 2H), 3.30-3.19 (m, 2H), 2.88 (t, J=6.2 Hz, 2H), 2.54 (dt, J=11.9, 5.9 Hz, 2H), 2.37 (s, 3H), 2.16 (s, 6H), 2.14-2.00 (m, 4H), 1.30 (t, J=7.1 Hz, 3H), 0.96-0.86 (m, 2H), −0.11 (s, 9H).

Step B: ethyl 2-{3-[(1,3-benzothiazol-2-yl)amino]-4-methyl-5H,6H,7H,8H-pyrido[2,3-c]pyridazin-8-yl}-5-(3-{4-[2-(dimethylamino)ethoxy]phenoxy}propyl)-1,3-thiazole-4-carboxylate To a solution of the product from Step A (35 mg, 0.04 mmol, 1 eq) in dichloromethane (2.7 mL), cooled to 0° C., was added trifluoroacetic acid (0.3 mL, 3.92 mmol, 90 eq) and the mixture was allowed to warm to ambient temperature and stir overnight. The reaction was diluted with dichloromethane, cooled to 0° C. and neutralised with aqueous ammonia, then the organic phase was separated (PTFE phase separator) and concentrated in vacuo. Purification by automated flash column chromatography (CombiFlash Rf, 4 g RediSep™ silica cartridge) eluting with a gradient of 0-10% methanol in dichloromethane afforded the desired product as a yellow solid (21 mg, 0.03 mmol, 72%).

LC/MS ($C_{34}H_{39}N_7O_4S_2$) 674 [M+H]$^+$; RT 2.12 (LCMS-V-C)

$^1$H NMR (400 MHz, DMSO-d6) δ 11.48 (br s, 1H), 7.88 (d, J=7.9 Hz, 1H), 7.50 (d, J=8.0 Hz, 1H), 7.38 (td, J=8.1, 7.7, 1.3 Hz, 1H), 7.24-7.15 (m, 1H), 6.93-6.82 (m, 4H), 5.77 (s, 1H), 4.33-4.23 (m, 4H), 4.02-3.90 (m, 4H), 3.31-3.23 (m, 2H), 2.89 (t, J=6.3 Hz, 2H), 2.58-2.51 (m, 2H), 2.35 (s, 3H), 2.17 (s, 6H), 2.13-2.01 (m, 4H), 1.31 (t, J=7.1 Hz, 3H).

Step C: 2-{3-[(1,3-benzothiazol-2-yl)amino]-4-methyl-5H,6H,7H,8H-pyrido[2,3-c]pyridazin-8-yl}-5-(3-{4-[2-(dimethylamino)ethoxy]phenoxy}propyl)-1,3-thiazole-4-carboxylic acid To a solution of the product from Step B (21 mg, 0.03 mmol, 1 eq) in 1,4-dioxane (2 mL) was added lithium hydroxide monohydrate (13.1 mg, 0.31 mmol, 10 eq) and the mixture was heated at reflux for 15 h. The reaction was allowed to cool to ambient temperature and concentrated in vacuo. Purification by automated flash column chromatography (CombiFlash Rf, 4 g RediSep™ silica cartridge) eluting with a gradient of 0-20% 7N methanolic ammonia in dichloromethane afforded the desired product as a white solid (14.6 mg, 0.02 mmol, 73%).

HRMS-ESI (m/z) [M+H]+ calcd for $C_{32}H_{36}N_7O_4S2$: 646.2270, found 646.2292 Example 45: 5-(3-{4-[3-(Azetidin-1-yl)prop-1-yn-1-yl]-2-fluorophenoxy}propyl)-2-{3-[(1,3-benzothiazol-2-yl)amino]-4-methyl-5H,6H,7H,8H-pyrido[2,3-c]pyridazin-8-yl}-1,3-thiazole-4-carboxylic acid

Step A: methyl 5-[3-[4-[3-(azetidin-1-yl)prop-1-ynyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylate Using Propargylic amine preparation General Procedure starting from 258 mg of Preparation 3d (0.40 mmol, 1 eq.) as the appropriate propargylic alcohol and azetidine (456.8 mg, 20 eq.), 36 mg of the desired product (36%) was obtained.

Step B: 5-(3-{4-[3-(azetidin-1-yl)prop-1-yn-1-yl]-2-fluorophenoxy}propyl)-2-{3-[(1,3-benzothiazol-2-yl)amino]-4-methyl-5H,6H,7H,8H-pyrido[2,3-c]pyridazin-8-yl}-1,3-thiazole-4-carboxylic acid Using Hydrolysis General Procedure starting from the product from Step A as the appropriate methyl ester, the desired product was obtained.

HRMS-ESI (m/z): [M+H]+ calcd for $C_{34}H_{33}FN_7O_3S_2$: 670.2064, found 670.2065.

Example 46: 2-[3-(1,3-Benzothiazol-2-ylamino)-4-methyl-6,7-dihydro-5H-pyrido[2,3-c]pyridazin-8-yl]-5-[3-[2-fluoro-4-[3-(1-piperidyl)prop-1-ynyl]phenoxy]propyl]thiazole-4-carboxylic acid

Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(1-piperidyl)prop-1-ynyl]phenoxy]propyl]thiazole-4-carboxylate Using Propargylic amine preparation General Procedure starting from 100 mg of Preparation 3d (0.155 mmol, 1 eq.) as the appropriate propargylic alcohol and piperidine (264.2 mg, 20 eq.), 55 mg of the desired product (50%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-(1-piperidyl)prop-1-ynyl]phenoxy]propyl]thiazole-4-carboxylic acid Using Hydrolysis General Procedure starting from the product of Step A as the appropriate methyl ester, the desired product was obtained.

HRMS-ESI (m/z): [M+H]+ calcd for $C_{36}H_{37}FN_7O_3S_2$: 698.2377, found 698.2373.

Example 47: 2-[3-(1,3-Benzothiazol-2-ylamino)-4-methyl-6,7-dihydro-5H-pyrido[2,3-c]pyridazin-8-yl]-5-[3-[2-fluoro-4-(3-morpholinoprop-1-ynyl)phenoxy]propyl]thiazole-4-carboxylic acid Example 48: 2-[3-(1,3-Benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)prop-1-ynyl]phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[2-fluoro-4-(3-morpholinoprop-1-ynyl)phenoxy]propyl]thiazole-4-carboxylate Using Propargylic amine preparation General Procedure starting from 100 mg of Preparation 3d (0.155 mmol, 1 eq.) as the appropriate propargylic alcohol and morpholine (270.3 mg, 20 eq.), 191 mg of the desired product (86%) was obtained.

Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)prop-1-ynyl]phenoxy]propyl]thiazole-4-carboxylate Using Propargylic amine preparation General Procedure starting from 100 mg of Preparation 3d (0.155 mmol, 1 eq.) as the appropriate propargylic alcohol and 1-methylpiperazine (310.7 mg, 20 eq.), 150 mg of the desired product (79%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-(3-morpholinoprop-1-ynyl)phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{35}H_{35}FN_7O_4S_2$: 700.2170, found 700.2163.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)prop-1-ynyl]phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{38}FN_8O_3S_2$: 713.2486, found 713.2474.

Example 49: 2-{3-[(1,3-Benzothiazol-2-yl)amino]-4-methyl-5H,6H,7H,8H-pyrido[2,3-c]pyridazin-8-yl}-5-(3-{4-[3-(4,4-difluoropiperidin-1-yl)prop-1-yn-1-yl]-2-fluorophenoxy}propyl)-1,3-thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[4-[3-(4,4-difluoro-1-piperidyl)prop-1-ynyl]-2-fluoro-phenoxy]propyl]thiazole-4-carboxylate Using Propargylic amine preparation General Procedure starting from 100 mg of Preparation 3d (0.155 mmol, 1 eq.) as the appropriate propargylic alcohol and 4,4-difluoropiperidine (20 eq.), 120 mg of the desired product (72%) was obtained.

Step B: 2-{3-[(1,3-benzothiazol-2-yl)amino]-4-methyl-5H,6H,7H,8H-pyrido[2,3-c]pyridazin-8-yl}-5-(3-{4-[3-(4,4-difluoropiperidin-1-yl)prop-1-yn-1-yl]-2-fluorophenoxy}propyl)-1,3-thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{35}F_3N_7O_3S_2$: 734.2189, found 734.2185.

Example 50: 2-{3-[(1,3-Benzothiazol-2-yl)amino]-4-methyl-5H,6H,7H,8H-pyrido[2,3-c]pyridazin-8-yl}-5-(3-{4-[3-(3,3-difluoropiperidin-1-yl)prop-1-yn-1-yl]-2-fluorophenoxy}propyl)-1,3-thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[4-[3-(3,3-difluoro-1-piperidyl)prop-1-ynyl]-2-fluoro-phenoxy]propyl]thiazole-4-carboxylate Using Propargylic amine preparation General Procedure starting from 100 mg of Preparation 3d (0.155 mmol, 1 eq.) as the appropriate propargylic alcohol and 3,3-difluoropiperidine, hydrogen chloride (1:1) (488.9 mg, 20 eq.), 30 mg of the desired product (26%) was obtained.

Step B: 2-{3-[(1,3-Benzothiazol-2-yl)amino]-4-methyl-5H,6H,7H,8H-pyrido[2,3-c]pyridazin-8-yl}-5-(3-{4-[3-(3,3-difuoropiperidin-1-yl)prop-1-yn-1-yl]-2-fluorophenoxy}propyl)-1,3-thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{35}F_3N_7O_3S_2$: 734.2189, found 734.2186.

Example 51: 2-{3-[(1,3-Benzothiazol-2-yl)amino]-4-methyl-5H,6H,7H,8H-pyrido[2,3-c]pyridazin-8-yl}-5-(3-{2-chloro-4-[3-(dimethylamino)prop-1-yn-1-yl]phenoxy}propyl)-1,3-thiazole-4-carboxylic acid Step A: methyl 5-[3-(2-chloro-4-iodophenoxy)pro-pyl]-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of product from Preparation 3b (225 mg, 0.32 mmol, 1 eq) in toluene (10 mL) was added 2-chloro-4-iodophenol (100 mg, 0.39 mmol, 1.22 eq), followed by triphenylphosphine (127 mg, 0.48 mmol, 1.5 eq) and diiso-propyl azodicarboxylate (0.1 ml, 0.48 mmol, 1.5 eq) and the mixture was stirred at ambient temperature for 3 h. Purifi-cation by flash column chromatography (20 g silica) eluting with a gradient of 0-30% ethyl acetate in iso-heptane afforded the desired product as a yellow solid (235 mg, 0.23 mmol, 72%).

LC/MS ($C_{35}H_{40}ClIN_6O_4SiS_2$) 863 [M+H]$^+$; RT 1.48 (LCMS-V-B2)

$^1$H NMR (400 MHz, CDCl$_3$) δ 7.65 (d, J=2.1 Hz, 1H), 7.59 (dt, J=7.7, 0.9 Hz, 1H), 7.47 (dd, J=8.6, 2.2 Hz, 1H), 7.39-7.35 (m, 2H), 7.24-7.17 (m, 1H), 6.67 (d, J=8.6 Hz, 1H), 5.84 (s, 2H), 4.47-4.35 (m, 2H), 4.13-4.06 (m, 2H), 3.90 (s, 3H), 3.80-3.70 (m, 2H), 3.43-3.34 (m, 2H), 2.87 (t, J=6.3 Hz, 2H), 2.38 (s, 3H), 2.34-2.22 (m, 2H), 2.19-2.06 (m, 2H), 1.02-0.91 (m, 2H), −0.07 (s, 9H).

Step B: methyl 5-(3-{2-chloro-4-[3-(dimethyl-amino)prop-1-yn-1-yl]phenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate Dimethyl(prop-2-yn-1-yl)amine (0.1 ml, 0.93 mmol, 4.0 eq) was added to a solution of the product from Step A (235 mg, 0.23 mmol, 1 eq), copper(I) iodide (8.81 mg, 0.05 mmol, 0.2 eq) and tetrakis(triphenylphosphine)palladium(0) (26.7 mg, 0.02 mmol, 0.1 eq) in 2-methyltetrahydrofuran (10 mL), then NN-diisopropylethylamine (0.15 ml, 0.69 mmol, 3 eq) was added and the mixture was heated at 75° C. for 18 h. The reaction was allowed to cool to ambient temperature and purification by flash column chromatography (20 g silica) eluting with a gradient of 0-100% ethyl acetate in iso-heptane afforded the desired product as a brown gum (75 mg, 0.09 mmol, 40%).

LC/MS ($C_{40}H_{48}ClN_7O_4SiS_2$) 818 [M+H]$^+$; RT 1.56 (LCMS-V-B1)

$^1$H NMR (400 MHz, CDCl$_3$) δ 7.70-7.63 (m, 1H), 7.59 (dt, J=7.6, 0.9 Hz, 1H), 7.48-7.44 (m, 1H), 7.40-7.35 (m, 2H), 7.23-7.16 (m, 1H), 6.84 (d, J=8.6 Hz, 1H), 5.84 (s, 2H), 4.46-4.36 (m, 2H), 4.18-4.05 (m, 2H), 3.90 (s, 3H), 3.79-3.69 (m, 2H), 3.49-3.34 (m, 4H), 2.87 (t, J=6.5 Hz, 2H), 2.39 (s, 3H), 2.35 (s, 6H), 2.32-2.25 (m, 2H), 2.18-2.08 (m, 2H), 1.01-0.93 (m, 2H), −0.07 (s, 9H).

Step C: 2-{3-[(1,3-benzothiazol-2-yl)amino]-4-methyl-5H,6H,7H,8H-pyrido[2,3-c]pyridazin-8-yl}-5-(3-{2-chloro-4-[3-(dimethylamino)prop-1-yn-1-yl]phenoxy}propyl)-1,3-thiazole-4-carboxylic acid To a solution of the product from Step B (75 mg, 0.09 mmol, 1 eq) in dichloromethane (1.8 mL), cooled to 0° C., was added trifluoroacetic acid (0.2 ml, 2.75 mmol, 30 eq) and the mixture was stirred for 36 h. The reaction was diluted with dichloromethane (20 mL), successively washed with 1M aqueous ammonia (10 mL), water (10 mL) and brine (10 mL), dried (magnesium sulfate) and concentrated in vacuo. The crude material was suspended in a mixture of water (1.5 mL) and methanol (0.5 mL), lithium hydroxide monohydrate (11.5 mg, 0.27 mmol, 3 eq) was added, and the suspension was heated at 80° C. for 18 h. The reaction was neutralised with acetic acid and the solids were collected by filtration and washed with water (20 mL). Purification by preparative HPLC (HPLC-V-A2) afforded the desired prod-uct as a pale yellow solid (7 mg, 0.01 mmol, 11%).

HRMS-ESI (m/z) [M+H]+ calcd for $C_{33}H_{33}C_1N_7O_3S_2$: 674.1775, found 674.1796.

Example 52: 2-{3-[(1,3-Benzothiazol-2-yl)amino]-4-methyl-5H,6H,7H,8H-pyrido[2,3-c]pyridazin-8-yl}-5-(3-{4-[2-(pyrrolidin-1-yl)ethoxy]phenoxy}propyl)-1,3-thiazole-4-carboxylic acid Step A: ethyl 2-(4-methyl-3-{[(2Z)-3-{[2-(trimeth-ylsilyl)ethoxy]methyl}-2,3-dihydro-1,3-benzothi-azol-2-ylidene]amino}-5H,6H,7H,8H-pyrido[2,3-c]pyridazin-8-yl)-5-(3-{4-[2-(pyrrolidin-1-yl)ethoxy]phenoxy}propyl)-1,3-thiazole-4-carboxylate To a solution of the product from Preparation 3g (150 mg, 0.23 mmol, 1 eq) and the product from Preparation 4f (97 mg, 0.47 mmol, 2 eq) in toluene (6 mL) was added triph-enylphosphine (123 mg, 0.47 mmol, 2 eq) and di-tert-butyl azodicarboxylate (108 mg, 0.47 mmol, 2 eq) and the mixture was heated at 50° C. overnight. The reaction was partitioned between dichloromethane and brine, and the organic phase was dried (magnesium sulfate) and concentrated in vacuo. Purification by automated flash column chromatography (CombiFlash Rf, 12 g RediSep™ silica cartridge) eluting with a gradient of 0-12% methanol in dichloromethane afforded the desired product as a yellow gum (165 mg, 0.2 mmol, 85%).

LC/MS (C$_{42}$H$_{55}$N$_7$O$_5$SiS$_2$) 831 [M+H]$^+$; RT 2.75 (LCMS-V-C)

$^1$H NMR (400 MHz, DMSO-d6) δ 7.82 (d, 1H), 7.48-7.39 (m, 2H), 7.28-7.20 (m, 1H), 6.92-6.82 (m, 4H), 5.84 (s, 2H), 4.34-4.21 (m, 4H), 4.02-3.91 (m, 4H), 3.76-3.66 (m, 2H), 3.26 (t, 2H), 2.87 (t, J=6.2 Hz, 2H), 2.71 (t, 1H), 2.48-2.42 (m, 4H), 2.37 (s, 3H), 2.13-2.00 (m, 4H), 1.71-1.60 (m, 4H), 1.30 (t, J=7.1 Hz, 3H), 0.95-0.86 (m, 2H), −0.11 (s, 9H).

Step B: ethyl 2-{3-[(1,3-benzothiazol-2-yl)amino]-4-methyl-5H,6H,7H,8H-pyrido[2,3-c]pyridazin-8-yl}-5-(3-{4-[2-(pyrrolidin-1-yl)ethoxy]phenoxy}propyl)-1,3-thiazole-4-carboxylate To a solution of the product from Step A (165 mg, 0.2 mmol, 1 eq) in dichloromethane (8.1 mL), cooled to 0° C., was added trifluoroacetic acid (0.91 mL, 11.9 mmol, 60 eq) and the mixture was stirred at ambient temperature overnight. The reaction was diluted with dichloromethane, cooled to 0° C., neutralised with aqueous ammonia and the organic phase was separated (PTFE phase separator) and concentrated in vacuo. Purification by automated flash column chromatography (CombiFlash Rf, 4 g RediSep™ silica cartridge) eluting with a gradient of 0-14% methanol in dichloromethane afforded the desired product as a yellow solid (84 mg, 0.12 mmol, 60%).

LC/MS (C$_{36}$H$_{41}$N$_7$O$_4$S$_2$) 700 [M+H]$^+$; RT 2.14 (LCMS-V-C)

$^1$H NMR (400 MHz, DMSO-d6) δ 11.48 (br s, 1H), 7.89 (d, J=7.7 Hz, 1H), 7.50 (d, J=7.9 Hz, 1H), 7.42-7.34 (m, 1H), 7.20 (td, J=7.5, 1.2 Hz, 1H), 6.94-6.83 (m, 4H), 4.34-4.21 (m, 4H), 3.98 (t, J=6.2 Hz, 4H), 3.32-3.23 (m, 2H), 2.89 (t, J=6.4 Hz, 2H), 2.85-2.74 (m, 2H), 2.65-2.53 (m, 4H), 2.35 (s, 3H), 2.16-1.99 (m, 4H), 1.70 (s, 4H), 1.31 (t, J=7.1 Hz, 3H).

Step C: 2-{3-[(1,3-benzothiazol-2-yl)amino]-4-methyl-5H,6H,7H,8H-pyrido[2,3-c]pyridazin-8-yl}-5-(3-{4-[2-(pyrrolidin-1-yl)ethoxy]phenoxy}propyl)-1,3-thiazole-4-carboxylic acid To a solution of the product from Step B (84 mg, 0.12 mmol, 1 eq) in 1,4-dioxane (4 mL) was added lithium hydroxide monohydrate (50.4 mg, 1.2 mmol, 10 eq) and the mixture was heated at reflux overnight. The reaction was allowed to cool to ambient temperature and concentrated in vacuo. Purification by automated flash column chromatography (CombiFlash Rf, 4 g RediSep™ silica cartridge) eluting with a gradient of 0-15% 7N methanolic ammonia in dichloromethane gave a solid that was triturated with diethyl ether, filtered and dried under vacuum to afford the desired product as a yellow solid (52.9 mg, 0.08 mmol, 66%).

LC/MS (C$_{34}$H$_{37}$N$_7$O$_4$S$_2$) 672 [M+H]$^+$; RT 1.93 (LCMS-V-C)

$^1$H NMR (400 MHz, DMSO-d6) δ 7.89 (dd, J=7.9, 1.2 Hz, 1H), 7.50 (d, J=8.1 Hz, 1H), 7.38 (td, J=7.7, 1.3 Hz, 1H), 7.20 (td, J=7.6, 1.2 Hz, 1H), 6.94-6.81 (m, 4H), 4.28 (dd, J=7.3, 4.3 Hz, 2H), 4.05-3.91 (m, 4H), 3.35-3.17 (m, 6H), 2.89 (t, J=6.2 Hz, 2H), 2.76 (t, J=5.9 Hz, 2H), 2.35 (s, 3H), 2.18-1.96 (m, 4H), 1.73-1.62 (m, 4H).

HRMS-ESI (m/z) [M+H]+ calcd for C$_{34}$H$_{38}$N$_7$O$_4$S2: 672.2427, found 672.2449 Example 53: 2-{3-[(1,3-Benzothiazol-2-yl)amino]-4-methyl-5H,6H,7H,8H-pyrido[2,3-c]pyridazin-8-yl}-5-(3-{4-[2-(dimethylamino)ethyl]-2-fluorophenoxy}propyl)-1,3-thiazole-4-carboxylic acid Step A: methyl 5-(3-{4-[2-(dimethylamino)ethyl]-2-fluorophenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3b (95 mg, 0.15 mmol, 1 eq) and the product from Preparation 4g (41 mg, 0.22 mmol, 1.48 eq) in toluene (5 mL) was added di-tert-butyl azodicarboxylate (69.8 mg, 0.3 mmol, 2 eq) and triphenylphosphine (79.5 mg, 0.3 mmol, 2 eq) and the mixture was heated at 50° C. for 20 h. The reaction was partitioned between dichloromethane and water, and the organic phase was separated (PTFE phase separator) and concentrated in vacuo. Purification by automated flash column chromatography (CombiFlash Rf, 4 g RediSep™ silica cartridge) eluting with a gradient of 0-5% methanol in dichloromethane afforded the desired product as a yellow oil (83 mg, 0.1 mmol, 69%).

LC/MS (C$_{39}$H$_{50}$FN$_7$O$_4$SiS$_2$) 792 [M+H]V; RT 2.69 (LCMS-V-C)

$^1$H NMR (400 MHz, DMSO-d6) δ 7.82 (dd, J=7.3, 1.1 Hz, 1H), 7.48-7.38 (m, 2H), 7.28-7.20 (m, 1H), 7.14-7.02 (m, 2H), 6.98-6.92 (m, 1H), 5.85 (s, 2H), 4.26 (dd, J=7.2, 4.4 Hz, 2H), 4.08 (t, J=6.2 Hz, 2H), 3.79 (s, 3H), 3.75-3.67 (m, 2H), 3.31-3.23 (m, 2H), 2.88 (t, J=6.4 Hz, 2H), 2.65-2.56 (m, 2H), 2.46-2.37 (m, 2H), 2.37 (s, 3H), 2.12 (s, 6H), 2.11-2.07 (m, 2H), 2.07-2.00 (m, 2H), 0.96-0.88 (m, 2H), −0.11 (s, 9H).

Step B: methyl 2-{3-[(1,3-benzothiazol-2-yl)amino]-4-methyl-5H,6H,7H,8H-pyrido[2,3-c]pyridazin-8-yl}-5-(3-{4-[2-(dimethylamino)ethyl]-2-fluorophenoxy}propyl)-1,3-thiazole-4-carboxylate To a solution of the product from Step A (83 mg, 0.1 mmol, 1 eq) in dichloromethane (5 mL) was added trifluoroacetic acid (1 mL, 12.99 mmol, 124 eq) and the mixture was stirred at ambient temperature overnight. The reaction was diluted with dichloromethane, cooled to 0° C., neutralised with aqueous ammonia, and the organic phase was separated (PTFE phase separator) and concentrated in vacuo. Purification by automated flash column chromatography (CombiFlash Rf, 4 g RediSep™ silica cartridge) eluting with a gradient of 0-8% methanol in dichloromethane afforded the desired product as a yellow solid (50 mg, 0.08 mmol, 72%).

LC/MS ($C_{33}H_{36}FN_7O_3S_2$) 662 [M+H]$^+$; RT 2.04 (LCMS-V-C)

$^1$H NMR (400 MHz, DMSO-d6) δ 11.48 (br s, 1H), 7.88 (d, J=7.9 Hz, 1H), 7.49 (d, J=8.0 Hz, 1H), 7.40-7.34 (m, 1H), 7.19 (td, J=7.6, 1.2 Hz, 1H), 7.13-7.02 (m, 2H), 6.98-6.92 (m, 1H), 4.30-4.21 (m, 2H), 4.08 (t, 2H), 3.78 (s, 3H), 3.32-3.24 (m, 2H), 2.87 (t, J=6.3 Hz, 2H), 2.62 (dd, J=8.6, 6.6 Hz, 2H), 2.46-2.38 (m, 2H), 2.34 (s, 3H), 2.14 (s, 6H), 2.13-2.09 (m, 2H), 2.08-2.01 (m, 2H).

Step C: 2-{3-[(1,3-benzothiazol-2-yl)amino]-4-methyl-5H,6H,7H,8H-pyrido[2,3-c]pyridazin-8-yl}-5-(3-{4-[2-(dimethylamino)ethyl]-2-fluorophenoxy}propyl)-1,3-thiazole-4-carboxylic acid To a solution of the product from Step B (50 mg, 0.08 mmol, 1 eq) in 1,4-dioxane (3 mL) was added lithium hydroxide monohydrate (31.7 mg, 0.76 mmol, 10 eq) and the mixture was heated at 70° C. overnight. The reaction was allowed to cool to ambient temperature and concentrated in vacuo. Purification by automated flash column chromatography (CombiFlash Rf, 4 g RediSep™ silica cartridge) eluting with a gradient of 0-15% 7N methanolic ammonia in dichloromethane afforded the desired product as a yellow solid (24.68 mg, 0.04 mmol, 50%).

LC/MS ($C_{32}H_{34}FN_7O_3S_2$) 648 [M+H]$^+$; RT 1.87 (LCMS-V-C)

$^1$H NMR (400 MHz, DMSO-d6) δ 7.89 (d, J=7.8 Hz, 1H), 7.50 (d, J=8.1 Hz, 1H), 7.38 (td, J=8.1, 7.7, 1.3 Hz, 1H), 7.20 (td, J=7.5, 1.2 Hz, 1H), 7.14-7.02 (m, 2H), 6.95 (dt, J=8.4, 1.4 Hz, 1H), 4.32-4.25 (m, 2H), 4.09 (t, J=6.3 Hz, 2H), 3.31-3.23 (m, 2H), 2.89 (t, J=6.3 Hz, 2H), 2.63 (t, J=7.6 Hz, 2H), 2.44 (dd, J=8.5, 6.6 Hz, 2H), 2.35 (s, 3H), 2.17 (s, 6H), 2.15-2.08 (m, 2H), 2.08-2.00 (m, 2H) HRMS-ESI (m/z) [M+H]+ calcd for $C_{32}H_{35}FN_7O_3S_2$: 648.2227, found 648.2269.

Example 54: 3-[2-[3-[4-[3-[2-[3-(1,3-Benzothiazol-2-ylamino)-4-methyl-6,7-dihydro-5H-pyrido[2,3-c]pyridazin-8-yl]-4-carboxy-thiazol-5-yl]propoxy]-3-fluoro-phenyl]prop-2-ynylamino]ethyl-dimethyl-ammonio]propane-1-sulfonate

Step A: 3-[2-[tert-butoxycarbonyl-[3-[4-[3-[2-(3-chloro-4-methyl-6,7-dihydro-5H-pyrido[2,3-c]pyridazin-8-yl)-4-methoxycarbonyl-thiazol-5-yl]propoxy]-3-fluoro-phenyl]prop-2-ynyl]amino]ethyl-dimethyl-ammonio]propane-1-sulfonate A mixture of 384 mg of Example 76 (Step A)(0.55 mmol, 1 eq.) and 1944 mg of oxathiolane 2,2-dioxide (15.92 mmol, 30 eq.) in acetonitrile (4 mL/mmol) and DMF (1 mL/mmol) was stirred at rt. After reaching appropriate conversion, the volatiles were removed under reduced pressure and purified via flash column chromatography (SiO$_2$, EtOAc:0.6 M NH$_3$ in MeOH) to obtain 94 mg (29%) of the desired product.

LC-MS-ESI (m/z): [M+H]+ calcd for C$_{37}$H$_{49}$ClFN$_6$O$_8$S$_2$: 823.3, found 823.2.

Step B: 3-[2-[3-[4-[3-[2-[3-(1,3-benzothiazol-2-ylamino)-4-methyl-6,7-dihydro-5H-pyrido[2,3-c]pyridazin-8-yl]-4-methoxycarbonyl-thiazol-5-yl]propoxy]-3-fluoro-phenyl]prop-2-ynyl-tert-butoxycarbonyl-amino]ethyl-dimethyl-ammonio]propane-1-sulfonate Using Buchwald General Procedure II starting from the product from Step A and 1,3-benzothiazol-2-amine, the desired product was obtained.

$^1$H NMR (500 MHz, DMSO-d$_6$) δ ppm 7.88 (d, 1H), 7.49 (d, 1H), 7.37 (t, 1H), 7.35 (d, 1H), 7.25 (dd, 1H), 7.20 (t, 1H), 7.18 (t, 1H), 4.27 (s, 2H), 4.26 (t, 2H), 4.15 (t, 2H), 3.77 (s, 3H), 3.69 (t, 2H), 3.46 (t, 2H), 3.45 (t, 2H), 3.28 (t, 2H), 3.07 (s, 6H), 2.88 (t, 2H), 2.46 (t, 2H), 2.34 (s, 3H), 2.13 (qn, 2H), 2.04 (qn, 2H), 2.02 (qn, 2H), 1.44 (s, 9H); $^{13}$C NMR (125 MHz, DMSO-d$_6$) δ ppm 129.2, 126.5, 122.6, 122.4, 119.3, 116.9, 115.5, 85.4, 82.5, 68.4, 63.3, 60.1, 52.0, 50.8, 48.0, 46.4, 40.8, 37.9, 31.0, 28.4, 23.9, 23.2, 20.4, 19.5, 13.0; HRMS-ESI (m/z): [M+H]$^+$ calcd for C$_{44}$H$_{54}$FN$_8$O$_8$S$_3$: 937.3205, found 937.3209.

Step C: 3-[2-[3-[4-[3-[2-[3-(1,3-Benzothiazol-2-ylamino)-4-methyl-6,7-dihydro-5H-pyrido[2,3-c]pyridazin-8-yl]-4-carboxy-thiazol-5-yl]propoxy]-3-fluoro-phenyl]prop-2-ynylamino]ethyl-dimethyl-ammonio]propane-1-sulfonate Using Deprotection and Hydrolysis General Procedure followed by repurification via reverse phase preparative chromatography (C18, 25 mM NH$_4$HCO$_3$ in water:MeCN) starting from the product from Step B, the desired product was obtained.

HRMS-ESI (m/z): [M+H]+ calcd for C$_{38}$H$_{44}$FN$_8$O$_6$S$_3$: 823.2524, found 823.2523.

Example 55: 2-[3-(1,3-Benzothiazol-2-ylamino)-4-methyl-6,7-dihydro-5H-pyrido[2,3-c]pyridazin-8-yl]-5-[3-[2-fluoro-4-[3-(3-hydroxy-1-piperidyl)prop-1-ynyl]phenoxy]propyl]thiazole-4-carboxylic acid

Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(3-hydroxy-1-piperidyl)prop-1-ynyl]phenoxy]propyl]thiazole-4-carboxylate Using Propargylic amine preparation General Procedure starting from 100 mg of Preparation 3d (0.155 mmol, 1 eq.) as the appropriate propargylic alcohol and piperidin-3-ol (313.8 mg, 20 eq.), 70 mg of the desired product (62%) was obtained.

Step B: 2-[3-(1,3-Benzothiazol-2-ylamino)-4-methyl-6,7-dihydro-5H-pyrido[2,3-c]pyridazin-8-yl]-5-[3-[2-fluoro-4-[3-(3-hydroxy-1-piperidyl)prop-1-ynyl]phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for C$_{36}$H$_{37}$FN$_7$O$_4$S$_2$: 714.2327, found 714.2323.

Example 56: 5-[3-[4-[3-[(1S,5R)-3-Azabicyclo[3.1.0]hexan-3-yl]prop-1-ynyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylic acid Step A: methyl 5-[3-[4-[3-[(1R,5S)-3-azabicyclo[3.1.0]hexan-3-yl]prop-1-ynyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylate Using Propargylic amine preparation General Procedure starting from 100 mg of Preparation 3d (0.155 mmol, 1 eq.) as the appropriate propargylic alcohol and (1R,5S)-3-azabicyclo[3.1.0]hexane (20 eq.), 150 mg of the desired product (81%) was obtained.

Step B: 5-[3-[4-[3-[(1S,5R)-3-Azabicyclo[3.1.0]hexan-3-yl]prop-1-ynyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{35}FN_7O_3S_2$: 696.2221, found 696.2227.

Example 57: 2-[3-(1,3-Benzothiazol-2-ylamino)-4-methyl-6,7-dihydro-5H-pyrido[2,3-c]pyridazin-8-yl]-5-[3-[2-fluoro-4-[3-[4-(1-piperidyl)-1-piperidyl]prop-1-ynyl]phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-[4-(1-piperidyl)-1-piperidyl]prop-1-ynyl]phenoxy]propyl]thiazole-4-carboxylate Using Propargylic amine preparation General Procedure starting from 100 mg of Preparation 3d (0.155 mmol, 1 eq.) as the appropriate propargylic alcohol and 1-(4-piperidyl)piperidine, hydrogen chloride (1:2) (748.3 mg, 20 eq.), 100 mg of the desired product (81%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-[4-(1-piperidyl)-1-piperidyl]prop-1-ynyl]phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{41}H_{46}FN_8O_3S_2$: 781.3112, found 781.3112.

Example 58: 2-[3-(1,3-Benzothiazol-2-ylamino)-4-methyl-6,7-dihydro-5H-pyrido[2,3-c]pyridazin-8-yl]-5-[3-[2-fluoro-4-[3-(3-oxo-2,8-diazaspiro[4.5]decan-8-yl)prop-1-ynyl]phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(3-oxo-2,8-diazaspiro[4.5]decan-8-yl)prop-1-ynyl]phenoxy]propyl]thiazole-4-carboxylate Using Propargylic amine preparation General Procedure starting from 100 mg of Preparation 3d (0.155 mmol, 1 eq.) as the appropriate propargylic alcohol and 2,8-diazaspiro[4.5]decan-3-one (478.4 mg, 20 eq.), 125 mg of the desired product (82%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-(3-oxo-2,8-diazaspiro[4.5]decan-8-yl)prop-1-ynyl]phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{39}H_{40}FN_8O_4S2$: 767.2592, found 767.2588.

Example 59: 2-{3-[(1,3-Benzothiazol-2-yl)amino]-
4-methyl-5H,6H,7H,8H-pyrido[2,3-c]pyridazin-8-
yl}-5-(3-{2-bromo-4-[3-(dimethylamino)prop-1-yn-
1-yl]phenoxy}propyl)-1,3-thiazole-4-carboxylic acid Step A: methyl 5-[3-(2-bromo-4-iodophenoxy)pro-
pyl]-2-(4-methyl-3-{[(2Z)-3-{[2-(trimethylsilyl)
ethoxy]methyl}-2,3-dihydro-1,3-benzothiazol-2-
ylidene]amino}-5H,6H,7H,8H-pyrido[2,3-c]
pyridazin-8-yl)-1,3-thiazole-4-carboxylate To a solution of the product from Preparation 3b (350 mg,
0.5 mmol, 1 eq) and 2-bromo-4-iodophenol (200 mg, 0.67
mmol, 1.33 eq) in toluene (10 mL) was added triphenylphos-
phine (198 mg, 0.75 mmol, 1.5 eq) and diisopropyl azodi-
carboxylate (0.15 ml, 0.75 mmol, 1.5 eq) and the mixture
was stirred at ambient temperature for 18 h. The reaction
was concentrated in vacuo and purification by flash column
chromatography (20 g silica) eluting with a gradient of
0-30% ethyl acetate in iso-heptane afforded the desired
product as a yellow solid (555 mg, 0.49 mmol, 97%).
LC/MS (C$_{35}$H$_{40}$BrIN$_6$O$_4$SiS$_2$) 907 [M+H]$^+$; RT 1.50
(LCMS-V-B2)
$^1$H NMR (400 MHz, CDCl$_3$) δ 7.82 (d, J=2.1 Hz, 1H),
7.59 (dt, J=7.6, 0.9 Hz, 1H), 7.50 (dd, J=8.6, 2.1 Hz, 1H),
7.39-7.34 (m, 2H), 7.24-7.16 (m, 1H), 6.65 (d, J=8.7 Hz,
1H), 5.84 (s, 2H), 4.47-4.36 (m, 2H), 4.17-4.05 (m, 2H),
3.90 (s, 3H), 3.80-3.69 (m, 2H), 3.39 (dd, J=8.4, 6.6 Hz, 2H),
2.87 (t, J=6.4 Hz, 2H), 2.38 (s, 3H), 2.34-2.23 (m, 2H),
2.18-2.07 (m, 2H), 1.00-0.92 (m, 2H), −0.07 (s, 9H).

Step B: methyl 5-(3-{2-bromo-4-[3-(dimethyl-
amino)prop-1-yn-1-yl]phenoxy}propyl)-2-(4-
methyl-3-{[(2Z)-3-{[2-(trimethylsilyl)ethoxy]
methyl}-2,3-dihydro-1,3-benzothiazol-2-ylidene]
amino}-5H,6H,7H,8H-pyrido[2,3-c]pyridazin-8-yl)-
1,3-thiazole-4-carboxylate To a solution of the product from Step A (550 mg, 0.52
mmol, 1 eq), copper (I) iodide (18.5 mg, 0.1 mmol, 0.2 eq)
and tetrakis(triphenylphosphine)palladium(0) (56 mg, 0.05
mmol, 0.1 eq) in 2-methyltetrahydrofuran (10 mL) was
added dimethyl(prop-2-yn-1-yl)amine (0.3 mL, 2.79 mmol,
5.75 eq) followed by N,N-diisopropylethylamine (0.3 ml,
1.45 mmol, 3 eq) and the mixture was heated at 75° C. for 3 h. The reaction was allowed to cool to ambient temperature
and concentrated in vacuo. Purification by flash column
chromatography (20 g silica) eluting with a gradient of
0-100% ethyl acetate in iso-heptane afforded the desired
product as a dark orange gum (220 mg, 0.25 mmol, 53%).
LC/MS (C$_{40}$H$_{48}$BrN$_7$O$_4$SiS$_2$) 862 [M+H]$^+$; RT 1.54
(LCMS-V-B2)
$^1$H NMR (400 MHz, CDCl$_3$) δ 7.64 (d, J=2.0 Hz, 1H),
7.60 (dt, J=7.7, 0.9 Hz, 1H), 7.38-7.37 (m, 2H), 7.34-7.30
(m, 1H), 7.23-7.16 (m, 1H), 6.81 (d, J=8.6 Hz, 1H), 5.84 (s,
2H), 4.48-4.35 (m, 2H), 4.16-4.07 (m, 2H), 3.90 (s, 3H),
3.78-3.69 (m, 2H), 3.50-3.35 (m, 4H), 2.87 (t, J=6.3 Hz,
2H), 2.38 (s, 3H), 2.35 (s, 6H), 2.33-2.26 (m, 2H), 2.18-2.07
(m, 2H), 1.01-0.88 (m, 2H), −0.07 (s, 9H).

Step C: 2-{3-[(1,3-benzothiazol-2-yl)amino]-4-
methyl-5H,6H,7H,8H-pyrido[2,3-c]pyridazin-8-yl}-
5-(3-{2-bromo-4-[3-(dimethylamino)prop-1-yn-1-yl]
phenoxy}propyl)-1,3-thiazole-4-carboxylic acid To a solution of the product from Step B (210 mg, 0.24
mmol, 1 eq) in dichloromethane (4.5 mL), cooled to 0° C.,
was added trifluoroacetic acid (0.5 ml, 6.08 mmol, 25 eq)
and the mixture was stirred for 24 h at ambient temperature.
The reaction was diluted with dichloromethane (40 mL),
successively washed with 1M aqueous ammonia (20 mL),
water (2×20 mL) and brine (20 mL), dried (magnesium
sulfate) and concentrated in vacuo. To a solution of the crude
product in methanol (1 mL) was added water (2 mL) and
lithium hydroxide monohydrate (30.6 mg, 0.73 mmol, 3 eq)
and the suspension was heated at 75° C. for 72 h. The
reaction was allowed to cool to ambient temperature, then
neutralised with acetic acid and the solids were collected by
filtration and washed with water (2×10 mL). Purification by
preparative HPLC (HPLC-V-A2) afforded the desired prod-
uct as a green solid (15 mg, 0.02 mmol, 9%).
LC/MS (C$_{33}$H$_{32}$BrN$_7$O$_3$S$_2$) 718 [M+H]$^+$; RT 1.18
(LCMS-V-B1)
$^1$H NMR (400 MHz, DMSO-d6) δ 7.87 (d, J=7.8 Hz, 1H),
7.63 (d, J=2.0 Hz, 1H), 7.49 (d, J=8.0 Hz, 1H), 7.42-7.33 (m,
2H), 7.20 (td, J=7.6, 1.1 Hz, 1H), 7.09 (d, J=8.6 Hz, 1H),
4.26 (t, J=5.5 Hz, 2H), 4.13 (t, J=6.1 Hz, 2H), 3.34-3.25 (m,
2H), 2.86 (t, J=6.1 Hz, 2H), 2.54 (s, 2H), 2.33 (s, 3H), 2.17
(s, 6H), 2.16-2.09 (m, 2H), 2.08-1.95 (m, 2H).

Example 60: 2-{3-[(1,3-Benzothiazol-2-yl)amino]-
4-methyl-5H,6H,7H,8H-pyrido[2,3-c]pyridazin-8-
yl}-5-{3-[2-fluoro-4-(4-methylpiperazin-1-yl)phe-
noxy]propyl}-1,3-thiazole-4-carboxylic acid Step A: methyl 5-[3-(2-fluoro-4-iodophenoxy)pro-
pyl]-2-(4-methyl-3-{[(2Z)-3-{[2-(trimethylsilyl)
ethoxy]methyl}-2,3-dihydro-1,3-benzothiazol-2-
ylidene]amino}-5H,6H,7H,8H-pyrido[2,3-c]
pyridazin-8-yl)-1,3-thiazole-4-carboxylate To a solution of the product from Preparation 3b (200 mg, 0.32 mmol, 1 eq) and 2-fluoro-4-iodophenol (152 mg, 0.64 mmol, 2 eq) in toluene (6 mL) was added triphenylphosphine (167 mg, 0.64 mmol, 2 eq) and diisopropyl azodicarboxylate (147 mg, 0.64 mmol, 2 eq) and the mixture was stirred at 50° C. for 17 h. The reaction was partitioned between dichloromethane and water, and the organic phase was separated (PTFE phase separator) and concentrated in vacuo. Purification by automated flash column chromatography (CombiFlash Rf, 12 g RediSep™ silica cartridge) eluting with a gradient of 0-100% ethyl acetate in isoheptane afforded the desired product as a yellow gum (161 mg, 0.19 mmol, 60%).

LC/MS ($C_{35}H_{40}FIN_6O_4SiS_2$) 847 [M+H]+; RT 3.33 (LCMS-V-C)

$^1$H NMR (400 MHz, DMSO-d6) δ 7.82 (dt, J=7.6, 0.9 Hz, 1H), 7.61 (dd, J=10.8, 2.1 Hz, 1H), 7.49-7.39 (m, 3H), 7.24 (ddd, J=8.3, 6.6, 1.9 Hz, 1H), 7.01 (t, J=8.8 Hz, 1H), 5.85 (s, 2H), 4.26 (t, J=5.7 Hz, 2H), 4.11 (t, J=6.2 Hz, 2H), 3.78 (s, 3H), 3.76-3.67 (m, 2H), 3.27 (t, 2H), 2.88 (t, J=6.3 Hz, 2H), 2.37 (s, 3H), 2.18-2.09 (m, 2H), 2.08-2.01 (m, 2H), 0.95-0.86 (m, 2H), −0.12 (s, 9H).

Step B: methyl 5-{3-[2-fluoro-4-(4-methylpiper-
azin-1-yl)phenoxy]propyl}-2-(4-methyl-3-{[(2Z)-3-
{[2-(trimethylsilyl)ethoxy]methyl}-2,3-dihydro-1,3-
benzothiazol-2-ylidene]amino}-5H,6H,7H,8H-
pyrido[2,3-c]pyridazin-8-yl)-1,3-thiazole-4-carboxy-
late 1-Methylpiperazine (14.5 μL, 0.13 mmol, 1.5 eq) was added to a solution of the product from Step A (74 mg, 0.09 mmol, 1 eq), copper(I) iodide (1.66 mg, 0.01 mmol, 0.1 eq), potassium phosphate tribasic (37.1 mg, 0.17 mmol, 2 eq) and [(2,6-dimethylphenyl)carbamoyl]formic acid (3.38 mg, 0.02 mmol, 0.2 eq) in DMSO (2 mL) and the mixture was heated at 120° C. for 2 h under microwave irradiation. The reaction was allowed to cool to ambient temperature, partitioned between ethyl acetate and water, and the organic phase was washed with brine, dried (magnesium sulfate) and concentrated in vacuo. Purification by automated flash column chromatography (CombiFlash Rf, 4 g RediSep™ silica cartridge) eluting with a gradient of 0-8% methanol in dichloromethane afforded the desired product as a brown gum (30 mg, 0.04 mmol, 42%).

LC/MS ($C_{40}H_{51}FN_8O_4SiS_2$) 819 [M+H]f; RT 2.71 (LCMS-V-C)

$^1$H NMR (400 MHz, DMSO-d6) δ 7.82 (d, 1H), 7.48-7.38 (m, 2H), 7.27-7.20 (m, 1H), 7.03 (t, 1H), 6.84 (dd, 1H), 6.67-6.61 (m, 1H), 5.84 (s, 2H), 4.26 (t, J=5.7 Hz, 2H), 4.02 (t, J=6.2 Hz, 2H), 3.79 (s, 3H), 3.76-3.66 (m, 2H), 3.26 (t, 2H), 3.04-2.95 (m, 4H), 2.92-2.82 (m, 2H), 2.42-2.32 (m, 7H), 2.18 (s, 3H), 2.12-1.99 (m, 4H), 0.95-0.86 (m, 2H), −0.11 (s, 9H).

Step C: methyl 2-{3-[(1,3-benzothiazol-2-yl)
amino]-4-methyl-5H,6H,7H,8H-pyrido[2,3-c]
pyridazin-8-yl}-5-{3-[2-fluoro-4-(4-methylpiper-
azin-1-yl)phenoxy]propyl}-1,3-thiazole-4-
carboxylate To a solution of the product from Step B (116 mg, 0.14 mmol, 1 eq) in dichloromethane (7.5 mL), cooled to 0° C., was added trifluoroacetic acid (1.52 mL, 19.8 mmol, 140 eq) and the mixture was stirred for 24 h at ambient temperature. The reaction was diluted with dichloromethane (40 mL), washed with aqueous ammonia, dried (PTFE phase separator) and concentrated in vacuo. Purification by automated flash column chromatography (CombiFlash Rf, 4 g RediSep™ silica cartridge) eluting with a gradient of 0-10% methanol in dichloromethane afforded the desired product as a yellow gum (72 mg, 0.1 mmol, 74%).

LC/MS ($C_{34}H_{37}FN_8O_3S_2$) 689 [M+H]+; RT 2.01 (LCMS-V-C)

$^1$H NMR (400 MHz, DMSO-d6) δ 11.46 (br s, 1H), 7.89 (d, J=7.8 Hz, 1H), 7.56-7.44 (m, 1H), 7.38 (ddd, J=8.3, 7.3, 1.3 Hz, 1H), 7.24-7.16 (m, 1H), 7.04 (dd, J=9.9, 9.0 Hz, 1H), 6.85 (dd, J=14.6, 2.8 Hz, 1H), 6.69-6.61 (m, 1H), 4.27 (t, J=5.8 Hz, 2H), 4.08-3.99 (m, 2H), 3.80 (s, 3H), 3.31-3.23 (m, 2H), 3.05-2.96 (m, 4H), 2.89 (t, J=6.3 Hz, 2H), 2.42-2.36 (m, 4H), 2.35 (s, 3H), 2.19 (s, 3H), 2.13-2.00 (m, 4H).

Step D: 2-{3-[(1,3-benzothiazol-2-yl)amino]-4-
methyl-5H,6H,7H,8H-pyrido[2,3-c]pyridazin-8-yl}-
5-{3-[2-fluoro-4-(4-methylpiperazin-1-yl)phenoxy]
propyl}-1,3-thiazole-4-carboxylic acid To a solution of the product from Step C (72 mg, 0.1 mmol, 1 eq) in 1,4-dioxane (3 mL) was added lithium hydroxide monohydrate (43.9 mg, 1.05 mmol, 10 eq) and the mixture was heated at reflux for 3 h. Purification by automated flash column chromatography (CombiFlash Rf, 4 g RediSep™ silica cartridge) eluting with a gradient of 0-15% 7N methanolic ammonia in dichloromethane gave a solid that was triturated with diethyl ether, filtered and dried under vacuum to afford the desired product as a yellow solid (35 mg, 0.05 mmol, 50%).

HRMS-ESI (m/z) [M+H]+ calcd for $C_{33}H_{36}FN_8O_3S_2$: 675.2336, found 675.2364 Example 61: 2-{3-[(1,3-Benzothiazol-2-yl)amino]-4-methyl-5H,6H,7H,8H-pyrido[2,3-c]pyridazin-8-yl}-5-[3-({3-[(dimethylamino)methyl]-5-fluoro-1-methyl-1H-indol-6-yl}oxy)propyl]-1,3-thiazole-4-carboxylic acid Step A: methyl 5-[3-({3-[(dimethylamino)methyl]-
5-fluoro-1-methyl-1H-indol-6-yl}oxy)propyl]-2-(4-
methyl-3-{[(2Z)-3-{[2-(trimethylsilyl)ethoxy]
methyl}-2,3-dihydro-1,3-benzothiazol-2-ylidene]
amino}-5H,6H,7H,8H-pyrido[2,3-c]pyridazin-8-yl)-
1,3-thiazole-4-carboxylate The product from Preparation 3b (120 mg, 0.19 mmol, 1 eq) was taken up in toluene (15 mL) and the product from Preparation 4h (67 mg, 0.26 mmol, 1.35 eq) was added, followed by triphenylphosphine (100 mg, 0.38 mmol, 2 eq) and di-tert-butyl azodicarboxylate (88.2 mg, 0.38 mmol, 2 eq) and the mixture was stirred at 50° C. overnight. The reaction was partitioned between dichloromethane and water, and the organic phase was washed with brine, dried (PTFE phase separator) and concentrated in vacuo. Purification by automated flash column chromatography (CombiFlash Rf, 4 g RediSep™ silica cartridge) eluting with a gradient of 0-10% methanol in dichloromethane afforded the desired product as a beige solid (18 mg, 0.02 mmol, 11%).

LC/MS ($C_{41}H_{51}FN_8O_4SiS_2$) 831 [M+H]V; RT 2.73 (LCMS-V-C)

$^1$H NMR (400 MHz, DMSO-d6) δ 7.81 (d, J=7.7 Hz, 1H), 7.47-7.43 (m, 2H), 7.40-7.33 (m, 1H), 7.28-7.21 (m, 1H), 7.15 (d, J=11.6 Hz, 1H), 6.84 (d, J=7.4 Hz, 1H), 5.85 (s, 2H), 4.28 (t, 2H), 4.16 (t, J=6.3 Hz, 2H), 3.79 (s, 3H), 3.76-3.71 (m, 2H), 3.69 (s, 2H), 3.63 (s, 3H), 3.48-3.41 (m, 4H), 3.88 (t, 2H), 2.38 (s, 3H), 2.08-2.00 (m, 2H), 1.46 (s, 6H), 1.35 0.95-0.86 (m, 2H), −0.11 (s, 9H).

Step B: 2-{3-[(1,3-benzothiazol-2-yl)amino]-4-methyl-5H,6H,7H,8H-pyrido[2,3-c]pyridazin-8-yl}-5-[3-({3-[(dimethylamino)methyl]-5-fluoro-1-methyl-1H-indol-6-yl}oxy)propyl]-1,3-thiazole-4-carboxylic acid A solution of the product from Step A (18 mg, 0.02 mmol, 1 eq) in dichloromethane (1 mL) was cooled to 0° C. and trifluoroacetic acid (1 mL, 13 mmol, 600 eq) was added and the mixture was stirred for 4 h at ambient temperature. Dichloromethane (10 mL) was added and the solution was cooled to 0° C., washed with aqueous ammonia, dried (PTFE phase separator) and concentrated in vacuo. The residue was suspended in 1,4-dioxane (2 mL), lithium hydroxide monohydrate (9.1 mg, 0.22 mmol, 10 eq) was added and the mixture was heated at 70° C. overnight. Purification by preparative HPLC (HPLC-V-B1) afforded the desired product as a yellow solid (4.5 mg, 0.01 mmol, 30%), as a formic acid salt.

HRMS-ESI (m/z) [M+H]+ calcd for $C_{34}H_{36}FN_8O_3S_2$: 687.2336, found 687.2362

Example 62: 2-{3-[(1,3-Benzothiazol-2-yl)amino]-4-methyl-5H,6H,7H,8H-pyrido[2,3-c]pyridazin-8-yl}-5-(3-{4-[4-(dimethylamino)butyl]-2-fluorophenoxy}propyl)-1,3-thiazole-4-carboxylic acid

Step A: methyl 5-(3-{4-[4-(dimethylamino)butyl]-2-fluorophenoxy}propyl)-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3b (120 mg, 0.19 mmol, 1 eq) in toluene (5 mL) was added the product from Preparation 4i (107 mg, 0.51 mmol, 2.65 eq), di-tert-butyl azodicarboxylate (88 mg, 0.38 mmol, 2 eq) and triphenylphosphine (100 mg, 0.38 mmol, 2 eq) and the mixture was heated at 50° C. for 20 h. The reaction was partitioned between dichloromethane and water, and the organic phase was dried (PTFE phase separator) and concentrated in vacuo. Purification by automated flash column chromatography (CombiFlash Rf, 4 g RediSep™ silica cartridge) eluting with a gradient of 0-8% methanol in dichloromethane afforded the desired product as a yellow oil (133 mg, 0.16 mmol, 85%).

LC/MS ($C_{14}H_{54}FN_7O_4SiS_2$) 821 [M+H]$^+$; RT 2.74 (LCMS-V-C)

$^1$H NMR (400 MHz, DMSO-d6) δ 7.85-7.78 (m, 1H), 7.48-7.38 (m, 2H), 7.27-7.20 (m, 1H), 7.11-7.01 (m, 2H), 6.95-6.89 (m, 1H), 5.84 (s, 2H), 4.26 (t, J=6.0 Hz, 2H), 4.07 (t, 2H), 3.78 (s, 3H), 3.71 (dd, 2H), 3.28 (dd, J=15.9, 8.4 Hz, 2H), 2.87 (t, J=6.2 Hz, 2H), 2.37 (s, 3H), 2.21-2.08 (m, 4H), 2.08-2.01 (m, 8H), 1.55-1.42 (m, 2H), 1.41-1.27 (m, 2H), 0.95-0.87 (m, 2H), −0.11 (s, 9H).

Step B: methyl 2-{3-[(1,3-benzothiazol-2-yl)amino]-4-methyl-5H,6H,7H,8H-pyrido[2,3-c]pyridazin-8-yl}-5-(3-{4-[4-(dimethylamino)butyl]-2-fluorophenoxy}propyl)-1,3-thiazole-4-carboxylate A solution of the product from Step A (133 mg, 0.16 mmol, 1 eq) in dichloromethane (6 mL) was cooled to 0° C. and trifluoroacetic acid (1.24 mL, 16.2 mmol, 100 eq) was added and the mixture was stirred for 24 h at ambient temperature. dichloromethane (40 mL) was added and the solution was washed with saturated aqueous ammonium chloride, dried (PTFE phase separator) and concentrated in vacuo. Purification by automated flash column chromatography (CombiFlash Rf, 4 g RediSep™ silica cartridge) eluting with a gradient of 0-14% methanol in dichloromethane afforded the desired product as a yellow gum (81 mg, 0.12 mmol, 72%).

LC/MS ($C_{35}H_{40}FN_7O_3S_2$) 690 [M+H]$^+$; RT 2.14 (LCMS-V-C)

$^1$H NMR (400 MHz, DMSO-d6) δ 7.87 (dd, J=7.8, 1.2 Hz, 1H), 7.49 (d, J=8.0 Hz, 1H), 7.37 (ddd, J=8.2, 7.2, 1.3 Hz, 1H), 7.19 (td, J=7.5, 1.2 Hz, 1H), 7.09-7.01 (m, 2H), 6.94-6.87 (m, 1H), 4.25 (dd, J=7.3, 4.5 Hz, 2H), 4.07 (t, J=6.2 Hz, 2H), 3.78 (s, 3H), 3.27 (t, J=7.7 Hz, 2H), 2.87 (t, J=6.3 Hz, 2H), 2.48-2.43 (m, 2H), 2.33 (s, 3H), 2.18-2.07 (m, 4H), 2.08-1.98 (m, 8H), 1.55-1.41 (m, 2H), 1.40-1.26 (m, 2H).

Step C: 2-{3-[(1,3-benzothiazol-2-yl)amino]-4-methyl-5H,6H,7H,8H-pyrido[2,3-c]pyridazin-8-yl}-5-(3-{4-[4-(dimethylamino)butyl]-2-fluorophenoxy}propyl)-1,3-thiazole-4-carboxylic acid To a solution of the product from Step B (81 mg, 0.12 mmol, 1 eq) in 1,4-dioxane (3 mL) was added lithium hydroxide monohydrate (49.3 mg, 1.17 mmol, 10 eq) and the mixture was heated at 70° C. overnight. Purification by automated flash column chromatography (CombiFlash Rf, 4 g RediSep™ silica cartridge) eluting with a gradient of 0-20% 7N methanolic ammonia in dichloromethane afforded the desired product as a yellow solid (48.3 mg, 0.07 mmol, 61%).

HRMS-ESI (m/z) [M+H]+ calcd for $C_{34}H_{39}FN_7O_3S_2$: 676.2540, found 676.2569

Example 63: 2-[3-(1,3-Benzothiazol-2-ylamino)-4-methyl-6,7-dihydro-5H-pyrido[2,3-c]pyridazin-8-yl]-5-[3-[4-[3-[(1S,5R)-6,6-difluoro-3-azabicyclo[3.1.0]hexan-3-yl]prop-1-ynyl]-2-fluoro-phenoxy]propyl]thiazole-4-carboxylic acid

Step A: methyl 2-[3-(1,3-benzothiazol-2-ylamino)-4-methyl-6,7-dihydro-5H-pyrido[2,3-c]pyridazin-8-yl]-5-[3-[4-[3-[(1S,5R)-6,6-difluoro-3-azabicyclo[3.1.0]hexan-3-yl]prop-1-ynyl]-2-fluoro-phenoxy]propyl]thiazole-4-carboxylate Using Propargylic amine preparation General Procedure starting from 100 mg of Preparation 3d (0.155 mmol, 1 eq.) as the appropriate propargylic alcohol and (1S,5R)-6,6-difluoro-3-azabicyclo[3.1.0]hexane (20 eq.), 61 mg of the desired product (52%) was obtained.

Step B: 2-[3-(1,3-Benzothiazol-2-ylamino)-4-methyl-6,7-dihydro-5H-pyrido[2,3-c]pyridazin-8-yl]-5-[3-[4-[3-[(1S,5R)-6,6-difluoro-3-azabicyclo[3.1.0]hexan-3-yl]prop-1-ynyl]-2-fluoro-phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{33}F_3N_7O_3S_2$: 732.2033, found 732.2023.

Example 64: 2-{3-[(1,3-Benzothiazol-2-yl)amino]-4-methyl-5H,6H,7H,8H-pyrido[2,3-c]pyridazin-8-yl}-5-(3-{2-fluoro-4-[2-(methylamino)ethyl]phenoxy}propyl)-1,3-thiazole-4-carboxylic acid

Step A: methyl 5-{3-[4-(2-{[(tert-butoxy)carbonyl](methyl)amino}ethyl)-2-fluorophenoxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3b (80 mg, 0.13 mmol, 1 eq) in toluene (5 mL) was added the product from Preparation 4j (48 mg, 0.18 mmol, 1.4 eq), di-tert-butyl azodicarboxylate (58.8 mg, 0.26 mmol, 2 eq) and triphenylphosphine (67 mg, 0.26 mmol, 2 eq) and the mixture was heated at 50° C. overnight. The reaction was partitioned between dichloromethane and water, separated (phase separator) and the organic phase was concentrated in vacuo. Purification by automated flash column chromatography (CombiFlash Rf, 4 g RediSep™ silica cartridge) eluting with a gradient of 0-100% ethyl acetate in iso-heptane afforded the desired product as a colourless gum (77 mg, 0.09 mmol, 69%).

LC/MS ($C_{43}H_{56}FN_7O_6SiS_2$) 878 [M+H]+; RT 3.28 (LCMS-V-C)

$^1$H NMR (400 MHz, DMSO-d6) δ 7.82 (dt, J=7.6, 0.9 Hz, 1H), 7.48-7.38 (m, 2H), 7.24 (ddd, J=8.3, 6.7, 1.8 Hz, 1H), 7.13-7.01 (m, 2H), 6.96-6.86 (m, 1H), 5.84 (s, 2H), 4.27 (t, J=5.7 Hz, 2H), 4.08 (t, 2H), 3.78 (s, 2H), 3.75-3.67 (m, 2H), 3.31-3.22 (m, 4H), 2.88 (t, J=6.2 Hz, 2H), 2.71 (s, 3H), 2.69-2.61 (m, 2H), 2.37 (s, 3H), 2.17-2.06 (m, 2H), 2.05-2.00 (m, 2H), 1.24 (s, 9H), 0.95-0.86 (m, 2H), −0.12 (s, 9H).

Step B: methyl 2-{3-[(1,3-benzothiazol-2-yl)amino]-4-methyl-5H,6H,7H,8H-pyrido[2,3-c]pyridazin-8-yl}-5-(3-{2-fluoro-4-[2-(methylamino)ethyl]phenoxy}propyl)-1,3-thiazole-4-carboxylate A solution of the product from Step A (77 mg, 0.09 mmol, 1 eq) in dichloromethane (4 mL) was cooled to 0° C. and trifluoroacetic acid (0.81 mL, 10.5 mmol, 120 eq) was added and the mixture was stirred for 24 h at ambient temperature. The reaction was diluted with dichloromethane, washed with aqueous ammonia, dried (PTFE phase separator) and concentrated in vacuo. Purification by automated flash column chromatography (CombiFlash Rf, 4 g RediSep™ silica cartridge) eluting with a gradient of 0-18% methanol in dichloromethane afforded the desired product as a yellow solid (39 mg, 0.06 mmol, 69%).

LC/MS ($C_{32}H_{34}FN_7O_3S_2$) 648 [M+H]$^+$; RT 2.02 (LCMS-V-C)

$^1$H NMR (400 MHz, DMSO-d6) δ 7.91-7.84 (m, 1H), 7.49 (d, J=8.0 Hz, 1H), 7.41-7.33 (m, 1H), 7.19 (td, J=7.5, 1.2 Hz, 1H), 7.12-7.03 (m, 2H), 6.94 (dd, J=8.8, 1.9 Hz, 1H), 4.27 (dd, J=7.1, 4.5 Hz, 2H), 4.09 (t, J=6.2 Hz, 2H), 3.79 (s, 3H), 3.31-3.21 (m, 2H), 2.88 (t, J=6.2 Hz, 2H), 2.68-2.57 (m, 4H), 2.35 (s, 3H), 2.25 (s, 3H), 2.17-2.01 (m, 4H).

Step C: 2-{3-[(1,3-benzothiazol-2-yl)amino]-4-methyl-5H,6H,7H,8H-pyrido[2,3-c]pyridazin-8-yl}-5-(3-{2-fluoro-4-[2-(methylamino)ethyl]phenoxy}propyl)-1,3-thiazole-4-carboxylic acid To a solution of the product from Step B (39 mg, 0.06 mmol, 1 eq) in 1,4-dioxane (2 mL) was added lithium hydroxide monohydrate (25.3 mg, 0.6 mmol, 10 eq) and the mixture was heated at reflux for 4 h. Purification by automated flash column chromatography (CombiFlash Rf, 4 g RediSep™ silica cartridge) eluting with a gradient of 0-25% 7N methanolic ammonia in dichloromethane afforded a solid that was suspended in ethyl acetate (2 mL) and hydrochloric acid (4M in 1,4-dioxane; 68.9 µL, 0.28 mmol, 4.58 eq) was added. The mixture was stirred for 10 mins before collecting the solids by filtration and drying under vacuum afforded the desired product as a yellow solid (17.2 mg, 0.03 mmol, 45%), as a hydrochloric acid salt.

HRMS-ESI (m/z) [M+H]+ calcd for $C_{31}H_{33}FN_7O_3S_2$: 634.2070, found 634.2093.

Example 65: 2-{3-[(1,3-Benzothiazol-2-yl)amino]-4-methyl-6-[2-(methylamino)ethoxy]-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylic acid

Step A: 4-methylmorpholin-3-one

A solution of 2-(methylamino)ethanol (5.32 mL, 66.6 mmol, 1 eq) in ethanol (100 mL) and 35% aqueous sodium hydroxide (6.25 mL) was cooled to 15-20° C. and chloroacetyl chloride (13.3 mL, 166 mmol, 2.5 eq) and 35% aqueous sodium hydroxide (22 mL) were added simultaneously with vigorous stirring over 1 h. The mixture was stirred for 20 min, then neutralised with aqueous hydrochloric acid and extracted with dichloromethane (3×100 mL). The combined organic extracts were washed with water, dried (PTFE phase separator) and concentrated in vacuo. Purification by automated flash column chromatography (CombiFlash Rf, 80 g RediSep™ silica cartridge) eluting with a gradient of 0-100% ethyl acetate in iso-heptane afforded the desired product as a colourless oil (4.4 g, 38.2 mmol, 58%).

$^1$H NMR (400 MHz, DMSO-d6) δ 4.00 (s, 2H), 3.84-3.78 (m, 2H), 3.36-3.29 (m, 2H), 2.86 (s, 3H).

Step B: 2-(but-2-yn-1-yl)-4-methylmorpholin-3-one

To a solution of diisopropylamine (6.45 mL, 45.9 mmol, 1.2 eq) in tetrahydrofuran (130 mL), cooled to −78° C., was added n-butyllithium (2.06M in hexanes; 20.4 mL, 42 mmol, 1.1 eq) dropwise. After 1 minute a solution of the product from Step A (4.4 g, 38.2 mmol, 1 eq) in tetrahydrofuran (30 mL) was added dropwise. After 15 minutes a solution of 1-bromo-2-butyne (4.02 mL, 45.9 mmol, 1.2 eq) in tetrahydrofuran (15 mL) was added dropwise and the mixture was stirred at −78° C. for 1 h then allowed to warm to ambient temperature. Saturated aqueous ammonium chloride was added and the mixture was extracted with ethyl acetate (×3), and the combined organic extracts were dried (magnesium sulfate) and concentrated in vacuo. Purification by automated flash column chromatography (CombiFlash Rf, 80 g RediSep™ silica cartridge) eluting with a gradient of 0-100% ethyl acetate in iso-heptane afforded the desired product as a yellow oil (5.15 g, 30.8 mmol, 81%).

$^1$H NMR (400 MHz, DMSO-d6) δ 4.09 (dd, J=7.6, 3.5 Hz, 1H), 4.01-3.94 (m, 1H), 3.76 (ddd, J=11.9, 10.0, 3.6 Hz, 1H), 3.52-3.41 (m, 1H), 3.26-3.18 (m, 1H), 2.86 (s, 3H), 2.67-2.58 (m, 1H), 2.57-2.44 (m, 1H), 1.73 (t, J=2.6 Hz, 3H).

Step C: 2-[2-(methylamino)ethoxy]hex-4-ynoic acid

To a solution of the product from Step B (3.25 g, 19.4 mmol, 1 eq) in methanol (110 mL) was added 1M aqueous lithium hydroxide (60.3 mL, 60.3 mmol, 3.1 eq) and the mixture was heated at reflux overnight. The reaction was concentrated in vacuo to afford the desired product as an orange gum (5.15 g, 27.8 mmol, 100%) that was used directly in the subsequent step without further characterisation.

Step D: 2-[2-({[(9H-fluoren-9-yl)methoxy]carbonyl}(methyl)amino)ethoxy]hex-4-ynoic acid To a solution of the product from Step C (5.15 g, 27.8 mmol, 1 eq) in 1,4-dioxane (45 mL) and water (160 mL) was added potassium carbonate (15.4 g, 111 mmol, 4 eq) at 0° C., followed by 9H-fluoren-9-yl-methyl chloroformate (7.19 g, 27.8 mmol, 1 eq) and the mixture was allowed to warm to ambient temperature and stir for 2 h. The reaction was partitioned between water and ethyl acetate, and the aqueous phase was acidified with aqueous hydrochloric acid to pH 2-3 and extracted with ethyl acetate (3×300 mL). The combined organic extracts were washed with brine, dried (magnesium sulfate) and concentrated in vacuo. Purification by automated flash column chromatography (CombiFlash Rf, 120 g RediSep™ silica cartridge) eluting with a gradient of 0-20% methanol in dichloromethane afforded the desired product as a dark yellow gum (7.06 g, 17.3 mmol, 62%).

LC/MS ($C_{24}H_{25}NO_5$) 408 [M+H]$^+$; RT 0.74 (LCMS-V-B2)

$^1$H NMR (400 MHz, DMSO-d6) δ 7.90 (t, J=6.8 Hz, 2H), 7.65 (dd, J=7.5, 1.1 Hz, 2H), 7.42 (td, J=7.4, 3.0 Hz, 2H), 7.34 (td, J=7.4, 1.3 Hz, 2H), 4.43-4.22 (m, 3H), 3.50-3.42 (m, 1H), 3.39-3.28 (m, 1H), 3.26-3.15 (m, 3H), 2.90-2.82 (m, 3H), 2.51-2.44 (m, 2H), 1.71 (dt, J=13.8, 2.5 Hz, 3H).

Step E: (9H-fluoren-9-yl)methyl N-{2-[(1-hydroxy-hex-4-yn-2-yl)oxy]ethyl}-N-methylcarbamate A solution of the product from Step D (7.06 g, 17.33 mmol, 1 eq) in tetrahydrofuran (120 mL) was cooled to −10° C., then triethylamine (2.65 mL, 19.1 mmol, 1.1 eq) and isobutyl chloroformate (2.7 mL, 20.8 mmol, 1.2 eq) in THF (40 mL) were added dropwise. The precipitate was removed by filtration and the solution was cooled to −10° C. Sodium borohydride (2.62 g, 69.3 mmol, 4 eq) in water (40 mL) was added dropwise and the mixture was stirred for 1 h at −10° C. The pH of the solution was adjusted to pH 5 using 1N aqueous hydrochloric acid, and then adjusted to pH 10 using saturated aqueous sodium bicarbonate. The layers were separated and the organic phase was successively washed water (100 mL) and brine (50 mL), dried (magnesium sulfate) and concentrated in vacuo. Purification by automated flash column chromatography (CombiFlash Rf, 80 g RediSep™ silica cartridge) eluting with a gradient of 0-100% ethyl acetate in iso-heptane afforded the desired product as a colourless gum (4.64 g, 11.8 mmol, 68%).

LC/MS ($C_{24}H_{27}NO_4$) 394 [M+H]$^+$; RT 0.77 (LCMS-V-B2)

$^1$H NMR (400 MHz, DMSO-d6) δ 7.90 (d, J=7.5 Hz, 2H), 7.65 (dt, J=7.4, 0.9 Hz, 2H), 7.43 (t, J=7.4 Hz, 2H), 7.35 (td, J=7.4, 1.2 Hz, 2H), 4.68-4.60 (m, 1H), 4.39 (d, J=6.0 Hz, 1H), 4.34 (d, J=6.7 Hz, 1H), 4.28 (t, J=6.4 Hz, 1H), 3.60-3.51 (m, 1H), 3.46-3.36 (m, 2H), 3.34-3.28 (m, 2H), 3.19 (dd, J=16.6, 5.5 Hz, 2H), 2.84 (d, J=10.8 Hz, 3H), 2.38-2.15 (m, 2H), 1.71 (t, J=2.5 Hz, 3H).

Step F: (9H-fluoren-9-yl)methyl N-[2-({1-[(tert-butyldiphenylsilyl)oxy]hex-4-yn-2-yl}oxy)ethyl]-N-methylcarbamate To a cooled solution of the product from Step E (4.64 g, 11.8 mmol, 1 eq) and imidazole (1.56 mL, 23.6 mmol, 2 eq) in dichloromethane (200 mL) was added tert-butyl(chloro)diphenylsilane (6.13 mL, 23.6 mmol, 2 eq) dropwise and the mixture was allowed to warm to ambient temperature and stir overnight. The reaction was quenched with 2M aqueous ammonium chloride and the mixture was extracted with dichloromethane (3×200 mL). The combined organic extracts were washed with brine, dried (PTFE phase separator) and concentrated in vacuo. Purification by automated flash column chromatography (CombiFlash Rf, 120 g RediSep™ silica cartridge) eluting with a gradient of 0-25% ethyl acetate in iso-heptane afforded the desired product as a colourless gum (5.86 g, 9.27 mmol, 79%).

LC/MS ($C_{40}H_{45}NO_4Si$) 632 [M+H]$^+$; RT 1.38 (LCMS-V-B2)

$^1$H NMR (400 MHz, DMSO-d6) δ 7.87 (dd, J=20.0, 7.5 Hz, 2H), 7.67-7.56 (m, 6H), 7.53-7.39 (m, 7H), 7.39-7.22 (m, 3H), 4.38 (t, J=4.8 Hz, 1H), 4.31 (s, 1H), 4.24 (t, J=5.7 Hz, 1H), 3.73-3.61 (m, 1H), 3.60-3.44 (m, 2H), 3.34-3.29 (m, 2H), 3.29-3.18 (m, 1H), 3.16-3.06 (m, 1H), 2.81 (d, J=14.1 Hz, 3H), 2.43-2.26 (m, 2H), 1.69 (t, J=2.4 Hz, 3H), 0.98 (s, 9H).

Step G: (9H-fluoren-9-yl)methyl N-[2-({1-[(tert-butyldiphenylsilyl)oxy]-3-(3,6-dichloro-5-methylpyridazin-4-yl)propan-2-yl}oxy)ethyl]-N-methylcarbamate A solution of the product from Step F (5.86 g, 9.27 mmol, 1 eq) and 3,6-dichloro-1,2,4,5-tetrazine (5.6 g, 37.1 mmol, 4 eq) in toluene (130 mL) was heated at 150° C. overnight in a sealed flask. The reaction was concentrated in vacuo and purification by automated flash column chromatography (CombiFlash Rf, 120 g RediSep™ silica cartridge) eluting with a gradient of 0-30% ethyl acetate in iso-heptane afforded the desired product as a pink foam (2.99 g, 3.97 mmol, 43%).

LC/MS ($C_{42}H_{45}Cl_2N_3O_4Si$) 754 [M+H]; RT 1.37 (LCMS-V-B2)

$^1$H NMR (400 MHz, DMSO-d6) δ 7.90 (d, J=7.7 Hz, 1H), 7.78 (d, J=7.4 Hz, 1H), 7.68-7.59 (m, 5H), 7.57-7.50 (m, 1H), 7.47-7.41 (m, 6H), 7.45-7.37 (m, 1H), 7.36-7.28 (m, 2H), 7.23 (t, J=7.5 Hz, 1H), 4.30 (d, J=5.7 Hz, 1H), 4.27-4.11 (m, 2H), 3.81-3.60 (m, 3H), 3.55-3.45 (m 1H), 3.20-2.98 (m, 4H), 2.89-2.77 (m, 1H), 2.58 (d, J=23.0 Hz, 3H), 2.39 (d, J=13.1 Hz, 3H), 1.01 (s, 9H).

Step H: 4-{3-[(tert-butyldiphenylsilyl)oxy]-2-[2-(methylamino)ethoxy]propyl}-3,6-dichloro-5-methylpyridazine A solution of the product from Step G (2.79 g, 3.7 mmol, 1 eq) and diethylamine (0.77 mL, 7.39 mmol, 2 eq) in acetonitrile (60 mL) was stirred at ambient temperature overnight. Water was added and the mixture was extracted with ethyl acetate (3×70 mL). The combined organic extracts were washed with brine (100 mL), dried (magnesium sulfate) and concentrated in vacuo. Purification by automated flash column chromatography (CombiFlash Rf, 40 g RediSep™ silica cartridge) eluting with a gradient of 0-16% methanol in dichloromethane afforded the desired product as an orange/pink gum (1.9 g, 3.57 mmol, 96%).

LC/MS ($C_{27}H_{35}Cl_2N_3O_2Si$) 532 [M+H]; RT 0.84 (LCMS-V-B2)

$^1$H NMR (400 MHz, DMSO-d6) δ 7.69-7.62 (m, 4H), 7.54-7.41 (m, 6H), 3.83-3.60 (m, 3H), 3.42-3.36 (m, 1H), 3.16-2.97 (m, 3H), 2.45 (s, 3H), 2.39-2.23 (m, 2H), 2.06 (s, 3H), 1.02 (s, 9H).

Step I: tert-butyl N-[2-({1-[(tert-butyldiphenylsilyl)oxy]-3-(3,6-dichloro-5-methylpyridazin-4-yl)propan-2-yl}oxy)ethyl]-N-methylcarbamate To a solution of the product from Step H (1.9 g, 3.57 mmol, 1 eq) in dichloromethane (100 mL) was added di-tert-butyl dicarbonate (1.53 mL, 7.14 mmol, 2 eq) followed by triethylamine (1.99 mL, 14.3 mmol, 4 eq) and the mixture was stirred at ambient temperature for 4 h. The reaction was partitioned between dichloromethane and water, and the aqueous phase was acidified to pH 4 and extracted with dichloromethane (3×80 mL). The combined organic extracts were washed with brine, dried (PTFE phase separator) and concentrated in vacuo. Purification by automated flash column chromatography (CombiFlash Rf, 40 g RediSep™ silica cartridge) eluting with a gradient of 0-25% ethyl acetate in iso-heptane afforded the desired product as a colourless gum (1.83 g, 2.9 mmol, 81%).

LC/MS ($C_{32}H_{43}Cl_2N_3O_4Si$) 532 [M-Boc+H]$^+$; RT 1.33 (LCMS-V-B2)

$^1$H NMR (400 MHz, DMSO-d6) δ 7.69-7.62 (m, 4H), 7.54-7.41 (m, 6H), 3.76 (qd, J=10.7, 4.7 Hz, 2H), 3.66 (d, J=5.5 Hz, 1H), 3.44 (q, J=7.9, 6.3 Hz, 1H), 3.20-3.10 (m, 3H), 3.04 (dd, J=14.0, 4.1 Hz, 2H), 2.58 (s, 3H), 2.44 (s, 3H), 1.31 (d, J=22.6 Hz, 9H), 1.02 (s, 9H).

Step J: tert-butyl N-(2-{[1-(3,6-dichloro-5-methylpyridazin-4-yl)-3-hydroxypropan-2-yl]oxy}ethyl)-N-methylcarbamate A solution of the product from Step I (1.83 g, 2.9 mmol, 1 eq) in tetrahydrofuran (75 mL) was cooled to 0° C. before the addition of tetrabutylammonium fluoride (1M in tetrahydrofuran; 2.9 mL, 2.9 mmol, 1 eq) and stirring at 0° C. for 30 min, then at ambient temperature for 1 h. The reaction was partitioned between dichloromethane and water, and the aqueous phase was extracted with dichloromethane (×2). The combined organic extracts were washed with brine, dried (PTFE phase separator) and concentrated in vacuo. Purification by automated flash column chromatography (CombiFlash Rf, 24 g RediSep™ silica cartridge) eluting with a gradient of 0-100% ethyl acetate in iso-heptane afforded the desired product as a pale orange gum (0.73 g, 1.86 mmol, 64%).

$^1$H NMR (400 MHz, DMSO-d6) δ 4.93 (t, J=5.5 Hz, 1H), 3.62-3.44 (m, 4H), 3.23 (dt, J=9.6, 6.0 Hz, 1H), 3.11 (d, J=23.9 Hz, 2H), 3.02 (dd, J=6.5, 2.0 Hz, 2H), 2.60 (d, J=8.1 Hz, 3H), 2.45 (s, 3H), 1.35 (d, J=13.0 Hz, 9H).

Step K: methyl 2-{[(tert-butoxy)carbonyl][2-(2-{[(tert-butoxy)carbonyl](methyl)amino}ethoxy)-3-(3,6-dichloro-5-methylpyridazin-4-yl)propyl]amino}-5-(3-{4-[3-(dimethylamino)prop-1-yn-1-yl]-2-fluorophenoxy}propyl)-1,3-thiazole-4-carboxylate To a solution of the product from Step J (125 mg, 0.32 mmol, 1 eq) in toluene (20 mL) was added the product from Preparation 1c (171 mg, 0.35 mmol, 1.1 eq), di-tert-butyl azodicarboxylate (146 mg, 0.63 mmol, 2 eq) and triphenylphosphine (166 mg, 0.63 mmol, 2 eq) and the mixture was stirred at 50° C. for 1 h. The reaction was partitioned between dichloromethane and water, and the aqueous phase was extracted with dichloromethane (×2), and the combined organic extracts were washed with brine, dried (magnesium sulfate) and concentrated in vacuo. Purification by automated flash column chromatography (CombiFlash Rf, 12 g RediSep™ silica cartridge) eluting with a gradient of 0-100% ethyl acetate in iso-heptane afforded the desired product as a pale yellow gum (282 mg, 0.32 mmol, 102%). LC/MS ($C_{40}H_{53}Cl_2FN_6O_8S$) 867 [M+H]$^+$; RT 0.97 (LCMS-V-B2)

$^1$H NMR (400 MHz, DMSO-d6) δ 7.30 (dd, 1H), 7.23-7.17 (m, 1H), 7.12 (t, 1H), 4.29 (dd, J=13.9, 5.7 Hz, 1H), 4.10 (t, J=6.0 Hz, 2H), 3.96-3.87 (m, 1H), 3.74 (s, 3H), 3.61-3.48 (m, 1H), 3.42 (s, 3H), 3.32 (s, 2H), 3.25 (dt, J=7.1, 3.9 Hz, 3H), 3.16-2.99 (m, 2H), 2.97-2.89 (m, 1H), 2.58 (d, J=11.6 Hz, 2H), 2.45 (s, 3H), 2.23 (s, 6H), 2.10 (t, J=6.9 Hz, 2H), 1.52 (s, 9H), 1.31 (d, J=39.6 Hz, 9H).

Step L: methyl 2-{[2-(2-{[(tert-butoxy)carbonyl](methyl)amino}ethoxy)-3-(3,6-dichloro-5-methylpyridazin-4-yl)propyl]amino}-5-(3-{4-[3-(dimethylamino)prop-1-yn-1-yl]-2-fluorophenoxy}propyl)-1,3-thiazole-4-carboxylate A solution of the product from Step K (275 mg, 0.32 mmol, 1 eq) in 1,1,1,3,3,3-hexafluoro-2-propanol (2.5 mL, 23.7 mmol, 74.7 eq) was heated at 100° C. for 60 min under microwave irradiation. The reaction was concentrated in vacuo and purification by automated flash column chromatography (CombiFlash Rf, 12 g RediSep™ silica cartridge) eluting with a gradient of 0-7% methanol in dichloromethane afforded the desired product as a white solid (154 mg, 0.2 mmol, 63%).

LC/MS ($C_{35}H_{45}Cl_2FN_6O_6S$) 767 [M+H]$^+$; RT 0.70 (LCMS-V-B2)

$^1$H NMR (400 MHz, DMSO-d6) δ 7.83 (br s, 1H), 7.30 (dd, J=11.9, 2.0 Hz, 1H), 7.24-7.17 (m, 1H), 7.12 (t, J=8.7 Hz, 1H), 4.08 (t, J=6.1 Hz, 2H), 3.82 (dt, J=9.0, 4.5 Hz, 1H), 3.70 (s, 3H), 3.60-3.49 (m, 1H), 3.46-3.39 (m, 4H), 3.33 (s, 2H), 3.29-3.18 (m, 1H), 3.14 (t, 2H), 3.10-3.02 (m, 2H), 2.98 (dd, J=13.9, 3.8 Hz, 1H), 2.64-2.53 (m, 2H), 2.44 (s, 3H), 2.23 (s, 6H), 2.07-1.95 (m, 2H), 1.32 (d, J=30.8 Hz, 9H).

Step M: methyl 2-[6-(2-{[(tert-butoxy)carbonyl](methyl)amino}ethoxy)-3-chloro-4-methyl-5H,6H,7H,8H-pyrido[2,3-c]pyridazin-8-yl]-5-(3-{4-[3-(dimethylamino)prop-1-yn-1-yl]-2-fluorophenoxy}propyl)-1,3-thiazole-4-carboxylate To a solution of the product from Step L (154 mg, 0.2 mmol, 1 eq) in 1,4-dioxane (14 mL) was added cesium carbonate (131 mg, 0.4 mmol, 2 eq), N,N-diisopropylethylamine (0.07 mL, 0.4 mmol, 2 eq) and bis(di-tert-butyl(4-dimethylaminophenyl)phosphine) dichloropalladium(II) (14.2 mg, 0.02 mmol, 0.1 eq) and the mixture was heated at 80° C. for 45 min. The reaction was partitioned between dichloromethane and water, and the aqueous phase was extracted with dichloromethane (×2). The combined organic extracts were washed with brine, dried (magnesium sulfate) and concentrated in vacuo. Purification by automated flash column chromatography (CombiFlash Rf, 12 g RediSep™ silica cartridge) eluting with a gradient of 0-8% methanol in dichloromethane afforded the desired product as a cream solid (136 mg, 0.19 mmol, 93%).

LC/MS ($C_{35}H_{44}ClFN_6O_6S$) 731 [M+H]$^+$; RT 0.75 (LCMS-V-B2)

$^1$H NMR (400 MHz, DMSO-d6) δ 7.31 (dt, J=12.0, 1.9 Hz, 1H), 7.25-7.19 (m, 1H), 7.14 (t, 1H), 4.86 (dd, 1H), 4.25 (s, 1H), 4.13 (t, J=6.2 Hz, 2H), 3.93 (d, J=13.5 Hz, 1H), 3.78 (s, 3H), 3.56 (t, J=5.6 Hz, 2H), 3.42 (s, 3H), 3.32 (s, 2H), 3.30-3.23 (m, 2H), 3.21-3.09 (m, 2H), 3.08-3.00 (m, 1H), 2.58-2.52 (m, 1H), 2.34 (s, 3H), 2.23 (s, 6H), 2.12 (p, J=6.7 Hz, 2H), 1.27 (d, J=28.5 Hz, 9H).

Step N: methyl 2-{3-[(1,3-benzothiazol-2-yl)amino]-6-(2-{[(tert-butoxy)carbonyl](methyl)amino}ethoxy)-4-methyl-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylate To a solution of the product from Step M (136 mg, 0.19 mmol, 1 eq) in cyclohexanol (4.5 mL) was added 2-aminobenzothiazole (55.7 mg, 0.37 mmol, 2 eq) and NN-diisopropylethylamine (0.1 mL, 0.56 mmol, 3 eq) and the mixture was sparged with nitrogen (10 min). Xantphos (21.5 mg, 0.04 mmol, 0.2 eq) and tris(dibenzylideneacetone)dipalladium(0) (17 mg, 0.02 mmol, 0.1 eq) were added and the mixture was heated at 140° C. for 1 h under microwave irradiation. The reaction was partitioned between dichloromethane and water, and the aqueous phase was extracted with dichloromethane (3×40 mL). The combined organic extracts were washed with brine, dried (PTFE phase separator) and concentrated in vacuo. Purification by reverse phase automated flash chromatography (CombiFlash Rf, C18 15.5 g Gold RediSep column) eluting with a gradient of 5-95% acetonitrile in water afforded the desired product as a yellow solid (70.8 mg, 0.08 mmol, 45%).

LC/MS ($C_{42}H_{49}FN_8O_6S_2$) 845 [M+H]$^+$; RT 0.86 (LCMS-V-B2)

$^1$H NMR (400 MHz, DMSO-d6) δ 11.52 (br s, 1H), 7.88 (d, J=7.8 Hz, 1H), 7.49 (d, J=8.1 Hz, 1H), 7.37 (ddd, J=8.2, 7.3, 1.3 Hz, 1H), 7.31 (dd, J=11.9, 1.9 Hz, 1H), 7.24-7.12 (m, 3H), 4.80 (dd, 1H), 4.22 (s, 1H), 4.15 (t, J=6.2 Hz, 2H), 3.94 (d, J=13.4 Hz, 1H), 3.78 (s, 3H), 3.56 (t, J=5.7 Hz, 2H), 3.44-3.37 (m, 1H), 3.31 (s, 2H), 3.28 (d, 1H), 3.24-3.14 (m, 2H), 3.12-2.97 (m, 2H), 2.58 (d, J=12.3 Hz, 3H), 2.33 (s, 3H), 2.19 (s, 6H), 2.14 (q, J=7.0 Hz, 2H), 1.27 (d, 9H).

Step O: methyl 2-{3-[(1,3-benzothiazol-2-yl) amino]-4-methyl-6-[2-(methylamino)ethoxy]-5H, 6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylate To a solution of the product from Step N (70.8 mg, 0.08 mmol, 1 eq) in dichloromethane (5 mL) was added trifluoroacetic acid (1 mL) slowly and the mixture was stirred at ambient temperature for 1 h. The reaction was partitioned between dichloromethane and saturated aqueous sodium bicarbonate and the aqueous phase was extracted with dichloromethane (3×30 mL). The combined organic extracts were washed with brine, dried (PTFE phase separator) and concentrated in vacuo to afford the desired product as a bright yellow solid (59.8 mg, 0.08 mmol, 96%).

LC/MS ($C_{37}H_{41}FN_8O_4S_2$) 745 [M+H]$^+$; RT 1.07 (LCMS-V-B1)

$^1$H NMR (400 MHz, DMSO-d6) δ 7.88 (dd, J=7.8, 1.2 Hz, 1H), 7.49 (d, J=8.1 Hz, 1H), 7.37 (ddd, J=8.2, 7.2, 1.3 Hz, 1H), 7.32 (dd, J=11.9, 1.9 Hz, 1H), 7.24-7.12 (m, 3H), 4.79-4.69 (m, 1H), 4.26-4.19 (m, 1H), 4.15 (t, J=6.2 Hz, 2H), 4.03 (dd, J=13.5, 2.4 Hz, 1H), 3.78 (s, 3H), 3.60 (t, J=5.5 Hz, 2H), 3.39 (s, 2H), 3.32-3.27 (m, 2H), 3.15 (d, J=14.6 Hz, 1H), 3.08-2.99 (m, 1H), 2.70 (t, J=5.5 Hz, 2H), 2.38 (s, 3H), 2.29 (s, 3H), 2.22 (s, 6H), 2.17-2.08 (m, 2H).

Step P: 2-{3-[(1,3-benzothiazol-2-yl)amino]-4-methyl-6-[2-(methylamino)ethoxy]-5H,6H,7H,8H-pyrido[2,3-c]pyridazin-8-yl}-5-(3-{4-[3-(dimethylamino)prop-1-yn-1-yl]-2-fluorophenoxy}propyl)-1,3-thiazole-4-carboxylic acid To a solution of the product from Step 0 (59.8 mg, 0.08 mmol, 1 eq) in 1,4-dioxane (2 mL) was added 1M aqueous lithium hydroxide (0.24 mL, 0.24 mmol, 3 eq) and the mixture was heated at 50° C. for 2 h. The solid was collected by filtration and dried under vacuum to afford the desired product as a bright yellow solid (43 mg, 0.06 mmol, 73%), as a lithium salt.

HRMS-ESI (m/z) [M+H]+ calcd for $C_{36}H_{40}FN_8O_4S_2$: 731.2598, found 731.2623.

Example 66: 2-{3-[(1,3-Benzothiazol-2-yl)amino]-4-methyl-5H,6H,7H,8H-pyrido[2,3-c]pyridazin-8-yl}-5-{3-[(6-fluoro-2-methyl-1,2,3,4-tetrahydroisoquinolin-7-yl)oxy]propyl}-1,3-thiazole-4-carboxylic acid Step A: methyl 5-{3-[(6-fluoro-2-methyl-1,2,3,4-tetrahydroisoquinolin-7-yl)oxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of 6-fluoro-2-methyl-3,4-dihydro-1H-isoquinolin-7-ol (52 mg, 0.29 mmol, 1.8 eq) and the product from Preparation 3b (100 mg, 0.16 mmol, 1 eq) in toluene (5 mL) was added triphenylphosphine (83.7 mg, 0.32 mmol, 2 eq) and di-tert-butyl azodicarboxylate (73.5 mg, 0.32 mmol, 2 eq) and the mixture was stirred at 50° C. overnight. The reaction was partitioned between dichloromethane and water, and the organic phase was washed with brine, dried (PTFE phase separator) and concentrated in vacuo. Purification by automated flash column chromatography (CombiFlash Rf, 4 g RediSep™ silica cartridge) eluting with a gradient of 0-10% methanol in dichloromethane afforded the desired product as a yellow solid (61 mg, 0.08 mmol, 48%).

LC/MS ($C_{39}H_{48}FN_7O_4SiS_2$) 790 [M+H]$^+$; RT 2.68 (LCMS-V-C)

$^1$H NMR (400 MHz, DMSO-d6) δ 7.82 (d, 1H), 7.48-7.37 (m, 2H), 7.28-7.19 (m, 1H), 6.94 (d, J=12.1 Hz, 1H), 6.82 (d, J=8.7 Hz, 1H), 5.84 (s, 2H), 4.27 (t, J=5.8 Hz, 2H), 4.05 (t, J=6.2 Hz, 2H), 3.79 (s, 3H), 3.76-3.68 (m, 2H), 3.42-3.34 (m, 4H), 3.27 (t, 2H), 2.88 (t, J=6.2 Hz, 2H), 2.69 (d, J=6.0 Hz, 2H), 2.38 (s, 3H), 2.26 (s, 3H), 2.17-1.99 (m, 4H), 0.95-0.87 (m, 2H), −0.011 (s, 9H).

Step B: methyl 2-{3-[(1,3-benzothiazol-2-yl)amino]-4-methyl-5H,6H,7H,8H-pyrido[2,3-c]pyridazin-8-yl}-5-{3-[(6-fluoro-2-methyl-1,2,3,4-tetrahydroisoquinolin-7-yl)oxy]propyl}-1,3-thiazole-4-carboxylate A solution of the product from Step A (67 mg, 0.08 mmol, 1 eq) in dichloromethane (4 mL) was cooled to 0° C. and trifluoroacetic acid (1.95 mL, 25.4 mmol, 300 eq) was added and the mixture was stirred for 6 h at ambient temperature. Dichloromethane (10 mL) was added and the solution was cooled to 0° C., washed with aqueous ammonia, and the organic phase was separated (phase separator) and concentrated in vacuo. Purification by automated flash column chromatography (CombiFlash Rf, 4 g RediSep™ silica cartridge) eluting with a gradient of 0-10% methanol in dichloromethane afforded the desired product as a yellow solid (39 mg, 0.06 mmol, 70%).

LC/MS ($C_{33}H_{34}FN_7O_3S_2$) 660 [M+H]⁺; RT 2.01 (LCMS-V-C)

¹H NMR (400 MHz, DMSO-d6) δ 7.89 (s, 1H), 7.51 (br s, 1H), 7.38 (t, J=7.5 Hz, 1H), 7.20 (t, J=7.5 Hz, 1H), 6.95 (d, J=12.1 Hz, 1H), 6.83 (d, J=8.7 Hz, 1H), 4.27 (t, J=5.7 Hz, 2H), 4.06 (t, J=6.3 Hz, 2H), 3.80 (s, 3H), 3.43-3.36 (m, 4H), 3.29 (t, 2H), 2.89 (t, J=6.3 Hz, 2H), 2.73-2.66 (m, 2H), 2.35 (s, 3H), 2.27 (s, 3H), 2.17-2.10 (m, 2H), 2.09-2.00 (m, 2H).

Step C: 2-{3-[(1,3-benzothiazol-2-yl)amino]-4-methyl-5H,6H,7H,8H-pyrido[2,3-c]pyridazin-8-yl}-5-{3-[(6-fluoro-2-methyl-1,2,3,4-tetrahydroisoquino-lin-7-yl)oxy]propyl}-1,3-thiazole-4-carboxylic acid To a solution of the product from Step B (39 mg, 0.06 mmol, 1 eq) in 1,4-dioxane (2 mL) was added lithium hydroxide monohydrate (24.8 mg, 0.59 mmol, 10 eq) and the mixture was heated at reflux overnight. The reaction was allowed to cool to ambient temperature and concentrated in vacuo. Purification by automated flash column chromatography (CombiFlash Rf, 4 g RediSep™ silica cartridge) eluting with a gradient of 0-20% 7N methanolic ammonia in dichloromethane afforded the desired product as an off-white solid (19.4 mg, 0.03 mmol, 51%) HRMS-ESI (m/z) [M+H]+ calcd for $C_{32}H_{33}FN_7O_3S_2$: 646.2070, found 646.2094

Example 67: 5-[3-[4-[3-(Azetidin-1-yl)propyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylic acid

Step A: methyl 5-[3-[4-[3-(azetidin-1-yl)propyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylate Using Propargylic amine preparation General Procedure starting from 50 mg of Preparation 3e (0.077 mmol, 1.0 eq.)

as the appropriate alcohol and azetidine (88.00 mg, 20 eq.), 35 mg of the desired product (75%) was obtained.

Step B: 5-[3-[4-[3-(azetidin-1-yl)propyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylic acid Using Hydrolysis General Procedure starting from the product from Step A as the appropriate methyl ester, the desired product was obtained.

HRMS-ESI (m/z): [M+H]+ calcd for $C_{34}H_{36}FN_7O_3S_2$: 674.2377, found 674.2386.

Example 68: 2-[3-(1,3-Benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)pro-pyl]phenoxy]propyl]thiazole-4-carboxylic acid

Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)pro-pyl]phenoxy]propyl]thiazole-4-carboxylate Using Propargylic amine preparation General Procedure starting from 50 mg of Preparation 3e (0.077 mmol, 1.0 eq.) as the appropriate alcohol and 1-methylpiperazine (154.4 mg, 20 eq.), 46 mg of the desired product (73%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-(4-methylpiperazin-1-yl)pro-pyl]phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{42}FN_8O_3S_2$: 717.2799, found 717.2808.

Example 69: 2-[3-(1,3-Benzothiazol-2-ylamino)-4-methyl-6,7-dihydro-5H-pyrido[2,3-c]pyridazin-8-yl]-5-[3-[2-fluoro-4-(3-pyrrolidin-1-ylpropyl)phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[2-fluoro-4-(3-pyrrolidin-1-ylpropyl)phenoxy]propyl]thiazole-4-carboxylate Using Propargylic amine preparation General Procedure starting from 50 mg of Preparation 3e (0.077 mmol, 1.0 eq.) as the appropriate alcohol and pyrrolidine (109.6 mg, 20 eq.), 53 mg of the desired product (98%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-(3-pyrrolidin-1-ylpropyl)phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{35}H_{39}FN_7O_3S_2$: 688.2534, found 688.2533.

Example 70: 2-[3-(1,3-Benzothiazol-2-ylamino)-4-methyl-6,7-dihydro-5H-pyrido[2,3-c]pyridazin-8-yl]-5-[3-[2-fluoro-4-(3-morpholinopropyl)phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[2-fluoro-4-(3-morpholinopropyl)phenoxy]propyl]thiazole-4-carboxylate Using Propargylic amine preparation General Procedure starting from 50 mg of Preparation 3e (0.077 mmol, 1.0 eq.) as the appropriate alcohol and morpholine (134.3 mg, 20 eq.), 46 mg of the desired product (83%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-(3-morpholinopropyl)phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{35}H_{39}FN_7O_4S_2$: 704.2483, found 704.2471.

Example 71: 2-[3-(1,3-Benzothiazol-2-ylamino)-4-methyl-6,7-dihydro-5H-pyrido[2,3-c]pyridazin-8-yl]-5-[3-[2-fluoro-4-[3-(1-piperidyl)propyl]phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(1-piperidyl)propyl]phenoxy]propyl]thiazole-4-carboxylate Using Propargylic amine preparation General Procedure starting from 50 mg of Preparation 3e (0.077 mmol, 1.0 eq.) as the appropriate alcohol and piperidine (131.2 mg, 20 eq.), 43 mg of the desired product (83%) was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-(1-piperidyl)propyl]phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{41}FN_7O_3S_2$: 702.2690, found 702.2703.

Example 72: 2-[3-(1,3-Benzothiazol-2-ylamino)-4-methyl-6,7-dihydro-5H-pyrido[2,3-c]pyridazin-8-yl]-5-[3-[4-[3-[(1R,5S)-6,6-difluoro-3-azabicyclo[3.1.0]hexan-3-yl]propyl]-2-fluoro-phenoxy]propyl]thiazole-4-carboxylic acid Example 73: 2-[3-(1,3-Benzothiazol-2-ylamino)-4-methyl-6,7-dihydro-5H-pyrido[2,3-c]pyridazin-8-yl]-5-[3-[2-fluoro-4-[3-(3-oxo-2,8-diazaspiro[4.5]decan-8-yl)propyl]phenoxy]propyl]thiazole-4-carboxylic acid Step A: methyl 2-[3-(1,3-benzothiazol-2-ylamino)-4-methyl-6,7-dihydro-5H-pyrido[2,3-c]pyridazin-8-yl]-5-[3-[4-[3-[(1S,5R)-6,6-difluoro-3-azabicyclo[3.1.0]hexan-3-yl]propyl]-2-fluoro-phenoxy]propyl]thiazole-4-carboxylate Using Propargylic amine preparation General Procedure starting from 50 mg of Preparation 3e (0.077 mmol, 1.0 eq.) as the appropriate alcohol and (1S,5R)-6,6-difluoro-3-azabicyclo[3.1.0]hexane (1.54 mmol, 20 eq.), 24 mg of the desired product (41%) was obtained.

Step A: methyl 2-[3-(1,3-benzothiazol-2-ylamino)-4-methyl-6,7-dihydro-5H-pyrido[2,3-c]pyridazin-8-yl]-5-[3-[2-fluoro-4-[3-(3-oxo-2,8-diazaspiro[4.5]decan-8-yl)propyl]phenoxy]propyl]thiazole-4-carboxylate Using Propargylic amine preparation General Procedure starting from 50 mg of Preparation 3e (0.077 mmol, 1.0 eq.) as the appropriate alcohol and 2,8-diazaspiro[4.5]decan-3-one (237.7 mg, 20 eq.), 35 mg of the desired product (58%) was obtained.

Step B: 2-[3-(1,3-benzothiazol-2-ylamino)-4-methyl-6,7-dihydro-5H-pyrido[2,3-c]pyridazin-8-yl]-5-[3-[4-[3-[(1R,5S)-6,6-difluoro-3-azabicyclo[3.1.0]hexan-3-yl]propyl]-2-fluoro-phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{36}H_{37}F_3N_7O_3S2$: 736.2345, found 736.2340.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-(3-oxo-2,8-diazaspiro[4.5]decan-8-yl)propyl]phenoxy]propyl]thiazole-4-carboxylic acid Using Hydrolysis General Procedure starting from the product from Step A as the appropriate methyl ester, the desired product was obtained.

HRMS-ESI (m/z): [M+H]+ calcd for $C_{39}H_{44}FN_8O_4S2$: 771.2905, found 771.2922.

Example 74: 2-{3-[(1,3-Benzothiazol-2-yl)amino]-4-methyl-5H,6H,7H,8H-pyrido[2,3-c]pyridazin-8-yl}-5-{3-[(7-fluoro-2-methyl-1,2,3,4-tetrahydroiso-quinolin-6-yl)oxy]propyl}-1,3-thiazole-4-carboxylic acid Step A: methyl 5-{3-[(7-fluoro-2-methyl-1,2,3,4-tetrahydroisoquinolin-6-yl)oxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3b (120 mg, 0.19 mmol, 1 eq) in toluene (5 mL) was added 7-fluoro-2-methyl-3,4-dihydro-1H-isoquinolin-6-ol (69.4 mg, 0.38 mmol, 2 eq), triphenylphosphine (100 mg, 0.38 mmol, 2 eq) and di-tert-butyl azodicarboxylate (88.2 mg, 0.38 mmol, 2 eq). The mixture was stirred at 50° C. overnight. The reaction was partitioned between dichloromethane and water, and the organic phase was washed with brine, dried (PTFE phase separator) and concentrated in vacuo. Purification by automated flash column chromatography (CombiFlash Rf, 4 g RediSep™ silica cartridge) eluting with a gradient of 0-14% methanol in dichloromethane afforded the desired product as a yellow gum (111 mg, 0.14 mmol, 73%).

LC/MS (C$_{39}$H$_{48}$FN$_7$O$_4$SiS$_2$) 790 [M+H]$^+$; RT 2.64 (LCMS-V-C)

$^1$H NMR (400 MHz, DMSO-d6) δ 7.82 (dd, J=7.6, 1.2 Hz, 1H), 7.48-7.38 (m, 2H), 7.28-7.20 (m, 1H), 6.94-6.84 (m, 2H), 5.85 (s, 2H), 4.27 (t, J=5.8 Hz, 2H), 4.06 (q, J=7.4, 6.8 Hz, 2H), 3.79 (s, 3H), 3.76-3.68 (m, 2H), 3.34-3.22 (m, 4H), 2.88 (t, J=6.3 Hz, 2H), 2.73 (t, J=6.0 Hz, 2H), 2.38 (s, 3H), 2.27 (s, 3H), 2.17-1.99 (m, 4H), 0.97-0.86 (m, 2H), −0.12 (s, 9H).

Step B: methyl 2-{3-[(1,3-benzothiazol-2-yl)amino]-4-methyl-5H,6H,7H,8H-pyrido[2,3-c]pyridazin-8-yl}-5-{3-[(7-fluoro-2-methyl-1,2,3,4-tetrahydroisoquinolin-6-yl)oxy]propyl}-1,3-thiazole-4-carboxylate A solution of the product from Step A (111 mg, 0.14 mmol, 1 eq) in dichloromethane (5 mL) was cooled to 0° C. and trifluoroacetic acid (1.02 mL, 13.4 mmol, 95 eq) was added and the mixture was stirred at ambient temperature overnight. Dichloromethane (10 mL) was added and the solution was cooled to 0° C., washed with aqueous ammonia, and the organic phase was separated (phase separator) and concentrated in vacuo. Purification by automated flash column chromatography (CombiFlash Rf, 4 g RediSep™ silica cartridge) eluting with a gradient of 0-7% methanol in dichloromethane afforded the desired product as a yellow gum (79 mg, 0.12 mmol, 85%).

LC/MS (C$_{33}$H$_{34}$FN$_7$O$_3$S$_2$) 660 [M+H]$^+$; RT 2.01 (LCMS-V-C)

$^1$H NMR (400 MHz, DMSO-d6) δ 7.88 (d, J=7.8 Hz, 1H), 7.50 (br s, 1H), 7.42-7.33 (m, 1H), 7.20 (t, J=7.7 Hz, 1H), 6.95-6.85 (m, 2H), 4.27 (t, J=5.7 Hz, 2H), 4.08 (t, J=6.2 Hz, 2H), 3.79 (s, 3H), 3.34-3.22 (m, 6H), 2.89 (t, J=6.3 Hz, 2H), 2.74 (t, J=5.9 Hz, 2H), 2.35 (s, 3H), 2.28 (s, 3H), 2.17-2.03 (m, 4H).

Step C: 2-{3-[(1,3-benzothiazol-2-yl)amino]-4-methyl-5H,6H,7H,8H-pyrido[2,3-c]pyridazin-8-yl}-5-{3-[(7-fluoro-2-methyl-1,2,3,4-tetrahydroisoquino-lin-6-yl)oxy]propyl}-1,3-thiazole-4-carboxylic acid To a solution of the product from Step B (79 mg, 0.12 mmol, 1 eq) in 1,4-dioxane (3 mL) was added lithium hydroxide monohydrate (50.2 mg, 1.2 mmol, 10 eq) and the mixture was heated at reflux for 4.5 h. The reaction was allowed to cool to ambient temperature and concentrated in vacuo. Purification by automated flash column chromatography (CombiFlash Rf, 4 g RediSep™ silica cartridge) eluting with a gradient of 0-20% 7N methanolic ammonia in dichloromethane afforded a solid that was triturated with diethyl ether, filtered, washed with diethyl ether and dried under vacuum to afford the desired product as a yellow solid (44.4 mg, 0.07 mmol, 57%).

HRMS-ESI (m/z) [M+H]+ calcd for C$_{32}$H$_{33}$FN$_7$O$_3$S$_2$: 646.2070, found 646.2103

Example 75: 2-{3-[(1,3-Benzothiazol-2-yl)amino]-4-methyl-5H,6H,7H,8H-pyrido[2,3-c]pyridazin-8-yl}-5-(3-{2-fluoro-4-[4-(methylamino)butyl]phenoxy}propyl)-1,3-thiazole-4-carboxylic acid Step A: methyl 5-{3-[4-(4-{[(tert-butoxy)carbonyl](methyl)amino}butyl)-2-fluorophenoxy]propyl}-2-(4-methyl-3-{[(2Z)-3-{[2-(trimethylsilyl)ethoxy]methyl}-2,3-dihydro-1,3-benzothiazol-2-ylidene]amino}-5H,6H,7H,8H-pyrido[2,3-c]pyridazin-8-yl)-1,3-thiazole-4-carboxylate To a solution of the product from Preparation 3b (50 mg, 0.08 mmol, 1 eq) in toluene (5 mL) was added the product from Preparation 4k (32.7 mg, 0.11 mmol, 1.38 eq), di-tert-butyl azodicarboxylate (36.7 mg, 0.16 mmol, 2 eq) and triphenylphosphine (41.8 mg, 0.16 mmol, 2 eq) and the mixture was heated at 50° C. overnight. The reaction was partitioned between dichloromethane and water, separated (PTFE phase separator) and concentrated in vacuo. Purification by automated flash column chromatography (CombiFlash Rf, 4 g RediSep™ silica cartridge) eluting with a gradient of 0-70% ethyl acetate in iso-heptane afforded the desired product as a clear gum (45 mg, 0.05 mmol, 62%).

LC/MS ($C_{45}H_{60}FN_7O_6SiS_2$) 906 [M+H]$^+$; RT 3.51 (LCMS-V-C)

$^1$H NMR (400 MHz, DMSO-d6) δ 7.82 (d, 1H), 7.48-7.38 (m, 2H), 7.24 (ddd, J=8.3, 6.8, 1.8 Hz, 1H), 7.11-7.01 (m, 2H), 6.91 (d, J=8.2 Hz, 1H), 5.85 (s, 2H), 4.27 (t, J=5.8 Hz, 2H), 4.07 (t, 2H), 3.78 (s, 3H), 3.76-3.68 (m, 2H), 3.32-23 (m, 4H), 3.16-3.05 (m, 2H), 2.88 (t, J=6.3 Hz, 2H), 2.70 (s, 3H), 2.38 (s, 3H), 2.17-2.01 (m, 4H), 1.51-1.39 (m, 4H), 1.34 (d, J=16.8 Hz, 9H), 0.95-0.86 (m, 2H), −0.11 (s, 9H).

Step B: methyl 2-{3-[(1,3-benzothiazol-2-yl)amino]-4-methyl-5H,6H,7H,8H-pyrido[2,3-c]pyridazin-8-yl}-5-(3-{2-fluoro-4-[4-(methylamino)butyl]phenoxy}propyl)-1,3-thiazole-4-carboxylate A solution of the product from Step A (45 mg, 0.05 mmol, 1 eq) in dichloromethane (3 mL) was cooled to 0° C. and trifluoroacetic acid (0.61 mL, 7.95 mmol, 160 eq) was added and the mixture was stirred for 24 h at ambient temperature. Dichloromethane (40 mL) was added and the solution was washed with aqueous ammonia and concentrated in vacuo. Purification by automated flash column chromatography (CombiFlash Rf, 4 g RediSep™ silica cartridge) eluting with a gradient of 0-20% methanol in dichloromethane afforded the desired product as a yellow solid (22 mg, 0.03 mmol, 66%).

LC/MS ($C_{34}H_{38}FN_7O_3S_2$) 676 [M+H]$^+$; RT 1.12 (LCMS-V-B1)

$^1$H NMR (400 MHz, DMSO-d6) δ 7.85 (d, J=7.9 Hz, 1H), 7.47 (d, J=8.0 Hz, 1H), 7.35 (t, J=7.5 Hz, 1H), 7.16 (t, J=7.5 Hz, 1H), 7.11-7.02 (m, 2H), 6.93 (d, J=8.8 Hz, 1H), 4.26 (dd, J=6.9, 4.3 Hz, 2H), 4.09 (t, J=6.1 Hz, 2H), 3.79 (s, 3H), 3.32-3.24 (m, 4H), 2.88 (t, J=6.3 Hz, 2H), 2.42 (t, 2H), 2.34 (s, 3H), 2.23 (s, 3H), 2.19-2.09 (m, 2H), 2.08-1.99 (m, 2H), 1.60-1.47 (m, 2H), 1.41-1.30 (m, 2H).

Step C: 2-{3-[(1,3-benzothiazol-2-yl)amino]-4-methyl-5H,6H,7H,8H-pyrido[2,3-c]pyridazin-8-yl}-5-(3-{2-fluoro-4-[4-(methylamino)butyl]phenoxy}propyl)-1,3-thiazole-4-carboxylic acid To a solution of the product from Step B (22 mg, 0.03 mmol, 1 eq) in 1,4-dioxane (3 mL) was added lithium hydroxide monohydrate (13.7 mg, 0.33 mmol, 10 eq) and the mixture was heated at reflux overnight. Purification by automated flash column chromatography (CombiFlash Rf, 4 g RediSep™ silica cartridge) eluting with a gradient of 0-25% 7N methanolic ammonia in dichloromethane afforded a solid that was suspended in ethyl acetate (1.5 mL) and hydrochloric acid (4M in 1,4-dioxane; 54.5 µL, 0.22 mmol, 6.7 eq) was added. The mixture was stirred for 10 min, then the solids were collected by filtration and dried under vacuum to afford the desired product as a yellow solid (11.4 mg, 0.02 mmol, 53%), as a hydrochloric acid salt.

HRMS-ESI (m/z) [M+H]+ calcd for $C_{33}H_{37}FN_7O_3S_2$: 662.2383, found 662.2414

Example 76: 2-[3-(1,3-Benzothiazol-2-ylamino)-4-methyl-6,7-dihydro-5H-pyrido[2,3-c]pyridazin-8-yl]-5-[3-[4-[3-[2-(dimethylamino)ethylamino]prop-1-ynyl]-2-fluoro-phenoxy]propyl]thiazole-4-carboxylic acid Step A: methyl 5-[3-[4-[3-[tert-butoxycarbonyl-[2-(dimethylamino)ethyl]amino]prop-1-ynyl]-2-fluoro-phenoxy]propyl]-2-(3-chloro-4-methyl-6,7-dihydro-5H-pyrido[2,3-c]pyridazin-8-yl)thiazole-4-carboxylate Using Sonogashira General Procedure starting from 1.00 g of Preparation 3a (1.66 mmol, 1 eq.) and 413 mg of tert-butyl N-[2-(dimethylamino)ethyl]-N-prop-2-ynyl-carbamate (1.83 mmol, 1.1 eq.) as the appropriate alkyne, the desired product was isolated as yellow solid.

$^1$H NMR (500 MHz, DMSO-d$_6$) δ ppm 7.30 (d, 1H), 7.21 (d, 1H), 7.15 (t, 1H), 4.27 (brt, 2H), 4.26 (t, 2H), 4.12 (t, 2H), 3.77 (s, 3H), 3.47 (brt, 2H), 3.26 (t, 2H), 2.89 (t, 2H), 2.82 (brs, 2H), 2.45 (brs, 6H), 2.32 (s, 3H), 2.11 (qn, 2H), 2.04 (qn, 2H), 1.43 (s, 9H); $^{13}$C NMR (125 MHz, DMSO-d$_6$) δ ppm 163.1, 155.4, 151.8, 151.4, 151.4, 147.5, 142.4, 136.2, 135, 129.1, 129.1, 119.2, 115.5, 114.8, 82.3, 80.3, 68.3, 56.3, 52.0, 46.4, 46.4, 44.6, 43.1, 30.7, 28.5, 24.2, 23, 19.7, 15.7; HRMS-ESI (m/z): [M+H]+ calcd for $C_{34}H_{43}ClFN_6O_5S$: 701.2683, found 701.2678.

Step B: methyl 2-[3-(1,3-benzothiazol-2-ylamino)-4-methyl-6,7-dihydro-5H-pyrido[2,3-c]pyridazin-8-yl]-5-[3-[4-[3-[tert-butoxycarbonyl-[2-(dimethyl-amino)ethyl]amino]prop-1-ynyl]-2-fluoro-phenoxy]propyl]thiazole-4-carboxylate Using Buchwald General Procedure II starting from the product from Step A and 1,3-benzothiazol-2-amine, the desired product was obtained.

LC-MS-ESI (m/z): [M+H]+ calcd for $C_{41}H_{48}FN_8O_5S_2$: 815.3, found 815.4.

Step C: 2-[3-(1,3-benzothiazol-2-ylamino)-4-methyl-6,7-dihydro-5H-pyrido[2,3-c]pyridazin-8-yl]-5-[3-[4-[3-[2-(dimethylamino)ethylamino]prop-1-ynyl]-2-fluoro-phenoxy]propyl]thiazole-4-carboxylic acid Using Deprotection and Hydrolysis General Procedure followed by repurification via reverse phase preparative chromatography (C18, 25 mM NH$_4$HCO$_3$ in water:MeCN) starting from the product from Step B, the desired product was obtained.

HRMS-ESI (m/z): [M+H]+ calcd for C$_{35}$H$_{38}$FN$_8$O$_3$S$_2$: 701.2487, found 701.2483.

Example 77: 2-[3-(1,3-Benzothiazol-2-ylamino)-4-methyl-6,7-dihydro-5H-pyrido[2,3-c]pyridazin-8-yl]-5-[3-(2-fluoro-4-iodo-phenoxy)propyl]thiazole-4-carboxylic acid Step A: methyl 5-[3-(2-fluoro-4-iodo-phenoxy)pro-pyl]-2-[4-methyl-3-[(Z)-[3-(2-trimethylsily-lethoxymethyl)-1,3-benzothiazol-2-ylidene]amino]-6,7-dihydro-5H-pyrido[2,3-c]pyridazin-8-yl]thiazole-4-carboxylate Using Mitsunobu General Procedure staring from 2.00 g of Preparation 3b (3.19 mmol, 1 eq.) and 835 mg of 2-fluoro-4-iodo-phenol (3.51 mmol, 1.1 eq.) as the appropriate phenol, 2.31 g (85% Yield) of the desired product was obtained.

$^1$H NMR (500 MHz, DMSO-d$_6$) δ ppm 7.81 (dm, 1H), 7.6 (dd, 1H), 7.45 (dm, 1H), 7.43 (dm, 1H), 7.41 (m, 1H), 7.23 (m, 1H), 7 (t, 1H), 5.83 (s, 2H), 4.25 (t, 2H), 4.1 (t, 2H), 3.77 (s, 3H), 3.71 (m, 2H), 3.26 (t, 2H), 2.84 (t, 2H), 2.34 (s, 3H), 2.11 (m, 2H), 2.03 (m, 2H), 0.9 (m, 2H),-0.11 (s, 9H); HRMS-ESI (m/z): [M+H]+ calcd for C$_{35}$H$_{41}$FIN$_6$O$_4$S$_2$Si: 847.1423, found 847.1396.

Step B: 2-[3-(1,3-benzothiazol-2-ylamino)-4-methyl-6,7-dihydro-5H-pyrido[2,3-c]pyridazin-8-yl]-5-[3-(2-fluoro-4-iodo-phenoxy)propyl]thiazole-4-carboxylic acid Using Deprotection and Hydrolysis General Procedure starting from the product from Step A as the appropriate carbamate, the desired product was obtained.

HRMS-ESI (m/z): [M+H]+ calcd for C$_{28}$H$_{25}$FIN$_6$O$_3$S$_2$: 703.0452, found 703.0427.

Example 78: 2-[3-(1,3-Benzothiazol-2-ylamino)-4-methyl-6,7-dihydro-5H-pyrido[2,3-c]pyridazin-8-yl]-5-[3-[5-[3-(dimethylamino)prop-1-ynyl]-2-fluoro-phenoxy]propyl]thiazole-4-carboxylic acid Step A: methyl 5-[3-(2-fluoro-5-iodo-phenoxy)pro-pyl]-2-[4-methyl-3-[(Z)-[3-(2-trimethylsily-lethoxymethyl)-1,3-benzothiazol-2-ylidene]amino]-6,7-dihydro-5H-pyrido[2,3-c]pyridazin-8-yl]thiazole-4-carboxylate Using Mitsunobu General Procedure staring from 390 mg of Preparation 3b (0.622 mmol, 1 eq.) and 177 mg of 2-fluoro-5-iodo-phenol (0.746 mmol, 1.2 eq.) as the appropriate phenol, 416 mg (79% Yield) of the desired product was obtained.

$^1$H NMR (500 MHz, DMSO-d$_6$) δ ppm 7.81 (dm, 1H), 7.46 (dd, 1H), 7.43 (dm, 1H), 7.41 (m, 1H), 7.27 (m, 1H), 7.23 (m, 1H), 7.05 (dd, 1H), 5.83 (s, 2H), 4.26 (t, 2H), 4.14 (t, 2H), 3.78 (s, 3H), 3.71 (m, 2H), 3.26 (t, 2H), 2.85 (t, 2H), 2.34 (s, 3H), 2.11 (m, 2H), 2.04 (m, 2H), 0.91 (m, 2H), –0.11 (s, 9H); HRMS-ESI (m/z): [M+H]+ calcd for C$_{28}$H$_{25}$FIN$_6$O$_3$S$_2$: 847.1423, found 847.1416.

Step B: methyl 5-[3-[5-[3-(dimethylamino)prop-1-ynyl]-2-fluoro-phenoxy]propyl]-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate Using Sonogashira General Procedure starting from 310 mg of the product from Step A (0.366 mmol, 1.0 eq.) and 91 mg NN-dimethylprop-2-yn-1-amine (1.10 mmol, 3 eq.) as the appropriate acetylene, 251 mg (85% Yield) of the desired product was obtained.

$^1$H NMR (500 MHz, DMSO-d$_6$) δ ppm 7.81 (dm, 1H), 7.43 (dm, 1H), 7.41 (m, 1H), 7.23 (m, 1H), 7.23 (m, 1H), 7.22 (dd, 1H), 7.03 (m, 1H), 5.82 (s, 2H), 4.25 (t, 2H), 4.15 (t, 2H), 3.78 (s, 3H), 3.71 (m, 2H), 3.50 (s, 2H), 3.27 (t, 2H), 2.84 (t, 2H), 2.33 (s, 3H), 2.28 (s, 6H), 2.12 (m, 2H), 2.03 (m, 2H), 0.9 (m, 2H), –0.11 (s, 9H); HRMS-ESI (m/z): [M+H]+ calcd for C$_{40}$H$_{49}$FN$_7$O$_4$S$_2$Si: 802.3035, found 802.3028.

Step C: 2-[3-(1,3-benzothiazol-2-ylamino)-4-methyl-6,7-dihydro-5H-pyrido[2,3-c]pyridazin-8-yl]-5-[3-[5-[3-(dimethylamino)prop-1-ynyl]-2-fluoro-phenoxy]propyl]thiazole-4-carboxylic acid Using Deprotection and Hydrolysis General Procedure starting from the product from Step B as the appropriate carbamate, the desired product was obtained.

HRMS-ESI (m/z): [M+H]+ calcd for $C_{33}H_{33}FN_7O_3S_2$: 658.2064, found 658.2045.

Example 79: 2-[3-(1,3-Benzothiazol-2-ylamino)-4-methyl-6,7-dihydro-5H-pyrido[2,3-c]pyridazin-8-yl]-5-[3-[2-fluoro-4-(3-piperazin-1-ylprop-1-ynyl)phenoxy]propyl]thiazole-4-carboxylic acid Step A: 2-[3-(1,3-benzothiazol-2-ylamino)-4-methyl-6,7-dihydro-5H-pyrido[2,3-c]pyridazin-8-yl]-5-[3-[4-[3-(4-tert-butoxycarbonylpiperazin-1-yl)prop-1-ynyl]-2-fluoro-phenoxy]propyl]thiazole-4-carboxylic acid Using Silver catalyzed propargylic amine preparation General Procedure starting from Preparation 3c, paraformaldehyde as the aldehyde and tert-butyl piperazine-1-carboxylate as the appropriate secondary amine, the desired product was obtained.

Step B: 2-[3-(1,3-benzothiazol-2-ylamino)-4-methyl-6,7-dihydro-5H-pyrido[2,3-c]pyridazin-8-yl]-5-[3-[2-fluoro-4-(3-piperazin-1-ylprop-1-ynyl)phenoxy]propyl]thiazole-4-carboxylic acid The mixture of the product from Step A (207 mg, 0.25 mmol) and HFxPyr (2.5 mmol, 10 eq.) in acetonitrile (4.3 mL) was stirred at 60° C. for 2.5 h. The product was purified via flash chromatography on 24 g silica gel column using DCM and MeOH (NH₃) as eluents to give 143 mg (79%) of the desired product.

HRMS-ESI (m/z): [M+H]+ calcd for $C_{35}H_{36}FN_8O_3S_2$: 699.2330, found 699.2322.

Example 80: 2-[3-(1,3-Benzothiazol-2-ylamino)-4-methyl-6,7-dihydro-5H-pyrido[2,3-c]pyridazin-8-yl]-5-[3-[4-[3-(methylamino)prop-1-ynyl]phenoxy]propyl]thiazole-4-carboxylic acid Step A: methyl 5-[3-(4-iodophenoxy)propyl]-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate Using Mitsunobu General Procedure staring from 313 mg of Preparation 3b (0.50 mmol, 1.0 eq.) and 110 mg of 4-iodo-phenol (0.50 mmol, 1.0 eq.) as the appropriate phenol, 328 mg (63% Yield) of the desired product was obtained.

$^1$H NMR (500 MHz, DMSO-d₆) δ ppm 7.81 (d, 1H), 7.58 (d, 2H), 7.43 (d, 1H), 7.42 (t, 1H), 7.24 (t, 1H), 6.81 (d, 2H), 5.83 (s, 2H), 4.25 (t, 2H), 4.02 (t, 2H), 3.78 (s, 3H), 3.71 (t, 2H), 3.26 (t, 2H), 2.85 (t, 2H), 2.35 (s, 3H), 2.1 (qn, 2H), 2.04 (qn, 2H), 0.9 (t, 2H), −0.11 (s, 9H); $^{13}$C NMR (125 MHz, DMSO-d₆) δ ppm 138.5, 127.1, 123.3, 123.1, 117.8, 111.8, 73, 67.3, 66.7, 52.0, 46.4, 31.1, 23.8, 23.2, 20.4, 17.8, 13.0, −0.9; HRMS-ESI (m/z): [M+H]+ calcd for $C_{35}H_{42}IN_6O_4S_2Si$: 829.1517, found 829.1517.

Step B: methyl 5-[3-[4-[3-[tert-butoxycarbonyl(methyl)amino]prop-1-ynyl]phenoxy]propyl]-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate Using Sonogashira General Procedure starting from 3304 mg of the product from Step A (0.294 mmol, 1.0 eq.) and 100 mg tert-butyl N-methyl-N-prop-2-ynyl-carbamate (0.588 mmol, 2 eq.) as the appropriate acetylene, 172 mg (67% Yield) of the desired product was obtained.

$^1$H NMR (500 MHz, DMSO-d₆) δ ppm 7.81 (d, 1H), 7.44 (d, 1H), 7.42 (t, 1H), 7.36 (d, 2H), 7.24 (t, 1H), 6.96 (d, 2H), 5.84 (s, 2H), 4.26 (t, 2H), 4.2 (brs, 2H), 4.06 (t, 2H), 3.78 (s, 3H), 3.72 (t, 2H), 3.28 (t, 2H), 2.86 (t, 2H), 2.84 (brs, 3H), 2.36 (s, 3H), 2.11 (qn, 2H), 2.04 (qn, 2H), 1.41 (s, 9H), 0.91 (t, 2H), −0.11 (s, 9H); $^{13}$C NMR (125 MHz, DMSO-d₆) δ ppm 133.5, 127.1, 123.3, 123.1, 115.3, 111.8, 72.9, 67.3, 66.7, 52.0, 46.3, 38.6, 33.7, 31.0, 28.5, 23.8, 23.2, 20.3, 17.8, 13.0, −0.9; HRMS-ESI (m/z): [M+H]+ calcd for $C_{44}H_{56}N_7O_6S_2Si$: 870.3497, found 870.349.

Step C: 2-[3-(1,3-benzothiazol-2-ylamino)-4-methyl-6,7-dihydro-5H-pyrido[2,3-c]pyridazin-8-yl]-5-[3-[4-[3-(methylamino)prop-1-ynyl]phenoxy]propyl]thiazole-4-carboxylic acid Using Deprotection and Hydrolysis General Procedure starting from the product from Step B as the appropriate carbamate, the desired product was obtained.

HRMS-ESI (m/z): [M+H]+ calcd for $C_{32}H_{32}N_7O_3S2$: 626.2002, found 626.2004.

Example 81: 2-[3-(1,3-Benzothiazol-2-ylamino)-4-methyl-6,7-dihydro-5H-pyrido[2,3-c]pyridazin-8-yl]-5-[3-[2-fluoro-4-(3-methyl-3-pyrrolidin-1-yl-but-1-ynyl)phenoxy]propyl]thiazole-4-carboxylic acid Using Silver catalyzed propargylic amine preparation General Procedure starting from Preparation 3c, acetone as the ketone and pyrrolidine as the appropriate secondary amine, the desired product was obtained.

HRMS-ESI (m/z): [M+H]+ calcd for $C_{37}H_{39}FN_7O_3S_2$: 712.2534, found 712.2522.

Example 82: 5-[3-[4-[3-(Dimethylamino)prop-1-ynyl]-2-fluoro-phenoxy]propyl]-2-[3-[(7-fluoro-1,3-benzothiazol-2-yl)amino]-4-methyl-6,7-dihydro-5H-pyrido[2,3-c]pyridazin-8-yl]thiazole-4-carboxylic acid Step A: methyl 2-(3-chloro-4-methyl-6,7-dihydro-5H-pyrido[2,3-c]pyridazin-8-yl)-5-[3-[4-[3-(dimethylamino)prop-1-ynyl]-2-fluoro-phenoxy]propyl]thiazole-4-carboxylate Using Sonogashira General Procedure starting from 500 mg of Preparation 3a (0.80 mmol, 1.0 eq.) and 100 mg NN-dimethylprop-2-yn-1-amine (1.2 mmol, 1.5 eq.) as the appropriate acetylene, 254 mg (50% Yield) of the desired product was obtained.

HRMS-ESI (m/z): [M+H]+ calcd for $C_{27}H_{30}ClFN_5O_3S$: 558.1736, found 558.1729.

Step B: methyl 5-[3-[4-[3-(dimethylamino)prop-1-ynyl]-2-fluoro-phenoxy]propyl]-2-[3-[(7-fluoro-1,3-benzothiazol-2-yl)amino]-4-methyl-6,7-dihydro-5H-pyrido[2,3-c]pyridazin-8-yl]thiazole-4-carboxylate Using Buchwald General Procedure II starting from 254 mg of the product from Step A (0.45 mmol, 1.0 eq.) and 153 mg 7-fluoro-1,3-benzothiazol-2-amine (0.91 mmol, 2.0 eq.), 161 mg (51% Yield) of the desired product was obtained.

$^1$H NMR (500 MHz, DMSO-d$_6$) δ ppm 11.59 (brs, 1H), 7.41 (dd, 1H), 7.4 (t, 1H), 7.31 (dd, 1H), 7.21 (dd, 1H), 7.15 (t, 1H), 7.08 (t, 1H), 4.26 (t, 2H), 4.13 (t, 2H), 3.78 (s, 3H), 3.49 (s, 2H), 3.28 (t, 2H), 2.87 (t, 2H), 2.34 (s, 3H), 2.27 (s, 6H), 2.13 (qn, 2H), 2.04 (qn, 2H); $^{13}$C NMR (125 MHz, DMSO-d$_6$) δ ppm 163.2, 157.0, 155.7, 151.6, 150.4, 149.1, 148.8, 147.5, 141.6, 134.9, 129.0, 128.3, 128.0, 127.9, 119.3, 117.2, 115.5, 115.0, 113.6, 108.4, 84.8, 84.3, 68.3, 51.8, 48.0, 46.4, 43.9, 30.8, 23.9, 22.9, 20.2, 12.8; HRMS-ESI (m/z): [M+H]+ calcd for $C_{34}H_{34}F_2N_7O_3S_2$: 690.2127, found 690.2110.

Step C: 5-[3-[4-[3-(dimethylamino)prop-1-ynyl]-2-fluoro-phenoxy]propyl]-2-[3-[(7-fluoro-1,3-benzo-thiazol-2-yl)amino]-4-methyl-6,7-dihydro-5H-pyrido[2,3-c]pyridazin-8-yl]thiazole-4-carboxylic acid Using Deprotection and Hydrolysis General Procedure starting from the product from Step B as the appropriate methyl ester, the desired product was obtained.

HRMS-ESI (m/z): [M+H]+ calcd for $C_{32}H_{31}FN_7O_3S_2$: 676.1970, found 676.1958.

Example 83: 2-[3-(1,3-Benzothiazol-2-ylamino)-4-methyl-6,7-dihydro-5H-pyrido[2,3-c]pyridazin-8-yl]-5-[3-[4-[3-(dimethylamino)-3-methyl-but-1-ynyl]-2-fluoro-phenoxy]propyl]thiazole-4-carboxylic acid Using Silver catalyzed propargylic amine preparation General Procedure starting from Preparation 3c, acetone as the ketone and dimethyl amine as the appropriate secondary amine, the desired product was obtained.

HRMS-ESI (m/z): [M+H]+ calcd for $C_{35}H_{37}FN_7O_3S_2$: 686.2377, found 686.2361.

Example 84: 2-[3-(1,3-Benzothiazol-2-ylamino)-4-methyl-6,7-dihydro-5H-pyrido[2,3-c]pyridazin-8-yl]-5-[3-[4-[2-[1-(dimethylamino)cyclohexyl]ethynyl]-2-fluoro-phenoxy]propyl]thiazole-4-carboxylic acid Using Silver catalyzed propargylic amine preparation General Procedure starting from Preparation 3c, cyclohexanone as the ketone and dimethyl amine as the appropriate secondary amine, the desired product was obtained.

HRMS-ESI (m/z): [M+H]+ calcd for $C_{38}H_{41}FN_7O_3S_2$: 726.2690, found 726.2676.

Example 85: 2-[3-(1,3-Benzothiazol-2-ylamino)-4-methyl-6,7-dihydro-5H-pyrido[2,3-c]pyridazin-8-yl]-5-[3-[4-[3-(diethylamino)prop-1-ynyl]-2-fluoro-phenoxy]propyl]thiazole-4-carboxylic acid Using Silver catalyzed propargylic amine preparation General Procedure starting from Preparation 3c, paraformaldehyde as the aldehyde and diethyl amine as the appropriate secondary amine, the desired product was obtained.

HRMS-ESI (m/z): [M+H]+ calcd for $C_{35}H_{37}FN_7O_3S_2$: 686.2377, found 686.2386.

Example 86: 2-[3-(1,3-Benzothiazol-2-ylamino)-4-methyl-6,7-dihydro-5H-pyrido[2,3-c]pyridazin-8-yl]-5-[3-[4-[3-(diisopropylamino)prop-1-ynyl]-2-fluoro-phenoxy]propyl]thiazole-4-carboxylic acid Using Silver catalyzed propargylic amine preparation General Procedure starting from Preparation 3c, paraformaldehyde as the aldehyde and diisopropyl amine as the appropriate secondary amine, the desired product was obtained.

HRMS-ESI (m/z): [M+H]+ calcd for $C_{37}H_{41}FN_7O_3S_2$: 714.2690, found 714.2681.

Example 87: 2-[3-(1,3-Benzothiazol-2-ylamino)-4-methyl-6,7-dihydro-5H-pyrido[2,3-c]pyridazin-8-yl]-5-[3-[4-[3-(diisobutylamino)prop-1-ynyl]-2-fluoro-phenoxy]propyl]thiazole-4-carboxylic acid Using Silver catalyzed propargylic amine preparation General Procedure starting from Preparation 3c, paraformaldehyde as the aldehyde and N-isobutyl-2-methyl-propan-1-amine as the appropriate secondary amine, the desired product was obtained.

HRMS-ESI (m/z): [M+H]+ calcd for $C_{39}H_{45}FN_7O_3S_2$: 742.3003, found 742.3001.

Example 88: 2-[3-(1,3-Benzothiazol-2-ylamino)-4-methyl-6,7-dihydro-5H-pyrido[2,3-c]pyridazin-8-yl]-5-[3-[4-[3-[ethyl(methyl)amino]prop-1-ynyl]-2-fluoro-phenoxy]propyl]thiazole-4-carboxylic acid Using Silver catalyzed propargylic amine preparation General Procedure starting from Preparation 3c, paraformaldehyde as the aldehyde and N-methylethanamine as the appropriate secondary amine, the desired product was obtained.

HRMS-ESI (m/z): [M+H]+ calcd for $C_{34}H_{35}FN_7O_3S_2$: 672.2221, found 672.2206.

Example 89: 2-[3-(1,3-Benzothiazol-2-ylamino)-4-methyl-6,7-dihydro-5H-pyrido[2,3-c]pyridazin-8-yl]-5-[3-[4-[3-[(3R,5S)-3,5-dimethylpiperazin-1-yl]prop-1-ynyl]-2-fluoro-phenoxy]propyl]thiazole-4-carboxylic acid Step A: 2-[3-(1,3-benzothiazol-2-ylamino)-4-methyl-6,7-dihydro-5H-pyrido[2,3-c]pyridazin-8-yl]-5-[3-[4-[3-[(3R,5S)-4-tert-butoxycarbonyl-3,5-dimethyl-piperazin-1-yl]prop-1-ynyl]-2-fluoro-phenoxy]propyl]thiazole-4-carboxylic acid Using Silver catalyzed propargylic amine preparation General Procedure starting from Preparation 3c, paraformaldehyde as the aldehyde and tert-butyl (2R,6S)-2,6-dimethylpiperazine-1-carboxylate as the appropriate secondary amine, 215 mg (62% Yield) of the desired product was obtained.

$^1$H NMR (500 MHz, DMSO-d$_6$) δ ppm 7.88 (dm, 1H), 7.49 (brs, 1H), 7.37 (m, 1H), 7.32 (dd, 1H), 7.2 (dm, 1H), 7.19 (m, 1H), 7.15 (t, 1H), 4.27 (t, 2H), 4.14 (t, 2H), 3.98 (m, 1H), 3.49 (s, 2H), 3.27 (t, 2H), 2.88 (t, 2H), 2.62/2.25 (dd+dd, 4H), 2.34 (s, 3H), 2.13 (m, 2H), 2.04 (m, 2H), 1.4 (s, 9H), 1.19 (d, 6H); HRMS-ESI (m/z): [M+H]+ calcd for $C_{42}H_{48}FN_8O_5S_2$: 827.3167, found 827.3186.

Step B: 2-[3-(1,3-benzothiazol-2-ylamino)-4-methyl-6,7-dihydro-5H-pyrido[2,3-c]pyridazin-8-yl]-5-[3-[4-[3-[(3R,5S)-3,5-dimethylpiperazin-1-yl]prop-1-ynyl]-2-fluoro-phenoxy]propyl]thiazole-4-carboxylic acid Using Deprotection and Hydrolysis General Procedure (without LiOH×H$_2$O hydrolysis) starting from the product from Step A as the appropriate carbamate, the desired product was obtained.

HRMS-ESI (m/z): [M+H]+ calcd for $C_{37}H_{40}FN_8O_3S2$: 727.2643, found 727.2641.

Example 90: 2-[3-(1,3-Benzothiazol-2-ylamino)-4-methyl-6,7-dihydro-5H-pyrido[2,3-c]pyridazin-8-yl]-5-[3-[4-[1-[(dimethylamino)methyl]-3-bicyclo[1.1.1]pentanyl]-2-fluoro-phenoxy]propyl]thiazole-4-carboxylic acid Step A: methyl 5-[3-[4-[1-[(dimethylamino)methyl]-3-bicyclo[1.1.1]pentanyl]-2-fluoro-phenoxy]propyl]-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate Using Mitsunobu General Procedure starting from Preparation 4a and Preparation 3b as the appropriate alcohol, the crude desired product was isolated and transferred into the next step without further purification.

HRMS-ESI (m/z): [M+H]+ calcd for $C_{43}H_{55}FN_7O_4S_2Si$: 844.3505, found 844.3485.

Step B: 2-[3-(1,3-benzothiazol-2-ylamino)-4-methyl-6,7-dihydro-5H-pyrido[2,3-c]pyridazin-8-yl]-5-[3-[4-[1-[(dimethylamino)methyl]-3-bicyclo[1.1.1]pentanyl]-2-fluoro-phenoxy]propyl]thiazole-4-carboxylic acid Using Deprotection and Hydrolysis General Procedure followed by repurification via reverse phase preparative chromatography (C18, 25 mM NH₄HCO₃ in water:MeCN) starting from the product from Step A, the desired product was obtained.

HRMS-ESI (m/z): [M+H]+ calcd for $C_{36}H_{39}FN_7O_3S_2$: 700.2534, found 700.2515.

Example 91: 2-[3-(1,3-Benzothiazol-2-ylamino)-4-methyl-6,7-dihydro-5H-pyrido[2,3-c]pyridazin-8-yl]-5-[3-[2-fluoro-4-[3-methyl-3-(methylamino)but-1-ynyl]phenoxy]propyl]thiazole-4-carboxylic acid

Step A: methyl 2-(3-chloro-4-methyl-6,7-dihydro-5H-pyrido[2,3-c]pyridazin-8-yl)-5-[3-[2-fluoro-4-[3-methyl-3-(methylamino)but-1-ynyl]phenoxy]propyl]thiazole-4-carboxylate Using Sonogashira General Procedure starting from Preparation 3a and N,2-dimethylbut-3-yn-2-amine, 417 mg of the desired product was obtained.

¹H NMR (500 MHz, DMSO-d₆) δ ppm 7.23 (dd, 1H), 7.16 (dd, 1H), 7.12 (t, 1H), 4.26 (t, 2H), 4.11 (t, 2H), 3.77 (s, 3H), 3.25 (t, 2H), 2.89 (t, 2H), 2.37 (s, 3H), 2.32 (s, 3H), 2.1 (m, 2H), 2.04 (m, 2H), 1.34 (s, 6H); ¹³C NMR (125 MHz, DMSO-d₆) δ ppm 163.1, 151.3, 136.2, 129.1, 128.9, 119.1, 115.4, 93.7, 81.5, 68.2, 52, 51, 46.4, 30.7, 30.4, 29, 24.2, 23, 19.7, 15.7; HRMS-ESI (m/z): [M+H]+ calcd for $C_{28}H_{32}ClFN_5O_3S$: 572.1898; found: 572.1888.

Step B: methyl 2-[3-(1,3-benzothiazol-2-ylamino)-4-methyl-6,7-dihydro-5H-pyrido[2,3-c]pyridazin-8-yl]-5-[3-[2-fluoro-4-[3-methyl-3-(methylamino)but-1-ynyl]phenoxy]propyl]thiazole-4-carboxylate Using Buchwald General Procedure II staring from the product from Step A and 1,3-benzothiazol-2-amine, 77 mg of the desired product was obtained.

HRMS-ESI (m/z): [M+H]+ calcd for $C_{35}H_{37}FN_7O_3S_2$: 686.2383; found 686.2380

Step C: 2-[3-(1,3-benzothiazol-2-ylamino)-4-methyl-6,7-dihydro-5H-pyrido[2,3-c]pyridazin-8-yl]-5-[3-[2-fluoro-4-[3-methyl-3-(methylamino)but-1-ynyl]phenoxy]propyl]thiazole-4-carboxylic acid Using Hydrolysis General Procedure starting from the product from Step B, 22 mg of the desired product was obtained.

HRMS-ESI (m/z): [M+H]+ calcd for $C_{34}H_{35}FN_7O_3S_2$: 672.2227; found: 672.2224.

Example 92: 6-{3-[(1,3-benzothiazol-2-yl)amino]-4-methyl-6,7-dihydropyrido[2,3-c]pyridazin-8(5H)-yl}-3-(1-{[3-(2-{[(3S)-3,4-dihydroxybutyl]amino}ethoxy)-5,7-dimethyladamantan-1-yl]methyl}-5-methyl-1H-pyrazol-4-yl)pyridine-2-carboxylic acid Using the Amine substitution and Hydrolysis General procedure starting from Preparation 12 and 2-[(4S)-2,2-dimethyl-1,3-dioxolan-4-yl]ethanamine as the appropriate amine, a compound with a dihydroxy protected amine was obtained. Hydrolysis with a 10% HCl solution (rt, 1 h) and purification by preparative HPLC (using acetonitrile and 5 mM aqueous NH₄HCO₃ solution as eluents) afforded the desired product.

HRMS-ESI (m/z): [M+H]+ calcd for $C_{44}H_{55}N_9O_5$: 822.4125, found: 822.4120.

233

Example 93: 6-{3-[(1,3-benzothiazol-2-yl)amino]-4-methyl-6,7-dihydropyrido[2,3-c]pyridazin-8(5H)-yl}-3-(1-{[3-(2-{[(3R)-3,4-dihydroxybutyl]amino}ethoxy)-5,7-dimethyladamantan-1-yl]methyl}-5-methyl-1H-pyrazol-4-yl)pyridine-2-carboxylic acid

234

Example 94: 6-{3-[(1,3-benzothiazol-2-yl)amino]-4-methyl-6,7-dihydropyrido[2,3-c]pyridazin-8(5H)-yl}-3-[1-({3,5-dimethyl-7-[2-(methylamino)ethoxy]adamantan-1-yl}methyl)-5-methyl-1H-pyrazol-4-yl]pyridine-2-carboxylic acid Using the Amine substitution and Hydrolysis General procedure starting from Preparation 12 and methylamine as the appropriate amine, the desired product was obtained.

HRMS-ESI (m/z): [M+H]+ calcd for $C_{41}H_{50}NO_3S$: 748.3757, found: 748.3746.

Example 95: 6-{3-[(1,3-benzothiazol-2-yl)amino]-4-methyl-6,7-dihydropyrido[2,3-c]pyridazin-8(5H)-yl}-3-[1-({3-[2-(dimethylamino)ethoxy]-5,7-dimethyladamantan-1-yl}methyl)-5-methyl-1H-pyrazol-4-yl]pyridine-2-carboxylic acid Using the Amine substitution and Hydrolysis General procedure starting from Preparation 12 and 2-[(4R)-2,2-dimethyl-1,3-dioxolan-4-yl]ethanamine as the appropriate amine, a compound with a dihydroxy protected amine was obtained. Hydrolysis with a 10% HCl solution (rt, 1 h) and purification by preparative HPLC (using acetonitrile and 5 mM aqueous $NH_4HCO_3$ solution as eluents) afforded the desired product.

HRMS-ESI (m/z): [M+H]+ calcd for $C_{44}H_{56}N_9O_5S$: 822.4125, found: 822.4124.

Using the Amine substitution and Hydrolysis General procedure starting from Preparation 12 and dimethylamine as the appropriate amine, the desired product was obtained.

HRMS-ESI (m/z): [M+H]+ calcd for $C_{42}H_{52}NO_3S$: 762.3914, found: 762.3912.

235

236

Example 96: 6-{3-[(1,3-benzothiazol-2-yl)amino]-4-methyl-6,7-dihydropyrido[2,3-c]pyridazin-8(5H)-yl}-3-{1-[(3,5-dimethyl-7-{2-[(2-sulfoethyl)amino]ethoxy}adamantan-1-yl)methyl]-5-methyl-1H-pyrazol-4-yl}pyridine-2-carboxylic acid Example 97: 6-{3-[(1,3-benzothiazol-2-yl)amino]-4-methyl-6,7-dihydropyrido[2,3-c]pyridazin-8(5H)-yl}-3-{1-[(3,5-dimethyl-7-{2-[methyl(2-sulfoethyl)amino]ethoxy}adamantan-1-yl)methyl]-5-methyl-1H-pyrazol-4-yl}pyridine-2-carboxylic acid Using the Amine substitution and Hydrolysis General procedure starting from Preparation 12 and taurine as the appropriate amine, and K$_2$CO$_3$ (10 eq) as base during the substitution step, the desired product was obtained.

HRMS-ESI (m/z): [M+H]+ calcd for C$_{42}$H$_{52}$NO$_6$S2: 842.3482, found: 842.3487.

Example 98: 2-{3-[(1,3-benzothiazol-2-yl)amino]-4-methyl-6,7-dihydropyrido[2,3-c]pyridazin-8(5H)-yl}-5-{3-[4-(3-{[(but-3-yn-1-yl)amino]methyl}bicyclo[1.1.1]pentan-1-yl)-2-fluorophenoxy]propyl}-1,3-thiazole-4-carboxylic acid

237

Example 99: 6-{3-[(1,3-benzothiazol-2-yl)amino]-4-methyl-6,7-dihydropyrido[2,3-c]pyridazin-8(5H)-yl}-3-[1-({3-[2-(dimethylamino)ethoxy]adamantan-1-yl}methyl)-5-methyl-1H-pyrazol-4-yl]pyridine-2-carboxylic acid

238

Example 100: 6-{3-[(1,3-benzothiazol-2-yl)amino]-4-methyl-6,7-dihydropyrido[2,3-c]pyridazin-8(5H)-yl}-3-(1-{[3,5-dimethyl-7-(4-methylpiperazin-1-yl)adamantan-1-yl]methyl}-5-methyl-1H-pyrazol-4-yl)pyridine-2-carboxylic acid Example 101: 5-{3-[4-(3-{[(3-azidopropyl)amino]methyl}bicyclo[11.1.1]pentan-1-yl)-2-fluorophe-noxy]propyl}-2-{3-[(1,3-benzothiazol-2-yl)amino]-4-methyl-6,7-dihydropyrido[2,3-c]pyridazin-8(5H)-yl}-1,3-thiazole-4-carboxylic acid 239 240

Example 102: 2-{3-[(1,3-benzothiazol-2-yl)amino]-4-methyl-6,7-dihydropyrido[2,3-c]pyridazin-8(5H)-yl}-5-(3-{4-[3-(ethylamino)-3-methylbut-1-yn-1-yl]-2-fluorophenoxy}propyl)-1,3-thiazole-4-carboxylic acid Step A: methyl 5-[3-[4-[3-(tert-butoxycarbo-nylamino)-3-methyl-but-1-ynyl]-2-fluoro-phenoxy]propyl]-2-(3-chloro-4-methyl-6,7-dihydro-5H-pyrido[2,3-c]pyridazin-8-yl)thiazole-4-carboxylate Using Sonogashira General Procedure starting from 1.00 g of the product from Preparation 3a (1.66 mmol) and 330 mg (1.1 eq) of tert-butyl N-(1,1-dimethylprop-2-ynyl)carbamate as the appropriate alkyne, 742 mg (68%) of the desired product was obtained.

$^1$H NMR (500 MHz, DMSO-d$_6$) δ ppm 7.17 (dd, 1H), 7.12 (t, 1H), 7.11 (dd, 1H), 7.07 (brs, 1H), 4.26 (t, 2H), 4.11 (t, 2H), 3.77 (s, 3H), 3.25 (t, 2H), 2.89 (t, 2H), 2.32 (s, 3H), 2.1 (qn, 2H), 2.04 (qn, 2H), 1.50 (s, 6H), 1.40 (s, 9H); $^{13}$C NMR (125 MHz, DMSO-d$_6$) δ ppm 163.1, 155.4, 151.7, 151.5, 151.3, 147.1, 142.5, 136.2, 134.9, 129.1, 128.7, 118.9, 115.7, 115.4, 94.2, 79.3, 78.7, 68.2, 52.0, 47.1, 46.4, 30.7, 29.8, 28.7, 24.2, 23.1, 19.7, 15.7; HRMS-ESI (m/z): [M+H]$^+$ calcd for C$_{32}$H$_{38}$ClFN$_5$O$_5$S: 658.2266, found: 658.2245

Step B: methyl 5-[3-[4-(3-amino-3-methyl-but-1-ynyl)-2-fluoro-phenoxy]propyl]-2-(3-chloro-4-methyl-6,7-dihydro-5H-pyrido[2,3-c]pyridazin-8-yl)thiazole-4-carboxylate The mixture of the product from Step A (740 mg, 1.12 mmol) and HFxPyr (3 eq) in acetonitrile (5 mL/mmol) was stirred at 50° C. for 1 h. After the volatiles were removed, purification by column chromatography (silica gel, using EtOAc and MeOH (NH$_3$) as eluents) afforded 560 mg (89%) of the desired product.

$^1$H NMR (500 MHz, DMSO-d$_6$) δ ppm 7.18 (dd, 1H), 7.11 (m, 1H), 7.11 (m, 1H), 4.25 (m, 2H), 4.10 (t, 2H), 3.77

(s, 3H), 3.25 (t, 2H), 2.88 (t, 2H), 2.31 (s, 3H), 2.10 (m, 2H), 2.04 (m, 2H), 1.35 (s, 6H); $^{13}$C NMR (125 MHz, DMSO-d$_6$) δ ppm 163.1, 128.6, 118.9, 115.3, 98.1, 78.4, 68.2, 52.0, 46.3, 46.3, 32.3, 30.7, 24.2, 23.1, 19.7, 15.7; HRMS-ESI (m/z): [M+H]+ calcd for C$_{27}$H$_{30}$ClFN$_5$O$_3$S: 558.1742, found: 558.1730.

Step C: methyl 2-(3-chloro-4-methyl-6,7-dihydro-5H-pyrido[2,3-c]pyridazin-8-yl)-5-[3-[4-[3-(ethyl-amino)-3-methyl-but-1-ynyl]-2-fluoro-phenoxy]propyl]thiazole-4-carboxylate The mixture of the product from Step B (550 mg, 0.98 mmol), N-ethyl-N-isopropyl-propan-2-amine (0.52 mL, 3 eq) and iodoethane (0.12 mL, 1.5 eq) in NN-dimethylformamide (5 mL/mmol) was stirred at rt for 3 h. After the volatiles were removed, the crude intermediate was purified by column chromatography (silica gel, using EtOAc and MeOH (NH$_3$) as eluents) to give 570 mg (99%) of the desired product.

$^1$H NMR (500 MHz, DMSO-d$_6$) δ ppm 9.07 (brm, 2H), 7.41 (dd, 1H), 7.29 (dd, 1H), 7.20 (t, 1H), 4.27 (t, 2H), 4.15 (t, 2H), 3.78 (s, 3H), 3.27 (t, 2H), 3.17 (m, 2H), 2.90 (t, 2H), 2.33 (s, 3H), 2.12 (qn, 2H), 2.05 (qn, 2H), 1.64 (s, 6H), 1.26 (t, 3H); $^{13}$C NMR (125 MHz, DMSO-d$_6$) δ ppm 163.1, 155.4, 151.7, 151.4, 151.3, 148.2, 142.4, 136.3, 135.0, 129.4, 129.1, 119.5, 115.5, 113.2, 86.8, 85.3, 68.3, 53.8, 52.0, 46.4, 38.2, 30.7, 26.5, 24.2, 23.1, 19.8, 15.7, 12.2; HRMS-ESI (m/z): [M+H]+ calcd for C$_{29}$H$_{34}$ClFN$_5$O$_3$S: 586.2055, found: 586.2048.

Step D: methyl 2-[3-(1,3-benzothiazol-2-ylamino)-4-methyl-6,7-dihydro-5H-pyrido[2,3-c]pyridazin-8-yl]-5-[3-[4-[3-(ethylamino)-3-methyl-but-1-ynyl]-2-fluoro-phenoxy]propyl]thiazole-4-carboxylate Using Buchwald General Procedure I starting from 570 mg of the product from Step C (0.98 mmol) and 292 mg (2 eq) of 1,3-benzothiazol-2-amine, 420 mg (61%) of the desired product was obtained.

$^1$H NMR (500 MHz, DMSO-d$_6$) δ ppm 8.98 (m, 2H), 7.88 (brs, 1H), 7.53 (brs, 1H), 7.42 (dd, 1H), 7.38 (m, 1H), 7.29 (dm, 1H), 7.22 (t, 1H), 7.20 (m, 1H), 4.26 (t, 2H), 4.16 (t, 2H), 3.77 (s, 3H), 3.29 (t, 2H), 3.14 (m, 2H), 2.88 (t, 2H), 2.34 (s, 3H), 2.15 (m, 2H), 2.04 (m, 2H), 1.60 (s, 6H), 1.23 (t, 3H); HRMS-ESI (m/z): [M+H]+ calcd for C$_{36}$H$_{39}$FN$_7$O$_3$S$_2$: 700.2540, found: 700.2532.

Step E: 2-[3-(1,3-benzothiazol-2-ylamino)-4-methyl-6,7-dihydro-5H-pyrido[2,3-c]pyridazin-8-yl]-5-[3-[4-[3-(ethylamino)-3-methyl-but-1-ynyl]-2-fluoro-phenoxy]propyl]thiazole-4-carboxylic acid To the product from Step D (420 mg, 0.60 mmol) in a 2:1 mixture of 1,4-dioxane and water (7.5 mL/mmol) was added 50 mg (2 eq) of LiOHxH$_2$O, and the mixture was stirred at rt for 3 h. After removal of the volatiles, purification by reverse phase preparative chromatography (C18, 0.1% TFA in water:MeCN) afforded 33 mg (8%) of the desired compound.

HRMS-ESI (m/z): [M+H]+ calcd for C$_{35}$H$_{37}$FN$_7$O$_3$S$_2$: 686.2383, found: 686.2378.

Example 103: 2-{3-[(1,3-benzothiazol-2-yl)amino]-
4-methyl-6,7-dihydropyrido[2,3-c]pyridazin-8(5H)-
yl}-5-(3-{2-fluoro-4-[3-methyl-3-(piperazin-1-yl)
but-1-yn-1-yl]phenoxy}propyl)-1,3-thiazole-4-
carboxylic acid Example 104: 5-[3-(4-{3-[(3-azidopropyl)amino]
prop-1-yn-1-yl}-2-fluorophenoxy)propyl]-2-{3-[(1,
3-benzothiazol-2-yl)amino]-4-methyl-6,7-dihydro-
pyrido[2,3-c]pyridazin-8(5H)-yl}-1,3-thiazole-4-
carboxylic acid Example 105: 5-[3-(4-{3-[(3-aminopropyl)amino]
prop-1-yn-1-yl}-2-fluorophenoxy)propyl]-2-{3-[(1,
3-benzothiazol-2-yl)amino]-4-methyl-6,7-dihydro-
pyrido[2,3-c]pyridazin-8(5H)-yl}-1,3-thiazole-4-
carboxylic acid Example 106: 2-{3-[(1,3-benzothiazol-2-yl)amino]-
4-methyl-6,7-dihydropyrido[2,3-c]pyridazin-8(5H)-
yl}-5-[3-(2-fluoro-4-{3-[(pent-4-yn-1-yl)amino]
prop-1-yn-1-yl}phenoxy)propyl]-1,3-thiazole-4-
carboxylic acid Example 107: 2-{3-[(1,3-benzothiazol-2-yl)amino]-4-methyl-6,7-dihydropyrido[2,3-c]pyridazin-8(5H)-yl}-5-{3-[2-fluoro-4-(3-{[2-(2-hydroxyethoxy)ethyl](methyl)amino}prop-1-yn-1-yl)phenoxy]propyl}-1,3-thiazole-4-carboxylic acid Example 108: 2-{3-[(1,3-benzothiazol-2-yl)amino]-4-methyl-6,7-dihydropyrido[2,3-c]pyridazin-8(5H)-yl}-5-[3-(2-fluoro-4-{3-methyl-3-[(pent-4-yn-1-yl)amino]but-1-yn-1-yl}phenoxy)propyl]-1,3-thiazole-4-carboxylic acid

40

Example 109: 2-{3-[(1,3-benzothiazol-2-yl)amino]-
4-methyl-6,7-dihydropyrido[2,3-c]pyridazin-8(5H)-
yl}-5-{3-[2-fluoro-4-(3-{[(prop-2-yn-1-yl)amino]
methyl}bicyclo[1.1.1]pentan-1-yl)phenoxy]propyl}-
1,3-thiazole-4-carboxylic acid Example 110: 2-{3-[(1,3-benzothiazol-2-yl)amino]-
4-methyl-6,7-dihydropyrido[2,3-c]pyridazin-8(5H)-
yl}-5-[3-(2-fluoro-4-{3-[(hex-5-yn-1-yl)amino]prop-
1-yn-1-yl}phenoxy)propyl]-1,3-thiazole-4-
carboxylic acid

35

Example 111: 5-[3-(4-{3-[(4-azidobutyl)amino]
prop-1-yn-1-yl}-2-fluorophenoxy)propyl]-2-{3-[(1,
3-benzothiazol-2-yl)amino]-4-methyl-6,7-dihydro-
pyrido[2,3-c]pyridazin-8(5H)-yl}-1,3-thiazole-4-
carboxylic acid Example 112: 5-[3-(4-{3-[(4-azidobutyl)(methyl)
amino]prop-1-yn-1-yl}-2-fluorophenoxy)propyl]-2-
{3-[(1,3-benzothiazol-2-yl)amino]-4-methyl-6,7-
dihydropyrido[2,3-c]pyridazin-8(5H)-yl}-1,3-
thiazole-4-carboxylic acid

40

Example 113: 2-{3-[(1,3-benzothiazol-2-yl)amino]-
4-methyl-6,7-dihydropyrido[2,3-c]pyridazin-8(5H)-
yl}-5-[3-(2-fluoro-4-{3-[(hex-5-yn-1-yl)(methyl)
amino]prop-1-yn-1-yl}phenoxy)propyl]-1,3-
thiazole-4-carboxylic acid Example 114: 2-{3-[(1,3-benzothiazol-2-yl)amino]-
4-methyl-6,7-dihydropyrido[2,3-c]pyridazin-8(5H)-
yl}-5-[3-(2-fluoro-4-{3-[methyl(pent-4-yn-1-yl)
amino]prop-1-yn-1-yl}phenoxy)propyl]-1,3-
thiazole-4-carboxylic acid Example 115: 5-[3-(4-{3-[(3-azidopropyl)(methyl)
amino]prop-1-yn-1-yl}-2-fluorophenoxy)propyl]-2-
{3-[(1,3-benzothiazol-2-yl)amino]-4-methyl-6,7-
dihydropyrido[2,3-c]pyridazin-8(5H)-yl}-1,3-
thiazole-4-carboxylic acid Example 116: 2-{3-[(1,3-benzothiazol-2-yl)amino]-
4-methyl-6,7-dihydropyrido[2,3-c]pyridazin-8(5H)-
yl}-5-{3-[2-fluoro-4-(3-{[methyl(pent-4-yn-1-yl)
amino]methyl}bicyclo[1.1.1]pentan-1-yl)phenoxy]
propyl}-1,3-thiazole-4-carboxylic acid

40

Example 117: 5-{3-[4-(3-{[(4-azidobutyl)(methyl)
amino]methyl}bicyclo[11.1.1]pentan-1-yl)-2-fluoro-
phenoxy]propyl}-2-{3-[(1,3-benzothiazol-2-yl)
amino]-4-methyl-6,7-dihydropyrido[2,3-c]pyridazin-
8(5H)-yl}-1,3-thiazole-4-carboxylic acid Example 118: 2-{3-[(1,3-benzothiazol-2-yl)amino]-
4-methyl-6,7-dihydropyrido[2,3-c]pyridazin-8(5H)-
yl}-5-{3-[4-(3-{1[(but-3-yn-1-yl)(methyl)amino]
methyl}bicyclo[1.1.1]pentan-1-yl)-2-fluorophenoxy]
propyl}-1,3-thiazole-4-carboxylic acid

40

Example 119: 5-{3-[4-(3-{[(3-azidopropyl)(methyl)
amino]methyl}bicyclo[11.1.1]pentan-1-yl)-2-fluoro-
phenoxy]propyl}-2-{3-[(1,3-benzothiazol-2-yl)
amino]-4-methyl-6,7-dihydropyrido[2,3-c]pyridazin-
8(5H)-yl}-1,3-thiazole-4-carboxylic acid Example 120: 5-{3-[4-(3-{[(4-azidobutyl)amino]
methyl}bicyclo[1.1.1]pentan-1-yl)-2-fluorophenoxy]
propyl}-2-{3-[(1,3-benzothiazol-2-yl)amino]-4-
methyl-6,7-dihydropyrido[2,3-c]pyridazin-8(5H)-
yl}-1,3-thiazole-4-carboxylic acid

40

Example 121: 2-{3-[(1,3-benzothiazol-2-yl)amino]-
4-methyl-6,7-dihydropyrido[2,3-c]pyridazin-8(5H)-
yl}-5-{3-[2-fluoro-4-(3-{[(pent-4-yn-1-yl)amino]
methyl}bicyclo[1.1.1]pentan-1-yl)phenoxy]propyl}-
1,3-thiazole-4-carboxylic acid Example 122: 2-[(6R)-3-[(1,3-benzothiazol-2-yl)
amino]-6-(2-hydroxyethyl)-4-methyl-6,7-dihydro-
pyrido[2,3-c]pyridazin-8(5H)-yl]-5-(3-{4-[3-(dim-
ethylamino)prop-1-yn-1-yl]-2-
fluorophenoxy}propyl)-1,3-thiazole-4-carboxylic
acid Example 123: 2-[(6S)-3-[(1,3-benzothiazol-2-yl)
amino]-6-(2-hydroxyethyl)-4-methyl-6,7-dihydro-
pyrido[2,3-c]pyridazin-8(5H)-yl]-5-(3-{4-[3-(dim-
ethylamino)prop-1-yn-1-yl]-2-
fluorophenoxy}propyl)-1,3-thiazole-4-carboxylic
acid Example 124: 2-[3-(1,3-benzothiazol-2-ylamino)-4-methyl-6,7-dihydro-5H-pyrido[2,3-c]pyridazin-8-yl]-5-[3-[2-fluoro-4-[3-(prop-2-ynylamino)prop-1-ynyl]phenoxy]propyl]thiazole-4-carboxylic acid Step A: methyl 5-[3-[2-fluoro-4-[3-(prop-2-ynylamino)prop-1-ynyl]phenoxy]propyl]-2-[4-methyl-3-[(Z)-[3-(2-trimethylsilylethoxymethyl)-1,3-benzothiazol-2-ylidene]amino]-6,7-dihydro-5H-pyrido[2,3-c]pyridazin-8-yl]thiazole-4-carboxylate Using Sonogashira General Procedure starting from the product from Example 77, Step A (2.30 g, 2.71 mmol, 1.0 eq.) and 1.26 g of N-prop-2-ynylprop-2-yn-1-amine (13.58 mmol, 5 eq.) as the appropriate acetylene, 793 mg (36%) of the desired product was obtained.

LC/MS ($C_{41}H_{47}FN_7O_4S_2Si$) 812 [M+H]+.

Step B: 2-[3-(1,3-benzothiazol-2-ylamino)-4-methyl-6,7-dihydro-5H-pyrido[2,3-c]pyridazin-8-yl]-5-[3-[2-fluoro-4-[3-(prop-2-ynylamino)prop-1-ynyl]phenoxy]propyl]thiazole-4-carboxylic acid Using Deprotection and Hydrolysis General Procedure starting from the product from Step A (900 mg, 1.10 mmol), 222 mg (30%) of the desired product was obtained.

$^1$H NMR (500 MHz, DMSO-$d_6$) δ ppm 7.88 (d, 1H), 7.48 (br., 1H), 7.37 (t, 1H), 7.28 (dd, 1H), 7.19 (d, 1H), 7.18 (t, 1H), 7.14 (t, 1H), 4.27 (br., 2H), 4.14 (t, 2H), 3.55 (s, 2H), 3.39 (d, 2H), 3.27 (t, 2H), 3.09 (t, 1H), 2.87 (t, 2H), 2.33 (s, 3H), 2.13 (m, 2H), 2.03 (m, 2H); $^{13}$C NMR (125 MHz, DMSO-$d_6$) δ ppm 128.9, 126.5, 122.5, 122.3, 119.2, 115.5, 87.8, 82.8, 82.2, 74.5, 68.5, 46.3, 37.2, 36.6, 31.0, 23.9, 23.1, 20.3, 12.9; HRMS-ESI (m/z): [M+H]+ calcd for $C_{34}H_{31}FN_7O_3S_2$: 668.1914, found: 668.1907.

Example 125: 2-{3-[(1,3-benzothiazol-2-yl)amino]-4-methyl-6,7-dihydro-5H-pyrido[2,3-c]pyridazin-8-yl}-5-{3-[4-(3-{bis[(3S)-3,4-dihydroxybutyl]amino}prop-1-yn-1-yl)-2-fluorophenoxy]propyl}-1,3-thiazole-4-carboxylic acid Step A: methyl 5-[3-[4-[3-(tert-butoxycarbo-nylamino)prop-1-ynyl]-2-fluoro-phenoxy]propyl]-2-(3-chloro-4-methyl-6,7-dihydro-5H-pyrido[2,3-c]pyridazin-8-yl)thiazole-4-carboxylate Using Sonogashira General Procedure starting from 3.00 g of Preparation 3a (5.0 mmol) and 1.55 g of tert-butyl N-prop-2-ynylcarbamate (2 eq.) as the appropriate acetylene, 2.79 g of the desired product (89%) was obtained.

$^1$H NMR (500 MHz, dmso-d6) δ ppm 7.34 (brt, 1H), 7.26 (dd, 1H), 7.17 (dm, 1H), 7.13 (t, 1H), 4.25 (t, 2H), 4.11 (t, 2H), 3.95 (brd, 2H), 3.77 (s, 3H), 3.25 (t, 2H), 2.88 (m, 2H), 2.31 (s, 3H), 2.10 (m, 2H), 2.03 (m, 2H), 1.39 (s, 9H); $^{13}$C NMR (500 MHz, dmso-d6) δ ppm 128.9, 119.1, 115.4, 68.2, 51.9, 46.3, 30.7, 30.5, 28.7, 24.1, 23.0, 19.7, 15.7; HRMS-ESI (m/z): [M+H]$^+$ calcd for $C_{30}H_{34}ClFN_5O_5S$: 630.1953, found 630.1945.

Step B: methyl 5-[3-[4-(3-aminoprop-1-ynyl)-2-fluoro-phenoxy]propyl]-2-(3-chloro-4-methyl-6,7-dihydro-5H-pyrido[2,3-c]pyridazin-8-yl)thiazole-4-carboxylate The mixture of the product from Step A (2.19 g, 3.47 mmol), pyridine and hydrogen fluoride (1:1) (3.44 g, 10.0 eq) in MeCN (17.3 mL) was stirred at 60° C. for 1.5 h. Purification by flash chromatography (silica gel, DCM and MeOH (1.2% NH₃) as eluents) afforded the desired product (1.81 g, 98.5%).

$^1$H NMR (500 MHz, dmso-d6) δ ppm 7.26 (dd, 1H), 7.18 (dd, 1H), 7.14 (t, 1H), 5.36 (NH₃+, br., 3H), 4.25 (m, 2H), 4.12 (t, 2H), 3.77 (s, 3H), 3.61 (s, 2H), 3.25 (t, 2H), 2.88 (t, 2H), 2.31 (s, 3H), 2.10 (m, 2H), 2.04 (m, 2H); $^{13}$C NMR (500 MHz, dmso-d6) δ ppm 163.1, 155.3, 151.7, 151.5, 151.3, 147.4, 142.5, 136.1, 136.1, 134.9, 128.9, 119.1, 115.5, 115.2, 89.2, 81.9, 68.2, 51.9, 46.3, 31.1, 30.7, 24.2, 23.0, 19.7, 15.7; HRMS-ESI (m/z): [M+H]+ calcd for $C_{25}H_{26}ClFN_5O_3S$: 530.1429, found 530.1410.

Step C: (4S)-4-(2-iodoethyl)-2,2-dimethyl-1,3-dioxolane

To the mixture of PPh₃ (11.84 g, 2.2 eq), imidazole (3.07 g, 2.2 eq) and 2-[(4S)-2,2-dimethyl-1,3-dioxolan-4-yl]ethanol (2.92 mL, 20.52 mmol) in dichloromethane (103 mL) was added iodine (11.46 g, 2.2 eq) portionwise at 0° C., then stirred at rt for 18 h. Then, the reaction was quenched with 100 mL of Na₂S₂O₃ solution and the phases were separated, the organic phase was washed with brine, dried, and purified via flash chromatography (silica gel, heptane and heptane-MTBE as eluents) to give the desired compound (2.90 g, 55%).

$^1$H NMR (500 MHz, dmso-d6) δ ppm 4.06 (m, 1H), 4.01/3.45 (dd+dd, 2H), 3.28/3.21 (dd+dd, 2H), 2.00/1.97 (m+m, 2H), 1.31 (s, 3H), 1.26 (s, 3H); $^{13}$C NMR (500 MHz, dmso-d6) δ ppm 108.7, 75.8, 68.3, 37.9, 27.3, 26.0, 3.5; GC-MS (E1, M+): 255.79.

Step D: methyl 5-[3-[4-[3-[bis[2-[(4S)-2,2-dim-ethyl-1,3-dioxolan-4-yl]ethyl]amino]prop-1-ynyl]-2-fluoro-phenoxy]propyl]-2-(3-chloro-4-methyl-6,7-dihydro-5H-pyrido[2,3-c]pyridazin-8-yl)thiazole-4-carboxylate The mixture of the product from Step B (500 mg, 0.94 mmol), the product from Step C (483.2 mg, 2.0 eq) and N-ethyl-N-isopropyl-propan-2-amine (1.0 mL, 6 eq) in N,N-dimethylformamide (4.7 mL) was stirred at rt for 6 h. 10 mL of a 2 M solution of dimethylamine was added and the reaction mixture was further stirred for 1 h. The mixture was diluted with water and saturated solution of NaHCO₃ and extracted with EtOAc. The combined organic phases were washed with brine, dried, concentrated and purified by preparative HPLC (MeCN, NH₄HCO₃) to give the desired compound (100 mg, 13%).

$^1$H NMR (500 MHz, dmso-d6) δ ppm 7.28 (dd, 1H), 7.18 (dm, 1H), 7.14 (t, 1H), 4.27 (t, 2H), 4.11 (t, 2H), 4.07 (m, 2H), 3.99/3.46 (dd+dd, 4H), 3.76 (s, 3H), 3.56 (s, 2H), 2.89 (t, 2H), 2.51 (m, 4H), 2.33 (s, 3H), 2.32 (t, 2H), 2.11 (m, 2H), 2.04 (m, 2H), 1.64 (m, 4H), 1.30 (s, 6H), 1.24 (s, 6H); HRMS-ESI (m/z): [M+H]+ calcd for $C_{39}H_{50}ClFN_5O_7S$: 786.3104, found 786.3111.

Step E: methyl 2-[3-(1,3-benzothiazol-2-ylamino)-4-methyl-6,7-dihydro-5H-pyrido[2,3-c]pyridazin-8-yl]-5-[3-[4-[3-[bis[2-[(4S)-2,2-dimethyl-1,3-dioxo-lan-4-yl]ethyl]amino]prop-1-ynyl]-2-fluoro-phenoxy]propyl]thiazole-4-carboxylate Using Buchwald General Procedure I starting from 100 mg of the product from Step D (0.127 mmol) and preparative HPLC purification (MeCN, NH₄HCO₃), 90 mg of the desired product (78%) was obtained.

$^1$H NMR (500 MHz, dmso-d6) δ ppm 7.90 (brs, 1H), 7.60 (brs, 1H), 7.37 (brm, 1H), 7.29 (dd, 1H), 7.20 (brm, 1H), 7.19 (dm, 1H), 7.16 (t, 1H), 4.45/3.98 (dd+dd, 4H), 4.26 (t, 2H), 4.14 (t, 2H), 4.05 (dd, 2H), 3.78 (s, 3H), 3.53 (s, 2H), 3.28 (t, 2H), 2.88 (t, 2H), 2.5 (m, 4H), 2.35 (s, 3H), 2.14 (m, 2H), 2.05 (m, 2H), 1.63 (m, 4H), 1.3 (s, 6H), 1.24 (s, 6H); HRMS-ESI (m/z): [M+H]+ calcd for $C_{46}H_{55}FN_7O_7S_2$: 900.3588, found 900.3591.

Step F: 2-[3-(1,3-benzothiazol-2-ylamino)-4-methyl-6,7-dihydro-5H-pyrido[2,3-c]pyridazin-8-yl]-5-[3-[4-[3-[bis[(3S)-3,4-dihydroxybutyl]amino]prop-1-ynyl]-2-fluoro-phenoxy]propyl]thiazole-4-carboxylic acid The mixture of the product from Step E (90 mg, 0.1 mmol) and LiOH×H₂O (95 mg, 22.6 eq) in 1,4-dioxane (1 mL) and water (1 mL) was stirred at rt for 1 h, and at 50° C. for 2 h. After treatment with hydrogen chloride (8 mmol) and stirring at rt for 4 h, a saturated solution of NaHCO₃ and a 1:1 mixture of water and brine were added, and the desired product was filtered out (33 mg, 40%).

HRMS-ESI (m/z) [M+H]+ calcd for $C_{39}H_{45}FN_7O_7S_2$: 806.2806, found 806.2803.

Example 126: methyl 5-[3-[4-(3-aminoprop-1-ynyl)-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylate Step A: methyl 2-[3-(1,3-benzothiazol-2-ylamino)-4-methyl-6,7-dihydro-5H-pyrido[2,3-c]pyridazin-8-yl]-5-[3-[4-[3-(tert-butoxycarbonylamino)prop-1-ynyl]-2-fluoro-phenoxy]propyl]thiazole-4-carboxylate Using Buchwald General Procedure I starting from 4.60 g of Example 125, Step A and 2.20 g (2 eq) of 2-amino-benzothiazole followed by a column chromatography purification (silica gel using heptane, EtOAc, and MeOH (1.2% NH3) as eluents), 4.02 g (74%) of the desired product was obtained.

$^1$H NMR (500 MHz, dmso-d6) δ ppm 7.90 (br., 1H), 7.61 (br., 1H), 7.37 (brt., 1H), 7.27 (dd, 1H), 7.19 (br., 1H), 7.19 (dd, 1H), 7.15 (t, 1H), 4.25 (t, 2H), 4.14 (t, 2H), 3.94 (d, 2H), 3.77 (s, 3H), 3.27 (t, 2H), 2.86 (t, 2H), 2.33 (s, 3H), 2.13 (m, 2H), 2.04 (m, 2H), 1.39 (s, 9H); $^{13}$C NMR (500 MHz, dmso-d6) δ ppm 163.2, 155.7, 129.0, 126.4, 122.5, 122.2, 119.2, 115.5, 68.4, 51.9, 46.3, 31.0, 30.5, 28.7, 23.9, 23.1, 20.3, 12.9; HRMS-ESI (m/z): [M+H]+ calcd for $C_{37}H_{39}FN_7O_5S_2$: 744.2438, found: 744.2425.

Step B: methyl 5-[3-[4-(3-aminoprop-1-ynyl)-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylate The mixture of the product from Step A (4.00 g, 5.38 mmol), pyridine and hydrogen fluoride (1:1) (5.33 g, 10 eq) in MeCN (27 mL) was stirred at 60 C for 16 h. Purification by column chromatography (silica gel, DCM and MeOH (NH3) as eluents) afforded the desired compound.

HRMS-ESI (m/z): [M+H]+ calcd for $C_{32}H_{31}FN_7O_3S_2$: 644.1914, found: 644.1913.

Example 127: 6-[3-(1,3-benzothiazol-2-ylamino)-4-methyl-6,7-dihydro-5H-pyrido[2,3-c]pyridazin-8-yl]-3-[1-[[3,5-dimethyl-7-(2-pyrrolidin-1-ylethoxy)-1-adamantyl]methyl]-5-methyl-pyrazol-4-yl]pyridine-2-carboxylic acid Using the Amine substitution and Hydrolysis General procedure starting from Preparation 12 and pyrrolidine as the appropriate amine, the desired product was obtained.

HRMS-ESI (m/z): [M+H]+ calcd for $C_{44}N_{54}NO_3S$: 788, 4070, found: 788.4068.

Example 128: 6-[3-(1,3-benzothiazol-2-ylamino)-4-methyl-6,7-dihydro-5H-pyrido[2,3-c]pyridazin-8-yl]-3-[1-[[3,5-dimethyl-7-[2-(4-methylpiperazin-1-yl)ethoxy]-1-adamantyl]methyl]-5-methyl-pyrazol-4-yl]pyridine-2-carboxylic acid Using the Amine substitution and Hydrolysis General procedure starting from Preparation 12 and 1-methylpiperazine as the appropriate amine, the desired product was obtained. HRMS-ESI (m/z): [M+2H]2+ calcd for $C_{45}H_{58}N_{10}O_3S$: 409.2207, found: 409.2208.

Example 129: 2-[3-(1,3-benzothiazol-2-ylamino)-4-methyl-6,7-dihydro-5H-pyrido[2,3-c]pyridazin-8-yl]-5-[3-[4-[3-[[(3S)-3,4-dihydroxybutyl]amino]prop-1-ynyl]-2-fluoro-phenoxy]propyl]thiazole-4-carboxylic acid The mixture of the product from Preparation 3c (400 mg, 0.67 mmol), paraformaldehyde (400 mg, 20 eq), (2S)-4-aminobutane-1,2-diol, hydrogen chloride (1:1) (754.3 mg, 8 eq), triethylamine (2.3 mL, 25 eq), CuI (127 mg, 1 eq) and molecular sieves (0.5 g) in ethanol (3.3 mL) was kept in an Anton-Paar microwave reactor at 120° C. for 1 h. Purification by column chromatography (silica gel, using heptane, EtOAc and MeOH/NH$_3$ (0.6N) as eluents) and RF HPLC (Gemini, using water with 0.1% TFA and acetonitrile as eluents) afforded 15.3 mg (3%) of the desired product.

HRMS-ESI (m/z): [M+H]+ calcd for C$_{35}$H$_{37}$FN$_7$O$_5$S$_2$: 718.2282, found: 718.2266.

Example 130: 6-[3-(1,3-benzothiazol-2-ylamino)-4-methyl-6,7-dihydro-5H-pyrido[2,3-c]pyridazin-8-yl]-3-[1-[[3-[2-[[(3R)-3,4-dihydroxybutyl]-methyl-amino]ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 2-[(4R)-2,2-dimethyl-1,3-dioxolan-4-yl]-N-methyl-ethanamine as the appropriate amine, a compound with a dihydroxy protected amine was obtained. Hydrolysis with a 10% HCl solution (rt, 1 h) and purification by preparative HPLC (using acetonitrile and 5 mM aqueous NH$_4$HCO$_3$ solution as eluents) afforded the desired product.

HRMS-ESI (m/z): [M+2H]$^{2+}$ calcd for C$_{45}$H$_{59}$N$_9$O$_5$S: 418.7180, found: 418.7167.

Example 131: 2-[3-(1,3-benzothiazol-2-ylamino)-4-methyl-6,7-dihydro-5H-pyrido[2,3-c]pyridazin-8-yl]-5-[3-[4-[3-[[(3R)-3,4-dihydroxybutyl]amino]prop-1-ynyl]-2-fluoro-phenoxy]propyl]thiazole-4-carboxylic acid

The mixture of the product from Preparation 3c (200 mg, 0.33 mmol), paraformaldehyde (200 mg, 20 eq), (2R)-4-aminobutane-1,2-diol, hydrogen chloride (1:1) (471 mg, 10 eq), triethylamine (1.2 mL, 25 eq), CuI (64 mg, 1 eq) and molecular sieves (0.25 g) in ethanol (1.6 mL) was kept in an Anton-Paar microwave reactor at 120° C. for 1 h. Purification by column chromatography (silica gel, using heptane, EtOAc and MeOH/NH₃ (0.6N) as eluents) and RF HPLC (Gemini, using water with 0.1% TFA and acetonitrile as eluents) afforded 43 mg (18%) of the desired product.

HRMS-ESI (m/z): [M+H]+ calcd for $C_{35}H_{37}FN_7O_5S_2$: 718.2282, found: 718.2281.

Example 132: 6-[3-(1,3-benzothiazol-2-ylamino)-4-methyl-6,7-dihydro-5H-pyrido[2,3-c]pyridazin-8-yl]-3-[1-[[3-[2-(4-hydroxybutylamino)ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 4-aminobutan-1-ol as the appropriate amine, the desired product was obtained.

HRMS-ESI (m/z): [M+H]+ calcd for $C_{44}H_{56}NO_4S$: 806.4176, found: 806.4174.

Example 133: 6-[3-(1,3-benzothiazol-2-ylamino)-4-methyl-6,7-dihydro-5H-pyrido[2,3-c]pyridazin-8-yl]-3-[1-[[3-[2-[[3-hydroxy-2-(hydroxymethyl)propyl]amino]ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and (2,2-dimethyl-1,3-dioxan-5-yl)methanamine as the appropriate amine a compound with a dihydroxy protected amine was obtained. Hydrolysis with a 10% HCl solution (rt, 1 h) and purification by preparative HPLC (using acetonitrile and 5 mM aqueous $NH_4HCO_3$ solution as eluents) afforded the desired product.

HRMS-ESI (m/z): [M+H]+ calcd for $C_{44}H_{56}N_9O_5S$: 822, 4125, found: 822.4099.

Example 134: 6-[3-(1,3-benzothiazol-2-ylamino)-4-methyl-6,7-dihydro-5H-pyrido[2,3-c]pyridazin-8-yl]-3-[1-[[3-[2-[bis(2-hydroxyethyl)amino]ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 2-(2-hydroxy-ethylamino)ethanol as the appropriate amine, the desired product was obtained.

HRMS-ESI (m/z): [M+H]+ calcd for $C_{44}H_{56}N_9O_5S$: 822, 4125, found: 822.4123.

Example 135: 6-[3-(1,3-benzothiazol-2-ylamino)-4-methyl-6,7-dihydro-5H-pyrido[2,3-c]pyridazin-8-yl]-3-[1-[[3-[2-[[2-hydroxy-1-(hydroxymethyl)ethyl]amino]ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 2-aminopropane-1,3-diol as the appropriate amine, the desired product was obtained.

HRMS-ESI (m/z): [M+H]+ calcd for $C_{43}H_{54}N_9O_5S$: 808.3969, found: 808.3965.

Example 136: 6-[3-(1,3-benzothiazol-2-ylamino)-4-methyl-6,7-dihydro-5H-pyrido[2,3-c]pyridazin-8-yl]-3-[1-[[3-[2-[2-(2-hydroxyethoxy)ethylamino] ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 2-(2-aminoethoxy)ethanol as the appropriate amine, the desired product was obtained.

HRMS-ESI (m/z): [M+H]+ calcd for $C_{44}H_{56}N_9O_5S$: 822.4125, found: 822.4116.

Example 137: 6-[3-(1,3-benzothiazol-2-ylamino)-4-methyl-6,7-dihydro-5H-pyrido[2,3-c]pyridazin-8-yl]-3-[1-[[3-[2-[bis(3-hydroxypropyl)amino]ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 3-(3-hydroxy-propylamino)propan-1-ol as the appropriate amine, the desired product was obtained.

HRMS-ESI (m/z): [M+H]+ calcd for $C_{46}H_{60}N_9O_5S$: 850.4438, found: 850.4436.

Example 138: 6-[3-(1,3-benzothiazol-2-ylamino)-4-methyl-6,7-dihydro-5H-pyrido[2,3-c]pyridazin-8-yl]-3-[1-[[3-[2-(3-hydroxypropylamino)ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 3-aminopropan-1-ol as the appropriate amine, the desired product was obtained.

HRMS-ESI (m/z): [M+H]+ calcd for $C_{43}H_{54}N_9O_4S$: 792.4019, found: 792.4012.

Example 139: 5-[3-[4-[3-[acetyl(methyl)amino]prop-1-ynyl]-2-fluoro-phenoxy]propyl]-2-[3-(1,3-benzothiazol-2-ylamino)-4-methyl-6,7-dihydro-5H-pyrido[2,3-c]pyridazin-8-yl]thiazole-4-carboxylic acid Step A: methyl 5-[3-[4-[3-[tert-butoxycarbonyl(methyl)amino]prop-1-ynyl]-2-fluoro-phenoxy]propyl]-2-(3-chloro-4-methyl-6,7-dihydro-5H-pyrido[2,3-c]pyridazin-8-yl)thiazole-4-carboxylate Using Sonogashira General Procedure starting from 4.00 g of Preparation 3a (6.63 mmol) and 2.24 g tert-butyl N-methyl-N-prop-2-ynyl-carbamate (13.3 mmol, 2 eq) as the appropriate acetylene, 2.40 g (55%) of the desired product was obtained.

$^1$H NMR (500 MHz, dmso-d6) δ ppm 7.30 (dd, 1H), 7.20 (dm, 1H), 7.13 (t, 1H), 4.24 (m, 2H), 4.23 (brs, 2H), 4.11 (t, 2H), 3.77 (s, 3H), 3.24 (t, 2H), 2.87 (m, 2H), 2.86 (s, 3H), 2.30 (s, 3H), 2.10 (m, 2H), 2.03 (m, 2H), 1.41 (s, 9H); $^{13}$C NMR (500 MHz, dmso-d6) δ ppm 129.1, 119.3, 115.4, 85.2, 82.4, 68.2, 51.9, 46.3, 38.6, 33.8, 30.7, 28.5, 24.1, 23.0, 19.7, 15.7; HRMS-ESI (m/z): [M+H]+ calcd for $C_{31}H_{36}ClFN_5O_5S$: 644.2110, found: 644.2094.

Step B: methyl 2-(3-chloro-4-methyl-6,7-dihydro-5H-pyrido[2,3-c]pyridazin-8-yl)-5-[3-[2-fluoro-4-[3-(methylamino)prop-1-ynyl]phenoxy]propyl]thiazole-4-carboxylate To 322 mg product from Step A (0.5 mmol) in 2.5 mL acetonitrile was added 0.9 mL of hydrogen fluoride in pyridine (20 eq). The reaction mixture was stirred at 60° C. until no further conversion was observed. Purification via flash chromatography (silica gel, using DCM and MeOH (1.2% NH$_3$)) afforded 258 mg (95%) of desired product.

$^1$H NMR (500 MHz, dmso-d6) δ ppm 7.25 (dd, 1H), 7.17 (dd, 1H), 7.12 (t, 1H), 4.25 (t, 2H), 4.11 (t, 2H), 3.77 (s, 3H), 3.46 (s, 2H), 3.25 (t, 2H), 2.88 (t, 2H), 2.32 (s, 3H), 2.31 (s, 3H), 2.10 (qn, 2H), 2.03 (qn, 2H), 1.99 (brs, 1H); $^{13}$C NMR (500 MHz, dmso-d6) δ ppm 163.1, 155.4, 151.7, 151.6, 151.3, 147.2, 142.5, 136.2, 134.9, 129.0, 128.8, 119.1, 115.7, 115.4, 88.7, 82.1, 68.3, 52.0, 46.4, 40.5, 35.4, 30.8, 24.2, 23.1, 19.7, 15.7; HRMS-ESI (m/z): [M+H]+ calcd for $C_{26}H_{28}ClFN_5O_3S$: 544.1585, found: 544.1570.

Step C: methyl 5-[3-[4-[3-[acetyl(methyl)amino]prop-1-ynyl]-2-fluoro-phenoxy]propyl]-2-(3-chloro-4-methyl-6,7-dihydro-5H-pyrido[2,3-c]pyridazin-8-yl)thiazole-4-carboxylate To 220 mg of the product from Step B (0.41 mmol) and 0.085 mL of TEA (1.5 eq) in 2 mL of dichloromethane was added 0.031 mL of acetyl chloride (1.1 eq). The reaction mixture was stirred until no further conversion was observed. Purification via flash chromatography (silica gel, using DCM and MeOH (1.2% NH$_3$) as eluents) afforded 174 mg (73%) of the desired product.

$^1$H NMR (500 MHz, dmso-d6) δ ppm 7.34/7.31 (dd/dd, 1H), 7.23/7.20 (brd/brd., 1H), 7.14/7.13 (t/t, 1H), 4.38/4.34 (s/s, 2H), 4.25 (m, 2H), 4.12 (t, 2H), 3.77 (s, 3H), 3.25 (t, 2H), 3.05/2.88 (s/s, 3H), 2.88 (t, 2H), 2.31 (s, 3H), 2.10 (m, 2H), 2.09/2.02 (s/s, 3H), 2.03 (m, 2H); $^{13}$C NMR (500 MHz, dmso-d6) δ ppm 170.2/170.1, 163.0, 155.4, 151.3, 142.4, 134.9, 129.2/129.1, 119.4/119.3, 115.4, 85.3/84.7, 82.9/81.9, 68.2, 51.9, 46.3, 40.6/36.3, 35.4/33.1, 30.7, 24.1, 23.0, 21.9/21.8, 19.7, 15.7. HRMS-ESI (m/z): [M+H]+ calcd for $C_{28}H_{30}ClFN_5O_3S$: 586.1691, found: 586.1690.

Step D: methyl 5-[3-[4-[3-[acetyl(methyl)amino]
prop-1-ynyl]-2-fluoro-phenoxy]propyl]-2-[3-(1,3-
benzothiazol-2-ylamino)-4-methyl-6,7-dihydro-5H-
pyrido[2,3-c]pyridazin-8-yl]thiazole-4-carboxylate Using Buchwald General Procedure I starting from 170
mg (0.29 mmol) of the product from Step C and 87 mg (2
eq) of 1, 3-benzothiazol-2-amine, 220 mg (98%) of the
desired product was obtained.

HRMS-ESI (m/z): [M+H]+ calcd for $C_{35}H_{35}FN_7O_4S_2$:
700.2176, found: 700.2180.

Step E: 5-[3-[4-[3-[acetyl(methyl)amino]prop-1-
ynyl]-2-fluoro-phenoxy]propyl]-2-[3-(1,3-benzothi-
azol-2-ylamino)-4-methyl-6,7-dihydro-5H-pyrido[2,
3-c]pyridazin-8-yl]thiazole-4-carboxylic acid Using Hydrolysis General Procedure starting from the
product of Step D as the appropriate methyl ester, the desired
product was obtained.

HRMS-ESI (m/z): [M+H]+ calcd for $C_{34}H_{33}FN_7O_4S_2$:
686.2023, found: 686.2019.

Example 140: 6-[3-(1,3-benzothiazol-2-ylamino)-4-
methyl-6,7-dihydro-5H-pyrido[2,3-c]pyridazin-8-
yl]-3-[1-[[3-[2-[bis(4-hydroxybutyl)amino]ethoxy]-
5,7-dimethyl-1-adamantyl]methyl]-5-methyl-
pyrazol-4-yl]pyridine-2-carboxylic acid Example 141: 2-[3-(1,3-benzothiazol-2-ylamino)-4-
methyl-6,7-dihydro-5H-pyrido[2,3-c]pyridazin-8-
yl]-5-[3-[4-[3-(dimethylamino)prop-1-ynyl]phe-
noxy]propyl]thiazole-4-carboxylic acid

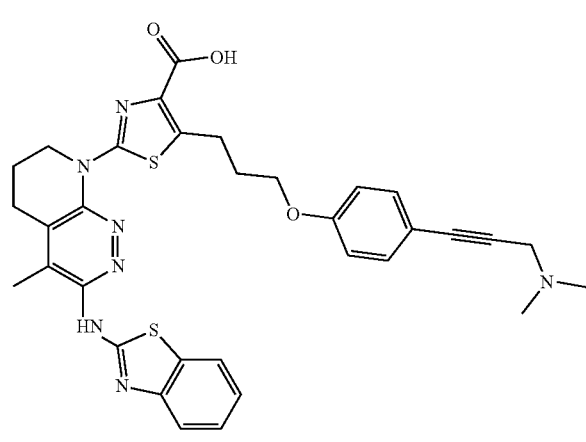 [SMILES: Cc1c(Nc2nc3ccccc3s2)nnc2c1CCCN2c1nc(C(=O)O)c(CCCOc2ccc(C#CCN(C)C)cc2)s1]

Step A: 4-[3-(dimethylamino)prop-1-ynyl]phenol

Using Sonogashira General Procedure starting from 10.0
g of 4-iodophenol (45.45 mmol) and 4.91 g (1.3 eq) of Using the Amine substitution and Hydrolysis General
procedure starting from Preparation 12 and 4-(4-hydroxy-
butylamino)butan-1-ol as the appropriate amine, the desired
product was obtained.

HRMS-ESI (m/z): [M+H]+ calcd for $C_{48}H_{64}N_9O_5S$:
878.4751, found: 878.4752.

NN-dimethylprop-2-yn-1-amine, 3.29 g (41%) of the
desired product was obtained.

$^1$H NMR (400 MHz, DMSO-d$_6$) δ ppm 9.83 (brs, 1H),
7.25 (d, 2H), 6.74 (d, 2H), 3.44 (s, 2H), 2.26 (s, 6H); LC/MS
($C_{11}H_{14}NO$) 176[M+H]+.

Step B: methyl 2-(tert-butoxycarbonylamino)-5-[3-[tert-butyl(diphenyl)silyl]oxypropyl]thiazole-4-carboxylate To the product of Preparation 1a, Step C (77.0 g, 243.7 mmol), imidazole (33.14 g, 2 eq) and DMAP (1.49 g, 0.05 eq) in DMF (973 mL) was added dropwise tert-butyl(chloro)diphenylsilane (93.5 mL, 1.5 eq) and the reaction mixture was stirred at rt for 16 h. After removal of the volatiles, purification by column chromatography (silica gel, using heptane and EtOAc as eluents) afforded 13.56 g (99%) of the desired product.

$^1$H NMR (500 MHz, DMSO-d$_6$) δ ppm 11.63 (s, 1H), 7.60 (d, 4H), 7.45 (t, 2H), 7.42 (t, 4H), 3.74 (s, 3H), 3.67 (t, 2H), 3.20 (t, 2H), 1.87 (qn, 2H), 1.47 (s, 9H), 0.99 (s, 9H); $^{13}$C NMR (125 MHz, DMSO-d$_6$) δ ppm 162.8, 156.0, 142.6, 135.6, 135.5, 133.5, 130.3, 128.3, 81.8, 62.9, 51.9, 34.0, 28.3, 27.1, 23.2, 19.2; HRMS-ESI (m/z): [M+H]+ calcd for C$_{29}$H$_{39}$N$_2$O$_5$SSi: 555.2349, found: 555.2336.

Step C: methyl 2-[tert-butoxycarbonyl-[3-(3,6-dichloro-5-methyl-pyridazin-4-yl)propyl]amino]-5-[3-[tert-butyl(diphenyl)silyl]oxypropyl]thiazole-4-carboxylate Using Alkylation General Procedure starting from 34.95 g (63 mmol) of the product from Step B and 25.0 g (1.2 eq) of 3,6-dichloro-4-(3-iodopropyl)-5-methyl-pyridazine as the appropriate iodine compound, 51.0 g (quantitative yield) of the desired product was obtained.

$^1$H NMR (500 MHz, DMSO-d$_6$) δ ppm 7.63-7.37 (m, 10H), 4.09 (t, 2H), 3.75 (s, 3H), 3.67 (t, 2H), 3.20 (t, 2H), 2.82 (m, 2H), 2.40 (s, 3H), 1.87 (m, 2H), 1.87 (m, 2H), 1.50 (s, 9H), 0.97 (s, 9H); $^{13}$C NMR (125 MHz, DMSO-d$_6$) δ ppm 62.9, 52.0, 46.1, 33.9, 28.1, 27.5, 27.1, 25.9, 23.8, 16.4; HRMS-ESI (m/z): [M+H]+ calcd for C$_{37}$H$_{47}$C$_{12}$N$_4$O$_5$SSi: 757.2413, found: 757.2395.

Step D: methyl 5-[3-[tert-butyl(diphenyl)silyl]oxypropyl]-2-[3-(3,6-dichloro-5-methyl-pyridazin-4-yl)propylamino]thiazole-4-carboxylate Using Deprotection with HFIP General Procedure starting from 51.70 g of the product from Step C (68 mmol), 36.32 g (81%) of the desired product was obtained.

$^1$H NMR (500 MHz, DMSO-d$_6$) δ ppm 7.71 (t, 1H), 7.63-7.37 (m, 10H), 3.69 (s, 3H), 3.67 (t, 2H), 3.30 (m, 2H), 3.10 (t, 2H), 2.85 (m, 2H), 2.83 (s, 3H), 1.79 (m, 2H), 1.78 (m, 2H), 0.98 (s, 9H); $^{13}$C NMR (125 MHz, DMSO-d$_6$) δ ppm 62.9, 51.7, 44.1, 34.2, 28.0, 27.1, 27.0, 23.4, 16.4; HRMS-ESI (m/z): [M+H]+ calcd for C$_{32}$H$_{39}$Cl$_2$N$_4$O$_3$SSi: 657.1889, found: 657.1875.

Step E: methyl 5-[3-[tert-butyl(diphenyl)silyl]oxypropyl]-2-(3-chloro-4-methyl-6,7-dihydro-5H-pyrido[2,3-c]pyridazin-8-yl)thiazole-4-carboxylate The mixture of 36.0 g (54.7 mmol) of the product from Step D and 35.7 g (2 eq) of Cs$_2$CO$_3$ in 1,4-dioxane (383 mL) was stirred at 90° C. for 18 h. After dilution with water, the precipitated solid was filtered off, washed with diethylether, and dried to give 34.0 g (99%) of the desired product.

$^1$H NMR (500 MHz, DMSO-d$_6$) δ ppm 7.61 (d, 4H), 7.43 (t, 2H), 7.42 (t, 4H), 4.26 (t, 2H), 3.77 (s, 3H), 3.70 (t, 2H), 3.23 (t, 2H), 2.90 (t, 2H), 2.33 (s, 3H), 2.04 (qn, 2H), 1.90 (qn, 2H), 1.00 (s, 9H); $^{13}$C NMR (125 MHz, DMSO-d$_6$) δ ppm 163.1, 155.3, 151.8, 151.4, 143.2, 136.2, 135.5, 134.7, 133.6, 130.3, 129.0, 128.3, 63.1, 51.9, 46.3, 34.1, 27.1, 24.2, 23.1, 19.8, 19.2, 15.7; HRMS-ESI (m/z): [M+H]V calcd for C$_{32}$H$_{38}$ClN$_4$O$_3$SSi: 621.2122, found: 621.2097.

Step F: methyl 2-(3-chloro-4-methyl-6,7-dihydro-5H-pyrido[2,3-c]pyridazin-8-yl)-5-(3-hydroxypropyl)thiazole-4-carboxylate The mixture of 23.36 g (37.6 mmol) of the product from Step E and 45 mL (1.2 eq.) of 1 M TBAF solution in THF (5 mL/mmol) was stirred at rt for 2 h. After the removal of the volatiles, purification by column chromatography (silica gel, using EtOAc and MeOH/NH$_3$ as eluents) afforded 12.88 g (89%) of the desired product.

$^1$H NMR (500 MHz, DMSO-d$_6$) δ ppm 4.54 (br., 1H), 4.25 (m, 2H), 3.80 (s, 3H), 3.45 (t, 2H), 3.11 (m, 2H), 2.88 (t, 2H), 2.31 (s, 3H), 2.04 (m, 2H), 1.77 (m, 2H); $^{13}$C NMR (125 MHz, DMSO-d$_6$) δ ppm 163.1, 155.2, 151.2, 143.8, 136.1, 134.5, 129.0, 60.5, 52.0, 46.3, 34.6, 24.2, 23.2, 19.7, 15.7; HRMS-ESI (m/z): [M+H]+ calcd for C$_{16}$H$_{20}$ClN$_4$O$_3$S: 383.0945, found: 383.0937.

Step G: methyl 2-(3-chloro-4-methyl-6,7-dihydro-5H-pyrido[2,3-c]pyridazin-8-yl)-5-[3-[4-[3-(dimethylamino)prop-1-ynyl]phenoxy]propyl]thiazole-4-carboxylate Using Mitsunobu General Procedure starting from 0.65 g (1.2 eq) of the product from Step F and 250 mg (1.43 mmol) of 4-[3-(dimethylamino)prop-1-ynyl]phenol in THF (9 mL/mmol), 0.28 g (37%) of the desired product was obtained.

$^1$H NMR (500 MHz, DMSO-d$_6$) δ ppm 7.34 (d, 2H), 6.91 (d, 2H), 4.26 (t, 2H), 4.03 (t, 2H), 3.78 (s, 3H), 3.40 (s, 2H), 3.25 (t, 2H), 2.88 (t, 2H), 2.31 (s, 3H), 2.22 (s, 6H), 2.08 (qn, 2H), 2.03 (qn, 2H); $^{13}$C NMR (125 MHz, DMSO-d$_6$) δ ppm 163.1, 158.9, 155.3, 151.7, 151.3, 142.7, 136.2, 134.9, 133.3, 129.0, 115.2, 115.0, 85.2, 84.1, 67.1, 52.0, 48.3, 46.3, 44.3, 30.8, 24.1, 23.1, 19.7, 15.7; HRMS-ESI (m/z): [M+H]+ calcd for C$_{27}$H$_{31}$C$_1$N$_5$O$_3$S: 540.1836, found: 540.1834.

Step H: methyl 2-[3-(1,3-benzothiazol-2-ylamino)-4-methyl-6,7-dihydro-5H-pyrido[2,3-c]pyridazin-8-yl]-5-[3-[4-[3-(dimethylamino)prop-1-ynyl]phenoxy]propyl]thiazole-4-carboxylate Using Buchwald General Procedure I starting from 0.27 g of the product from Step G (0.5 mmol), 0.29 g (89%) of the desired product was obtained.

$^1$H NMR (500 MHz, DMSO-d$_6$) δ ppm 7.83 (dm, 1H), 7.50 (dm, 1H), 7.36 (m, 1H), 7.35 (m, 2H), 7.18 (m, 1H), 6.94 (m, 2H), 4.28 (m, 2H), 4.09 (t, 2H), 3.80 (s, 3H), 3.39 (s, 2H), 3.29 (t, 2H), 2.88 (t, 2H), 2.35 (s, 3H), 2.23 (s, 6H), 2.13 (m, 2H), 2.07 (m, 2H); HRMS-ESI (m/z): [M+H]+ calcd for C$_{34}$H$_{36}$N$_7$O$_3$S$_2$: 654.2321, found: 654.2322.

Step I: 2-[3-(1,3-benzothiazol-2-ylamino)-4-methyl-6,7-dihydro-5H-pyrido[2,3-c]pyridazin-8-yl]-5-[3-[4-[3-(dimethylamino)prop-1-ynyl]phenoxy]propyl]thiazole-4-carboxylic acid To the product from Step H (280 mg, 0.43 mmol) in a 1:1 mixture of THF and water (10 mL/mmol) was added 90 mg (5 eq) of LiOHxH$_2$O, and the reaction mixture was stirred at 50° C. for 18 h. After the removal of the volatiles, purification by reverse phase preparative chromatography (C18, 0.1% TFA in water and MeCN as eluents) afforded 132 mg (48%) of the desired compound.

HRMS-ESI (m/z): [M+H]+ calcd for C$_{33}$H$_{34}$N$_7$O$_3$S$_2$: 640.2165, found: 640.2160.

Example 142: 6-[3-(1,3-benzothiazol-2-ylamino)-4-methyl-6,7-dihydro-5H-pyrido[2,3-c]pyridazin-8-yl]-3-[1-[[3,5-dimethyl-7-(2-morpholinoethoxy)-1-adamantyl]methyl]-5-methyl-pyrazol-4-yl]pyridine-2-carboxylic acid Using the Amine substitution and Hydrolysis General procedure starting from Preparation 12 and morpholine as the appropriate amine, the desired product was obtained.

HRMS-ESI (m/z): [M+H]+ calcd for $C_{44}H_{54}NO_4S$: 804.4019, found: 804.4012.

Example 143: 6-[3-(1,3-benzothiazol-2-ylamino)-4-methyl-6,7-dihydro-5H-pyrido[2,3-c]pyridazin-8-yl]-3-[1-[[3,5-dimethyl-7-[2-(1-piperidyl)ethoxy]-1-adamantyl]methyl]-5-methyl-pyrazol-4-yl]pyridine-2-carboxylic acid Using the Amine substitution and Hydrolysis General procedure starting from Preparation 12 and piperidine as the appropriate amine, the desired product was obtained.

HRMS-ESI (m/z): [M+H]+ calcd for $C_{45}H_{56}NO_3S$: 802.4227, found: 802.4223.

Example 144: 6-[3-(1,3-benzothiazol-2-ylamino)-4-methyl-6,7-dihydro-5H-pyrido[2,3-c]pyridazin-8-yl]-3-[1-[[3,5-dimethyl-7-(2-piperazin-1-ylethoxy)-1-adamantyl]methyl]-5-methyl-pyrazol-4-yl]pyridine-2-carboxylic acid Using the Amine substitution and Hydrolysis General procedure starting from Preparation 12 and piperazine as the appropriate amine, the desired product was obtained.

HRMS-ESI (m/z): [M+H]+ calcd for $C_{44}H_{55}N_{10}O_3S$: 803.4179, found: 803.4177.

Example 145: 3-[1-[[3-[2-(azepan-1-yl)ethoxy]-5,7-dimethyl-1-adamantyl]methyl]-5-methyl-pyrazol-4-yl]-6-[3-(1,3-benzothiazol-2-ylamino)-4-methyl-6,7-dihydro-5H-pyrido[2,3-c]pyridazin-8-yl]pyridine-2-carboxylic acid Using the Amine substitution and Hydrolysis General procedure starting from Preparation 12 and azepane as the appropriate amine, the desired product was obtained.

HRMS-ESI (m/z): [M+H]+ calcd for $C_{46}H_{58}NO_3S$: 816.4383, found: 816.4379.

Example 146: 6-[3-(1,3-benzothiazol-2-ylamino)-4-methyl-6,7-dihydro-5H-pyrido[2,3-c]pyridazin-8-yl]-3-[1-[[3-[2-(4-isopropylpiperazin-1-yl)ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 1-isopropylpiperazine as the appropriate amine, the desired product was obtained.

HRMS-ESI (m/z): [M+H]+ calcd for $C_{47}H_{61}N_{10}O_3S$: 845.4649, found: 845.4646.

Example 147: 2-[3-(1,3-benzothiazol-2-ylamino)-4-methyl-6,7-dihydro-5H-pyrido[2,3-c]pyridazin-8-yl]-5-[3-[2-fluoro-4-[3-(3-hydroxypropylamino)prop-1-ynyl]phenoxy]propyl]thiazole-4-carboxylic acid Step A: 3-[tert-butyl(dimethyl)silyl]oxy-N-prop-2-ynyl-propan-1-amine The mixture of 0.70 mL (3.0 mmol) of 3-bromopropoxy-tert-butyl-dimethyl-silane, 1.9 mL (10 eq) of propargylic amine and 1.6 mL (3 eq) of DIPEA in acetonitrile (15 mL) was stirred at 50° C. until no further conversion was observed. The reaction mixture was concentrated, diluted with DCM, and extracted with saturated NaHCO$_3$ and brine. The combined organic layers were dried and concentrated to give the desired product in quantitative yield.

$^1$H NMR (500 MHz, dmso-d6) δ ppm 3.62 (t, 2H), 3.27 (d, 2H), 3.02 (t, 1H), 2.59 (t, 2H), 2.19 (brs, 1H), 1.57 (m, 2H), 0.86 (s, 9H), 0.02 (s, 6H); $^{13}$C NMR (500 MHz, dmso-d6) δ ppm 73.9, 61.5, 45.2, 37.9, 32.7, 26.3, −4.8; HRMS (EI) (m/z): [M-CH3]+ calcd for C$_{11}$H$_{22}$NOSi: 212.1471, found: 212.1467.

Step B: ethyl 5-[3-[4-[3-[3-[tert-butyl(dimethyl)silyl]oxypropylamino]prop-1-ynyl]-2-fluoro-phenoxy]propyl]-2-(3-chloro-4-methyl-6,7-dihydro-5H-pyrido[2,3-c]pyridazin-8-yl)thiazole-4-carboxylate Using Sonogashira General Procedure starting from 1.0 g (1.64 mmol) of the product of Preparation 15 and 737 mg (2 eq.) of the product from Step A as the appropriate acetylene, 1.16 g (96%) of the desired product was obtained.

$^1$H NMR (500 MHz, dmso-d6) δ ppm 45.2 (t, 2H), 7.24 (dd, 1H), 7.17 (dd, 1H), 7.14 (t, 1H), 4.27 (br., 2H), 4.25 (q, 2H), 4.12 (t, 2H), 3.65 (t, 2H), 3.6 (s, 2H), 3.25 (t, 2H), 2.89 (t, 2H), 2.32 (s, 3H), 2.11 (m, 2H), 2.04 (m, 2H), 1.63 (m, 2H), 1.28 (t, 3H), 0.84 (s, 9H), 0.02 (s, 6H); 13C NMR (500 MHz, dmso-d6) δ ppm 128.8, 119.1, 115.4, 68.3, 61.3, 60.7, 46.3, 45.2, 38.4, 32.4, 30.8, 26.3, 24.2, 23.1, 19.7, 15.7, 14.6, −4.8; HRMS-ESI (m/z): [M+H]+ calcd for C$_{35}$H$_{48}$ClFN$_5$O$_4$SSi: 716.2869, found: 716.2868.

Step C: ethyl 2-[3-(1,3-benzothiazol-2-ylamino)-4-methyl-6,7-dihydro-5H-pyrido[2,3-c]pyridazin-8-yl]-5-[3-[4-[3-[3-[tert-butyl(dimethyl)silyl]oxypropylamino]prop-1-ynyl]-2-fluoro-phenoxy]propyl]thiazole-4-carboxylate Using Buchwald General Procedure I starting from 1.16 g (1.57 mmol) of the product from Step B and 730 mg (2 eq) of 1,3-benzothiazol-2-amine, 598 mg (45%) of the desired product was obtained.

$^1$H NMR (500 MHz, dmso-d6) δ ppm 7.87 (d, 1H), 7.49 (d, 1H), 7.37 (td, 1H), 7.25 (dd, 1H), 7.19 (t, 1H), 7.17 (t, 1H), 7.17 (m, 1H), 4.26 (br., 2H), 4.25 (q, 2H), 4.14 (t, 2H), 3.63 (t, 2H), 3.57 (s, 2H), 3.27 (t, 2H), 2.87 (t, 2H), 2.69 (t, 2H), 2.34 (s, 3H), 2.13 (m, 2H), 2.04 (m, 2H), 1.61 (m, 2H), 1.28 (t, 3H), 0.84 (s, 9H), 0.02 (s, 6H); $^{13}$C NMR (500 MHz, dmso-d6) δ ppm 128.9, 126.5, 122.5, 122.3, 119.1, 116.3, 115.5, 68.4, 61.3, 60.6, 46.3, 45.2, 38.4, 32.4, 31.1, 26.3, 23.9, 23.2, 20.3, 14.6, 12.9, −4.9; HRMS-ESI (m/z): [M+H]+ calcd for C$_{42}$H$_{53}$FN$_7$O$_4$S$_2$Si: 830.3354, found: 830.3347.

Step D: 2-[3-(1,3-benzothiazol-2-ylamino)-4-methyl-6,7-dihydro-5H-pyrido[2,3-c]pyridazin-8-yl]-5-[3-[2-fluoro-4-[3-(3-hydroxypropylamino)prop-1-ynyl]phenoxy]propyl]thiazole-4-carboxylic acid The mixture of 590 mg (0.71 mmol) of the product from Step C and 298 mg of LiOHxH$_2$O (10 eq) in 7 mL of THF/water (1:1) was stirred at 60° C. until no further conversion was observed.

The reaction mixture was treated with 0.71 mL (12 eq) of concentrated hydrogen chloride at 0° C. (pH=2-3) and stirred until no further conversion was observed. After the reaction mixture was concentrated to remove THF and lyophilization, the solid was dissolved in a 6N NH$_3$ solution in MeOH and purified by reverse phase chromatography (using 25 mM NH$_4$HCO$_3$ and MeCN as eluents) to give 100 mg (21%) of the desired product.

HRMS-ESI (m/z): [M+H]+ calcd for C$_{34}$H$_{35}$FN$_7$O$_4$S$_2$: 688.2176, found: 688.2179.

Example 148: 2-[3-(1,3-benzothiazol-2-ylamino)-4-methyl-6,7-dihydro-5H-pyrido[2,3-c]pyridazin-8-yl]-5-[3-[4-[3-[[(3S)-3,4-dihydroxybutyl]-methyl-amino]prop-1-ynyl]-2-fluoro-phenoxy]propyl]thiazole-4-carboxylic acid

Step A: 2-[(4S)-2,2-dimethyl-1,3-dioxolan-4-yl]ethyl 4-methylbenzenesulfonate To 1.0 g (6.8 mmol) of 2-[(4S)-2,2-dimethyl-1,3-dioxo-lan-4-yl]ethanol and 3.8 mL (4 eq) of triethylamine in 34 mL of DCM was added 4.5 g (2 eq) of p-tolylsulfonyl 4-meth-ylbenzenesulfonate at 0° C. The reaction mixture was stirred until no further conversion was observed, concentrated and treated with diisopropyl ether. Then, the precipitated hydro-chloric salt was filtered off and the mother liqueur was concentrated and purified via flash chromatography (silica gel, using heptane and EtOAc as eluents) to give 1.6 g (81%) of desired product.

$^1$H NMR (500 MHz, dmso-d6) δ ppm 7.79 (dm, 2H), 7.49 (dm, 2H), 4.08 (m, 2H), 4.00 (m, 1H), 3.91/3.44 (dd+dd, 2H), 2.42 (s, 3H), 1.83/1.77 (m+m, 2H), 1.24/1.20 (s+s, 6H); $^{13}$C NMR (500 MHz, dmso-d6) δ ppm 132.7, 132.7, 130.7, 128.1, 108.6, 72.3, 68.7, 68.4, 32.9, 27.2/25.9, 21.6; HRMS-ESI (m/z): [M+H]+ calcd for $C_{14}H_{21}O_5S$: 301.1110, found: 301.1107.

Step B: N-[2-[(4S)-2,2-dimethyl-1,3-dioxolan-4-yl]ethyl]prop-2-yn-1-amine

The mixture of the product from Step A (7.6 g, 25.3 mmol), prop-2-yn-1-amine (16 mL, 10 eq) and DIPEA (13.22 mL, 3 eq) in 127 mL of MeCN was stirred at 50° C. for 16 h. After concentration, taken up in DCM and extrac-tion with cc. NaHCO$_3$ solution and brine, the combined organic layers were dried and concentrated to give 5.0 g (107%) of the desired product, which was used without any further purification.

$^1$H NMR (500 MHz, dmso-d6) δ ppm 4.07 (m, 1H), 3.98/3.43 (dd+t, 2H), 3.28 (m, 2H), 3.05 (t, 1H), 2.62/2.55 (m+m, 2H), 2.23 (brs, 1H), 1.63/1.59 (m+m, 2H), 1.30 (s, 3H), 1.25 (s, 3H); $^{13}$C NMR (500 MHz, dmso-d6) δ ppm 108.2, 83.4, 74.6, 74.1, 69.2, 45.1, 37.8, 33.6, 27.3, 26.2; HRMS (EI) (m/z): [M]+ calcd for $C_{10}H_{17}NO_2$: 183.1259, found: 183.1260.

Step C: N-[2-[(4S)-2,2-dimethyl-1,3-dioxolan-4-yl]ethyl]-N-methyl-prop-2-yn-1-amine To the product from Step B (500 mg, 2.73 mmol) in NN-dimethylformamide (14 mL) was added portionwise sodium hydride (120 mg, 1.1 eq) at 0° C. After stirring at 0° C. for 0.5 h, the mixture was treated with iodomethane (0.17 mL, 1 eq) and stirred at rt for 18 h. After quenching with a saturated solution of NH$_4$Cl and water, the mixture was extracted with Et$_2$O. The combined organic phases were dried and concentrated to give the desired product (362 mg, 67%). GC/MS ($C_{11}H_{19}NO_2$) 197 [M$^+$].

Step D: ethyl 2-(3-chloro-4-methyl-6,7-dihydro-5H-pyrido[2,3-c]pyridazin-8-yl)-5-[3-[4-[3-[2-[(4S)-2,2-dimethyl-1,3-dioxolan-4-yl]ethyl-methyl-amino]prop-1-ynyl]-2-fluoro-phenoxy]propyl]thiazole-4-carboxylate Using Sonogashira General Procedure starting from 0.548 g (0.89 mmol) of the product of Preparation 15 and 350 mg (2 eq) of the product from Step C as the appropriate acetylene, 510 mg (82%) of the desired product was obtained. LC/MS ($C_{34}H_{42}ClFN_5O_5S$) 686 [M+H]$^+$.

Step E: ethyl 2-[3-(1,3-benzothiazol-2-ylamino)-4-methyl-6,7-dihydro-5H-pyrido[2,3-c]pyridazin-8-yl]-5-[3-[4-[3-[2-[(4S)-2,2-dimethyl-1,3-dioxolan-4-yl]ethyl-methyl-amino]prop-1-ynyl]-2-fluoro-phenoxy]propyl]thiazole-4-carboxylate Using Buchwald General Procedure I starting from 510 mg (0.52 mmol) of the product from Step D and 234 mg (3 eq) of 1,3-benzothiazol-2-amine, 200 mg (48%) of the desired product was obtained.

$^1$H NMR (500 MHz, dmso-d6) δ ppm 7.88 (dm, 1H), 7.49 (brd, 1H), 7.37 (m, 1H), 7.3 (dd, 1H), 7.20 (dm, 1H), 7.19 (m, 1H), 7.16 (t, 1H), 4.26 (m, 2H), 4.25 (q, 2H), 4.14 (t, 2H), 4.04 (m, 1H), 3.98/3.45 (dd+dd, 2H), 3.46 (s, 2H), 3.28 (m, 2H), 2.87 (t, 2H), 2.45/2.39 (m+m, 2H), 2.34 (s, 3H), 2.21 (s, 3H), 2.13 (m, 2H), 2.04 (m, 2H), 1.63 (m, 2H), 1.29 (t, 3H), 1.29 (s, 3H), 1.24 (s, 3H); HRMS (ESI) (m/z): [M+H]+ calcd for $C_{41}H_{47}FN_7O_5S_2$: 800.3064, found: 800.3064.

Step F: 2-[3-(1,3-benzothiazol-2-ylamino)-4-methyl-6,7-dihydro-5H-pyrido[2,3-c]pyridazin-8-yl]-5-[3-[4-[3-[[(3S)-3,4-dihydroxybutyl]-methyl-amino]prop-1-ynyl]-2-fluoro-phenoxy]propyl]thiazole-4-carboxylic acid The mixture of 200 mg (0.25 mmol) of product from Step E and 53 mg of LiOHxH$_2$O (5 eq) in 5 mL of THF/water (1:1) was stirred at 60° C. for 18 h. The reaction mixture was treated with 0.125 mL (6 eq) of concentrated hydrogen chloride at 0° C. (pH=2-3) and stirred at rt, then at 60° C. for 0.5 h. After the reaction mixture was concentrated to remove THF and lyophilization, the solid was dissolved in 6 N NH$_3$ solution in MeOH and purified by reverse phase chromatography (using 5 mM NH$_4$HCO$_3$ and MeCN as eluents) to give 47 mg (25%) of the desired product.

HRMS (ESI) (m/z): [M+H]+ calcd for $C_{36}H_{39}FN_7O_5S_2$: 732.2438, found: 732.2441.

Example 149: 6-[3-(1,3-benzothiazol-2-ylamino)-4-methyl-6,7-dihydro-5H-pyrido[2,3-c]pyridazin-8-yl]-3-[1-[[3-2-[(4-hydroxyphenyl)methylamino]ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 4-(aminomethyl)phenol as the appropriate amine, the desired product was obtained.

HRMS-ESI (m/z): [M+H]+ calcd for $C_{47}H_{54}NO_4S$: 840.4019, found: 840.4016.

Example 150: 6-[3-(1,3-benzothiazol-2-ylamino)-4-methyl-6,7-dihydro-5H-pyrido[2,3-c]pyridazin-8-yl]-3-[1-[[3-[2-[2-hydroxyethyl(methyl)amino]ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 2-(methylamino) ethanol as the appropriate amine, the desired product was obtained.

HRMS-ESI (m/z): [M+H]+ calcd for $C_{43}H_{54}N_9O_4S$: 792.4019, found: 792.4019.

Example 151: 6-[3-(1,3-benzothiazol-2-ylamino)-4-methyl-6,7-dihydro-5H-pyrido[2,3-c]pyridazin-8-yl]-3-[1-[[3-[2-[3-methoxypropyl(methyl)amino] ethoxy]-5,7-dimethyl-1-adamantyl]methyl]-5-methyl-pyrazol-4-yl]pyridine-2-carboxylic acid Using the Amine substitution and Hydrolysis General procedure starting from Preparation 12 and 3-methoxy-N-methyl-propan-1-amine as the appropriate amine, the desired product was obtained.

HRMS-ESI (m/z): [M+H]+ calcd for $C_{45}H_{58}N_9O_4S$: 820.4332, found: 820.4328.

Example 152: 3-[1-[[3,5-dimethyl-7-(2-pyrrolidin-1-ylethoxy)-1-adamantyl]methyl]-5-methyl-pyrazol-4-yl]-6-[3-[(5-hydroxy-1,3-benzothiazol-2-yl)amino]-4-methyl-6,7-dihydro-5H-pyrido[2,3-c]pyridazin-8-yl]pyridine-2-carboxylic acid

Step A: 5-[tert-butyl(dimethyl)silyl]oxy-1,3-benzo-thiazol-2-amine

To a mixture of 2-amino-1,3-benzothiazol-5-ol (750 mg, 4.51 mmol), DMAP (110 mg, 0.2 eq), and imidazole (399 mg, 1.3 eq) in DMF (23 mL) was added tert-butyl(chloro) diphenylsilane (816 mg, 1.2 eq) and the reaction mixture was stirred for 18 h. After quenching with water and extraction with EtOAc, the combined organic phases were dried, concentrated, and purified by column chromatography (silica gel, heptane and EtOAc as eluents) to give the desired product (1.07 g, 84.5%).

$^1$H NMR (400 MHz, DMSO-d$_6$): δ ppm 7.46 (d, 1H), 7.44 (s, 2H), 6.78 (d, 1H), 6.53 (dd, 1H), 0.95 (s, 9H), 0.17 (s, 6H); $^{13}$C NMR (100 MHz, DMSO-d$_6$) δ ppm 168.1, 154.5, 154.1, 124.0, 121.5, 114.0, 109.6, 26.1, 18.4, −4.0; $^{15}$N NMR (100 MHz, DMSO-d$_6$) δ ppm 237, 79.

Step B: methyl 6-[3-[[5-[tert-butyl(dimethyl)silyl] oxy-1,3-benzothiazol-2-yl]amino]-4-methyl-6,7-dihydro-5H-pyrido[2,3-c]pyridazin-8-yl]-3-[1-[[3-(2-hydroxyethoxy)-5,7-dimethyl-1-adamantyl] methyl]-5-methyl-pyrazol-4-yl]pyridine-2-carboxylate Using Buchwald General Procedure I at 130° C. for 1 h, starting from 1.0 g (1.57 mmol) of the product from Preparation 12, Step C and 883 mg (2 eq) of the product from Step A, 1.1 g (80%) of the desired product was obtained.

$^1$H NMR (400 MHz, DMSO-d$_6$): δ ppm 7.95 (d, 1H), 7.7 (d, 1H), 7.65 (br, 1H), 7.38 (s, 1H), 6.95 (br, 1H), 6.71 (brd, 1H), 4.45 (t, 1H), 4.00 (t, 2H), 3.88 (s, 2H), 3.70 (s, 3H), 3.41 (q, 2H), 3.35 (t, 2H), 2.85 (t, 2H), 2.31 (s, 3H), 2.16 (s, 3H), 1.98 (qn, 2H), 1.39 (s, 2H), 1.32/1.25 (d+d, 4H), 1.18/1.12 (d+d, 4H), 1.08/1.00 (d+d, 4H), 0.97 (s, 9H), 0.87 (s, 6H), 0.21 (s, 6H); $^{13}$C NMR (100 MHz, DMSO-d$_6$) δ ppm 139.9, 137.5, 122.3, 119.1, 115.3, 62.1, 61.5, 58.9, 52.6, 50.1, 47.0, 46.1, 45.4, 43.3, 30.2, 26.1, 24.3, 21.7, 12.6, 10.9, −4.0; HRMS-ESI (m/z): [M+H]$^+$ calcd for C$_{47}$H$_3$N$_8$O$_5$SSi: 879.4411, found: 879.4412.

Step C: methyl 6-[3-[[5-[tert-butyl(dimethyl)silyl] oxy-1,3-benzothiazol-2-yl]amino]-4-methyl-6,7-dihydro-5H-pyrido[2,3-c]pyridazin-8-yl]-3-[1-[[3,5-dimethyl-7-[2-(p-tolylsulfonyloxy)ethoxy]-1-adamantyl]methyl]-5-methyl-pyrazol-4-yl]pyridine-2-carboxylate To the product from Step B (1.1 g, 1.26 mmol) and triethylamine (0.53 mL, 3 eq) in DCM (13 mL) was added p-tolylsulfonyl 4-methylbenzenesulfonate (618 mg, 1.5 eq) and the reaction mixture was stirred for 2 h. Purification by column chromatography (silica gel, DCM and EtOAc as eluents) afforded the desired product (590 mg, 45%).

$^1$H NMR (400 MHz, DMSO-d$_6$): δ ppm 7.96 (d, 1H), 7.90-6.40 (brs, 3H), 7.70 (d, 10H), 7.70 (m, 2H), 7.46 (m, 2H), 7.38 (s, 1H), 4.07 (m, 2H), 4.00 (m, 2H), 3.85 (s, 2H), 3.69 (s, 3H), 3.49 (m, 2H), 2.85 (t, 2H), 2.40 (s, 3H), 2.31 (s, 3H), 2.15 (s, 3H), 1.98 (m, 2H), 1.33-0.91 (m, 12H), 0.97 (s, 9H), 0.84 (s, 6H), 0.21 (s, 6H); HRMS-ESI (m/z): [M+H]+ calcd for C$_{54}$H$_{69}$N$_8$O$_7$S$_2$Si: 1033.4500, found: 1033.4504.

Step D: methyl 6-[3-[[5-[tert-butyl(dimethyl)silyl] oxy-1,3-benzothiazol-2-yl]amino]-4-methyl-6,7-dihydro-5H-pyrido[2,3-c]pyridazin-8-yl]-3-[1-[[3,5-dimethyl-7-(2-pyrrolidin-1-ylethoxy)-1-adamantyl] methyl]-5-methyl-pyrazol-4-yl]pyridine-2-carboxylate To the product from Step C (180 mg, 0.17 mmol) in MeCN (1.7 mL) and NMP (1.0 mL) was added pyrrolidine (0.10 mL, 7 eq) and the reaction mixture was stirred at 60° C. for 18 h. Purification by column chromatography (silica gel, DCM and 0.6 M NH$_3$ in MeOH as eluents) afforded the desired product (144 mg, 89%).

$^1$H NMR (400 MHz, DMSO-d$_6$): δ ppm 11.24 (brs, 1H), 7.95 (d, 1H), 7.69 (d, 1H), 7.63 (d, 1H), 7.37 (s, 1H), 6.92 (br, 1H), 6.70 (dd, 1H), 4.00 (t, 2H), 3.87 (s, 2H), 3.70 (s, 3H), 3.43 (t, 2H), 2.85 (t, 2H), 2.46 (t, 2H), 2.41 (t, 4H), 2.31 (s, 3H), 2.16 (s, 3H), 1.98 (qn, 2H), 1.63 (t, 4H), 1.38 (s, 2H), 1.30/1.25 (d+d, 4H), 1.19/1.12 (d+d, 4H), 1.08/0.99 (d+d, 2H), 0.97 (s, 9H), 0.86 (s, 6H), 0.21 (s, 6H); $^{13}$C NMR (100 MHz, DMSO-d$_6$) δ ppm 139.8, 137.5, 122.6, 119.0, 115.3, 59.5, 58.9, 56.6, 54.5, 52.6, 50.1, 47.0, 46.0, 46.0, 43.3, 30.2, 26.0, 24.2, 23.6, 21.7, 12.6, 10.9, −4.0; HRMS-ESI (m/z): [M+H]+ calcd for C$_{51}$H$_{70}$N$_9$O$_4$SSi: 932.5041, found: 932.5014.

Step E: 3-[1-[[3,5-dimethyl-7-(2-pyrrolidin-1-ylethoxy)-1-adamantyl]methyl]-5-methyl-pyrazol-4-yl]-6-[3-[(5-hydroxy-1,3-benzothiazol-2-yl)amino]-4-methyl-6,7-dihydro-5H-pyrido[2,3-c]pyridazin-8-yl]pyridine-2-carboxylic acid To the product of Step D (70 mg, 0.075 mmol) in THF (1.2 mL) and water (0.30 mL), was added LiOHxH$_2$O (25.2 mg, 8 eq) and the reaction mixture was stirred at 60° C. for 1.5 h. Purification by preparative reversed-phase HPLC (C18, 5 mM NH$_4$HCO$_3$ (aqueous) and IPA as eluents) afforded the desired product (45 mg, 74%).

HRMS-ESI (m/z): [M+H]+ calcd for C$_{44}$H$_{54}$NO$_4$S: 804, 4019, found: 804.4019.

Example 153: 6-[3-(1,3-benzothiazol-2-ylamino)-4-
methyl-6,7-dihydro-5H-pyrido[2,3-c]pyridazin-8-
yl]-3-[1-[[3-[2-[4-hydroxybutyl(methyl)amino]
ethoxy]-5,7-dimethyl-1-adamantyl]methyl]-5-
methyl-pyrazol-4-yl]pyridine-2-carboxylic acid Using the Amine substitution and Hydrolysis General
procedure starting from Preparation 12 and 4-(methylamino)
butan-1-ol as the appropriate amine, the desired product was
obtained.

HRMS-ESI (m/z): [M+H]+ calcd for $C_{45}H_{58}N_9O_4S$:
820.4332, found: 820.4339.

Example 154: 6-[3-(1,3-benzothiazol-2-ylamino)-4-
methyl-6,7-dihydro-5H-pyrido[2,3-c]pyridazin-8-
yl]-3-[1-[[3-[2-(dimethylamino)ethoxy]-1-adaman-
tyl]methyl]-5-methyl-pyrazol-4-yl]pyridine-2-
carboxylic acid Using the Amine substitution and Hydrolysis General
procedure starting from Preparation 14 and dimethylamine
as the appropriate amine, the desired product was obtained.

HRMS-ESI (m/z): [M+H]+ calcd for $C_{40}H_{48}N_9O_3S$:
734.3601, found: 734.3589.

Example 155: 6-[3-(1,3-benzothiazol-2-ylamino)-4-
methyl-6,7-dihydro-5H-pyrido[2,3-c]pyridazin-8-
yl]-3-[5-methyl-1-[[3-(2-pyrrolidin-1-ylethoxy)-1-
adamantyl]methyl]pyrazol-4-yl]pyridine-2-
carboxylic acid Using the Amine substitution and Hydrolysis General
procedure starting from Preparation 14 and pyrrolidine as
the appropriate amine, the desired product was obtained.
HRMS-ESI (m/z): [M+H]+ calcd for $C_{42}H_{50}NO_3S$:
760.3757, found: 760.3730.

Example 156: 6-[3-(1,3-benzothiazol-2-ylamino)-4-
methyl-6,7-dihydro-5H-pyrido[2,3-c]pyridazin-8-
yl]-3-[5-methyl-1-[[3-[2-(4-methylpiperazin-1-yl)
ethoxy]-1-adamantyl]methyl]pyrazol-4-yl]pyridine-
2-carboxylic acid Using the Amine substitution and Hydrolysis General
procedure starting from Preparation 14 and 1-methylpipera-
zine as the appropriate amine, the desired product was
obtained.

HRMS-ESI (m/z): [M+H]+ calcd for $C_{43}H_{53}N_{10}O_3S$:
789.4017, found: 789.4023.

Example 157: 6-[3-(1,3-benzothiazol-2-ylamino)-4-methyl-6,7-dihydro-5H-pyrido[2,3-c]pyridazin-8-yl]-3-[5-methyl-1-[[3-(2-morpholinoethoxy)-1-adamantyl]methyl]pyrazol-4-yl]pyridine-2-carboxylic acid Using the Amine substitution and Hydrolysis General procedure starting from Preparation 14 and morpholine as the appropriate amine, the desired product was obtained.

HRMS-ESI (m/z): [M+H]+ calcd for $C_{42}H_{50}NO_4S$: 776.3706, found: 776.3697.

Example 158: 6-[3-(1,3-benzothiazol-2-ylamino)-4-methyl-6,7-dihydro-5H-pyrido[2,3-c]pyridazin-8-yl]-3-[1-[[3-[2-(3-hydroxypropylamino)ethoxy]-1-adamantyl]methyl]-5-methyl-pyrazol-4-yl]pyridine-2-carboxylic acid Using the Amine substitution and Hydrolysis General procedure starting from Preparation 14 and 3-aminopropan-1-ol as the appropriate amine, the desired product was obtained.

HRMS-ESI (m/z): [M+H]+ calcd for $C_{41}H_{50}NO_4S$: 764.3706, found: 764.3700.

Example 159: 6-[3-(1,3-benzothiazol-2-ylamino)-4-methyl-6,7-dihydro-5H-pyrido[2,3-c]pyridazin-8-yl]-3-[1-[[3-[2-(4-hydroxybutylamino)ethoxy]-1-adamantyl]methyl]-5-methyl-pyrazol-4-yl]pyridine-2-carboxylic acid Using the Amine substitution and Hydrolysis General procedure starting from Preparation 14 and 4-aminobutan-1-ol as the appropriate amine, the desired product was obtained.

HRMS-ESI (m/z): [M+H]+ calcd for $C_{42}H_{52}NO_4S$: 778.3863, found: 778.3859.

Example 160: 6-[3-(1,3-benzothiazol-2-ylamino)-4-methyl-6,7-dihydro-5H-pyrido[2,3-c]pyridazin-8-yl]-3-[1-[[3-[2-[[(3S)-3,4-dihydroxybutyl]amino]ethoxy]-1-adamantyl]methyl]-5-methyl-pyrazol-4-yl]pyridine-2-carboxylic acid Using the Amine substitution and Hydrolysis General procedure starting from Preparation 14 and 2-[(4S)-2,2-dimethyl-1,3-dioxolan-4-yl]ethanamine as the appropriate amine, the desired product was obtained.

HRMS-ESI (m/z): [M+H]+ calcd for $C_{42}H_{52}N_9O_5S$: 794.3812, found: 794.3807.

Example 161: 6-[3-(1,3-benzothiazol-2-ylamino)-4-methyl-6,7-dihydro-5H-pyrido[2,3-c]pyridazin-8-yl]-3-[1-[[3-[2-[[3-hydroxy-2-(hydroxymethyl)propyl]amino]ethoxy]-1-adamantyl]methyl]-5-methyl-pyrazol-4-yl]pyridine-2-carboxylic acid Using the Amine substitution and Hydrolysis General procedure starting from Preparation 14 and 2-(aminomethyl)propane-1,3-diol as the appropriate amine, the desired product was obtained.

HRMS-ESI (m/z): [M+H]+ calcd for $C_{42}H_{52}NO_5S$: 794.3812, found: 794.3808.

Example 162: 6-[3-(1,3-benzothiazol-2-ylamino)-4-
methyl-6,7-dihydro-5H-pyrido[2,3-c]pyridazin-8-
yl]-3-[1-[[3-[2-[4-hydroxybutyl(methyl)amino]
ethoxy]-1-adamantyl]methyl]-5-methyl-pyrazol-4-
yl]pyridine-2-carboxylic acid Using the Amine substitution and Hydrolysis General
procedure starting from Preparation 14 and 4-(methylamino)
butan-1-ol as the appropriate amine, the desired product was
obtained.

HRMS-ESI (m/z): [M+H]+ calcd for $C_{43}H_{54}NO_4S$:
792.4019, found: 792.4020.

Example 163: 6-[3-(1,3-benzothiazol-2-ylamino)-4-
methyl-6,7-dihydro-5H-pyrido[2,3-c]pyridazin-8-
yl]-3-[1-[[3-[2-[3-hydroxypropyl(methyl)amino]
ethoxy]-1-adamantyl]methyl]-5-methyl-pyrazol-4-
yl]pyridine-2-carboxylic acid Using the Amine substitution and Hydrolysis General
procedure starting from Preparation 14 and 3-(methylamino)
propan-1-ol as the appropriate amine, the desired product
was obtained.

HRMS-ESI (m/z): [M+H]+ calcd for $C_{42}H_{52}NO_4S$:
778.3863, found: 778.3858.

Example 164: 6-[3-(1,3-benzothiazol-2-ylamino)-4-methyl-6,7-dihydro-5H-pyrido[2,3-c]pyridazin-8-yl]-3-[1-[[3-[2-[bis(3-hydroxypropyl)amino]ethoxy]-1-adamantyl]methyl]-5-methyl-pyrazol-4-yl]pyridine-2-carboxylic acid Using the Amine substitution and Hydrolysis General procedure starting from Preparation 14 and 3-(3-hydroxy-propylamino)propan-1-ol as the appropriate amine, the desired product was obtained.

HRMS-ESI (m/z): [M+H]+ calcd for $C_{44}H_{56}N_9O_5S$: 822.4125, found: 822.4121.

Example 165: 6-[3-(1,3-benzothiazol-2-ylamino)-4-methyl-6,7-dihydro-5H-pyrido[2,3-c]pyridazin-8-yl]-3-[5-methyl-1-[[3-(2-piperazin-1-ylethoxy)-1-adamantyl]methyl]pyrazol-4-yl]pyridine-2-carboxylic acid Using the Amine substitution and Hydrolysis General procedure starting from Preparation 14 and piperazine as the appropriate amine, the desired product was obtained.

HRMS-ESI (m/z): [M+H]+ calcd for $C_{44}H_{56}N_9O_5S$: 775.3866, found: 775.3859.

Example 166: 6-[3-(1,3-benzothiazol-2-ylamino)-4-methyl-6,7-dihydro-5H-pyrido[2,3-c]pyridazin-8-yl]-3-[1-[[3,5-dimethyl-7-(3-pyrrolidin-1-ylpropyl)-1-adamantyl]methyl]-5-methyl-pyrazol-4-yl]pyridine-2-carboxylic acid Example 167: 6-[3-(1,3-benzothiazol-2-ylamino)-4-methyl-6,7-dihydro-5H-pyrido[2,3-c]pyridazin-8-yl]-3-[1-[[3-[3-(dimethylamino)propyl]-5,7-dimethyl-1-adamantyl]methyl]-5-methyl-pyrazol-4-yl]pyridine-2-carboxylic acid Using the Amine substitution and Hydrolysis General procedure starting from Preparation 13 and dimethylamine as the appropriate amine, the desired product was obtained.

HRMS-ESI (m/z): [M+H]+ calcd for $C_{43}H_{54}NO_2S$: 760.4115, found: 760.4121.

Using the Amine substitution and Hydrolysis General procedure starting from Preparation 13 and pyrrolidine as the appropriate amine, the desired product was obtained.

HRMS-ESI (m/z): [M+H]+ calcd for $C_{45}H_{56}N_9O_2S$: 786.4278, found: 786.4273.

Example 168: 6-[3-(1,3-benzothiazol-2-ylamino)-4-methyl-6,7-dihydro-5H-pyrido[2,3-c]pyridazin-8-yl]-3-[1-[[3,5-dimethyl-7-[3-(4-methylpiperazin-1-yl)propyl]-1-adamantyl]methyl]-5-methyl-pyrazol-4-yl]pyridine-2-carboxylic acid Using the Amine substitution and Hydrolysis General procedure starting from Preparation 13 and 1-methylpiperazine as the appropriate amine, the desired product was obtained.

HRMS-ESI (m/z): [M+H]+ calcd for $C_{46}H_{59}N_{10}O_2S$: 815.4543, found: 815.4534.

Example 169: 6-[3-(1,3-benzothiazol-2-ylamino)-4-methyl-6,7-dihydro-5H-pyrido[2,3-c]pyridazin-8-yl]-3-[1-[[3,5-dimethyl-7-(3-morpholinopropyl)-1-adamantyl]methyl]-5-methyl-pyrazol-4-yl]pyridine-2-carboxylic acid Using the Amine substitution and Hydrolysis General procedure starting from Preparation 13 and morpholine as the appropriate amine, the desired product was obtained.

HRMS-ESI (m/z): [M+H]+ calcd for $C_{45}H_{56}N_9O_3S$: 802.4227, found: 802.4221.

Example 170: 6-[3-(1,3-benzothiazol-2-ylamino)-4-methyl-6,7-dihydro-5H-pyrido[2,3-c]pyridazin-8-yl]-3-[1-[[3-[3-(3-hydroxypropylamino)propyl]-5,7-dimethyl-1-adamantyl]methyl]-5-methyl-pyrazol-4-yl]pyridine-2-carboxylic acid Using the Amine substitution and Hydrolysis General procedure starting from Preparation 13 and 3-aminopropan-1-ol as the appropriate amine, the desired product was obtained.

HRMS-ESI (m/z): [M+H]+ calcd for $C_{44}H_{56}N_9O_3S$: 790.4227, found: 790.4220.

Example 171: 6-[3-(1,3-benzothiazol-2-ylamino)-4-methyl-6,7-dihydro-5H-pyrido[2,3-c]pyridazin-8-yl]-3-[1-[[3-[3-(4-hydroxybutylamino)propyl]-5,7-dimethyl-1-adamantyl]methyl]-5-methyl-pyrazol-4-yl]pyridine-2-carboxylic acid Using the Amine substitution and Hydrolysis General procedure starting from Preparation 13 and 4-(amino)butan-1-ol as the appropriate amine, the desired product was obtained.

HRMS-ESI (m/z): [M+H]+ calcd for $C_{45}H_{58}N_9O_3S$: 804.4383, found: 804.4377.

Example 172: 6-[3-(1,3-benzothiazol-2-ylamino)-4-methyl-6,7-dihydro-5H-pyrido[2,3-c]pyridazin-8-yl]-3-[1-[[3-[3-[[(3S)-3,4-dihydroxybutyl]amino]propyl]-5,7-dimethyl-1-adamantyl]methyl]-5-methyl-pyrazol-4-yl]pyridine-2-carboxylic acid Using the Amine substitution and Hydrolysis General procedure starting from Preparation 13 and 2-[(4S)-2,2-dimethyl-1,3-dioxolan-4-yl]ethanamine as the appropriate amine, the desired product was obtained.

HRMS-ESI (m/z): [M+H]+ calcd for $C_{42}H_{52}NO_5S$: 820.4332, found: 820.4328.

Example 173: 6-[3-(1,3-benzothiazol-2-ylamino)-4-
methyl-6,7-dihydro-5H-pyrido[2,3-c]pyridazin-8-
yl]-3-[1-[[3-[3-[[3-hydroxy-2-(hydroxymethyl)pro-
pyl]amino]propyl]-5,7-dimethyl-1-adamantyl]
methyl]-5-methyl-pyrazol-4-yl]pyridine-2-
carboxylic acid

5

Using the Amine substitution and Hydrolysis General
procedure starting from Preparation 13 and 2-(aminomethyl)
propane-1,3-diol as the appropriate amine, the desired prod-
uct was obtained.

HRMS-ESI (m/z): [M+H]+ calcd for $C_{42}H_{52}NO_5S$:
820.4332, found: 820.4329.

Example 174: 6-[3-(1,3-benzothiazol-2-ylamino)-4-
methyl-6,7-dihydro-5H-pyrido[2,3-c]pyridazin-8-
yl]-3-[1-[[3-[3-[4-hydroxybutyl(methyl)amino]pro-
pyl]-5,7-dimethyl-1-adamantyl]methyl]-5-methyl-
pyrazol-4-yl]pyridine-2-carboxylic acid Using the Amine substitution and Hydrolysis General procedure starting from Preparation 13 and 4-(methylamino)butan-1-ol as the appropriate amine, the desired product was obtained.

HRMS-ESI (m/z): [M+H]+ calcd for $C_{43}H_{54}N_9O_4S$: 818.4540, found: 818.4536.

Example 175: 6-[3-(1,3-benzothiazol-2-ylamino)-4-methyl-6,7-dihydro-5H-pyrido[2,3-c]pyridazin-8-yl]-3-[1-[[3-[3-[3-hydroxypropyl(methyl)amino]propyl]-5,7-dimethyl-1-adamantyl]methyl]-5-methyl-pyrazol-4-yl]pyridine-2-carboxylic acid Using the Amine substitution and Hydrolysis General procedure starting from Preparation 13 and 3-(methylamino)propan-1-ol as the appropriate amine, the desired product was obtained.

HRMS-ESI (m/z): [M+H]+ calcd for $C_{42}H_{52}N_9O_4S$: 804.4383, found: 804.4380.

Example 176: 6-[3-(1,3-benzothiazol-2-ylamino)-4-methyl-6,7-dihydro-5H-pyrido[2,3-c]pyridazin-8-yl]-3-[1-[[3-[3-[bis(3-hydroxypropyl)amino]propyl]-5,7-dimethyl-1-adamantyl]methyl]-5-methyl-pyrazol-4-yl]pyridine-2-carboxylic acid Using the Amine substitution and Hydrolysis General procedure starting from Preparation 13 and 3-(3-hydroxy-propylamino)propan-1-ol as the appropriate amine, the desired product was obtained.

HRMS-ESI (m/z): [M+H]+ calcd for $C_{44}H_{56}N_9O_5S$: 848.4645, found: 848.4645.

Example 177: 6-[3-(1,3-benzothiazol-2-ylamino)-4-methyl-6,7-dihydro-5H-pyrido[2,3-c]pyridazin-8-yl]-3-[1-[[3,5-dimethyl-7-(3-piperazin-1-ylpropyl)-1-adamantyl]methyl]-5-methyl-pyrazol-4-yl]pyridine-2-carboxylic acid Using the Amine substitution and Hydrolysis General procedure starting from Preparation 13 and piperazine as the appropriate amine, the desired product was obtained.

HRMS-ESI (m/z): [M+H]+ calcd for $C_{44}H_{56}N_9O_5S$: 801.4387, found: 801.4370.

Example 178: 3-[1-[[3,5-dimethyl-7-(2-pyrrolidin-1-ylethoxy)-1-adamantyl]methyl]-5-methyl-pyrazol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid Step A: methyl 6-[3-[(7-fluoro-1,3-benzothiazol-2-yl)amino]-4-methyl-6,7-dihydro-5H-pyrido[2,3-c]pyridazin-8-yl]-3-[1-[[3-(2-hydroxyethoxy)-5,7-dimethyl-1-adamantyl]methyl]-5-methyl-pyrazol-4-yl]pyridine-2-carboxylate Using Buchwald General Procedure I at 130° C. for 2 h, starting from 130 mg (0.2 mmol) of the product from Preparation 12, Step C and 52 mg (1.5 eq) of the 7-fluoro-1,3-benzothiazol-2-amine, 139 mg (88%) of the desired product was obtained.

$^1$H NMR (500 MHz, dmso-d6) δ ppm 7.95 (d, 1H), 7.71 (d, 1H), 7.45-7.35 (m, 1H), 7.45-7.35 (br., 1H), 7.38 (s, 1H), 7.05 (m, 1H), 4.46 (br., 1H), 4 (t, 2H), 3.88 (s, 2H), 3.71 (s, 3H), 3.41 (q, 2H), 3.35 (t, 2H), 2.87 (t, 2H), 2.33 (s, 3H), 2.16 (s, 3H), 1.99 (m, 2H), 1.39 (s, 2H), 1.30/1.25 (d+d, 4H), 1.18/1.12 (d+d, 4H), 1.07/1.00 (d+d, 2H), 0.87 (s, 6H); $^{13}$C NMR (500 MHz, dmso-d6) δ ppm 157.1, 140.0, 137.5, 127.7, 119.3, 108.3, 62.1, 61.5, 59.0, 52.7, 50.1, 47.0, 46.0, 45.5, 43.3, 30.2, 24.3, 21.6, 12.5, 10.9; HRMS-ESI (m/z): [M+H]+ calcd for $C_{41}H_{48}FN_8O_4S$: 767.3482, found: 767.3503.

Step B: methyl 3-[1-[[3,5-dimethyl-7-[2-(p-tolylsulfonyloxy)ethoxy]-1-adamantyl]methyl]-5-methyl-pyrazol-4-yl]-6-[3-[(7-fluoro-1,3-benzothi-azol-2-yl)amino]-4-methyl-6,7-dihydro-5H-pyrido[2,3-c]pyridazin-8-yl]pyridine-2-carboxylate To the product from Step A (130 mg, 0.17 mmol) and triethylamine (0.071 mL, 3 eq) in DCM (2 mL) was added p-tolylsulfonyl 4-methylbenzenesulfonate (83 mg, 1.5 eq) and the reaction mixture was stirred for 1 h. Purification by column chromatography (silica gel, DCM and EtOAc as eluents) afforded the desired product (54 mg, 34%).

$^1$H NMR (500 MHz, dmso-d6) δ ppm 7.96 (d, 1H), 7.77 (d, 2H), 7.71 (d, 1H), 7.63-7.26 (br., 1H), 7.46 (d, 2H), 7.40 (br., 1H), 7.39 (s, 1H), 7.05 (br., 1H), 4.06 (m, 2H), 4.00 (t, 2H), 3.85 (s, 2H), 3.69 (s, 3H), 3.49 (m, 2H), 2.87 (t, 2H), 2.41 (s, 3H), 2.33 (s, 3H), 2.15 (s, 3H), 1.99 (m, 2H), 1.28 (s, 2H), 1.20-1.06 (m, 4H), 1.20-1.06 (m, 4H), 1.02/0.97 (d+d, 2H), 0.84 (s, 6H); 13C NMR (500 MHz, dmso-d6) δ ppm 140.0, 137.6, 130.6, 128.1, 127.6, 119.3, 108.3, 71.5, 58.9, 58.4, 52.6, 49.9, 46.6, 45.9, 45.5, 43.0, 30.1, 24.3, 21.6, 21.6, 12.5, 10.9; HRMS-ESI (m/z): [M+H]+ calcd for $C_{41}H_{48}FN_8O_4S$: 921.3592, found: 921.3567.

Step C: 3-[1-[[3,5-dimethyl-7-(2-pyrrolidin-1-ylethoxy)-1-adamantyl]methyl]-5-methyl-pyrazol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid Using the Amine substitution and Hydrolysis General procedure starting from the product from Step B and pyrrolidine as the appropriate amine, the desired product was obtained.

HRMS-ESI (m/z): [M+H]+ calcd for $C_{44}H_{53}FN_9O_3S$: 806.3976, found: 806.3974.

Example 179: 3-[1-[[3,5-dimethyl-7-(2-pyrrolidin-1-ylethoxy)-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Preparation 12, Step C and 54.3 mg (1.5 eq) of the 5-methyl-1,3-benzothiazol-2-amine, 126 mg (75%) of the desired product was obtained.

$^1$H NMR (500 MHz, dmso-d6) δ ppm 12.08/10.89 (brs/brs, 1H), 7.95 (d, 1H), 7.69 (d, 1H), 7.67 (br, 1H), 7.38 (s, 1H), 7.30 (br, 1H), 7.00 (d, 1H), 4.46 (brs, 1H), 4.00 (t, 2H), 3.88 (s, 2H), 3.70 (s, 3H), 3.41 (t, 2H), 3.35 (t, 2H), 2.85 (t, 2H), 2.39 (s, 3H), 2.32 (s, 3H), 2.16 (s, 3H), 1.98 (qn, 2H), 1.39 (s, 2H), 1.30/1.25 (d+d, 4H), 1.18/1.12 (d+d, 4H), 1.08/1.02 (d+d, 2H), 0.87 (s, 6H); $^{13}$C NMR (500 MHz, dmso-d6) δ ppm 139.8, 137.5, 123.6, 121.6, 119.0, 62.1, 61.5, 59.0, 52.7, 50.1, 47.0, 46.0, 45.4, 43.3, 30.2, 24.3, 21.7, 21.6, 12.6, 10.9; HRMS-ESI (m/z): [M+H]$^+$ calcd for $C_{42}H_{51}N_8O_4S$: 763.3760, found: 763.3754.

Step B: methyl 3-[1-[[3,5-dimethyl-7-[2-(p-tolylsulfonyloxy)ethoxy]-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylate To the product from Step A (119 mg, 0.16 mmol) and triethylamine (0.066 mL, 3 eq) in DCM (2 mL) was added p-tolylsulfonyl 4-methylbenzenesulfonate (76 mg, 1.5 eq) and the reaction mixture was stirred for 1 h. Purification by column chromatography (silica gel, DCM and EtOAc as eluents) afforded the desired product (93 mg, 65%).

$^1$H NMR (500 MHz, dmso-d6) δ ppm 12.17/10.83 (brs/brs, 1H), 7.95 (d, 1H), 7.77 (d, 2H), 7.7 (d, 1H), 7.69 (br, 1H), 7.46 (d, 2H), 7.42 (br, 1H), 7.39 (s, 1H), 7.00 (d, 1H), 4.07 (t, 2H), 4 (t, 2H), 3.96 (s, 3H), 3.85 (s, 2H), 3.49 (t, 2H), 2.85 (t, 2H), 2.40 (s, 3H), 2.39 (s, 3H), 2.32 (s, 3H), 2.15 (s, 3H), 1.99 (qn, 2H), 1.29 (s, 2H), 1.17/1.1 (d+d, 4H), 1.12/1.1 (d+d, 4H), 1.02/0.97 (d+d, 2H), 0.84 (s, 6H); $^{13}$C NMR (500 MHz, dmso-d6) δ ppm 139.8, 137.6, 130.6, 128.1, 123.6, 119.0, 71.5, 58.8, 58.4, 52.7, 49.9, 46.6, 45.9, 45.4, 43.0, 30.1, 24.3, 21.6, 21.6, 21.6, 12.6, 10.9; HRMS-ESI (m/z): [M+H]+ calcd for $C_{49}H_{57}N_8O_6S2$: 917.3842, found: 917.3840.

Step A: methyl 3-[1-[[3-(2-hydroxyethoxy)-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylate Using Buchwald General Procedure I at 130° C. for 1.5 h, starting from 140 mg (0.22 mmol) of the product from Step C: 3-[1-[[3,5-dimethyl-7-(2-pyrrolidin-1-ylethoxy)-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Using the Amine substitution and Hydrolysis General procedure starting from the product from Step B and pyrrolidine as the appropriate amine, the desired product was obtained.

HRMS-ESI (m/z): [M+H]+ calcd for $C_{45}H_{56}N_9O_3S$: 802.4227, found: 802.4220.

Example 180: 3-[1-[[3,5-dimethyl-7-(2-pyrrolidin-1-ylethoxy)-1-adamantyl]methyl]-5-methyl-pyrazol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid Step A: methyl 3-[1-[[3-(2-hydroxyethoxy)-5,7-dimethyl-1-adamantyl]methyl]-5-methyl-pyrazol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylate Using Buchwald General Procedure I at 130° C. for 2.5 h, starting from 140 mg (0.22 mmol) of the product from Preparation 12, Step C and 60 mg (1.5 eq) of the 5-methyl-1,3-benzothiazol-2-amine, 129 mg (75%) of the desired product was obtained.

$^1$H NMR (500 MHz, dmso-d6) δ ppm 7.95 (d, 1H), 7.69 (d, 1H), 7.67 (br., 1H), 7.38 (s, 1H), 7.02 (br., 1H), 6.80 (dd, 1H), 4.46 (br., 1H), 4.00 (t, 2H), 3.88 (s, 2H), 3.80 (s, 3H), 3.70 (s, 3H), 3.41 (t, 2H), 3.35 (t, 2H), 2.85 (t, 2H), 2.32 (s, 3H), 2.16 (s, 3H), 1.98 (m, 2H), 1.39 (s, 2H), 1.30/1.25 (d+d, 4H), 1.18/1.12 (d+d, 4H), 1.08/1 (d+d, 2H), 0.87 (s, 6H); $^{13}$C NMR (500 MHz, dmso-d6) δ ppm 139.8, 137.5, 122.6, 119.0, 110.5, 62.1, 61.5, 58.9, 55.8, 52.6, 50.1, 47.0, 46.0, 45.4, 43.3, 30.2, 24.3, 21.7, 12.6, 10.9; HRMS-ESI (m/z): [M+H]+ calcd for $C_{42}H_{51}N_8O_5S$: 779.3703, found: 779.3687.

Step B: methyl 3-[1-[[3,5-dimethyl-7-[2-(p-tolylsulfonyloxy)ethoxy]-1-adamantyl]methyl]-5-methyl-pyrazol-4-yl]-6-[3-[(5-methoxy-1,3-benzo-thiazol-2-yl)amino]-4-methyl-6,7-dihydro-5H-pyrido[2,3-c]pyridazin-8-yl]pyridine-2-carboxylate To the product from Step A (122 mg, 0.16 mmol) and triethylamine (0.066 mL, 3 eq) in DCM (2 mL) was added p-tolylsulfonyl 4-methylbenzenesulfonate (77 mg, 1.5 eq) and the reaction mixture was stirred for 1 h. Purification by column chromatography (silica gel, DCM and EtOAc as eluents) afforded the desired product (79 mg, 54%).

$^1$H NMR (500 MHz, dmso-d6) δ ppm 12.17/10.83 (brs/brs, 1H), 7.95 (d, 1H), 7.77 (d, 2H), 7.72 (d, 1H), 7.67 (brd, 1H), 7.46 (d, 2H), 7.39 (s, 1H), 7.02 (br, 1H), 6.80 (d, 1H), 4.07 (t, 2H), 4.00 (t, 2H), 3.86 (s, 2H), 3.80 (s, 3H), 3.69 (s, 3H), 3.49 (t, 2H), 2.86 (t, 2H), 2.41 (s, 3H), 2.33 (s, 3H), 2.15 (s, 3H), 1.99 (qn, 2H), 1.29 (s, 2H), 1.17/1.1 (d+d, 4H), 1.12/1.10 (d+d, 4H), 1.02/0.97 (d+d, 2H), 0.84 (s, 6H); $^{13}$C NMR (500 MHz, dmso-d6) δ ppm 139.9, 137.6, 130.6, 128.1, 119.0, 110.6, 71.5, 58.8, 58.4, 55.9, 52.6, 49.9, 46.6, 45.9, 45.8, 43.0, 30.1, 24.3, 21.6, 21.6, 12.7, 10.9; HRMS-ESI (m/z): [M+H]+ calcd for $C_{49}H_{57}N_8O_7S2$: 933.3792, found: 933.3794.

Step C: 3-[1-[[3,5-dimethyl-7-(2-pyrrolidin-1-ylethoxy)-1-adamantyl]methyl]-5-methyl-pyrazol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid Using the Amine substitution and Hydrolysis General procedure starting from the product from Step B and pyrrolidine as the appropriate amine, the desired product was obtained.

HRMS-ESI (m/z): [M+H]+ calcd for $C_{45}H_{57}N_9O_4S$: 818.4176, found: 818.4172.

The compounds of the following Examples 181-219 are synthesised using the Amine Substitution and Hydrolysis General procedure starting from one of the Preparation 12, 13, 14 or analogs benzothiazole derivatives and the appropriate amine.

Example 181: 3-[1-[[3,5-dimethyl-7-[2-(methyl-amino)ethoxy]-1-adamantyl]methyl]-5-methyl-pyra-zol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid

326

Example 183: 3-[1-[[3,5-dimethyl-7-[2-(4-meth-ylpiperazin-1-yl)ethoxy]-1-adamantyl]methyl]-5-methyl-pyrazol-4-yl]-6-[3-[(7-fluoro-1,3-benzothi-azol-2-yl)amino]-4-methyl-6,7-dihydro-5H-pyrido[2,3-c]pyridazin-8-yl]pyridine-2-carboxylic acid Example 182: 3-[1-[[3-[2-(dimethylamino)ethoxy]-5,7-dimethyl-1-adamantyl]methyl]-5-methyl-pyra-zol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid Example 184: 6-[3-[(7-fluoro-1,3-benzothiazol-2-yl)amino]-4-methyl-6,7-dihydro-5H-pyrido[2,3-c]pyridazin-8-yl]-3-[1-[[3-[2-(3-hydroxypropylamino)ethoxy]-5,7-dimethyl-1-adamantyl]methyl]-5-methyl-pyrazol-4-yl]pyridine-2-carboxylic acid

327

Example 185: 6-[3-[(7-fluoro-1,3-benzothiazol-2-yl)amino]-4-methyl-6,7-dihydro-5H-pyrido[2,3-c]pyridazin-8-yl]-3-[1-[[3-[2-(4-hydroxybutylamino)ethoxy]-5,7-dimethyl-1-adamantyl]methyl]-5-methyl-pyrazol-4-yl]pyridine-2-carboxylic acid

328

Example 187: 3-[1-[[3-[2-[[(3S)-3,4-dihydroxy-butyl]amino]ethoxy]-5,7-dimethyl-1-adamantyl]methyl]-5-methyl-pyrazol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid Example 186: 3-[1-[[3-[2-[[(3R)-3,4-dihydroxy-butyl]amino]ethoxy]-5,7-dimethyl-1-adamantyl]methyl]-5-methyl-pyrazol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid Example 188: 3-[1-[[3,5-dimethyl-7-(2-piperazin-1-ylethoxy)-1-adamantyl]methyl]-5-methyl-pyrazol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid

US 12,570,648 B2

329

Example 189: 3-[1-[[3,5-dimethyl-7-(2-morpholino-
ethoxy)-1-adamantyl]methyl]-5-methyl-pyrazol-4-
yl]-6-[3-[(7-fluoro-1,3-benzothiazol-2-yl)amino]-4-
methyl-6,7-dihydro-5H-pyrido[2,3-c]pyridazin-8-yl]
pyridine-2-carboxylic acid

330

Example 191: 6-[3-[(7-fluoro-1,3-benzothiazol-2-yl)
amino]-4-methyl-6,7-dihydro-5H-pyrido[2,3-c]
pyridazin-8-yl]-3-[1-[[3-[2-[4-hydroxybutyl(methyl)
amino]ethoxy]-5,7-dimethyl-1-adamantyl]methyl]-5-
methyl-pyrazol-4-yl]pyridine-2-carboxylic acid Example 190: 6-[3-[(7-fluoro-1,3-benzothiazol-2-yl)
amino]-4-methyl-6,7-dihydro-5H-pyrido[2,3-c]
pyridazin-8-yl]-3-[1-[[3-[2-[3-hydroxypropyl
(methyl)amino]ethoxy]-5,7-dimethyl-1-adamantyl]
methyl]-5-methyl-pyrazol-4-yl]pyridine-2-
carboxylic acid Example 192: 6-[3-[(7-fluoro-1,3-benzothiazol-2-yl)
amino]-4-methyl-6,7-dihydro-5H-pyrido[2,3-c]
pyridazin-8-yl]-3-[1-[[3-[2-[[3-hydroxy-2-(hy-
droxymethyl)propyl]amino]ethoxy]-5,7-dimethyl-1-
adamantyl]methyl]-5-methyl-pyrazol-4-yl]pyridine-
2-carboxylic acid

331

Example 193: 3-[1-[[3-[2-[bis(3-hydroxypropyl)amino]ethoxy]-5,7-dimethyl-1-adamantyl]methyl]-5-methyl-pyrazol-4-yl]-6-[3-[(7-fluoro-1,3-benzothiazol-2-yl)amino]-4-methyl-6,7-dihydro-5H-pyrido[2,3-c]pyridazin-8-yl]pyridine-2-carboxylic acid Example 194: 3-[1-[[3,5-dimethyl-7-[2-(methylamino)ethoxy]-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid

332

Example 195: 3-[1-[[3-[2-(dimethylamino)ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 196: 3-[1-[[3,5-dimethyl-7-[2-(4-methylpiperazin-1-yl)ethoxy]-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid

333

Example 197: 3-[1-[[3-[2-(3-hydroxypropylamino)ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid

334

Example 199: 3-[1-[[3-[2-[[(3R)-3,4-dihydroxybutyl]amino]ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 198: 3-[1-[[3-[2-(4-hydroxybutylamino)ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 200: 3-[1-[[3-[2-[[(3S)-3,4-dihydroxybutyl]amino]ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid

335

336

Example 201: 3-[1-[[3,5-dimethyl-7-(2-piperazin-1-ylethoxy)-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 203: 3-[1-[[3-[2-[3-hydroxypropyl(methyl)amino]ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 202: 3-[1-[[3,5-dimethyl-7-(2-morpholino-ethoxy)-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 204: 3-[1-[[3-[2-[4-hydroxybutyl(methyl)amino]ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid

337

338

Example 205: 3-[1-[[3-[2-[[3-hydroxy-2-(hy-droxymethyl)propyl]amino]ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 207: 3-[1-[[3,5-dimethyl-7-[2-(methyl-amino)ethoxy]-1-adamantyl]methyl]-5-methyl-pyra-zol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid Example 206: 3-[1-[[3-[2-[bis(3-hydroxypropyl)amino]ethoxy]-5,7-dimethyl-1-adamantyl]methyl]-5-methyl-pyrazol-4-yl]-6-[4-methyl-3-[(5-methyl-1,3-benzothiazol-2-yl)amino]-6,7-dihydro-5H-pyrido[2,3-c]pyridazin-8-yl]pyridine-2-carboxylic acid Example 208: 3-[1-[[3-[2-(dimethylamino)ethoxy]-5,7-dimethyl-1-adamantyl]methyl]-5-methyl-pyra-zol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid

339

Example 209: 3-[1-[[3,5-dimethyl-7-[2-(4-meth-ylpiperazin-1-yl)ethoxy]-1-adamantyl]methyl]-5-methyl-pyrazol-4-yl]-6-[3-[(5-methoxy-1,3-benzo-thiazol-2-yl)amino]-4-methyl-6,7-dihydro-5H-pyrido[2,3-c]pyridazin-8-yl]pyridine-2-carboxylic acid

340

Example 211: 3-[1-[[3-[2-(4-hydroxybutylamino)ethoxy]-5,7-dimethyl-1-adamantyl]methyl]-5-methyl-pyrazol-4-yl]-6-[3-[(5-methoxy-1,3-benzo-thiazol-2-yl)amino]-4-methyl-6,7-dihydro-5H-pyrido[2,3-c]pyridazin-8-yl]pyridine-2-carboxylic acid Example 210: 3-[1-[[3-[2-(3-hydroxypropylamino)ethoxy]-5,7-dimethyl-1-adamantyl]methyl]-5-methyl-pyrazol-4-yl]-6-[3-[(5-methoxy-1,3-benzo-thiazol-2-yl)amino]-4-methyl-6,7-dihydro-5H-pyrido[2,3-c]pyridazin-8-yl]pyridine-2-carboxylic acid Example 212: 3-[1-[[3-[2-[[(3R)-3,4-dihydroxy-butyl]amino]ethoxy]-5,7-dimethyl-1-adamantyl]methyl]-5-methyl-pyrazol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid

341

Example 213: 3-[1-[[3-[2-[[(3S)-3,4-dihydroxy-butyl]amino]ethoxy]-5,7-dimethyl-1-adamantyl] methyl]-5-methyl-pyrazol-4-yl]-6-[3-[(5-methoxy-1, 3-benzothiazol-2-yl)amino]-4-methyl-6,7-dihydro-5H-pyrido[2,3-c]pyridazin-8-yl]pyridine-2-carboxylic acid

342

Example 215: 3-[1-[[3,5-dimethyl-7-(2-morpholino-ethoxy)-1-adamantyl]methyl]-5-methyl-pyrazol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid Example 214: 3-[1-[[3,5-dimethyl-7-(2-piperazin-1-ylethoxy)-1-adamantyl]methyl]-5-methyl-pyrazol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid Example 216: 3-[1-[[3-[2-[3-hydroxypropyl(methyl) amino]ethoxy]-5,7-dimethyl-1-adamantyl]methyl]-5-methyl-pyrazol-4-yl]-6-[3-[(5-methoxy-1,3-benzo-thiazol-2-yl)amino]-4-methyl-6,7-dihydro-5H-pyrido [2,3-c]pyridazin-8-yl]pyridine-2-carboxylic acid

343

344

Example 217: 3-[1-[[3-[2-[4-hydroxybutyl(methyl)amino]ethoxy]-5,7-dimethyl-1-adamantyl]methyl]-5-methyl-pyrazol-4-yl]-6-[3-[(5-methoxy-1,3-benzo-thiazol-2-yl)amino]-4-methyl-6,7-dihydro-5H-pyrido[2,3-c]pyridazin-8-yl]pyridine-2-carboxylic acid Example 219: 3-[1-[[3-[2-[bis(3-hydroxypropyl)amino]ethoxy]-5,7-dimethyl-1-adamantyl]methyl]-5-methyl-pyrazol-4-yl]-6-[3-[(5-methoxy-1,3-benzo-thiazol-2-yl)amino]-4-methyl-6,7-dihydro-5H-pyrido[2,3-c]pyridazin-8-yl]pyridine-2-carboxylic acid Example 218: 3-[1-[[3-[2-[[3-hydroxy-2-(hy-droxymethyl)propyl]amino]ethoxy]-5,7-dimethyl-1-adamantyl]methyl]-5-methyl-pyrazol-4-yl]-6-[3-[(5-methoxy-1,3-benzothiazol-2-yl)amino]-4-methyl-6,7-dihydro-5H-pyrido[2,3-c]pyridazin-8-yl]pyridine-2-carboxylic acid Example 220: 5-[3-[4-[3-(dimethylamino)prop-1-ynyl]-2-fluoro-phenoxy]propyl]-2-[4-methyl-3-[(5-methyl-1,3-benzothiazol-2-yl)amino]-6,7-dihydro-5H-pyrido[2,3-c]pyridazin-8-yl]thiazole-4-carboxylic acid Example 221: 5-[3-[4-[3-(dimethylamino)prop-1-ynyl]-2-fluoro-phenoxy]propyl]-2-[3-[(5-methoxy-1,3-benzothiazol-2-yl)amino]-4-methyl-6,7-dihydro-5H-pyrido[2,3-c]pyridazin-8-yl]thiazole-4-carboxylic acid Pharmacological Study Example A: Fluorescence Polarisation Assay Data Fluorescence polarization measures the rotation of a fluorescing species in solution, the larger the molecule the more polarized the fluorescence emission.

The fluorescent PUMA (UniProtKB® primary accession number Q9BXH1-SEQ ID:01) based probe Fluorescein-betaAla-Ahx-AREIGAQLRRMADDLNAQY-OH from Biopeptides binds to GST(1-218)-(FACTOR_XA)-hsBCLXL(2-209) having an aminoacid sequence (SEQ ID:02):

[MSPILGYWKIKGLVQPTRLLLEYLEEKYEEHLYE

RDEGDKWRNKKFELGLEFPNLPYYIDGDVKLTQSM

AIIRYIADKHNMLGGCPKERAEISMLEGAVLDIRY

GVSRIAYSKDFETLKVDFLSKEPEMLKMFEDRLCH

KTYENGDHVTHPDFMLYDALDVVLYMDPMCLDAFP

KLVCFKKRIEAIPQIDKYLKSSKYIAWPLQGWQAT

FGGGDHPPKSDLIEGRGIPEFEFSQSNRELVVDFL

SYKLSQKGYSWSQFSDVEENRTEAPEGTESEMETP

SAINGNPSWHLADSPAVNGATGHSSSLDAREVIPM

AAVKQALREAGDEFELRYRRAFSDLTSQLHITPGT

AYQSFEQVVNELFRDGVNWGRIVAFFSFGGALCVE

SVDKEMQVLVSRIAAWMATYLNDHLEMMENGGWDT

FVELYGNNAAAESRKGQER]

(GST UniProtKB® primary accession number P08515 and BCLXL UniProtKB® primary accession number Q07817-1), resulting in an increase in anisotropy. If a compound is added which competitively binds to the same site as the probe, thereby releasing it, anisotropy decreases due to the increased amount of free probe.

An 11-point serial dilution of each compound was prepared in DMSO, the final buffer conditions were 10 mM 4-(2-hydroxyethyl)-1-piperazineethanesulfonic acid [HEPES], 150 mM NaCl, 0.05% Tween 20, pH 7.4 and 5% DMSO. The final protein concentration in the assay was 20 nM with the fluorescent probe present at 10 nM. The experiments were incubated for 2 hours at 23° C. before fluorescence polarization was measured on a Biotek SynergyNeo plate reader (Excitation 485 nm, emission 525 nm, parallel and perpendicular reads). The dose response curves were plotted with XL-Fit software using a 4-Parameter Logistic Model (Sigmoidal DoseResponse Model) and the inhibitory concentrations that gave a 50% increase in fluorescence intensity was determined ($IC_{50}$). The $K_I$ values were determined from the $IC_{50}$ values according to Cer et al, *Nucleic Acids Res,* 2009, Jul. 1; 37 (WebServer issue): W441-W445.

The results are summarised in Table 1. They show that the compounds of the invention inhibit the interaction between the Bcl-xL protein and the fluorescent peptide described hereinbefore.

TABLE 1

| Example | Ki (M) |
|---|---|
| 1 | 3.7E−05 |
| 2 | >1E−05 |
| 3 | 3.6E−05 |
| 4 | >1E−05 |
| 5 | >1E−05 |
| 6 | >1E−05 |
| 7 | 9.9E−06 |
| 8 | 1.1E−06 |
| 9 | 1.3E−08 |
| 10 | 2.1E−07 |
| 11 | 9.2E−09 |
| 12 | 3.0E−08 |
| 13 | 9.2E−09 |
| 14 | 5.5E−09 |
| 15 | 2.3E−09 |
| 16 | 1.2E−07 |
| 17 | 2.0E−09 |
| 18 | 5.0E−06 |
| 19 | 3.3E−06 |
| 20 | 8.5E−08 |
| 21 | 1.6E−06 |
| 22 | 3.0E−09 |
| 23 | 1.1E−09 |
| 24 | <1E−09 |
| 25 | 1.2E−07 |
| 26 | 1.5E−05 |
| 27 | <1E−09 |
| 28 | 1.4E−08 |
| 29 | 9.6E−09 |
| 30 | <1E−09 |
| 31 | <1E−09 |
| 32 | <1E−09 |
| 33 | 5.5E−09 |
| 35 | <1E−09 |
| 36 | <1E−09 |

Example B: Quench Assay Data

Fluorescence quenching assay measures the change in fluorescence intensity of C-terminally Cy5-labelled BCL-xL protein, His-His-(EK)-hsBCLXL(2-197)[N197C] (UniProtKB®

```
[MHHHHHHHHGATGSTAGSGTAGSTGASGASTGGT

GATHHHHHHHHDDDDKSPMGSQSNRELVVDFLSYK

LSQKGYSWSQFSDVEENRTEAPEGTESEMEIPSAI

NGNPSWHLADSPAVNGATGEISSSLDAREVIPMAA

VKQALREAGDEFELRYRRAFSDLTSQLHITPGTAY

QSFEQVVNELFRDGVNWGRIVAFFSFGGALCVESV

DKEMQVLVSRIAAWMATYLNDHLEPWIQENGGWDT

FVELYG]
``` which is linked in C-terminal region to the amino acid X which corresponds to a cysteine labelled on the sulfur with Sulfo-Cyanine5 from Lumiprobe GmbH catalogue number 13380, upon binding of a C-terminally labelled peptide derived from PUMA (UniProtKB® primary accession number Q9BXH1) having an aminoacid sequence (SEQ ID:04): [QWAREIGAQLRRMADDLNAQY] which is linked in C-terminal region to the amino acid X' where X' is cysteine labelled on the sulfur with TQ5WS from AAT Bioquest catalogue number 2079.

The addition of a compound which binds competitively to the same site as the peptide will result in an increase in the fluorescence intensity of the protein due to displacement of the fluorescence quencher.

An 11-point serial dilution of each compound was prepared in DMSO, the final buffer conditions were 10 mM 4-(2-hydroxyethyl)-1-piperazineethanesulfonic acid [HEPES], 150 mM NaCl, 0.05% Tween 20, pH 7.4 and 5% DMSO. The final protein concentration in the assay was 1 nM with the peptide present at 400 nM. The experiments were incubated for 2 hours at 23° C. before fluorescence intensity was measured on a Biotek SynergyNeo plate reader (Excitation 620 nm, emission 680 nm). The dose response curves were plotted with XL-Fit software using a 4-Parameter Logistic Model (Sigmoidal DoseResponse Model) and the inhibitory concentrations that gave a 50% increase in fluorescence intensity was determined ($IC_{50}$). The $K_1$ values were determined from the $IC_{50}$ values according to Cer et al, *Nucleic Acids Res*, 2009, Jul. 1; 37 (WebServer issue): W441-W445.

The results are summarised in Table 2.

TABLE 2

| Example | Ki (M) |
|---|---|
| 22 | 2.5E−11 |
| 23 | 5.1E−11 |
| 24 | 8.0E−12 |
| 27 | 8.5E−12 |
| 30 | 3.6E−12 |
| 31 | 8.2E−12 |
| 32 | 4.6E−12 |
| 33 | 1.4E−09 |
| 34 | 1.9E−12 |
| 35 | 7.7E−12 |
| 36 | 1.7E−12 |
| 37 | 7.7E−12 |

TABLE 2-continued

| Example | Ki (M) |
|---|---|
| 38 | 2.9E−12 |
| 39 | 9.8E−12 |
| 40 | 5.7E−11 |
| 41 | 2.5E−12 |
| 42 | 2.8E−12 |
| 43 | 3.1E−12 |
| 44 | 1.5E−12 |
| 45 | 4.9E−12 |
| 46 | 1.5E−11 |
| 47 | 8.9E−12 |
| 48 | 1.6E−12 |
| 49 | 6.4E−11 |
| 50 | 7.1E−11 |
| 51 | 1.2E−11 |
| 52 | 1.3E−12 |
| 53 | 6.6E−12 |
| 54 | 1.2E−12 |
| 55 | 9.2E−12 |
| 56 | 4.9E−11 |
| 57 | 3.0E−12 |
| 58 | 4.8E−12 |
| 59 | 2.3E−11 |
| 60 | 8.9E−12 |
| 61 | 3.3E−11 |
| 62 | 3.4E−12 |
| 63 | 8.1E−11 |
| 64 | 5.2E−12 |
| 65 | 5.0E−12 |
| 66 | 1.2E−11 |
| 67 | 3.2E−12 |
| 68 | 3.8E−12 |
| 69 | 3.7E−12 |
| 70 | 1.7E−11 |
| 71 | 4.5E−12 |
| 72 | 8.0E−11 |
| 73 | 2.5E−12 |
| 74 | 1.0E−11 |
| 75 | 3.3E−12 |
| 76 | 1.8E−12 |
| 77 | 1.7E−10 |
| 78 | 2.3E−11 |
| 79 | 5.2E−12 |
| 80 | 6.5E−12 |
| 81 | 1.5E−11 |
| 82 | 2.3E−11 |
| 83 | 2.6E−11 |
| 84 | 5.3E−11 |
| 85 | 4.4E−11 |
| 86 | 1.9E−11 |
| 87 | 4.4E−11 |
| 88 | 1.0E−11 |
| 89 | 2.8E−12 |
| 90 | 2.2E−12 |
| 91 | 5.7E−12 |
| 92 | 1.7E−12 |
| 93 | 2.4E−12 |
| 94 | 1.5E−12 |
| 95 | 5.6E−12 |
| 96 | 2.2E−12 |
| 102 | 4.5E−12 |
| 125 | 6.7E−12 |
| 126 | 6.7E−11 |
| 127 | 2.1E−12 |
| 128 | 1.8E−12 |
| 129 | 4.7E−12 |
| 130 | 2.3E−12 |
| 131 | 4.5E−12 |
| 132 | 2.0E−12 |
| 133 | 2.1E−12 |
| 134 | 2.8E−12 |
| 135 | 1.8E−12 |
| 136 | 1.4E−12 |
| 137 | 9.9E−13 |
| 138 | 7.1E−13 |
| 139 | 2.0E−11 |
| 140 | 3.2E−12 |
| 141 | 8.5E−12 |
| 142 | 2.6E−12 |

TABLE 2-continued

| Example | Ki (M) |
| --- | --- |
| 143 | 1.4E–12 |
| 144 | 1.4E–12 |
| 145 | 1.8E–12 |
| 146 | 3.2E–12 |
| 147 | 4.6E–12 |
| 148 | 5.9E–12 |
| 149 | 3.7E–12 |
| 150 | 1.5E–12 |
| 151 | 1.5E–12 |
| 152 | 1.7E–12 |
| 153 | 1.2E–12 |
| 154 | #N/A |
| 155 | #N/A |
| 156 | #N/A |
| 157 | #N/A |
| 158 | #N/A |
| 159 | #N/A |
| 160 | #N/A |
| 161 | #N/A |
| 162 | #N/A |
| 163 | #N/A |
| 164 | #N/A |
| 165 | #N/A |
| 166 | 2.7E–12 |
| 167 | 1.9E–12 |
| 168 | 2.9E–12 |
| 169 | #N/A |
| 170 | 2.7E–12 |
| 171 | #N/A |
| 172 | 2.0E–12 |
| 173 | #N/A |
| 174 | #N/A |
| 175 | #N/A |
| 176 | #N/A |
| 177 | #N/A |
| 178 | 2.2E–12 |
| 179 | 2.9E–12 |
| 180 | 1 2E–12 |

The results of Tables 1 and 2 show that most of the compounds of the invention are potent inhibitors of the Bcl-xL protein.

Example C: Effect of Bcl-xL inhibitors in MOLT-4 or H146 cell viability using MTT assay MTT colorimetric assay is based on the mitochondrial reduction of tetrazolium salt by living cells. The viable cell number is proportional to the production of formazan salts, which can be read spectrophotometrically at 540 nm.

MOLT-4 and H146 cells were purchased from ATCC and cultivated in RPMI 1640 supplemented with 10% heat inactivated fetal bovine serum, penicillin (100 IU/ml), streptomycin (100 µg/ml) and L-glutamine (2 mM). Cells were cultured at 37° C. in a humidified atmosphere containing 5% $CO_2$. Cells were seeded in 96 microwell plates (150p per well) and exposed to the compounds for 48 h (3.16 fold serially diluted; 9 concentrations each, triplicates). At the end of incubation time, 15 µL of MTT solution (5 mg/ml) were added per well and the cells were incubated for another 4 h. Then, 100 µL of 10% Sodium Dodecyl Sulfate (SDS)/HCl 10 mM were added per well and the plate was incubated overnight, before measurement of optical density at 540 nm. $IC_{50}$s were calculated using standard four-parametric curve fitting. $IC_{50}$ is defined as the compound concentration at which the MTT signal is reduced to 50% of that measured for the control. Results represent the mean of at least 2 independent experiments and are presented in Table 3 below.

TABLE 3

| Example | H146 $IC_{50}$ (M) | MOLT-4 $IC_{50}$ (M) |
| --- | --- | --- |
| 9 | 2.34E–06 | #N/A |
| 10 | >1.5E–05 | >1.5E–05 |
| 11 | 6.36E–06 | 2.43E–06 |
| 13 | 7.9E–07 | 1.26E–07 |
| 14 | 3.08E–06 | 4.53E–07 |
| 15 | 2.6E–06 | 1.05E–06 |
| 17 | 3.93E–07 | 1.28E–07 |
| 20 | 3.1E–06 | 1.62E–07 |
| 21 | >1.5E–05 | 4.23E–06 |
| 22 | 1.27E–08 | 3.42E–09 |
| 23 | 2.77E–09 | 9.48E–10 |
| 24 | 3.27E–08 | 4.85E–09 |
| 26 | >1.5E–05 | >=1.34E–05 |
| 27 | 6.53E–09 | 1.46E–09 |
| 28 | 3.14E–06 | 8.80E–07 |
| 30 | 6.55E–09 | 7.75E–10 |
| 31 | 8.82E–08 | 1.48E–08 |
| 32 | #N/A | 9.87E–10 |
| 35 | 6.28E–08 | 3.02E–08 |
| 36 | 5.51E–09 | #N/A |
| 37 | 1.02E–08 | 4.61E–09 |
| 38 | 2.21E–08 | 5.94E–08 |
| 39 | 3.36E–08 | 3.71E–08 |
| 40 | 2.08E–08 | 8.16E–09 |
| 41 | 3.67E–09 | 3.6E–10 |
| 42 | 3.02E–09 | 3.27E–10 |
| 43 | 1.17E–08 | 1.71E–09 |
| 44 | 1.07E–08 | 4.04E–09 |
| 45 | 1.06E–08 | 5.51E–10 |
| 46 | 1.11E–08 | 1.2E–09 |
| 47 | 7.31E–09 | 9.57E–10 |
| 48 | 2.25E–09 | 3.09E–10 |
| 49 | 3.34E–08 | 2.13E–09 |
| 50 | 8.77E–08 | 3.71E–09 |
| 51 | 9.6E–09 | 2.54E–09 |
| 52 | 1.07E–08 | 2.42E–09 |
| 53 | 1.49E–08 | 9.74E–09 |
| 54 | 5.95E–07 | 4.72E–08 |
| 55 | 5.65E–09 | 9.49E–10 |
| 56 | 1.29E–08 | 1.46E–09 |
| 57 | 5.54E–09 | 5.92E–10 |
| 58 | 6.65E–09 | 8.17E–10 |
| 59 | 1.73E–08 | 3.36E–09 |
| 60 | 8.86E–09 | 2.75E–09 |
| 61 | 1.2E–07 | 1.22E–07 |
| 62 | 6.9E–08 | 2.02E–08 |
| 63 | 2.02E–08 | #N/A |
| 64 | 1.18E–08 | 3.05E–08 |
| 65 | 3.98E–09 | 2.66E–08 |
| 66 | 8.22E–09 | 2.01E–09 |
| 67 | 1.46E–08 | 7.4E–09 |
| 68 | 1.04E–08 | 2.91E–09 |
| 69 | #N/A | 4.11E–09 |
| 70 | 1.69E–08 | 3.08E–09 |
| 71 | 9.3E–09 | 2.11E–09 |
| 72 | #N/A | 1.39E–08 |
| 73 | 1.47E–08 | 6.54E–09 |
| 75 | #N/A | 9.78E–09 |
| 76 | #N/A | 7.4E–10 |
| 77 | #N/A | 2.26E–07 |
| 78 | #N/A | 2.46E–09 |
| 79 | #N/A | 1.01E–09 |
| 80 | #N/A | 5.75E–10 |
| 81 | #N/A | 1.75E–10 |
| 82 | #N/A | 1.21E–09 |
| 83 | #N/A | 5.73E–10 |
| 84 | #N/A | 1.83E–09 |
| 85 | #N/A | 4.16E–10 |
| 86 | #N/A | 1.5E–09 |
| 88 | #N/A | 1.81E–10 |
| 89 | #N/A | 5.7E–10 |
| 90 | #N/A | 4.6E–10 |
| 91 | #N/A | 3.59E–10 |

These data show that the majority of these compounds are active in cells and can induce a dose dependent decrease in the viability of H146 and Molt-4 cell lines.

| Example | MOLT-4 $IC_{50}$ (M) |
|---|---|
| 92 | 4.58E−09 |
| 93 | 1.42E−08 |
| 94 | 6.16E−10 |
| 95 | 2.05E−10 |
| 96 | 8.27E−09 |
| 102 | 2.68E−10 |
| 125 | 9.53E−09 |
| 126 | 5.33E−08 |
| 127 | 1.37E−10 |
| 128 | 2.84E−10 |
| 129 | 3.11E−09 |
| 130 | 1.94E−09 |
| 131 | 2.75E−10 |
| 132 | 1.32E−09 |
| 133 | 1.68E−09 |
| 134 | 1.57E−09 |
| 135 | 3.05E−09 |
| 136 | 1.25E−09 |
| 137 | 5.78E−09 |
| 138 | 1.01E−09 |
| 139 | 9.95E−10 |
| 140 | 2.85E−09 |
| 141 | 9.8E−11 |
| 142 | 5.13E−11 |
| 143 | 5.46E−11 |
| 144 | 1.32E−08 |
| 145 | 2.65E−10 |
| 146 | 2.47E−10 |
| 147 | 8.52E−10 |
| 148 | 2.77E−10 |
| 149 | 9.82E−10 |
| 150 | 2.19E−10 |
| 151 | 8.24E−11 |
| 152 | #N/A |
| 153 | 2.29E−10 |
| 154 | 4.49E−10 |
| 155 | 5.43E−10 |
| 160 | >1.0E−07 |
| 166 | 4.29E−10 |
| 167 | 5.32E−11 |
| 168 | 2.91E−10 |
| 170 | 7.87E−10 |
| 172 | 3.25E−09 |
| 178 | 6.41E−10 |
| 179 | 9.16E−11 |
| 180 | 1.3E−10 |

Example D: Pharmacodynamics and Tumor Regression Study

The in vivo therapeutic and pharmacodynamic effects of Bcl-xL-targeting small molecules were determined in MOLT-4 T-cell Acute Lymphoblastic Leukemia (T-ALL) model upon intravenous (IV) or oral (PO) administration.

Materials and methods

MOLT-4 cells (ATCC No. CRL-1582) were cultured in RPMI supplemented with 10% FBS. Cells were re-suspended in 50% matrigel (BD Biosciences) and 0.1 mL containing 5×10⁶ cells was subcutaneously inoculated into the right flank of female NOD SCID mice (Charles River).

For efficacy studies, when tumors reached the appropriate volume, mice were randomized (7 animals per group) using Easy stat software. Control vehicle (HPBCD/HCl) or Example 24 (2.5, 5 or 7.5 mg/kg) were injected IV (twice weekly for 3 weeks—Q3D6). Mice body weight was monitored three times a week and tumor size was measured using electronic calipers. Tumor volume was estimated by measuring the minimum and maximum tumor diameters using the formula: (minimum diameter)$^2$(maximum diameter)/2. The last day with at least half of control animals still present in the study (day 31), tumor growth inhibition was calculated using the formula:

$$\left(1 - \frac{\text{Median } (TV \text{ at } Dx \text{ in treated group})}{\text{Median } (TV \text{ at } Dx \text{ in Control group})}\right) \times 100$$

Response was evaluated as follows: CR (Complete Response) if tumor size was <25 mm³ for at least three consecutive measurements, PR (Partial Response) if tumor size was comprised between 25 mm³ and half of the starting size for at least three consecutive measurements. Mice were sacrificed at the first measurement for which tumor volume exceeded 2000 mm³ or at the first signs of animal health deterioration.

For pharmacodynamics studies, when tumors reached the appropriate volume, mice were randomized (3 animals per group) using Easy stat software. Example 24 (7.5 mg/kg) was dosed IV (once per day—QD) in HPBCD/HCl or PO (once per day—QD) in PEG300/EtOH/Phosal (30/10/60). Tumor samples were collected 6 h after dosing and lysed (10 mM HEPES pH 7.4, 142.5 mM KCl, 5 mM MgCl₂, 1 mM EDTA, 1% NP40, protease and phosphatase inhibitors cocktails—Calbiochem). Cleared lysates were prepared for immunodetection of cleaved PARP and Caspase 3 by using the MSD apoptosis panel whole cell lysate kit (MSD) in 96-well plates according to manufacturer's instructions, and were analyzed on the QuickPlex SQ 120. Whole blood samples were analyzed on the Hematology Analyzer Coulter Ac•T diff (Beckman Coulter).

All experiments were conducted in accordance with the French regulations in force after approval by Servier Research Institute (IdRS) Ethical Committee. NOD SCID mice were maintained according to institutional guidelines.

Results

Efficacy of Example 24 on MOLT-4 xenografts is illustrated in FIG. 1. Treatment was started 12 days post tumor cells inoculation (average size: 235 mm³). Vehicle (HPBCD/HCl) or Example 24 (2.5, 5 and 7.5 mg/kg) were dosed IV each 3 days for a total of 6 administrations. On day 31 after treatment start, the Tumor Growth Inhibition (% TGI) induced by Example 24 was of 77.1% at 2.5 mg/kg, 78.7% at 5 mg/kg and 94.7% at 7.5 mg/kg (p<0.05), as depicted in FIG. 1 and Table 4. Partial regression (PR) was achieved in 28.6%, 71.4% and 100% of the cases, respectively. Complete regression (CR) was observed in 14.3% of the animals treated at the highest dose.

No clinically relevant body weight loss due to the treatment was observed (FIG. 2).

TABLE 4

MOLT-4 tumor growth inhibition upon treatment with Example 24 (2.5, 5 and 7.5 mg/kg, administered IV, Q3D6).

| Group | Dose (mg/kg) | % TGI (d31) | % CR | % PR |
|---|---|---|---|---|
| Example 24 | 2.5 | 77.1* | 0 | 28.6 |
| Example 24 | 5 | 78.7* | 0 | 71.4 |
| Example 24 | 7.5 | 94.7* | 14.3 | 100 |

*p value <0.05 compared to control group.

The effect of Example 24 on apoptosis induction in MOLT-4 tumor cells and number of circulating platelets is illustrated in Table 5. Treatment was started 18 days post tumor cells inoculation (average size: 461 mm³). Example 24 (7.5 mg/kg) was dosed once PO or IV and samples were collected 6 h later. The compound showed an induction of apoptosis markers, namely cleaved PARP (24.1-38.6-fold over non-treated control) and cleaved Caspase 3 (7.2-18.9-fold over non-treated control) cleavage, independently on the administration route. In addition, given the well-described role of Bcl-xL in regulating platelets life-span, it also caused a significant reduction in platelet numbers (to 1% of control values).

these data indicate that there is a possible therapeutic margin for the use of these Bcl-xL-targeting small molecules in cancer treatment.

Example E: In Vivo Pharmacodynamic Profile of the Compounds of Formula (I)

The pharmacokinetic profile of the compounds of formula (I) is evaluated in rodent (mouse, rat) after PO and/or IV route. The formulation is selected based on the physico-chemical properties of the tested drug as well as the route of administration. A single dose of the drug (<5 mg/kg) prepared in the adapted formulation is administered by IV (bolus or 10 min infusion) or PO (gavage) route to animals (3 animals/route). Blood samples from each animal (up to 6 samples/animal) are collected over 24 h after dosing and plasma concentrations of the tested compound are determined after extraction followed by a liquid chromatography coupled with tandem mass spectrometry detection (LC/MS-MS).

In some cases, the following experimental protocol is used to determine the pharmacokinetic profile of the compounds of the invention in the Wistar rat: The drug is prepared in a formulation composed by a mixture of polyethylene glycol 300/anhydrous Ethanol/NaCl 0.9% (40/10/

TABLE 5

Cleaved PARP and cleaved Caspase 3 activation in tumor cells and platelet loss in MOLT-4-grafted female NOD SCID mice 6 h after treatment (PO or IV) with Example 24 at 7.5 mg/kg.

| Compound tested | Dose (mg/kg) and route | Time-point (h) | Cleaved PARP (fold increase over control) | Cleaved Caspase 3 (fold increase over control) | Platelet count (×10³/µl) | % remaining platelets (vs controls) |
|---|---|---|---|---|---|---|
| Example 24 | 7.5, PO | 6 | 24.1 | 7.1 | 7 | 1 |
| Example 24 | 7.5, IV | 6 | 38.6 | 18.9 | 8 | 1 |

In conclusion, we show here that the Bcl-xL-targeting small molecule described in Example 24 is active in vivo after intravenous or oral administration. We observed tumor regression, apoptosis induction in tumor cells and a strong reduction in circulating platelets, in agreement with the previously described role of Bcl-xL in apoptosis control and platelets life-span regulation (Youle and Strasser, Nat. Rev. Mol. Cell Biol. 2008 Jan.; 9(1):47-59; Zhang et al., Cell Death Differ. 2007 May; 14(5):943-51; Mason et al., Cell 2007 Mar. 23; 128(6):1173-86). In addition, no clinically relevant body weight loss was observed upon treatment with efficacious doses and platelets loss was recovered after treatment discontinuation (data not shown). Altogether, 50 v/v/v). The formulation is administered by IV route to male Wistar rat (3 animals) at a dose of 0.75 mg/kg (10 min inf, 5 mL/kg). Blood samples are taken at the following time points from each animal: end of infusion (10 min), 0.5 h, 1 h, 3 h, 6 h and 24 h after dosing. The plasma concentrations of the tested compound are determined after extraction followed by a liquid chromatography coupled with tandem mass spectrometry detection (LC/MS-MS).

The lower limit of quantification is 2.5 ng/mL.

The results allow to rank the compounds of the invention based on their plasma exposure, elimination rate constant, clearance and volume of distribution in order to evaluate the therapeutic range of the compounds in animal model.

The invention claimed is:

1. A compound of formula (IA):

wherein:

n represents 0, 1 or 2,

------ represents a single or a double bond, $A_4$ and $A_5$, independently of one another, represent a carbon or a nitrogen atom, $Z_1$ represents a bond, $-N(R)-$, or $-O-$, wherein R represents hydrogen or linear or branched $C_1$-$C_6$alkyl, $R_1$ represents a group selected from: hydrogen; linear or branched $C_1$-$C_6$alkyl optionally substituted by a hydroxyl or a $C_1$-$C_6$alkoxy group; $C_3$-$C_6$cycloalkyl; trifluoromethyl; linear or branched $C_1$-$C_6$alkylene-heterocycloalkyl wherein the heterocycloalkyl group is optionally substituted by a linear or branched $C_1$-$C_6$alkyl group;

$R_2$ represents hydrogen or methyl;

$R_3$ represents a group selected from: hydrogen; linear or branched $C_1$-$C_4$alkyl; $-X_1-NR_aR_b$; $-X_1-N^+R_aR_bR_c$; $-X_1-O-R_c$; $-X_1-COOR_c$; $-X_1-PO(OH)_2$; $-X_1-SO_2(OH)$; $-X_1-N_3$ and:

$$-X_1-\!\!\equiv\!\!CH,$$

$R_a$ and $R_b$, independently of one another, represent a group selected from: hydrogen; heterocycloalkyl; $-SO_2$-phenyl, wherein the phenyl may be substituted by a linear or branched $C_1$-$C_6$alkyl; linear or branched $C_1$-$C_6$alkyl optionally substituted by one or two hydroxyl groups; $C_1$-$C_6$alkylene-$SO_2OH$; $C_1$-$C_6$alkylene-$SO_2O-$; $C_1$-$C_6$alkylene-COOH; $C_1$-$C_6$alkylene-$PO(OH)_2$; $C_1$-$C_6$alkylene-$NR_dR_e$; $C_1$-$C_6$alkylene-$N^+R_dR_eR_f$; $C_1$-$C_6$alkylene-phenyl wherein the phenyl may be substituted by a $C_1$-$C_6$alkoxy group; and the group:

or $R_a$ and $R_b$, together with the nitrogen atom carrying them, form a cycle $B_1$;

or $R_a$, $R_b$ and $R_c$, together with the nitrogen atom carrying them, form a bridged $C_3$-$C_8$heterocycloalkyl, $R_c$, $R_d$, $R_e$, $R_f$ independently of one another, represent hydrogen or linear or branched $C_1$-$C_6$alkyl, or $R_d$ and $R_e$, together with the nitrogen atom carrying them, form a a cycle $B_2$, or $R_d$, $R_e$ and $R_f$, together with the nitrogen atom carrying them, form a bridged $C_3$-$C_8$heterocycloalkyl, $Het_1$ represents a group selected from:

361

-continued

Het$_2$ represents a group selected from:

A$_1$ represents —NH—, —N(C$_1$-C$_3$alkyl), O, S or Se,
A$_2$ represents N, CH or C(R$_5$),
G is selected from:
—C(O)OR$_{G3}$, —C(O)NR$_{G1}$R$_{G2}$, —C(O)R$_{G2}$, —NR$_{G1}$C(O)R$_{G2}$, —NR$_{G1}$C(O)NR$_{G1}$R$_{G2}$, —OC(O)NR$_{G1}$R$_{G2}$, —NR$_{G1}$C(O)OR$_{G3}$, —C(=NOR$_{G1}$)NR$_{G1}$R$_{G2}$, —NR$_{G1}$C(=NCN)NR$_{G1}$R$_{G2}$, —NR$_{G1}$S(O)$_2$NR$_{G1}$R$_{G2}$, —S(O)$_2$R$_{G3}$, —S(O)$_2$NR$_{G1}$R$_{G2}$, —NR$_{G1}$S(O)$_2$R$_{G2}$, —NR$_{G1}$C(=NR$_{G2}$)NR$_{G1}$R$_{G2}$, —C(=S)NR$_{G1}$R$_{G2}$, —C(=NR$_{G1}$)NR$_{G1}$R$_{G2}$, halogen, —NO$_2$, and —CN, wherein:

$R_{G1}$ and $R_{G2}$, at each occurrence, are each independently selected from the group consisting of hydrogen, $C_1$-$C_5$alkyl optionally substituted by 1 to 3 halogen atoms, $C_2$-$C_6$alkenyl, $C_2$-$C_6$alkynyl, $C_3$-$C_6$cycloalkyl, phenyl and —$(CH_2)_{1-4}$-phenyl;

$R_{G3}$ is selected from the group consisting of $C_1$-$C_6$alkyl optionally substituted by 1 to 3 halogen atoms, $C_2$-$C_6$alkenyl, $C_2$-$C_6$alkynyl, $C_3$-$C_6$cycloalkyl, phenyl and —$(CH_2)_{1-4}$-phenyl; or $R_{G1}$ and $R_{G2}$, together with the atom to which each is attached, form a $C_3$-$C_8$heterocycloalkyl; or G is selected from:

-continued wherein $R_{G4}$ is selected from $C_1$-$C_6$alkyl optionally substituted by 1 to 3 halogen atoms, $C_2$-$C_6$alkenyl, $C_2$-$C_6$alkynyl and $C_3$-$C_6$cycloalkyl, $R_4$ represents hydrogen, fluorine, chlorine, bromine, methyl, hydroxyl or methoxy, $R_5$ represents a group selected from: $C_1$-$C_6$alkyl optionally substituted by 1 to 3 halogen atoms; $C_2$-$C_6$alkenyl; $C_2$-$C_6$alkynyl; halogen and —CN, $R_6$ represents a group selected from:
hydrogen;
—$C_2$-$C_6$alkenyl;
—$X_2$—O—$R_7$;

—$X_2$—$NSO_2$—$R_7$;
—C=C($R_9$)—$Y_1$—O—$R_7$;
$C_3$-$C_6$cycloalkyl;
$C_3$-$C_6$heterocycloalkyl optionally substituted by a hydroxyl group;
$C_3$-$C_6$cycloalkylene-$Y_2$—$R_7$;
$C_3$-$C_6$heterocycloalkylene-$Y_2$—$R_7$; and
a heteroarylene-$R_7$ group optionally substituted by a linear or branched $C_1$-$C_6$alkyl group, $R_7$ represents a group selected from: linear or branched $C_1$-$C_6$alkyl; $(C_3$-$C_6)$cycloalkylene-$R_8$; and:

-continued $(CH_2)_p$—$OCH_3$,

Cy $R_8$, $R_{14}$ $R_{15}$ $R_{10}$ $R_8$, $R_{14}$ $R_{15}$ $R_{10}$ $R_{14}$ $R_8$, $R_{10}$ $R_{14}$ $R_{10}$ $R_{14}$, $R_{10}$ $R_{11}$ $R_{10}$ $R_{12}$ $R_8$ $R_{13}$, $R_{12}$ $R_{12}$ $R_{13}$, $R_8$ $R_{13}$ $R_8$, $R_{12}$ wherein Cy represents a $C_3$-$C_8$cycloalkyl, $R_8$ represents a group selected from: hydrogen; linear or branched $C_1$-$C_6$alkyl, —$NR'_aR'_b$; —$NR'_a$—CO—$OR'_c$; —$NR'_a$—CO—$R'_c$; —$N^+R'_aR'_bR'_c$; —O—$R'_c$; —NH—$X'_2$—$N^+R'_aR'_bR'_c$; —O—$X'_2$—$NR'_aR'b$, —$X'_2$—$NR'_aR'_b$, —$NR'_c$—$X'_2$—$N_3$ and:

~$NR'_c$—$X'_2$≡CH, $R_9$ represents a group selected from linear or branched $C_1$-$C_6$alkyl, trifluoromethyl, hydroxyl, halogen, $C_1$-$C_6$alkoxy, $R_{10}$ represents a group selected from hydrogen, fluorine, chlorine, bromine, —$CF_3$ and methyl, $R_{11}$ represents a group selected from hydrogen, halogen, $C_1$-$C_3$alkylene-$R_8$, —O—$C_1$-$C_3$alkylene-$R_8$, —CO—$NR_hR_i$ and —CH=CH—$C_1$-$C_4$alkylene-$NR_hR_i$, —CH=CH—CHO, $C_3$-$C_8$cycloalkylene-$CH_2$—$R_8$ and $C_3$-$C_8$heterocycloalkylene-$CH_2$—$R_8$, $R_{12}$ and $R_{13}$, independently of one another, represent hydrogen or methyl, $R_{14}$ and $R_{15}$, independently of one another, represent hydrogen or methyl, or $R_{14}$ and $R_{15}$, together with the carbon atom carrying them, form a a cyclohexyl group, $R_h$ and $R_i$, independently of one another, represent hydrogen or linear or branched $C_1$-$C_6$alkyl, $X_1$ represents a linear or branched $C_1$-$C_4$alkylene group optionally substituted by one or two groups selected from trifluoromethyl, hydroxyl, halogen and $C_1$-$C_6$alkoxy, $X_2$ represents a linear or branched $C_1$-$C_6$alkylene group optionally substituted by one or two groups selected from trifluoromethyl, hydroxyl, halogen and $C_1$-$C_6$alkoxy, $X'_2$ represents linear or branched $C_1$-$C_6$alkylene, $R'_a$ and $R'_b$, independently of one another, represent a group selected from: hydrogen; heterocycloalkyl; —$SO_2$-phenyl wherein the phenyl may be substituted by a linear or branched $C_1$-$C_6$alkyl; linear or branched $C_1$-$C_6$alkyl optionally substituted by one or two hydroxyl or $C_1$-$C_6$alkoxy groups; $C_1$-$C_6$alkylene-$SO_2OH$; $C_1$-$C_6$alkylene-$SO_2O$—; $C_1$-$C_6$alkylene-COOH; $C_1$-$C_6$alkylene-PO(OH)$_2$; $C_1$-$C_6$alkylene-$NR'_dR'_e$; $C_1$-$C_6$alkylene-$N^+R'_dR'_eR'_f$; $C_1$-$C_6$alkylene-O—$C_1$-$C_6$alkylene-OH; $C_1$-$C_6$alkylene-phenyl, wherein the phenyl may be substituted by a hydroxyl or a $C_1$-$C_6$alkoxy group;

the group:

$CF_3$

N

N or $R'_a$ and $R'_b$, together with the nitrogen atom carrying them, form a cycle $B_3$, or $R'_a$, $R'_b$ and $R'_c$, together with the nitrogen atom carrying them, form a bridged $C_3$-$C_8$heterocycloalkyl, $R'_c$, $R'_d$, $R'_e$, $R'_f$, independently of one another, represents a hydrogen or a linear or branched $C_1$-$C_6$alkyl group, or $R'_d$ and $R'_e$, together with the nitrogen atom carrying them, form a cycle $B_4$, or $R'_d$, $R'_e$ and $R'_f$, together with the nitrogen atom carrying them, form a bridged $C_3$-$C_8$heterocycloalkyl, $Y_1$ represents linear or branched $C_1$-$C_4$alkylene, $Y_2$ represents a bond, —O—, —O—$CH_2$—, —O—CO—, —O—$SO_2$—, —$CH_2$—, —$CH_2$—O, —$CH_2$—CO—, —$CH_2$—$SO_2$—, —$C_2H_5$—, —CO—, —CO—O—, —CO—$CH_2$—, —CO—NH—$CH_2$—, —$SO_2$—, —$SO_2$—$CH_2$—, —NH—CO— or —NH—$SO_2$—, m represents 0, 1 or 2, p represents 1, 2, 3 or 4, $B_1$, $B_2$, $B_3$ and $B_4$, independently of one another, represent a $C_3$-$C_8$heterocycloalkyl group, which group: (i) is a mono- or bi-cyclic group, wherein bicyclic group includes fused, bridged or spiro ring system, (ii) may have, in addition to the nitrogen atom, one or two hetero atoms selected independently from oxygen, sulphur and nitrogen and (iii) may optionally be substituted by one or two groups selected from: fluorine, bromine, chlorine, linear or branched $C_1$-$C_6$alkyl, hydroxyl, —$NH_2$, oxo and piperidinyl, its enantiomers and diastereoisomers, and salts thereof with a pharmaceutically acceptable acid or base.

2. The compound according to claim 1, wherein $A_4$ and $A_5$ represent each a nitrogen atom.

3. The compound according to claim 1, wherein $Z_1$ represents —NH— or —O—.

4. The compound according to claim 1, wherein $R_3$ represents —$X_1$—$NR_aR_b$.

5. The compound according to claim 4, wherein $R_3$ represents —$C_2H_5$—NH—$CH_3$.

6. The compound according to claim 1, which is selected from:

-continued

7. The compound according to claim 6, which is a compound of formula (IB):

8. The compound according to claim 1, wherein $R_1$ represents hydrogen, methyl or cyclopropyl.

9. The compound according to claim 1, wherein $Het_1$ represents:

10. The compound according to claim 1, wherein $Het_2$ represents:

11. The compound according to claim 1, wherein $Het_2$ represents:

12. The compound according to claim 1 wherein R$_6$ represents a —X$_2$—O—R$_7$ group wherein X$_2$ is a propylene group.

13. The compound according to claim 12, wherein R$_7$ represents the following group:

14. The compound according to claim 12, wherein R$_7$ represents the following group:

15. The compound according to claim 13, wherein R$_8$ represents a group selected from: dimethylamino, diethylamino, diisopropylamino, diisobutylamino, methylamino, ethylamino, ethyl(methyl)amino, 4-methyl-piperazin-1-yl, piperazin-1-yl, pyrrolidin-1-yl, azetidin-1-yl, 1-piperidyl, 4-morpholinyl, 4,4-difluoropiperidin-1-yl, 3,3-difluoropiperidin-1-yl, 3-hydroxy-1-piperidyl, (1S,5R)-3-azabicyclo[3.1.0]hexan-3-yl, 4-(1-piperidyl)-1-piperidyl, 3-oxo-2,8-diazaspiro[4.5]decan-8-yl, (1S,5R)-6,6-difluoro-3-azabicyclo[3.1.0]hexan-3-yl, 2-(dimethylamino)ethylamino, 3-piperazin-1-yl, (3R,5S)-3,5-dimethylpiperazin-1-yl, (but-3-yn-1-yl)amino, (but-3-yn-1-yl)(methyl)amino, (3-azidopropyl)amino, (3-azidopropyl)(methyl)amino (3-aminopropyl)amino, (pent-4-yn-1-yl)amino, methyl(pent-4-yn-1-yl)amino, (prop-2-yn-1-yl)amino, (hex-5-yn-1-yl)amino, 3-[(hex-5-yn-1-yl)(methyl)amino, (4-azidobutyl)amino, (4-azidobutyl)(methyl)amino, [2-(2-hydroxyethoxy)ethyl](methyl)amino,
and:

16. The compound according to claim 14, wherein R$_8$ represents a group selected from: dimethylamino, diethylamino, diisopropylamino, diisobutylamino, methylamino, ethylamino, ethyl(methyl)amino, 4-methyl-piperazin-1-yl, piperazin-1-yl, pyrrolidin-1-yl, azetidin-1-yl, 1-piperidyl, 4-morpholinyl, 4,4-difluoropiperidin-1-yl, 3,3-difluoropiperidin-1-yl, 3-hydroxy-1-piperidyl, (1S,5R)-3-azabicyclo[3.1.0]hexan-3-yl, 4-(1-piperidyl)-1-piperidyl, 3-oxo-2,8-diazaspiro[4.5]decan-8-yl, (1S,5R)-6,6-difluoro-3-azabicyclo[3.1.0]hexan-3-yl, 2-(dimethylamino)ethylamino, 3-piperazin-1-yl, (3R,5S)-3,5-dimethylpiperazin-1-yl, (but-3-yn-1-yl)amino, (but-3-yn-1-yl)(methyl)amino, (3-azidopropyl)amino, (3-azidopropyl)(methyl)amino (3-aminopropyl)amino, (pent-4-yn-1-yl)amino, methyl(pent-4-yn-1-yl)amino, (prop-2-yn-1-yl)amino, (hex-5-yn-1-yl)amino, 3-[(hex-5-yn-1-yl)(methyl)amino, (4-azidobutyl)amino, (4-azidobutyl)(methyl)amino, [2-(2-hydroxyethoxy)ethyl](methyl)amino, and:

17. The compound according to claim 13, wherein R$_8$ represents a group selected from: bis[(3S)-3,4-dihydroxybutyl]amino, amino, [(3S)-3,4-dihydroxybutyl]amino, [(3R)-3,4-dihydroxybutyl]amino, acetyl(methyl)amino, 3-hydroxypropylamino.

18. The compound according to claim 14, wherein R$_8$ represents a group selected from: bis[(3S)-3,4-dihydroxybutyl]amino, amino, [(3S)-3,4-dihydroxybutyl]amino, [(3R)-3,4-dihydroxybutyl]amino, acetyl(methyl)amino, 3-hydroxypropylamino.

19. The compound according to claim 12, wherein R$_7$ represents:

wherein R$_{11}$ is selected from 3-(dimethylamino)propyl, 3-(methylamino)propyl, aminomethyl, 2-(dimethylamino)ethyl, 4-(dimethylamino)butyl, 2-(methylamino)ethyl, 4-(methylamino)butyl, 3-(azetidin-1-yl)propyl, 3-(4-methylpiperazin-1-yl)propyl, 3-pyrrolidin-1-ylpropyl, 3-morpholinopropyl, 3-(1-piperidyl)propyl, 3-[(1R,5S)-6,6-difluoro-3-azabicyclo[3.1.0]hexan-3-yl and 3-(3-oxo-2,8-diazaspiro[4.5]decan-8-yl)propyl.

20. The compound according to claim 12, wherein R$_7$ represents a group selected from:

21. The compound according to claim 11, wherein R$_6$ represents:

22. The compound according to claim 21, wherein $R_7$ represents a group selected from:

wherein $R_8$ represents a group selected from: hydrogen, 2-(methylamino)ethoxy, 2-(dimethylamino)ethoxy, 2-[(2-sulfoethyl)amino]ethoxy, 2-[methyl(2-sulfoethyl)amino] ethoxy, 4-methylpiperazin-1-yl and:

23. The compound according to claim 21, wherein $R_7$ represents a group selected from:

wherein $R_8$ represents a group selected from: 2-pyrrolidin-1-ylethoxy, 2-(4-methylpiperazin-1-yl)ethoxy, 2-[[(3R)-3,4- dihydroxybutyl]-methyl-amino]ethoxy, 2-(4-hydroxybuty-lamino)ethoxy, 2-[[3-hydroxy-2-(hydroxymethyl)propyl] amino]ethoxy, 2-[bis(2-hydroxyethyl)amino]ethoxy, 2-[[2-hydroxy-1-(hydroxymethyl)ethyl]amino]ethoxy, 2-[2-(2-hydroxyethoxy)ethylamino]ethoxy, 2-[bis(3-hydroxypropyl)amino]ethoxy, 2-(3-hydroxypropylamino) ethoxy, 2-[bis(4-hydroxybutyl)amino]ethoxy, 2-morpholinoethoxy, 2-(1-piperidyl)ethoxy, 2-piperazin-1-ylethoxy, 2-(azepan-1-yl)ethoxy, 2-(4-isopropylpiperazin-1-yl)ethoxy, 2-[(4-hydroxyphenyl)methylamino]ethoxy, 2-[2-hydroxyethyl(methyl)amino]ethoxy, 2-[3-methoxypropyl (methyl)amino]ethoxy, 2-[4-hydroxybutyl(methyl)amino] ethoxy, 3-pyrrolidin-1-ylpropyl, 3-(dimethylamino)propyl, 3-(4-methylpiperazin-1-yl)propyl, 3-morpholinopropyl, 3-(3-hydroxypropylamino)propyl, 3-(4-hydroxybuty-lamino)propyl, 3-[[(3S)-3,4-dihydroxybutyl]amino]propyl, 3-hydroxy-2-(hydroxymethyl)propyl]amino]propyl, 3-[4-hydroxybutyl(methyl)amino]propyl, 3-[3-hydroxypropyl (methyl)amino]propyl, 3-[3-[bis(3-hydroxypropyl)amino] propyl, 3-piperazin-1-ylpropyl.

24. The compound according to claim 1, wherein $R_3$ represents $-X_1-PO(OH)_2$, $-X_1-SO_2(OH)$, $-X_1-NR_aR_b$; $-X_1-N^+R_aR_bR_c$, wherein $R_a$ or $R_b$, or both of them, represent a group selected from $C_1$-$C_6$alkylene-$SO_2OH$, $C_1$-$C_6$alkylene-$SO_2O^-$ and $C_1$-$C_6$alkylene-$PO(OH)_2$.

25. The compound according to claim 7, wherein $R_3$ represents $-X_1-PO(OH)_2$, $-X_1-SO_2(OH)$, $-X_1-NR_aR_b$; $-X_1-N^+R_aR_bR_c$, wherein $R_a$ or $R_b$, or both of them, represent a group selected from $C_1$-$C_6$alkylene-$SO_2OH$, $C_1$-$C_6$alkylene-$SO_2O^-$ and $C_1$-$C_6$alkylene-$PO(OH)_2$.

26. The compound according to claim 1, wherein $R_8$ represents $-NR'_aR'_b$; $-N^+R'_aR'_bR'_c$; $-NH-X'_2-N^+R'_aR'_bR'_c$, wherein $R'_a$ and $R'_b$, or both of them, represent a group selected from $C_1$-$C_6$alkylene-$SO_2OH$ and $C_1$-$C_6$alkylene-$PO(OH)_2$.

27. The compound according to claim 7, wherein $R_8$ represents $-NR'_aR'_b$; $-N^+R'_aR'_bR'_c$; $-NH-X'_2-N^+R'_aR'_bR'_c$, wherein $R'_a$ and $R'_b$, or both of them, represent a group selected from $C_1$-$C_6$alkylene-$SO_2OH$ and $C_1$-$C_6$alkylene-$PO(OH)_2$.

28. The compound according to claim 1, which is selected from:

2-[3-(1,3-Benzothiazol-2-ylamino)-4-methyl-6,7-di-hydro-5H-pyrido[2,3-c]pyridazin-8-yl]-5-[3-[4-[3-(di-methylamino)prop-1-ynyl]-2-fluoro-phenoxy]propyl] thiazole-4-carboxylic acid, 2-{3-[(1,3-Benzothiazol-2-yl)amino]-4-methyl-5H,6H, 7H,8H-pyrido[2,3-c]pyridazin-8-yl}-5-(3-{2-fluoro-4-[3-(methylamino)prop-1-yn-1-yl]phenoxy}propyl)-1, 3-thiazole-4-carboxylic acid, 2-{3-[(1,3-Benzothiazol-2-yl)amino]-4-methyl-5H,6H, 7H,8H-pyrido[2,3-c]pyridazin-8-yl}-5-(3-{4-[3-(dim-ethylamino)propyl]-2-fluorophenoxy}propyl)-1,3-thi-azole-4-carboxylic acid, 2-[3-(1,3-Benzothiazol-2-ylamino)-4-methyl-6,7-di-hydro-5H-pyrido[2,3-c]pyridazin-8-yl]-5-[3-[2-fluoro-4-[3-(4-methylpiperazin-1-yl)but-1-ynyl]phenoxy]pro-pyl]thiazole-4-carboxylic acid, 2-[3-(1,3-Benzothiazol-2-ylamino)-4-methyl-6,7-di-hydro-5H-pyrido[2,3-c]pyridazin-8-yl]-5-[3-[2-fluoro-4-(3-pyrrolidin-1-ylprop-1-ynyl)phenoxy]propyl]thi-azole-4-carboxylic acid, 5-(3-{4-[3-(Azetidin-1-yl)prop-1-yn-1-yl]-2-fluorophenoxy}propyl)-2-{3-[(1,3-benzothiazol-2-yl)

amino]-4-methyl-5H,6H,7H,8H-pyrido[2,3-c]
pyridazin-8-yl}-1,3-thiazole-4-carboxylic acid, 2-[3-(1,3-Benzothiazol-2-ylamino)-4-methyl-6,7-di-
hydro-5H-pyrido[2,3-c]pyridazin-8-yl]-5-[3-[2-fluoro-
4-[3-(4-methylpiperazin-1-yl)prop-1-ynyl]phenoxy]
propyl]thiazole-4-carboxylic acid, 2-{3-[(1,3-Benzothiazol-2-yl)amino]-4-methyl-5H,6H,
7H,8H-pyrido[2,3-c]pyridazin-8-yl}-5-(3-{4-[3-(4,4-
difluoropiperidin-1-yl)prop-1-yn-1-yl]-2-
fluorophenoxy}propyl)-1,3-thiazole-4-carboxylic acid, 2-{3-[(1,3-Benzothiazol-2-yl)amino]-4-methyl-5H,6H,
7H,8H-pyrido[2,3-c]pyridazin-8-yl}-5-(3-{4-[3-(3,3-
difluoropiperidin-1-yl)prop-1-yn-1-yl]-2-
fluorophenoxy}propyl)-1,3-thiazole-4-carboxylic acid, 2-[3-(1,3-Benzothiazol-2-ylamino)-4-methyl-6,7-di-
hydro-5H-pyrido[2,3-c]pyridazin-8-yl]-5-[3-[2-fluoro-
4-[3-(3-oxo-2,8-diazaspiro[4.5]decan-8-yl)prop-1-
ynyl]phenoxy]propyl]thiazole-4-carboxylic acid, 2-[3-(1,3-Benzothiazol-2-ylamino)-4-methyl-6,7-di-
hydro-5H-pyrido[2,3-c]pyridazin-8-yl]-5-[3-[4-[3-
[(1S,5R)-6,6-difluoro-3-azabicyclo[3.1.0]hexan-3-yl]
prop-1-ynyl]-2-fluoro-phenoxy]propyl]thiazole-4-
carboxylic acid, 2-[3-(1,3-Benzothiazol-2-ylamino)-4-methyl-6,7-di-
hydro-5H-pyrido[2,3-c]pyridazin-8-yl]-5-[3-[2-fluoro-
4-(3-piperazin-1-ylprop-1-ynyl)phenoxy]propyl]thiaz-
ole-4-carboxylic acid, 2-[3-(1,3-Benzothiazol-2-ylamino)-4-methyl-6,7-di-
hydro-5H-pyrido[2,3-c]pyridazin-8-yl]-5-[3-[4-[3-
[(3R,5S)-3,5-dimethylpiperazin-1-yl]prop-1-ynyl]-2-
fluoro-phenoxy]propyl]thiazole-4-carboxylic acid, 2-[3-(1,3-Benzothiazol-2-ylamino)-4-methyl-6,7-di-
hydro-5H-pyrido[2,3-c]pyridazin-8-yl]-5-[3-[4-[3-(di-
ethylamino)prop-1-ynyl]-2-fluoro-phenoxy]propyl]thi-
azole-4-carboxylic acid, 2-[3-(1,3-Benzothiazol-2-ylamino)-4-methyl-6,7-di-
hydro-5H-pyrido[2,3-c]pyridazin-8-yl]-5-[3-[4-[3-(di-
isopropylamino)prop-1-ynyl]-2-fluoro-phenoxy]pro-
pyl]thiazole-4-carboxylic acid, 2-[3-(1,3-Benzothiazol-2-ylamino)-4-methyl-6,7-di-
hydro-5H-pyrido[2,3-c]pyridazin-8-yl]-5-[3-[4-[3-[2-
(dimethylamino)ethylamino]prop-1-ynyl]-2-fluoro-
phenoxy]propyl]thiazole-4-carboxylic acid, 2-{3-[(1,3-Benzothiazol-2-yl)amino]-4-methyl-6-[2-
(methylamino)ethoxy]-5H,6H,7H,8H-pyrido[2,3-c]
pyridazin-8-yl}-5-(3-{4-[3-(dimethylamino)prop-1-
yn-1-yl]-2-fluorophenoxy}propyl)-1,3-thiazole-4-
carboxylic acid, 2-[3-(1,3-Benzothiazol-2-ylamino)-4-methyl-6,7-di-
hydro-5H-pyrido[2,3-c]pyridazin-8-yl]-5-[3-[4-[1-
[(dimethylamino)methyl]-3-bicyclo[1.1.1]pentanyl]-2-
fluoro-phenoxy]propyl]thiazole-4-carboxylic acid, 2-[3-(1,3-Benzothiazol-2-ylamino)-4-methyl-6,7-di-
hydro-5H-pyrido[2,3-c]pyridazin-8-yl]-5-[3-[2-fluoro-
4-[3-methyl-3-(methylamino)but-1-ynyl]phenoxy]pro-
pyl]thiazole-4-carboxylic acid, 2-[3-(1,3-benzothiazol-2-ylamino)-4-methyl-6,7-di-
hydro-5H-pyrido[2,3-c]pyridazin-8-yl]-5-[3-[2-fluoro-
4-[3-(prop-2-ynylamino)prop-1-ynyl]phenoxy]propyl]
thiazole-4-carboxylic acid, 6-{3-[(1,3-benzothiazol-2-yl)amino]-4-methyl-6,7-dihy-
dropyrido[2,3-c]pyridazin-8(5H)-yl}-3-[1-({3-[2-(di-
methylamino)ethoxy]-5,7-dimethyladamantan-1-
yl}methyl)-5-methyl-1H-pyrazol-4-yl]pyridine-2-
carboxylic acid, 6-{3-[(1,3-benzothiazol-2-yl)amino]-4-methyl-6,7-dihy-
dropyrido[2,3-c]pyridazin-8(5H)-yl}-3-[1-({3,5-dimethyl-7-[2-(methylamino)ethoxy]adamantan-1-
yl}methyl)-5-methyl-1H-pyrazol-4-yl]pyridine-2-
carboxylic acid, 2-{3-[(1,3-benzothiazol-2-yl)amino]-4-methyl-6,7-dihy-
dropyrido[2,3-c]pyridazin-8(5H)-yl}-5-(3-{4-[3-(eth-
ylamino)-3-methylbut-1-yn-1-yl]-2-
fluorophenoxy}propyl)-1,3-thiazole-4-carboxylic acid, 3-{1-[(Adamantan-1-yl)methyl]-5-methyl-1H-pyrazol-4-
yl}-6-{3-[(1,3-benzothiazol-2-yl)amino]-4-methyl-5H,
6H,7H,8H-pyrido[2,3-c]pyridazin-8-yl}pyridine-2-
carboxylic acid, its enantiomers and diastereoisomers, and salts thereof
with a pharmaceutically acceptable acid or base.

29. The compound according to claim 1, which is selected
from:

6-{3-[(1,3-benzothiazol-2-yl)amino]-4-methyl-6,7-dihy-
dropyrido[2,3-c]pyridazin-8(5H)-yl}-3-[1-({3-[2-(di-
methylamino)ethoxy]-5,7-dimethyladamantan-1-
yl}methyl)-5-methyl-1H-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3,5-di-
methyl-7-(2-pyrrolidin-1-ylethoxy)-1-adamantyl]
methyl]-5-methyl-pyrazol-4-yl]pyridine-2-carboxylic
acid, 6-[3-(1,3-benzothiazol-2-ylamino)-4-methyl-6,7-di-
hydro-5H-pyrido[2,3-c]pyridazin-8-yl]-3-[1-[[3,5-di-
methyl-7-[2-(4-methylpiperazin-1-yl)ethoxy]-1-ada-
mantyl]methyl]-5-methyl-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3-[2-(3-
hydroxypropylamino)ethoxy]-5,7-dimethyl-1-adaman-
tyl]methyl]-5-methyl-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3-[2-(4-
hydroxybutylamino)ethoxy]-5,7-dimethyl-1-adaman-
tyl]methyl]-5-methyl-pyrazol-4-yl]pyridine-2-
carboxylic acid, 6-{3-[(1,3-benzothiazol-2-yl)amino]-4-methyl-6,7-dihy-
dropyrido[2,3-c]pyridazin-8(5H)-yl}-3-(1-{[3-(2-{
[(3S)-3,4-dihydroxybutyl]amino}ethoxy)-5,7-dimeth-
yladamantan-1-yl]methyl}-5-methyl-1H-pyrazol-4-yl)
pyridine-2-carboxylic acid, 6-{3-[(1,3-benzothiazol-2-yl)amino]-4-methyl-6,7-dihy-
dropyrido[2,3-c]pyridazin-8(5H)-yl}-3-(1-{[3-(2-{
[(3R)-3,4-dihydroxybutyl]amino}ethoxy)-5,7-dimeth-
yladamantan-1-yl]methyl}-5-methyl-1H-pyrazol-4-yl)
pyridine-2-carboxylic acid, 6-[3-(1,3-benzothiazol-2-ylamino)-4-methyl-6,7-di-
hydro-5H-pyrido[2,3-c]pyridazin-8-yl]-3-[1-[[3-[2-[2-
hydroxyethyl(methyl)amino]ethoxy]-5,7-dimethyl-1-
adamantyl]methyl]-5-methyl-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3-[2-[4-
hydroxybutyl(methyl)amino]ethoxy]-5,7-dimethyl-1-
adamantyl]methyl]-5-methyl-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3-[2-
[[(3R)-3,4-dihydroxybutyl]-methyl-amino]ethoxy]-5,
7-dimethyl-1-adamantyl]methyl]-5-methyl-pyrazol-4-
yl]pyridine-2-carboxylic acid, 6-[3-(1,3-benzothiazol-2-ylamino)-4-methyl-6,7-di-
hydro-5H-pyrido[2,3-c]pyridazin-8-yl]-3-[1-[[3,5-dimethyl-7-(2-piperazin-1-ylethoxy)-1-adamantyl]
methyl]-5-methyl-pyrazol-4-yl]pyridine-2-carboxylic
acid, 6-{3-[(1,3-benzothiazol-2-yl)amino]-4-methyl-6,7-dihy-
dropyrido[2,3-c]pyridazin-8(5H)-yl}-3-[1-({3,5-dim-
ethyl-7-[2-(methylamino)ethoxy]adamantan-1-
yl}methyl)-5-methyl-1H-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3,5-di-
methyl-7-[2-(1-piperidyl)ethoxy]-1-adamantyl]
methyl]-5-methyl-pyrazol-4-yl]pyridine-2-carboxylic
acid, 3-[1-[[3-[2-(azepan-1-yl)ethoxy]-5,7-dimethyl-1-ada-
mantyl]methyl]-5-methyl-pyrazol-4-yl]-6-[3-(1,3-ben-
zothiazol-2-ylamino)-4-methyl-6,7-dihydro-5H-pyrido
[2,3-c]pyridazin-8-yl]pyridine-2-carboxylic acid, 6-[3-(1,3-benzothiazol-2-ylamino)-4-methyl-6,7-di-
hydro-5H-pyrido[2,3-c]pyridazin-8-yl]-3-[1-[[3-[2-(4-
isopropylpiperazin-1-yl)ethoxy]-5,7-dimethyl-1-ada-
mantyl]methyl]-5-methyl-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3,5-di-
methyl-7-(2-morpholinoethoxy)-1-adamantyl]methyl]-
5-methyl-pyrazol-4-yl]pyridine-2-carboxylic acid, 6-[3-(1,3-benzothiazol-2-ylamino)-4-methyl-6,7-di-
hydro-5H-pyrido[2,3-c]pyridazin-8-yl]-3-[1-[[3-[2-[3-
methoxypropyl(methyl)amino]ethoxy]-5,7-dimethyl-
1-adamantyl]methyl]-5-methyl-pyrazol-4-yl]pyridine-
2-carboxylic acid, 6-[3-(1,3-benzothiazol-2-ylamino)-4-methyl-6,7-di-
hydro-5H-pyrido[2,3-c]pyridazin-8-yl]-3-[1-[[3-[2-[2-
(2-hydroxyethoxy)ethylamino]ethoxy]-5,7-dimethyl-
1-adamantyl]methyl]-5-methyl-pyrazol-4-yl]pyridine-
2-carboxylic acid, 6-[3-(1,3-benzothiazol-2-ylamino)-4-methyl-6,7-di-
hydro-5H-pyrido[2,3-c]pyridazin-8-yl]-3-[1-[[3-[2-
[[2-hydroxy-1-(hydroxymethyl)ethyl]amino]ethoxy]-
5,7-dimethyl-1-adamantyl]methyl]-5-methyl-pyrazol-
4-yl]pyridine-2-carboxylic acid, 6-[3-(1,3-benzothiazol-2-ylamino)-4-methyl-6,7-di-
hydro-5H-pyrido[2,3-c]pyridazin-8-yl]-3-[1-[[3-[2-
[[3-hydroxy-2-(hydroxymethyl)propyl]amino]ethoxy]-
5,7-dimethyl-1-adamantyl]methyl]-5-methyl-pyrazol-
4-yl]pyridine-2-carboxylic acid, 6-[3-(1,3-benzothiazol-2-ylamino)-4-methyl-6,7-di-
hydro-5H-pyrido[2,3-c]pyridazin-8-yl]-3-[1-[[3-[2-
[bis(2-hydroxyethyl)amino]ethoxy]-5,7-dimethyl-1-
adamantyl]methyl]-5-methyl-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3-[2-
[bis(3-hydroxypropyl)amino]ethoxy]-5,7-dimethyl-1-
adamantyl]methyl]-5-methyl-pyrazol-4-yl]pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3-[2-
[bis(4-hydroxybutyl)amino]ethoxy]-5,7-dimethyl-1-
adamantyl]methyl]-5-methyl-pyrazol-4-yl]pyridine-2-
carboxylic acid, 6-{3-[(1,3-benzothiazol-2-yl)amino]-4-methyl-6,7-dihy-
dropyrido[2,3-c]pyridazin-8(5H)-yl}-3-{1-[(3,5-dim-
ethyl-7-{2-[(2-sulfoethyl)amino]ethoxy}adamantan-1-
yl)methyl]-5-methyl-1H-pyrazol-4-yl}pyridine-2-
carboxylic acid, 6-[3-(1,3-benzothiazol-2-ylamino)-4-methyl-6,7-di-
hydro-5H-pyrido[2,3-c]pyridazin-8-yl]-3-[1-[[3-[2-
[(4-hydroxyphenyl)methylamino]ethoxy]-5,7-dim-
ethyl-1-adamantyl]methyl]-5-methyl-pyrazol-4-yl]
pyridine-2-carboxylic acid, 2-[3-(1,3-Benzothiazol-2-ylamino)-4-methyl-6,7-di-
hydro-5H-pyrido[2,3-c]pyridazin-8-yl]-5-[3-[4-[3-(di-
methylamino)prop-1-ynyl]-2-fluoro-phenoxy]propyl]
thiazole-4-carboxylic acid, 2-[3-(1,3-benzothiazol-2-ylamino)-4-methyl-6,7-di-
hydro-5H-pyrido[2,3-c]pyridazin-8-yl]-5-[3-[4-[3-
[[(3S)-3,4-dihydroxybutyl]amino]prop-1-ynyl]-2-
fluoro-phenoxy]propyl]thiazole-4-carboxylic acid, 2-[3-(1,3-benzothiazol-2-ylamino)-4-methyl-6,7-di-
hydro-5H-pyrido[2,3-c]pyridazin-8-yl]-5-[3-[2-fluoro-
4-[3-(3-hydroxypropylamino)prop-1-ynyl]phenoxy]
propyl]thiazole-4-carboxylic acid, its enantiomers and diastereoisomers, and addition-salts
thereof with a pharmaceutically acceptable acid or
base.

30. A pharmaceutical composition comprising the com-
pound according to claim 1, or a salt thereof with a phar-
maceutically acceptable acid or base, in combination with
one or more pharmaceutically acceptable excipients.

31. A method of treating a condition selected from a
haemotological malignancy and a solid tumor, wherein the
haemotological malignancy is T-cell Acute Lymphoblastic
Leukemia (T-ALL) and the solid tumor is lung cancer, in a
subject in need thereof, comprising administration of the
compound according to claim 1, alone or in combination
with one or more pharmaceutically acceptable excipients.

32. The method according to claim 31, wherein the
condition is T-cell Acute Lymphoblastic Leukemia (T-ALL).

33. The method according to claim 31, wherein the the
condition is lung cancer.

34. A combination of the compound according to claim 1
with an anti-cancer agent selected from genotoxic agents,
mitotic poisons, anti-metabolites, proteasome inhibitors,
kinase inhibitors and antibodies.

35. A pharmaceutical composition comprising the com-
bination according to claim 34 in combination with one or
more pharmaceutically acceptable excipients.

36. A method of treating cancer in a subject in need
thereof, comprising administration of an effective amount of
the combination according to claim 34, alone or in combi-
nation with one or more pharmaceutically acceptable excipi-
ents.

37. A method of treating cancer requiring radiotherapy in
a subject in need thereof, comprising administration of the
compound according to claim 1.

38. A compound selected from:

(VI)

377
-continued (VIII)

(IX)

wherein R$_7$ represents a group selected from: linear or branched C$_1$-C$_6$alkyl; (C$_3$-C$_6$)cycloalkylene-R$_8$; and:

378
-continued wherein Cy represents a C$_3$-C$_8$cycloalkyl, and

G1 represents a C$_1$-C$_6$alkyl group or a (4-methoxyphenyl) methyl group.

39. A compound selected from:

(XIV-a)

(XIV-b)

379

-continued (XV-a)

(XV-b)

380 wherein $R_6$ represents a group selected from:

hydrogen;

—$C_2$-$C_6$alkenyl;

—$X_2$—O—$R_7$;

—$X_2$—$NSO_2$—$R_7$;

—C=C($R_9$)—$Y_1$—O—$R_7$;

$C_3$-$C_6$cycloalkyl;

$C_3$-$C_6$heterocycloalkyl optionally substituted by a hydroxyl group;

$C_3$-$C_6$cycloalkylene-$Y_2$—$R_7$;

$C_3$-$C_6$heterocycloalkylene-$Y_2$—$R_7$; and a heteroarylene-$R_7$ group optionally substituted by a linear or branched $C_1$-$C_6$alkyl group, and G1 represents a $C_1$-$C_6$alkyl group or a (4-methoxyphenyl) methyl group.

\* \* \* \* \*

SEQUENCE LISTING

```
<160> NUMBER OF SEQ ID NOS: 4

<210> SEQ ID NO 1
<211> LENGTH: 19
<212> TYPE: PRT
<213> ORGANISM: Homo sapiens

<400> SEQUENCE: 1

Ala Arg Glu Ile Gly Ala Gln Leu Arg Arg Met Ala Asp Asp Leu Asn
1               5                   10                  15

Ala Gln Tyr

<210> SEQ ID NO 2
<211> LENGTH: 440
<212> TYPE: PRT
<213> ORGANISM: Homo sapiens

<400> SEQUENCE: 2

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Ile Glu Gly
        210                 215                 220

Arg Gly Ile Pro Glu Phe Glu Phe Ser Gln Ser Asn Arg Glu Leu Val
225                 230                 235                 240

Val Asp Phe Leu Ser Tyr Lys Leu Ser Gln Lys Gly Tyr Ser Trp Ser
                245                 250                 255

Gln Phe Ser Asp Val Glu Glu Asn Arg Thr Glu Ala Pro Glu Gly Thr
                260                 265                 270

Glu Ser Glu Met Glu Thr Pro Ser Ala Ile Asn Gly Asn Pro Ser Trp
            275                 280                 285

His Leu Ala Asp Ser Pro Ala Val Asn Gly Ala Thr Gly His Ser Ser
    290                 295                 300
```

-continued

```
Ser Leu Asp Ala Arg Glu Val Ile Pro Met Ala Ala Val Lys Gln Ala
305             310             315             320

Leu Arg Glu Ala Gly Asp Glu Phe Glu Leu Arg Tyr Arg Arg Ala Phe
            325             330             335

Ser Asp Leu Thr Ser Gln Leu His Ile Thr Pro Gly Thr Ala Tyr Gln
            340             345             350

Ser Phe Glu Gln Val Val Asn Glu Leu Phe Arg Asp Gly Val Asn Trp
            355             360             365

Gly Arg Ile Val Ala Phe Phe Ser Phe Gly Gly Ala Leu Cys Val Glu
            370             375             380

Ser Val Asp Lys Glu Met Gln Val Leu Val Ser Arg Ile Ala Ala Trp
385             390             395             400

Met Ala Thr Tyr Leu Asn Asp His Leu Glu Pro Trp Ile Gln Glu Asn
                405             410             415

Gly Gly Trp Asp Thr Phe Val Glu Leu Tyr Gly Asn Asn Ala Ala Ala
                420             425             430

Glu Ser Arg Lys Gly Gln Glu Arg
            435             440

<210> SEQ ID NO 3
<211> LENGTH: 249
<212> TYPE: PRT
<213> ORGANISM: Homo sapiens

<400> SEQUENCE: 3

Met His His His His His His His His Gly Ala Thr Gly Ser Thr Ala
1               5               10              15

Gly Ser Gly Thr Ala Gly Ser Thr Gly Ala Ser Gly Ala Ser Thr Gly
            20              25              30

Gly Thr Gly Ala Thr His His His His His His His Asp Asp Asp
            35              40              45

Asp Lys Ser Pro Met Gly Ser Gln Ser Asn Arg Glu Leu Val Val Asp
    50              55              60

Phe Leu Ser Tyr Lys Leu Ser Gln Lys Gly Tyr Ser Trp Ser Gln Phe
65              70              75              80

Ser Asp Val Glu Glu Asn Arg Thr Glu Ala Pro Glu Gly Thr Glu Ser
            85              90              95

Glu Met Glu Thr Pro Ser Ala Ile Asn Gly Asn Pro Ser Trp His Leu
            100             105             110

Ala Asp Ser Pro Ala Val Asn Gly Ala Thr Gly His Ser Ser Ser Leu
            115             120             125

Asp Ala Arg Glu Val Ile Pro Met Ala Ala Val Lys Gln Ala Leu Arg
    130             135             140

Glu Ala Gly Asp Glu Phe Glu Leu Arg Tyr Arg Arg Ala Phe Ser Asp
145             150             155             160

Leu Thr Ser Gln Leu His Ile Thr Pro Gly Thr Ala Tyr Gln Ser Phe
                165             170             175

Glu Gln Val Val Asn Glu Leu Phe Arg Asp Gly Val Asn Trp Gly Arg
            180             185             190

Ile Val Ala Phe Phe Ser Phe Gly Gly Ala Leu Cys Val Glu Ser Val
            195             200             205

Asp Lys Glu Met Gln Val Leu Val Ser Arg Ile Ala Ala Trp Met Ala
    210             215             220

Thr Tyr Leu Asn Asp His Leu Glu Pro Trp Ile Gln Glu Asn Gly Gly
```

-continued 225          230          235          240

Trp Asp Thr Phe Val Glu Leu Tyr Gly
             245

<210> SEQ ID NO 4
<211> LENGTH: 21
<212> TYPE: PRT
<213> ORGANISM: Homo sapiens

<400> SEQUENCE: 4

Gln Trp Ala Arg Glu Ile Gly Ala Gln Leu Arg Arg Met Ala Asp Asp
1               5                   10                  15

Leu Asn Ala Gln Tyr
            20